(12) United States Patent
Klein et al.

(10) Patent No.: US 12,103,982 B2
(45) Date of Patent: Oct. 1, 2024

(54) T CELL ACTIVATING BISPECIFIC ANTIGEN BINDING MOLECULES

(71) Applicant: Hoffmann-La Roche Inc., Little Falls, NJ (US)

(72) Inventors: Christian Klein, Bonstetten (CH); Ekkehard Moessner, Kreuzlingen (CH); Ralf Hosse, Cham (CH); Peter Bruenker, Hittnau (CH); Pablo Umana, Wollerau (CH); Christiane Neumann, Niederweningen (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 352 days.

(21) Appl. No.: 17/470,778

(22) Filed: Sep. 9, 2021

(65) Prior Publication Data

US 2022/0213224 A1    Jul. 7, 2022

Related U.S. Application Data

(60) Division of application No. 16/541,258, filed on Aug. 15, 2019, now abandoned, which is a division of application No. 15/600,015, filed on May 19, 2017, now abandoned, which is a continuation of application No. PCT/EP2015/076745, filed on Nov. 17, 2015.

(30) Foreign Application Priority Data

Nov. 20, 2014    (EP) .................................. 14194097

(51) Int. Cl.
| | |
|---|---|
| C07K 16/46 | (2006.01) |
| A61K 39/00 | (2006.01) |
| A61K 39/385 | (2006.01) |
| C07K 16/28 | (2006.01) |
| C07K 16/30 | (2006.01) |
| C12N 15/73 | (2006.01) |

(52) U.S. Cl.
CPC .... C07K 16/464 (2013.01); A61K 39/001102 (2018.08); A61K 39/00117 (2018.08); A61K 39/385 (2013.01); C07K 16/28 (2013.01); C07K 16/2809 (2013.01); C07K 16/2878 (2013.01); C07K 16/30 (2013.01); C07K 16/468 (2013.01); C12N 15/73 (2013.01); *A61K 2039/5158* (2013.01); *C07K 16/46* (2013.01); *C07K 2317/24* (2013.01); *C07K 2317/31* (2013.01); *C07K 2317/33* (2013.01); *C07K 2317/41* (2013.01); *C07K 2317/515* (2013.01); *C07K 2317/71* (2013.01); *C07K 2317/73* (2013.01); *C07K 2317/92* (2013.01); *C07K 2319/00* (2013.01)

(58) Field of Classification Search
CPC .. C07K 16/464; C07K 16/28; C07K 16/2809; C07K 16/30; C07K 16/468; A61K 39/001102; C12N 15/73
See application file for complete search history.

(56) References Cited

U.S. PATENT DOCUMENTS

| | | |
|---|---|---|
| 5,547,668 A | 8/1996 | Kranz et al. |
| 5,571,894 A | 11/1996 | Wels et al. |
| 5,587,458 A | 12/1996 | King et al. |
| 5,591,828 A | 1/1997 | Bosslet et al. |
| 5,731,168 A | 3/1998 | Carter et al. |
| 5,821,337 A | 10/1998 | Carter et al. |
| 5,869,046 A | 2/1999 | Presta et al. |
| 6,248,516 B1 | 6/2001 | Winter et al. |
| 6,737,056 B1 | 5/2004 | Presta |
| 6,809,185 B1 | 10/2004 | Schoonjans et al. |
| 7,332,581 B2 | 2/2008 | Presta |
| 7,608,413 B1 | 10/2009 | Joseloff et al. |
| 7,695,936 B2 | 4/2010 | Carter et al. |
| 8,227,577 B2 | 7/2012 | Klein et al. |
| 8,242,247 B2 | 8/2012 | Klein et al. |
| 8,703,132 B2 | 4/2014 | Imhof-Jung et al. |
| 8,709,421 B2 | 4/2014 | Heiss et al. |
| 8,796,424 B2 | 8/2014 | Croasdale et al. |
| 8,834,877 B2 | 9/2014 | O'Shannessy |
| 8,969,526 B2 | 3/2015 | Baehner et al. |
| 9,068,008 B2 | 6/2015 | Mossner et al. |

(Continued)

FOREIGN PATENT DOCUMENTS

| | | |
|---|---|---|
| EA | 201791121 A1 | 4/2018 |
| EP | 0404097 B1 | 9/1996 |

(Continued)

OTHER PUBLICATIONS

Lee et al., Mc Gill Newsromm, Feb. 2016. (Year: 2016).*

(Continued)

*Primary Examiner* — Lei Yao
(74) *Attorney, Agent, or Firm* — Clark & Elbing LLP; Karen L. Elbing

(57) ABSTRACT

The present invention generally relates to novel bispecific antigen binding molecules for T cell activation and re-direction to specific target cells comprising a common light chain. In addition, the present invention relates to polynucleotides encoding such bispecific antigen binding molecules, and vectors and host cells comprising such polynucleotides. The invention further relates to methods for producing the bispecific antigen binding molecules of the invention, and to methods of using these bispecific antigen binding molecules in the treatment of disease.

14 Claims, 79 Drawing Sheets

Specification includes a Sequence Listing.

(56) References Cited

U.S. PATENT DOCUMENTS

| | | |
|---|---|---|
| 9,266,938 B2 | 2/2016 | Ast et al. |
| 9,266,967 B2 | 2/2016 | Klein et al. |
| 9,382,323 B2 | 7/2016 | Brinkmann et al. |
| 9,447,159 B2 | 9/2016 | Ast et al. |
| 9,526,797 B2 | 12/2016 | Gerdes et al. |
| 2007/0111281 A1 | 5/2007 | Sondermann et al. |
| 2008/0241152 A1 | 10/2008 | Alitalo et al. |
| 2009/0252683 A1 | 10/2009 | Kischel et al. |
| 2010/0015133 A1 | 1/2010 | Igawa et al. |
| 2010/0150918 A1 | 6/2010 | Kufer et al. |
| 2010/0310571 A1 | 12/2010 | Cheung |
| 2010/0316645 A1 | 12/2010 | Imhof-Jung et al. |
| 2011/0293613 A1 | 12/2011 | Brinkmann et al. |
| 2012/0164137 A1 | 6/2012 | Sass et al. |
| 2012/0189620 A1 | 7/2012 | Oyesiku |
| 2012/0225071 A1 | 9/2012 | Klein et al. |
| 2012/0276125 A1 | 11/2012 | Ast et al. |
| 2013/0022601 A1 | 1/2013 | Brinkmann et al. |
| 2013/0045492 A1 | 2/2013 | Babb et al. |
| 2013/0058936 A1 | 3/2013 | Bruenker et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0171095 A1 | 7/2013 | Bernett et al. |
| 2013/0266579 A1 | 10/2013 | Wei et al. |
| 2014/0088295 A1 | 3/2014 | Smith et al. |
| 2014/0099254 A1 | 4/2014 | Chang et al. |
| 2014/0112914 A1 | 4/2014 | Nezu et al. |
| 2014/0120096 A1 | 5/2014 | Bakker et al. |
| 2014/0154254 A1 | 6/2014 | Kannan et al. |
| 2014/0205610 A1 | 7/2014 | Ando et al. |
| 2014/0242079 A1 | 8/2014 | Bacac et al. |
| 2014/0242080 A1 | 8/2014 | Jaeger et al. |
| 2014/0288275 A1 | 9/2014 | Moore et al. |
| 2014/0294823 A1 | 10/2014 | Moore et al. |
| 2014/0294833 A1 | 10/2014 | Desjarlais et al. |
| 2014/0302064 A1 | 10/2014 | Moore |
| 2014/0308285 A1 | 10/2014 | Yan et al. |
| 2014/0322217 A1 | 10/2014 | Moore et al. |
| 2014/0363426 A1 | 12/2014 | Moore et al. |
| 2014/0370013 A1 | 12/2014 | Desjarlais et al. |
| 2014/0377270 A1 | 12/2014 | Moore et al. |
| 2015/0079088 A1 | 3/2015 | Lowman et al. |
| 2015/0094451 A1 | 4/2015 | Fischer et al. |
| 2015/0166661 A1 | 6/2015 | Chen et al. |
| 2015/0218274 A1 | 8/2015 | Sabatos-Peyton et al. |
| 2015/0274845 A1 | 10/2015 | Bruenker et al. |
| 2015/0315296 A1 | 11/2015 | Schaefer et al. |
| 2015/0368351 A1 | 12/2015 | Vu et al. |
| 2015/0376287 A1 | 12/2015 | Vu et al. |
| 2016/0075785 A1 | 3/2016 | Ast et al. |
| 2016/0130347 A1 | 5/2016 | Bruenker et al. |
| 2016/0145354 A1 | 5/2016 | Bacac et al. |
| 2016/0175397 A1 | 6/2016 | Umana et al. |
| 2016/0208017 A1 | 7/2016 | Ast et al. |
| 2016/0208019 A1 | 7/2016 | Bacac et al. |
| 2016/0263240 A1 | 9/2016 | Ast et al. |
| 2016/0297881 A1 | 10/2016 | Vu et al. |
| 2016/0368985 A1 | 12/2016 | Hotzel et al. |
| 2017/0008971 A1 | 1/2017 | Dennis et al. |
| 2017/0096485 A1 | 4/2017 | Bacac et al. |
| 2017/0096495 A1 | 4/2017 | Bacac et al. |
| 2017/0114146 A1 | 4/2017 | Klein et al. |
| 2017/0174786 A1 | 6/2017 | Bacac et al. |
| 2017/0190783 A1 | 7/2017 | Bacac et al. |
| 2017/0209573 A1 | 7/2017 | Bacac et al. |
| 2017/0253670 A1 | 9/2017 | Klein et al. |
| 2017/0267783 A1 | 9/2017 | Nezu et al. |
| 2017/0306018 A1 | 10/2017 | Vu et al. |
| 2017/0306036 A1 | 10/2017 | Vu et al. |
| 2017/0306044 A1 | 10/2017 | Vu et al. |
| 2017/0327579 A1 | 11/2017 | Vu et al. |
| 2017/0327580 A1 | 11/2017 | Vu et al. |

FOREIGN PATENT DOCUMENTS

| | | |
|---|---|---|
| EP | 1870459 A1 | 12/2007 |
| EP | 1870459 A4 | 9/2010 |
| EP | 2578230 A1 | 4/2013 |
| EP | 2647707 A1 | 10/2013 |
| EP | 2647707 A4 | 4/2014 |
| EP | 2982694 A1 | 2/2016 |
| EP | 1870459 B1 | 6/2016 |
| JP | 2012-522523 A | 9/2012 |
| WO | WO-91/03493 A1 | 3/1991 |
| WO | WO-93/16185 A2 | 8/1993 |
| WO | WO-96/01126 A1 | 1/1996 |
| WO | WO-96/27011 A1 | 9/1996 |
| WO | WO-96/40210 A1 | 12/1996 |
| WO | WO-98/50431 A2 | 11/1998 |
| WO | WO-98/50431 A3 | 1/1999 |
| WO | WO-02/09573 A2 | 2/2002 |
| WO | WO-2004/113388 A2 | 12/2004 |
| WO | WO-2005/044859 A2 | 5/2005 |
| WO | WO-2005/080431 A2 | 9/2005 |
| WO | WO-2006/082515 A2 | 8/2006 |
| WO | WO-2006/099141 A2 | 9/2006 |
| WO | WO-2006/116592 A2 | 11/2006 |
| WO | WO-2007/024715 A2 | 3/2007 |
| WO | WO-2007/042261 A2 | 4/2007 |
| WO | WO-2007/075270 A2 | 7/2007 |
| WO | WO-2007/110205 A2 | 10/2007 |
| WO | WO-2007/146968 A2 | 12/2007 |
| WO | WO-2007/147901 A1 | 12/2007 |
| WO | WO-2008/031577 A1 | 3/2008 |
| WO | WO-2007/024715 A3 | 10/2008 |
| WO | WO-2008/119566 A2 | 10/2008 |
| WO | WO-2008/119567 A2 | 10/2008 |
| WO | WO-2007/024715 A9 | 4/2009 |
| WO | WO-2009/070642 A1 | 6/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/089004 A1 | 7/2009 |
| WO | WO-2010/115551 A1 | 10/2010 |
| WO | WO-2010/115589 A1 | 10/2010 |
| WO | WO-2010/129304 A2 | 11/2010 |
| WO | WO-2010/136172 A1 | 12/2010 |
| WO | WO-2010/145792 A1 | 12/2010 |
| WO | WO-2010/145793 A1 | 12/2010 |
| WO | WO-2010/129304 A3 | 2/2011 |
| WO | WO-2011/028952 A1 | 3/2011 |
| WO | WO-2011/090754 A1 | 7/2011 |
| WO | WO-2011/090762 A1 | 7/2011 |
| WO | WO-2011/106528 A1 | 9/2011 |
| WO | WO-2011/143545 A1 | 11/2011 |
| WO | WO-2012/054654 A2 | 4/2012 |
| WO | WO-2012/058768 A1 | 5/2012 |
| WO | WO-2012/061759 A2 | 5/2012 |
| WO | WO-2012/058768 A8 | 6/2012 |
| WO | WO-2012/073985 A1 | 6/2012 |
| WO | WO-2012/130831 A1 | 10/2012 |
| WO | WO-2012/135675 A2 | 10/2012 |
| WO | WO-2012/158818 A2 | 11/2012 |
| WO | WO-2012/162067 A2 | 11/2012 |
| WO | WO-2013/012722 A1 | 1/2013 |
| WO | WO-2013/026831 A1 | 2/2013 |
| WO | WO-2013/026833 A1 | 2/2013 |
| WO | WO-2013/026837 A1 | 2/2013 |
| WO | WO-2013/072406 A1 | 5/2013 |
| WO | WO-2013/096291 A2 | 6/2013 |
| WO | WO-2013/157953 A1 | 10/2013 |
| WO | WO-2013/157954 A1 | 10/2013 |
| WO | WO-2013/172951 A1 | 11/2013 |
| WO | WO-2014/004549 A1 | 1/2014 |
| WO | WO-2014/022540 A1 | 2/2014 |
| WO | WO-2014/028560 A2 | 2/2014 |
| WO | WO-2014/047231 A1 | 3/2014 |
| WO | WO-2014/051433 A1 | 4/2014 |
| WO | WO-2014/056783 A1 | 4/2014 |
| WO | WO-2014/028560 A3 | 5/2014 |
| WO | WO-2014/081955 A1 | 5/2014 |

(56) References Cited

FOREIGN PATENT DOCUMENTS

| | | |
|---|---|---|
| WO | WO-2014/087863 A1 | 6/2014 |
| WO | WO-2014/104270 A1 | 7/2014 |
| WO | WO-2014/110601 A1 | 7/2014 |
| WO | WO-2014/122143 A1 | 8/2014 |
| WO | WO-2014/122144 A1 | 8/2014 |
| WO | WO-2014/122251 A2 | 8/2014 |
| WO | WO-2014/131694 A1 | 9/2014 |
| WO | WO-2014/131712 A1 | 9/2014 |
| WO | WO-2014/141152 A2 | 9/2014 |
| WO | WO-2014/144357 A1 | 9/2014 |
| WO | WO-2014/144722 A2 | 9/2014 |
| WO | WO-2014/151910 A1 | 9/2014 |
| WO | WO-2014/153002 A1 | 9/2014 |
| WO | WO-2014/122251 A3 | 10/2014 |
| WO | WO-2014/161845 A1 | 10/2014 |
| WO | WO-2014/167022 A1 | 10/2014 |
| WO | WO-2014/141152 A3 | 12/2014 |
| WO | WO-2014/191113 A1 | 12/2014 |
| WO | WO-2015/001085 A1 | 1/2015 |
| WO | WO-2015/013671 A1 | 1/2015 |
| WO | WO-2014/191113 A8 | 2/2015 |
| WO | WO-2015/018085 A1 | 2/2015 |
| WO | WO-2015/048272 A1 | 4/2015 |
| WO | WO-2015/150447 A1 | 10/2015 |
| WO | WO-2016/014974 A2 | 1/2016 |
| WO | WO-2016/020065 A1 | 2/2016 |
| WO | WO-2016/020332 A1 | 2/2016 |
| WO | WO-2016/036678 A1 | 3/2016 |
| WO | WO-2016/055592 A1 | 4/2016 |
| WO | WO-2016/055593 A1 | 4/2016 |
| WO | WO-2016/077505 A2 | 5/2016 |
| WO | WO-2016/079076 A1 | 5/2016 |
| WO | WO-2016/079081 A1 | 5/2016 |
| WO | WO-2016/079177 A1 | 5/2016 |
| WO | WO-2016/087531 A1 | 6/2016 |
| WO | WO-2016/146894 A1 | 9/2016 |
| WO | WO-2016/179003 A1 | 11/2016 |
| WO | WO-2017/021450 A1 | 2/2017 |

OTHER PUBLICATIONS

Labrador et al., Natue vol. 409; p. 1000 Feb. 2001 (Year: 2001).*
Atwell et al., "Stable heterodimers from remodeling the domain interface of a homodimer using a phage display library," J Mol Biol. 270(1):26-35 (1997).
Booy et al., "Monoclonal and bispecific antibodies as novel therapeutics," Arch Immunol Ther Exp (Warsz). 54(2):85-101 (2006).
Bosch et al., "MCSP/CD3-bispecific single-chain antibody construct engages CD4+ and CD8+ T cells for lysis of MCSP-expressing human uveal melanoma cells," AACR 101st Annual Meeting. April 17-21, Washington, DC. 70(8 Suppl) Abstract 5621 (2010).
Carreno et al., "Cross-species reactivity of the anti-idiotype anti-OKT3 cascade between mice and humans," Hum Immunol. 33(4):249-58 (1992).
Carreno et al., "First step toward the murine idiotypic network generated by OKT3," Human Immunology. 32:12:8.4 (1991) (Abstract only) (1 page).
Carter, "Bispecific human IgG by design," J Immunol Methods. 248(1-2):7-15 (2001).
Casset et al., "A peptide mimetic of an anti-CD4 monoclonal antibody by rational design," Biochem Biophys Res Commun. 307(1):198-205 (2003).
Chan et al., "Variable region domain exchange in human IgGs promotes antibody complex formation with accompanying structural changes and altered effector functions," Mol Immunol. 41(5):527-38 (2004).
Chen et al., "Selection and analysis of an optimized anti-VEGF antibody: crystal structure of an affinity-matured Fab in complex with antigen," J Mol Biol. 293(4):865-81 (1999).
Cui et al., "Chemically programmed bispecific antibodies that recruit and activate T cells," J Biol Chem. 287(34):28206-14 (10 Pages) (2012).
De Pascalis et al., "Grafting of 'abbreviated' complementarity-determining regions containing specificity-determining residues essential for ligand contact to engineer a less immunogenic humanized monoclonal antibody," J Immunol. 169(6):3076-84 (2002).
Deyev et al., "Modern Technologies for Creating Synthetic Antibodies for Clinical application," Acta Naturae. 1(1):32-50 (2009) (19 pages).
Edelman et al., "The covalent structure of an entire gammaG immunoglobulin molecule," Proc Natl Acad Sci U S A. 63(1):78-85 (1969).
Garcia-Bennett et al., "In search of the Holy Grail: Folate-targeted nanoparticles for cancer therapy," Biochem Pharmacol. 81(8):976-84 (2011) (9 pages).
Hasemann et al., "Mutational analysis of arsonate binding by a CRIA+ antibody. VH and VL junctional diversity are essential for binding activity," J Biol Chem. 266(12):7626-32 (1991) (7 pages).
Holliger et al., "'Diabodies': small bivalent and bispecific antibody fragments," Proc Natl Acad Sci U S A. 90(14):6444-8 (1993).
Holliger et al., "Specific killing of lymphoma cells by cytotoxic T-cells mediated by a bispecific diabody," Protein Eng. 9(3):299-305 (1996).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Hudson et al., "Engineered antibodies," Nat Med. 9(1):129-34 (2003).
Jackman et al., "Development of a two-part strategy to identify a therapeutic human bispecific antibody that inhibits IgE receptor signaling," J Biol Chem. 285(27):20850-9 (2010) (11 pages).
Kang et al., "Antibody redesign by chain shuffling from random combinatorial immunoglobulin libraries," Proc Natl Acad Sci U.S.A. 88(24):11120-3 (1991).
Katayose et al., "MUC1-specific targeting immunotherapy with bispecific antibodies: inhibition of xenografted human bile duct carcinoma growth," Cancer Res. 56(18):4205-12 (1996) (9 pages).
Kimura et al., "Molecular cloning of a human MafF homologue, which specifically binds to the oxytocin receptor gene in term myometrium," Biochem Biophys Res Commun. 264(1):86-92 (1999).
Kipriyanov et al., "Bispecific tandem diabody for tumor therapy with improved antigen binding and pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," MAbs. 4(2):182-97 (2012).
Kopantzev et al., "Differences in gene expression levels between early and later stages of human lung development are opposite to those between normal lung tissue and non-small lung cell carcinoma," Lung Cancer. 62(1):23-34 (2008) (12 pages).
Lamminmäki et al., "Crystal Structure of a Recombinant Anti-Estradiol Fab Fragment in Complex With 17beta-Estradiol," J Biol Chem. 276(39):36687-94 (2001).
Luiten et al., "Chimeric bispecific OC/TR monoclonal antibody mediates lysis of tumor cells expressing the folate-binding protein (MOv18) and displays decreased immunogenicity in patients," J Immunother. 20(6):496-504 (1997).
MacCallum et al., "Antibody-antigen interactions: contact analysis and binding site topography," J Mol Biol. 262(5):732-45 (1996) (14 pages).
Merchant et al., "An efficient route to human bispecific IgG," Nat Biotechnol. 16(7):677-81 (1998).
Mezzanzanica et al., "Human ovarian carcinoma lysis by cytotoxic T cells targeted by bispecific monoclonal antibodies: analysis of the antibody components," Int J Cancer. 41(4):609-15 (1988).
Miller et al., "Design, construction, and in vitro analyses of multivalent antibodies," J Immunol. 170(9):4854-61 (2003).
Moore et al., "A novel bispecific antibody format enables simultaneous bivalent and monovalent co-engagement of distinct target antigens," MAbs. 3(6):546-57 (2011).
Moore et al., "Application of dual affinity retargeting molecules to achieve optimal redirected T-cell killing of B-cell lymphoma," Blood. 117(17):4542-51 (2011) (11 pages).

(56) References Cited

OTHER PUBLICATIONS

Nagorsen et al., "Immunomodulatory therapy of cancer with T cell-engaging BiTE antibody blinatumomab," Exp Cell Res. 317(9):1255-60 (2011).
Osada et al., "CEA/CD3-bispecific T Cell-Engaging (BiTE) Antibody-Mediated T Lymphocyte Cytotoxicity Maximized by Inhibition of Both PD1 and PD-L1," Cancer Immunol Immunother. 64(6):677-88 (2015).
Oshimi et al., "Increased lysis of patient CD10-positive leukemic cells by T cells coated with anti-CD3 Fab' antibody cross-linked to anti-CD10 Fab' antibody," Blood. 77(5):1044-9 (1991).
Padlan et al., "Structure of an antibody-antigen complex: crystal structure of the HyHEL-10 Fab-lysozyme complex," Proc Natl Acad Sci USA. 86(15):5938-5942 (1989).
Paul, Chapter 9: Structure and Function of Immunoglobulins, *Fundamental Immunology*, Third Edition. Raven Press Ltd., 292-295 (1993) (6 pages).
Pessano et al., "The T3/T cell receptor complex: antigenic distinction between the two 20-kd T3 (T3-delta and T3-epsilon) subunits," Embo J. 4(2):337-44 (1985).
Ridgway et al., "'Knobs-into-holes' engineering of antibody CH3 domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Riemer et al., "Matching of trastuzumab (Herceptin®) epitope mimics onto the surface of Her-2_neu—a new method of epitope definition—ScienceDirect", Mol. Immunol. 42(9):1121-1124 (2005).
Rudikoff et al., "Single amino acid substitution altering antigen-binding specificity," Proc Natl Acad Sci U S A. 79(6):1979-83 (1982).
Schaefer et al., "Immunoglobulin domain crossover as a generic approach for the production of bispecific IgG antibodies," Proc Natl Acad Sci U S A. 108(27):11187-92 (2011).
Seimetz et al., "Development and approval of the trifunctional antibody catumaxomab (anti-EpCAM x anti-CD3) as a targeted cancer immunotherapy," Cancer Treat Rev. 36(6):458-67 (2010).
Stancovski et al., "Mechanistic aspects of the opposing effects of monoclonal antibodies to the ERBB2 receptor on tumor growth," Proc Natl Acad Sci U S A. 88(19):8691-8695 (1991).
Stubenrauch et al., "Impact of molecular processing in the hinge region of therapeutic IgG4 antibodies on disposition profiles in cynomolgus monkeys," Drug Metab Dispos. 38(1):84-91 (2010).
Sun et al., "Anti-CD20/CD3 T cell-dependent bispecific antibody for the treatment of B cell malignancies," Sci Transl Med. 7(287):287ra70 (2015) (11 pages).
Torisu-Itakura et al., "Redirected lysis of human melanoma cells by a MCSP/CD3-bispecific BiTE antibody that engages patient-derived T cells," J Immunother. 34(8):597-605 (2011).
Tutt et al., "Trispecific F(ab')3 derivatives that use cooperative signaling via the TCR/CD3 complex and CD2 to activate and redirect resting cytotoxic T cells," J Immunol. 147(1):60-9 (1991).
Vajdos et al., "Comprehensive functional maps of the antigen-binding site of an anti-ErbB2 antibody obtained with shotgun scanning mutagenesis," J Mol Biol. 320(2):415-28 (2002).
Weidle et al., "The intriguing options of multispecific antibody formats for treatment of cancer," Cancer Genomics Proteomics. 10(1):1-18 (2013).
Wolf et al., "BiTEs: bispecific antibody constructs with unique anti-tumor activity," Drug Discov Today. 10(18):1237-44 (2005).
Wu et al., "Humanization of a murine monoclonal antibody by simultaneous optimization of framework and CDR residues," J Mol Biol. 294(1):151-62 (1999).
Zhu et al., "Identification of heavy chain residues in a humanized anti-CD3 antibody important for efficient antigen binding and T cell activation," J Immunol. 155(4):1903-10 (1995).
English Translation of Office Action for Russian Patent Application No. 2017121326, dated Jan. 28, 2019 (3 pages).
English Translation of Office Action for Russian Patent Application No. 2017121326, dated Jun. 13, 2019 (3 pages).
First Office Action for Chinese Patent Application No. 201580073062.8, dated Jul. 3, 2020 (21 pages).
International Preliminary Report on Patentability for International Patent Application No. PCT/EP2015/076745, issued May 23, 2017 (12 pages).
International Search Report and Written Opinion for International Patent Application No. PCT/EP2015/076745, mailed Apr. 11, 2016 (20 pages).
Office Action for U.S. Appl. No. 15/600,015, dated Feb. 20, 2019 (19 pages).
Office Action for U.S. Appl. No. 15/600,011, dated Sep. 17, 2019 (43 pages).
Office Action for Chinese Patent Application No. 201580059475.0, dated Jun. 22, 2020 (15 pages).
Office Action for Chinese Patent Application No. 201580073564.0, dated Jun. 22, 2020 (5 pages).
Office Action for Ukrainian Patent Application No. 201706105, dated Jul. 22, 2020 (6 pages).
Office Action for U.S. Appl. No. 16/138,417, dated May 18, 2020 (20 pages).
Search Report for Chinese Patent Application No. 201580073062.8, dated Jun. 28, 2020 (3 pages).
Search Report for Chinese Patent Application No. 201580073564.0, dated Nov. 17, 2015 (1 page).
Search Report and Written Opinion for Brazilian Patent Application No. BR112017007086-3, dated Oct. 4, 2020 (4 pages).
Search Report and Written Opinion for Singaporean Patent Application No. 11201808085, dated Mar. 3, 2020 (10 pages).

* cited by examiner

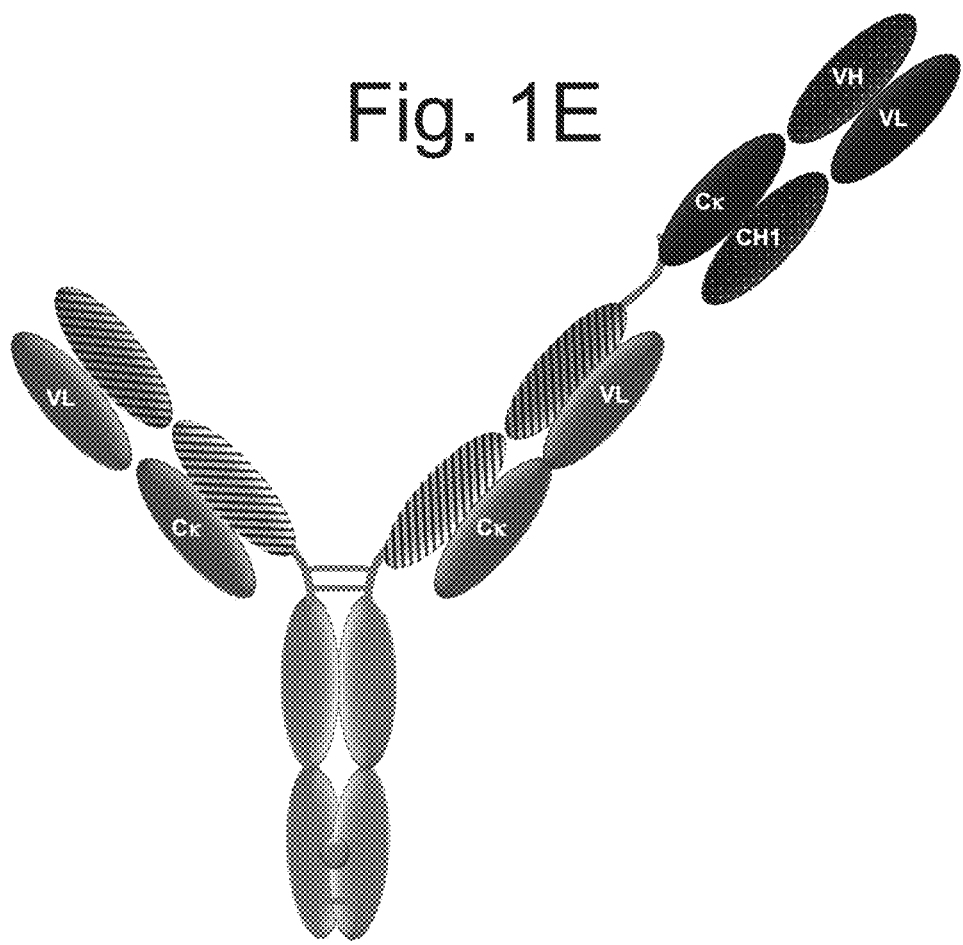

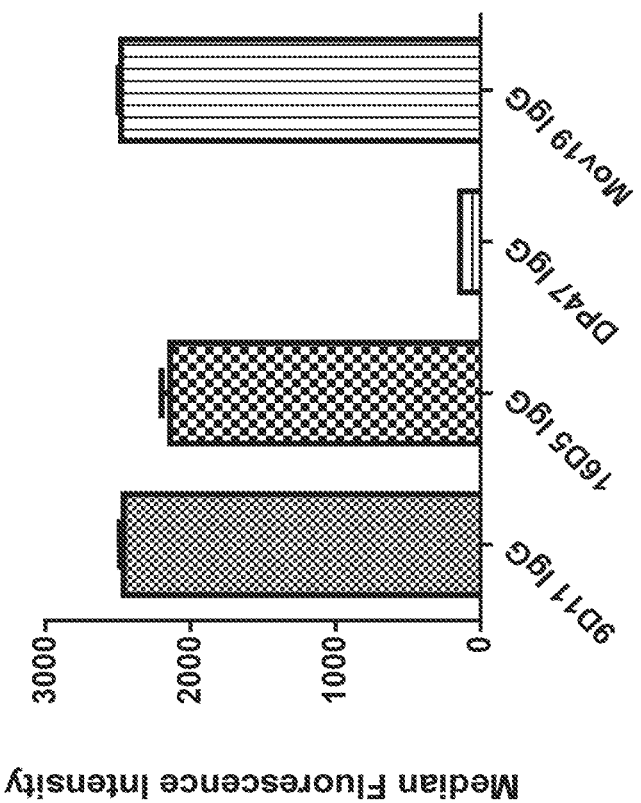
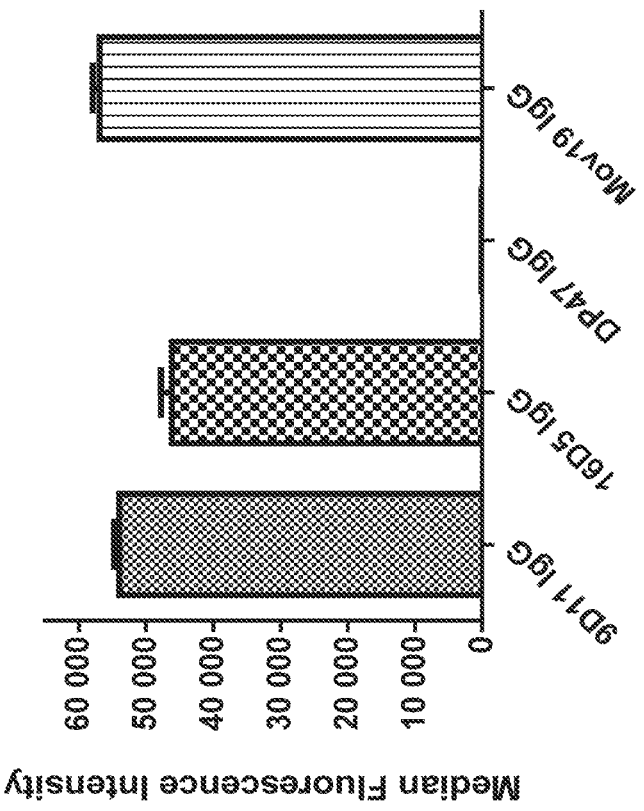

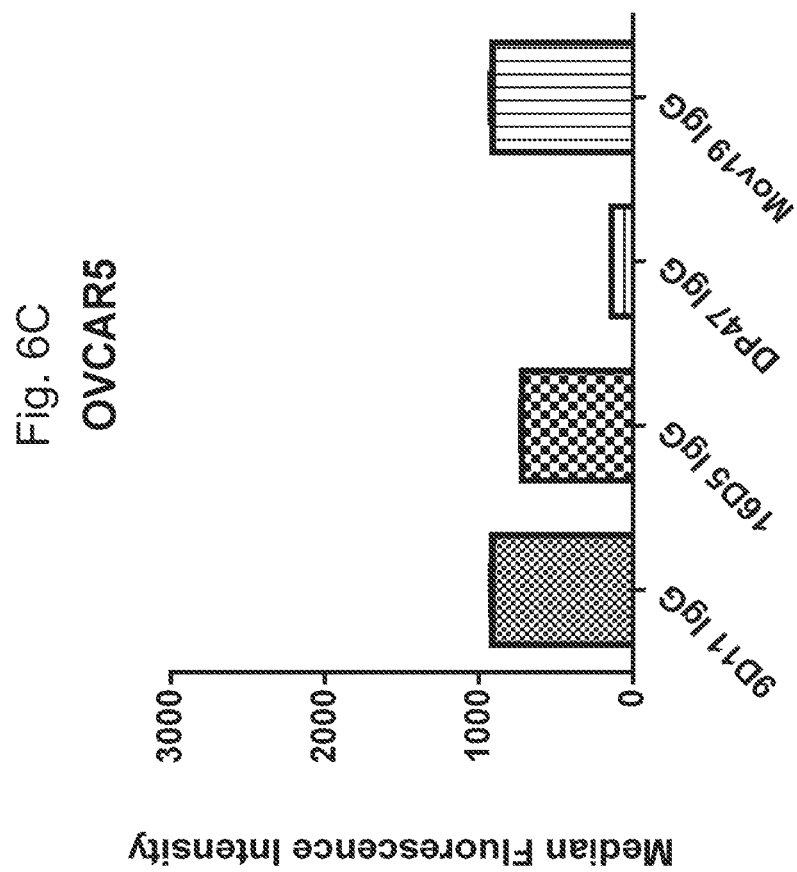

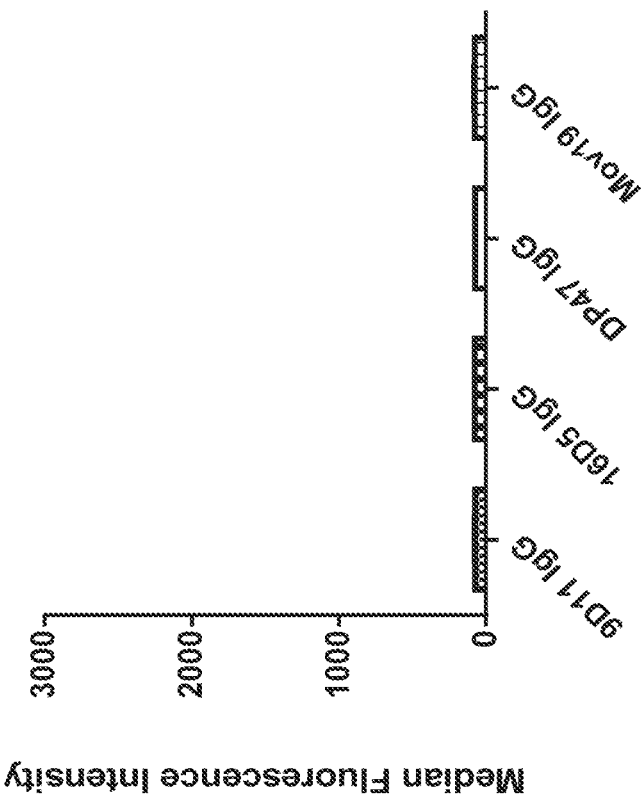
Fig. 6E MKN45
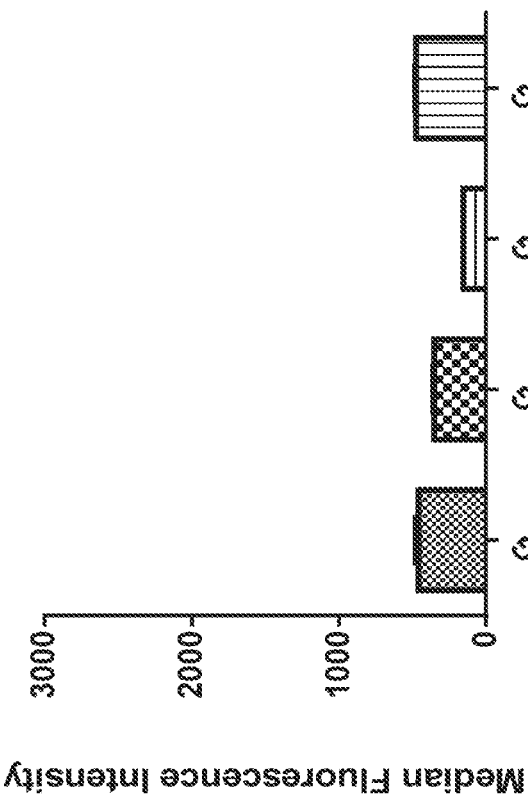
Fig. 6D HT29

16D5 FolR1 TCB    9D11 FolR1 TCB    DP47 TCB

Mov19 TCB    9D11 TCB    16D5 TCB    DP47 TCB

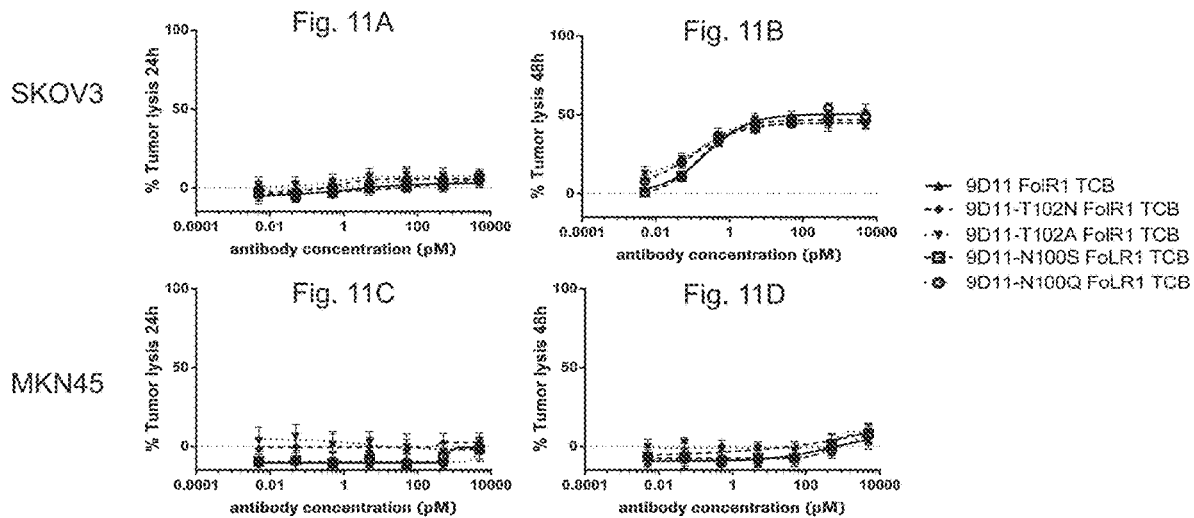

HT29 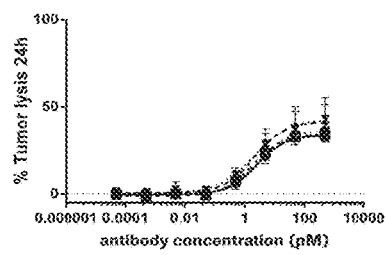 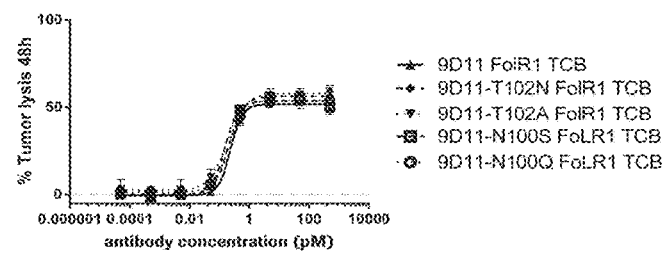

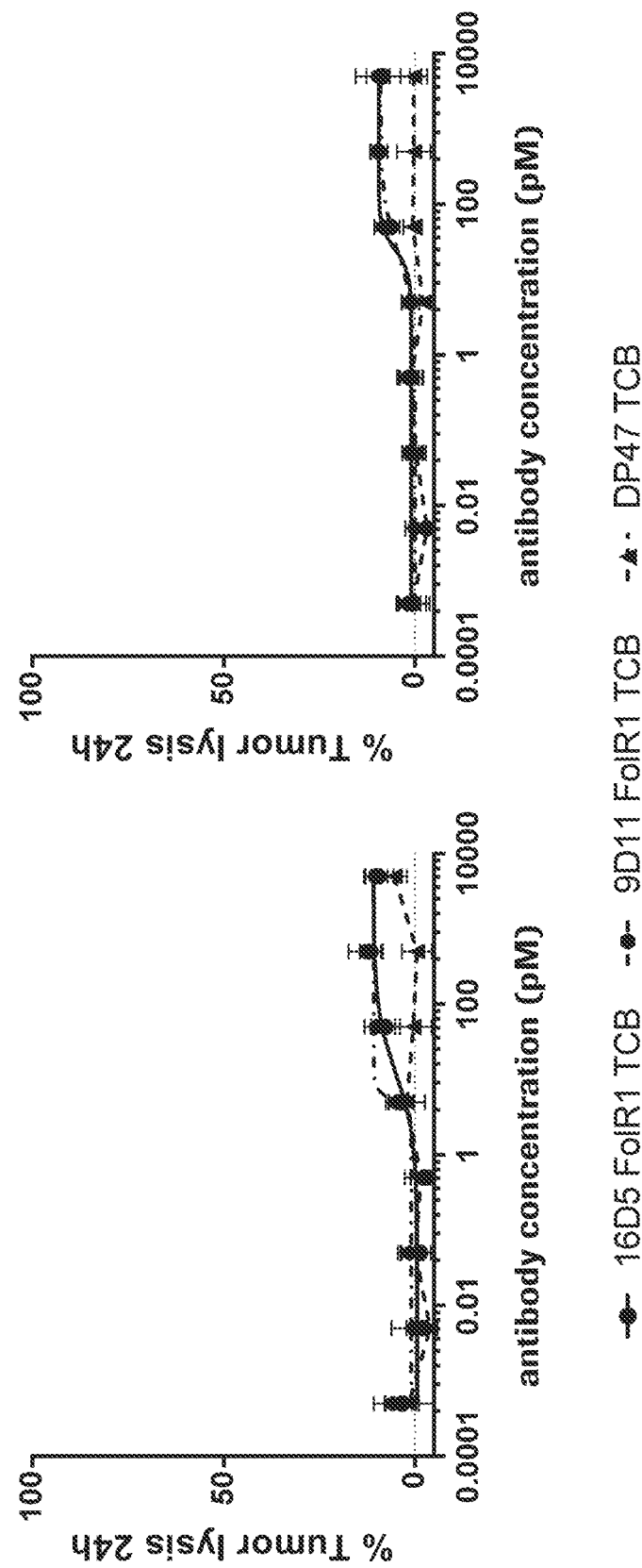

HT29

HB

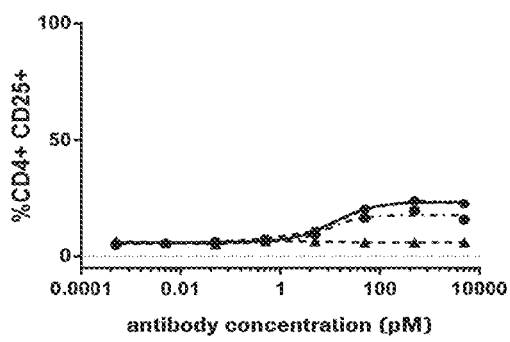
Fig. 12I
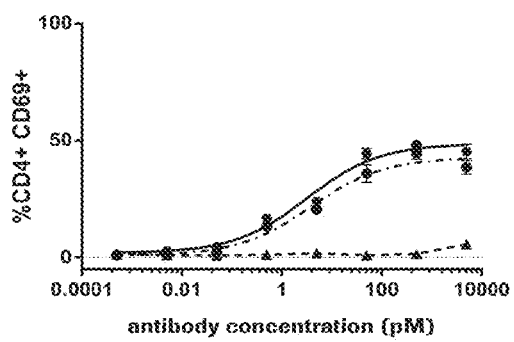
Fig. 12J  HRP
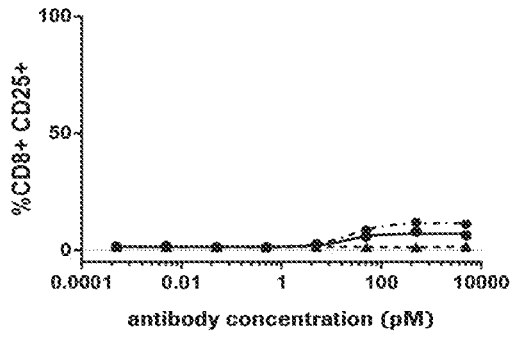
Fig. 12K
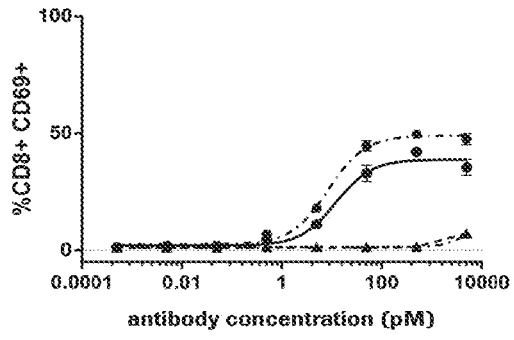
Fig. 12L

HRC

—●— 16D5 FolR1 TCB  —●— 9D11 FolR1 TCB  -▲- DP47 TCB

HB

— 16D5 FolR1 TCB    —•— 9D11 FolR1 TCB    —▲— DP47 TCB

HT29

— 16D5 FolR1 TCB   — 9D11 FolR1 TCB   — DP47 TCB

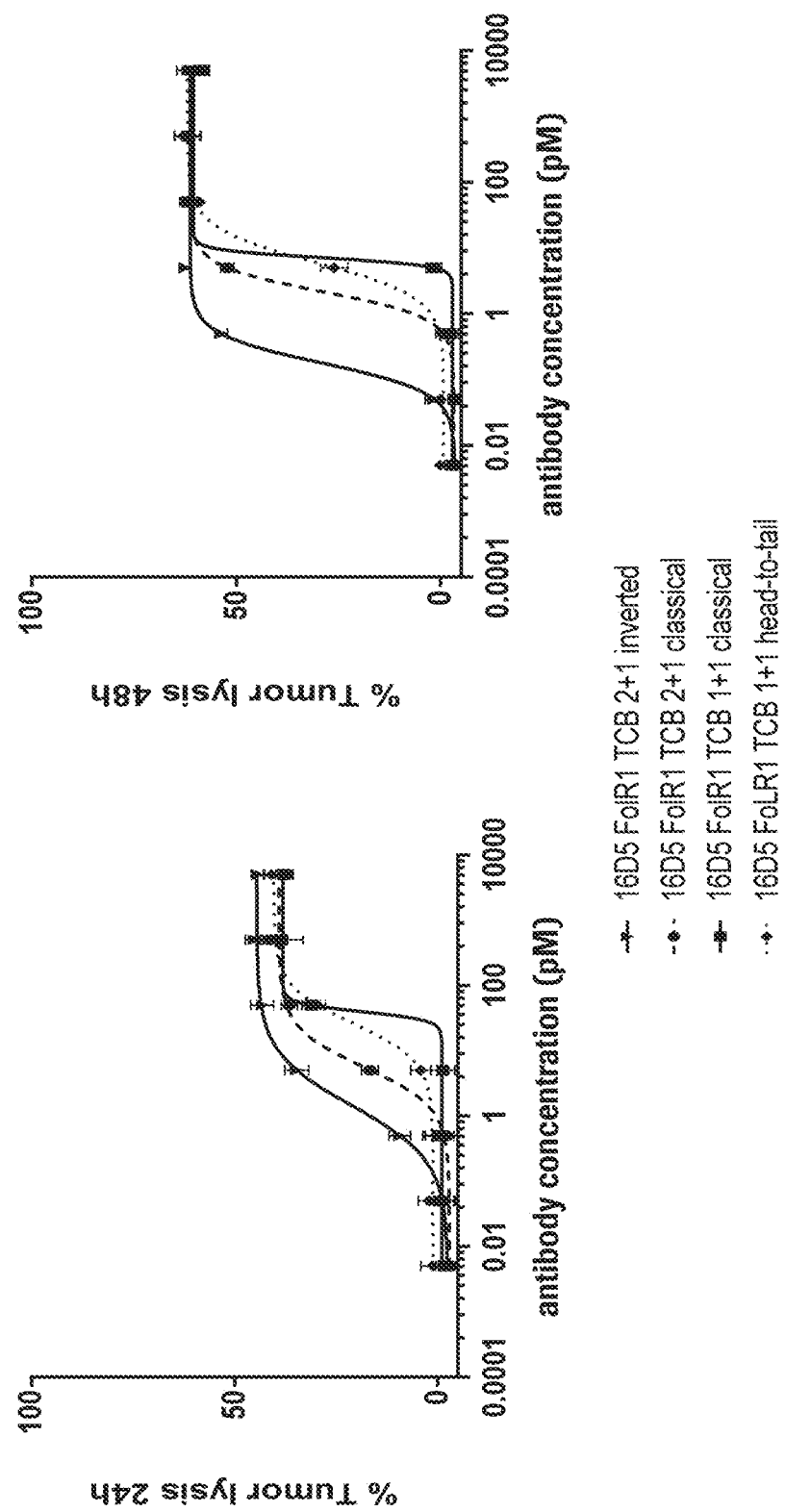

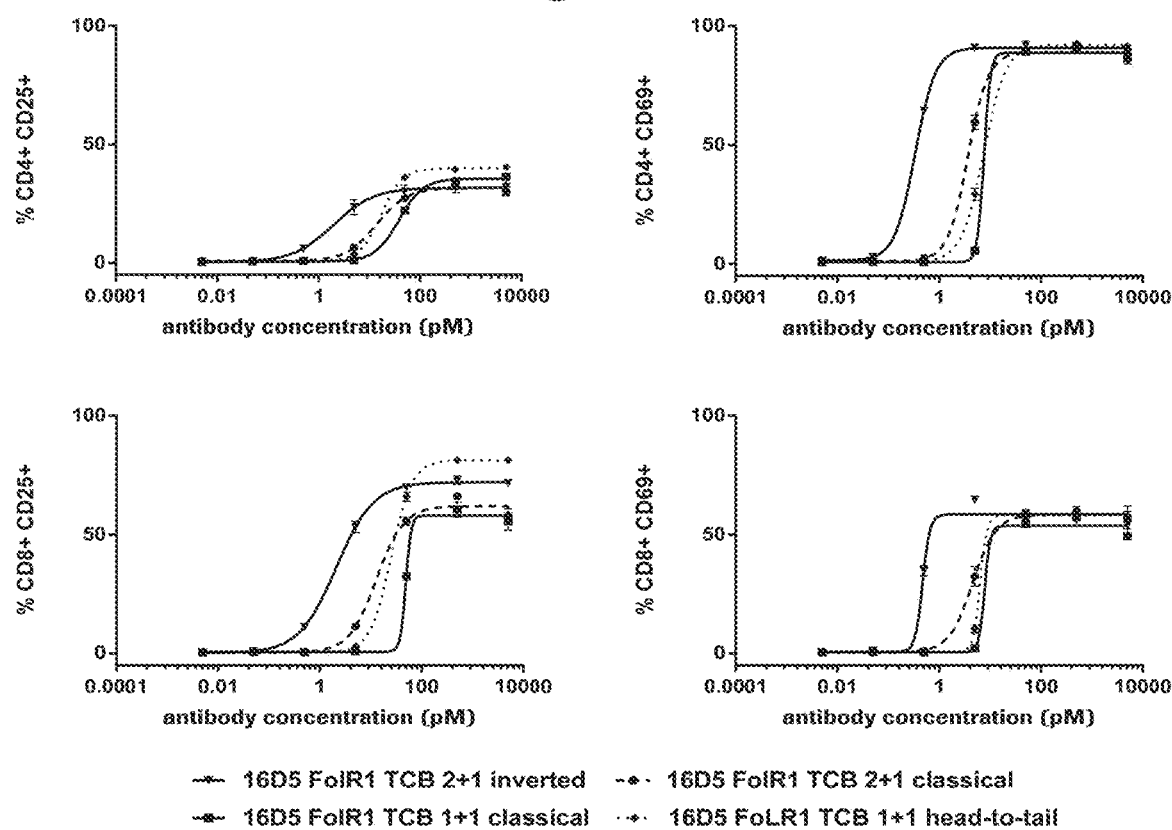

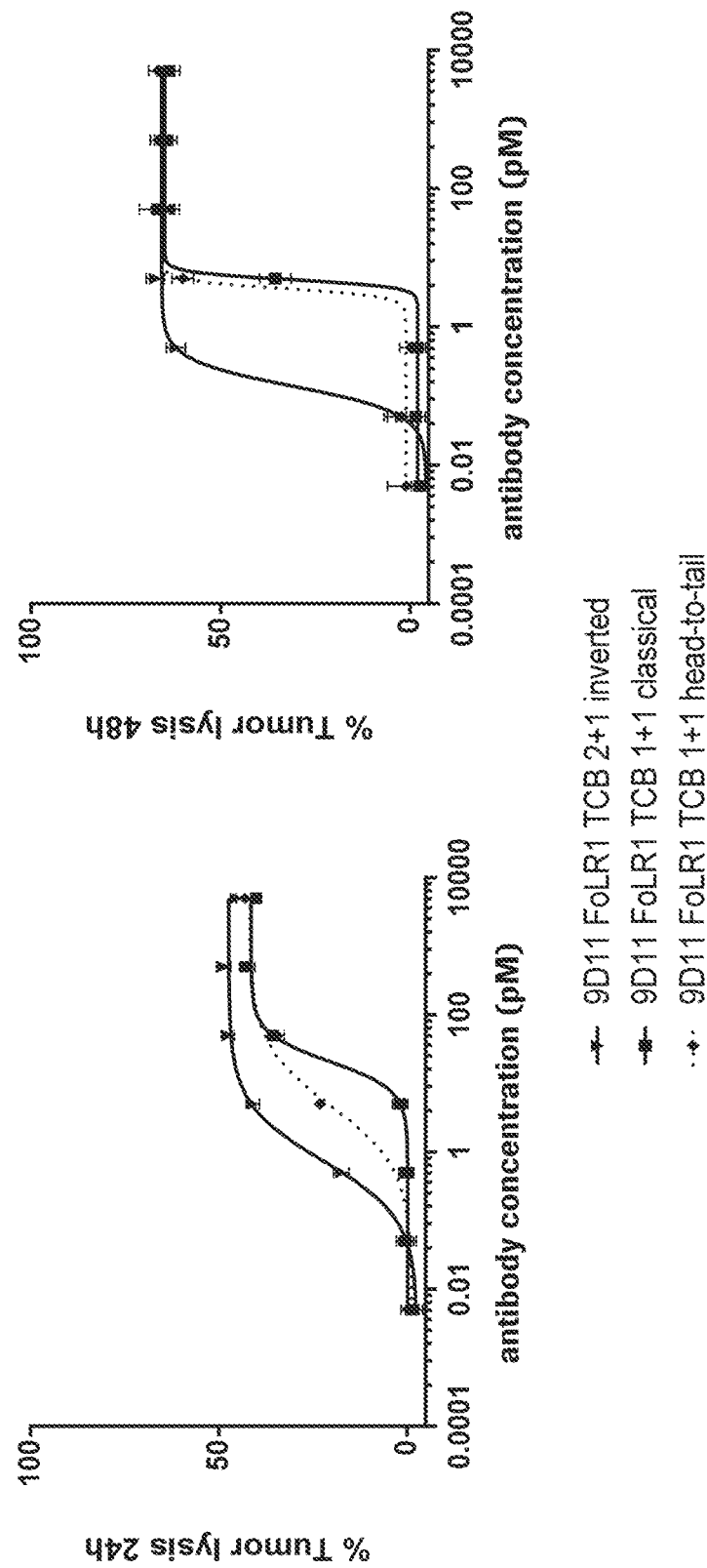

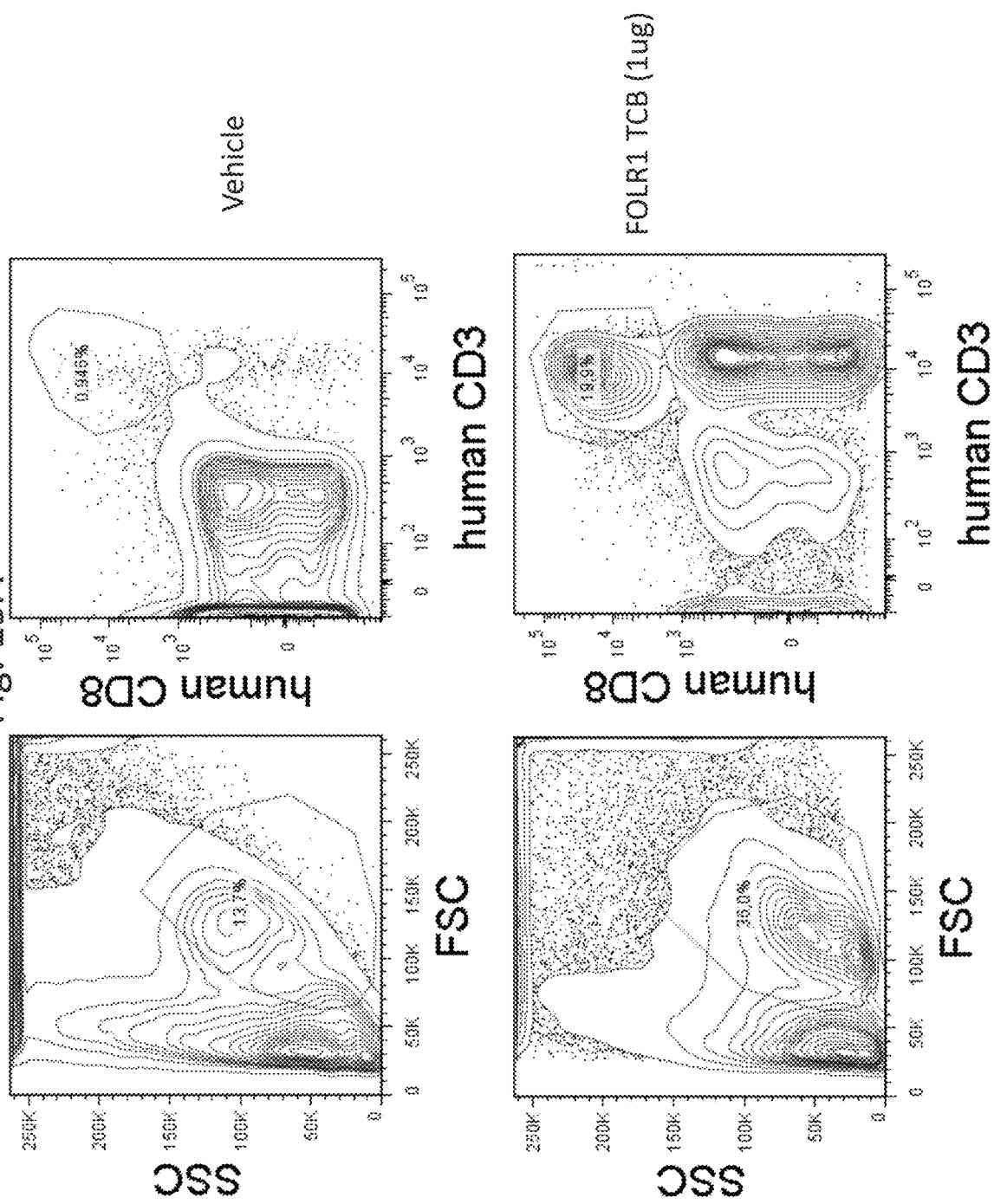

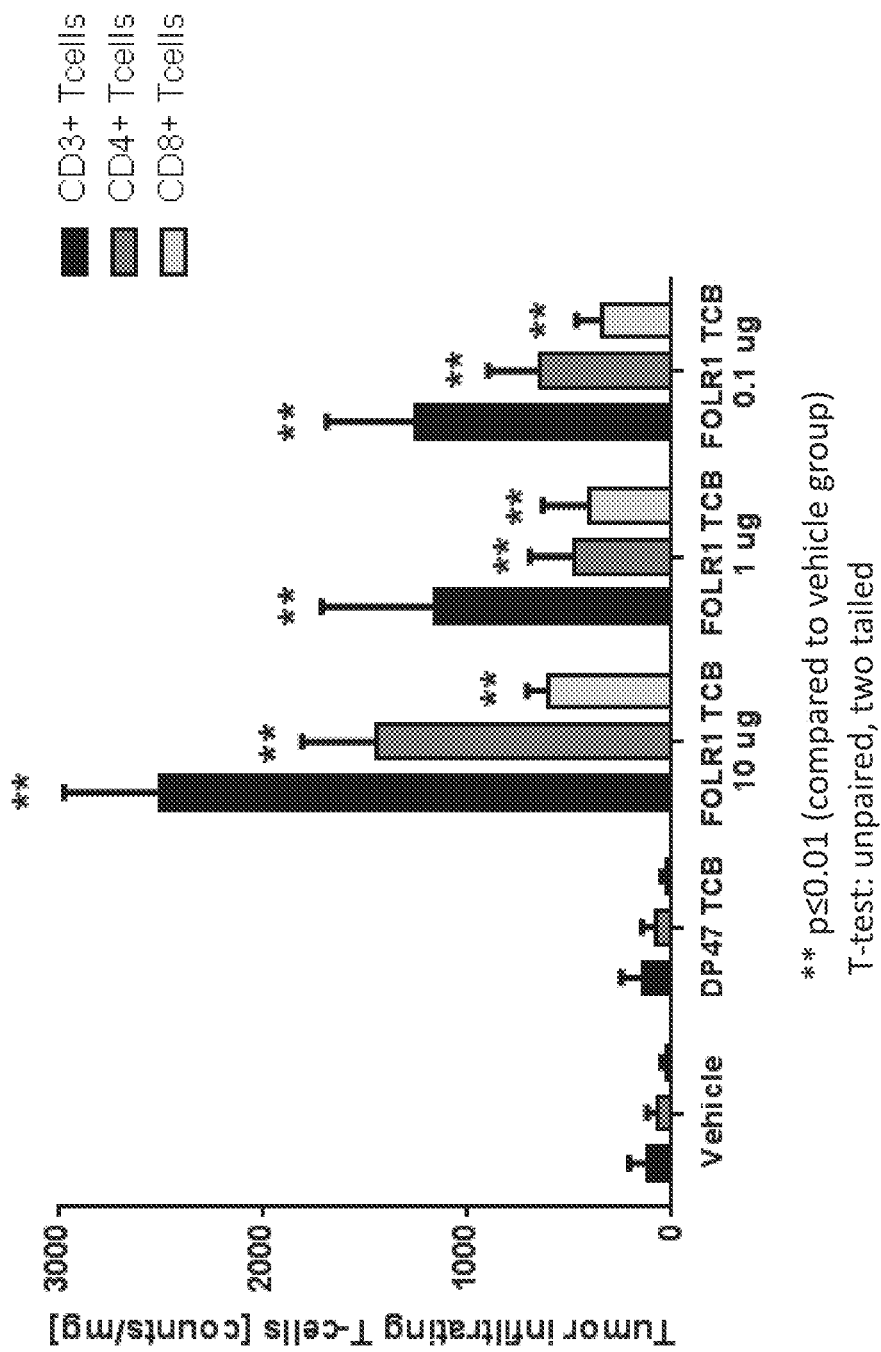

— DP47 TCB   — kappa lambda FolR1 TCB

- 36F2 TCB
- 16D5 TCB
- 16D5 TCB classical
- 16D5 HT
- 16D5 1+1
- DP47 TCB

Fig. 27

| Cell line | Binding sites | Cell line | Binding sites |
|---|---|---|---|
| Hela | 2'240'716 | Bronchial epithelium | 492 |
| Skov3 | 91'510 | Choroid plexus epithelium | 104 |
| OVCAR5 | 22'077 | Renal cortical epithelium | 312 |
| HT29 | 10'135 | Retinal pigment epithelium | 822 |
| MKN45 | 54 | Skov3 | 69'890 |

Fig. 31

| Clone | ka(1/Ms) | kd(1/s) | $K_D$ (M) |
|---|---|---|---|
| 58D6 | 3.40E+04 | 7.98E-4 | 2.35E-8 |
| 106D2 | 0.98E+04 | 2.95E-4 | 3.00E-8 |
| 110A5 | 1.22E+04 | 16.4E-4 | 13.4E-8 |

Fig. 32B

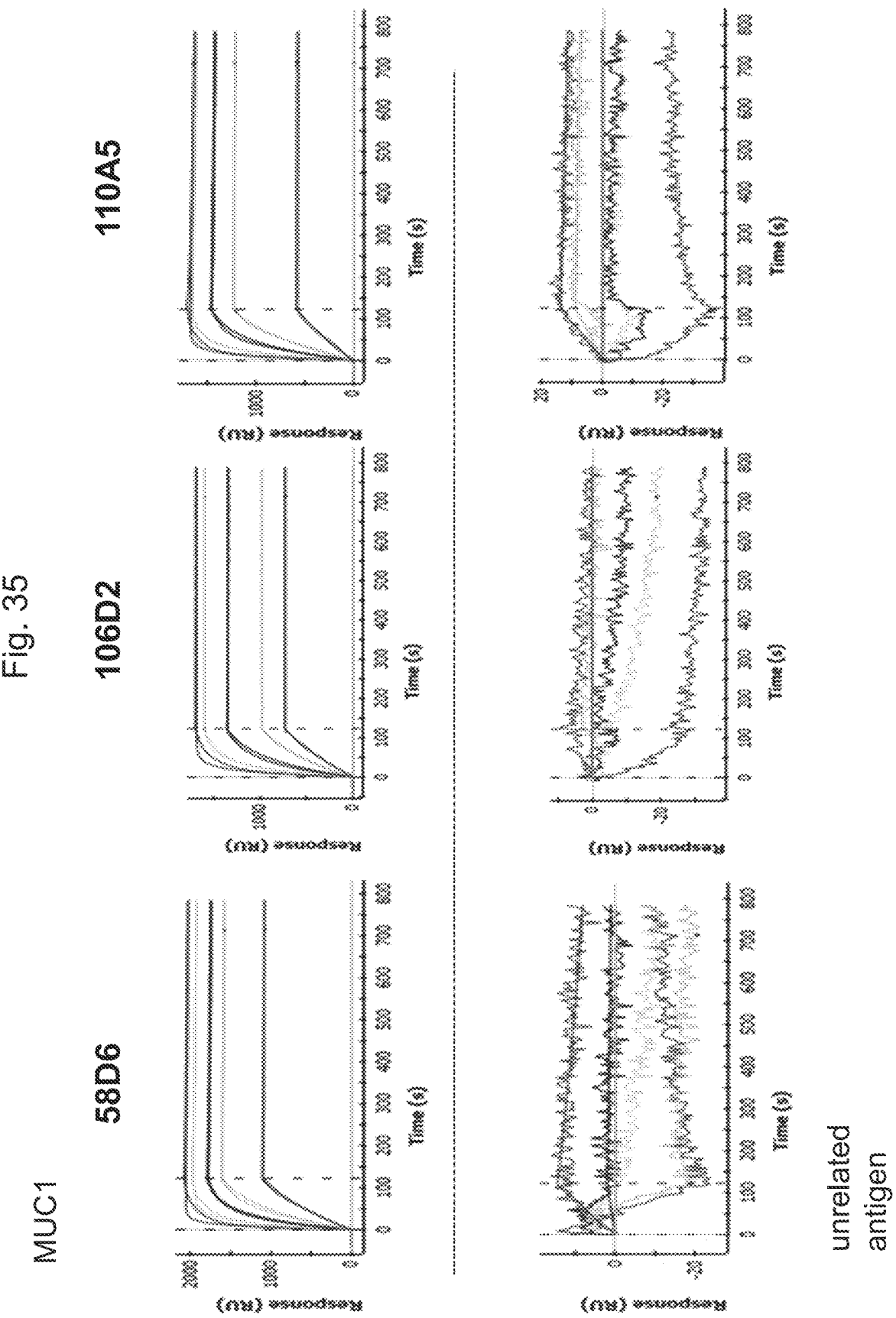

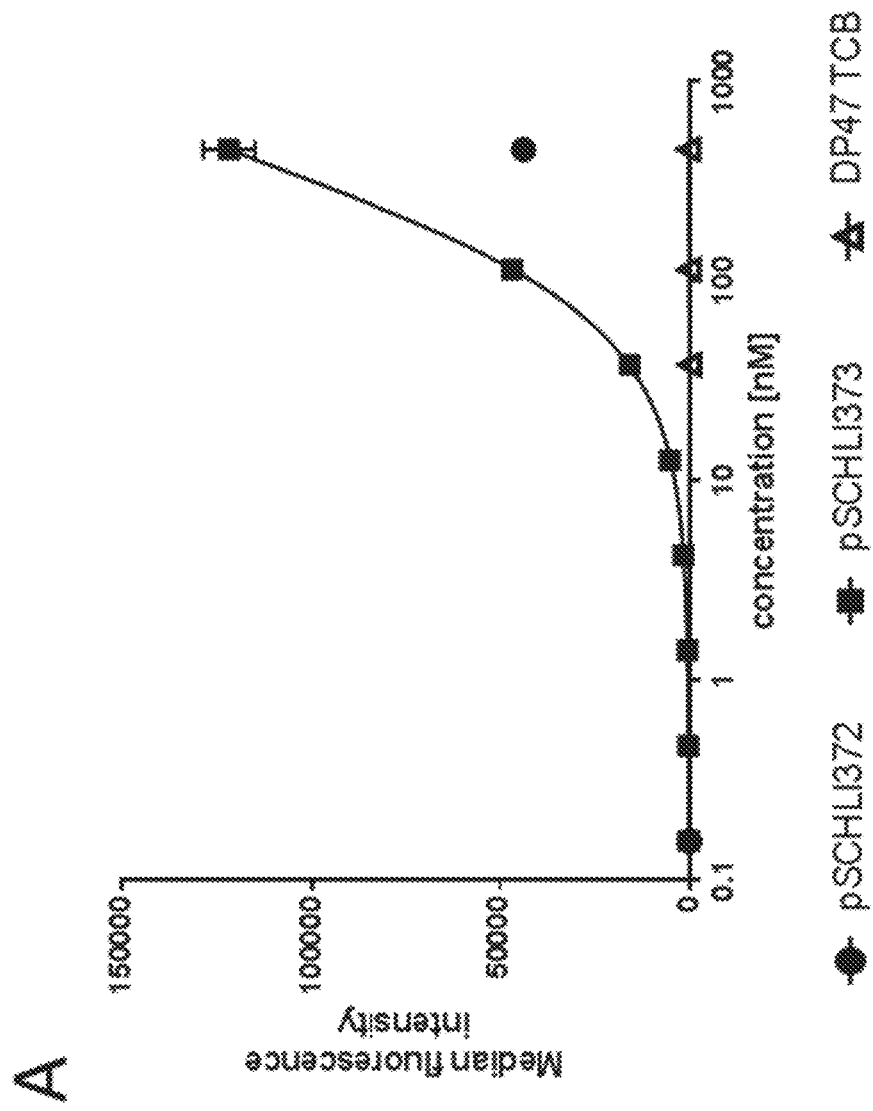

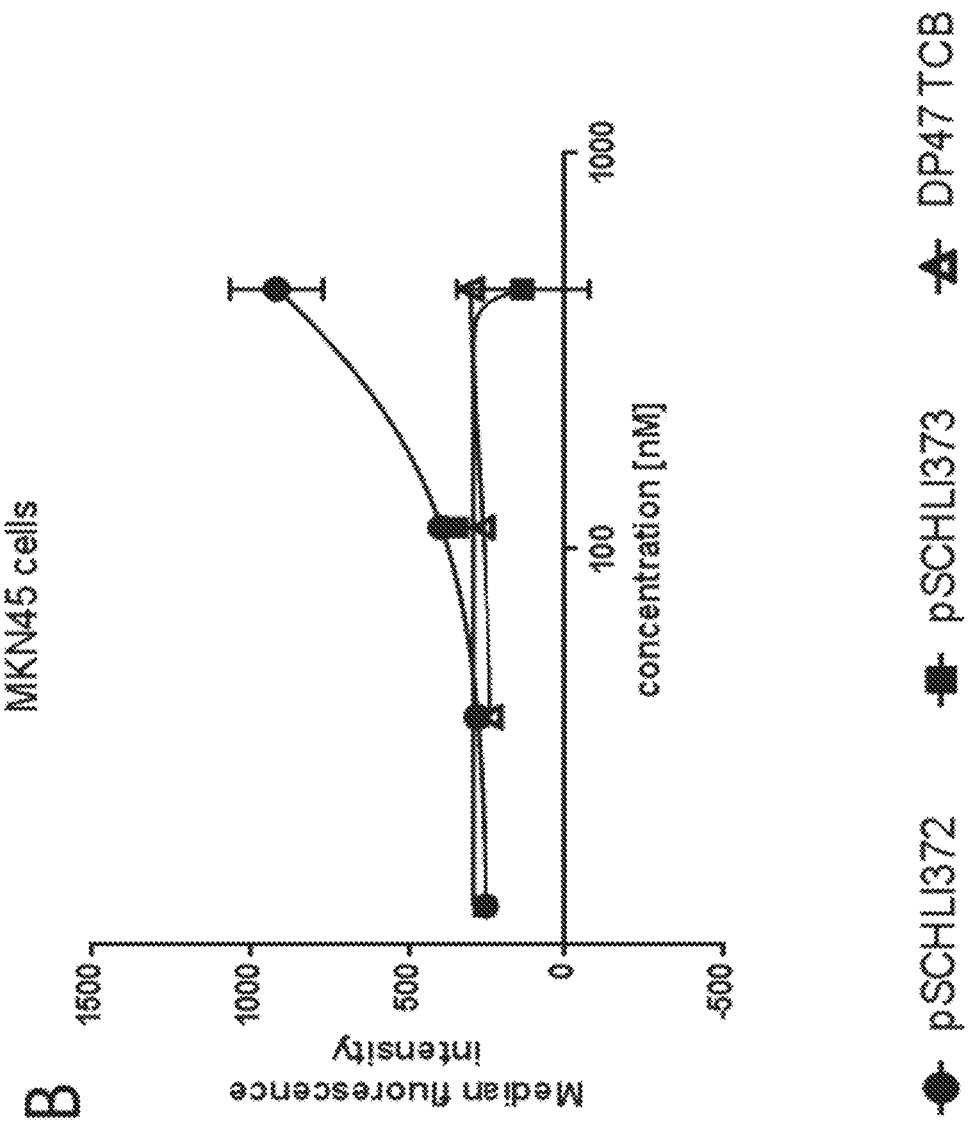

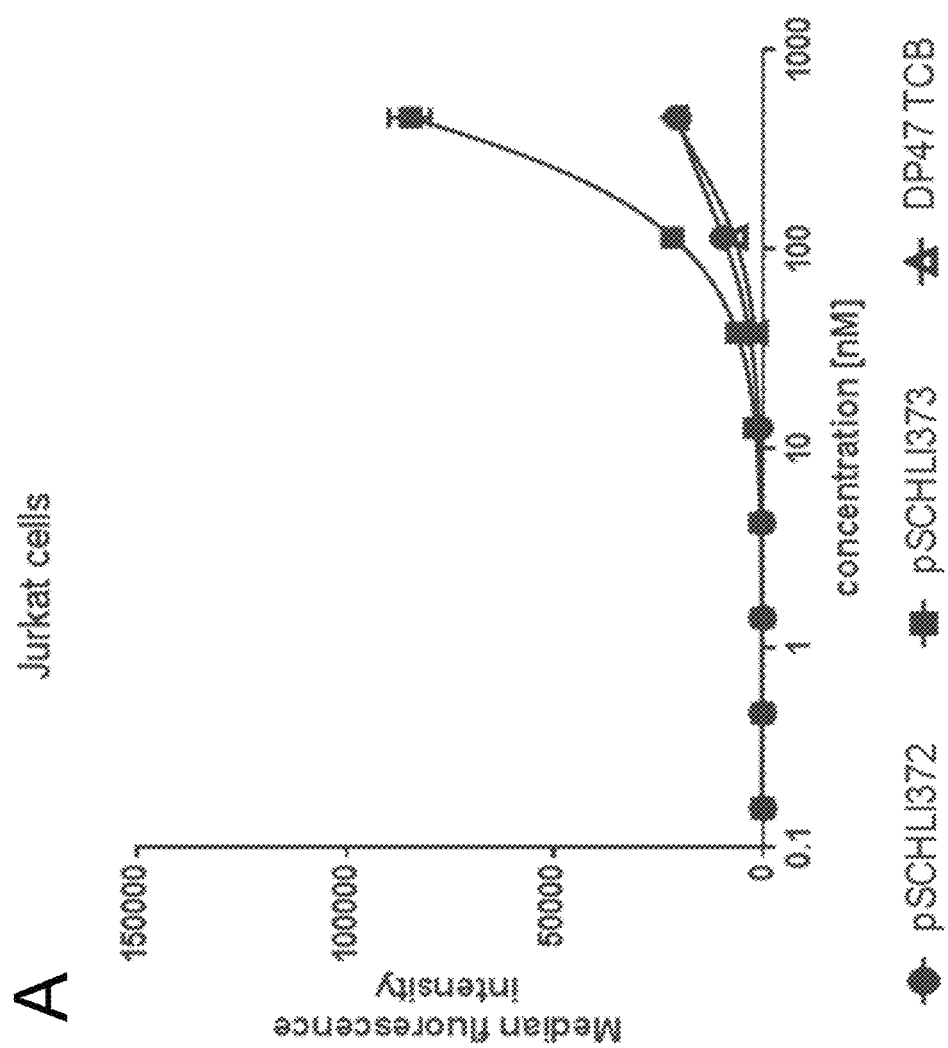

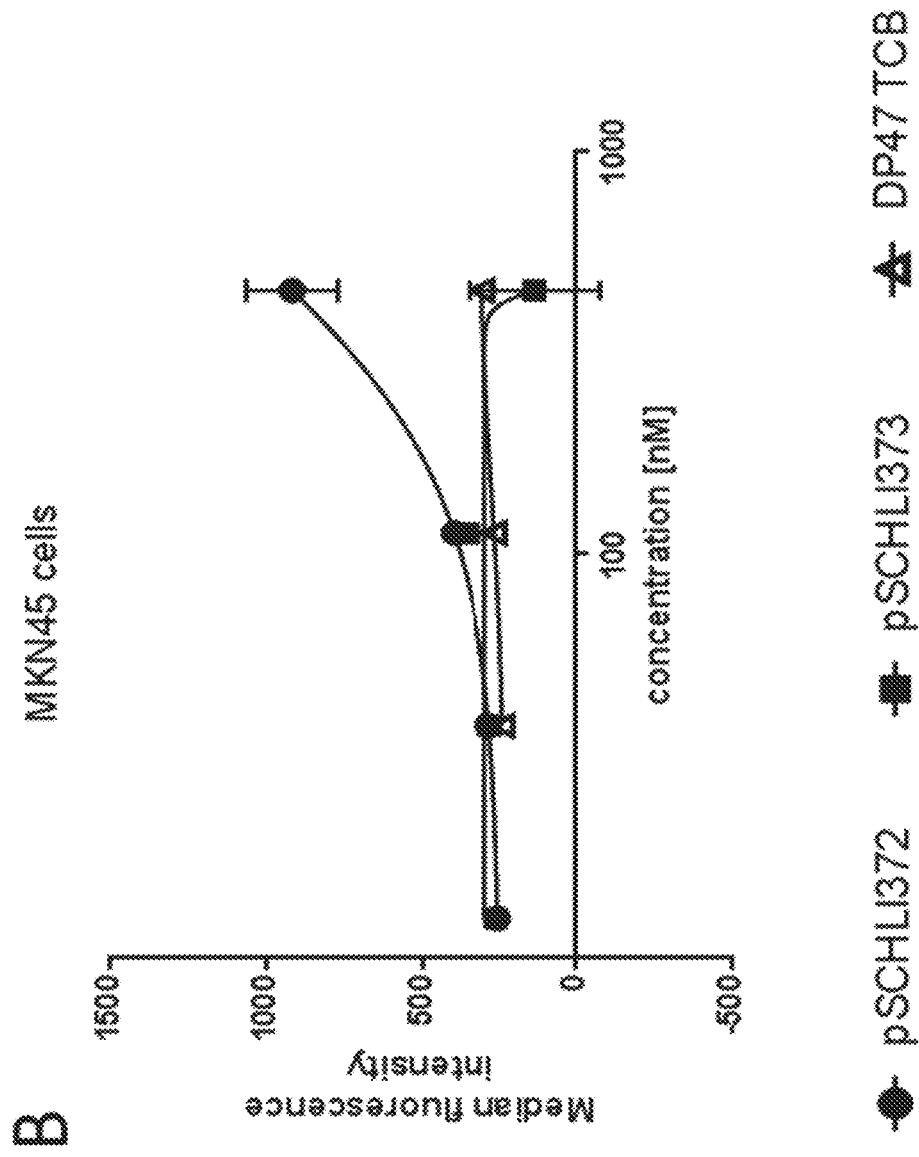

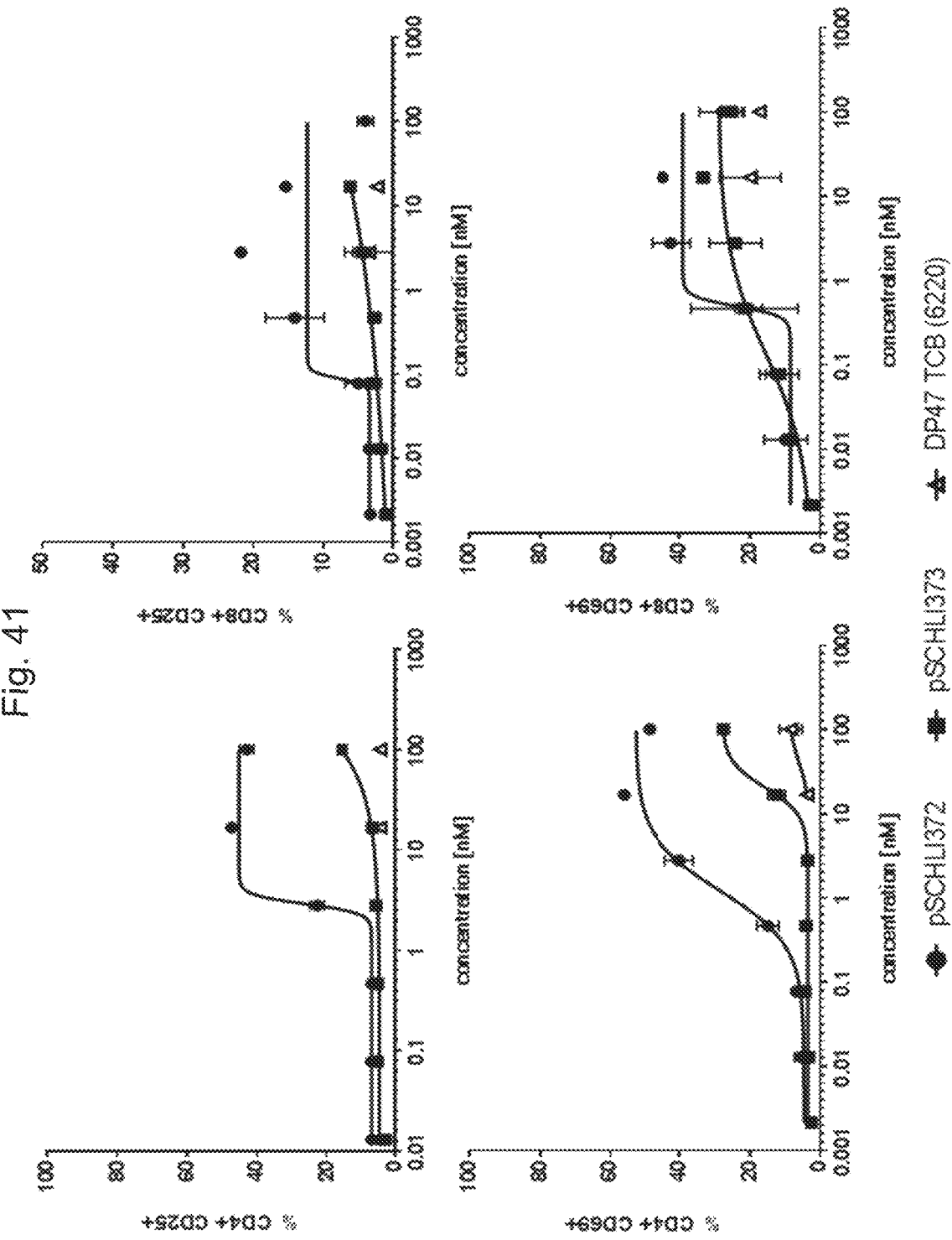

T CELL ACTIVATING BISPECIFIC ANTIGEN BINDING MOLECULES

CROSS REFERENCE TO RELATED APPLICATIONS

This application is a divisional of U.S. patent application Ser. No. 16/541,258 filed Aug. 15, 2019, which is a divisional of U.S. patent application Ser. No. 15/600,015, filed May 19, 2017, now abandoned, which is a continuation of International Application No. PCT/EP2015/076745, Publication No. WO2016/079081, filed Nov. 17, 2015, which claims priority to European Patent Application No. 14194097.3, filed Nov. 20, 2014, the disclosures of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Sep. 2, 2021, is named 51177-010003_Sequence_Listing_9_2_21_ST25.txt and is 537,784 bytes in size.

FIELD OF THE INVENTION

The present invention generally relates to bispecific antigen binding molecules for activating T cells. In addition, the present invention relates to polynucleotides encoding such bispecific antigen binding molecules, and vectors and host cells comprising such polynucleotides. The invention further relates to methods for producing the bispecific antigen binding molecules of the invention, and to methods of using these bispecific antigen binding molecules in the treatment of disease.

BACKGROUND

The selective destruction of an individual cell or a specific cell type is often desirable in a variety of clinical settings. For example, it is a primary goal of cancer therapy to specifically destroy tumor cells, while leaving healthy cells and tissues intact and undamaged.

An attractive way of achieving this is by inducing an immune response against the tumor, to make immune effector cells such as natural killer (NK) cells or cytotoxic T lymphocytes (CTLs) attack and destroy tumor cells. CTLs constitute the most potent effector cells of the immune system, however they cannot be activated by the effector mechanism mediated by the Fc domain of conventional therapeutic antibodies.

In this regard, bispecific antibodies designed to bind with one "arm" to a surface antigen on target cells, and with the second "arm" to an activating, invariant component of the T cell receptor (TCR) complex, have become of interest in recent years. The simultaneous binding of such an antibody to both of its targets forces a temporary interaction between target cell and T cell, causing activation of any cytotoxic T cell and subsequent lysis of the target cell. Hence, the immune response is re-directed to the target cells and is independent of peptide antigen presentation by the target cell or the specificity of the T cell as would be relevant for normal MHC-restricted activation of CTLs. In this context it is crucial that CTLs are only activated when the bispecific antibody binds to a target cell and the CTL, i.e. the immunological synapse is mimicked. Particularly desirable are bispecific antibodies that do not require lymphocyte preconditioning or co-stimulation in order to elicit efficient lysis of target cells.

Several bispecific antibody formats have been developed and their suitability for T cell mediated immunotherapy investigated. Out of these, the so-called BiTE (bispecific T cell engager) molecules have been very well characterized and already shown some promise in the clinic (reviewed in Nagorsen and Bsuerle, Exp Cell Res 317, 1255-1260 (2011)). BiTEs are tandem scFv molecules wherein two scFv molecules are fused by a flexible linker. Further bispecific formats being evaluated for T cell engagement include diabodies (Holliger et al., Prot Eng 9, 299-305 (1996)) and derivatives thereof, such as tandem diabodies (Kipriyanov et al., J Mol Biol 293, 41-66 (1999)). A more recent development are the so-called DART (dual affinity retargeting) molecules, which are based on the diabody format but feature a C-terminal disulfide bridge for additional stabilization (Moore et al., Blood 117, 4542-51 (2011)). The so-called triomabs, which are whole hybrid mouse/rat IgG molecules and also currently being evaluated in clinical trials, represent a larger sized format (reviewed in Seimetz et al., Cancer Treat Rev 36, 458-467 (2010)).

The variety of formats that are being developed shows the great potential attributed to T cell re-direction and activation in immunotherapy. The task of generating bispecific antibodies suitable therefor is, however, by no means trivial, but involves a number of challenges that have to be met related to efficacy, toxicity, applicability and produceability of the antibodies.

Small constructs such as, for example, BiTE molecules—while being able to efficiently crosslink effector and target cells—have a very short serum half life requiring them to be administered to patients by continuous infusion. IgG-like formats on the other hand—while having the great benefit of a long half life—suffer from toxicity associated with the native effector functions inherent to IgG molecules. Their immunogenic potential constitutes another unfavorable feature of IgG-like bispecific antibodies, especially non-human formats, for successful therapeutic development. Finally, a major challenge in the general development of bispecific antibodies has been the production of bispecific antibody constructs at a clinically sufficient quantity and purity, due to the mispairing of antibody heavy and light chains of different specificities upon co-expression, which decreases the yield of the correctly assembled construct and results in a number of non-functional side products from which the desired bispecific antibody may be difficult to separate.

Given the difficulties and disadvantages associated with currently available bispecific antibodies for T cell mediated immunotherapy, there remains a need for novel, improved formats of such molecules.

SUMMARY OF THE INVENTION

In a first aspect the present invention provides a T cell activating bispecific antigen binding molecule comprising a first and a second antigen binding moiety, wherein the first antigen binding moiety comprises a first light chain and wherein the first antigen binding moiety is capable of specific binding to an activating T cell antigen and the second antigen binding moiety comprises a second light chain and wherein the second antigen binding moiety is capable of specific binding to a target cell antigen, wherein the amino acid sequence of the first and the second light chain is identical. In one embodiment, the first antigen binding moiety is a Fab. In one embodiment, the second antigen binding moiety is a Fab. In one embodiment, the first and the second antigen binding moiety is a Fab.

In one aspect the invention provides a T cell activating bispecific antigen binding molecule comprising a first and a second antigen binding moiety, one of which is a Fab molecule capable of specific binding to an activating T cell antigen and the other one of which is a Fab molecule capable of specific binding to a target cell antigen, wherein the first and the second Fab molecule have identical VLCL light chains.

In one embodiment said T cell activating bispecific antigen binding molecule further comprises an Fc domain composed of a first and a second subunit capable of stable association.

In one embodiment said T cell activating bispecific antigen binding molecule comprises a light chain comprising the light chain CDRs of SEQ ID NO: 32, SEQ ID NO: 33 and SEQ ID NO: 34.

In one embodiment said T cell activating bispecific antigen binding molecule comprises a light chain comprising SEQ ID NO: 31.

In one embodiment said Fab molecule capable of specific binding to an activating T cell antigen comprises a heavy chain comprising the heavy chain CDR of SEQ ID NO: 37, SEQ ID NO: 38 and SEQ ID NO: 39.

In a particular embodiment, not more than one antigen binding moiety capable of specific binding to an activating T cell antigen is present in the T cell activating bispecific antigen binding molecule (i.e. the T cell activating bispecific antigen binding molecule provides monovalent binding to the activating T cell antigen).

In some embodiments, the first and the second antigen binding moiety of the T cell activating bispecific antigen binding molecule are fused to each other, optionally via a peptide linker. In one such embodiment, the second antigen binding moiety is fused at the C-terminus of the Fab heavy chain to the N-terminus of the Fab heavy chain of the first antigen binding moiety. In another such embodiment, the first antigen binding moiety is fused at the C-terminus of the Fab heavy chain to the N-terminus of the Fab heavy chain of the second antigen binding moiety.

In yet another such embodiment, the second antigen binding moiety is fused at the C-terminus of the Fab light chain to the N-terminus of the Fab light chain of the first antigen binding moiety. In yet another such embodiment, the first antigen binding moiety is fused at the C-terminus of the Fab light chain to the N-terminus of the Fab light chain of the second antigen binding moiety.

In one embodiment, the first antigen binding moiety of the T cell activating bispecific antigen binding molecule is fused at the C-terminus of the Fab heavy chain to the N-terminus of the first or the second subunit of the Fc domain.

In one embodiment, the second antigen binding moiety of the T cell activating bispecific antigen binding molecule is fused at the C-terminus of the Fab heavy chain to the N-terminus of the first or the second subunit of the Fc domain.

In another embodiment, the first antigen binding moiety is fused at the C-terminus of the Fab heavy chain to the N-terminus of the first or second subunit of the Fc domain.

In one embodiment, the first and the second antigen binding moiety of the T cell activating bispecific antigen binding molecule are each fused at the C-terminus of the Fab heavy chain to the N-terminus of one of the subunits of the Fc domain.

In certain embodiments, the T cell activating bispecific antigen binding molecule comprises a third antigen binding moiety which is a Fab molecule capable of specific binding to a target cell antigen. In one embodiment said third antigen binding moiety is a Fab molecule comprising an identical VLCL light chain as the first and the second antigen binding moiety.

In one such embodiment the first, second and third antigen binding moiety are each a Fab molecule comprising the light chain CDRs of SEQ ID NO: 32, SEQ ID NO: 33 and SEQ ID NO: 34.

In one such embodiment the first, second and third antigen binding moiety are each a Fab molecule comprising a light chain comprising SEQ ID NO: 31.

In one embodiment, the third antigen binding moiety is fused at the C-terminus of the Fab heavy chain to the N-terminus of the first or second subunit of the Fc domain. In a particular embodiment, the second and the third antigen binding moiety of the T cell activating antigen binding molecule are each fused at the C-terminus of the Fab heavy chain to the N-terminus of one of the subunits of the Fc domain, and the first antigen binding moiety is fused at the C-terminus of the Fab heavy chain to the N-terminus of the Fab heavy chain of the second antigen binding moiety. In another particular embodiment, the first and the third antigen binding moiety of the T cell activating antigen binding molecule are each fused at the C-terminus of the Fab heavy chain to the N-terminus of one of the subunits of the Fc domain, and the second antigen binding moiety is fused at the C-terminus of the Fab heavy chain to the N-terminus of the Fab heavy chain of the first antigen binding moiety. The components of the T cell activating bispecific antigen binding molecule may be fused directly or through suitable peptide linkers. In one embodiment the second and the third antigen binding moiety and the Fc domain are part of an immunoglobulin molecule. In one embodiment the first and the third antigen binding moiety and the Fc domain are part of an immunoglobulin molecule. In a particular embodiment the immunoglobulin molecule is an IgG class immunoglobulin. In an even more particular embodiment the immunoglobulin is an IgG$_1$ subclass immunoglobulin. In another embodiment, the immunoglobulin is an IgG$_4$ subclass immunoglobulin.

In a particular embodiment, the Fc domain is an IgG Fc domain. In a specific embodiment, the Fc domain is an IgG$_1$ Fc domain. In another specific embodiment, the Fc domain is an IgG$_4$ Fc domain. In an even more specific embodiment, the Fc domain is an IgG$_4$ Fc domain comprising the amino acid substitution S228P. In an even more specific embodiment, the Fc domain is an IgG$_4$ Fc domain comprising the amino acid substitutions L235E and S228P (SPLE). In particular embodiments the Fc domain is a human Fc domain.

In particular embodiments the Fc domain comprises a modification promoting the association of the first and the second Fc domain subunit. In a specific such embodiment, an amino acid residue in the CH3 domain of the first subunit of the Fc domain is replaced with an amino acid residue having a larger side chain volume, thereby generating a protuberance within the CH3 domain of the first subunit which is positionable in a cavity within the CH3 domain of the second subunit, and an amino acid residue in the CH3 domain of the second subunit of the Fc domain is replaced with an amino acid residue having a smaller side chain volume, thereby generating a cavity within the CH3 domain of the second subunit within which the protuberance within the CH3 domain of the first subunit is positionable.

In a particular embodiment the Fc domain exhibits reduced binding affinity to an Fc receptor and/or reduced effector function, as compared to a native IgG$_1$ Fc domain. In certain embodiments the Fc domain is engineered to have reduced binding affinity to an Fc receptor and/or reduced effector function, as compared to a non-engineered Fc domain. In one embodiment, the Fc domain comprises one or more amino acid substitution that reduces binding to an Fc receptor and/or effector function. In one embodiment, the one or more amino acid substitution in the Fc domain that reduces binding to an Fc receptor and/or effector function is at one or more position selected from the group of L234, L235, and P329 (Kabat numbering). In particular embodiments, each subunit of the Fc domain comprises three amino acid substitutions that reduce binding to an Fc receptor and/or effector function wherein said amino acid substitutions are L234A, L235A and P329G. In one such embodiment, the Fc domain is an IgG$_1$ Fc domain, particularly a human IgG$_1$ Fc domain. In other embodiments, each subunit of the Fc domain comprises two amino acid substitutions that reduce binding to an Fc receptor and/or effector function wherein said amino acid substitutions are L235E and P329G. In one such embodiment, the Fc domain is an IgG$_4$ Fc domain, particularly a human IgG$_4$ Fc domain.

In one embodiment the Fc receptor is an Fcγ receptor. In one embodiment the Fc receptor is a human Fc receptor. In one embodiment, the Fc receptor is an activating Fc receptor. In a specific embodiment, the Fc receptor is human FcγRIIa, FcγRI, and/or FcγRIIIa. In one embodiment, the effector function is antibody-dependent cell-mediated cytotoxicity (ADCC).

In a particular embodiment, the activating T cell antigen that the bispecific antigen binding molecule is capable of binding is CD3. In other embodiments, the target cell antigen that the bispecific antigen binding molecule is capable of binding is a tumor cell antigen. In one embodiment, the target cell antigen is selected from the group consisting of: Folate Receptor 1 (FolR1), Mucin-1 (MUC1), and B Cell Maturation Antigen (BCMA). In one specific embodiment, the target cell antigen is not BCMA.

In another aspect, the invention provides for a light chain comprising the amino acid sequence of SEQ ID NO: 32, SEQ ID NO: 33 and SEQ ID NO: 34 for use in a T cell activating bispecific antigen binding molecule. In one embodiment, the light chain comprises the amino acid sequence of SEQ ID NO: 31. In one embodiment, the light chain comprises the amino acid sequence of SEQ ID NO: 35.

In another aspect, the invention provides for a light chain comprising the amino acid sequence of SEQ ID NO: 32, SEQ ID NO: 33 and SEQ ID NO: 34 for use in a library for production of T cell activating bispecific antigen binding molecule. In one embodiment, the light chain comprises the amino acid sequence of SEQ ID NO: 31. In one embodiment, the light chain comprises the amino acid sequence of SEQ ID NO: 35.

In another aspect, the invention provides for an isolated polypeptide comprising the amino acid sequence of SEQ ID NO: 31.

In another aspect, the invention provides for an isolated polypeptide comprising the amino acid sequence of SEQ ID NO: 35.

According to another aspect of the invention there is provided an isolated polynucleotide encoding a T cell activating bispecific antigen binding molecule of the invention or a fragment thereof. The invention also encompasses polypeptides encoded by the polynucleotides of the invention. The invention further provides an expression vector comprising the isolated polynucleotide of the invention, and a host cell comprising the isolated polynucleotide or the expression vector of the invention. In some embodiments the host cell is a eukaryotic cell, particularly a mammalian cell.

In another aspect is provided a method of producing the T cell activating bispecific antigen binding molecule of the invention, comprising the steps of a) culturing the host cell of the invention under conditions suitable for the expression of the T cell activating bispecific antigen binding molecule and b) recovering the T cell activating bispecific antigen binding molecule. The invention also encompasses a T cell activating bispecific antigen binding molecule produced by the method of the invention.

The invention further provides a pharmaceutical composition comprising the T cell activating bispecific antigen binding molecule of the invention and a pharmaceutically acceptable carrier.

Also encompassed by the invention are methods of using the T cell activating bispecific antigen binding molecule and pharmaceutical composition of the invention. In one aspect the invention provides a T cell activating bispecific antigen binding molecule or a pharmaceutical composition of the invention for use as a medicament. In one aspect is provided a T cell activating bispecific antigen binding molecule or a pharmaceutical composition according to the invention for use in the treatment of a disease in an individual in need thereof. In a specific embodiment the disease is cancer.

Also provided is the use of a T cell activating bispecific antigen binding molecule of the invention for the manufacture of a medicament for the treatment of a disease in an individual in need thereof; as well as a method of treating a disease in an individual, comprising administering to said individual a therapeutically effective amount of a composition comprising the T cell activating bispecific antigen binding molecule according to the invention in a pharmaceutically acceptable form. In a specific embodiment the disease is cancer. In any of the above embodiments the individual preferably is a mammal, particularly a human.

The invention also provides a method for inducing lysis of a target cell, particularly a tumor cell, comprising contacting a target cell with a T cell activating bispecific antigen binding molecule of the invention in the presence of a T cell, particularly a cytotoxic T cell.

In another aspect, the invention provides for a method for identifying a variable heavy chain for use in a bispecific antigen binding molecule specific for a T cell activation antigen and a target cell antigen, comprising the step of screening a combinatorial library comprising variable heavy chains with a light chain comprising the amino acid sequence of SEQ ID NO: 32, SEQ ID NO: 33 and SEQ ID NO: 34. In one embodiment, the light chain comprises the amino acid sequence of SEQ ID NO: 31. In one embodiment, the light chain comprises the amino acid sequence of SEQ ID NO: 35.

BRIEF DESCRIPTION OF THE DRAWINGS

FIGS. 1A-I illustrate exemplary configurations of the T cell activating bispecific antigen binding molecules (TCBs) disclosed herein. All constructs except the kappa-lambda format in (FIG. 1I) have P329G LALA mutations and comprise knob-into-hole Fc fragments with knob-into-hole modifications. (FIG. 1A) Illustration of the "FolR1 TCB 2+1 inverted (common light chain)". The FolR1 binder is fused at the C-terminus of the Fab heavy chain to the N-terminus of the first subunit of the Fc domain comprising the knob modification. These constructs are not crossed and have three times the same VLCL light chain. (FIG. 1B) Illustration of the "FolR1 TCB 1+1 head-to-tail (common light chain)". These constructs are not crossed and have two times the same VLCL light chain. (FIG. 1C) Illustration of the "FolR1 TCB 1+1 classical (common light chain)". These constructs are not crossed and have two times the same VLCL light chain. (FIG. 1D) Illustration of the "FolR1 TCB 2+1 classical (common light chain)". The CD3 binder is fused at the C-terminus of the Fab heavy chain to the N-terminus of the first subunit of the Fc domain comprising the knob modification. These constructs are not crossed and have three times the same VLCL light chain. (FIG. 1E) Illustration of the "FolR1 TCB 2+1 crossfab classical". These constructs comprise a Ck-VH chain for the CD3 binder instead of the conventional CH1-VH chain. The CD3 binder is fused at the C-terminus of the Fab heavy chain to the N-terminus of the first subunit of the Fc domain comprising the knob modification. (FIG. 1F) Illustration of the "FolR1 TCB 2+1 crossfab inverted". These constructs comprise a Ck-VH chain for the CD3 binder instead of the conventional CH1-VH chain. The FolR1 binder is fused at the C-terminus of the Fab heavy chain to the N-terminus of the first subunit of the Fc domain comprising the knob modification. (FIG. 1G) Illustration of the "FolR1 TCB 1+1 crossfab head-to-tail". These constructs comprise a Ck-VH chain for the CD3 binder instead of the conventional CH1-VH chain. (FIG. 1H) Illustration of the "FolR1 TCB 1+1 crossfab classical". These constructs comprise a Ck-VH chain for the CD3 binder instead of the conventional CH1-VH chain. FIG. 1I illustrates the CD3/FolR1 kappa-lambda antibody format. These constructs comprise a crossed common light chain VLCH1 and one crossed VHCL chain specific for CD3 and one crossed VHCL chain specific for FolR1.

FIGS. 6A-E depict graphs summarizing binding of FolR1 IgGs to cells with different FolR1 expression levels. Binding of 9D11, 16D5 and Mov19 IgG to tumor cells with different FolR1 expression levels was analyzed by flow cytometry. DP47 IgG was included as isotype control and MKN-45 were included as FolR1 negative cell line. The antibodies were detected with a fluorescently labeled anti-human secondary antibody.

(FIGS. 7A-D) T cell mediated killing of HT-29 and SKOV3 cells in the presence of 9D11 FolR1 TCB and 16D5 FolR1 TCB was measured by LDH release after 24 h and 48 h. DP47 TCB was included as negative control. After 48 h incubation upregulation of the activation marker CD25 and CD69 on CD8 T cells and CD4 T cells upon killing of SKOV3 (FIGS. 7E-H) or HT-29 (FIGS. 7I-L) tumor cells was assessed by flow cytometry.

FIGS. 11A-F depict graphs summarizing T cell mediated killing with 9D11 FolR1 TCB a-glyco variants of tumor cells. 9D11 FolR1 TCB a-glyco variants were used to test T cell mediated killing of (FIGS. 11A-D) SKOV3, MKN-45 (as FolR1 negative control) and (FIGS. 11E-F) HT-29 tumor cells in comparison to killing with the original 9D11 FolR1 TCB. As read-out LDH release after 24 h and 48 h was used.

FIGS. 12A-X depict graphs summarizing T cell mediated killing of primary epithelial cells. Primary epithelial cells with very low levels of FolR1 were used to test T cell mediated killing with 16D5 FolR1 TCB and 9D11 FolR1 TCB, DP47 TCB was included as a negative control and HT29 cells were included as positive control. (FIGS. 12A-H) LDH release of human retinal pigment (HRP), human renal cortical (HRC), human bronchial (HB) and of HT29 cells was determined after 24 h and 48 h. CD25 and CD69 activation marker upregulation on CD4 T cells and CD8 T cells upon killing of (FIGS. 12I-L) HRP, (FIGS. 12M-P) HRC, (FIGS. 12Q-T) HB and (FIGS. 12 U-X) HT29 was determined after 48 h by flow cytometry.

FIGS. 13A-C show a comparison of different TCB formats with 16D5. Four different TCB formats containing the FolR1 binder 16D5 were compared in FIG. 13A binding to HeLa cells, in FIG. 14 B T cell mediated killing of SKOV3 cells after 24 h and 48 h and in FIG. 14C CD25 and CD69 activation marker upregulation on CD4 T cells and CD8 T cells 48 h after killing.

FIGS. 14A-C depict a comparison of different TCB formats with 9D11. Three different TCB formats containing the FolR1 binder 9D11 were compared in A) binding to HeLa cells, in B) T cell mediated killing of SKOV3 cells after 24 h and 48 h and in C) CD25 and CD69 activation marker upregulation on CD4 T cells and CD8 T cells 48 h after killing.

(FIG. 17A) Mean values and SEM of tumor volumes in the different treatment groups. (FIG. 17B) Tumor growth of single mice in all treatment groups. TGI (tumor growth inhibition) give the percentage of the Mean tumor volume compared to vehicle group.

FIGS. 19A-B show FACS analysis of tumor infiltrating T-cells at study day 32. (FIG. 19A) Tumor single cells suspensions were stained with anti-human CD3/CD4/CD8 and analyzed by flow cytometry. (FIG. 19B) Mean values and SEM of T-cell counts per mg tumor tissue in different treatment groups.

FIG. 27 depicts a table summarizing quantification of FolR1 binding sites on various normal and cancer cells lines.

FIG. 31 shows a sequence alignment of the VH domains of the 3 identified MUC1-specific binders. All three clones are derivatives of the IGHV3-23 germline (SEQ ID NO: 136). Clone 58D6 (SEQ ID NO: 60) and 110A5 (SEQ ID NO: 64) originate from a library that was only randomized in CDR3, while clone 106D2 (SEQ ID NO: 62) was identified from a library randomized in all 3 CDRs. Positions in CDR1 and 2 that deviate from the germline sequence are printed italic.

FIGS. 32A-B shows results of characterization of CLC binders. (FIG. 32A) SPR analysis. SPR-based kinetic analyses of 3 clones specifically binding to MUC1. Smooth lines represent a global fit of the data to a 1:1 interaction model. (FIG. 32B) Summary of kinetic and thermodynamic parameters.

FIG. 35 depicts SPR analysis of the MUC1-specific binders in the TCB format. Shown is the binding of 2 MUC1-specific TCBs at different concentrations (see text) to either MUC1 or an unrelated antigen. Smooth lines represent a global fit of the data to a 1:1 interaction model

FIGS. 39A-B show binding of BCMA-TCB CLC antibodies on BCMAhi-positive H929 cells by flow cytometry. The median fluorescence intensity of BCMA-TCB CLC antibodies were plotted in function of antibody concentrations (0.12 to 500 nM); (A) pSCHLI372-TCB CLC and pSCHLI373-TCB CLC on H929 cells (A) and MKN45 cells (B). DP47-TCB is a negative control TCB which did not bind to BCMA at concentrations below 100 nM (see Example 7).

FIGS. 40A-B show binding of BCMA-TCB CLC antibodies on CD3-positive Jurkat T cells as measured by flow cytometry. Median fluorescence intensity for BCMA-TCB CLC antibodies (pSCHLI372-TCB CLC and pSCHLI373-TCB CLC) binding to Jurkat T cells and plotted in function of antibody concentration. Non-binding to BCMA-negative and CD3-negative MKN45 cells at concentrations below 100 nM.

FIG. 41 shows T-cell activation mediated by BCMA-TCB CLC antibodies in presence of H929 cells as detected by flow cytometry. Expression level of the early activation marker CD69 and the late activation marker CD25 on CD4+ and CD8+ T cells after 48 hours of incubation. pSCHL1372-TCB CLC and pSCHL1373-TCB CLC antibodies induced an up-regulation of CD69 and CD25 activation markers in a concentration-dependent and specific manner in the presence of BCMA-positive target cells. E:T ratio used as 10 PBMCs:1 H929 cell; cells were incubated for 48 h before measurement of CD69 and CD25 upregulation. DP47-TCB which is a negative control TCB did not induce T-cell activation. Representative results are from two independent experiments.

DETAILED DESCRIPTION OF THE INVENTION

Definitions

Figure 1A:
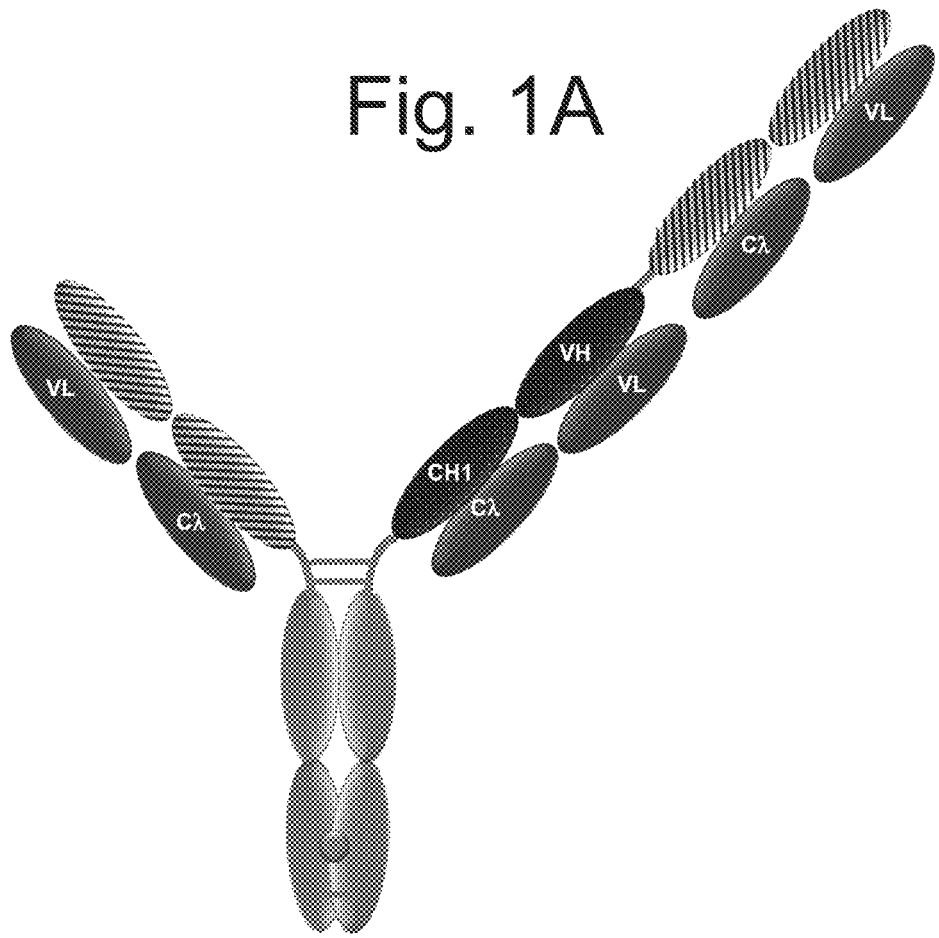
Figure 1B:
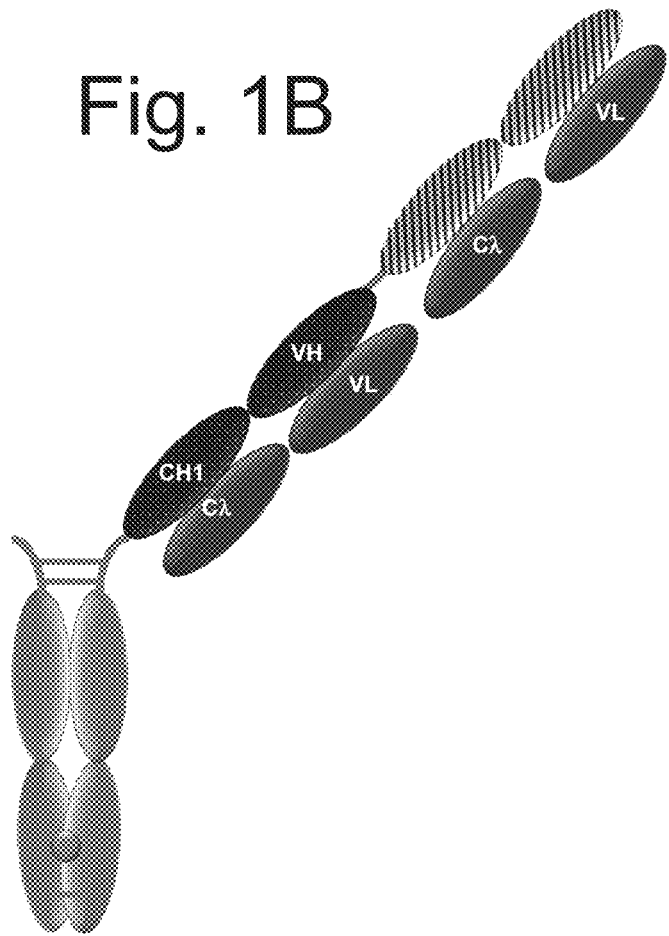
Figure 1C:
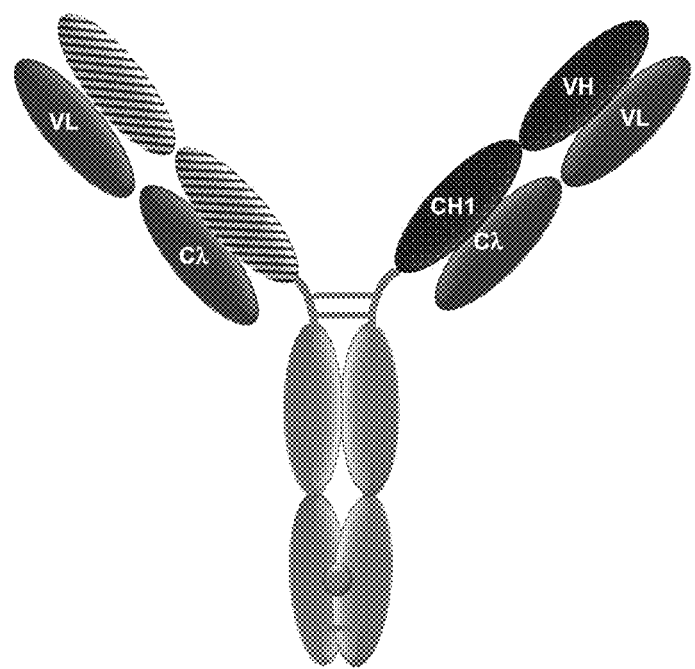
Figure 1D:
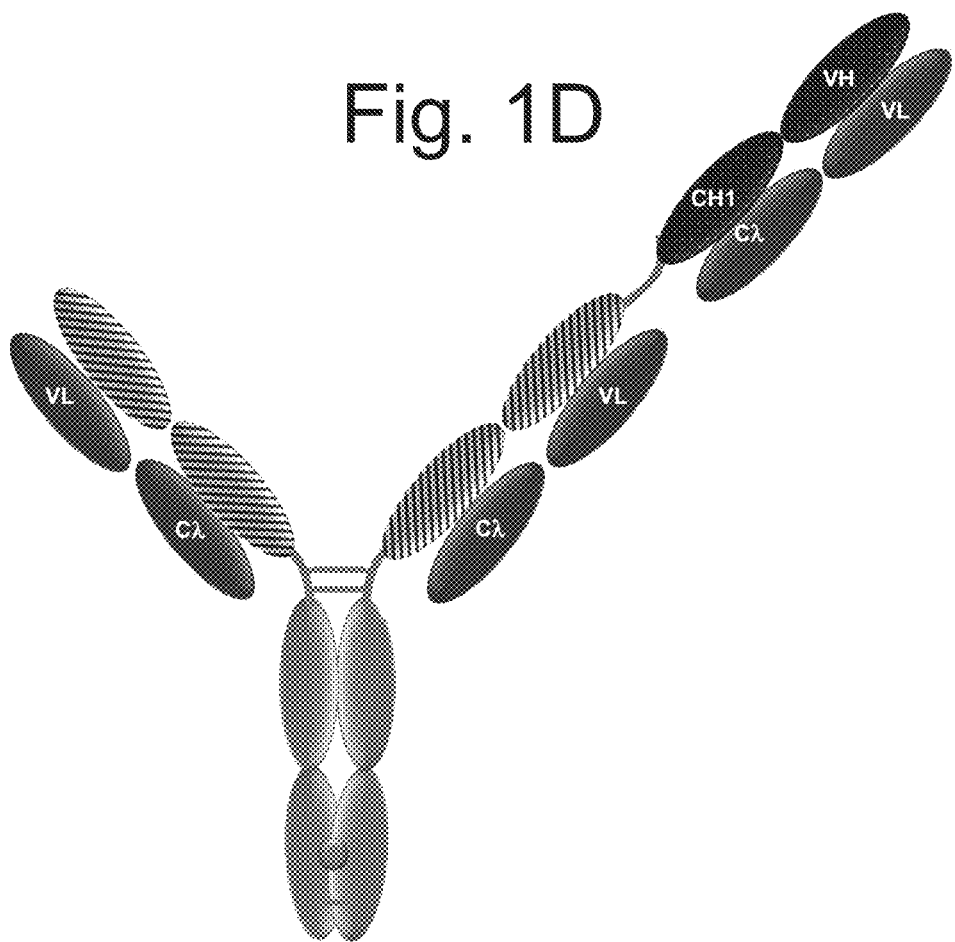
Figure 1F:
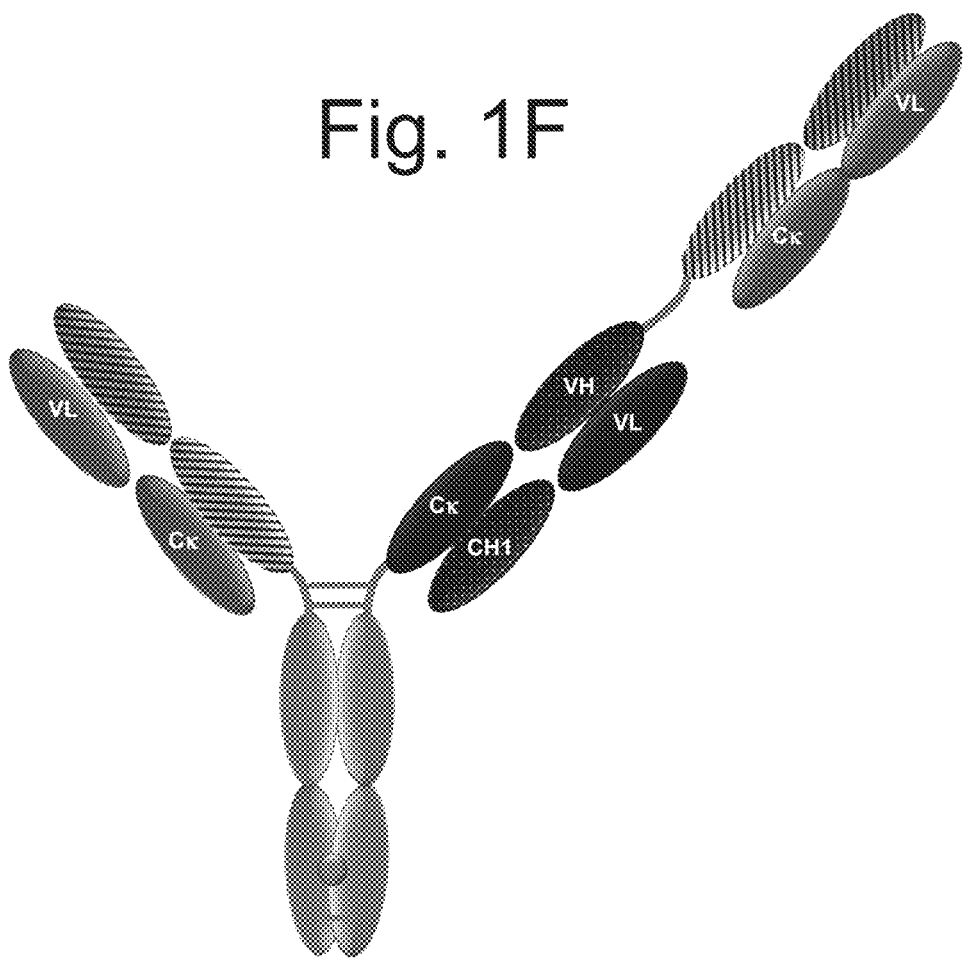
Figure 1G:
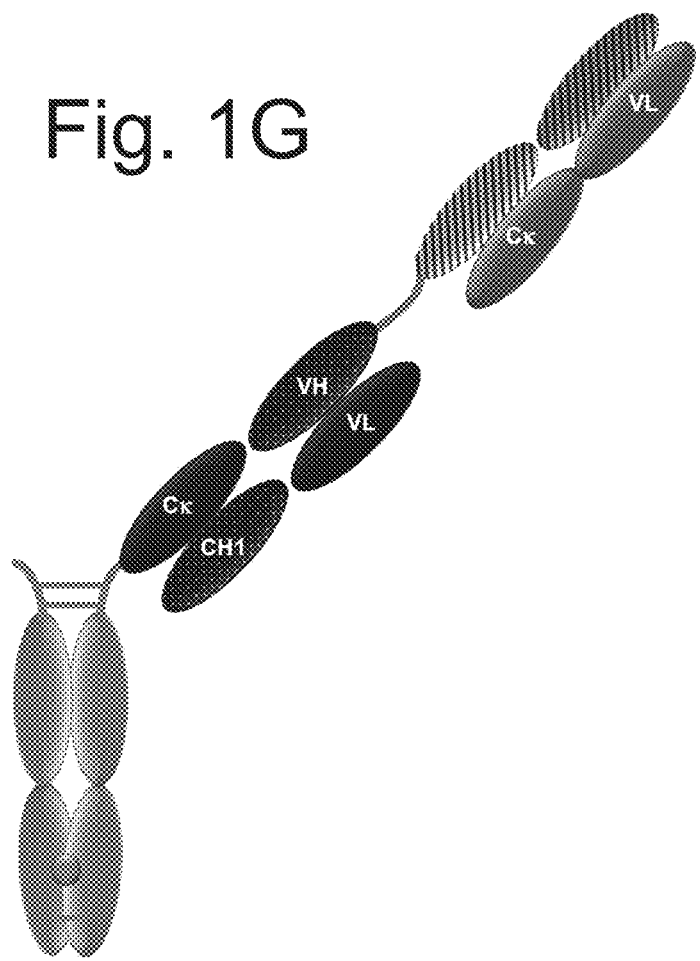
Figure 1H:
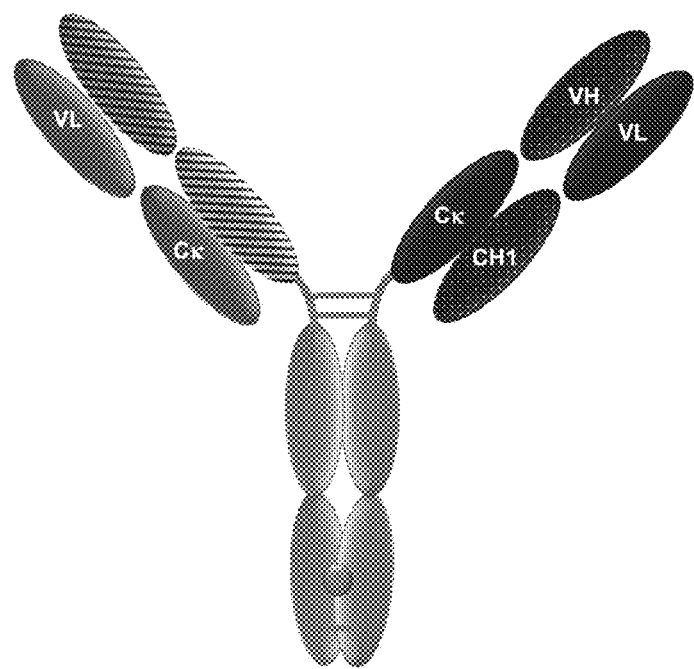
Figure 1I:
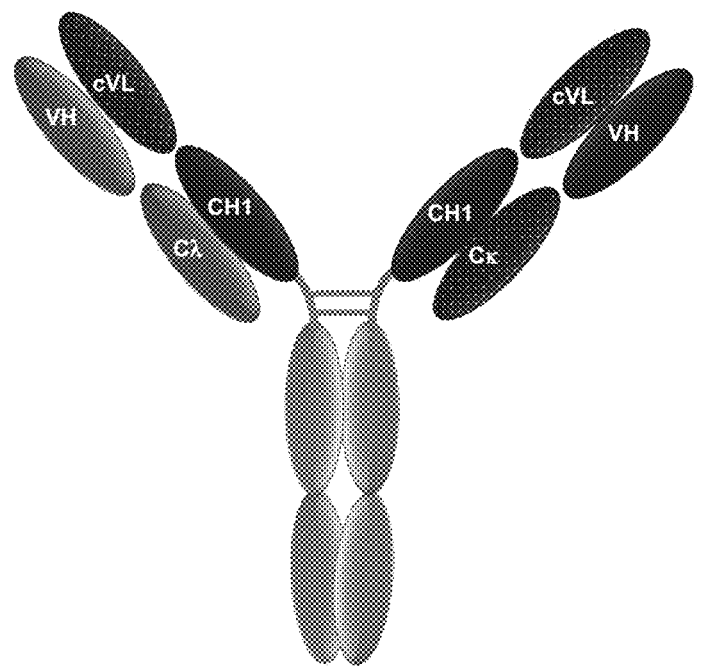

Terms are used herein as generally used in the art, unless otherwise defined in the following.

As used herein, the term "antigen binding molecule" refers in its broadest sense to a molecule that specifically binds an antigenic determinant. Examples of antigen binding molecules are immunoglobulins and derivatives, e.g. fragments, thereof.

The term "bispecific" means that the antigen binding molecule is able to specifically bind to at least two distinct antigenic determinants. Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e. one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

As used herein, the term "antigen binding moiety" refers to a polypeptide molecule that specifically binds to an antigenic determinant. In one embodiment, an antigen binding moiety is able to direct the entity to which it is attached (e.g. a second antigen binding moiety) to a target site, for example to a specific type of tumor cell or tumor stroma bearing the antigenic determinant. In another embodiment an antigen binding moiety is able to activate signaling through its target antigen, for example a T cell receptor complex antigen. Antigen binding moieties include antibodies and fragments thereof as further defined herein. Particular antigen binding moieties include an antigen binding domain of an antibody, comprising an antibody heavy chain variable region and an antibody light chain variable region. In certain embodiments, the antigen binding moieties may comprise antibody constant regions as further defined herein and known in the art. Useful heavy chain constant regions include any of the five isotypes: α, δ, ε, γ, or μ. Useful light chain constant regions include any of the two isotypes: κ and λ.

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins referred to as antigens herein (e.g. MCSP, FAP, CEA, EGFR, CD33, CD3) can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants. Exemplary human proteins useful as antigens include, but are not limited to Folate Receptor 1 (FolR1, Folate receptor alpha (FRA); Folate binding protein (FBP); human FolR1 UniProt no.: P15328; murine FolR1 UniProt no.: P35846; cynomolgus FolR1 UniProt no.: G7PR14), Mucin-1 (MUC1), and B Cell Maturation Antigen (BCMA), and CD3, particularly the epsilon subunit of CD3 (see UniProt no. P07766 (version 130), NCBI RefSeq no. NP_000724.1 for the human sequence; or UniProt no. Q95L15 (version 49), NCBI GenBank no. BAB71849.1 for the cynomolgus [*Macaca fascicularis*] sequence).

In certain embodiments the T cell activating bispecific antigen binding molecule of the invention binds to an epitope of an activating T cell antigen or a target cell antigen that is conserved among the activating T cell antigen or target antigen from different species.

By "specific binding" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g. surface plasmon resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an antigen binding molecule comprising that antigen binding moiety, has a dissociation constant ($K_D$) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., an antigen binding moiety and an antigen, or a receptor and its ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well established methods known in the art, including those described herein. A particular method for measuring affinity is Surface Plasmon Resonance (SPR).

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

An "activating T cell antigen" as used herein refers to an antigenic determinant expressed on the surface of a T lymphocyte, particularly a cytotoxic T lymphocyte, which is capable of inducing T cell activation upon interaction with an antigen binding molecule. Specifically, interaction of an antigen binding molecule with an activating T cell antigen may induce T cell activation by triggering the signaling cascade of the T cell receptor complex. In a particular embodiment the activating T cell antigen is CD3.

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The T cell activating bispecific antigen binding molecules of the invention are capable of inducing T cell activation. Suitable assays to measure T cell activation are known in the art described herein.

A "target cell antigen" as used herein refers to an antigenic determinant presented on the surface of a target cell, for example a cell in a tumor such as a cancer cell or a cell of the tumor stroma.

As used herein, the terms "first" and "second" with respect to antigen binding moieties etc., are used for convenience of distinguishing when there is more than one of each type of moiety. Use of these terms is not intended to confer a specific order or orientation of the T cell activating bispecific antigen binding molecule unless explicitly so stated.

The term "BCMA" as used herein relates to human B cell maturation target, also known as BCMA, TR17_HUMAN, TNFRSF17 (UniProt Q02223), which is a member of the tumor necrosis receptor superfamily that is preferentially expressed in differentiated plasma cells. The extracellular domain of BCMA consists according to UniProt of amino acids 1-54 (or 5-51). The term "antibody against BCMA, anti BCMA antibody" as used herein relates to an antibody specifically binding to BCMA.

The term "CD3ε or CD3" as used herein relates to human CD3ε described under UniProt P07766 (CD3E_HUMAN). The term "antibody against CD3, anti CD3 antibody" relates to an antibody binding to CD3ε.

A "Fab molecule" refers to a protein consisting of the VH and CH1 domain of the heavy chain (the "Fab heavy chain") and the VL and CL domain of the light chain (the "Fab light chain") of an immunoglobulin. The term "Fab molecules having identical VLCL light chains" as used therein refers to binders that share one light chain but still have separate specificities. T-cell activating bispecific molecules of the invention comprise at least two Fab molecules having identical VLCL light chains. The corresponding heavy chains are remodeled and confer specific binding to a T cell activating bispecific antigen and a target cell antigen, respectively.

By "fused" is meant that the components (e.g. a Fab molecule and an Fc domain subunit) are linked by peptide bonds, either directly or via one or more peptide linkers.

The term "common light chain" as used herein refers to a light chain that within a bispecific or multispecific molecule pairs with more than one heavy chain or fragment thereof to form at least a first and a second antigen binding site, e.g., a Fab, each specific for a different antigen. For example, the common light chain pairs with a first heavy chain or fragment thereof within an antigen binding molecule to form a first binding site specific for a tumor antigen, and another copy of the common light chain pairs with a second heavy chain or fragment thereof within an antigen binding molecule to form a second binding site specific for a T cell activating antigen, e.g., CD3.

The term "immunoglobulin molecule" refers to a protein having the structure of a naturally occurring antibody. For example, immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five types, called α (IgA), δ (IgD), ε (IgE), γ (IgG), or μ (IgM), some of which may be further divided into subtypes, e.g. $\gamma_1$ (IgG$_1$), $\gamma_2$ (IgG$_2$), $\gamma_3$ (IgG$_3$), $\gamma_4$ (IgG$_4$), $\alpha_1$ (IgA$_1$) and $\alpha_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "antibody" herein is used in the broadest sense and encompasses various antibody structures, including but not limited to monoclonal antibodies, polyclonal antibodies, and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Particularly, an antigen binding domain comprises an antibody light chain variable region (VL) and an antibody heavy chain variable region (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6$^{th}$ ed., W.H. Freeman and Co., page 91 (2007). A single VH or VL domain may be sufficient to confer antigen-binding specificity.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

| CDR Definitions[1] | | | |
|---|---|---|---|
| CDR | Kabat | Chothia | AbM[2] |
| V$_H$ CDR1 | 31-35 | 26-32 | 26-35 |
| V$_H$ CDR2 | 50-65 | 52-58 | 50-58 |
| V$_H$ CDR3 | 95-102 | 95-102 | 95-102 |
| V$_L$ CDR1 | 24-34 | 26-32 | 24-34 |

TABLE A-continued

CDR Definitions[1]

| CDR | Kabat | Chothia | AbM[2] |
|---|---|---|---|
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

The polypeptide sequences of the sequence listing are not numbered according to the Kabat numbering system. However, it is well within the ordinary skill of one in the art to convert the numbering of the sequences of the Sequence Listing to Kabat numbering.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\epsilon$, $\gamma$, and $\mu$, respectively.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991. A "subunit" of an Fc domain as used herein refers to one of the two polypeptides forming the dimeric Fc domain, i.e. a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e. the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g. antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor, or increased association with another peptide. Amino acid sequence deletions and insertions include amino- and/or carboxy-terminal deletions and insertions of amino acids. Particular amino acid mutations are amino acid substitutions. For the purpose of altering e.g. the binding characteristics of an Fc region, non-conservative amino acid substitutions, i.e. replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g. 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc domain to glycine can be indicated as 329G, G329, G329, P329G, or Pro329Gly.

As used herein, term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

By an "isolated" polypeptide or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "activating Fc receptor" is an Fc receptor that following engagement by an Fc domain of an antibody elicits signaling events that stimulate the receptor-bearing cell to perform effector functions. Human activating Fc receptors include FcγRIIIa (CD16a), FcγRI (CD64), FcγRIIa (CD32), and FcαRI (CD89).

Antibody-dependent cell-mediated cytotoxicity (ADCC) is an immune mechanism leading to the lysis of antibody-coated target cells by immune effector cells. The target cells are cells to which antibodies or derivatives thereof comprising an Fc region specifically bind, generally via the protein part that is N-terminal to the Fc region. As used herein, the term "reduced ADCC" is defined as either a reduction in the number of target cells that are lysed in a given time, at a given concentration of antibody in the medium surrounding the target cells, by the mechanism of ADCC defined above, and/or an increase in the concentration of antibody in the medium surrounding the target cells, required to achieve the lysis of a given number of target cells in a given time, by the mechanism of ADCC. The reduction in ADCC is relative to the ADCC mediated by the same antibody produced by the same type of host cells, using the same standard production, purification, formulation and storage methods (which are known to those skilled in the art), but that has not been engineered. For example the reduction in ADCC mediated by an antibody comprising in its Fc domain an amino acid substitution that reduces ADCC, is relative to the ADCC mediated by the same antibody without this amino acid substitution in the Fc domain. Suitable assays to measure ADCC are well known in the art (see e.g. PCT publication no. WO 2006/082515 or PCT patent application no. PCT/EP2012/055393).

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, T cell activating bispecific antigen binding molecules of the invention are used to delay development of a disease or to slow the progression of a disease.

The term "package insert" is used to refer to instructions customarily included in commercial packages of therapeutic products, that contain information about the indications, usage, dosage, administration, combination therapy, contraindications and/or warnings concerning the use of such therapeutic products.

DETAILED DESCRIPTION OF THE EMBODIMENTS

The present invention provides bispecific antigen binding molecules designed for T cell activation and re-direction that combine good efficacy and produceability and methods of making and using the same. In particular this invention relates to bispecific molecules wherein at least two binding moieties have identical light chains and, in some embodiments, corresponding remodeled heavy chains that confer the specific binding to a T cell activating bispecific antigen and a target cell antigen, respectively. The use of this so-called 'common light chain' principle, i.e. combining two binders that share one light chain but still have separate specificities, prevents light chain mispairing. Thus, there are less side products during production, facilitating the homogenous preparation of T cell activating bispecific antigen binding molecules.

The present invention particularly pertains to a predefined rare light chain which contributes significantly to antigen binding and heteromultimeric pairing with different binding partners, e.g., heavy chains and fragments thereof. This common light chain is, thus, suitable as for use in a library from which new bi- or multispecific antigen binding molecules can be prepared. Advantageously, the common light chain used in connection with antigen binding molecules and methods disclosed herein can be used to form an antigen binding molecule useful for T cell activation. One of skill in the art can recognize the advantageous efficiency of having such light chain that can function in both, T cell activating antigen binding moieties and target antigen binding moieties. This allows for efficient production of T cell activating bispecific antigen binding molecules that comprise the T cell activation component and a target antigen binding component. In a particular embodiment, the common light chain a lambda constant light chain domain. In a particular embodiment, the common light chain is a human or humanized lambda light chain. In a particular embodiment, the common light chain is of the rare human lambda 7 family of light chain. Using a light chain of the lambda, particularly, the rare lambda 7 family was an uncommon approach and would have been expected to decrease the likelihood of identifying suitable heavy chain binding partners to create antigen binding molecules specific for a variety of targets. Thus, prior to the inventor's work disclosed herein, it was not known that a lambda 7 light chain with suitable properties could be developed for a variety of different unrelated target antigens such as, e.g., FolR1, MUC1, and BCMA. It was further not known that a lambda light chain could be developed to generate stable, functional, high affinity binders to improve production of T cell activating bispecific antigen binding molecules with CD3 specificity and a target antigen specificity, where the target antigens are unrelated, e.g., FolR1, MUC1, and BCMA. In one embodiment, such common light chain can be used to construct a common light chain (CLC) library which is based on a specific CD3 binder, not a germline antibody, to generate specifically CD3 binders contributing to the binder, as described below. The advantage of this approach is that it allows for maintaining the previously identified and validated CD3 binder such that merely a new target antigen binder for the target antigen binding moiety of a T cell activating bispecific antigen binding molecules has to be identified based on the heavy chain. This allows for a module approach to generating different T cell activating bispecific antigen binding molecules with identical or highly homologous chains. While the light chain is identical within a given T cell activating antigen binding molecule, the light chains of different T cell activating bispecific antigen binding molecules might be identical or highly homologous. By "highly homologous" is meant that the light chains of different T cell activating bispecific antigen binding molecules produced by this module approach comprise an amino acid sequence that is at least about 95%, 96%, 97%, 98%, or 99% identical. Preferably, highly homologous light chains of the invention have identical variable light chain regions and differ only on their constant region. For example, in some embodiments, the amino acid variance is confined to the linker region. In some embodiment, the common light chain comprises a kappa constant light chain domain.

In addition to the foregoing advantages, yield of correctly paired heteromultimeric molecules using this approach is enhanced, as explained above, because the light chain used within the antigen binding moieties of a T cell activating bispecific antigen binding molecule is identical. Stated another way, using a common light chain the production of these molecules is facilitated as any mispairing of a light chain to the incorrect heavy chain is abolished. Thus, the isolation of a highly pure T cell activating bispecific antigen binding molecule species is facilitated. In a particular embodiment, the T cell activating bispecific antigen binding molecule uses Fabs as building blocks. Compared to other formats the use of Fab fragments as building blocks as opposed to, e.g., the use of scFv fragments results in higher thermal stability and the lack of scFv aggregation and intermolecular scFv formation.

Prior to the inventors' work described herein, it was not known that a common light chain could be generated that can not only serve as common light chain in a bi- or multispecific molecule but also support the functional property of T cell activation of a T cell activating bispecific antigen binding molecule. Furthermore, prior to the inventors' work described herein, it was not known that a common light chain could be generated that significantly contributes to antigen binding properties of the antigen binding moiety within a T cell activating bispecific antigen binding molecule. A well-established strategy is to identify heavy chains or fragments thereof that contribute most of the binding properties, such as strength and specificity. According to the present invention, the common light chain significantly contributes to the binding properties.

Accordingly, in a first aspect the invention provides a T cell activating bispecific antigen binding molecule comprising a first and a second antigen binding moiety, wherein the first antigen binding moiety comprises a first light chain and wherein the first antigen binding moiety is capable of specific binding to an activating T cell antigen, wherein the second antigen binding moiety comprises a second light chain and wherein the second antigen binding moiety is capable of specific binding to a target cell antigen, wherein the amino acid sequence of the first and the second light chain is identical. In one embodiment, the first antigen binding moiety is a Fab. In one embodiment, the second antigen binding moiety is a Fab. In one aspect, the invention provides a T cell activating bispecific antigen binding molecule comprising a first and a second antigen binding moiety, one of which is a Fab molecule capable of specific binding to an activating T cell antigen and the other one of which is a Fab molecule capable of specific binding to a target cell antigen, wherein the first and the second Fab molecule have identical light chains (variable light chain and constant light chain region, VLCL). In one embodiment, the light chain (VLCL) comprises the light chain CDRs of SEQ ID NO: 32, SEQ ID NO: 33 and SEQ ID NO: 34. In one embodiment said identical light chain (VLCL) comprises SEQ ID NO. 35.

T Cell Activating Bispecific Antigen Binding Molecule Formats

The components of the T cell activating bispecific antigen binding molecule can be fused to each other in a variety of configurations. Exemplary configurations include but are not limited to those depicted in FIGS. 1A-D.

In some embodiments, said T cell activating bispecific antigen binding molecule further comprises an Fc domain composed of a first and a second subunit capable of stable association. Below exemplary embodiments of T cell activating bispecific antigen binding molecule comprising an Fc domain are described. All these T cell activating bispecific antigen binding molecules comprise at least two Fab fragments having identical light chains (VLCL) and having different heavy chains (VHCL) which confer the specifities to two different antigens, i.e. one Fab fragment is capable of specific binding to a T cell activating antigen and the other Fab fragment is capable of specific binding to a target cell antigen.

In some embodiments, the first and the second antigen binding moiety of the T cell activating bispecific antigen binding molecule are fused to each other, optionally via a peptide linker. In one such embodiment, the second antigen binding moiety is fused at the C-terminus of the Fab heavy chain to the N-terminus of the Fab heavy chain of the first antigen binding moiety. In another such embodiment, the first antigen binding moiety is fused at the C-terminus of the Fab heavy chain to the N-terminus of the Fab heavy chain of the second antigen binding moiety. In yet another such embodiment, the second antigen binding moiety is fused at the C-terminus of the Fab light chain to the N-terminus of the Fab light chain of the first antigen binding moiety. In yet another such embodiment, the first antigen binding moiety is fused at the C-terminus of the Fab light chain to the N-terminus of the Fab light chain of the second antigen binding moiety.

In one embodiment the second antigen binding moiety is fused at the C-terminus of the Fab heavy chain to the N-terminus of the first or the second subunit of the Fc domain.

In a particular such embodiment, the first antigen binding moiety is fused at the C-terminus of the Fab heavy chain to the N-terminus of the Fab heavy chain of the second antigen binding moiety. In a specific such embodiment, the T cell activating bispecific antigen binding molecule essentially consists of a first and a second antigen binding moiety which comprise identical (VLCL) light chains, an Fc domain composed of a first and a second subunit, and optionally one or more peptide linkers, wherein the first antigen binding moiety is fused at the C-terminus of the Fab heavy chain to the N-terminus of the Fab heavy chain of the second antigen binding moiety, and the second antigen binding moiety is fused at the C-terminus of the Fab heavy chain to the N-terminus of the first or the second subunit of the Fc domain.

In an alternative such embodiment, the first antigen binding moiety is fused at the C-terminus of the Fab heavy chain to the N-terminus of the first or second subunit of the Fc domain. In a specific such embodiment, the T cell activating bispecific antigen binding molecule essentially consists of a first and a second antigen binding moiety which comprise identical (VLCL) light chains, an Fc domain composed of a first and a second subunit, and optionally one or more peptide linkers, wherein the first and the second antigen binding moiety are each fused at the C-terminus of the Fab heavy chain to the N-terminus of one of the subunits of the Fc domain.

In yet another such embodiment, the second antigen binding moiety is fused at the C-terminus of the Fab light chain to the N-terminus of the Fab light chain of the first antigen binding moiety. In a specific such embodiment, the T cell activating bispecific antigen binding molecule essentially consists of a first and a second antigen binding moiety which comprise identical (VLCL) light chains, an Fc domain composed of a first and a second subunit, and optionally one or more peptide linkers, wherein the first antigen binding moiety is fused at the N-terminus of the Fab light chain to the C-terminus of the Fab light chain of the second antigen binding moiety, and the second antigen binding moiety is fused at the C-terminus of the Fab heavy chain to the N-terminus of the first or the second subunit of the Fc domain.

In other embodiments, the first antigen binding moiety is fused at the C-terminus of the Fab heavy chain to the N-terminus of the first or second subunit of the Fc domain.

In a particular such embodiment, the second antigen binding moiety is fused at the C-terminus of the Fab heavy chain to the N-terminus of the Fab heavy chain of the first antigen binding moiety. In a specific such embodiment, the T cell activating bispecific antigen binding molecule essentially consists of a first and a second antigen binding moiety which comprise identical (VLCL) light chains, an Fc domain composed of a first and a second subunit, and optionally one or more peptide linkers, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first or the second subunit of the Fc domain.

In particular of these embodiments, the first antigen binding moiety is capable of specific binding to an activating T cell antigen. In other embodiments, the first antigen binding moiety is capable of specific binding to a target cell antigen.

The antigen binding moieties may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, $(G_4S)_n$ (SEQ ID NO: 41), $(SG_4)_n$ (SEQ ID NO: 42), $(G_4S)_n$ (SEQ ID NO: 41) or $G_4(SG_4)_n$ (SEQ ID NO: 43) peptide linkers. "n" is generally a number between 1 and 10, typically between 2 and 4. A particularly suitable peptide linker for fusing the Fab light chains of the first and the second antigen binding moiety to each other is (G$_4$S)$_2$ (SEQ ID NO: 44). Additionally, linkers may comprise (a portion of) an immunoglobulin hinge region. Particularly where an antigen binding moiety is fused to the N-terminus of an Fc domain subunit, it may be fused via an immunoglobulin hinge region or a portion thereof, with or without an additional peptide linker.

A T cell activating bispecific antigen binding molecule with a single antigen binding moiety capable of specific binding to a target cell antigen is useful, particularly in cases where internalization of the target cell antigen is to be expected following binding of a high affinity antigen binding moiety. In such cases, the presence of more than one antigen binding moiety specific for the target cell antigen may enhance internalization of the target cell antigen, thereby reducing its availability.

In many other cases, however, it will be advantageous to have a T cell activating bispecific antigen binding molecule comprising two or more antigen binding moieties specific for a target cell antigen, for example to optimize targeting to the target site or to allow crosslinking of target cell antigens.

Accordingly, in certain embodiments, the T cell activating bispecific antigen binding molecule of the invention further comprises a third antigen binding moiety which is a Fab molecule capable of specific binding to a target cell antigen. In one embodiment, the third antigen binding moiety is capable of specific binding to the same target cell antigen as the first or second antigen binding moiety. In a particular embodiment, the first antigen binding moiety is capable of specific binding to an activating T cell antigen, and the second and third antigen binding moieties are capable of specific binding to a target cell antigen. In a preferred embodiment, the first, second and third antigen binding moiety comprise identical (VLCL) light chains.

In one embodiment, the third antigen binding moiety is fused at the C-terminus of the Fab heavy chain to the N-terminus of the first or second subunit of the Fc domain.

In one embodiment, the first and the third antigen binding moiety are each fused at the C-terminus of the Fab heavy chain to the N-terminus of one of the subunits of the Fc domain, and the second antigen binding moiety is fused at the C-terminus of the Fab heavy chain to the N-terminus of the Fab heavy chain of the first antigen binding moiety. In a specific such embodiment, the T cell activating bispecific antigen binding molecule essentially consists of a first, a second and a third antigen binding moiety (Fab fragment), an Fc domain composed of a first and a second subunit, and optionally one or more peptide linkers, wherein the second antigen binding moiety is fused at the C-terminus of the Fab heavy chain to the N-terminus of the Fab heavy chain of the first antigen binding moiety, and the first antigen binding moiety is fused at the C-terminus of the Fab heavy chain to the N-terminus of the first subunit of the Fc domain, and wherein the third antigen binding moiety is fused at the C-terminus of the Fab heavy chain to the N-terminus of the second subunit of the Fc domain. Preferably in said embodiment the first antigen binding moiety is capable of specific binding to an activating T cell antigen, and the second and third antigen binding moieties are capable of specific binding to a target cell antigen, wherein the first, second and third antigen binding moeities are Fab fragments which comprise identical (VLCL) light chains.

In one embodiment, the second and the third antigen binding moiety are each fused at the C-terminus of the Fab heavy chain to the N-terminus of one of the subunits of the Fc domain, and the first antigen binding moiety is fused at the C-terminus of the Fab heavy chain to the N-terminus of the Fab heavy chain of the second antigen binding moiety.

In one embodiment, the T cell activating bispecific antigen binding molecule essentially consists of an immunoglobulin molecule capable of specific binding to a target cell antigen, and a Fab molecule capable of specific binding to an activating T cell antigen, fused to the N-terminus of one of the immunoglobulin heavy chains, optionally via a peptide linker. Preferably in said embodiment the immunoglobulin molecule capable of specific binding to a target cell antigen and the Fab molecule capable of specific binding to an activating T cell antigen comprise identical (VLCL) light chains.

The first and the third antigen binding moiety (or the second and the third antigen binding moiety, respectively) may be fused to the Fc domain directly or through a peptide linker. In a particular embodiment first and the third antigen binding moiety (or the second and the third antigen binding moiety, respectively) are each fused to the Fc domain through an immunoglobulin hinge region.

In a specific embodiment, the immunoglobulin hinge region is a human IgG$_1$ hinge region. In one embodiment first and the third antigen binding moiety (or the second and the third antigen binding moiety, respectively) and the Fc domain are part of an immunoglobulin molecule. In a particular embodiment the immunoglobulin molecule is an IgG class immunoglobulin. In an even more particular embodiment the immunoglobulin is an IgG$_1$ subclass immunoglobulin. In another embodiment the immunoglobulin is an IgG$_4$ subclass immunoglobulin. In a further particular embodiment the immunoglobulin is a human immunoglobulin. In other embodiments the immunoglobulin is a chimeric immunoglobulin or a humanized immunoglobulin.

Fc Domain

The Fc domain of the T cell activating bispecific antigen binding molecule consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one embodiment the T cell activating bispecific antigen binding molecule of the invention comprises not more than one Fc domain.

In one embodiment according the invention the Fc domain of the T cell activating bispecific antigen binding molecule is an IgG Fc domain. In a particular embodiment the Fc domain is an IgG$_1$ Fc domain. In another embodiment the Fc domain is an IgG$_4$ Fc domain. In a more specific embodiment, the Fc domain is an IgG$_4$ Fc domain comprising an amino acid substitution at position S228 (Kabat numbering), particularly the amino acid substitution S228P. This amino acid substitution reduces in vivo Fab arm exchange of IgG$_4$ antibodies (see Stubenrauch et al., Drug Metabolism and Disposition 38, 84-91 (2010)). In a further particular embodiment the Fc domain is human.

Fc Domain Modifications Promoting Heterodimerization

T cell activating bispecific antigen binding molecules according to the invention comprise different antigen binding moieties, fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of T cell activating bispecific antigen binding molecules in recombinant production, it will thus be advantageous to introduce in the Fc domain of the T cell activating bispecific antigen binding molecule a modification promoting the association of the desired polypeptides.

Accordingly, in particular embodiments the Fc domain of the T cell activating bispecific antigen binding molecule according to the invention comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

In a specific embodiment said modification is a so-called "knob-into-hole" modification, comprising a "knob" modification in one of the two subunits of the Fc domain and a "hole" modification in the other one of the two subunits of the Fc domain.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in a particular embodiment, in the CH3 domain of the first subunit of the Fc domain of the T cell activating bispecific antigen binding molecule an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

The protuberance and cavity can be made by altering the nucleic acid encoding the polypeptides, e.g. by site-specific mutagenesis, or by peptide synthesis.

In a specific embodiment, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A).

In yet a further embodiment, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). Introduction of these two cysteine residues results in formation of a disulfide bridge between the two subunits of the Fc domain, further stabilizing the dimer (Carter, J Immunol Methods 248, 7-15 (2001)).

In a particular embodiment the antigen binding moiety capable of binding to an activating T cell antigen is fused (optionally via the antigen binding moiety capable of binding to a target cell antigen) to the first subunit of the Fc domain (comprising the "knob" modification). Without wishing to be bound by theory, fusion of the antigen binding moiety capable of binding to an activating T cell antigen to the knob-containing subunit of the Fc domain will (further) minimize the generation of antigen binding molecules comprising two antigen binding moieties capable of binding to an activating T cell antigen (steric clash of two knob-containing polypeptides).

In an alternative embodiment a modification promoting association of the first and the second subunit of the Fc domain comprises a modification mediating electrostatic steering effects, e.g. as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

Fc Domain Modifications Reducing Fc Receptor Binding and/or Effector Function

The Fc domain confers to the T cell activating bispecific antigen binding molecule favorable pharmacokinetic properties, including a long serum half-life which contributes to good accumulation in the target tissue and a favorable tissue-blood distribution ratio. At the same time it may, however, lead to undesirable targeting of the T cell activating bispecific antigen binding molecule to cells expressing Fc receptors rather than to the preferred antigen-bearing cells. Moreover, the co-activation of Fc receptor signaling pathways may lead to cytokine release which, in combination with the T cell activating properties and the long half-life of the antigen binding molecule, results in excessive activation of cytokine receptors and severe side effects upon systemic administration. Activation of (Fc receptor-bearing) immune cells other than T cells may even reduce efficacy of the T cell activating bispecific antigen binding molecule due to the potential destruction of T cells e.g. by NK cells.

Accordingly, in particular embodiments the Fc domain of the T cell activating bispecific antigen binding molecules according to the invention exhibits reduced binding affinity to an Fc receptor and/or reduced effector function, as compared to a native $IgG_1$ Fc domain. In one such embodiment the Fc domain (or the T cell activating bispecific antigen binding molecule comprising said Fc domain) exhibits less than 50%, preferably less than 20%, more preferably less than 10% and most preferably less than 5% of the binding affinity to an Fc receptor, as compared to a native $IgG_1$ Fc domain (or a T cell activating bispecific antigen binding molecule comprising a native $IgG_1$ Fc domain), and/or less than 50%, preferably less than 20%, more preferably less than 10% and most preferably less than 5% of the effector function, as compared to a native $IgG_1$ Fc domain domain (or a T cell activating bispecific antigen binding molecule comprising a native $IgG_1$ Fc domain). In one embodiment, the Fc domain domain (or the T cell activating bispecific antigen binding molecule comprising said Fc domain) does not substantially bind to an Fc receptor and/or induce effector function. In a particular embodiment the Fc receptor is an Fcγ receptor. In one embodiment the Fc receptor is a human Fc receptor. In one embodiment the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment the effector function is one or more selected from the group of CDC, ADCC, ADCP, and cytokine secretion. In a particular embodiment the effector function is ADCC. In one embodiment the Fc domain domain exhibits substantially similar binding affinity to neonatal Fc receptor (FcRn), as compared to a native IgG$_1$ Fc domain domain. Substantially similar binding to FcRn is achieved when the Fc domain (or the T cell activating bispecific antigen binding molecule comprising said Fc domain) exhibits greater than about 70%, particularly greater than about 80%, more particularly greater than about 90% of the binding affinity of a native IgG$_1$ Fc domain (or the T cell activating bispecific antigen binding molecule comprising a native IgG$_1$ Fc domain) to FcRn.

In certain embodiments the Fc domain is engineered to have reduced binding affinity to an Fc receptor and/or reduced effector function, as compared to a non-engineered Fc domain. In particular embodiments, the Fc domain of the T cell activating bispecific antigen binding molecule comprises one or more amino acid mutation that reduces the binding affinity of the Fc domain to an Fc receptor and/or effector function. Typically, the same one or more amino acid mutation is present in each of the two subunits of the Fc domain. In one embodiment the amino acid mutation reduces the binding affinity of the Fc domain to an Fc receptor. In one embodiment the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment the T cell activating bispecific antigen binding molecule comprising an engineered Fc domain exhibits less than 20%, particularly less than 10%, more particularly less than 5% of the binding affinity to an Fc receptor as compared to a T cell activating bispecific antigen binding molecule comprising a non-engineered Fc domain. In a particular embodiment the Fc receptor is an Fcγ receptor. In some embodiments the Fc receptor is a human Fc receptor. In some embodiments the Fc receptor is an activating Fc receptor. In a specific embodiment the Fc receptor is an activating human Fcγ receptor, more specifically human FcγRIIIa, FcγRI or FcγRIIa, most specifically human FcγRIIIa. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the Fc domain to said receptor, is achieved when the Fc domain (or the T cell activating bispecific antigen binding molecule comprising said Fc domain) exhibits greater than about 70% of the binding affinity of a non-engineered form of the Fc domain (or the T cell activating bispecific antigen binding molecule comprising said non-engineered form of the Fc domain) to FcRn. The Fc domain, or T cell activating bispecific antigen binding molecules of the invention comprising said Fc domain, may exhibit greater than about 80% and even greater than about 90% of such affinity. In certain embodiments the Fc domain of the T cell activating bispecific antigen binding molecule is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming. In one embodiment the reduced effector function is one or more selected from the group of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or a T cell activating bispecific antigen binding molecule comprising a non-engineered Fc domain).

In one embodiment the amino acid mutation that reduces the binding affinity of the Fc domain to an Fc receptor and/or effector function is an amino acid substitution. In one embodiment the Fc domain comprises an amino acid substitution at a position selected from the group of E233, L234, L235, N297, P331 and P329. In a more specific embodiment the Fc domain comprises an amino acid substitution at a position selected from the group of L234, L235 and P329. In some embodiments the Fc domain comprises the amino acid substitutions L234A and L235A. In one such embodiment, the Fc domain is an IgG$_1$ Fc domain, particularly a human IgG$_1$ Fc domain. In one embodiment the Fc domain comprises an amino acid substitution at position P329. In a more specific embodiment the amino acid substitution is P329A or P329G, particularly P329G. In one embodiment the Fc domain comprises an amino acid substitution at position P329 and a further amino acid substitution at a position selected from E233, L234, L235, N297 and P331. In a more specific embodiment the further amino acid substitution is E233P, L234A, L235A, L235E, N297A, N297D or P331S. In particular embodiments the Fc domain comprises amino acid substitutions at positions P329, L234 and L235. In more particular embodiments the Fc domain comprises the amino acid mutations L234A, L235A and P329G ("P329G LALA"). In one such embodiment, the Fc domain is an IgG$_1$ Fc domain, particularly a human IgG$_1$ Fc domain. The "P329G LALA" combination of amino acid substitutions almost completely abolishes Fcγ receptor binding of a human IgG$_1$ Fc domain, as described in PCT patent application no. PCT/EP2012/055393, incorporated herein by reference in its entirety. PCT/EP2012/055393 also describes methods of preparing such mutant Fc domains and methods for determining its properties such as Fc receptor binding or effector functions.

IgG$_4$ antibodies exhibit reduced binding affinity to Fc receptors and reduced effector functions as compared to IgG$_1$ antibodies. Hence, in some embodiments the Fc domain of the T cell activating bispecific antigen binding molecules of the invention is an IgG$_4$ Fc domain, particularly a human IgG$_4$ Fc domain. In one embodiment the IgG$_4$ Fc domain comprises amino acid substitutions at position S228, specifically the amino acid substitution S228P. To further reduce its binding affinity to an Fc receptor and/or its effector function, in one embodiment the IgG$_4$ Fc domain comprises an amino acid substitution at position L235, specifically the amino acid substitution L235E. In another embodiment, the IgG$_4$ Fc domain comprises an amino acid substitution at position P329, specifically the amino acid substitution P329G. In a particular embodiment, the IgG$_4$ Fc domain comprises amino acid substitutions at positions S228, L235 and P329, specifically amino acid substitutions S228P, L235E and P329G. Such IgG$_4$ Fc domain mutants and their Fcγ receptor binding properties are described in PCT patent application no. PCT/EP2012/055393, incorporated herein by reference in its entirety.

In a particular embodiment the Fc domain exhibiting reduced binding affinity to an Fc receptor and/or reduced effector function, as compared to a native IgG$_1$ Fc domain, is a human IgG$_1$ Fc domain comprising the amino acid substitutions L234A, L235A and optionally P329G, or a human IgG$_4$ Fc domain comprising the amino acid substitutions S228P, L235E and optionally P329G.

In certain embodiments N-glycosylation of the Fc domain has been eliminated. In one such embodiment the Fc domain comprises an amino acid mutation at position N297, particularly an amino acid substitution replacing asparagine by alanine (N297A) or aspartic acid (N297D).

In addition to the Fc domains described hereinabove and in PCT patent application no. PCT/EP2012/055393, Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor.

Effector function of an Fc domain, or a T cell activating bispecific antigen binding molecule comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, CA); and CytoTox 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the T cell activating bispecific antigen binding molecule is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

Antigen Binding Moieties

The antigen binding molecule of the invention is bispecific, i.e. it comprises at least two antigen binding moieties capable of specific binding to two distinct antigenic determinants. According to one embodiment of the invention, the antigen binding moieties are Fab molecules (i.e. antigen binding domains composed of a heavy and a light chain, each comprising a variable and a constant region), wherein the light chain (VLCL) of the at least two Fab molecules comprises identical sequences. In one embodiment said VLCL light chain of the Fab molecules capable of specific binding to a target cell antigen and a T cell activating antigen, respectively, comprises the light chain CDRs of SEQ ID NO: 32, SEQ ID NO: 33 and SEQ ID NO: 34.

In one embodiment said VLCL light chain of the Fab molecules capable of specific binding to a target cell antigen and a T cell activating antigen, respectively, comprises SEQ ID NO: 31.

In one embodiment said Fab molecules are human. In another embodiment said Fab molecules are humanized. In yet another embodiment said Fab molecules comprise human heavy and light chain constant regions.

In a particular embodiment according to the invention, the T cell activating bispecific antigen binding molecule is capable of simultaneous binding to a target cell antigen, particularly a tumor cell antigen, and an activating T cell antigen. In one embodiment, the T cell activating bispecific antigen binding molecule is capable of crosslinking a T cell and a target cell by simultaneous binding to a target cell antigen and an activating T cell antigen. In an even more particular embodiment, such simultaneous binding results in lysis of the target cell, particularly a tumor cell. In one embodiment, such simultaneous binding results in activation of the T cell. In other embodiments, such simultaneous binding results in a cellular response of a T lymphocyte, particularly a cytotoxic T lymphocyte, selected from the group of: proliferation, differentiation, cytokine secretion, cytotoxic effector molecule release, cytotoxic activity, and expression of activation markers. In one embodiment, binding of the T cell activating bispecific antigen binding molecule to the activating T cell antigen without simultaneous binding to the target cell antigen does not result in T cell activation.

In one embodiment, the T cell activating bispecific antigen binding molecule is capable of re-directing cytotoxic activity of a T cell to a target cell. In a particular embodiment, said re-direction is independent of MHC-mediated peptide antigen presentation by the target cell and and/or specificity of the T cell.

Particularly, a T cell according to any of the embodiments of the invention is a cytotoxic T cell. In some embodiments the T cell is a CD4$^+$ or a CD8$^+$ T cell, particularly a CD8$^+$ T cell.

Activating T Cell Antigen Binding Moiety

The T cell activating bispecific antigen binding molecule of the invention comprises at least one antigen binding moiety capable of binding to an activating T cell antigen (also referred to herein as an "activating T cell antigen binding moiety"). In a particular embodiment, the T cell activating bispecific antigen binding molecule comprises not more than one antigen binding moiety capable of specific binding to an activating T cell antigen. In one embodiment the T cell activating bispecific antigen binding molecule provides monovalent binding to the activating T cell antigen. The activating T cell antigen binding moiety is a Fab molecule and comprises an identical VLCL light chain as the antigen binding moiety capable of specific binding to a target cell antigen.

In a particular embodiment the activating T cell antigen is CD3, particularly human CD3 or cynomolgus CD3, most particularly human CD3. In a particular embodiment the activating T cell antigen binding moiety is cross-reactive for (i.e. specifically binds to) human and cynomolgus CD3. In some embodiments, the activating T cell antigen is the epsilon subunit of CD3 (SEQ ID NO: 56).

In one embodiment, the activating T cell antigen binding moiety can compete with monoclonal antibody H2C (described in PCT publication no. WO2008/119567) for binding an epitope of CD3. In another embodiment, the activating T cell antigen binding moiety can compete with monoclonal antibody V9 (described in Rodrigues et al., Int J Cancer Suppl 7, 45-50 (1992) and U.S. Pat. No. 6,054,297) for binding an epitope of CD3. In yet another embodiment, the activating T cell antigen binding moiety can compete with monoclonal antibody FN18 (described in Nooij et al., Eur J Immunol 19, 981-984 (1986)) for binding an epitope of CD3. In a particular embodiment, the activating T cell antigen binding moiety can compete with monoclonal antibody SP34 (described in Pessano et al., EMBO J 4, 337-340 (1985)) for binding an epitope of CD3. In one embodiment, the activating T cell antigen binding moiety binds to the same epitope of CD3 as monoclonal antibody SP34.

In one embodiment, the activating T cell antigen binding moiety comprises the heavy chain CDR1 of SEQ ID NO: 14, the heavy chain CDR2 of SEQ ID NO: 15, the heavy chain CDR3 of SEQ ID NO: 16, the light chain CDR1 of SEQ ID NO: 32, the light chain CDR2 of SEQ ID NO: 33, and the light chain CDR3 of SEQ ID NO: 34. In a further embodiment, the activating T cell antigen binding moiety comprises a heavy chain variable region sequence that is at least about 80%, 85%, 90%, 95%, 96%, 97%, 98%, 99% or 100% identical to SEQ ID NO: 36, or variants thereof that retain functionality.

In a further embodiment, the activating T cell antigen binding moiety comprises a light chain variable region sequence that is at least about 80%, 85%, 90%, 95%, 96%, 97%, 98%, 99% or 100% identical to SEQ ID NO: 31, or variants thereof that retain functionality.

In one embodiment the activating T cell antigen binding moiety comprises a heavy chain comprising the sequence of SEQ ID NO: 36 and a light chain comprising the sequence of SEQ ID NO: 31.

In one embodiment the activating T cell antigen binding moiety comprises a heavy chain of SEQ ID NO: 40 and a light chain comprising of SEQ ID NO: 35.

Target Cell Antigen Binding Moiety

The T cell activating bispecific antigen binding molecule of the invention comprises at least one antigen binding moiety capable of binding to a target cell antigen (also referred to herein as an "target cell antigen binding moiety").

In certain embodiments, the T cell activating bispecific antigen binding molecule comprises two antigen binding moieties capable of binding to a target cell antigen. In a particular such embodiment, each of these antigen binding moieties specifically binds to the same antigenic determinant. In one embodiment, the T cell activating bispecific antigen binding molecule comprises an immunoglobulin molecule capable of specific binding to a target cell antigen. In one embodiment the T cell activating bispecific antigen binding molecule comprises not more than two antigen binding moieties capable of binding to a target cell antigen.

The target cell antigen binding moiety is generally a Fab molecule that binds to a specific antigenic determinant and is able to direct the T cell activating bispecific antigen binding molecule to a target site, for example to a specific type of tumor cell that bears the antigenic determinant. Said Fab molecule has an identical VLCL light chain as the Fab molecule capable of specific binding to a T cell activating antigen. In a preferred embodiment said VLCL light chain of the Fab molecule capable of specific binding to a target cell antigen and the Fab molecule capable of specific binding to a T cell activating antigen comprise the light chain CDR1 of SEQ ID NO: 32, the light chain CDR2 of SEQ ID NO: 33, and the light chain CDR3 of SEQ ID NO: 34. In a preferred embodiment said VLCL light chain of the Fab molecule capable of specific binding to a target cell antigen and the Fab molecule capable of specific binding to a T cell activating antigen comprise a VLCL light chain of SEQ ID NO. 31.

In a further embodiment, the target cell antigen binding moiety comprises a light chain variable region sequence that is at least about 80%, 85%, 90%, 95%, 96%, 97%, 98%, 99% or 100% identical to SEQ ID NO: 31, or variants thereof that retain functionality.

In a further embodiment, the target cell antigen binding moiety comprises a light chain sequence that is at least about 80%, 85%, 90%, 95%, 96%, 97%, 98%, 99% or 100% identical to SEQ ID NO: 35, or variants thereof that retain functionality.

In certain embodiments the target cell antigen binding moiety is directed to an antigen associated with a pathological condition, such as an antigen presented on a tumor cell or on a virus-infected cell. Suitable antigens are cell surface antigens, for example, but not limited to, cell surface receptors. In particular embodiments the antigen is a human antigen. In a specific embodiment the target cell antigen is selected from the group of Folate Receptor 1 (FolR1), Mucin-1 (MUC1), and B Cell Maturation Antigen (BCMA).

In a specific embodiment the T cell activating bispecific antigen binding molecule comprises a polypeptide sequence encoded by a polynucleotide sequence that is at least about 80%, 85%, 90%, 95%, 96%, 97%, 98%, 99% or 100% identical to a sequence selected from the group of SEQ ID NO: 183, SEQ ID NO: 193, SEQ ID NO: 263, SEQ ID NO: 264, SEQ ID NO: 191, SEQ ID NO: 198, SEQ ID NO: 267, and SEQ ID NO: 272, including functional fragments or variants thereof.

Polynucleotides

The invention further provides isolated polynucleotides encoding a T cell activating bispecific antigen binding molecule as described herein or a fragment thereof.

Polynucleotides of the invention include those that are at least about 80%, 85%, 90%, 95%, 96%, 97%, 98%, 99%, or 100% identical to the sequences set forth in SEQ ID NO: 183, SEQ ID NO: 193, SEQ ID NO: 263, SEQ ID NO: 264, SEQ ID NO: 191, SEQ ID NO: 198, SEQ ID NO: 267, and SEQ ID NO: 272, including functional fragments or variants thereof.

The polynucleotides encoding T cell activating bispecific antigen binding molecules of the invention may be expressed as a single polynucleotide that encodes the entire T cell activating bispecific antigen binding molecule or as multiple (e.g., two or more) polynucleotides that are co-expressed. Polypeptides encoded by polynucleotides that are co-expressed may associate through, e.g., disulfide bonds or other means to form a functional T cell activating bispecific antigen binding molecule. For example, the light chain portion of an antigen binding moiety may be encoded by a separate polynucleotide from the portion of the T cell activating bispecific antigen binding molecule comprising the heavy chain portion of the antigen binding moiety, an Fc domain subunit and optionally (part of) another antigen binding moiety. When co-expressed, the heavy chain polypeptides will associate with the light chain polypeptides to form the antigen binding moiety. In another example, the portion of the T cell activating bispecific antigen binding molecule comprising one of the two Fc domain subunits and optionally (part of) one or more antigen binding moieties could be encoded by a separate polynucleotide from the portion of the T cell activating bispecific antigen binding molecule comprising the other of the two Fc domain subunits and optionally (part of) an antigen binding moiety. When co-expressed, the Fc domain subunits will associate to form the Fc domain.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

T cell activating bispecific antigen binding molecules of the invention may be obtained, for example, by solid-state peptide synthesis (e.g. Merrifield solid phase synthesis) or recombinant production. For recombinant production one or more polynucleotide encoding the T cell activating bispecific antigen binding molecule (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of a T cell activating bispecific antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., Molecular Cloning: A Laboratory Manual, Cold Spring Harbor Laboratory, N.Y. (1989); and Ausubel et al., Current Protocols in Molecular Biology, Greene Publishing Associates and Wiley Interscience, N.Y (1989). The expression vector can be part of a plasmid, virus, or may be a nucleic acid fragment. The expression vector includes an expression cassette into which the polynucleotide encoding the T cell activating bispecific antigen binding molecule (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the T cell activating bispecific antigen binding molecule (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit A-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the T cell activating bispecific antigen binding molecule is desired, DNA encoding a signal sequence may be placed upstream of the nucleic acid encoding a T cell activating bispecific antigen binding molecule of the invention or a fragment thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the T cell activating bispecific antigen binding molecule may be included within or at the ends of the T cell activating bispecific antigen binding molecule (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes (part of) a T cell activating bispecific antigen binding molecule of the invention. As used herein, the term "host cell" refers to any kind of cellular system which can be engineered to generate the T cell activating bispecific antigen binding molecules of the invention or fragments thereof. Host cells suitable for replicating and for supporting expression of T cell activating bispecific antigen binding molecules are well known in the art. Such cells may be transfected or transduced as appropriate with the particular expression vector and large quantities of vector containing cells can be grown for seeding large scale fermenters to obtain sufficient quantities of the T cell activating bispecific antigen binding molecule for clinical applications. Suitable host cells include prokaryotic microorganisms, such as E. coli, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr⁻ CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B.K.C. Lo, ed., Humana Press, Totowa, NJ), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell).

Standard technologies are known in the art to express foreign genes in these systems. Cells expressing a polypeptide comprising either the heavy or the light chain of an antigen binding domain such as an antibody, may be engineered so as to also express the other of the antibody chains such that the expressed product is an antibody that has both a heavy and a light chain.

In one embodiment, a method of producing a T cell activating bispecific antigen binding molecule according to the invention is provided, wherein the method comprises culturing a host cell comprising a polynucleotide encoding the T cell activating bispecific antigen binding molecule, as provided herein, under conditions suitable for expression of the T cell activating bispecific antigen binding molecule, and recovering the T cell activating bispecific antigen binding molecule from the host cell (or host cell culture medium).

The components of the T cell activating bispecific antigen binding molecule are genetically fused to each other. T cell activating bispecific antigen binding molecule can be designed such that its components are fused directly to each other or indirectly through a linker sequence. The composition and length of the linker may be determined in accordance with methods well known in the art and may be tested for efficacy. Examples of linker sequences between different components of T cell activating bispecific antigen binding molecules are found in the sequences provided herein. Additional sequences may also be included to incorporate a cleavage site to separate the individual components of the fusion if desired, for example an endopeptidase recognition sequence.

In certain embodiments the one or more antigen binding moieties of the T cell activating bispecific antigen binding molecules comprise at least an antibody variable region capable of binding an antigenic determinant. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of antibody, antibody fragment, antigen binding domain or variable region can be used in the T cell activating bispecific antigen binding molecules of the invention. Non-limiting antibodies, antibody fragments, antigen binding domains or variable regions useful in the present invention can be of murine, primate, or human origin. If the T cell activating bispecific antigen binding molecule is intended for human use, a chimeric form of antibody may be used wherein the constant regions of the antibody are from a human. A humanized or fully human form of the antibody can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, *Front Biosci* 13, 1619-1633 (2008), and are further described, e.g., in Riechmann et al., *Nature* 332, 323-329 (1988); Queen et al., *Proc Natl Acad Sci USA* 86, 10029-10033 (1989); U.S. Pat. Nos. 5,821,337, 7,527,791, 6,982,321, and 7,087,409; Jones et al., *Nature* 321, 522-525 (1986); Morrison et al., *Proc Natl Acad Sci* 81, 6851-6855 (1984); Morrison and Oi, *Adv Immunol* 44, 65-92 (1988); Verhoeyen et al., *Science* 239, 1534-1536 (1988); Padlan, *Molec Immun* 31(3), 169-217 (1994); Kashmiri et al., *Methods* 36, 25-34 (2005) (describing SDR (a-CDR) grafting); Padlan, *Mol Immunol* 28, 489-498 (1991) (describing "resurfacing"); Dall'Acqua et al., *Methods* 36, 43-60 (2005) (describing "FR shuffling"); and Osbourn et al., *Methods* 36, 61-68 (2005) and Klimka et al., *Br J Cancer* 83, 252-260 (2000) (describing the "guided selection" approach to FR shuffling). Human antibodies and human variable regions can be produced using various techniques known in the art. Human antibodies are described generally in van Dijk and van de Winkel, *Curr Opin Pharmacol* 5, 368-74 (2001) and Lonberg, *Curr Opin Immunol* 20, 450-459 (2008). Human variable regions can form part of and be derived from human monoclonal antibodies made by the hybridoma method (see e.g. *Monoclonal Antibody Production Techniques and Applications*, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, *Nat Biotech* 23, 1117-1125 (2005). Human antibodies and human variable regions may also be generated by isolating Fv clone variable region sequences selected from human-derived phage display libraries (see e.g., Hoogenboom et al. in *Methods in Molecular Biology* 178, 1-37 (O'Brien et al., ed., Human Press, Totowa, NJ, 2001); and McCafferty et al., *Nature* 348, 552-554; Clackson et al., *Nature* 352, 624-628 (1991)). Phage typically display antibody fragments, either as single-chain Fv (scFv) fragments or as Fab fragments.

In certain embodiments, the antigen binding moieties useful in the present invention are engineered to have enhanced binding affinity according to, for example, the methods disclosed in U.S. Pat. Appl. Publ. No. 2004/0132066, the entire contents of which are hereby incorporated by reference. The ability of the T cell activating bispecific antigen binding molecule of the invention to bind to a specific antigenic determinant can be measured either through an enzyme-linked immunosorbent assay (ELISA) or other techniques familiar to one of skill in the art, e.g. surface plasmon resonance technique (analyzed on a BIA-CORE T100 system) (Liljeblad, et al., *Glyco J* 17, 323-329 (2000)), and traditional binding assays (Heeley, *Endocr Res* 28, 217-229 (2002)). Competition assays may be used to identify an antibody, antibody fragment, antigen binding domain or variable domain that competes with a reference antibody for binding to a particular antigen, e.g. an antibody that competes with the V9 antibody for binding to CD3. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols," in Methods in Molecular Biology vol. 66 (Humana Press, Totowa, NJ). In an exemplary competition assay, immobilized antigen (e.g. CD3) is incubated in a solution comprising a first labeled antibody that binds to the antigen (e.g. V9 antibody) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) *Antibodies: A Laboratory Manual* ch. 14 (Cold Spring Harbor Laboratory, Cold Spring Harbor, NY).

T cell activating bispecific antigen binding molecules prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the T cell activating bispecific antigen binding molecule binds. For example, for affinity chromatography purification of T cell activating bispecific antigen binding molecules of the invention, a matrix with protein A or protein G may be used. Sequential Protein A or G affinity chromatography and size exclusion chromatography can be used to isolate a T cell activating bispecific antigen binding molecule essentially as described in the Examples. The purity of the T cell activating bispecific antigen binding molecule can be determined by any of a variety of well known analytical methods including gel electrophoresis, high pressure liquid chromatography, and the like. For example, the heavy chain fusion proteins expressed as described in the Examples were shown to be intact and properly assembled as demonstrated by reducing SDS-PAGE. Three bands were resolved at approximately Mr 25,000, Mr 50,000 and Mr 75,000, corresponding to the predicted molecular weights of the T cell activating bispecific antigen binding molecule light chain, heavy chain and heavy chain/light chain fusion protein.

Assays

T cell activating bispecific antigen binding molecules provided herein may be identified, screened for, or characterized for their physical/chemical properties and/or biological activities by various assays known in the art.

Affinity Assays

The affinity of the T cell activating bispecific antigen binding molecule for an Fc receptor or a target antigen can be determined in accordance with the methods set forth in the Examples by surface plasmon resonance (SPR), using standard instrumentation such as a BIAcore instrument (GE Healthcare), and receptors or target proteins such as may be obtained by recombinant expression. Alternatively, binding of T cell activating bispecific antigen binding molecules for different receptors or target antigens may be evaluated using cell lines expressing the particular receptor or target antigen, for example by flow cytometry (FACS). A specific illustrative and exemplary embodiment for measuring binding affinity is described in the following and in the Examples below.

According to one embodiment, $K_D$ is measured by surface plasmon resonance using a BIACORE® T100 machine (GE Healthcare) at 25° C.

To analyze the interaction between the Fc-portion and Fc receptors, His-tagged recombinant Fc-receptor is captured by an anti-Penta His antibody (Qiagen) ("Penta His" disclosed as SEQ ID NO: 45) immobilized on CM5 chips and the bispecific constructs are used as analytes. Briefly, carboxymethylated dextran biosensor chips (CM5, GE Healthcare) are activated with N-ethyl-N'-(3-dimethylaminopropyl)-carbodiimide hydrochloride (EDC) and N-hydroxysuccinimide (NHS) according to the supplier's instructions. Anti Penta-His antibody ("Penta His" disclosed as SEQ ID NO: 45) is diluted with 10 mM sodium acetate, pH 5.0, to 40 µg/ml before injection at a flow rate of 5 µl/min to achieve approximately 6500 response units (RU) of coupled protein. Following the injection of the ligand, 1 M ethanolamine is injected to block unreacted groups. Subsequently the Fc-receptor is captured for 60 s at 4 or 10 nM. For kinetic measurements, four-fold serial dilutions of the bispecific construct (range between 500 nM and 4000 nM) are injected in HBS-EP (GE Healthcare, 10 mM HEPES, 150 mM NaCl, 3 mM EDTA, 0.05% Surfactant P20, pH 7.4) at 25° C. at a flow rate of 30 µl/min for 120 s.

To determine the affinity to the target antigen, bispecific constructs are captured by an anti human Fab specific antibody (GE Healthcare) that is immobilized on an activated CM5-sensor chip surface as described for the anti Penta-His antibody ("Penta His" disclosed as SEQ ID NO: 45). The final amount of coupled protein is approximately 12000 RU. The bispecific constructs are captured for 90 s at 300 nM. The target antigens are passed through the flow cells for 180 s at a concentration range from 250 to 1000 nM with a flowrate of 30 µl/min. The dissociation is monitored for 180 s.

Bulk refractive index differences are corrected for by subtracting the response obtained on reference flow cell. The steady state response was used to derive the dissociation constant $K_D$ by non-linear curve fitting of the Langmuir binding isotherm. Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999).

Activity Assays

Biological activity of the T cell activating bispecific antigen binding molecules of the invention can be measured by various assays as described in the Examples. Biological activities may for example include the induction of proliferation of T cells, the induction of signaling in T cells, the induction of expression of activation markers in T cells, the induction of cytokine secretion by T cells, the induction of lysis of target cells such as tumor cells, and the induction of tumor regression and/or the improvement of survival.

Compositions, Formulations, and Routes of Administration

In a further aspect, the invention provides pharmaceutical compositions comprising any of the T cell activating bispecific antigen binding molecules provided herein, e.g., for use in any of the below therapeutic methods. In one embodiment, a pharmaceutical composition comprises any of the T cell activating bispecific antigen binding molecules provided herein and a pharmaceutically acceptable carrier. In another embodiment, a pharmaceutical composition comprises any of the T cell activating bispecific antigen binding molecules provided herein and at least one additional therapeutic agent, e.g., as described below.

Further provided is a method of producing a T cell activating bispecific antigen binding molecule of the invention in a form suitable for administration in vivo, the method comprising (a) obtaining a T cell activating bispecific antigen binding molecule according to the invention, and (b) formulating the T cell activating bispecific antigen binding molecule with at least one pharmaceutically acceptable carrier, whereby a preparation of T cell activating bispecific antigen binding molecule is formulated for administration in vivo.

Pharmaceutical compositions of the present invention comprise a therapeutically effective amount of one or more T cell activating bispecific antigen binding molecule dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one T cell activating bispecific antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it need to be sterile for such routes of administration as injection. T cell activating bispecific antigen binding molecules of the present invention (and any additional therapeutic agent) can be administered intravenously, intradermally, intraarterially, intraperitoneally, intralesionally, intracranially, intraarticularly, intraprostatically, intrasplenically, intrarenally, intrapleurally, intratracheally, intranasally, intravitreally, intravaginally, intrarectally, intratumorally, intramuscularly, intraperitoneally, subcutaneously, subconjunctivally, intravesicularlly, mucosally, intrapericardially, intraumbilically, intraocularally, orally, topically, locally, by inhalation (e.g. aerosol inhalation), injection, infusion, continuous infusion, localized perfusion bathing target cells directly, via a catheter, via a lavage, in cremes, in lipid compositions (e.g. liposomes), or by other method or any combination of the forgoing as would be known to one of ordinary skill in the art (see, for example, Remington's Pharmaceutical Sciences, 18th Ed. Mack Printing Company, 1990, incorporated herein by reference). Parenteral administration, in particular intravenous injection, is most commonly used for administering polypeptide molecules such as the T cell activating bispecific antigen binding molecules of the invention.

Parenteral compositions include those designed for administration by injection, e.g. subcutaneous, intradermal, intralesional, intravenous, intraarterial intramuscular, intrathecal or intraperitoneal injection. For injection, the T cell activating bispecific antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the T cell activating bispecific antigen binding molecules may be in powder form for constitution with a suitable vehicle, e.g., sterile pyrogen-free water, before use. Sterile injectable solutions are prepared by incorporating the T cell activating bispecific antigen binding molecules of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

In addition to the compositions described previously, the T cell activating bispecific antigen binding molecules may also be formulated as a depot preparation. Such long acting formulations may be administered by implantation (for example subcutaneously or intramuscularly) or by intramuscular injection. Thus, for example, the T cell activating bispecific antigen binding molecules may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the T cell activating bispecific antigen binding molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The T cell activating bispecific antigen binding molecules may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

Therapeutic Methods and Compositions

Any of the T cell activating bispecific antigen binding molecules provided herein may be used in therapeutic methods. T cell activating bispecific antigen binding molecules of the invention can be used as immunotherapeutic agents, for example in the treatment of cancers.

For use in therapeutic methods, T cell activating bispecific antigen binding molecules of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, T cell activating bispecific antigen binding molecules of the invention for use as a medicament are provided. In further aspects, T cell activating bispecific antigen binding molecules of the invention for use in treating a disease are provided. In certain embodiments, T cell activating bispecific antigen binding molecules of the invention for use in a method of treatment are provided. In one embodiment, the invention provides a T cell activating bispecific antigen binding molecule as described herein for use in the treatment of a disease in an individual in need thereof. In certain embodiments, the invention provides a T cell activating bispecific antigen binding molecule for use in a method of treating an individual having a disease comprising administering to the individual a therapeutically effective amount of the T cell activating bispecific antigen binding molecule. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. In further embodiments, the invention provides a T cell activating bispecific antigen binding molecule as described herein for use in inducing lysis of a target cell, particularly a tumor cell. In certain embodiments, the invention provides a T cell activating bispecific antigen binding molecule for use in a method of inducing lysis of a target cell, particularly a tumor cell, in an individual comprising administering to the individual an effective amount of the T cell activating bispecific antigen binding molecule to induce lysis of a target cell. An "individual" according to any of the above embodiments is a mammal, preferably a human.

In a further aspect, the invention provides for the use of a T cell activating bispecific antigen binding molecule of the invention in the manufacture or preparation of a medicament. In one embodiment the medicament is for the treatment of a disease in an individual in need thereof. In a further embodiment, the medicament is for use in a method of treating a disease comprising administering to an individual having the disease a therapeutically effective amount of the medicament. In certain embodiments the disease to be treated is a proliferative disorder. In a particular embodiment the disease is cancer. In one embodiment, the method further comprises administering to the individual a therapeutically effective amount of at least one additional therapeutic agent, e.g., an anti-cancer agent if the disease to be treated is cancer. In a further embodiment, the medicament is for inducing lysis of a target cell, particularly a tumor cell. In still a further embodiment, the medicament is for use in a method of inducing lysis of a target cell, particularly a tumor cell, in an individual comprising administering to the individual an effective amount of the medicament to induce lysis of a target cell. An "individual" according to any of the above embodiments may be a mammal, preferably a human.

In a further aspect, the invention provides a method for treating a disease. In one embodiment, the method comprises administering to an individual having such disease a therapeutically effective amount of a T cell activating bispecific antigen binding molecule of the invention. In one embodiment a composition is administered to said individual, comprising the T cell activating bispecific antigen binding molecule of the invention in a pharmaceutically acceptable form. In certain embodiments the disease to be treated is a proliferative disorder. In a particular embodiment the disease is cancer. In certain embodiments the method further comprises administering to the individual a therapeutically effective amount of at least one additional therapeutic agent, e.g., an anti-cancer agent if the disease to be treated is cancer. An "individual" according to any of the above embodiments may be a mammal, preferably a human.

In a further aspect, the invention provides a method for inducing lysis of a target cell, particularly a tumor cell. In one embodiment the method comprises contacting a target cell with a T cell activating bispecific antigen binding molecule of the invention in the presence of a T cell, particularly a cytotoxic T cell. In a further aspect, a method for inducing lysis of a target cell, particularly a tumor cell, in an individual is provided. In one such embodiment, the method comprises administering to the individual an effective amount of a T cell activating bispecific antigen binding molecule to induce lysis of a target cell. In one embodiment, an "individual" is a human.

In certain embodiments the disease to be treated is a proliferative disorder, particularly cancer. Non-limiting examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using a T cell activating bispecific antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. A skilled artisan readily recognizes that in many cases the T cell activating bispecific antigen binding molecule may not provide a cure but may only provide partial benefit. In some embodiments, a physiological change having some benefit is also considered therapeutically beneficial. Thus, in some embodiments, an amount of T cell activating bispecific antigen binding molecule that provides a physiological change is considered an "effective amount" or a "therapeutically effective amount". The subject, patient, or individual in need of treatment is typically a mammal, more specifically a human.

In some embodiments, an effective amount of a T cell activating bispecific antigen binding molecule of the invention is administered to a cell. In other embodiments, a therapeutically effective amount of a T cell activating bispecific antigen binding molecule of the invention is administered to an individual for the treatment of disease.

For the prevention or treatment of disease, the appropriate dosage of a T cell activating bispecific antigen binding molecule of the invention (when used alone or in combination with one or more other additional therapeutic agents) will depend on the type of disease to be treated, the route of administration, the body weight of the patient, the type of T cell activating bispecific antigen binding molecule, the severity and course of the disease, whether the T cell activating bispecific antigen binding molecule is administered for preventive or therapeutic purposes, previous or concurrent therapeutic interventions, the patient's clinical history and response to the T cell activating bispecific antigen binding molecule, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The T cell activating bispecific antigen binding molecule is suitably administered to the patient at one time or over a series of treatments. Depending on the type and severity of the disease, about 1 μg/kg to 15 mg/kg (e.g. 0.1 mg/kg-10 mg/kg) of T cell activating bispecific antigen binding molecule can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the T cell activating bispecific antigen binding molecule would be in the range from about 0.005 mg/kg to about 10 mg/kg. In other non-limiting examples, a dose may also comprise from about 1 microgram/kg body weight, about 5 microgram/kg body weight, about 10 microgram/kg body weight, about 50 microgram/kg body weight, about 100 microgram/kg body weight, about 200 microgram/kg body weight, about 350 microgram/kg body weight, about 500 microgram/kg body weight, about 1 milligram/kg body weight, about 5 milligram/kg body weight, about 10 milligram/kg body weight, about 50 milligram/kg body weight, about 100 milligram/kg body weight, about 200 milligram/kg body weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 microgram/kg body weight to about 500 milligram/kg body weight, etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the T cell activating bispecific antigen binding molecule). An initial higher loading dose, followed by one or more lower doses may be administered. However, other dosage regimens may be useful. The progress of this therapy is easily monitored by conventional techniques and assays.

The T cell activating bispecific antigen binding molecules of the invention will generally be used in an amount effective to achieve the intended purpose. For use to treat or prevent a disease condition, the T cell activating bispecific antigen binding molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the T cell activating bispecific antigen binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the T cell activating bispecific antigen binding molecules may not be related to plasma concentration. One having skill in the art will be able to optimize therapeutically effective local dosages without undue experimentation.

A therapeutically effective dose of the T cell activating bispecific antigen binding molecules described herein will generally provide therapeutic benefit without causing substantial toxicity. Toxicity and therapeutic efficacy of a T cell activating bispecific antigen binding molecule can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. T cell activating bispecific antigen binding molecules that exhibit large therapeutic indices are preferred. In one embodiment, the T cell activating bispecific antigen binding molecule according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The *Pharmacological Basis of Therapeutics*, Ch. 1, p. 1, incorporated herein by reference in its entirety).

The attending physician for patients treated with T cell activating bispecific antigen binding molecules of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The T cell activating bispecific antigen binding molecules of the invention may be administered in combination with one or more other agents in therapy. For instance, a T cell activating bispecific antigen binding molecule of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an immunomodulatory agent, a cytostatic agent, an inhibitor of cell adhesion, a cytotoxic agent, an activator of cell apoptosis, or an agent that increases the sensitivity of cells to apoptotic inducers. In a particular embodiment, the additional therapeutic agent is an anti-cancer agent, for example a microtubule disruptor, an antimetabolite, a topoisomerase inhibitor, a DNA intercalator, an alkylating agent, a hormonal therapy, a kinase inhibitor, a receptor antagonist, an activator of tumor cell apoptosis, or an antiangiogenic agent.

Such other agents are suitably present in combination in amounts that are effective for the purpose intended. The effective amount of such other agents depends on the amount of T cell activating bispecific antigen binding molecule used, the type of disorder or treatment, and other factors discussed above. The T cell activating bispecific antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the T cell activating bispecific antigen binding molecule of the invention can occur prior to, simultaneously, and/or following, administration of the additional therapeutic agent and/or adjuvant. T cell activating bispecific antigen binding molecules of the invention can also be used in combination with radiation therapy.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a T cell activating bispecific antigen binding molecule of the invention. The label or package insert indicates that the composition is used for treating the condition of choice. Moreover, the article of manufacture may comprise (a) a first container with a composition contained therein, wherein the composition comprises a T cell activating bispecific antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Screening Methods

Described herein is the advantageous efficiency of using a single light chain or highly homologous variants thereof for methods of identifying appropriate heavy chain variable regions to construct a T cell activating bispecific antigen binding molecules. To construct these binders, the light chain not only has to be able to pair with various heavy chains to produce binding moieties of different specificity but also retain the ability to form a binding moiety that can activate the T cells to which it binds.

The light chain described herein can be used as a common light chain (CLC) for identifying appropriate heavy chain variable regions, e.g., by screening a library of heavy chain variable regions. This allows for maintaining the previously identified and validated CD3 binder such that merely a new target antigen binder for the target antigen binding moiety of a T cell activating bispecific antigen binding molecules has to be identified.

Accordingly, in another aspect, the invention provides for a method for identifying a variable heavy chain for use in a bispecific antigen binding molecule specific for a T cell activation antigen and a target cell antigen, comprising the step of screening a combinatorial library comprising variable heavy chains with a light chain comprising the amino acid sequence of SEQ ID NO: 32, SEQ ID NO: 33 and SEQ ID NO: 34. In one embodiment, the light chain comprises the amino acid sequence of SEQ ID NO: 31. In one embodiment, the light chain comprises the amino acid sequence of SEQ ID NO: 35. This method can be used to develop stable, functional, high affinity binders to improve production of T cell activating bispecific antigen binding molecules with, e.g., CD3 specificity and a target antigen specificity, where the target antigens are unrelated, e.g., FolR1, MUC1, and BCMA.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

EXAMPLES

General Methods
Recombinant DNA Techniques

Standard methods were used to manipulate DNA as described in Sambrook et al., *Molecular cloning: A laboratory manual*; Cold Spring Harbor Laboratory Press, Cold Spring Harbor, New York, 1989. The molecular biological reagents were used according to the manufacturers' instructions. General information regarding the nucleotide sequences of human immunoglobulins light and heavy chains is given in: Kabat, E. A. et al., (1991) *Sequences of Proteins of Immunological Interest*, 5th ed., NIH Publication No. 91-3242.

DNA Sequencing

DNA sequences were determined by standard double strand sequencing at Synergene (Schlieren).

Gene Synthesis

Desired gene segments where required were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Isolation of Primary Human Pan T Cells from PBMCs

Peripheral blood mononuclear cells (PBMCs) were prepared by Histopaque density centrifugation from enriched lymphocyte preparations (buffy coats) obtained from local blood banks or from fresh blood from healthy human donors. Briefly, blood was diluted with sterile PBS and carefully layered over a Histopaque gradient (Sigma, H8889). After centrifugation for 30 minutes at 450×g at room temperature (brake switched off), part of the plasma above the PBMC containing interphase was discarded. The PBMCs were transferred into new 50 ml Falcon tubes and tubes were filled up with PBS to a total volume of 50 ml. The mixture was centrifuged at room temperature for 10 minutes at 400×g (brake switched on). The supernatant was discarded and the PBMC pellet washed twice with sterile PBS (centrifugation steps at 4° C. for 10 minutes at 350×g). The resulting PBMC population was counted automatically (Vi-Cell) and stored in RPM11640 medium, containing 10% FCS and 1% L-alanyl-L-glutamine (Biochrom, K0302) at 37° C., 5% $CO_2$ in the incubator until assay start.

T cell enrichment from PBMCs was performed using the Pan T Cell Isolation Kit II (Miltenyi Biotec #130-091-156), according to the manufacturer's instructions. Briefly, the cell pellets were diluted in 40 µl cold buffer per 10 million cells (PBS with 0.5% BSA, 2 mM EDTA, sterile filtered) and incubated with 10 µl Biotin-Antibody Cocktail per 10 million cells for 10 min at 4° C. 30 µl cold buffer and 20 µl Anti-Biotin magnetic beads per 10 million cells were added, and the mixture incubated for another 15 min at 4° C. Cells were washed by adding 10-20× the current volume and a subsequent centrifugation step at 300×g for 10 min. Up to 100 million cells were resuspended in 500 µl buffer. Magnetic separation of unlabeled human pan T cells was performed using LS columns (Miltenyi Biotec #130-042-401) according to the manufacturer's instructions. The resulting T cell population was counted automatically (ViCell) and stored in AIM-V medium at 37° C., 5% $CO_2$ in the incubator until assay start (not longer than 24 h).

Isolation of Primary Human Naive T Cells from PBMCs

Peripheral blood mononuclear cells (PBMCs) were prepared by Histopaque density centrifugation from enriched lymphocyte preparations (buffy coats) obtained from local blood banks or from fresh blood from healthy human donors. T-cell enrichment from PBMCs was performed using the Naive $CD8^+$ T cell isolation Kit from Miltenyi Biotec (#130-093-244), according to the manufacturer's instructions, but skipping the last isolation step of CD8+ T cells (also see description for the isolation of primary human pan T cells).

Isolation of Murine Pan T Cells from Splenocytes

Spleens were isolated from C57BL/6 mice, transferred into a GentleMACS C-tube (Miltenyi Biotech #130-093-237) containing MACS buffer (PBS+0.5% BSA+2 mM EDTA) and dissociated with the GentleMACS Dissociator to obtain single-cell suspensions according to the manufacturer's instructions. The cell suspension was passed through a pre-separation filter to remove remaining undissociated tissue particles. After centrifugation at 400×g for 4 min at 4° C., ACK Lysis Buffer was added to lyse red blood cells (incubation for 5 min at room temperature). The remaining cells were washed with MACS buffer twice, counted and used for the isolation of murine pan T cells. The negative (magnetic) selection was performed using the Pan T Cell Isolation Kit from Miltenyi Biotec (#130-090-861), following the manufacturer's instructions. The resulting T cell population was automatically counted (ViCell) and immediately used for further assays.

Isolation of Primary Cynomolgus PBMCs from Heparinized Blood

Peripheral blood mononuclear cells (PBMCs) were prepared by density centrifugation from fresh blood from healthy cynomolgus donors, as follows: Heparinized blood was diluted 1:3 with sterile PBS, and Lymphoprep medium (Axon Lab #1114545) was diluted to 90% with sterile PBS. Two volumes of the diluted blood were layered over one volume of the diluted density gradient and the PBMC fraction was separated by centrifugation for 30 min at 520×g, without brake, at room temperature. The PBMC band was transferred into a fresh 50 ml Falcon tube and washed with sterile PBS by centrifugation for 10 min at 400×g at 4° C. One low-speed centrifugation was performed to remove the platelets (15 min at 150×g, 4° C.), and the resulting PBMC population was automatically counted (ViCell) and immediately used for further assays.

Exemplary Antigen Generation

The antigen is expressed in two different versions. For a non-Fc containing construct the extracellular domain is fused to an avi-His tag attached to its C-terminus. For an Fc containing antigen an Fc fusion using the knob-into-hole technology to the N-terminus of a heterodimeric Fc part is applied (Merchant et al.) to have only one molecule of the protein of interest per Fc dimer. This is done to avoid the formation of any artificial dimeric structures of the protein of interest. The avi-tag is here attached to the C-terminus of the Fc. Those proteins can easily be transiently expressed in mammalian cells like HEK or CHO, purified via ProteinA chromatography, biotinylted and can be attached to streptavidin beads for phage selections via the biotinylated avi-tag according to standard methods.

Affinity Maturation

Affinity maturation of the Fab fragments coming out of a CLC-library has to be limited to the heavy chain only, in order to retain the light chain in an unchanged manner to have the CD3e binding affinity retained. Since our initial library is randomized in the CDR3 of the heavy chain only, we focus for the maturation step on the CDRs 1 and 2. For this we design PCR primers for each framework that will introduce randomization in to CDR1 and CDR2 separately. Each primer is designed to bind to one of the six heavy chain frameworks and can be used in a generic way for each antibody clone coming from that particular phage library. The process of maturation is carried out as described by Knappik, or by Steidl (Knappik et al., *J. Mol. Biol.* (2000) 296, 57-86). S. Steidl et al.; *Molecular Immunology* 46 (2008) 135-144).

Phage panning is carried out as described above, with the difference that the concentrations of the soluble antigen is used at $2\times10^{-8}$M and is decreased to a final concentration to $2\times10^{-10}$M.

Cloning, Production, Purification and Biochemical Characterization of CLC TCB

The resulting variable region of heavy and light chain DNA sequences are subcloned in frame with either the constant heavy chain or the constant light chain pre-inserted into the respective recipient mammalian expression vector. The antibody expression is driven by an MPSV promoter and carries a synthetic polyA signal sequence at the 3' end of the CDS. In addition each vector contains an EBV OriP sequence for transient expression in HEK293-EBNA cells. As antibody isotypes IgG1 P329G LALA or IgG4 SPLE PG are used.

The CLC TCB is produced by co-transfecting HEK293-EBNA cells with the mammalian expression vectors using polyethylenimine. The cells are transfected with the corresponding expression vectors in a 1:1:3 ratio ("vector heavy chain Fc(hole)":"vector heavy chain Fc(knob)-FabCrossfab"):"vector common light chain".

For transfection HEK293 EBNA cells are cultivated in suspension serum free in CD CHO culture medium. For the production in 500 ml shake flask 400 million HEK293 EBNA cells are seeded 24 hours before transfection. For transfection cells are centrifuged for 5 min by 210×g, supernatant is replaced by pre-warmed 20 ml CD CHO medium. Expression vectors are mixed in 20 ml CD CHO medium to a final amount of 200 g DNA. After addition of 540 µl PEI solution is vortexed for 15 s and subsequently incubated for 10 min at room temperature. Afterwards cells are mixed with the DNA/PEI solution, transferred to a 500 ml shake flask and incubated for 3 hours by 37° C. in an incubator with a 5% CO2 atmosphere. After incubation time 160 ml F17 medium is added and cell are cultivated for 24 hours. One day after transfection 1 mM valporic acid and 7% Feed 1 is added. After 7 days cultivation supernatant is collected for purification by centrifugation for 15 min at 210×g, the solution is sterile filtered (0.22 µm filter) and sodium azide in a final concentration of 0.01% w/v is added, and kept at 4° C.

The secreted protein is purified from cell culture supernatants by affinity chromatography using ProteinA. Supernatant is loaded on a HiTrap ProteinA HP column (CV=5 mL, GE Healthcare) equilibrated with 40 ml 20 mM sodium phosphate, 20 mM sodium citrate, 0.5 M sodium chloride, pH 7.5. Unbound protein is removed by washing with at least 10 column volume 20 mM sodium phosphate, 20 mM sodium citrate, 0.5 M sodium chloride, pH 7.5. Target protein is eluted during a gradient over 20 column volume from 20 mM sodium citrate, 0.5 M sodium chloride, pH 7.5 to 20 mM sodium citrate, 0.5 M sodium chloride, pH 2.5. Protein solution is neutralized by adding 1/10 of 0.5 M sodium phosphate, pH 8. Target protein is concentrated and filtrated prior loading on a HiLoad Superdex 200 column (GE Healthcare) equilibrated with 20 mM Histidine, 140 mM sodium chloride solution of pH 6.0.

The protein concentration of purified protein samples is determined by measuring the optical density (OD) at 280 nm, using the molar extinction coefficient calculated on the basis of the amino acid sequence.

Purity and molecular weight of molecules are analyzed by CE-SDS analyses in the presence and absence of a reducing agent. The Caliper LabChip GXII system (Caliper lifescience) is used according to the manufacturer's instruction. 2 ug sample is used for analyses.

The aggregate content of antibody samples is analyzed using a TSKgel G3000 SW XL analytical size-exclusion column (Tosoh) in 25 mM K2HPO4, 125 mM NaCl, 200 mM L-Arginine Monohydrocloride, 0.02% (w/v) NaN3, pH 6.7 running buffer at 25° C.

CLC TCB Characterization in Cell-Based Assays

Binding of CLC TCB to ECD Tumor Antigen- and CD3-Expressing Cells

The binding of CLC TCB is tested using tumor cells expressing the antigen X of interest and a CD3e-expressing immortalized T lymphocyte line (Jurkat). Briefly, cells are harvested, counted, checked for viability and resuspended at 2×106 cells/ml in FACS buffer (100 µl PBS 0.1% BSA). 100 µl of cell suspension (containing 0.2×106 cells) is incubated in round-bottom 96-well plate for 30 min at 4° C. with increasing concentrations of the CLC TCB (3 pM-200 nM), washed twice with cold PBS 0.1% BSA, re-incubated for further 30 min at 4° C. with the PE-conjugated AffiniPure F(ab')2 Fragment goat anti-human IgG Fcg Fragment Specific secondary antibody (Jackson Immuno Research Lab PE #109-116-170), washed twice with cold PBS 0.1% BSA and immediately analyzed by FACS using a FACS Cantoll (Software FACS Diva) by gating live, DAPI-negative, cells. Binding curves are obtained using GraphPadPrism5.

Example 1

Purification of Biotinylated Folate Receptor-Fc Fusions

To generate new antibodies against human FolR1 the following antigens and screening tools were generated as monovalent Fc fusion proteins (the extracellular domain of the antigen linked to the hinge region of Fc-knob which is co-expressed with an Fc-hole molecule). The antigen genes were synthesized (Geneart, Regensburg, Germany) based on sequences obtained from GenBank or SwissProt and inserted into expression vectors to generate fusion proteins with Fc-knob with a C-terminal Avi-tag for in vivo or in vitro biotinylation. In vivo biotinylation was achieved by co-expression of the bacterial birA gene encoding a bacterial biotin ligase during production. Expression of all genes was under control of a chimeric MPSV promoter on a plasmid containing an oriP element for stable maintenance of the plasmids in EBNA containing cell lines.

For preparation of the biotinylated monomeric antigen/Fc fusion molecules, exponentially growing suspension HEK293 EBNA cells were co-transfected with three vectors encoding the two components of fusion protein (knob and hole chains) as well as BirA, an enzyme necessary for the biotinylation reaction. The corresponding vectors were used at a 9.5:9.5:1 ratio ("antigen ECD-Fc knob-avi tag":"Fc hole":"BirA").

For protein production in 500 ml shake flasks, 400 million HEK293 EBNA cells were seeded 24 hours before transfection. For transfection cells were centrifuged for 5 minutes at 210 g, and supernatant was replaced by pre-warmed CD CHO medium. Expression vectors were resuspended in 20 mL of CD CHO medium containing 200 µg of vector DNA. After addition of 540 µL of polyethylenimine (PEI), the solution was mixed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere. After the incubation, 160 mL of F17 medium was added and cells were cultured for 24 hours. One day after transfection, 1 mM valproic acid and 7% Feed 1 (Lonza) were added to the culture. The production medium was also supplemented with 100 µM biotin. After 7 days of culturing, the cell supernatant was collected by spinning down cells for 15 min at 210 g. The solution was sterile filtered (0.22 µm filter), supplemented with sodium azide to a final concentration of 0.01% (w/v), and kept at 4° C.

Secreted proteins were purified from cell culture supernatants by affinity chromatography using Protein A, followed by size exclusion chromatography. For affinity chromatography, the supernatant was loaded on a HiTrap ProteinA HP column (CV=5 mL, GE Healthcare) equilibrated with 40 mL 20 mM sodium phosphate, 20 mM sodium citrate pH 7.5. Unbound protein was removed by washing with at least 10 column volumes of 20 mM sodium phosphate, 20 mM sodium citrate pH 7.5. The bound protein was eluted using a linear pH-gradient created over 20 column volumes of 20 mM sodium citrate, 100 mM sodium chloride, 100 mM glycine, pH 3.0. The column was then washed with 10 column volumes of 20 mM sodium citrate, 100 mM sodium chloride, 100 mM glycine, pH 3.0.

pH of collected fractions was adjusted by adding 1/10 (v/v) of 0.5 M sodium phosphate, pH 8.0. The protein was concentrated and filtered prior to loading on a HiLoad Superdex 200 column (GE Healthcare) equilibrated with 20 mM histidine, 140 mM sodium chloride, pH 6.0.

The protein concentration was determined by measuring the optical density (OD) at 280 nm, using the molar extinction coefficient calculated on the basis of the amino acid sequence. Purity and molecular weight of the FolR1-Fc-fusion was analyzed by SDS capillary electrophoresis in the presence and absence of a reducing agent following the manufacturer instructions (instrument Caliper LabChipGX, Perkin Elmer). The aggregate content of samples was analyzed using a TSKgel G3000 SW XL analytical size-exclusion column (Tosoh) equilibrated in 25 mM K2HPO4, 125 mM NaCl, 200 mM L-arginine monohydrochloride, 0.02% (w/v) NaN3, pH 6.7 running buffer at 25° C.

Purified antigen-Fc-fusion proteins were analyzed by surface plasmon resonance assays using commercially available antibodies to confirm correct and natural conformation of the antigens (data not shown).

TABLE 1

Antigens produced for isolation, selection and counter selection of human FolR1 antibodies

| Antigen | ECD (aa) | Accession number | Sequence | Seq ID No |
|---|---|---|---|---|
| human FolR1 | 25-234 | P15328 | RIAWARTELLNVCMNAKHHKEKPGPEDKLHEQ CRPWRKNACCSTNTSQEAHKDVSYLYRFNWNH CGEMAPACKRHFIQDTCLYECSPNLGPWIQQV DQSWRKERVLNVPLCKEDCEQVWVEDCRTSYT | 227 |

TABLE 1-continued

Antigens produced for isolation, selection and counter selection of human FcIR1 antibodies

| Antigen | ECD (aa) | Accession number | Sequence | Seq ID No |
|---|---|---|---|---|
| | | | CKSNWHKGWNVVTSGFNKCAVGAACQPFHFYF PTPTVLCNEIWTHSYKVSNYSRGSGRCIQMWF DPAQGNPNEEVARFYAAAM | |
| human FcIR2 | 17-230 | P14207 | TMCSAQDRTDLLNVCMDAKHHKTKPGPEDKLH DQCSPWKKNACCTASTSQELHKDTSRLYNFNW DHCGKMEPACKRHFIQDTCLYECSPNLGPWIQ QVNQSWRKERFLDVPLCKEDCQRVWVEDCHTS HTCKSNWHRGWDVVTSGVNKCPAGALCRTFES YFPTPAALCEGLWSHSYKVSNYSRGSGRCIQM WFDSAQGNPNEEVARFYAAAMHVN | 228 |
| human FcIR3 | 24-243 | P41439 | SARARTDLLNVCMNAKHHKTQPSPEDELYGQC SPWKKNACCTASTSQELHKDTSRLYNFNWDHC GKMEPTCKRHFIQDSCLYECSPNLGPWIRQVN QSWRKERILNVPLCKEDCERVWVEDCRTSYTC KSNWHKGWNVVTSGINECPAGALCSTFESYFP TPAALCEGLWSHSFKVSNYSRGSGRCIQMWFD SAQGNPNEEVAKFYAAAMNAGAPSRGIIDS | 229 |
| murine FcIR1 | 25-232 | P35846 | TRARTELLNVCMDAKHHKEKPGPEDNLHDQCS PWKTNSCCSTNTSQEAHKDISYLYRFNWNHCG TMTSECKRHFIQDTCLYECSPNLGPWIQQVDQ SWRKERILDVPLCKEDCQQVWVEDCQSSFTCK SNWHKGWNWSSGHNECPVGASCHPFTFYFPTS AALCEEIWSHSYKLSNYSRGSGRCIQMWFDPA QGNPNEEVARFYAEAMS | 230 |
| cynomolgus FcIR1 | 25-234 | G7PR14 | EAQTRTARARTELLNVCMNAKHHKEKPGPEDK LHEQCRPWKKNACCSTNTSQEAHKDVSYLYRF NWNHCGEMAPACKRHFIQDTCLYECSPNLGPW IQQVDQSWRKERVLNVPLCKEDCERVWVEDCR TSYCKSNWHKGWNWTSGFNKCPVGAACQPFHF YFPTPTVLCNEIWTYSYKVSNYSRGSGRCIQM WFDPAQGNPNEEVARFYAAAMS | 231 |

TABLE 2

Summary of the yield and final monomer content of the FcIR- Fc- fusions.

| Antigen | Monomer [%] (SEC) | Yield |
|---|---|---|
| huFcIR1 | 100 | 30 mg/L |
| cyFcIR1 | 100 | 32 mg/L |
| muFcIR1 | 100 | 31 mg/L |
| huFcIR2 | 100 | 16 mg/L |
| huFcIR3 | 95 | 38 mg/L |

Example 2

Generation of Common Light Chain with CD3ε Specificity

The T cell activating bispecific molecules described herein comprise at least one CD3 binding moiety. This moiety can be generated by immunizing laboratory animals, screening phage library or using known anti-CD3 antibodies. The common light chain with CD3ε specificity was generated by humanizing the light chain of a murine parental anti-CD3ε antibody (CH2527). For humanization of an antibody of non-human origin, the CDR residues from the non-human antibody (donor) have to be transplanted onto the framework of a human (acceptor) antibody. Generally, acceptor framework sequences are selected by aligning the sequence of the donor to a collection of potential acceptor sequences and choosing one that has either reasonable homology to the donor, or shows similar amino acids at some positions critical for structure and activity. In the present case, the search for the antibody acceptor framework was performed by aligning the mouse VL-domain sequence of the parental antibody to a collection of human germline sequences and choosing the human sequence that showed high sequence identity. Surprisingly, a good match in terms of framework sequence homology was found in a rather infrequent human light chain belonging to the V-domain family 7 of the lambda type, more precisely, hVL_7_46 (IMGT nomenclature, GenBank Acc No. Z73674). This infrequent human light chain was subsequently chosen as acceptor framework for humanization of the light chain of CH2527. The three complementarity determining regions (CDRs) of the mouse light chain variable domain were grafted onto this acceptor framework. Since the framework 4 region is not part of the variable region of the germline V-gene, the alignment for this region (J-element) was done individually. Hence the IGLJ3-02 sequence was chosen for humanization of this light chain.

Thirteen humanized variants were generated (CH2527-VL7_46-1 to VL7_46-10, VL7_46-12 to VL7_46-14). These differ in framework residues (and combinations thereof) that were back-mutated to the murine V-domain sequence or in CDR-residues (Kabat definition) that could be kept identical to the human germline sequence. The following framework residues outside the CDRs were back-mutated to the murine residues in the final humanized VL-domain variant VL7_46-13 (murine residues listed): V36, E38, F44, G46, G49, and G57, respectively. The human J-element IGLJ3-02 was 100% identical to the J-element of the murine parental antibody.

Example 3

SPR Assessment of Humanized Variants with CD3ε Specificity

Humanized VL variants were assessed as chimera in a 2+1 classical format (FIG. 1D), i.e. humanized light chain V-domains were paired with murine heavy chain V-domains. SPR assessment was carried out on a ProteOn XPR36 instrument (Bio-Rad). More precisely, the variants were captured directly from the culture supernatant on an anti-Fab derivatized GLM sensorchip (Goat Anti-Human IgG, F(ab')2 Fragment Specific, Jackson ImmunoResearch) in vertical orientation. The following analytes were subsequently injected horizontally as single concentrations to assess binding to human and cynomolgus CD3ε: 3 μM hu CD3ε(-1-26)-Fc (knob)-avi (ID807) and 2.5 μM cy CD3ε-(-1-26)-Fc(knob)-Avi-Fc(hole) (ID873), respectively. Binding responses were qualitatively compared to binding of the murine control construct and graded+(comparable binding observed), +/– (reduced binding observed) and –(no binding observed). The capture antibody was regenerated after each cycle of ligand capture and analyte binding and the murine construct was re-injected at the end of the study to confirm the activity of the capture surface. The results are summarized in Table 3.

TABLE 3

Qualitative binding assessment based on SPR for the humanized light chain variants combined with the murine heavy chain of CH2527. Only the humanized light chain variant that was finally chosen, CH2527-VL7_46-13, highlighted in bold letters, exhibited comparable binding to human and cynomolgus CD3ε.

| Humanized VL variant | Binding to $CD3_\varepsilon$ |
|---|---|
| Murine CH2527-VL | + |
| CH2527-VL7 46-1 | – |
| CH2527-VL7 46-2 | – |
| CH2527-VL7 46-3 | – |
| CH2527-VL7 46-4 | – |
| CH2527-VL7 46-5 | – |
| CH2527-VL7 46-6 | – |
| CH2527-VL7 46-7 | – |
| CH2527-VL7 46-8 | – |
| CH2527-VL7 46-9 | – |
| CH2527-VL7 46-10 | – |
| CH2527-VL7 46-12 | +/– |
| CH2527-VL7 46-13 | + |
| CH2527-VL7 46-14 | – |

Example 4

Properties of Humanized Common Light Chain with CD3ε Specificity

The light chain V-domain variant that was chosen for the humanized lead molecule is VL7_46-13. The degree of humanness, i.e. the sequence homology of the humanized V-domain to the human germline V-domain sequence was determined. For VL7_46-13, the overall sequence identity with the closest human germline homolog is 65% before humanization and 80% afterwards. Omitting the CDR regions, the sequence identity is 92% to the closest human germline homolog. As can be seen from Table 3, VL7_46-13 is the only humanized VL variant out of a panel of 13 variants that showed comparable binding to the parental murine antibody and also retained its cross-reactivity to cynomolgus CD3ε. This result indicates that it was not trivial to humanize the murine VL-domain without losing binding affinity to CD3ε which required several back-mutations to murine framework residues (in particular G46) while retaining G24 in CDR1. In addition, this result shows that the VL-domain plays a crucial role in target recognition. Importantly, the humanized VL-domain VL7_46-13 based on an infrequent human germline belonging to the V-domain family 7 of the lambda type and retaining affinity and specificity for CD3ε, is also suitable to be used as a common light chain in phage-displayed antibody libraries of the Fab-format and enables successful selection for novel specificities which greatly facilitates the generation and production of bispecific molecules binding to CD3ε and e.g. a tumor target and sharing the same 'common' light chain.

Example 5

Generation of a Phage Displayed Antibody Library Using a Human Germ-Line Common Light Chain Derived from HVK1-39

Several approaches to generate bispecific antibodies that resemble full length human IgG utilize modifications in the Fc region that induce heterodimerization of two distinct heavy chains. Such examples include knobs-into-holes (Merchant et al., *Nat Biotechnol.* 1998 July; 16(7):677-81) SEED (Davis et al., *Protein Eng Des Sel.* 2010 April; 23(4):195-202) and electrostatic steering technologies (Gunasekaran et al., *J Biol Chem.* 2010 Jun. 18; 285(25):19637-46). Although these approaches enable effective heterodimerization of two distinct heavy chains, appropriate pairing of cognate light and heavy chains remains a problem. Usage of a common light chain (LC) can solve this issue (Merchant, et al. Nat Biotech 16, 677-681 (1998)).

Here, we describe the generation of an antibody library for the display on a M13 phage. Essentially, we designed a multi framework library for the heavy chain with one constant (or "common") light chain. This library is designed for generating multispecific antibodies without the need to use sophisticated technologies to avoid light chain mispairing.

By using a common light chain the production of these molecules can be facilitated as no mispairing occurs any longer and the isolation of a highly pure bispecific antibody is facilitated. As compared to other formats the use of Fab fragments as building blocks as opposed to e.g. the use of scFv fragments results in higher thermal stability and the lack of scFv aggregation and intermolecular scFv formation.

Library Generation

In the following the generation of an antibody library for the display on M13 phage is described. Essentially, we designed a multi framework library for the heavy chain with one constant (or "common") light chain.

We used these heavy chains in the library (GenBank Accession Numbers in brackets):
IGHV1-46*01 (X92343) (SEQ ID NO:104),
IGHV1-69*06 (L22583), (SEQ ID NO:105)
IGHV3-15*01 (X92216), (SEQ ID NO:106)
IGHV3-23*01 (M99660), (SEQ ID NO:107)
IGHV4-59*01 (AB019438), (SEQ ID NO:108)
IGHV5-51*01 (M99686), (SEQ ID NO:109)

All heavy chains use the IGHJ2 as J-element, except the IGHV1-69*06 which uses IGHJ6 sequence. The design of the randomization included the CDR-H1, CDR-H2, and CDR-H3. For CDR-H1 and CDR-H2 a "soft" randomization strategy was chosen, and the randomization oligonucleotides were such that the codon for the amino acid of the germ-line sequence was present at 50%. All other amino acids, except cysteine, were summing up for the remaining 50%. In CDR-H3, where no germ-line amino acid is present due to the presence of the genetic D-element, oligonucleotides were designed that allow for the usage of randomized inserts between the V-element and the J-element of 4 to 9 amino acids in length. Those oligonucleotides contained in their randomized part e.g. The three amino acids G/Y/S are present to 15% each, those amino acids A/D/T/R/P/L/V/N/W/F/I/E are present to 4.6% each.

Exemplary methods for generation of antibody libraries are described in Hoogenboom et al., *Nucleic Acids Res.* 1991, 19, 4133-413; Lee et., al *J. Mol. Biol.* (2004) 340, 1073-1093.

The light chain is derived from the human sequence hVK1-39, and is used in an unmodified and non-randomized fashion. This will ensure that the same light chain can be used for other projects without additional modifications.

Exemplary Library Selection:

Selections with all affinity maturation libraries are carried out in solution according to the following procedure using a monomeric and biotinylated extracellular domain of a target antigen X.

1. 10^12 phagemid particles of each library are bound to 100 nM biotinylated soluble antigen for 0.5 h in a total volume of 1 ml. 2. Biotinylated antigen is captured and specifically bound phage particles are isolated by addition of ~5×10^7 streptavidin-coated magnetic beads for 10 min. 3. Beads are washed using 5-10×1 ml PBS/Tween20 and 5-10×1 ml PBS. 4. Elution of phage particles is done by addition of 1 ml 100 mM TEA (triethylamine) for 10 min and neutralization by addition of 500 ul 1 M Tris/HCl pH 7.4 and 5. Re-infection of exponentially growing *E. coli* TG1 bacteria, infection with helper phage VCSM13 and subsequent PEG/NaCl precipitation of phagemid particles is applied in subsequent selection rounds. Selections are carried out over 3-5 rounds using either constant or decreasing (from 10^-7M to 2×10^-9M) antigen concentrations. In round 2, capture of antigen/phage complexes is performed using neutravidin plates instead of streptavidin beads. All binding reactions are supplemented either with 100 nM bovine serum albumin, or with non-fat milk powder in order to compete for unwanted clones arising from mere sticky binding of the antibodies to the plastic support.

Selections are being carried out over three or four rounds using decreasing antigen concentrations of the antigen starting from 100 nM and going down to 5 nM in the final selection round. Specific binders are defined as signals ca. 5× higher than background and are identified by ELISA. Specific binders are identified by ELISA as follows: 100 µl of 10 nM biotinylated antigen per well are coated on neutravidin plates. Fab-containing bacterial supernatants are added and binding Fabs are detected via their Flag-tags by using an anti-Flag/HRP secondary antibody. ELISA-positive clones are bacterially expressed as soluble Fab fragments in 96-well format and supernatants are subjected to a kinetic screening experiment by SPR-analysis using ProteOn XPR36 (BioRad). Clones expressing Fabs with the highest affinity constants are identified and the corresponding phagemids are sequenced. For further characterization, the Fab sequences are amplified via PCR from the phagemid and cloned via appropriate restriction sites into human IgG1 expression vectors for mammalian production.

Generation of a Phage Displayed Antibody Library Using a Humanized CD3ε Specific Common Light Chain Here, the generation of an antibody library for the display on M13 phage is described. Essentially, we designed a multi framework library for the heavy chain with one constant (or "common") light chain. This library was designed for the generation of Fc-containing, but FcgR binding inactive T cell bispecific antibodies of IgG1 P329G LALA or IgG4 SPLE PG isotype in which one or two Fab recognize a tumor surface antigen expressed on a tumor cell whereas the remaining Fab arm of the antibody recognizes CD3e on a T cell.

Library Generation

In the following the generation of an antibody library for the display on M13 phage is described. Essentially, we designed a multi framework library for the heavy chain with one constant (or "common") light chain. This library is designed solely for the generation of Fc-containing, but FcgR binding inactive T cell bispecific antibodies of IgG1 P329G LALA or IgG4 SPLE PG isotype.

Diversity was introduced via randomization oligonucleotides only in the CDR3 of the different heavy chains. Methods for generation of antibody libraries are well known in the art and are described in (Hoogenboom et al., Nucleic Acids Res. 1991, 19, 4133-413; or in: Lee et., al J. Mol. Biol. (2004) 340, 1073-1093).

We used these heavy chains in the library:
IGHV1-46*01 (X92343), (SEQ ID NO:104)
IGHV1-69*06 (L22583), (SEQ ID NO:105)
IGHV3-15*01 (X92216), (SEQ ID NO:106)
IGHV3-23*01 (M99660), (SEQ ID NO:107)
IGHV4-59*01 (AB019438), (SEQ ID NO:108)
IGHV5-51*01 (M99686), (SEQ ID NO:109)

We used the light chain derived from the humanized human and Cynomolgus CD3 ε specific antibody CH2527 in the library: (VL7_46-13; SEQ ID NO:112). This light chain was not randomized and used without any further modifications in order to ensure compatibility with different bispecific binders.

All heavy chains use the IGHJ2 as J-element, except the IGHV1-69*06 which uses IGHJ6 sequence. The design of the randomization focused on the CDR-H3 only, and PCR oligonucleotides were designed that allow for the usage of randomized inserts between the V-element and the J-element of 4 to 9 amino acids in length.

Example 6

Selection of Antibody Fragments from Common Light Chain Libraries (Comprising Light Chain with CD3ε Specificity) to FolR1

The antibodies 16A3, 15A1, 18D3, 19E5, 19A4, 15H7, 15B6, 16D5, 15E12, 21D1, 16F12, 21A5, 21G8, 19H3, 20G6, and 20H7 comprising the common light chain VL7_46-13 with CD3ε specificity were obtained by phage display selections against different species (human, cynomolgus and murine) of FolR1. Clones 16A3, 15A1, 18D3, 19E5, 19A4, 15H7, 15B6, 21D1, 16F12, 19H3, 20G6, and 20H7 were selected from a sub-library in which the common light chain was paired with a heavy chain repertoire based on the human germline VH1_46. In this sub-library, CDR3 of VH1_46 has been randomized based on 6 different CDR3 lengths. Clones 16D5, 15E12, 21A5, and 21G8 were selected from a sub-library in which the common light chain was paired with a heavy chain repertoire based on the human germline VH3_15. In this sub-library, CDR3 of VH3_15 has been randomized based on 6 different CDR3 lengths. In order to obtain species cross-reactive (or murine FolR1-reactive) antibodies, the different species of FolR1 were alternated (or kept constant) in different ways over 3 rounds of biopanning: 16A3 and 15A1 (human—cynomolgus—human FolR1); 18D3 (cynomolgus—human—murine FolR1); 19E5 and 19A4 (3 rounds against murine FolR1); 15H7, 15B6, 16D5, 15E12, 21D1, 16F12, 21A5, 21G8 (human—cynomolgus—human FolR1); 19H3, 20G6, and 20H7 (3 rounds against murine FolR1).

Human, murine and cynomolgus FolR1 as antigens for the phage display selections as well as ELISA- and SPR-based screenings were transiently expressed as N-terminal monomeric Fc-fusion in HEK EBNA cells and in vivo site-specifically biotinylated via co-expression of BirA biotin ligase at the avi-tag recognition sequence located at the C-terminus of the Fc portion carrying the receptor chain (Fc knob chain). In order to assess the specificity to FolR1, two related receptors, human FolR2 and FolR3 were generated in the same way.

Selection rounds (biopanning) were performed in solution according to the following pattern:
1. Pre-clearing of ~1012 phagemid particles on maxisorp plates coated with 10 ug/ml of an unrelated human IgG to deplete the libraries of antibodies recognizing the Fc-portion of the antigen.
2. Incubating the non-Fc-binding phagemid particles with 100 nM biotinylated human, cynomolgus, or murine FolR1 for 0.5h in the presence of 100 nM unrelated non-biotinylated Fc knob-into-hole construct for further depletion of Fc-binders in a total volume of 1 ml.
3. Capturing the biotinylated FolR1 and attached specifically binding phage by transfer to 4 wells of a neutravidin pre-coated microtiter plate for 10 min (in rounds 1 & 3).
4. Washing the respective wells using 5×PBS/Tween20 and 5×PBS.
5. Eluting the phage particles by addition of 250 ul 100 mM TEA (triethylamine) per well for 10 min and neutralization by addition of 500 ul 1 M Tris/HCl pH 7.4 to the pooled eluates from 4 wells.
6. Post-clearing of neutralized eluates by incubation on neutravidin pre-coated microtiter plate with 100 nM biotin-captured FolR2 or FolR3 for final removal of Fc- and unspecific binders.
7. Re-infection of log-phase E. coli TG1 cells with the supernatant of eluted phage particles, infection with helperphage VCSM13, incubation on a shaker at 30° C. over night and subsequent PEG/NaCl precipitation of phagemid particles to be used in the next selection round.

Selections were carried out over 3 rounds using constant antigen concentrations of 100 nM. In round 2, in order to avoid enrichment of binders to neutravidin, capture of antigen:phage complexes was performed by addition of $5.4 \times 10^7$ streptavidin-coated magnetic beads. Specific binders were identified by ELISA as follows: 100 ul of 25 nM biotinylated human, cynomolgus, or murine FolR1 and 10 ug/ml of human IgG were coated on neutravidin plates and maxisorp plates, respectively. Fab-containing bacterial supernatants were added and binding Fabs were detected via their Flag-tags using an anti-Flag/HRP secondary antibody. Clones exhibiting signals on human FolR1 and being negative on human IgG were short-listed for further analyses and were also tested in a similar fashion against the remaining two species of FolR1. They were bacterially expressed in a 0.5 liter culture volume, affinity purified and further characterized by SPR-analysis using BioRad's ProteOn XPR36 biosensor.

Affinities ($K_D$) of selected clones were measured by surface plasmon resonance (SPR) using a ProteOn XPR36 instrument (Biorad) at 25° C. with biotinylated human, cynomolgus, and murine FolR1 as well as human FolR2 and FolR3 (negative controls) immobilized on NLC chips by neutravidin capture. Immobilization of antigens (ligand): Recombinant antigens were diluted with PBST (10 mM phosphate, 150 mM sodium chloride pH 7.4, 0.005% Tween 20) to 10 µg/ml, then injected at 30 µl/minute in vertical orientation. Injection of analytes: For 'one-shot kinetics' measurements, injection direction was changed to horizontal orientation, two-fold dilution series of purified Fab (varying concentration ranges) were injected simultaneously along separate channels 1-5, with association times of 200 s, and dissociation times of 600 s. Buffer (PBST) was injected along the sixth channel to provide an "in-line" blank for referencing. Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$. Table 4 lists the equilibrium dissociation constants ($K_D$) of the selected clones specific for FolR1.

TABLE 4

Equilibrium dissociation constants (KD) for anti-FolR1 antibodies (Fab-format) selected by phage display from common light chain sub-libraries comprising VL7_46-13, a humanized light chain specific for CD3ε KD in nM.

| Clone | huFolR1 [nM] | cyFolR1 [nM] | muFolR1 [nm] | huFolR2 [nM] | huFolR3 [nM] |
|---|---|---|---|---|---|
| 16A3 | 21.7 | 18 | very weak | no binding | no binding |
| 15A1 | 30.9 | 17.3 | very weak | no binding | no binding |
| 18D3 | 93.6 | 40.2 | very weak | no binding | no binding |
| 19E5 | 522 | 276 | 19.4 | no binding | no binding |
| 19A4 | 2050 | 4250 | 43.1 | no binding | no binding |
| 15H7 | 13.4 | 72.5 | no binding | no binding | no binding |
| 15B6 | 19.1 | 13.9 | no binding | no binding | no binding |
| 16D5 | 39.5 | 114 | no binding | no binding | no binding |
| 15E12 | 55.7 | 137 | no binding | no binding | no binding |
| 21D1 | 62.6 | 32.1 | no binding | no binding | no binding |
| 16F12 | 68 | 90.9 | no binding | no binding | no binding |
| 21A5 | 68.8 | 131 | no binding | no binding | no binding |
| 21G8 | 130 | 261 | no binding | no binding | no binding |

TABLE 4-continued

Equilibrium dissociation constants (KD) for anti-FolR1 antibodies (Fab-format) selected by phage display from common light chain sub-libraries comprising VL7_46-13, a humanized light chain specific for CD3ε KD in nM.

| Clone | huFolR1 [nM] | oyFolR1 [nM] | muFolR1 [nm] | huFolR2 [nM] | huFolR3 [nM] |
|---|---|---|---|---|---|
| 19H3 | no binding | no binding | 89.7 | no binding | no binding |
| 20G6 | no binding | no binding | 78.5 | no binding | no binding |

Example 7

Selection of Antibody Fragments from Generic Multi-Framework Libraries to FolR1

The antibodies 11F8, 36F2, 9D11, 5D9, 6B6, and 14E4 were obtained by phage display selections based on generic multi-framework sub-libraries against different species (human, cynomolgus and murine) of FolR1. In these multi-framework sub-libraries, different VL-domains with randomized CDR3 (3 different lengths) are paired with different VH-domains with randomized CDR3 (6 different lengths). The selected clones are of the following VL/VH pairings: 11F8 (Vk_1_5/VH_1_69), 36F2 (Vk_3_20/VH_1_46), 9D11 (Vk2D_28/VH1_46), 5D9 (Vk3_20/VH1_46), 6B6 (Vk3_20/VH1_46), and 14E4 (Vk3_20/VH3_23). In order to obtain species cross-reactive (or murine FolR1-reactive) antibodies, the different species of FolR1 were alternated (or kept constant) in different ways over 3 or 4 rounds of biopanning: 11F8 (cynomolgus—murine—human FolR1); 36F2 (human—murine—cynomolgus—murine FolR1); 9D11 (cynomolgus—human—cynomolgus FolR1); 5D9 (human—cynomolgus—human FolR1); 6B6 (human—cynomolgus—human FolR1) and 14E4 (3 rounds against murine FolR1).

Human, murine and cynomolgus FolR1 as antigens for the phage display selections as well as ELISA- and SPR-based screenings were transiently expressed as N-terminal monomeric Fc-fusion in HEK EBNA cells and in vivo site-specifically biotinylated via co-expression of BirA biotin ligase at the avi-tag recognition sequence located at the C-terminus of the Fc portion carrying the receptor chain (Fc knob chain). In order to assess the specificity to FolR1, two related receptors, human FolR2 and FolR3 were generated in the same way.

Selection rounds (biopanning) were performed in solution according to the following pattern:
1. Pre-clearing of ~$10^{12}$ phagemid particles on maxisorp plates coated with 10 ug/ml of an unrelated human IgG to deplete the libraries of antibodies recognizing the Fc-portion of the antigen.
2. Incubating the non-Fc-binding phagemid particles with 100 nM biotinylated human, cynomolgus, or murine FolR1 for 0.5h in the presence of 100 nM unrelated non-biotinylated Fc knob-into-hole construct for further depletion of Fc-binders in a total volume of 1 ml.
3. Capturing the biotinylated FolR1 and attached specifically binding phage by transfer to 4 wells of a neutravidin pre-coated microtiter plate for 10 min (in rounds 1 & 3).
4. Washing the respective wells using 5×PBS/Tween20 and 5×PBS.
5. Eluting the phage particles by addition of 250 ul 100 mM TEA (triethylamine) per well for 10 min and neutralization by addition of 500 ul 1 M Tris/HCl pH 7.4 to the pooled eluates from 4 wells.
6. Post-clearing of neutralized eluates by incubation on neutravidin pre-coated microtiter plate with 100 nM biotin-captured FolR2 or FolR3 for final removal of Fc- and unspecific binders.
7. Re-infection of log-phase E. coli TG1 cells with the supernatant of eluted phage particles, infection with helperphage VCSM13, incubation on a shaker at 30° C. over night and subsequent PEG/NaCl precipitation of phagemid particles to be used in the next selection round.

Selections were carried out over 3 rounds using constant antigen concentrations of 100 nM. In round 2 and 4, in order to avoid enrichment of binders to neutravidin, capture of antigen:phage complexes was performed by addition of $5.4 \times 10^7$ streptavidin-coated magnetic beads. Specific binders were identified by ELISA as follows: 100 ul of 25 nM biotinylated human, cynomolgus, or murine FolR1 and 10 ug/ml of human IgG were coated on neutravidin plates and maxisorp plates, respectively. Fab-containing bacterial supernatants were added and binding Fabs were detected via their Flag-tags using an anti-Flag/HRP secondary antibody. Clones exhibiting signals on human FolR1 and being negative on human IgG were short-listed for further analyses and were also tested in a similar fashion against the remaining two species of FolR1. They were bacterially expressed in a 0.5 liter culture volume, affinity purified and further characterized by SPR-analysis using BioRad's ProteOn XPR36 biosensor. Affinities ($K_D$) of selected clones were measured by surface plasmon resonance (SPR) using a ProteOn XPR36 instrument (Biorad) at 25° C. with biotinylated human, cynomolgus, and murine FolR1 as well as human FolR2 and FolR3 (negative controls) immobilized on NLC chips by neutravidin capture. Immobilization of antigens (ligand): Recombinant antigens were diluted with PBST (10 mM phosphate, 150 mM sodium chloride pH 7.4, 0.005% Tween 20) to 10 µg/ml, then injected at 30 µl/minute in vertical orientation. Injection of analytes: For 'one-shot kinetics' measurements, injection direction was changed to horizontal orientation, two-fold dilution series of purified Fab (varying concentration ranges) were injected simultaneously along separate channels 1-5, with association times of 150 or 200 s, and dissociation times of 200 or 600 s, respectively. Buffer (PBST) was injected along the sixth channel to provide an "in-line" blank for referencing. Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$. Table 5 lists the equilibrium dissociation constants ($K_D$) of the selected clones specific for FolR1.

TABLE 5

Equilibrium dissociation constants ($K_D$) for anti-FolR1 antibodies (Fab-format) selected by phage display from generic multi-framework sub-libraries. $K_D$ in nM.

| Clone | KD (nM) | | | | |
| --- | --- | --- | --- | --- | --- |
| | huFolR1 | cyFolR1 | muFolR1 | huFOlR2 | huFOlR3 |
| 11F8 | 632 | 794 | 1200 | no binding | no binding |
| 36F2 | 1810 | 1640 | 737 | no binding | no binding |
| 9D11 | 8.64 | 5.29 | no binding | no binding | no binding |
| 5D9 | 8.6 | 5.9 | no binding | no binding | no binding |
| 6B6 | 14.5 | 9.4 | no binding | no binding | no binding |
| 14E4 | no binding | no binding | 6.09 | no binding | no binding |

Example 8

Production and Purification of Novel FolR1 Binders in IgG and T-Cell Bispecific Formats To identify FolR1 binders which are able to induce T-cell dependent killing of selected target cells the antibodies isolated from a common light chain- or Fab-library were converted into the corresponding human $IgG_1$ format. In brief, the variable heavy and variable light chains of unique FolR1 binders from phage display were amplified by standard PCR reactions using the Fab clones as the template. The PCR products were purified and inserted (either by restriction endonuclease and ligase based cloning, or by 'recombineering' using the InFusion kit from Invitrogen) into suitable expression vectors in which they are fused to the appropriate human constant heavy or human constant light chain. The expression cassettes in these vectors consist of a chimeric MPSV promoter and a synthetic polyadenylation site. In addition, the plasmids contain the oriP region from the Epstein Barr virus for the stable maintenance of the plasmids in HEK293 cells harboring the EBV nuclear antigen (EBNA). After PEI mediated transfection the antibodies were transiently produced in HEK293 EBNA cells and purified by standard ProteinA affinity chromatography followed by size exclusion chromatography as described:

Transient Transfection and Production

All (bispecific) antibodies (if not obtained from a commercial source) used herein were transiently produced in HEK293 EBNA cells using a PEI mediated transfection procedure for the required vectors as described below. HEK293 EBNA cells are cultivated in suspension serum free in CD CHO culture medium. For the production in 500 ml shake flask 400 million HEK293 EBNA cells are seeded 24 hours before transfection (for alternative scales all amounts were adjusted accordingly). For transfection cells are centrifuged for 5 min by 210×g, supernatant is replaced by pre-warmed 20 ml CD CHO medium. Expression vectors are mixed in 20 ml CD CHO medium to a final amount of 200 µg DNA. After addition of 540 µl PEI solution is vortexed for 15 s and subsequently incubated for 10 min at room temperature. Afterwards cells are mixed with the DNA/PEI solution, transferred to a 500 ml shake flask and incubated for 3 hours by 37° C. in an incubator with a 5% CO2 atmosphere. After incubation time 160 ml F17 medium is added and cell are cultivated for 24 hours. One day after transfection 1 mM valporic acid and 7% Feed 1 is added. After 7 days cultivation supernatant is collected for purification by centrifugation for 15 min at 210×g, the solution is sterile filtered (0.22 µm filter) and sodium azide in a final concentration of 0.01% w/v is added, and kept at 4° C. After production the supernatants were harvested and the antibody containing supernatants were filtered through 0.22 µm sterile filters and stored at 4° C. until purification.

Antibody Purification

All molecules were purified in two steps using standard procedures, such as protein A affinity purification (Äkta Explorer) and size exclusion chromatography. The supernatant obtained from transient production was adjusted to pH 8.0 (using 2 M TRIS pH 8.0) and applied to HiTrap PA FF (GE Healthcare, column volume (cv)=5 ml) equilibrated with 8 column volumes (cv) buffer A (20 mM sodium phosphate, 20 mM sodium citrate, pH 7.5). After washing with 10 cv of buffer A, the protein was eluted using a pH gradient to buffer B (20 mM sodium citrate pH 3, 100 mM NaCl, 100 mM glycine) over 12 cv. Fractions containing the protein of interest were pooled and the pH of the solution was gently adjusted to pH 6.0 (using 0.5 M $Na_2HPO_4$ pH 8.0). Samples were concentrated to 2 ml using ultra-concentrators (Vivaspin 15R 30.000 MWCO HY, Sartorius) and subsequently applied to a HiLoad™ 16/60 Superdex™ 200 preparative grade (GE Healthcare) equilibrated with 20 mM Histidine, pH 6.0, 140 mM NaCl, 0.01% Tween-20. The aggregate content of eluted fractions was analyzed by analytical size exclusion chromatography. Therefore, 30 µl of each fraction was applied to a TSKgel G3000 SW XL analytical size-exclusion column (Tosoh) equilibrated in 25 mM $K_2HPO_4$, 125 mM NaCl, 200 mM L-arginine monohydrochloride, 0.02% (w/v) $NaN_3$, pH 6.7 running buffer at 25° C. Fractions containing less than 2% oligomers were pooled and concentrated to final concentration of 1-1.5 mg/ml using ultra concentrators (Vivaspin 15R 30.000 MWCO HY, Sartorius). The protein concentration was determined by measuring the optical density (OD) at 280 nm, using the molar extinction coefficient calculated on the basis of the amino acid sequence. Purity and molecular weight of the constructs were analyzed by SDS capillary electrophoresis in the presence and absence of a reducing agent following the manufacturer instructions (instrument Caliper LabChipGX, Perkin Elmer). Purified proteins were frozen in liquid $N_2$ and stored at −80° C.

Based on in vitro characterization results selected binders were converted into a T-cell bispecific format. In these molecules the FolR1:CD3 binding moieties are arranged in a 2:1 order with the FolR1 Fabs being located at the N-terminus. For clones isolated from the standard Fab library the CD3 binding part was generated as a CrossFab (CH1CK crossing) while for the clones from the common light chain library no crossing was necessary. These bispecific molecules were produced and purified analogously to the IgGs.

TABLE 6

Yield and monomer content of novel FolR1 binders in IgG and TCB format, respectively.

| | | | IgG | | TCB | |
|---|---|---|---|---|---|---|
| # | Clone | Library | Yield [mg/L] | Monomer [%] | Yield [mg/L} | Monomer [%] |
| 1 | 11F8 | Fab | 8.03 | 96.26 | — | — |
| 2 | 14E4 | Fab | 8.90 | 98.12 | — | — |
| 3 | 15B6 | CLC | 7.72 | 100.00 | — | — |
| 4 | 15E12 | CLC | 6.19 | 100.00 | — | — |
| 5 | 15H7 | CLC | 8.94 | 100.00 | — | — |
| 6 | 16A3 | CLC | 0.60 | n.d. | — | — |
| 7 | 16D5 | CLC | 36.50 | 96.96 | 4.36 | 97.19 |
| 8 | 16F12 | CLC | 5.73 | 97.17 | — | — |
| 9 | 18D3 | CLC | 0.90 | n.d. | — | — |
| 10 | 19A4 | CLC | 38.32 | 100.00 | 37.50 | 100.00 |
| 11 | 19E5 | CLC | 46.09 | 100.00 | — | — |
| 12 | 19H3 | CLC | 7.64 | 100.00 | — | — |
| 13 | 20G6 | CLC | 24.00 | 100.00 | — | — |
| 14 | 20H7 | CLC | 45.39 | 100.00 | — | — |
| 15 | 21A5 | CLC | 1.38 | 98.56 | 47.31 | 95.08 |
| 16 | 21D1 | CLC | 5.47 | 100.00 | — | — |
| 17 | 21G8 | CLC | 6.14 | 97.28 | 9.27 | 100.00 |
| 18 | 36F2 | Fab | 11.22 | 100.00 | 18.00 | 100.00 |
| 19 | 5D9 | Fab | 20.50 | 100.00 | 0.93 | 97.32 |
| 20 | 6B6 | Fab | 3.83 | 100.00 | 4.17 | 91.53 |
| 21 | 9D11 | Fab | 14.61 | 100.00 | 2.63 | 100.00 |

CLC: Common light chain

Example 9

2+1 and 1+1 T-Cell Bispecific Formats

Four different T-cell bispecific formats were prepared for one common light chain binder (16D5) and three formats for one binder from the Fab library (9D11) to compare their killing properties in vitro.

The standard format is the 2+1 inverted format as already described (FolR1:CD3 binding moieties arranged in a 2:1 order with the FolR1 Fabs located at the N-terminus). In the 2+1 classical format the FolR1:CD3 binding moieties are arranged in a 2:1 order with the CD3 Fab being located at the N-terminus. Two monovalent formats were also prepared. The 1+1 head-to-tail has the FolR1:CD3 binding moieties arranged in a 1:1 order on the same arm of the molecule with the FolR1 Fab located at the N-terminus. In the 1+1 classical format the FolR1:CD3 binding moieties are present once, each on one arm of the molecule. For the 9D11 clone isolated from the standard Fab library the CD3 binding part was generated as a CrossFab (CH1Cκ crossing) while for the 16D5 from the common light chain library no crossing was necessary. These bispecific molecules were produced and purified analogously to the standard inverted T-cell bispecific format.

TABLE 7

Summary of the yield and final monomer content of the different T-cell bispecific formats.

| Construct | Monomer [%] (SEC) | Yield |
|---|---|---|
| 16D5 FolR1 TCB 2+1 (inverted) | 96% | 5.4 mg/L |
| 16D5 FolR1 TCB 2+1 (classical) | 90% | 4.6 mg/L |
| 16D5 FolR1 TCB 1+1 (head-to-tail) | 100% | 5.4 mg/L |
| 16D5 FolR1 TCB 1+1 (classical) | 100% | 0.7 mg/L |
| 9D11 FolR1 TCB 2+1 (inverted) | 100% | 2.6 mg/L |
| 9D11 FolR1 TCB 1+1 (head-to-tail) | 100% | 6.1 mg/L |
| 9D11 FolR1 TCB 1+1 (classical) | 96% | 1.3 mg/L |
| Mov19 FolR1 TCB 2+1 (inverted) | 98% | 3 mg/L |
| Mov19 FolR1 TCB 1+1 (head-to-tail) | 100% | 5.2 mg/L |

Example 10

Biochemical Characterization of FolR1 Binders by Surface Plasmon Resonance

Binding of FolR1 binders as IgG or in the T-cell bispecific format to different recombinant folate receptors (human FolR1, 2 and 3, murine FolR1 and cynomolgus FolR1; all as Fc fusions) was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany).

Single Injections

First the anti-FolR1 IgGs were analyzed by single injections (Table 1) to characterize their crossreactivity (to human, murine and cyno FolR1) and specificity (to human FolR1, human FolR2, human FolR3). Recombinant biotinylated monomeric Fc fusions of human, cynomolgus and murine Folate Receptor 1 (FolR1-Fc) or human Folate Receptor 2 and 3 (FolR2-Fc, FolR3-Fc) were directly coupled on a SA chip using the standard coupling instruction (Biacore, Freiburg/Germany). The immobilization level was about 300-400 RU. The IgGs were injected for 60 seconds at a concentration of 500 nM. IgGs binding to huFolR2 and huFolR3 were rejected for lack of specificity. Most of the binders are only crossreactive between human and cyno FolR1, additional crossreactivity to murine FolR1 went most of the time hand in hand with loss of specificity.

TABLE 8

Crossreactivity and specificity of 25 new folate receptor 1 binders (as IgGs) as well as of two control IgGs (Mov19 and Farletuzumab).

| Clone name | Binding to huFolR1 | Binding to cyFolR1 | Binding to muFolR1 | Binding to huFolR2 | Binding to huFolR3 |
|---|---|---|---|---|---|
| Mov19 | + | + | − | − | − |
| Farletuzumab | + | + | − | − | − |
| 16A3 | + | + | +/− | − | − |
| 18D3 | + | + | − | − | − |
| 19E5 | + | + | + | + | + |
| 19A4 | − | − | + | + | + |
| 15H7 | + | + | + | − | − |

TABLE 8-continued

Crossreactivity and specificity of 25 new folate receptor 1 binders (as IgGs) as well as of two control IgGs (Mov19 and Farletuzumab).

| Clone name | Binding to huFolR1 | Binding to cyFolR1 | Binding to muFolR1 | Binding to huFolR2 | Binding to huFolR3 |
|---|---|---|---|---|---|
| 15B6 | + | + | − | − | − |
| 16D5 | + | + | − | − | − |
| 15E12 | + | + | +/− | + | + |
| 21D1 | + | + | +/− | − | − |
| 16F12 | + | + | − | − | − |
| 21A5 | + | + | − | − | +/− |
| 21G8 | + | + | − | + | + |
| 19H3 | − | − | + | − | − |
| 20G6 | − | − | + | − | − |
| 20H7 | − | − | + | − | − |
| 9D11 | + | + | − | − | − |
| 5D9 | + | + | − | + | + |
| 6B6 | + | + | − | + | + |
| 11F8 | + | + | + | + | + |
| 36F2 | + | + | + | − | − |
| 14E4 | − | − | + | − | − |

+ means binding, − means no binding, +/− means weak binding.

Avidity to Folate Receptor 1

The avidity of the interaction between the anti-FolR1 IgGs or T cell bispecifics and the recombinant folate receptors was determined as described below (Table 9).

Recombinant biotinylated monomeric Fc fusions of human, cynomolgus and murine Folate Receptor 1 (FolR1-Fc) were directly coupled on a SA chip using the standard coupling instruction (Biacore, Freiburg/Germany). The immobilization level was about 300-400 RU. The anti-FolR1 IgGs or T cell bispecifics were passed at a concentration range from 2.1 to 500 nM with a flow of 30 μL/minutes through the flow cells over 180 seconds. The dissociation was monitored for 600 seconds. Bulk refractive index differences were corrected for by subtracting the response obtained on reference flow cell immobilized with recombinant biotinylated IL2 receptor Fc fusion. For the analysis of the interaction of 19H3 IgG and murine folate receptor 1, folate (Sigma F7876) was added in the HBS-EP running buffer at a concentration of 2.3 μM. The binding curves resulting from the bivalent binding of the IgGs or T cell bispecifics were approximated to a 1:1 Langmuir binding and fitted with that model (which is not correct, but gives an idea of the avidity). The apparent avidity constants for the interactions were derived from the rate constants of the fitting using the Bia Evaluation software (GE Healthcare).

TABLE 9

Bivalent binding (avidity with apparent KD) of selected FolR1 binders as IgGs or as T-cell bispecifics (TCB) on human and cyno FolR1.

| Analyte | Ligand | ka (1/Ms) | kd (1/s) | Apparent KD (M) |
|---|---|---|---|---|
| 16D5 TCB | huFolR1 | 8.31E+04 | 3.53E−04 | 4.24E−09 |
|  | cyFolR1 | 1.07E+05 | 3.70E−04 | 3.45E−09 |
| 9D11 TCB | huFolR1 | 1.83E+05 | 9.83E−05 | 5.36E−10 |
|  | cyFolR1 | 2.90E+05 | 6.80E−05 | 2.35E−10 |
| 21A5 TCB | huFolR1 | 2.43E+05 | 2.64E−04 | 1.09E−09 |
|  | cyFolR1 | 2.96E+05 | 2.76E−04 | 9.32E−10 |
| 36F2 IgG | huFolR1 | 2.62E+06 | 1.51E−02 | 5.74E−9 |
|  | cyFolR1 | 3.02E+06 | 1.60E−02 | 5.31E−9 |
|  | muFolR1 | 3.7E+05 | 6.03E−04 | 1.63E−9 |
| Mov19 IgG | huFolR1 | 8.61E+05 | 1.21E−04 | 1.4E−10 |
|  | cyFolR1 | 1.29E+06 | 1.39E−04 | 1.08E−10 |

TABLE 9-continued

Bivalent binding (avidity with apparent KD) of selected FolR1 binders as IgGs or as T-cell bispecifics (TCB) on human and cyno FolR1.

| Analyte | Ligand | ka (1/Ms) | kd (1/s) | Apparent KD (M) |
|---|---|---|---|---|
| Farletuzumab | huFolR1 | 1.23E+06 | 9E−04 | 7.3E−10 |
|  | cyFolR1 | 1.33E+06 | 8.68E−04 | 6.5E−10 |
| 19H3 IgG | muFolR1 | 7.1E+05 | 1.1E−03 | 1.55E−09 |

1. Affinity to Folate Receptor 1

The affinity of the interaction between the anti-FolR1 IgGs or the T cell bispecifics and the recombinant folate receptors was determined as described below (Table 10).

For affinity measurement, direct coupling of around 6000-7000 resonance units (RU) of the anti-human Fab specific antibody (Fab capture kit, GE Healthcare) was performed on a CM5 chip at pH 5.0 using the standard amine coupling kit (GE Healthcare). Anti-FolR1 IgGs or T cell bispecifics were captured at 20 nM with a flow rate of 10 μl/min for 20 or 40 sec, the reference flow cell was left without capture. Dilution series (6.17 to 500 nM or 12.35 to 3000 nM) of human or cyno Folate Receptor 1 Fc fusion were passed on all flow cells at 30 μl/min for 120 or 240 sec to record the association phase. The dissociation phase was monitored for 240 s and triggered by switching from the sample solution to HBS-EP. The chip surface was regenerated after every cycle using a double injection of 60 sec 10 mM Glycine-HCl pH 2.1 or pH 1.5. Bulk refractive index differences were corrected for by subtracting the response obtained on the reference flow cell 1. The affinity constants for the interactions were derived from the rate constants by fitting to a 1:1 Langmuir binding using the Bia Evaluation software (GE Healthcare).

TABLE 10

Monovalent binding (affinity) of selected FolR1 binders as IgGs or as T-cell bispecifics (TCB) on human and cyno FolR1.

| Ligand | Analyte | ka (1/Ms) | kd (1/s) | KD (M) |
|---|---|---|---|---|
| 16D5 TCB | huFolR1 | 1.53E+04 | 6.88E−04 | 4.49E−08 |
|  | cyFolR1 | 1.32E+04 | 1.59E−03 | 1.21E−07 |
| 9D11 TCB | huFolR1 | 3.69E+04 | 3.00E−04 | 8.13E−09 |
|  | cyFolR1 | 3.54E+04 | 2.06E−04 | 5.82E−09 |

TABLE 10-continued

Monovalent binding (affinity) of selected FoIR1 binders as IgGs or as T-cell bispecifics (TCB) on human and cyno FoIR1.

| Ligand | Analyte | ka (1/Ms) | kd (1/s) | KD (M) |
|---|---|---|---|---|
| 21A5 TCB | huFoIR1 | 1.79E+04 | 1.1E−03 | 6.16E−08 |
| | cyFoIR1 | 1.48E+04 | 2.06E−03 | 1.4E−07 |
| Mov19 IgG | huFoIR1 | 2.89E+05 | 1.59E−04 | 5.5E−10 |
| | cyFoIR1 | 2.97E+05 | 1.93E−04 | 6.5E−10 |
| Farletuzumab | huFoIR1 | 4.17E+05 | 2.30E−02 | 5.53E−08 |
| | cyFoIR1 | 5.53E+05 | 3.73E−02 | 6.73E−08 |

2. Affinity to CD3

The affinity of the interaction between the anti-FolR1 T cell bispecifics and the recombinant human CD386-Fc was determined as described below (Table 11).

For affinity measurement, direct coupling of around 9000 resonance units (RU) of the anti-human Fab specific antibody (Fab capture kit, GE Healthcare) was performed on a CM5 chip at pH 5.0 using the standard amine coupling kit (GE Healthcare). Anti-FolR1 T cell bispecifics were captured at 20 nM with a flow rate of 10 µl/min for 40 sec, the reference flow cell was left without capture. Dilution series (6.17 to 500 nM) of human CD386-Fc fusion were passed on all flow cells at 30 µl/min for 240 sec to record the association phase. The dissociation phase was monitored for 240 s and triggered by switching from the sample solution to HBS-EP. The chip surface was regenerated after every cycle using a double injection of 60 sec 10 mM Glycine-HCl pH 2.1. Bulk refractive index differences were corrected for by subtracting the response obtained on the reference flow cell 1. The affinity constants for the interactions were derived from the rate constants by fitting to a 1:1 Langmuir binding using the Bia Evaluation software (GE Healthcare).

TABLE 11

Monovalent binding (affinity) of selected FoIR1 T-cell bispecifics (TCB) on human CD3-Fc.

| Ligand | Analyte | ka (1/Ms) | kd (1/s) | KD (M) |
|---|---|---|---|---|
| 16D5 TCB | huCD3 | 4.25E+04 | 3.46E−03 | 8.14E−08 |
| 21A5 TCB | huCD3 | 3.72E+04 | 3.29E−03 | 8.8E−08 |

The CD3 binding part is identical for all constructs and the affinity is similar for the measured T cell bispecifics ($K_D$ range between 60 and 90 nM).

Example 11

Simultaneous Binding T Cell Bispecifics on Folate Receptor 1 and CD3

Simultaneous binding of the anti-FolR1 T cell bispecifics on recombinant Folate Receptor 1 and recombinant human CD386-Fc was determined by surface plasmon resonance as described below. Recombinant biotinylated monomeric Fc fusions of human, cynomolgus and murine Folate Receptor 1 (FolR1-Fc) were directly coupled on a SA chip using the standard coupling instruction (Biacore, Freiburg/Germany). The immobilization level was about 300-400 RU. The anti-FolR1 T cell bispecifics were injected for 60 s at 500 nM with a flow of 30 µL/minutes through the flow cells, followed by an injection of hu CD88-Fc for 60 s at 500 nM. Bulk refractive index differences were corrected for by subtracting the response obtained on reference flow cell immobilized with recombinant biotinylated IL2 receptor Fc fusion. The four T cell bispecifics tested (16D5 TCB, 21A5 TCB, 51C7 TCB and 45D2 TCB) were able to bind simultaneously to Folate Receptor 1 and human CD3 as expected.

Example 12

Epitope Binning

For epitope binning, the anti-FolR1 IgGs or T cell bispecifics were directly immobilized on a CM5 chip at pH 5.0 using the standard amine coupling kit (GE Healthcare), with a final response around 700 RU. 500 nM huFolR1-Fc was then captured for 60 s, followed by 500 nM of the different binders for 30 s. The surface was regenerated with two injections of 10 mM glycine pH 2 for 30 s each. It is assessed if the different binders can bind to huFolR1 captured on immobilized binders (Table 12).

TABLE 12

Epitope characterization of selected FolR1 binders as IgGs or as T-cell bispecifics (TCB) on human FolR1.

| On huFolR1 | | Analytes in solution | | | | |
|---|---|---|---|---|---|---|
| | | 16D5 TCB | 21A5 TCB | 9D11 TCB | 36F2 IgG | Mov19 IgG | Farletuzumab |
| Immobilized | 16D5 TCB | − | − | − | + | + | + |
| | 21A5 TCB | − | − | − | + | + | + |
| | 9D11 TCB | No additional binding on FolR1 possible once captured on 9D11 | | | | | |
| | 36F2 IgG | Measure not possible, huFolR1 dissociates too rapidly | | | | | |

TABLE 12-continued

Epitope characterization of selected FolR1 binders as IgGs or as T-cell bispecifics (TCB) on human FolR1.

| On huFolR1 | Analytes in solution | | | | | |
|---|---|---|---|---|---|---|
| | 16D5 TCB | 21A5 TCB | 9D11 TCB | 36F2 IgG | Mov19 IgG | Farletuzumab |
| Mov19 IgG | + | + | +/− | − | − | − |

+ means binding, − means no binding, +/− means weak binding

Based on these results and additional data with simultaneous binding on immobilized huFolR1, the binders were separated in three groups. It is not clear if 9D11 has a separate epitope because it displaces all the other binders. 16D5 and 21A5 seem to be in the same group and Mov19, Farletuzumab (Coney et al., Cancer Res. 1991 Nov. 15; 51(22):6125-32; Kalli et al., Curr Opin Investig Drugs. 2007 December; 8(12):1067-73) and 36F2 in another (Table 13). However, 36F2 binds to a different epitope than Mov 19 and Farletuzumab as it binds to human, cynomous and murine FolR1.

TABLE 13

Epitope grouping of selected FolR1 binders as
IgGs or as T-cell bispecifics (TCB) on human
FolR1

| Epitope 1 | Epitope 2 | Epitope 3 |
|---|---|---|
| 16D5 | 9D11 | Mov19 |
| 21A5 | | Farletuzumab |
| | | 36F2 |

Example 13

Selection of Binders

FolR1 binders in the IgG formats were screened by surface plasmon resonance (SPR) and by in vitro assay on cells to select the best candidates.

The anti-FolR1 IgGs were analyzed by SPR to characterize their crossreactivity (to human, murine and cynomolgus FolR1) and specificity (to human FolR1, human FolR2, human FolR3). Unspecific binding to human FolR2 and 3 was considered an exclusion factor. Binding and specificity to human FolR1 was confirmed on cells. Some binders did not bind on cells expressing FolR1 even though they recognized the recombinant human FolR1 in SPR. Aggregation temperature was determined but was not an exclusion factor because the selected binders were all stable. Selected binders were tested in a polyreactivity ELISA to check for unspecific binding, which led to the exclusion of four binders. This process resulted in an initial selection of three binders: 36F2 (Fab library), 9D11 (Fab library) and 16D5 (common light chain). 36F2 dissociated rapidly from huFolR1 and was, therefore, initially not favored.

Example 14

Figure 2A:
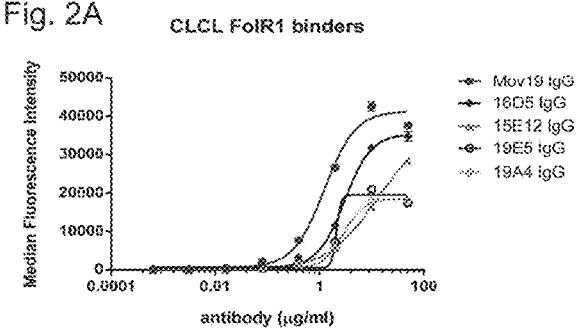
FIGS. 2A-C depict graphs summarizing Binding of FolR1 IgG binders to HeLa cells. Binding of newly generated FolR1 binders to FolR1 expressed on HeLa cells were determined by flow cytometry. Bound antibodies were detected with a fluorescently labeled anti-human secondary antibody.
Figure 2B:
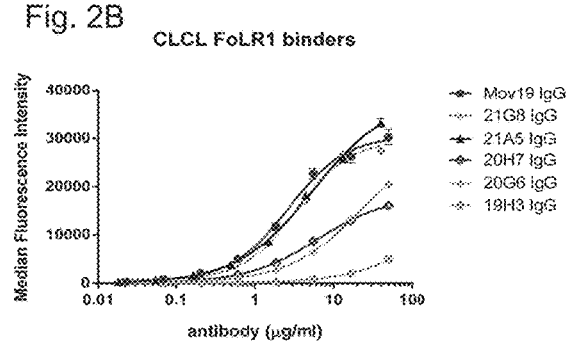
Figure 2C:
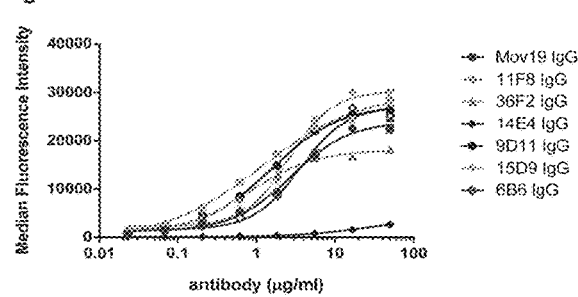
Figure 3A:
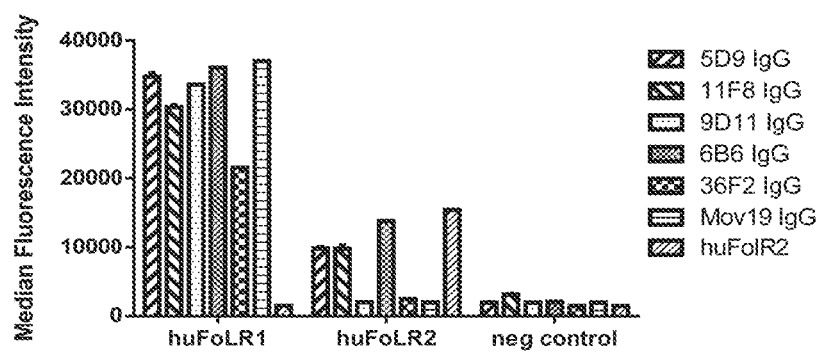
FIGS. 3A-B depict graphs summarizing specificity of FolR1 binders for FolR1. Binding of FolR1 IgGs to HEK cells transiently transfected with either FolR1 or FolR2 was analyzed by flow cytometry to identify clones which bind specifically to FolR1 and not to FolR2. The antibodies were detected with a fluorescently labeled anti-human secondary antibody.
Figure 3B:
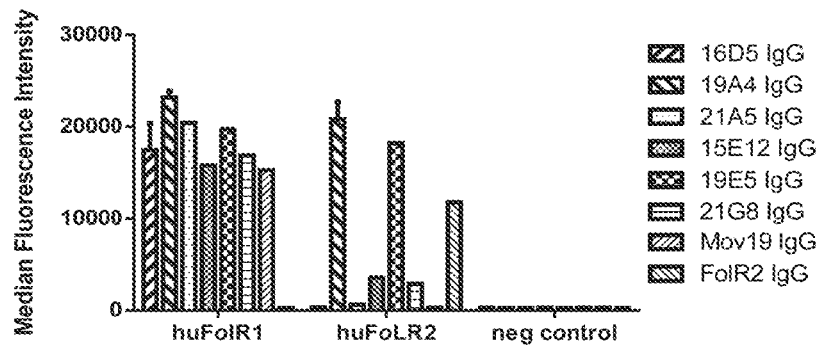
Figure 4A:
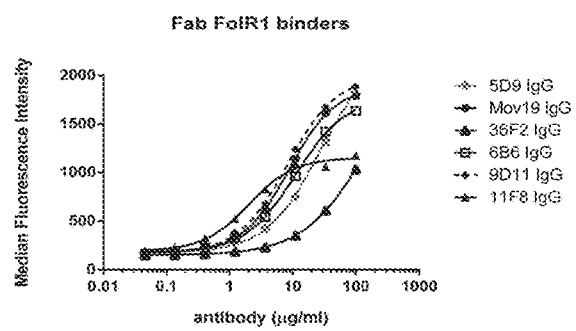
FIGS. 4A-B depict graphs summarizing cross-reactivity of FolR1 binders to cyFoLR1. Cross-reactivity of the FolR1 antibodies to cyno FolR1 was addressed on HEK cells transiently transfected with cyFolR1 by flow cytometry. The antibodies were detected with a fluorescently labeled anti-human secondary antibody.
Figure 4B:
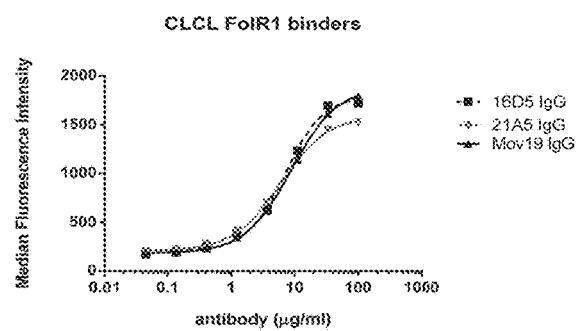
Figure 5:
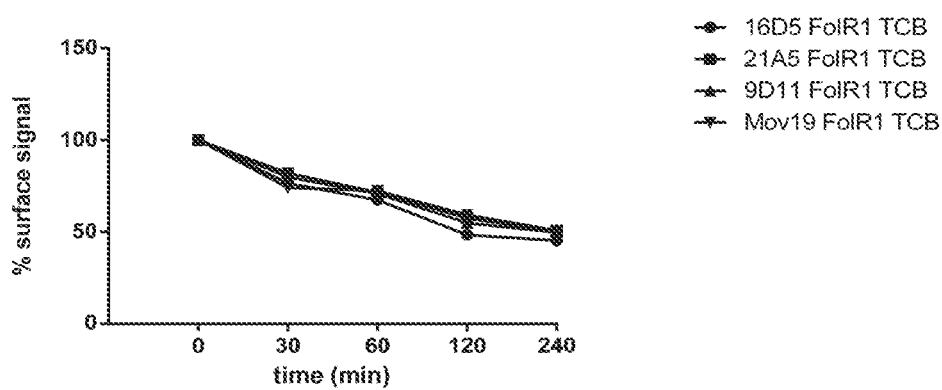
FIG. 5 depicts a graph illustrating internalization of FolR1 TCBs after binding. Internalization of the four FolR1 TCBs after binding to FolR1 was tested on HeLa cells. Remaining FolR1 TCBs on the surface were detected with a fluorescently labeled anti-human secondary antibody after indicated time points of incubation at 37° C. Percentage of internalization was calculated.
Figure 7A:
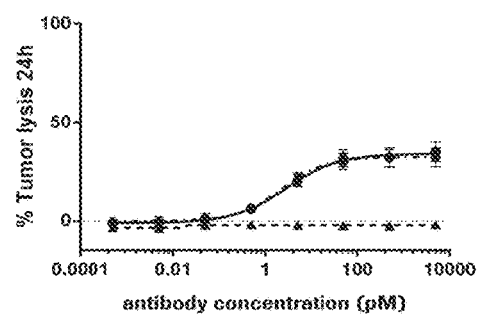
FIGS. 7A-L depict graphs summarizing T cell mediated killing of HT-29 and SKOV3 cells. FolR1 TCBs were used to test T cell mediated killing of HT-29 and SKOV3 tumor cells and upregulation of activation marker on T cells upon killing.
Figure 7B:
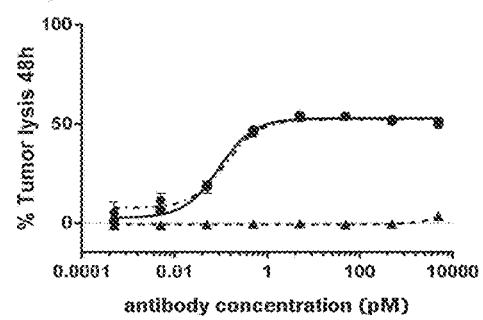
Figure 7C:
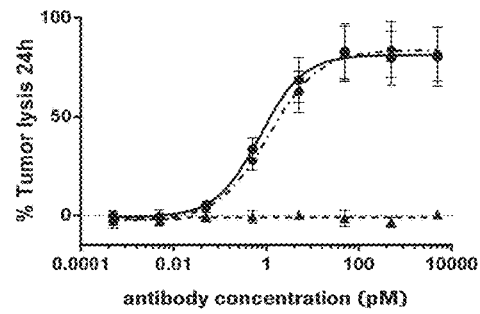
Figure 7D:
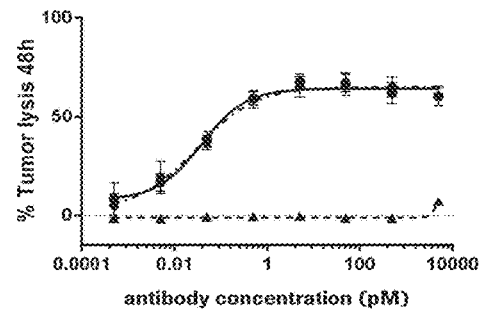
Figure 7E:
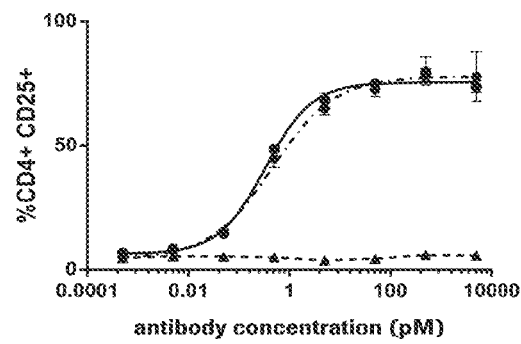
Figure 7F:
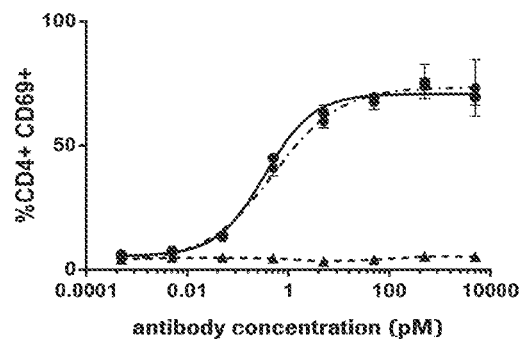
Figure 7G:
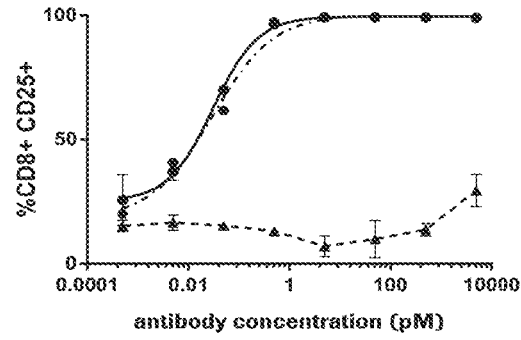
Figure 7H:
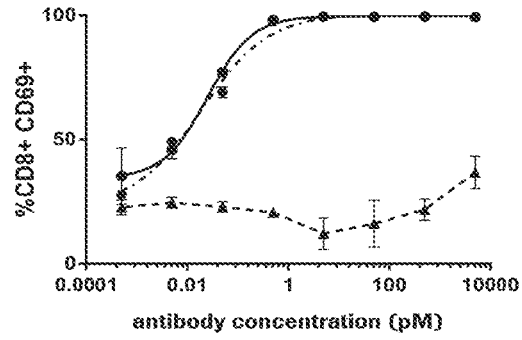
Figure 7I:
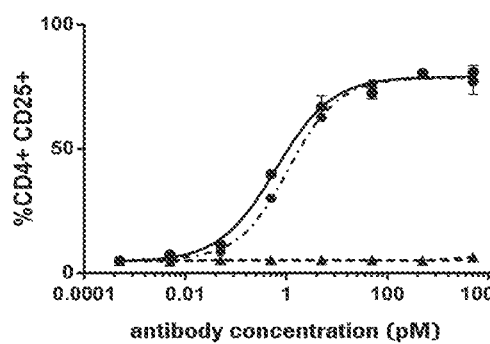
Figure 7J:
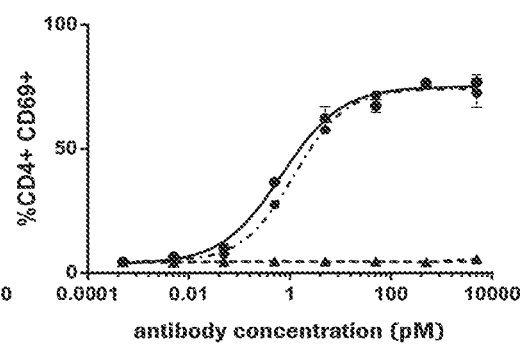
Figure 7K:
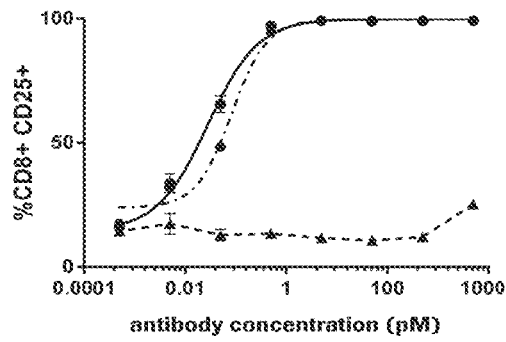
Figure 7L:
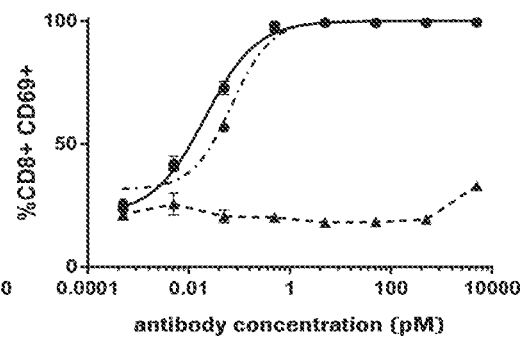

Specific Binding of Newly Generated FolR1
Binders to Human FolR1 Positive Tumor Cells New FolR1 binders were generated via Phage Display using either a Fab library or a common light chain library using the CD3 light chain. The identified binders were converted into a human IgG1 format and binding to FolR1 high expressing HeLa cells was addressed. As reference molecule the human FolR1 binder Mov19 was included. Most of the binders tested in this assay showed intermediate to good binding to FolR1 with some clones binding equally well as Mov19 (see FIG. 2). The clones 16A3, 18D3, 15H7, 15B6, 21D1, 14E4 and 16F12 were excluded because binding to FolR1 on cells could not be confirmed by flow cytometry. In a next step the selected clones were tested for specificity to human FolR1 by excluding binding to the closely related human FolR2. HEK cells were transiently transfected with either human FolR1 or human FolR2 to address specificity. The clones 36F2 and 9D11 derived from the Fab library and the clones 16D5 and 21A5 derived from the CLC library bind specifically to human FolR1 and not to human FolR2 (see FIGS. 3A-B). All the other tested clones showed at least some binding to human FolR2 (see FIGS. 3A-B). Therefore these clones were excluded from further characterization. In parallel cross-reactivity of the FolR1 clones to cyno FolR1 was addressed by performing binding studies to HEK cells transiently transfected with cyno FolR1. All tested clones were able to bind cyno FolR1 and the four selected human FoLR1 specific clones 36F2, 9D11, 16D5 and 21A5 bind comparably well human and cyno FoLR1 (FIG. 4). Subsequently three human FolR1 specific cyno cross-reactive binders were converted into TCB format and tested for induction of T cell killing and T cell activation. These clones were 9D11 from the Fab library and 16D5 and 21A5 from the CLC library. As reference molecule Mov19 FolR1 TCB was included in all studies. These FolR1 TCBs were then used to compare induction of internalization after binding to FolR1 on HeLa cells. All three tested clones are internalized upon binding to FolR1 comparable to internalization upon binding of Mov19 FoLR1 TCB (FIG. 5). 21A5 FolR1 TCB was discontinued due to signs of polyreactivity.

Example 15

T Cell-Mediated Killing of FolR1-Expressing
Tumor Target Cells Induced by FolR1 TCB
Antibodies The FolR1 TCBs were used to determine T cell mediated killing of tumor cells expressing FoLR1. A panel of potential target cell lines was used to determine FoLR1 binding sites by Qifikit analysis.

The used panel of tumor cells contains FolR1 high, intermediate and low expressing tumor cells and a FolR1 negative cell line.

TABLE 14

FolR1 binding sites on tumor cells

| Cell line | Origin | FolR1 binding sites |
|---|---|---|
| Hela | Cervix adenocarcinoma | 2'240'716 |
| Skov3 | Ovarian adenocarcinoma | 91'510 |
| OVCAR5 | Ovarian adenocarcinoma | 22'077 |
| HT29 | Colorectal adenocarcinoma | 10'135 |
| MKN45 | Gastric adenocarcinoma | 54 |

Binding of the three different FoLR1 TCBs (containing 9D11, 16D5 and Mov19 binders) to this panel of tumor cell lines was determined showing that the FolR1 TCBs bind specifically to FolR1 expressing tumor cells and not to a FoLR1 negative tumor cell line. The amount of bound construct is proportional to the FoLR1 expression level and there is still good binding of the constructs to the FoLR1 low cell line HT-29 detectable. In addition there is no binding of the negative control DP47 TCB to any of the used cell lines (FIGS. 6A-E).

The intermediate expressing cell line SKOV3 and the low expressing cell line HT-29 were further on used to test T cell mediated killing and T cell activation using 16D5 TCB and 9D11 TCB; DP47 TCB was included as negative control. Both cell lines were killed in the presence of already very low levels of 16D5 TCB and 9D11 TCB and there was no difference in activity between both TCBs even though 9D11 TCB binds stronger to FolR1 than 16D5 TCB. Overall killing of SKOV3 cells was higher compared to HT-29 which reflects the higher expression levels of FolR1 on SKOV3 cells (FIGS. 7A-D). In line with this, a strong upregulation of the activation marker CD25 and CD69 on CD4+ T cells and CD8+ T cells was detected. Activation of T cells was very similar in the presence of SKOV3 cells and HT-29 cells. The negative control DP47 TCB does not induce any killing at the used concentrations and there was no significant upregulation of CD25 and CD69 on T cells.

TABLE 15

EC50 values of tumor cell killing and T cell activation with SKOV3 cells

| Construct | Killing 24 h (pM) | Killing 48 h (pM) | CD4+ CD69+ (%) | CD4+ CD25+ (%) | CD8+ CD69+ (%) | CD8+ CD25+ (%) |
|---|---|---|---|---|---|---|
| 9D11 FolR1 TCB | 1.1 | 0.03 | 0.51 | 0.46 | 0.019 | 0.03 |
| 16D5 FolR1 TCB | 0.7 | 0.04 | 0.34 | 0.33 | 0.025 | 0.031 |

TABLE 16

EC50 values of tumor cell killing and T cell activation with HT-29 cells

| Construct | Killing 24 h (pM) | Killing 48 h (pM) | CD4+ CD69+ (%) | CD4+ CD25+ (%) | CD8+ CD69+ (%) | CD8+ CD25+ (%) |
|---|---|---|---|---|---|---|
| 9D11 FolR1 TCB | 2.3 | 0.1 | 1.22 | 1.11 | 0.071 | 0.084 |
| 16D5 FolR1 TCB | 2.8 | 0.1 | 0.69 | 0.62 | 0.021 | 0.028 |

Example 16

Binding to Erythrocytes and T Cell Activation in Whole Blood

Figure 8:
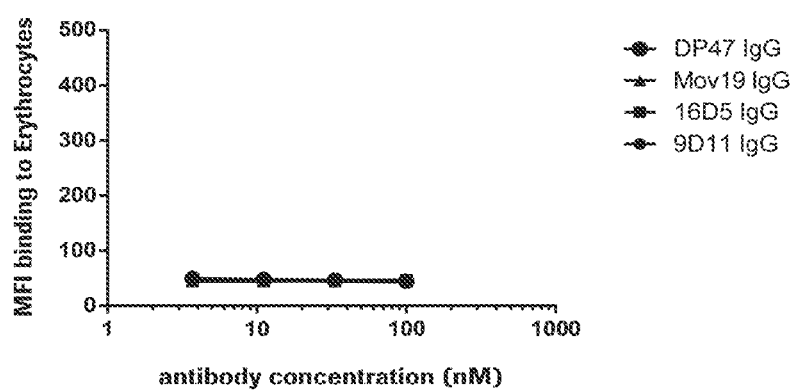
FIG. 8 depicts a graph showing absence of anti-FolR1 binding to erythrocytes. Erythrocytes were gated as CD235a positive population and binding of 9D11 IgG, 16D5 IgG, Mov19 IgG and DP47 IgG to this population was determined by flow cytometry. The antibodies were detected with a fluorescently labeled anti-human secondary antibody.
Figure 9A:
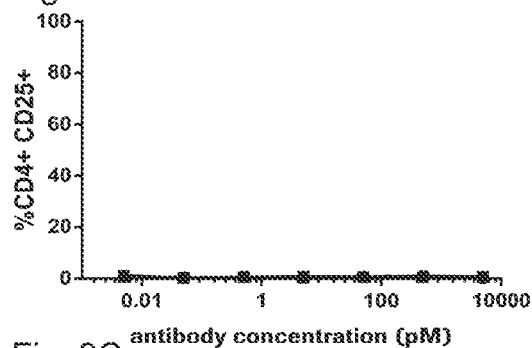
FIGS. 9A-D depict graphs summarizing activation marker upregulation in whole blood. CD25 and CD69 activation marker upregulation of CD4 T cells and CD8 T cells 24 h after addition of 9D11 FolR1 TCB, 16D5 FolR1 TCB, Mov19 FolR1 TCB and DP47 TCB was analyzed by flow cytometry.
Figure 9B:
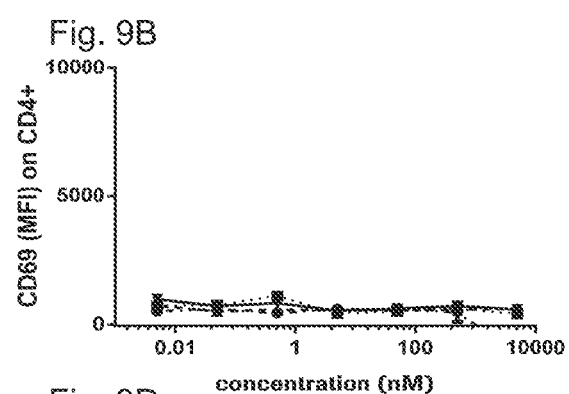
Figure 9C:
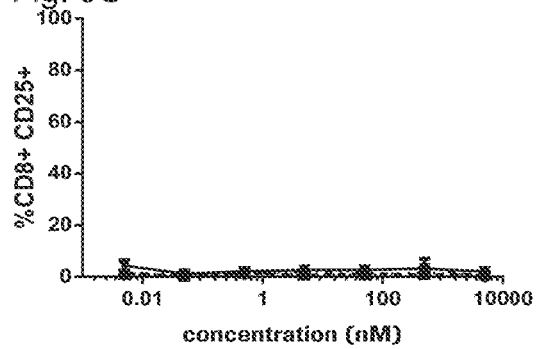
Figure 9D:
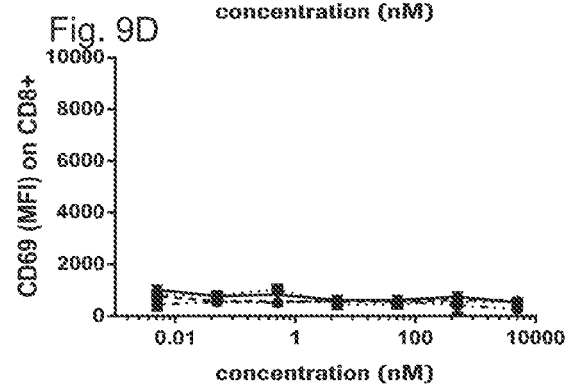

To prove that there is no spontaneous activation in the absence of FoLR1 expressing tumor cells we tested if there is binding of the FolR1 clones to erythrocytes which might potentially express FolR1. We could not observe any specific binding of 9D11 IgG, 16D5 IgG and Mov19 IgG to erythrocytes, as negative control DP47 IgG was included (FIG. 8).

To exclude any further unspecific binding to blood cells or unspecific activation via FoLR1 TCB, 9D11 TCB, 16D5 TCB and Mov19 TCB were added into whole blood and upregulation of CD25 and CD69 on CD4+ T cells and CD8+ T cells was analyzed by flow cytometry. DP47 TCB was included as negative control. No activation of T cells with any of the tested constructs could be observed by analyzing upregulation of CD25 and CD69 on CD4+ T cells and CD8+ T cells (FIG. 9).

Example 17

Removal of the N-Glycosylation Site in 9D11 Light Chain

During analysis of the different FolR1 binders to identify potential sequence hot spots, at the end of CDR L3 of the clone 9D11 a putative N-glycosylation site was identified. Usually the consensus motif for N-glycosylation is defined as N-X-S/T-X (where X is not P). The sequence of CDR L3 (MQASIMNRT (SEQ ID NO: 46)) perfectly matches this consensus motif having the sequence N-R-T. Since glycosylation might not be completely reproducible among different production batches this could have an impact on FolR1 binding, if the glycosylation in CDR L3 contributes to antigen binding. To evaluate if this N-glycosylation site is important for FolR1 binding, or could be replaced without impairing binding, different variants of the 9D11 light chain were generated in which the N-glycosylation site was exchanged by site specific mutagenesis.

1. Transient Transfection and Production

The four T cell bispecifics were transiently produced in HEK293 EBNA cells using a PEI mediated transfection procedure for the required vectors as described below. HEK293 EBNA cells were cultivated in suspension serum free in CD CHO culture medium. For the production in 500 ml shake flask 400 million HEK293 EBNA cells were seeded 24 hours before transfection (for alternative scales all amounts were adjusted accordingly). For transfection cells were centrifuged for 5 min by 210×g, supernatant was replaced by pre-warmed 20 ml CD CHO medium. Expression vectors were mixed in 20 ml CD CHO medium to a final amount of 200 µg DNA. After addition of 540 µl PEI solution was vortexed for 15 s and subsequently incubated for 10 min at room temperature. Afterwards cells were mixed with the DNA/PEI solution, transferred to a 500 ml shake flask and incubated for 3 hours by 37° C. in an incubator with a 5% CO2 atmosphere. After incubation time 160 ml F17 medium was added and cell were cultivated for 24 hours. One day after transfection 1 mM valporic acid and 7% Feed 1 was added. After 7 days cultivation supernatant was collected for purification by centrifugation for 15 min at 210×g, the solution is sterile filtered (0.22 µm filter) and sodium azide in a final concentration of 0.01% w/v was added, and kept at 4° C. After production the supernatants were harvested and the antibody containing supernatants were filtered through 0.22 µm sterile filters and stored at 4° C. until purification.

2. Antibody Purification

All molecules were purified in two steps using standard procedures, such as protein A affinity purification (Äkta Explorer) and size exclusion chromatography. The supernatant obtained from transient production was adjusted to pH 8.0 (using 2 M TRIS pH 8.0) and applied to HiTrap PA HP (GE Healthcare, column volume (cv)=5 ml) equilibrated with 8 column volumes (cv) buffer A (20 mM sodium phosphate, 20 mM sodium citrate, 0.5 M NaCl, 0.01% Tween-20, pH 7.5). After washing with 10 cv of buffer A, the protein was eluted using a pH gradient to buffer B (20 mM sodium citrate pH 2.5, 0.5 M NaCl, 0.01% Tween-20) over 20 cv. Fractions containing the protein of interest were pooled and the pH of the solution was gently adjusted to pH 6.0 (using 2 M Tris pH 8.0). Samples were concentrated to 1 ml using ultra-concentrators (Vivaspin 15R 30.000 MWCO HY, Sartorius) and subsequently applied to a Superdex™ 200 10/300 GL (GE Healthcare) equilibrated with 20 mM Histidine, pH 6.0, 140 mM NaCl, 0.01% Tween-20. The aggregate content of eluted fractions was analyzed by analytical size exclusion chromatography. Therefore, 30 µl of each fraction was applied to a TSKgel G3000 SW XL analytical size-exclusion column (Tosoh) equilibrated in 25 mM $K_2HPO_4$, 125 mM NaCl, 200 mM L-arginine monohydrochloride, 0.02% (w/v) $NaN_3$, pH 6.7 running buffer at 25° C. Fractions containing less than 2% oligomers were pooled and concentrated to final concentration of 1-1.5 mg/ml using ultra concentrators (Vivaspin 15R 30.000 MWCO HY, Sartorius). The protein concentration was determined by measuring the optical density (OD) at 280 nm, using the molar extinction coefficient calculated on the basis of the amino acid sequence. Purity and molecular weight of the constructs were analyzed by SDS capillary electrophoresis in the presence and absence of a reducing agent following the manufacturer instructions (instrument Caliper LabChipGX, Perkin Elmer). Purified proteins were frozen in liquid $N_2$ and stored at −80° C.

3. Aggregation Temperature

Stability of the four constructs was tested on an Optim1000 (Avacta, PALL Corporation) by a gradient heating from 250 to 800 at 0.1° C./min. The temperature at onset of aggregation is recorded.

TABLE 34

Yield, monomer content and aggregation temperature of four N-glycosylation site knock-out mutant of the 9D11 binder in the 2 + 1 inverted T-cell bispecific format. All four mutants behaved similarly to the wild-type 9D11 binder

| Clone | Mutation | Yield [mg/L] | Monomer [%] | Aggregation temperature |
|---|---|---|---|---|
| 9D11 | T102N | 1.34 | 97 | 56° |
| 9D11 | T102A | 1.29 | 100 | 56° |
| 9D11 | N100Q | 2.5 | 100 | 56° |
| 9D11 | N100S | 2.05 | 100 | 56° |
| 9D11 | — | 2.6 | 100 | 57° |

The following variants were generated: N100S (N95S); N100Q (N95Q), T102A (T97A) and T102N (T97N) (Kabat numbering indicated in parenthesis) and converted into the T-cell bispecific format. After transient production in HEK293 EBNA cells and purification the different variants were analyzed for target binding and cell killing activity in comparison to the original 9D11 clone.

TABLE 17 primers used for removal of N-glycosylation site in CDR L3 of 9D11 (sequences see below)

| # | Amino acid exchange | Mutagenesis primer |
|---|---|---|
| 1 | N95S | GAB-7735 |
| 2 | N95Q | GAB-7734 |
| 3 | T97A | GAB7736 |
| 4 | T97N | GAB-7737 |

Example 18

Binding and T Cell Mediated Killing with 9D11 a-Glyco Variants

Figure 10:
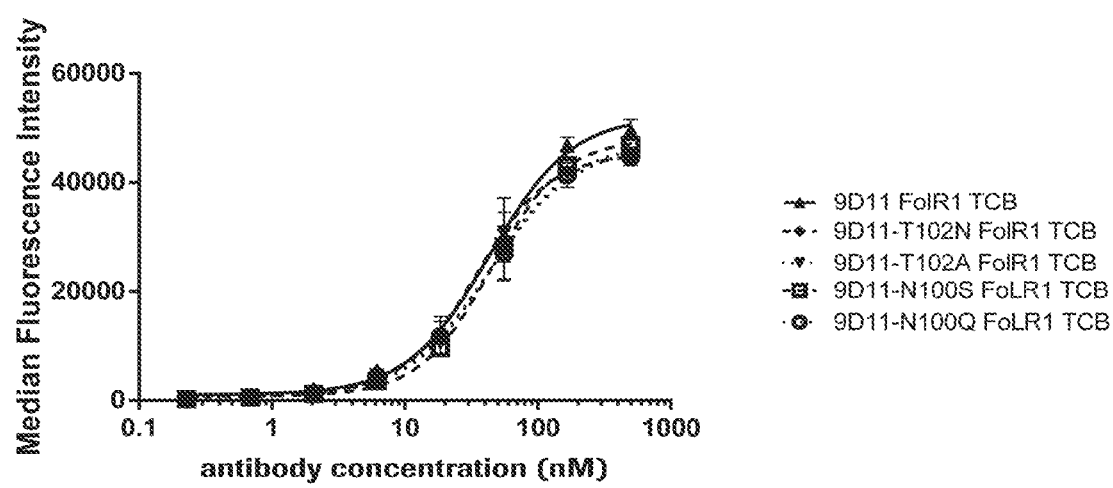
FIG. 10 Binding of 9D11 TCB a-glyco variants to HeLa cells. Binding of 9D11 FolR1 TCB a-glyco variants to Hela cells was compared to binding of the original 9D11 TCB on HeLa cells. The antibodies were detected with a fluorescently labeled anti-human secondary antibody and binding was determined by flow cytometry.

Due to a glycosylation site in the CDRs four different 9D11 variants were produced with a mutation removing the glycosylation site (Example 17). These four variants were tested in comparison to the original 9D11 for binding to FolR1 on HeLa cells (FIG. 10) and induction of tumor cell killing on SKOV3 and HT-29 (FIGS. 11A-B, E-F). None of the variants showed differences in binding or induction of tumor cell killing. In parallel unspecific killing of the FolR1 negative cell lines MKN-45 was addressed (FIGS. 11C-D). Also, no differences between the variants and the original binder could be observed. None of the constructs induced unspecific killing on FoLR1 negative tumor cells.

Example 19

FolR1 Expression on Primary Epithelial Cells

FolR1 is expressed at low levels on primary epithelial cells. Here we wanted to test if these levels are sufficient to induce T cell mediated killing in the presence of the FolR1 TCBs. To test this we used primary human bronchial epithelial cells, primary human choroid plexus epithelial cell, primary human renal cortical epithelial cells and primary human retinal pigment epithelial cells. As positive control either FolR1 positive SKOV3 cells or HT-29 cells were included. First we verified FolR1 expression on the used primary cells and determined the amount of FolR1 binding sites on these cells. Bronchial epithelial cells, renal cortical epithelial cells and retinal pigment epithelial cells express very low but significant levels of FolR1 compared to the levels expressed on tumor cells. The choroid plexus epithelial cells do not express significant levels of FolR1.

TABLE 18

FolR1 binding sites on primary epithelial cells

| Cell line | Binding sites |
|---|---|
| Bronchial epithelium | 492 |
| Choroid plexus epithelium | 104 |
| Renal cortical epithelium | 312 |
| Retinal pigment epithelium | 822 |
| Skov3 | 69'890 |

Figure 12D:
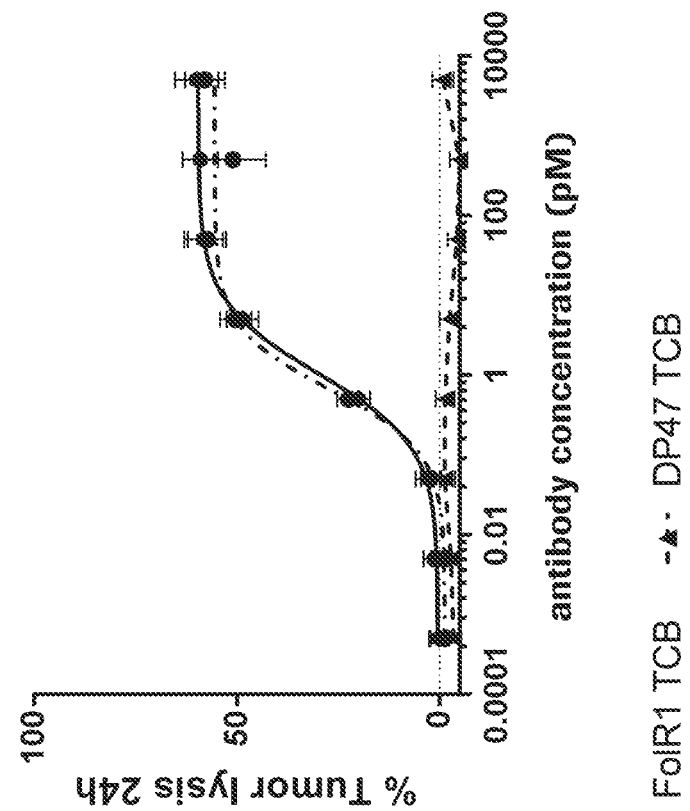
Figure 12C:
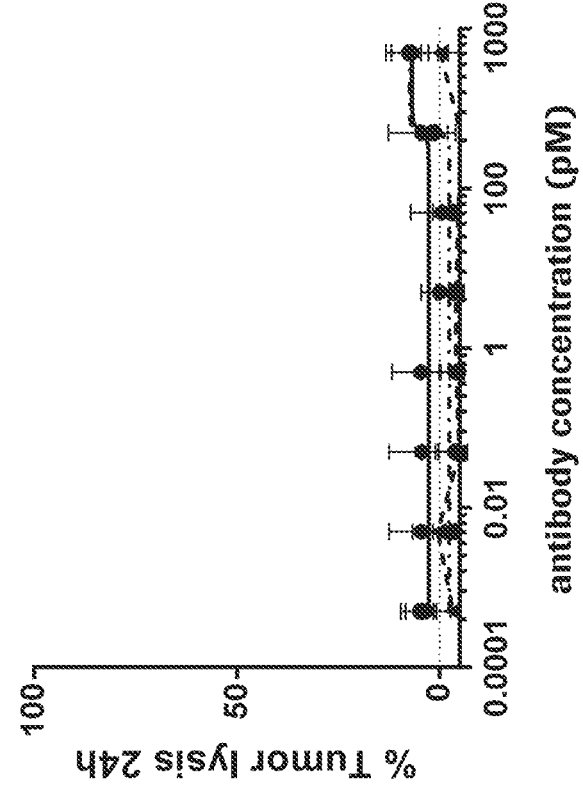
Figure 12E:
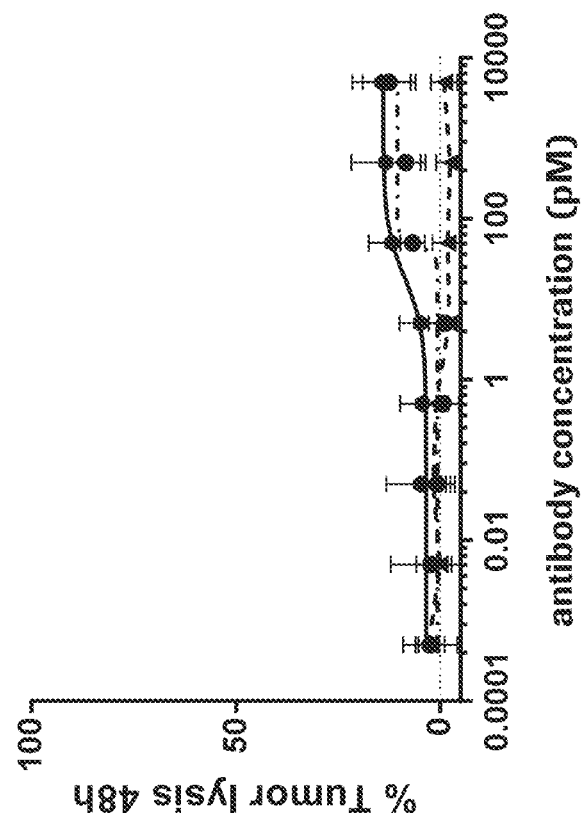
Figure 12F:
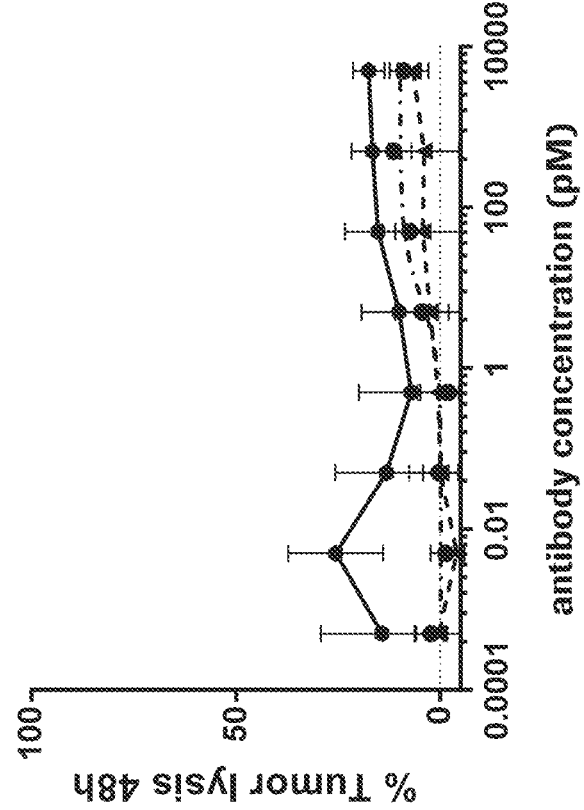
Figure 12H:
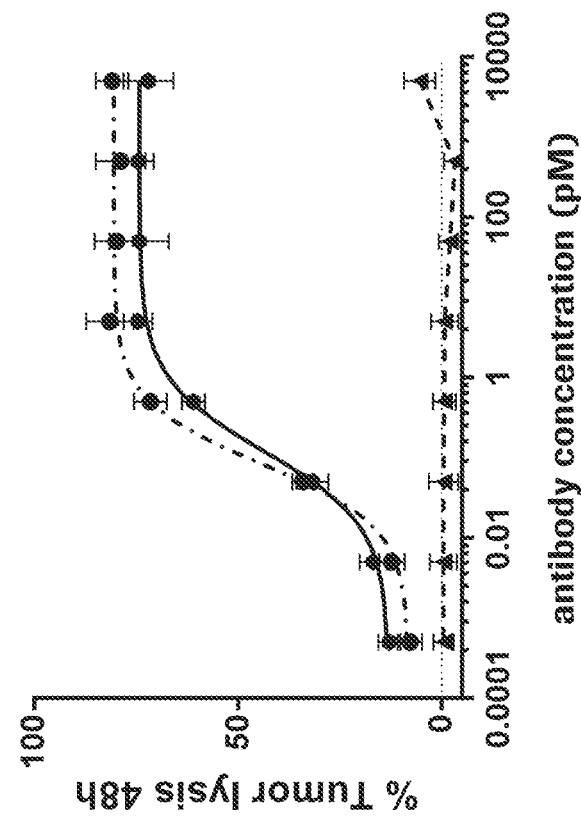
Figure 12G:
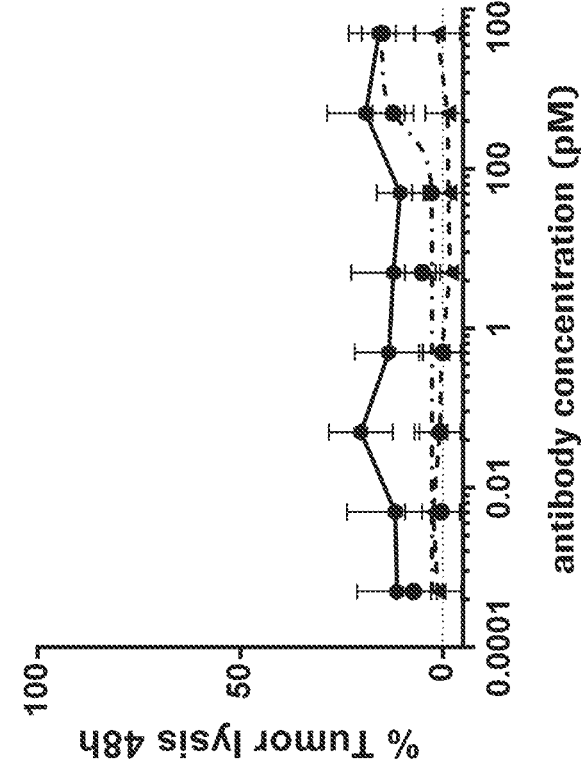
Figure 12M:
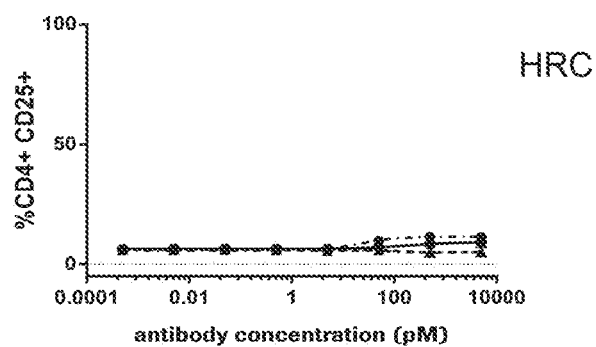
Figure 12N:
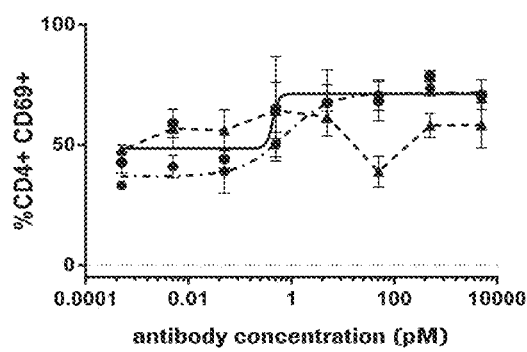
Figure 12O:
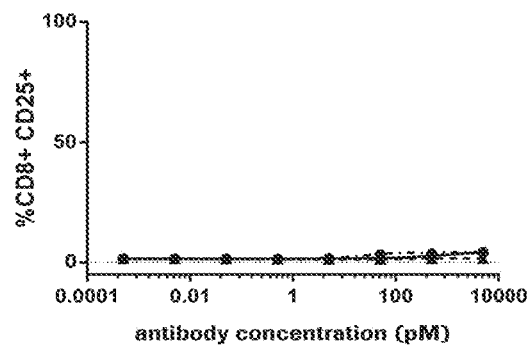
Figure 12P:
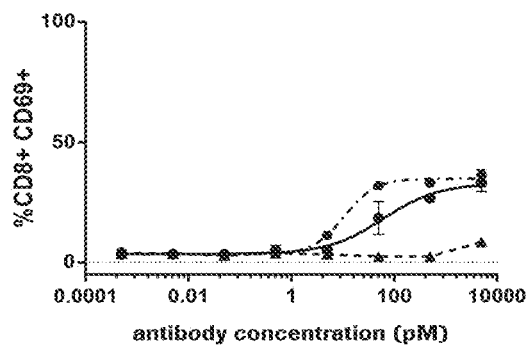
Figure 12Q:
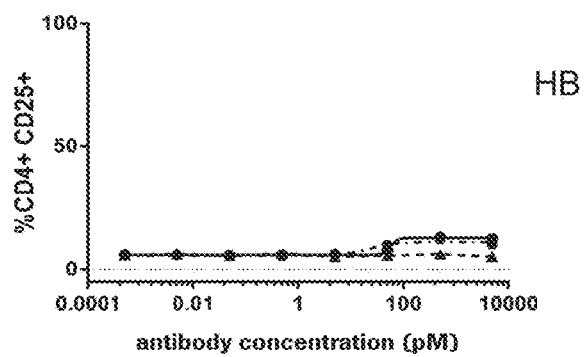
Figure 12R:
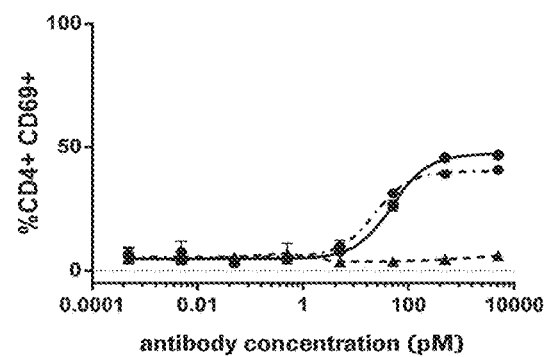
Figure 12S:
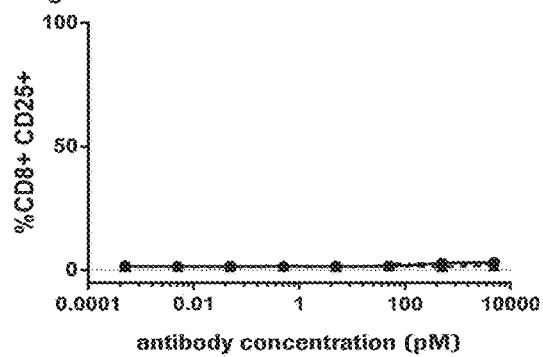
Figure 12T:
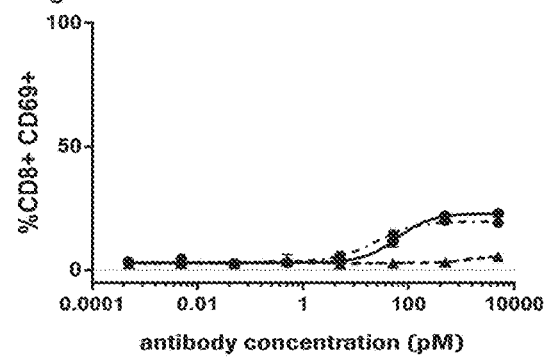
Figure 12U:
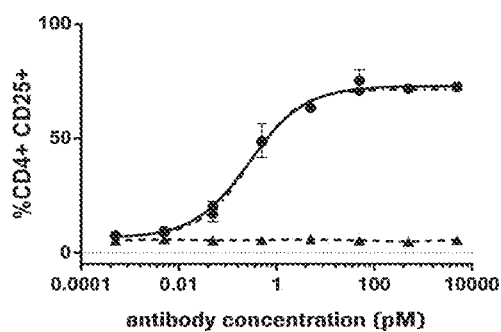
Figure 12V:
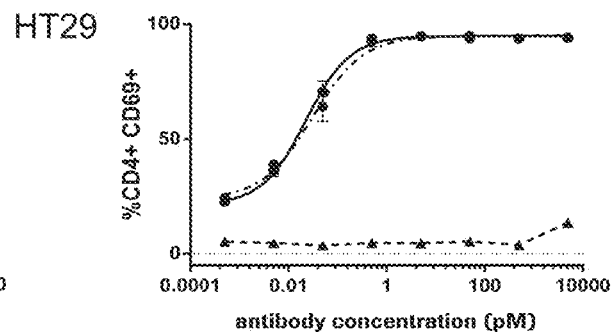
Figure 12W:
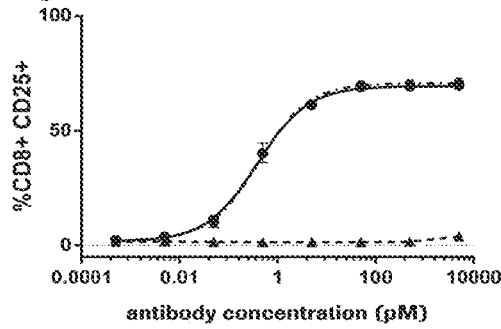
Figure 12X:
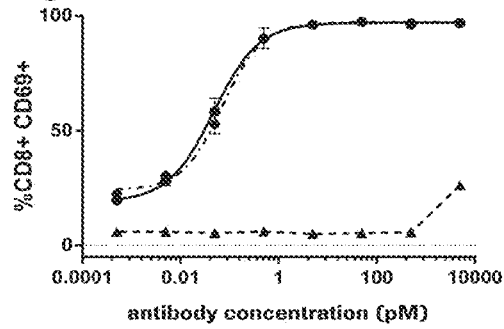
Figure 13A:
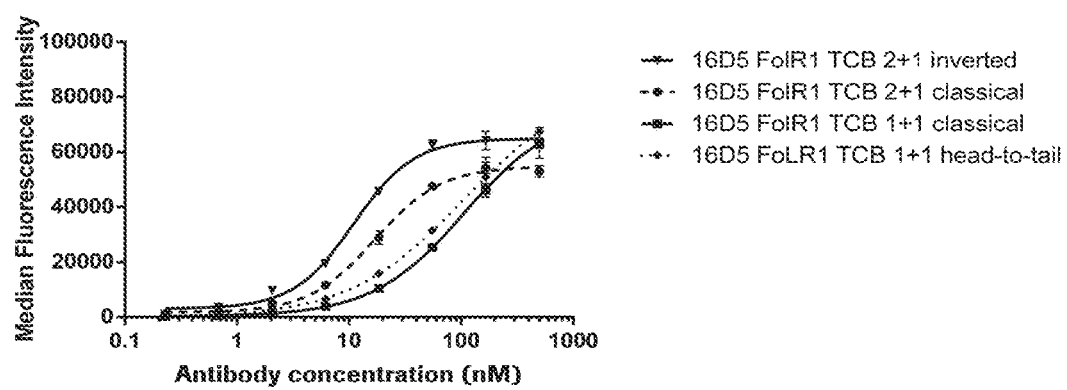
Figure 14A:
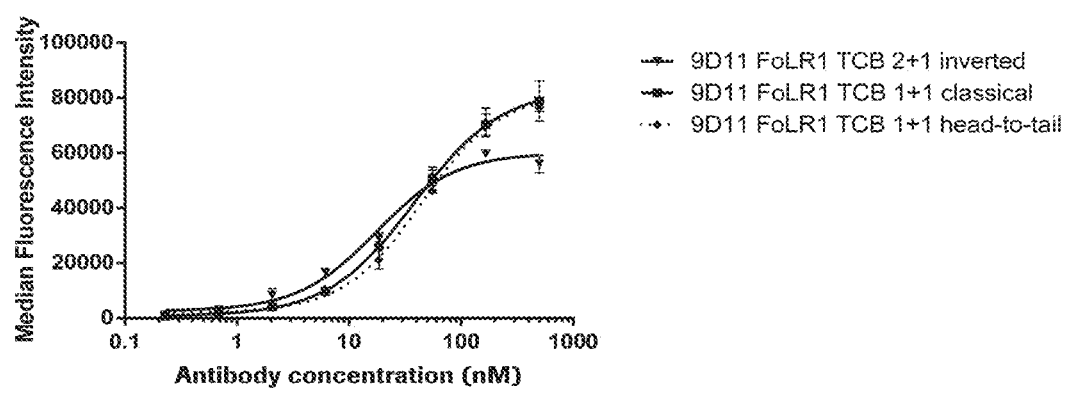
Figure 14C:
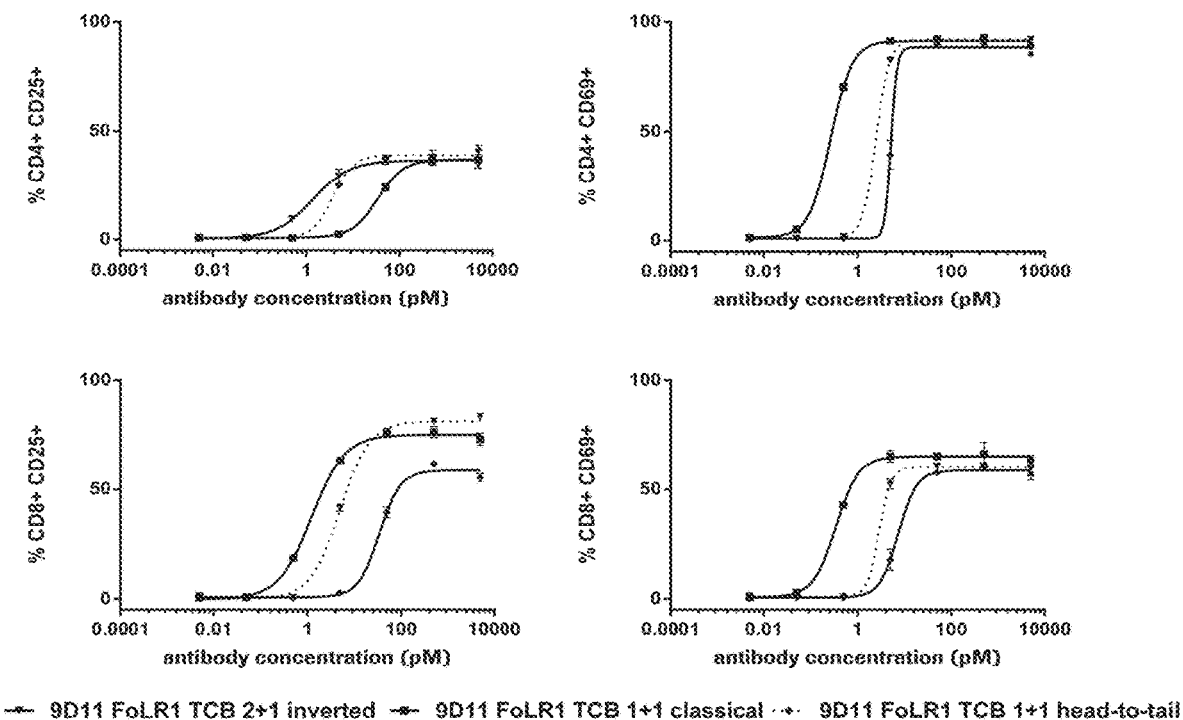

The primary epithelial cells that demonstrated FolR1 expression on the surface were used to address the question if these cells can be killed by T cells in the presence of FoLR1 TCBs. No significant levels of killing could be measured but induction of T cell activation in the presence of retinal pigment epithelial cells, bronchial epithelial cells and renal cortical cells resulting in upregulation of CD25 and CD69 was detected. The strongest activation is seen with retinal pigment epithelial cells resulting in upregulation of CD25 and CD69 both on CD4$^+$ T cells and CD8$^+$ T cells. In the presence of bronchial epithelial cells lower activation of T cells is induced with upregulation of CD69 on CD4$^+$ T cells and CD8$^+$ T cells but very low upregulation of CD25 only on CD4$^+$ T cells but not on CD8$^+$ T cells. The lowest activation of T cells is obtained in the presence of renal epithelial cells with no upregulation of CD25 on CD4 T$^+$ cells and CD8+ T cells and CD69 been only upregulated on CD8+ T cells (FIGS. 12A-X).

Example 20

Comparison of Different TCB Formats Containing Either 16D5 or 9D11 Binder

To determine if the TCB 2+1 inverted format is the most active format with the selected FolR1 binder, different formats containing either 16D5 or 9D11 were produced and compared in target cell binding, T cell mediated killing and T cell activation. The 16D5 binder was tested in the TCB 2+1 inverted (FIG. 1A), TCB 2+1 classical (FIG. 1D), TCB 1+1 classical (FIG. 1C) and TCB 1+1 head-to-tail (FIG. 1B) format; the 9D11 binder was tested in the TCB 2+1 inverted (FIG. 1A), TCB 1+1 classical (FIG. 1C) and TCB 1+1 head-to-tail (FIG. 1B) format.

All constructs were tested for binding to FolR1 on HeLa cells. The molecules bivalent for binding to FolR1 bind stronger compared to the monovalent constructs due to avidity. The difference between the bivalent vs. monovalent constructs is more pronounced for 16D5. The reason might be that due to the lower affinity of 16D5 the avidity effect for this binder is stronger. Between the two 1+1 TCBs there is no significant difference in binding but there is a difference between the two 2+1 constructs. The inverted 2+1 construct binds stronger to FolR1 than the classical 2+1 construct. This indicates that in the classical 2+1 construct the binding to FoLR1 is influenced by the presence of the CD3 Fab whereas in the inverted construct binding is less influenced.

By testing T cell mediated killing with these constructs we could show that stronger binding of the 2+1 inverted TCB in converted into stronger tumor cell killing and T cell activation compared to the 2+1 classical TCB. The 16D5 FolR1 TCB 2+1 classical is only a little bit more active than the respective 1+1 head-to-tail construct. The 1+1 head-to-tail construct is significantly more active than the 1+1 classical construct. This does not reflect the situation seen in binding and might be due to better crosslinking with the head-to-tail construct. Overall tumor cell killing and T cell activation is comparable with all tested constructs, the differences in potency seen with the differences are only in terms of EC50 values. In general it can be concluded that the FolR1 TCB 2+1 inverted independent of the used binder is the preferred format to induce T cell mediated tumor cell killing and T cell activation (see FIGS. 13A-C and FIGS. 14A-C).

TABLE 19

EC50 values of target cell binding and T cell mediated killing with different TCB formats

| Construct | Binding EC50 (nM) | Killing 24 h (pM) | Killing 48 h (pM) |
|---|---|---|---|
| 16D5 FolR1 TCB 2 + 1 inverted | 11.03 | 1.43 | 0.18 |
| 16D5 FolR1 TCB 2 + 1 classical | 17.07 | 5.60 | 2.18 |
| 16D5 FolR1 TCB 1 + 1 classical | 107.3 | n.d. | n.d. |
| 16D5 FoLR1 TCB 1 + 1 head-to-tail | 102.6 | 26.24 | 6.06 |
| 9D11 FoLR1 TCB 2 + 1 inverted | 17.52 | 0.74 | 0.14 |
| 9D11 FoLR1 TCB 1 + 1 classical | 38.57 | 20.92 | n.d. |
| 9D11 FoLR1 TCB 1 + 1 head-to-tail | 44.20 | 4.73 | n.d. |

TABLE 20

EC50 values of T cell activation in the presence of SKOV3 cells with different TCB formats

| Construct | CD4+ CD25+ (%) | CD4+ CD69+ (%) | CD8+ CD25+ (%) | CD8+ CD69+ (%) |
|---|---|---|---|---|
| 16D5 FolR1 TCB 2 + 1 inverted | 1.96 | 0.33 | 2.10 | n.d. |
| 16D5 FolR1 TCB 2 + 1 classical | 13.83 | 3.67 | 12.88 | 4.47 |
| 16D5 FolR1 TCB 1 + 1 classical | 38.54 | n.d. | n.d. | n.d. |
| 16D5 FolR1 TCB 1 + 1 head-to-tail | 17.14 | 7.47 | 25.15 | n.d. |
| 9D11 FolR1 TCB 2 + 1 inverted | 1.41 | 0.27 | 1.24 | 0.35 |
| 9D11 FolR1 TCB 1 + 1 classical | 34.01 | n.d. | 34.39 | 7.40 |
| 9D11 FolR1 TCB 1 + 1 head-to-tail | 3.73 | 2.47 | 4.98 | 2.89 |

Example 21

Tumor Cell Lines and Primary Cells

HeLa cells (CCL-2) were obtained from ATCC and cultured in DMEM with 10% FCS and 2 mM Glutamine, SKOV3 (HTB-77) were obtained from ATCC and cultured in RPMI with 10% FCS and 2 mM Glutamine, OVCAR5 were obtained from NCI and cultured in RPMI with 10% FCS and 2 mM Glutamine, HT-29 (ACC-299) were obtained from DSMZ and cultured in McCoy's 5A medium with 10% FCS and 2 mM Glutamine, MKN-45 (ACC-409) were obtained from DSMZ and cultured in RPMI with 10% FCS and 2 mM Glutamine.

All tested primary epithelial cells were obtained from ScienCell Research Laboratories. Human Bronchial Epithelium Cells (HBEpiC, Catalog Number 3210 were cultured in Bronchial Epithelial Cell Medium (BEpiCM, Cat. No. 3211, ScienCell). Human Colonic Epithelial Cells (HCoEpiC), Catalog Number 2950 were cultured in Colonic Epithelial Cell Medium (CoEpiCM, Cat. No. 2951, ScienCell). Human Retinal Pigment Epithelial Cells (HRPEpiC), Catalog Number 6540 were cultured in Epithelial Cell Medium (EpiCM, Cat. No. 4101, ScienCell). Human Renal Cortical Epithelial Cells (HRCEpiC), Catalog Number 4110, were cultured in Epithelial Cell Medium (EpiCM, Cat. No. 4101, ScienCell). Human Choroid Plexus Epithelial Cells (HCPEpiC), Catalog Number 1310 were cultured in Epithelial Cell Medium (EpiCM, Cat. No. 4101, ScienCell).

Example 22

Target Binding by Flow Cytometry

Target cells as indicated were harvested with Cell Dissociation Buffer, washed with PBS and resuspended in FACS buffer. The antibody staining was performed in a 96 well round bottom plate. Therefore 200,000 cells were seeded per well. The plate was centrifuged for 4 min at 400 g and the supernatant was removed. The test antibodies were diluted in FACS buffer and 20 µl of the antibody solution were added to the cells for 30 min at 4° C. To remove unbound antibody the cells were washed twice with FACS buffer before addition of the diluted secondary antibody (FITC conjugated AffiniPure F(ab')2 fragment goat anti-human IgG, Fcg Fragment, Jackson ImmunoResearch #109-096-098 or PE-conjugated AffiniPure F(ab')2 Fragment goat anti-human IgG Fcg Fragment Specific, Jackson ImmunoResearch #109-116-170. After 30 min incubation on 4° C. unbound secondary antibody was washed away. Before measurement the cells were resuspended in 200 µl FACS buffer and analyzed by flow cytometry using BD Canto II or BD Fortessa.

Example 23

Internalization

The cells were harvested and the viability was determined. The cells were re-suspended in fresh cold medium at 2 Mio cells per ml and the cell suspension was transferred in a 15 ml falcon tube for each antibody. The antibodies that should be tested for internalization were added with a final concentration of 20 µg per ml to the cells. The tubes were incubated for 45 min in the cold room on a shaker. After incubation the cells were washed three times with cold PBS to remove unbound antibodies. 0.2 Mio cells per well were transfer to the FACS plate as time point zero. The labeled cells were re-suspended in warm medium and incubated at 37° C. At the indicated time-points 0.2 Mio cells per well were transferred in cold PBS, washed in plated on the FACS plate. To detect the constructs that remain on the surface the cells were stained with PE-labeled anti-human Fc secondary antibody. Therefore 20 µl of the diluted antibody were added per well and the plate was incubated for 30 min at 4° C. Then the cells were washed twice to remove unbound antibodies and then fixed with 1% PFA to prevent any further internalization. The fluorescence was measured using BD FACS CantoII.

Example 24

QIFIKIT® Analysis

QIFIKIT® contains a series of beads, 10 µm in diameter and coated with different, but well-defined quantities of mouse Mab molecules (high-affinity anti-human CD5, Clone CRIS-1, isotype IgG2a). The beads mimic cells with different antigen densities which have been labeled with a primary mouse Mab, isotype IgG. Briefly, cells were labeled with primary mouse monoclonal antibody directed against the antigen of interest. In a separate test well, cells were labeled with irrelevant mouse monoclonal antibody (isotype control). Then, cells, Set-Up Beads and Calibration Beads were labeled with a fluorescein-conjugated anti-mouse secondary antibody included in the kit. The primary antibody used for labeling of the cells has to be used at saturating concentration. The primary antibody may be of any mouse IgG isotype. Under these conditions, the number of bound primary antibody molecules corresponds to the number of antigenic sites present on the cell surface. The secondary antibody is also used at saturating concentration. Consequently, the fluorescence is correlated with the number of bound primary antibody molecules on the cells and on the beads.

Example 25

T Cell Mediated Tumor Cell Killing and T Cell Activation

Target cells were harvested with Trypsin/EDTA, counted and viability was checked. The cells were resuspended in their respective medium with a final concentration of 300,000 cells per ml. Then 100 µl of the target cell suspension was transferred into each well of a 96-flat bottom plate. The plate was incubated overnight at 37° C. in the incubator to allow adherence of the cells to the plate. On the next day PBMCs were isolated from whole blood from healthy donors. The blood was diluted 2:1 with PBS and overlayed on 15 ml Histopaque-1077 (#10771, Sigma-Aldrich) in Leucosep tubes and centrifuged for 30 min at 450 g without break. After centrifugation the band containing the cells was collected with a 10 ml pipette and transferred into 50 ml tubes. The tubes were filled up with PBS until 50 ml and centrifuged (400 g, 10 min, room temperature). The supernatant was removed and the pellet resuspended in PBS. After centrifugation (300 g, 10 min, room temperature), supernatants were discarded, 2 tubes were pooled and the washing step was repeated (this time centrifugation 350×g, 10 min, room temperature). Afterwards the cells were resuspended and the pellets pooled in 50 ml PBS for cell counting. After counting cells were centrifuged (350 g, 10 min, room temperature) and resuspended at 6 Mio cells per ml in RPMI with 2% FCS and 2 nM Glutamine. Medium was removed from plated target cells and the test antibodies diluted in RPMI with 2% FCS and 2 nM Glutamine were added as well as. 300,000 cells of the effector cell solution were transferred to each well resulting in a E:T ratio of 10:1. To determine the maximal release target cells were lysed with Triton X-100. LDH release was determined after 24 h and 48 h using Cytotoxicity Detection Kit (#1644793, Roche Applied Science). Activation marker upregulation on T cells after tumor cell killing was measured by flow cytometry. Briefly PBMCs were harvested, transferred into a 96 well round bottom plate and stained with CD4 PE-Cy7 (#3557852, BD Bioscience), CD8 FITC (#555634, BD Bioscience), CD25 APC (#555434, BD Bioscience), CD69 PE (#310906, BioLegend) antibodies diluted in FACS buffer. After 30 min incubation at 4° C. the cells were washed twice with FACS buffer. Before measuring the fluorescence using BD Canto II the cells were resuspended in 200 µl FACS buffer.

Example 26

T Cell Activation in Whole Blood

280 µl of fresh blood were added into a 96 well conical deep well plate. Then 20 µl of the diluted TCBs were added to the blood and mixed well by shaking the plate. After 24 h incubation at 37° C. in an incubator the blood was mixed and 35 µl were transferred to a 96 well round bottom plate. Then 20 µl of the antibody staining mix were added consisting of CD4 PE-Cy7 (#3557852, BD Bioscience), CD8 FITC (#555634, BD Bioscience), CD25 APC (#555434, BD Bioscience), CD69 PE (#310906, BioLegend) and CD45 V500 (#560777, BD Horizon) and incubated for 15 min in the dark at room temperature. Before measuring 200 µl of the freshly prepared BD FACS lysing solution (#349202,

Example 27

SDPK (Single Dose Pharmacokinetics) Study of Humanized FOLR1 TCB (Clone 16D5) in Immunodeficient NOD/Shi-scid/IL-2Rγnull (NOG) Mice Female NOD/Shi-scid/IL-2Rγnull (NOG) mice, age 6-7 weeks at start of the experiment (bred at Taconic, Denmark) were maintained under specific-pathogen-free condition with daily cycles of 12 h light/12 h darkness according to committed guidelines (GV-Solas; Felasa; TierschG). The experimental study protocol was reviewed and approved by local government (P 2011/128). After arrival, animals were maintained for one week to get accustomed to the new environment and for observation. Continuous health monitoring was carried out on a regular basis.

Mice were injected i.v. with 10/1/0.1 µg/mouse of the FOLR1 TCB whereas 3 mice were bled per group and time point. All mice were injected with a total volume of 200 µl of the appropriate solution. To obtain the proper amount of the FOLR1 TCB per 200 µl, the stock solutions were diluted with PBS when necessary. Serum samples were collected 5 min, 1h, 3h, 8h, 24h, 48 h, 72h, 96h and 168h after therapy injection.

Figure 15:
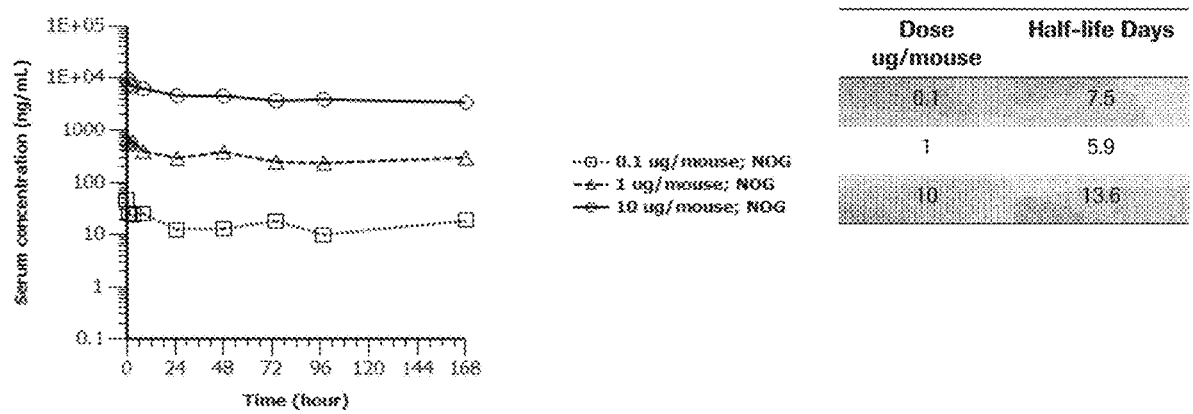
FIG. 15 depicts a PK-profile of FOLR1 TCB in NOG mice for three different doses.

FIG. 15 shows that the 16D5 FOLR1 TCB shows typical and dose proportional IgG-like PK properties in NOG mice with slow clearance.

TABLE 21

| Compound | Dose | Formulation buffer | Concentration (mg/mL) |
|---|---|---|---|
| FOLR1 TCB (16D5) | 10 µg (corresponding to ca. 0.5 mg/kg) | 20 mM Histidine, 140 mM NaCl, pH 6.0 | 5.43 (= stock solution) |
| FOLR1 TCB (16D5) | 1 µg (corresponding to ca. 0.05 mg/kg) | 20 mM Histidine, 140 mM NaCl, pH 6.0 | 5.43 (= stock solution) |
| FOLR1 TCB (16D5) | 0.1 µg (corresponding to ca. 0.005 mg/kg) | 20 mM Histidine, 140 mM NaCl, pH 6.0 | 5.43 (= stock solution) |

Example 28

In Vivo Efficacy of FOLR1 TCB (Clone 16D5) after Human PBMC Transfer in Skov3-Bearing NOG Mice The FOLR1 TCB was tested in the human ovarian carcinoma cell line Skov3, injected s.c. into PBMC engrafted NOG mice.

The Skov3 ovarian carcinoma cells were obtained from ATCC (HTB-77). The tumor cell line was cultured in RPMI containing 10% FCS (Gibco) at 37° C. in a water-saturated atmosphere at 5% $CO_2$. Passage 35 was used for transplantation, at a viability>95%. $5 \times 10^6$ cells per animal were injected s.c. into the right flank of the animals in a total of 100 µl of RPMI cell culture medium (Gibco).

Female NOD/Shi-scid/IL-2Rγnull (NOG) mice, age 6-7 weeks at start of the experiment (bred at Taconic, Denmark) were maintained under specific-pathogen-free condition with daily cycles of 12 h light/12 h darkness according to committed guidelines (GV-Solas; Felasa; TierschG). The experimental study protocol was reviewed and approved by local government (P 2011/128). After arrival, animals were maintained for one week to get accustomed to the new environment and for observation. Continuous health monitoring was carried out on a regular basis.

Figure 16:
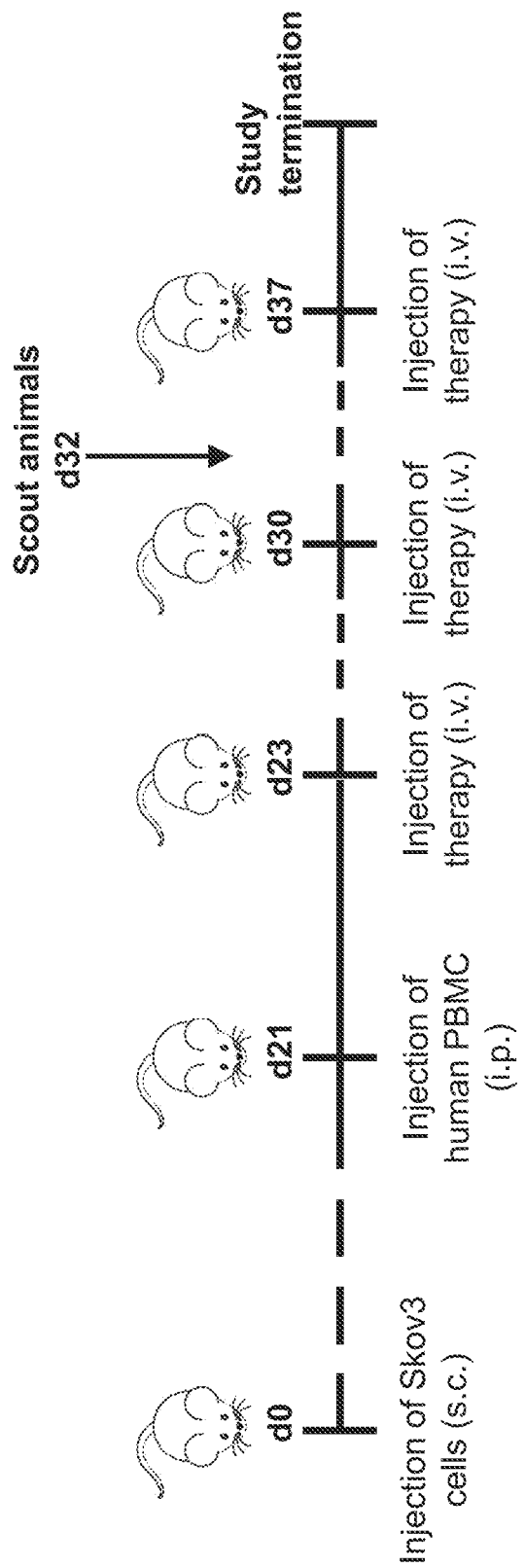
FIG. 16 illustrates an experimental protocol for efficacy study with FOLR1 TCB.

According to the protocol (FIG. 16), mice were injected s.c. on study day 0 with $5 \times 10^6$ of the Skov3. At study day 21, human PBMC of a healthy donor were isolated via the Ficoll method and $10 \times 10^6$ cells were injected i.p. into the tumor-bearing mice. Two days after, mice were randomized and equally distributed in five treatment groups (n=12) followed by i.v. injection with either 10/1/0.1 µg/mouse of the FOLR1 TCB or 10 µg/mouse of the DP47 control TCB once weekly for three weeks. All mice were injected i.v. with 200 µl of the appropriate solution. The mice in the vehicle group were injected with PBS. To obtain the proper amount of TCB per 200 µl, the stock solutions were diluted with PBS when necessary. Tumor growth was measured once weekly using a caliper (FIG. 17) and tumor volume was calculated as followed:

$$T_v: (W^2/2) \times L \text{ (W: Width, L: Length)}$$

Figure 17A:
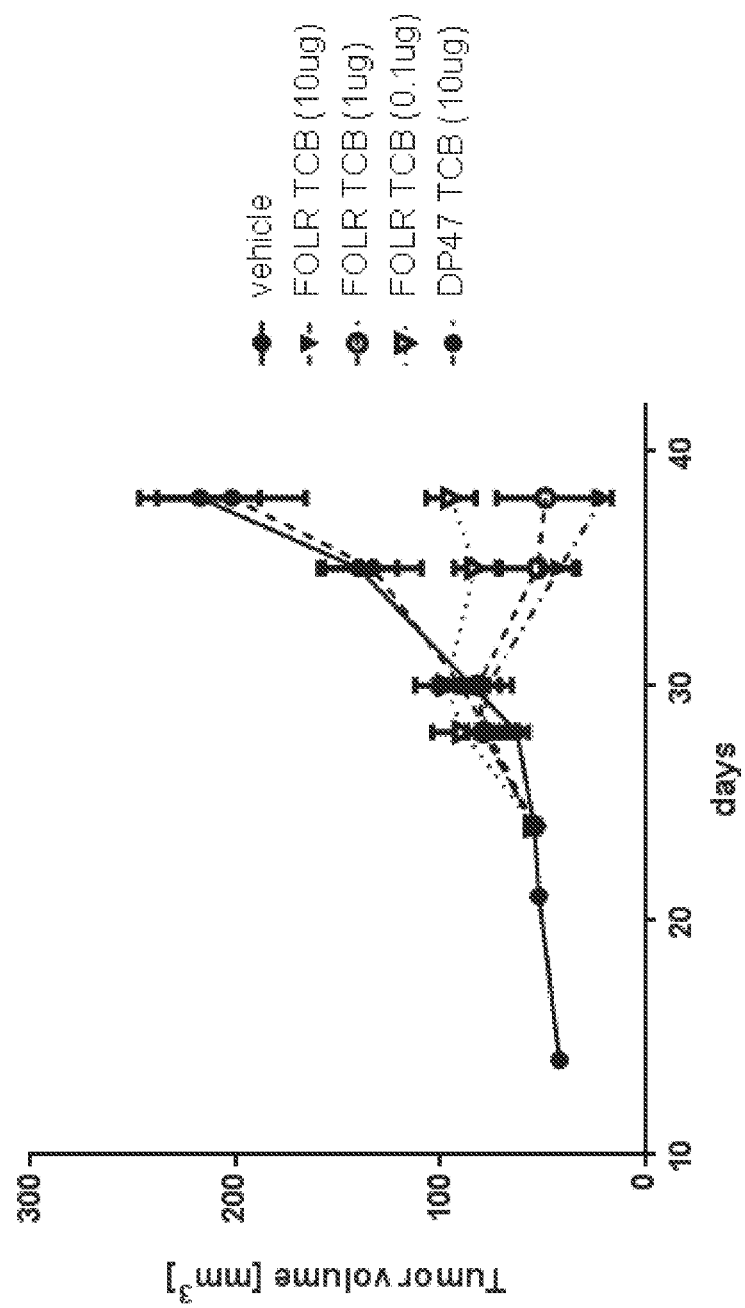
FIGS. 17A-B depict tumor growth curves.
Figure 17B:
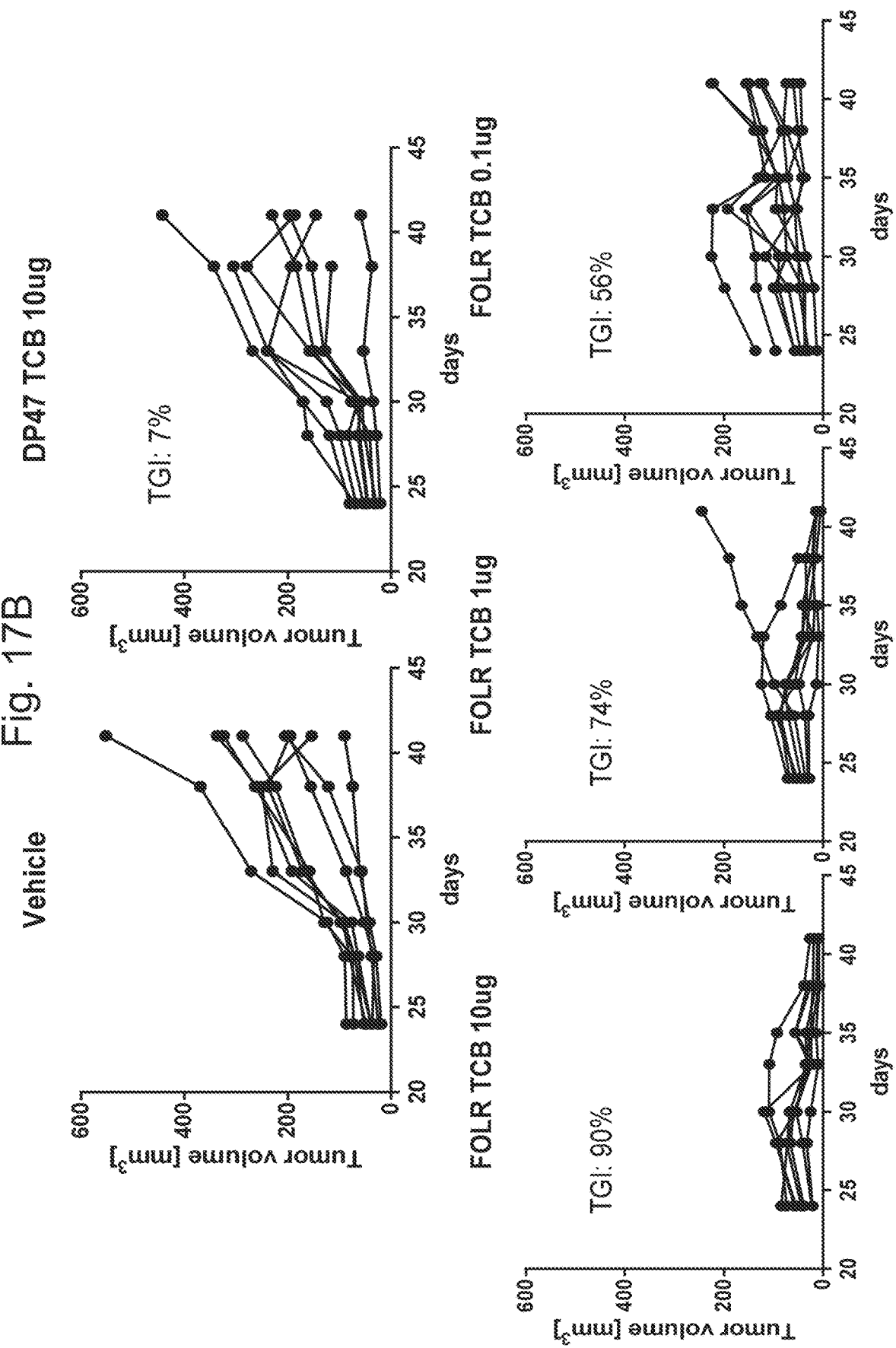

The once weekly injection of the FOLR1 TCB resulted in a dose-dependent anti-tumoral effect. Whereas a dose of 10 µg/mouse and 1 µg/mouse induced tumor shrinkage and 0.1 µg/mouse a tumor stasis (FIG. 17, Table 22). Maximal tumor shrinkage was achieved at a dose of 10 µg/mouse as compared to a non-targeted control DP47 TCB.

TABLE 22

| Compound | Dose | Tumor growth inhibition |
|---|---|---|
| DP47 TCB control TCB | 10 µg (corresponding to ca. 0.5 mg/kg) | 7% |
| FOLR1 TCB (16D5) | 10 µg (corresponding to ca. 0.5 mg/kg) | 90% |
| FOLR1 TCB (16D5) | 1 µg (corresponding to ca. 0.05 mg/kg) | 74% |
| FOLR1 TCB (16D5) | 0.1 µg (corresponding to ca. 0.005 mg/kg) | 56% |

Figure 20A:
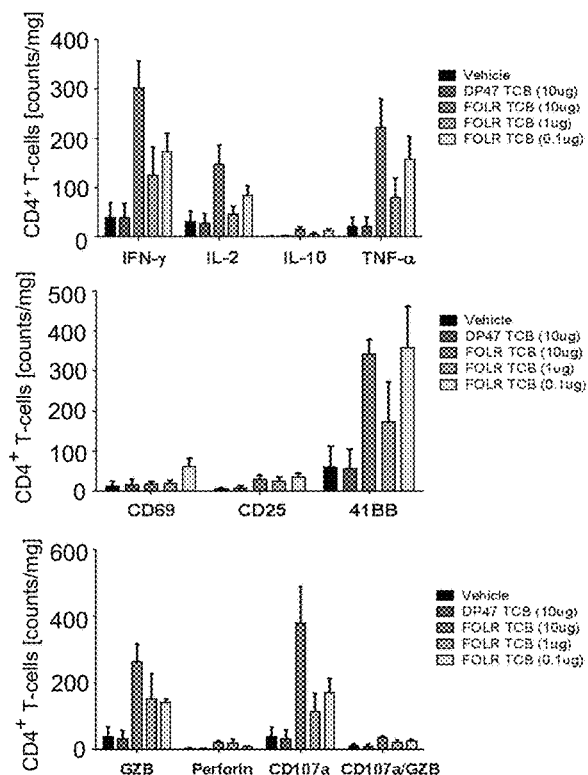
FIGS. 20A-B show FACS analysis for T-cell activation/degranulation and cytokine secretion at study day 32. CD4+ (FIG. 20A) and CD8+ (FIG. 20B) tumor infiltrating T-cells were stained for cytokines, activation and degranulation markers. Displayed are the mean values and SEM of T-cell counts per mg tumor tissue in different treatment groups.
Figure 20B:
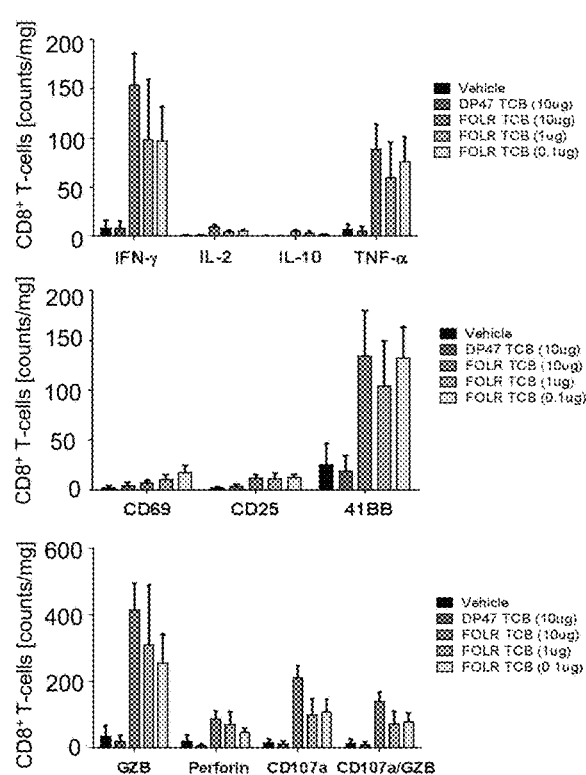

For PD read-outs, three mice per treatment group were sacrificed at study day 32, tumors were removed and single cell suspensions were prepared through an enzymatic digestion with Collagenase V, Dispase II and DNAse for subsequent FACS-analysis (FIGS. 19 and 20). Single cells where either used directly for staining of extracellular antigens and activation markers or were re-stimulated using 5 ng/ml PMA and 500 ng/ml Ionomycin in the presence of a protein transport inhibitor Monensin for 5h in normal culture medium. After re-stimulation, cells were stained for surface antigens, followed by a fixation and permeabilization step. Fix samples were then stained intracellulary for TNF-α, IFN-γ, IL-10 and IL-2 and analyzed by flow cytometry. Same procedure was used for the degranulation of cells, but an anti-CD107a antibody was added during the restimulation period and fixed samples were staining for intracellular perforin and granzyme-B contents. The FACS analysis revealed statistically higher number of infiltrating $CD4^+$ and $CD8^+$ T-cells in the tumor tissue upon treatment with FOLR1 TCB compared to vehicle and untargeted control TCB. Furthermore, higher numbers of TNF-1, IFN-Q and IL-2 producing as well as $perforin^+/granzym-B^+$ $CD4^+$ and CD8+ T-cells were detected in FOLR1 TCB treated tumors. Tumor infiltrating T-cells treated with FOLR1 TCB also showed higher degranulation rates compared to control groups.

Figure 18:
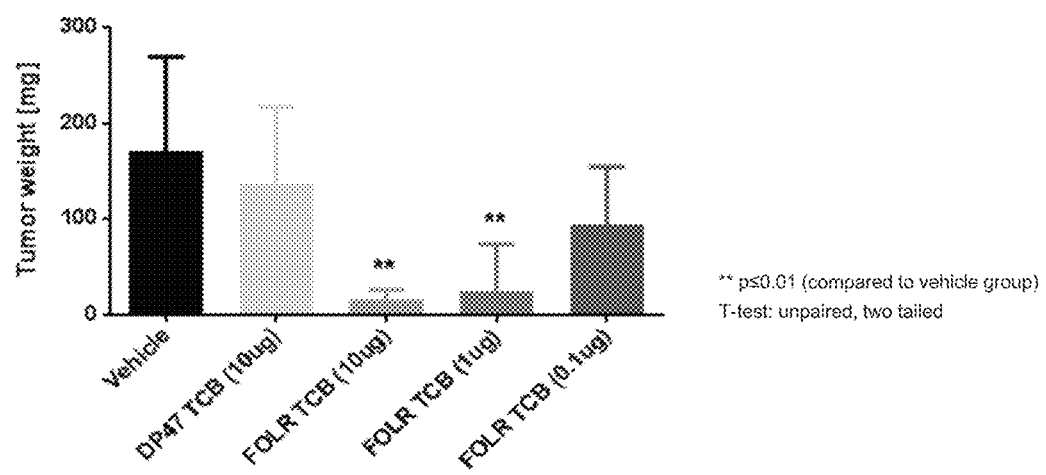
FIG. 18 shows tumor weights at study termination.

At study termination day 38, all animals were sacrificed; tumors were removed and weight (FIG. 18). The weight of the tumors treated with 10 and 1 µg/mouse of the FOLR1 TCB showed a statistically significant difference compared to the control groups.

TABLE 23

| Compound | Dose | Formulation buffer | Concentration (mg/mL) |
|---|---|---|---|
| PBS | | | |
| FOLR1 TCB (16D5) | 10 µg | 20 mM Histidine, 140 mM NaCl, pH 6.0 | 3.88 (= stock solution) |
| FOLR1 TCB (16D5) | 1 µg | 20 mM Histidine, 140 mM NaCl, pH6.0 | 3.88 (= stock solution) |
| FOLR1 TCB (16D5) | 0.1 µg | 20 mM Histidine, 140 mM NaCl, pH6.0 | 3.88 (= stock solution) |
| DP47 TCB | 10 µg | 20 mM Histidine, 140 mM NaCl, pH6.0 | 4.35 (= stock solution) |

Example 29

Generation of a Bispecific FolR1/CD3-kappa-lambda Antibody

To generate a bispecific antibody (monovalent for each antigen) that simultaneously can bind to human CD3 and human folate receptor alpha (FolR1) without using any hetero-dimerization approach (e.g. knob-into-hole technology), a combination of a common light chain library with the so-called CrossMab technology was applied: The variable region of the humanized CD3 binder (CH2527_VL7_46/13) was fused to the CH1 domain of a standard human IgG1 antibody to form the VLVH crossed molecule (fused to Fc) which is common for both specificities. To generate the crossed counterparts (VHCL), a CD3 specific variable heavy chain domain (CH2527_VH_23/12) was fused to a constant human κ light chain whereas a variable heavy chain domain specific for human FolR1 (clone 16D5, isolated from common light chain library) was fused to a constant human λ light chain. This enables the purification of the desired bispecific antibody by applying subsequent purification steps with KappaSelect and LambdaFabSelect columns (GE Healthcare) to remove undesired homodimeric antibodies.

All antibody expression vectors were generated using standard recombinant DNA technology as described in Sambrook, J. et al., Molecular cloning: A laboratory manual; Cold Spring Harbor Laboratory Press, Cold Spring Harbor, New York, 1989. Molecular biological reagents were used according the manufacturer's recommendations. Genes or gene fragments were either amplified by polymerase chain reaction (PCR) or generated from synthetic oligonucleotides at Geneart AG (Regensburg, Germany) by automated gene synthesis. PCR-amplified or subcloned DNA fragments were confirmed by DNA sequencing (Synergene GmbH, Switzerland). Plasmid DNA was transformed into and amplified in suitable E. coli host strains for preparation of transfection-grade plasmid DNA using standard Maxiprep kits (Qiagen). For production of the bispecific molecules HEK293 EBNA cells were transfected with plasmids encoding the respective genes using a standard polyethlenimine (PEI) based method. The used plasmid ratio of the three expression vectors was 1:1:1. Transfected cells were cultivated for 7 days before supernatants were harvested for purification. The bispecific FolR1/CD3-kappa-lambda antibodies were produced and purified as follows.

1. Transient Transfection and Production

The kappa-lambda bispecific antibody was transiently produced in HEK293 EBNA cells using a PEI mediated transfection procedure for the required vectors as described below. HEK293 EBNA cells were cultivated in suspension serum free in CD CHO culture medium. For the production in 500 ml shake flask 400 million HEK293 EBNA cells were seeded 24 hours before transfection (for alternative scales all amounts were adjusted accordingly). For transfection cells were centrifuged for 5 min by 210×g, supernatant is replaced by pre-warmed 20 ml CD CHO medium. Expression vectors were mixed in 20 ml CD CHO medium to a final amount of 200 µg DNA. After addition of 540 µl PEI solution is vortexed for 15 s and subsequently incubated for 10 min at room temperature. Afterwards cells were mixed with the DNA/PEI solution, transferred to a 500 ml shake flask and incubated for 3 hours by 37° C. in an incubator with a 5% $CO_2$ atmosphere. After incubation time 160 ml F17 medium was added and cell were cultivated for 24 hours. One day after transfection 1 mM valporic acid and 7% Feed 1 was added. After 7 days cultivation supernatant was collected for purification by centrifugation for 15 min at 210×g, the solution is sterile filtered (0.22 µm filter) and sodium azide in a final concentration of 0.01% w/v was added, and kept at 4° C.

2. Purification

The kappa-lambda bispecific antibody was purified in three steps, using an affinity step specific for kappa light chains, followed by an affinity step specific for lambda light chains and finally by a size exclusion chromatography step for removal of aggregates. The supernatant obtained from transient production was adjusted to pH 8.0 (using 2 M TRIS pH 8.0) and applied to Capture Select kappa affinity matrix, or HiTrap KappaSelect, GE Healthcare, column volume (cv)=1 ml, equilibrated with 5 column volumes (cv) buffer A (50 mM Tris, 100 mM glycine, 150 mM NaCl, pH 8.0). After washing with 15 cv of buffer A, the protein was eluted using a pH gradient to buffer B (50 mM Tris, 100 mM glycine, 150 mM NaCl, pH 2.0) over 25 cv. Fractions containing the protein of interest were pooled and the pH of the solution was adjusted to pH 8.0 (using 2 M Tris pH 8.0). The neutralized pooled fractions were applied to Capture Select lambda affinity matrix (now: HiTrap LambdaFabSelect, GE Healthcare, column volume (cv)=1 ml) equilibrated with 5 column volumes (cv) buffer A (50 mM Tris, 100 mM glycine, 150 mM NaCl, pH 8.0). After washing with 15 cv of buffer A, the protein was eluted using a pH gradient to buffer B (50 mM Tris, 100 mM glycine, 150 mM NaCl, pH 2.0) over 25 cv. Fractions containing the protein of interest were pooled and the pH of the solution was adjusted to pH 8.0 (using 2 M Tris pH 8.0). This solution was concentrated using ultra-concentrators (Vivaspin 15R 30.000 MWCO HY, Sartorius) and subsequently applied to a Superdex™ 200 10/300 GL (GE Healthcare) equilibrated with 20 mM Histidine, pH 6.0, 140 mM NaCl, 0.01% Tween-20. The pooled fractions after size exclusion were again concentrated using ultra-concentrators (Vivaspin 15R 30.000 MWCO HY, Sartorius).

The protein concentration was determined by measuring the optical density (OD) at 280 nm, using the molar extinction coefficient calculated on the basis of the amino acid sequence. Purity and molecular weight of the constructs were analyzed by SDS capillary electrophoresis in the presence and absence of a reducing agent following the manufacturer instructions (instrument Caliper LabChipGX, Perkin Elmer). Only small amounts of protein could be purified with a final yield of 0.17 mg/L.

Example 30

T cell mediated killing with bispecific FolR1/CD3-kappa-lambda antibody Activity of kappa lambda FolR1 TCB was tested on SKOV3 cells in the presence of freshly isolated PBMCs. As negative control DP47 TCB was included. T cell mediated killing of SKOV3 cells was determined after 24 h and 48 h by LDH release. After 48 h the T cells were harvested and CD69 and CD25 upregulation on CD4 T cells and CD8 T cells was measured by flow cytometry.

The kappa lambda FolR1 construct induces killing of SKOV3 cells in a concentration dependent manner which is accompanied by CD69 and CD25 upregulation both on CD4 T cells and on CD8 T cells.

Figure 21A:
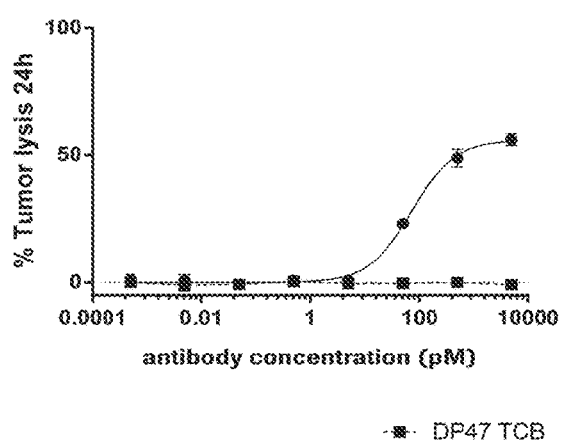
FIGS. 21A-B show percent tumor lysis. SKOV3 cells were incubated with PBMCs in the presence of either kappa lambda FoLR1 TCB or DP47 TCB. After 24 h (FIG. 21A) and 48 h (FIG. 21B) killing of tumor cells was determined by measuring LDH release
Figure 21B:
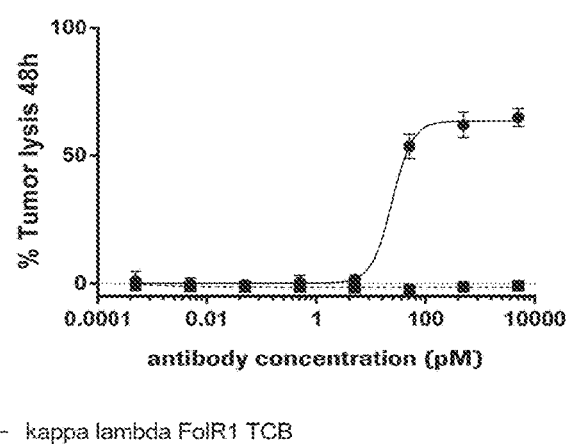
Figure 22A:
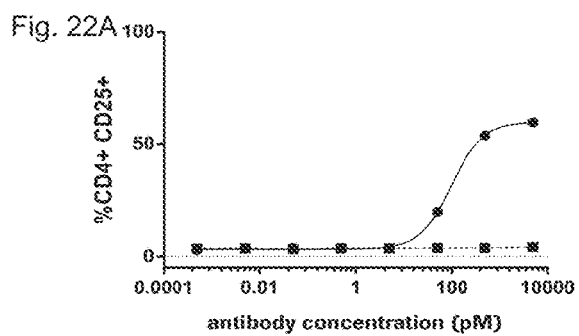
FIGS. 22A-D show CD25 and CD69 upregulation on CD4 T cells. SKOV3 cells were incubated with PBMCs in the presence of either kappa lambda FoLR1 TCB or DP47 TCB. After 48 h CD25 and CD69 upregulation on CD4 T cells (FIGS. 22A-B) and CD8 T cells (FIGS. 22C-D) was measured by flow cytometry.
Figure 22B:
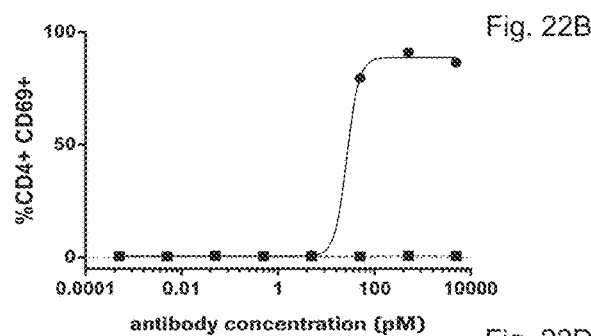
Figure 22C:
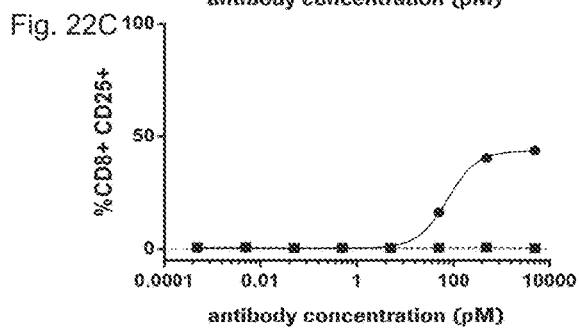
Figure 22D:
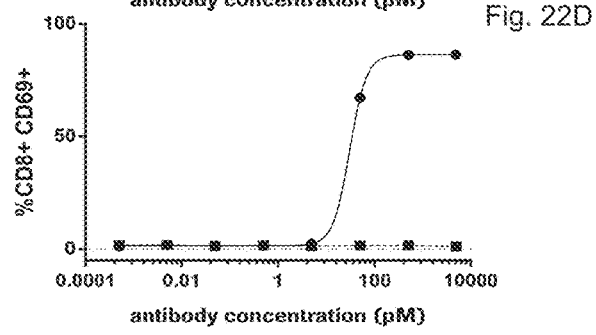

SKOV3 cells were incubated with PBMCs in the presence of either kappa lambda FoLR1 TCB or DP47 TCB. After 24 h and 48 h killing of tumor cells was determined by measuring LDH release (FIG. 21). SKOV3 cells were incubated with PBMCs in the presence of either kappa lambda FoLR1 TCB or DP47 TCB. After 48 h CD25 and CD69 upregulation on CD4 T cells and CD8 T cells was measured by flow cytometry (FIG. 22).

Example 31

Biochemical Characterization of 16D5 and 36F2 FolR1 Binders by Surface Plasmon Resonance Binding of anti-FolR1 16D5 in different monovalent or bivalent T-cell bispecific formats and of anti-FolR1 36F2 as IgG or as T-cell bispecific to recombinant human, cynomolgus and murine folate receptor 1 (all as Fc fusions) was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, GE Healthcare).

1. Molecules Tested

The molecules used for affinity and avidity determination are described in Table 24.

TABLE 24

Name and description of the 6 constructs used in SPR analysis

| Name | Description |
|---|---|
| 16D5 TCB | 2 + 1 T-cell bispecific, inverted format (common light chain) |
| 16D5 TCB classical | 2 + 1 T-cell bispecific, classical format (common light chain) |
| 16D5 TCB 1 + 1 | 1 + 1 T-cell bispecific (common light chain) |
| 16D5 TCB 1 + 1 HT | 1 + 1 T-cell bispecific head-to-tail (common light chain) |
| 36F2 IgG | Human IgG1 with P329G LALA |
| 36F2 TCB | 2 + 1 T-cell bispecific, inverted format, crossfab |

2. Avidity to Folate Receptor 1

The avidity of the interaction between the anti-FolR1 IgG or T cell bispecifics and the recombinant folate receptors was determined as described below (Table 25).

Recombinant biotinylated monomeric Fc fusions of human, cynomolgus and murine Folate Receptor 1 (FolR1-Fc) were directly coupled on a SA chip using the standard coupling instruction (Biacore, GE Healthcare). The immobilization level was about 300-400 RU. The anti-FolR1 IgGs or T cell bispecifics were passed at a concentration range from 3.7 to 900 nM with a flow of 30 µL/minutes through the flow cells over 180 seconds. The dissociation was monitored for 240 or 600 seconds. The chip surface was regenerated after every cycle using a double injection of 30 sec 10 mM Glycine-HCl pH 2. Bulk refractive index differences were corrected for by subtracting the response obtained on reference flow cell immobilized with recombinant biotinylated murine CD134 Fc fusion. The binding curves resulting from the bivalent binding of the IgG or T cell bispecifics were approximated to a 1:1 Langmuir binding (even though it is a 1:2 binding) and fitted with that model to get an apparent $K_D$ representing the avidity of the bivalent binding. The apparent avidity constants for the interactions were derived from the rate constants of the fitting using the Bia Evaluation software (GE Healthcare). For the 1+1 T cell bispecifics format the interaction is a real 1:1 and the $K_D$ represents affinity since there is only one FolR1 binder in this construct.

TABLE 25

Bivalent binding (avidity with apparent KD) of anti-FolR1 16D5 and 36F2 as IgG or as T-cell bispecifics (TCB) on human, cyno and murine FolR1.

| Analyte | Ligand | ka (1/Ms) | kd (1/s) | Apparent KD |
|---|---|---|---|---|
| 36F2 IgG | huFolR1 | 2.07E+06 | 1.3E-02 | 6 nM |
|  | cyFolR1 | 2.78E+06 | 1.75E-02 | 6 nM |
|  | muFolR1 | 4.28E+05 | 8.23E-04 | 2 nM |
| 36F2 TCB | huFolR1 | 2.45E+06 | 9.120E-03 | 4 nM |
|  | cyFolR1 | 4.31E+06 | 1.45E-02 | 3 nM |
|  | muFolR1 | 6.97E+05 | 9.51E-04 | 1 nM |
| 16D5 TCB | huFolR1 | 1.57E+05 | 3.92E-04 | 3 nM |
|  | cyFolR1 | 2.01E+05 | 3.81E-04 | 2 nM |
| 16D5 TCB classical | huFolR1 | 2.04E+05 | 1.84E-04 | 0.9 nM |
|  | cyFolR1 | 2.50E+05 | 3.05E-04 | 1 nM |
| 16D5 TCB 1 + 1 HT | huFolR1 | 5.00E+04 | 2.25E-03 | 45 nM |
|  | cyFolR1 | 5.75E+04 | 4.10E-03 | 70 nM |
| 16D5 TCB 1 + 1 | huFolR1 | 3.65E+04 | 2.04E-03 | 56 nM |
|  | cyFolR1 | 4.09E+04 | 3.60E-03 | 90 nM |

3. Affinity to Folate Receptor 1

The affinity of the interaction between the anti-FolR1 IgG or T cell bispecifics and the recombinant folate receptors was determined as described below (Table 26).

For affinity measurement, direct coupling of around 12000 resonance units (RU) of the anti-human Fab specific antibody (Fab capture kit, GE Healthcare) was performed on a CM5 chip at pH 5.0 using the standard amine coupling kit (GE Healthcare). Anti-FolR1 IgG or T cell bispecifics were captured at 20 nM with a flow rate of 10 µl/min for 40 sec, the reference flow cell was left without capture. Dilution series (12.3 to 3000 nM) of human, cyno or murine Folate Receptor 1 Fc fusion were passed on all flow cells at 30 µl/min for 240 sec to record the association phase. The dissociation phase was monitored for 300 s and triggered by switching from the sample solution to HBS-EP. The chip surface was regenerated after every cycle using a double injection of 60 sec 10 mM Glycine-HCl pH 1.5. Bulk refractive index differences were corrected for by subtracting the response obtained on the reference flow cell 1. The affinity constants for the interactions were derived from the rate constants by fitting to a 1:1 Langmuir binding using the Bia Evaluation software (GE Healthcare).

TABLE 26

Monovalent binding (affinity) of anti-FolR1 16D5 and 36F2 as IgG or as T-cell bispecifics (TCB) on human, cyno and murine FolR1.

| Analyte | Ligand | ka (1/Ms) | kd (1/s) | KD |
|---|---|---|---|---|
| 36F2 IgG | huFolR1 | 9.10E+04 | 6.65E-02 | 730 nM |
| | cyFolR1 | 1.02E+05 | 5.78E-02 | 570 nM |
| | muFolR1 | 8.32E+04 | 1.78E-02 | 210 nM |
| 36F2 TCB | huFolR1 | 5.94E+04 | 6.13E-02 | 1000 nM |
| | cyFolR1 | 6.29E+04 | 5.42E-02 | 860 nM |
| | muFolR1 | 5.68E+04 | 1.75E-02 | 300 nM |
| 16D5 TCB | huFolR1 | 2.23E+04 | 7.33E-04 | 33 nM |
| | cyFolR1 | 1.57E+04 | 1.60E-03 | 100 nM |
| 16D5 TCB classical | huFolR1 | 1.03E+04 | 7.59E-04 | 74 nM |
| | cyFolR1 | 9.18E+03 | 1.61E-03 | 175 nM |
| 16D5 TCB 1 + 1 HT | huFolR1 | 2.05E+04 | 7.08E-04 | 35 nM |
| | cyFolR1 | 1.67E+04 | 1.53E-03 | 92 nM |
| 16D5 TCB 1 + 1 | huFolR1 | 1.43E+04 | 9.91E-04 | 69 nM |
| | cyFolR1 | 1.20E+04 | 1.80E-03 | 150 nM |

The affinity (monovalent binding) to human and cyno FolR1-Fc of 36F2 TCB is similar and around 1000 nM for both, whereas the affinity to murine FolR1-Fc is slightly better and around 300 nM. The 36F2 can be used in murine and primate models, there is no need for a surrogate.

The avidity (apparent $K_D$) of 36F2 TCB to human FolR1 is around 30 times lower than the affinity of the 16D5 TCB to human FolR1. In the bivalent format, 36F2 TCB is in the low nanomolar range, whereas 16D5 TCB is in the low picomolar range (1000 fold difference).

FolR1 is expressed on tumor cells overexpressed, at intermittent and high levels, on the surface of cancer cells in a spectrum of epithelial malignancies, including ovarian, breast, renal, colorectal, lung and other solid cancers and is also expressed on the apical surface of a limited subset of polarized epithelial cells in normal tissue. These non-tumorous, normal cells express FolR1 only at low levels, and include, e.g., bronchiolal epithelial cells on alveolar surface, renal cortical luminal border of tubular cells, retinal pigment epithelium (basolateral membrane) and choroid plexus.

16D5 TCB binds to normal tissues cells expressing low amounts of FolR1 which results in their T cell mediated killing. This might, at least in part, account for limited tolerance observed at 10 µg/kg in cynomolgus monkeys. The inventors wanted to determine if lowering the affinity of the T cell bispecific molecule could increase the differentiation between high and low target density tissues and, thereby, lower toxicity by making use of bivalent binding and avidity. Low affinity binders are ordinarily not selected as suitable candidates for further analysis because low affinity is often associated with low potency and efficacy. Nevertheless, the low affinity FolR1 binder 36F2 was developed in several formats and characterized for its biological properties. For the 36F2 used in the bivalent T cell bispecific format the avidity effect (difference between monovalent and bivalent binding) is around 250 fold (1000 nM versus 4 nM). At low target density the affinity defined the interaction and with 1000 nM led to a low potency of the TCB. However, at high target density the molecule's avidity comes into play and with 4 nM led to a high activity of the TCB (see Example 32).

In an alternatively approach, the inventors generated monovalent formats of 16D5 and low affinity variant of 16D5 (affinity about 10-40 nM) in a bivalent format. The 16D5 binder used in a monovalent format (1+1) has an affinity of about 50 nM. The differentiation between high and low target density tissues can be better achieved by taking advantage of the avidity effect.

Example 32

T-Cell Killing of SKov-3 Cells Induced by 36F2 TCB, Mov19 TCB and 21A5 TCB

T-cell killing mediated by 36F2 TCB, Mov19 TCB and 21A5 TCB was assessed on SKov-3 cells (medium FolR1). Human PBMCs were used as effectors and the killing was detected at 24 h and 48 h of incubation with the bispecific antibodies. Briefly, target cells were harvested with Trypsin/EDTA, washed, and plated at density of 25 000 cells/well using flat-bottom 96-well plates. Cells were left to adhere overnight. Peripheral blood mononuclear cells (PBMCs) were prepared by Histopaque density centrifugation of enriched lymphocyte preparations (buffy coats) obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and stored in RPMI1640 medium containing 10% FCS and 1% L-alanyl-L-glutamine (Biochrom, K0302) at 37° C., 5% CO2 in cell incubator until further use (no longer than 24 h). For the killing assay, the antibody was added at the indicated concentrations (range of 0.005 pM-5 nM in triplicates). PBMCs were added to target cells at final E:T ratio of 10:1. Target cell killing was assessed after 24 h and 48 h of incubation at 37° C., 5% $CO_2$ by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct.

Figure 23A:
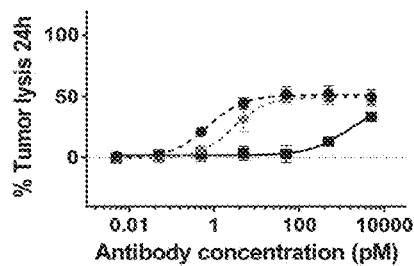
FIGS. 23A-B show percent tumor lysis. T-cell killing of SKov-3 cells (medium FolR1) induced by 36F2 TCB, Mov19 TCB and 21A5 TCB after 24 h (FIG. 23A) and 48 h (FIG. 23B) of incubation (E:T=10:1, effectors human PBMCs).
Figure 23B:
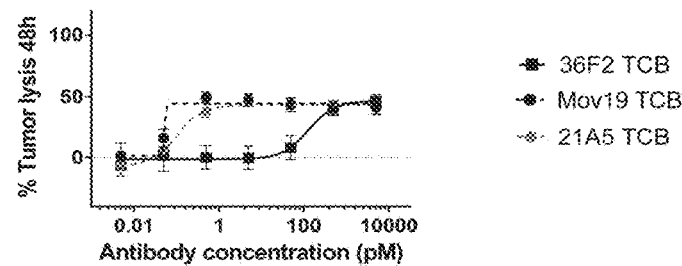

The results show that the killing induced by 36F2 is strongly reduced in comparison to Mov19 TCB and 21A5 TCB (FIGS. 23A-B). The EC50 values related to killing assays, calculated using GraphPadPrism6 are summarized in Table 27.

TABLE 27

EC50 values (pM) for T-cell mediated killing of FolR1-expressing SKov-3 cells induced by 36F2 TCB, Mov19 TCB and 21A5 TCB.

| | EC50 [pM] | |
|---|---|---|
| Antibody | 24 h | 48 h |
| 36F2 TCB | 1406.07* | 134.5 |
| Mov19 TCB | 0.75 | 0.05 |
| 21A5 TCB | 2.83 | 0.10 |

*curve did not reach saturation, value is hypothetical

Example 33

T-Cell Killing Induced by 36F2 TCB and 16D5 TCB in Different Monovalent and Bivalent T-Cell Bispecific Formats T-cell killing mediated by 36F2 TCB, 16D5 TCB, 16D5 TCB classical, 16D5 TCB 1+1 and 16D5 TCB HT antibodies of Hela (high FolR1, about 2 million copies, Table 14, FIG. 27), Skov-3 (medium FolR1, about 70000-90000 copies, Table 14, FIG. 27) and HT-29 (low FolR1, about 10000, Table 14, FIG. 27) human tumor cells was assessed. DP47 TCB antibody was included as negative control. Human PBMCs were used as effectors and the killing was detected at 24 h of incubation with the bispecific antibody. Briefly, target cells were harvested with Trypsin/EDTA, washed, and plated at density of 25 000 cells/well using flat-bottom 96-well plates. Cells were left to adhere overnight. Peripheral blood mononuclear cells (PBMCs) were prepared by Histopaque density centrifugation of enriched lymphocyte preparations (buffy coats) obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and stored in RPM11640 medium containing 10% FCS and 1% L-alanyl-L-glutamine (Biochrom, K0302) at 37° C., 5% CO2 in cell incubator until further use (no longer than 24 h). For the killing assay, the antibody was added at the indicated concentrations (range of 0.01 pM-100 nM in triplicates). PBMCs were added to target cells at final E:T ratio of 10:1. Target cell killing was assessed after 24 h of incubation at 37° C., 5% $CO_2$ by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct.

Figure 24A:
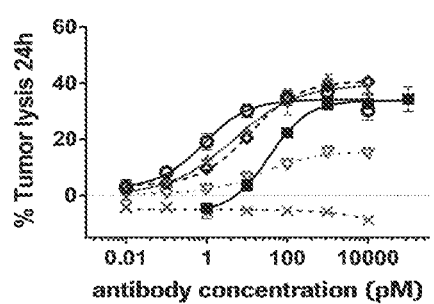
FIGS. 24A-C show T-cell killing induced by 36F2 TCB, 16D5 TCB, 16D5 TCB classical, 16D5 TCB 1+1 and 16D5 TCB HT of Hela (high FolR1) (FIG. 24A), Skov-3 (medium FolR1) (FIG. 24B) and HT-29 (low FolR1) (FIG. 24C) human tumor cells (E:T=10:1, effectors human PBMCs, incubation time 24 h). DP47 TCB was included as non-binding control.
Figure 24B:
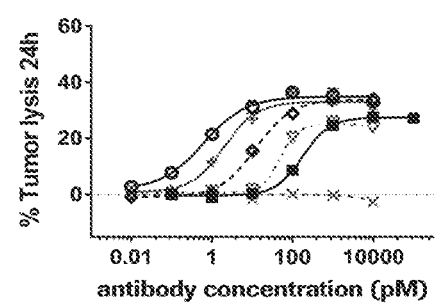
Figure 24C:
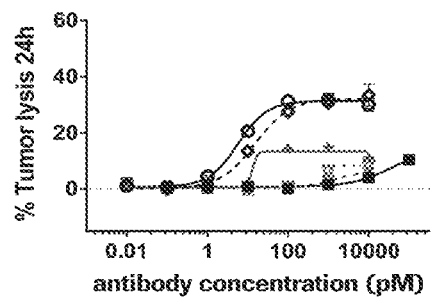
Figure 26A:
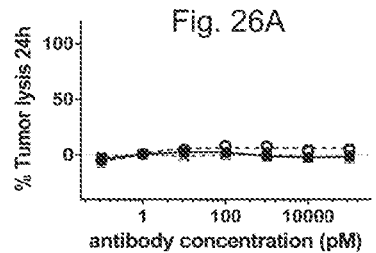
FIGS. 26A-F show T-cell killing induced by 36F2 TCB, 16D5 TCB and DP47 TCB of human Renal Cortical Epithelial Cells (FIGS. 26A, B), human Retinal Pigment Epithelial Cells (FIGS. 26C, D) and HT-29 cells (FIGS. 26E, F) cells after 24 h (FIGS. 26A, C, E) and 48 h (FIGS. 26B, D, F) of incubation (E:T=10:1, effectors human PBMCs).
Figure 26B:
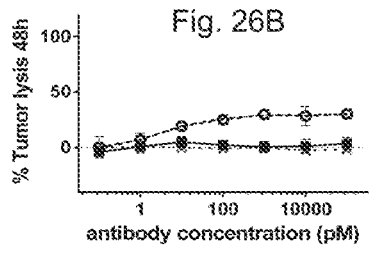
Figure 26C:
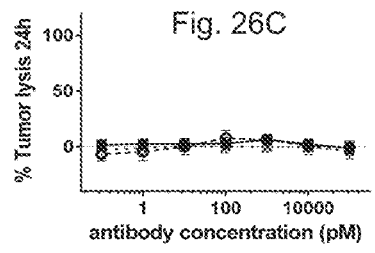
Figure 26D:
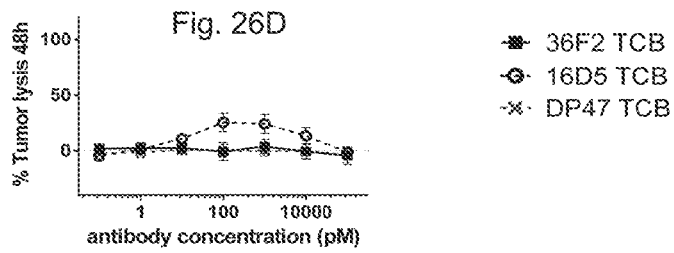

The results show that target-specific killing of all three FolR1+ target cell lines induced by 36F2 TCB is much weaker compared to the killing induced by 16D5 TCB (FIGS. 24A-C, Table 29). Target-specific killing induced by the monovalent 16D5 TCBs (16D5 HT and 16D5 1+1) is worse compared to the bivalent 16D5 TCBs (16D5 TCB and 16D5 TCB classical). The EC50 values related to killing assays, calculated using GraphPadPrism6, are summarized in Table 28. Importantly, this data shows that using the 36F2 FolR1 binder in the bivalent 2+1 TCB format widens the therapeutic window compared to the 16D5 FOLR1 TCB (FIGS. 24A-C). Whereas the potency reduction between 16D5 and 36F2 FOLR1 TCB is approximately 45-fold for Hela cells (high FOLR1 expression, see Table 28: 16D5 TCB=0.8 versus 36F2 TCB 36.0) and approximately 297-fold for Skov3 cells (medium FOLR1 expression, see Table 28: 16D5 TCB=0.6 versus 36F2 TCB 178.4), this reduction is almost 7000-fold for HT29 with low FOLR1 expression (see Table 28: 16D5 TCB=5.7 versus 36F2 TCB 39573). Thus, the 36F2 FOLR1 TCB differentiates between high and low expressing cells which is of special importance to reduce toxicity as the cells of some normal, non-tumorous tissues express very low levels of FolR1 (approximately less than 1000 copies per cell). Consistent with this observation, the results discussed in Example 35 below show that 36F2 TCB does not induce T-cell killing of primary cells (FIGS. 26A-D) whereas for 16D5 TCB some killing can be observed on HRCEpiC and HRPEpiC cells after 48 h of incubation (FIGS. 26B and C). This important characteristic of 36F2 TCB allows for dosing for the treatment of FolR1-positive tumors so that it mediates potent killing of tumor tissues with high or medium FOLR1 expression, but not of normal tissues with low (partially polarized) expression. Notably, this characteristic appears to be mediated by the avidity of 36F2 TCB in the bivalent 2+1 inverted format, as it was not observed when using the 1+1 monovalent formats carrying the same low affinity 36F2 binder.

Stated another way, 36F2 TCB in the bivalent 2+1 format comprises FolR1 binding moieties of relatively low affinity but it possesses an avidity effect which allows for differentiation between high and low FolR1 expressing cells. Because tumor cells express FolR1 at high or intermediate levels, this TCB selectively binds to tumor cells and not normal, non-cancerous cells that express FolR1 at low levels or not at all.

In addition to the above advantageous characteristics, the 36F2 TCB in the bivalent 2+1 inverted format also has the advantage that it does not require chemical cross linking or other hybrid approach. This makes it suitable for manufacture of a medicament to treat patients, for example patients having FolR1-positive cancerous tumors. The 36F2 TCB in the bivalent 2+1 inverted format can be produced using standard CHO processes with low aggregates. Further, the 36F2 TCB in the bivalent 2+1 comprises human and humanized sequences making it superior to molecules that employ rat and murine polypeptides that are highly immunogenic when administered to humans. Furthermore, the 36F2 TCB in the bivalent 2+1 format was engineered to abolish FcgR binding and, as such, does not cause FcgR crosslinking and infusion reactions, further enhancing its safety when administered to patients.

As demonstrated by the results described above, its head-to-tail geometry make the 36F2 TCB in the bivalent 2+1 inverted format a highly potent molecule that induces absolute target cell killing. Its bivalency enhance avidity and potency, but also allow for differentiation between high and low expressing cells. Its preference for high or medium target expressing cells due to its avidity affect reduce toxicity resulting from T cell mediated killing of normal cells that express FolR1 at low levels.

A further advantage of the 36F2 TCB in the bivalent 2+1 format and other embodiments disclosed herein is that their clinical development does not require the use of surrogate molecules as they bind to human, cynomous and murine FolR1. As such, the molecules disclosed herein recognize a different epitope than antibodies to FolR1 previously described that do not recognize FolR1 from all three species.

TABLE 28

EC50 values (pM) for T-cell mediated killing of FolR1-expressing tumor cells induced by 36F2 TCB and 16D5 TCB in different monovalent and bivalent T-cell bispecific formats after 24 h of incubation.

| Antibody | Hela (FolR1 high) | Skov-3 (FolR1 medium) | HT-29 (FolR1 low) |
|---|---|---|---|
| 16D5 TCB | 0.8 | 0.6 | 5.7 |
| 16D5 TCB classical | 4.6 | 2.0 | 13.0 |

TABLE 28-continued

EC50 values (pM) for T-cell mediated killing
of FolR1-expressing tumor cells induced by 36F2
TCB and 16D5 TCB in different monovalent
and bivalent T-cell bispecific formats after 24 h of
incubation.

| Antibody | Hela (FolR1 high) | Skov-3 (FolR1 medium) | HT-29 (FolR1 low) |
|---|---|---|---|
| 16D5 TCB HT | 11.6 | 12.3 | 15.1 |
| 16D5 TCB 1 + 1 | 23.8 | 48.9 | 883.8* |
| 36F2 TCB | 36.0 | 178.4 | 39573.0* |

*curve did not reach saturation, only hypothetical value

Table 29 shows a comparison of EC50 values of 16D5 TCB and 36F2 TCB on the different cell lines tested. Out of the obtained EC50 values the delta (EC50 of 16D5 TCB minus EC50 of 36F2 TCB) and the x-fold difference (EC50 of 16D5 TCB divided by the EC50 of 36F2 TCB) was calculated.

TABLE 29

Comparison of EC50 values of 16D5 TCB and 36F2 TCB.

| Antibody | Hela (FolR1 high) | Skov-3 (FolR1 medium) | HT-29 (FolR1 low) |
|---|---|---|---|
| 16D5 TCB | 0.82 | 0.63 | 5.73 |
| 36F2 TCB | 35.99 | 178.40 | 39573.00* |
| Δ | 35.17 | 177.77 | 39567.27 |
| x-fold | 43.83 | 284.61 | 6906.58 |

*curve did not reach saturation, only hypothetical value

The calculated EC50 values clearly show that the difference between 36F2 TCB and 16D5 TCB gets larger the lower the FolR1 expression on the target cells is.

The same calculations as done for the comparison of the EC50 values of 16D5 TCB and 36F2 TCB were done for 16D5 TCB and the two monovalent 16D5 TCBs (16D5 TCB HT and 16D5 1+1). Tables 30 and 31 show the comparisons of the EC50 values of 16D5 TCB vs 16D5 TCB HT (Table 30) and 16D5 TCB vs 16D5 TCB 1+1 (Table 31) as well as the corresponding deltas (EC50 of 16D5 TCB minus EC50 of 16D5 TCB HT/1+1) and the x-fold differences (EC50 of 16D5 TCB divided by the EC50 of 16D5 TCB HT/1+1).

TABLE 30

Comparison of EC50 values of 16D5 TCB (2 + 1 inverted) and 16D5 TCB HT.

| Antibody | Hela (FolR1 high) | Skov-3 (FolR1 medium) | HT-29 (FolR1 low) |
|---|---|---|---|
| 16D5 TCB | 0.82 | 0.63 | 5.73 |
| 16D5 TCB HT | 11.61 | 12.27 | 15.11 |
| Δ | 10.79 | 11.65 | 9.38 |
| x-fold | 14.14 | 19.58 | 2.64 |

TABLE 31

Comparison of EC50 values of 16D5 TCB and 16D5 TCB 1 + 1.

| Antibody | Hela (FolR1 high) | Skov-3 (FolR1 medium) | HT-29 (FolR1 low) |
|---|---|---|---|
| 16D5 TCB | 0.82 | 0.63 | 5.73 |
| 16D5 TCB 1 + 1 | 23.84 | 48.86 | 883.78* |

TABLE 31-continued

Comparison of EC50 values of 16D5 TCB and 16D5 TCB 1 + 1.

| Antibody | Hela (FolR1 high) | Skov-3 (FolR1 medium) | HT-29 (FolR1 low) |
|---|---|---|---|
| Δ | 23.02 | 48.24 | 878.05 |
| x-fold | 29.03 | 77.95 | 154.24 |

*curve did not reach saturation, only hypothetical value

The comparison of the EC50 values of 16D5 TCB and 36F2 TCB (Table 29) shows that the difference in the EC50 values gets larger the lower the FolR1 expression on the target cells is. This effect cannot be seen in the comparison of 16D5 TCB and the monovalent 16D5 TCBs (Table 29 and Table 30). For 16D5 TCB 1+1 (Table 31) there is also a slight increase in the difference between the EC50 of 16D5 TCB and 16D5 TCB 1+1 with decreasing FolR1 expression but by far not as pronounced as can be seen in the comparison of 16D5 TCB vs 36F2 TCB.

Example 34

CD25 and CD69 Upregulation on CD8+ and CD4+ Effector Cells after T Cell-Killing of FolR1-Expressing Tumor Cells Induced by 36F2 TCB and 16D5 TCB Antibody Activation of $CD8^+$ and $CD4^+$ T cells after T-cell killing of FolR1-expressing Hela, SKov-3 and HT-29 tumor cells mediated by 36F2 TCB and 16D5 TCB was assessed by FACS analysis using antibodies recognizing the T cell activation markers CD25 (late activation marker) and CD69 (early activation marker). DP47 TCB was included as non-binding control. The antibody and the killing assay conditions were essentially as described above (Example 32) using the same antibody concentration range (0.01 pM-100 nM in triplicates), E:T ratio 10:1 and an incubation time of 48 h.

After the incubation, PBMCs were transferred to a round-bottom 96-well plate, centrifuged at 400×g for 4 min and washed twice with PBS containing 0.1% BSA. Surface staining for CD8 (PE anti-human CD8, BD #555635), CD4 (Brilliant Violet 421™ anti-human CD4, Biolegend #300532), CD69 (FITC anti-human CD69, BD #555530) and CD25 (APC anti-human CD25 BD #555434) was performed according to the manufacturer's instructions. Cells were washed twice with 150 µl/well PBS containing 0.1% BSA. After centrifugation, the samples were resuspended in 200 µl/well PBS 0.1% for the FACS measurement. Samples were analyzed at BD FACS Canto II.

Figure 25A:
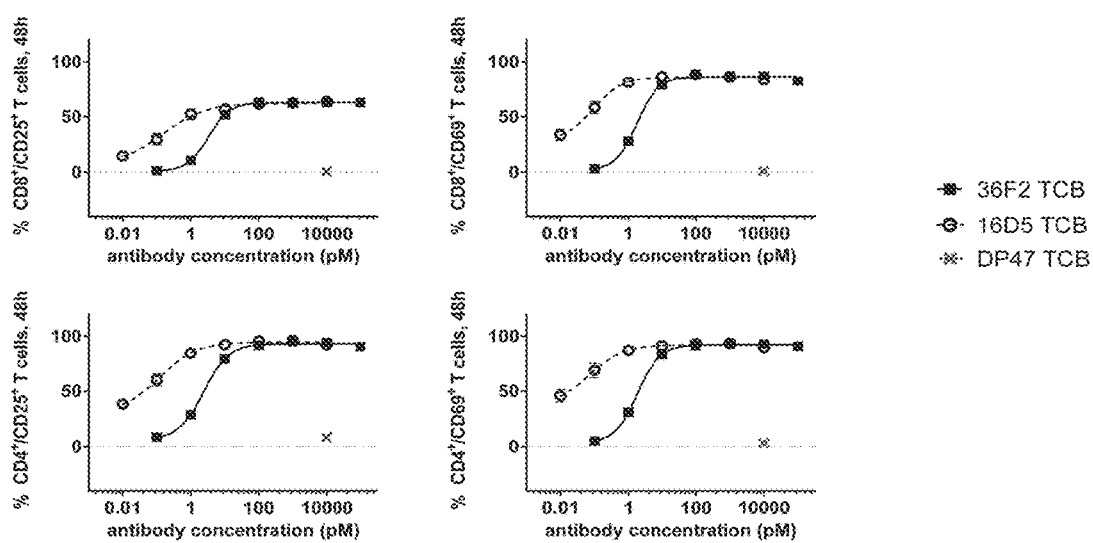
FIGS. 25A-C show upregulation of CD25 and CD69 on human CD8+ (FIGS. 25A, B) and CD4+ (FIG. 25C), T cells after T cell-mediated killing of Hela cells (high FolR1) (FIG. 25A), SKov-3 cells (medium FolR1) (FIG. 25B) and HT-29 cells (low FolR1) (FIG. 25C) (E:T=10:1, 48 h incubation) induced by 36F2 TCB, 16D5 TCB and DP47 TCB (non-binding control).
Figure 25B:
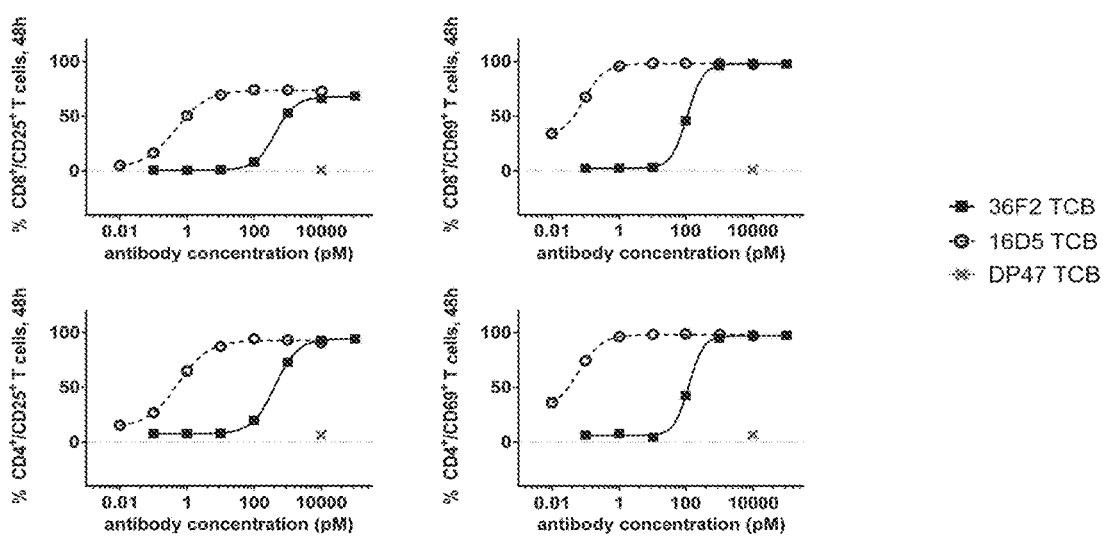

36F2 TCB induced a target-specific up-regulation of activation markers (CD25, CD69) on CD8+ and $CD4^+$ T cells after killing of Hela (FIG. 25A) and SKov-3 (FIG. 25B) cells. In comparison to 16D5 TCB the up-regulation of CD25 and CD69 on CD8+ and $CD4^+$ T cells induced by 36F2 is much weaker.

Figure 25C:
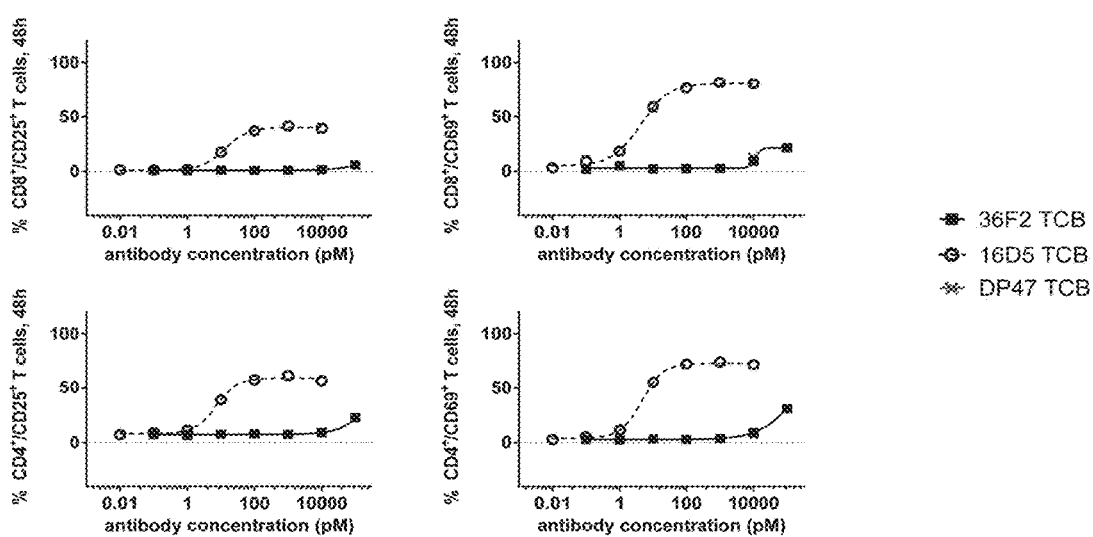

On HT-29 (low FolR1) an up-regulation of activation markers can only be seen at the highest concentration of 36F2 TCB. In contrast, with 16D5 TCB up-regulation of CD25 and CD69 can be seen already at much lower antibody concentrations (FIG. 25C).

As seen as well in the tumor lysis experiment, the analysis of activation markers (CD25 and CD69) on T cells (CD4+ and CD8+) after killing clearly shows that the difference between 16D5 TCB and 36F2 TCB becomes larger the lower the FolR1 expression level on the target cells is.

Example 35

T-Cell Killing of Primary Cells Induced by 36F2 TCB and 16D5 TCB

T-cell killing mediated by 36F2 TCB and 16D5 TCB was assessed on primary cells (Human Renal Cortical Epithelial Cells (HRCEpiC) (ScienCell Research Laboratories; Cat No 4110) and Human Retinal Pigment Epithelial Cells (HRPEpiC) (ScienCell Research Laboratories; Cat No 6540)). HT-29 cells (low FolR1) were included as control cell line. DP47 TCB served as non-binding control. Human PBMCs were used as effectors and the killing was detected at 24 h and 48 h of incubation with the bispecific antibodies. Briefly, target cells were harvested with Trypsin/EDTA, washed, and plated at density of 25 000 cells/well using flat-bottom 96-well plates. Cells were left to adhere overnight. Peripheral blood mononuclear cells (PBMCs) were prepared by Histopaque density centrifugation of enriched lymphocyte preparations (buffy coats) obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and stored in RPMI1640 medium containing 10% FCS and 1% L-alanyl-L-glutamine (Biochrom, K0302) at 37° C., 5% $CO_2$ in cell incubator until further use (no longer than 24 h). For the killing assay, the antibody was added at the indicated concentrations (range of 0.01 pM-10 nM in triplicates). PBMCs were added to target cells at final E:T ratio of 10:1. Target cell killing was assessed after 24 h and 48 h of incubation at 37° C., 5% $CO_2$ by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct.

Figure 26E:
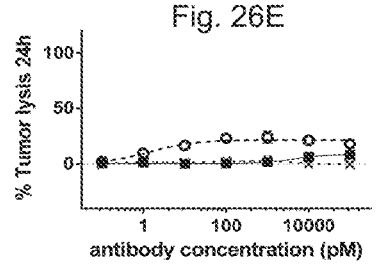
Figure 26F:
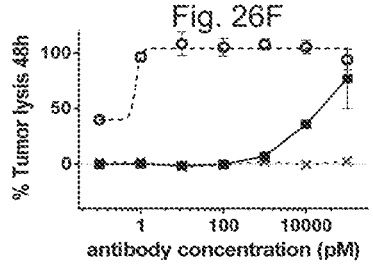

The results show that 36F2 TCB does not induce T-cell killing of primary cells (FIGS. 26A-D) whereas for 16D5 TCB some killing can be observed on HRCEpiC and HRPEpiC cells after 48 h of incubation (FIGS. 26B and D). As described above, a strong difference in T-cell killing between of HT-29 cells was observed between 16D5 TCB and 36F2 TCB (FIGS. 26E, F).

Example 36

Preparation of DP47 GS TCB (2+1 Crossfab-IgG P329G LALA Inverted="Untargeted TCB")

The "untargeted TCB" was used as a control in the above experiments. The bispecific antibody engages CD3e but does not bind to any other antigen and therefore cannot crosslink T cells to any target cells (and subsequently cannot induce any killing). It was therefore used as negative control in the assays to monitor any unspecific T cell activation. This untargeted TCB was prepared as described in WO2014/131712. In brief, the variable region of heavy and light chain DNA sequences have been subcloned in frame with either the constant heavy chain or the constant light chain pre-inserted into the respective recipient mammalian expression vector. The antibody expression was driven by an MPSV promoter and carries a synthetic polyA signal sequence at the 3' end of the CDS. In addition each vector contains an EBV OriP sequence.

The molecule was produced by co-transfecting HEK293-EBNA cells with the mammalian expression vectors using polyethylenimine. The cells were transfected with the corresponding expression vectors in a 1:2:1:1 ratio ("vector heavy chain Fc(hole)":"vector light chain":"vector light chain Crossfab":"vector heavy chain Fc(knob)-FabCrossfab").

For transfection HEK293 EBNA cells were cultivated in suspension serum free in CD CHO culture medium. For the production in 500 ml shake flask 400 million HEK293 EBNA cells were seeded 24 hours before transfection. For transfection cells were centrifuged for 5 min by 210×g, supernatant is replaced by pre-warmed 20 ml CD CHO medium. Expression vectors were mixed in 20 ml CD CHO medium to a final amount of 200 g DNA. After addition of 540 µl PEI solution was vortexed for 15 s and subsequently incubated for 10 min at room temperature. Afterwards cells were mixed with the DNA/PEI solution, transferred to a 500 ml shake flask and incubated for 3 hours by 37° C. in an incubator with a 5% CO2 atmosphere. After incubation time 160 ml F17 medium was added and cell were cultivated for 24 hours. One day after transfection 1 mM valporic acid and 7% Feed 1 was added. After 7 days cultivation supernatant was collected for purification by centrifugation for 15 min at 210×g, the solution was sterile filtered (0.22·m filter) and sodium azide in a final concentration of 0.01% w/v was added, and kept at 4° C.

The secreted protein was purified from cell culture supernatants by affinity chromatography using ProteinA. Supernatant was loaded on a HiTrap ProteinA HP column (CV=5 mL, GE Healthcare) equilibrated with 40 ml 20 mM sodium phosphate, 20 mM sodium citrate, 0.5 M sodium chloride, pH 7.5. Unbound protein was removed by washing with at least 10 column volume 20 mM sodium phosphate, 20 mM sodium citrate, 0.5 M sodium chloride, pH 7.5. Target protein was eluted during a gradient over 20 column volume from 20 mM sodium citrate, 0.5 M sodium chloride, pH 7.5 to 20 mM sodium citrate, 0.5 M sodium chloride, pH 2.5. Protein solution was neutralized by adding 1/10 of 0.5 M sodium phosphate, pH 8. Target protein was concentrated and filtrated prior loading on a HiLoad Superdex 200 column (GE Healthcare) equilibrated with 20 mM Histidine, 140 mM sodium chloride solution of pH 6.0.

The protein concentration of purified protein samples was determined by measuring the optical density (OD) at 280 nm, using the molar extinction coefficient calculated on the basis of the amino acid sequence.

Purity and molecular weight of molecules were analyzed by CE-SDS analyses in the presence and absence of a reducing agent. The Caliper LabChip GXII system (Caliper lifescience) was used according to the manufacturer's instruction. 2 ug sample is used for analyses.

The aggregate content of antibody samples was analyzed using a TSKgel G3000 SW XL analytical size-exclusion column (Tosoh) in 25 mM K2HPO4, 125 mM NaCl, 200 mM L-Arginine Monohydrocloride, 0.02% (w/v) NaN3, pH 6.7 running buffer at 25° C.

TABLE 32

Summary production and purification of DP47 GS TCB.

| Construct | Titer [mg/l] | Yield [mg/l] | Aggregate after 1st purification step [%] | HMW [%] | LMW [%] | Monomer [%] |
|---|---|---|---|---|---|---|
| DP47 GS TCB | 103.7 | 8.04 | 8 | 2.3 | 6.9 | 91.8 |

TABLE 33

CE-SDS analyses of DP47 GS TCB.

| | Peak | kDa | Corresponding Chain |
|---|---|---|---|
| DP47 GS TCB non reduced (A) | 1 | 165.22 | Molecule with 2 missing light chains |
| | 2 | 181.35 | Molecule with 1 missing light chain |
| | 3 | 190.58 | Correct molecule without N-linked glycosylation |
| | 4 | 198.98 | Correct molecule |
| DP47 GS TCB reduced (B) | 1 | 27.86 | Light chain DP47 GS |
| | 2 | 35.74 | Light chain huCH2527 |
| | 3 | 63.57 | Fc(hole) |
| | 4 | 93.02 | Fc(knob) |

Example 37

Figure 28A:
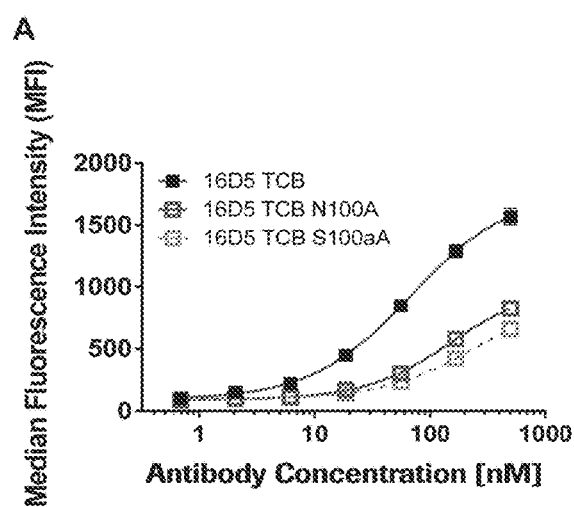
FIGS. 28A-B show binding of 16D5 TCB and its corresponding CD3 deamidation variants 16D5 TCB N100A and 16D5 TCB S100aA and 9D11 TCB and its demidation variants 9D11 TCB N100A and 9D11 TCB S100aA to human CD3 expressed on Jurkat cells.

Binding of 16D5 TCB and 9D11 TCB and their Corresponding CD3 Deamidation Variants N100A and S100aA to CD3-Expressing Jurkat Cells The binding of 16D5 TCB and the corresponding CD3 deamidation variants 16D5 TCB N100A and 16D5 TCB S100aA and 9D11 TCB and the deamidation variants 9D11 TCB N100A and 9D11 TCB S100aA to human CD3 was assessed on a CD3-expressing immortalized T lymphocyte line (Jurkat). Briefly, cells were harvested, counted, checked for viability and resuspended at 2×10⁶ cells/ml in FACS buffer (100 µl PBS 0.1% BSA). 100 µl of cell suspension (containing 0.2×10⁶ cells) was incubated in round-bottom 96-well plates for 30 min at 4° C. with different concentrations of the bispecific antibodies (686 pM-500 nM). After two washing steps with cold PBS 0.1% BSA, samples were re-incubated for further 30 min at 4° C. with a PE-conjugated AffiniPure F(ab')2 Fragment goat anti-human IgG Fcg Fragment Specific secondary antibody (Jackson Immuno Research Lab PE #109-116-170). After washing the samples twice with cold PBS 0.1% BSA they were immediately analyzed by FACS using a FACS Cantoll (Software FACS Diva). Binding curves were obtained using GraphPadPrism6 (FIGS. 28A-B).

Figure 28B:
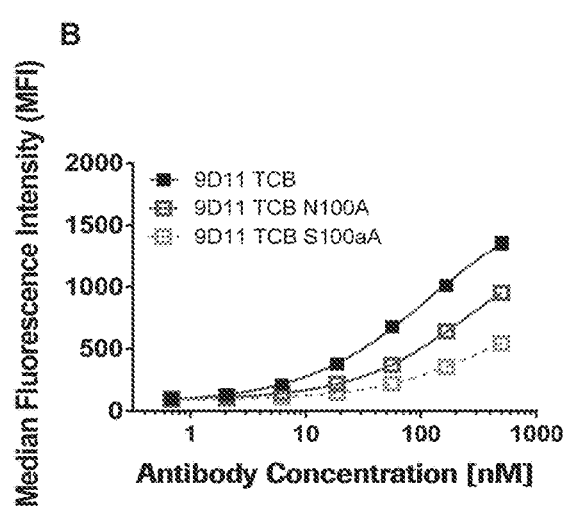

The results show reduced binding of the deamidation variants N100A and S100aA to CD3 compared to the parental antibodies 16D5 TCB (FIG. 28A) and 9D11 TCB (FIG. 28B).

Example 38

T-Cell Killing of SKov-3 and HT-29 Cells Induced by 16D5 TCB and 9D11 TCB and their CD3 Deamidation Variants N100A and S100aA T-cell killing mediated by 16D5 TCB and the corresponding CD3 deamidation variants 16D5 TCB N100A and 16D5 TCB S100aA and 9D11 TCB and the deamidation variants 9D11 TCB N100A and 9D11 TCB S100aA was assessed on SKov-3 (medium FolR1) and HT-29 (low FolR1) cells. Human PBMCs were used as effectors and the killing was detected at 24 h of incubation with the bispecific antibodies. Briefly, target cells were harvested with Trypsin/EDTA, washed, and plated at a density of 25 000 cells/well using flat-bottom 96-well plates. Cells were left to adhere overnight. Peripheral blood mononuclear cells (PBMCs) were prepared by Histopaque density centrifugation of enriched lymphocyte preparations (buffy coats) obtained from healthy human donors. Fresh blood was diluted with sterile PBS and layered over Histopaque gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (ViCell) and stored in RPM11640 medium containing 10% FCS and 1% L-alanyl-L-glutamine (Biochrom, K0302) at 37° C., 5% CO2 in cell incubator until further use (no longer than 24 h). For the killing assay, the antibody was added at the indicated concentrations (range of 0.01 pM-10 nM in triplicates). PBMCs were added to target cells at final E:T ratio of 10:1. Target cell killing was assessed after 24 h of incubation at 37° C., 5% $CO_2$ by quantification of LDH released into cell supernatants by apoptotic/necrotic cells (LDH detection kit, Roche Applied Science, #11 644 793 001). Maximal lysis of the target cells (=100%) was achieved by incubation of target cells with 1% Triton X-100. Minimal lysis (=0%) refers to target cells co-incubated with effector cells without bispecific construct.

Figure 29A:
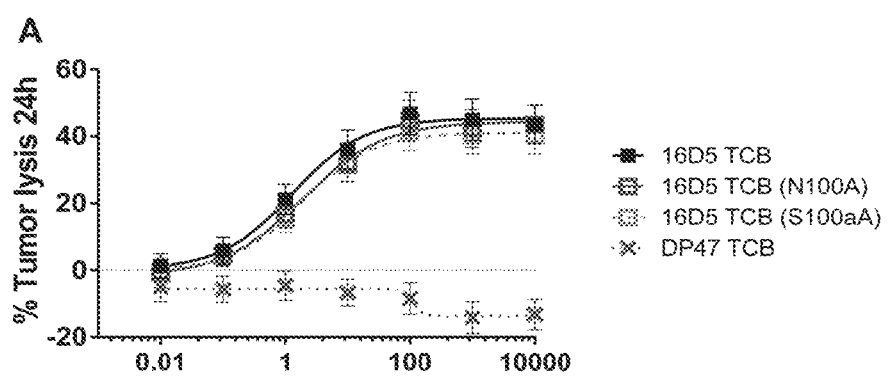
FIGS. 29A-B show T-cell killing of SKov-3 (medium FolR1) human tumor cells induced by 16D5 TCB and its corresponding CD3 deamidation variants 16D5 TCB N100A and 16D5 TCB S100aA (FIG. 29A) and 9D11 TCB and its demidation variants 9D11 TCB N100A and 9D11 TCB S100aA (FIG. 29B) (E:T=10:1, effectors human PBMCs, incubation time 24 h). DP47 TCB was included as non-binding control.
Figure 29B:
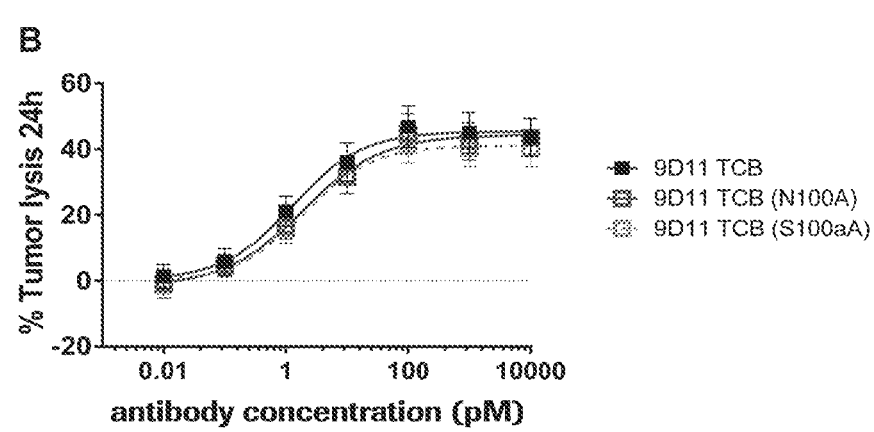
Figure 30A:
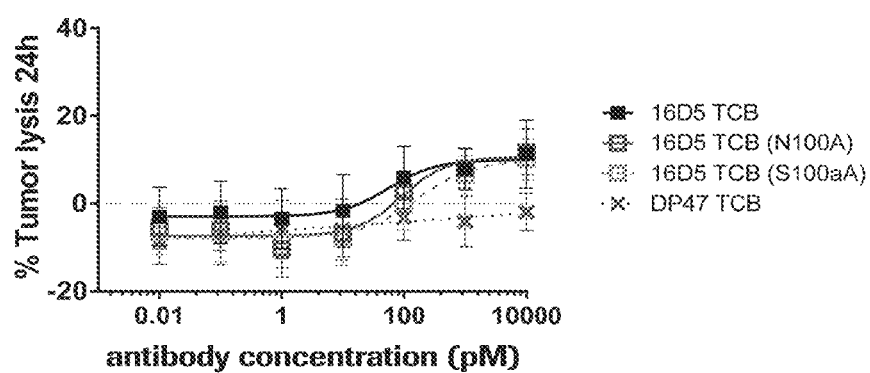
FIGS. 30A-B show T-cell killing of HT-29 (low FolR1) human tumor cells induced by 16D5 TCB and its corresponding CD3 deamidation variants 16D5 TCB N100A and 16D5 TCB S100aA (FIG. 30A) and 9D11 TCB and its demidation variants 9D11 TCB N100A and 9D11 TCB S100aA (FIG. 30B) (E:T=10:1, effectors human PBMCs, incubation time 24 h). DP47 TCB was included as non-binding control.
Figure 30B:
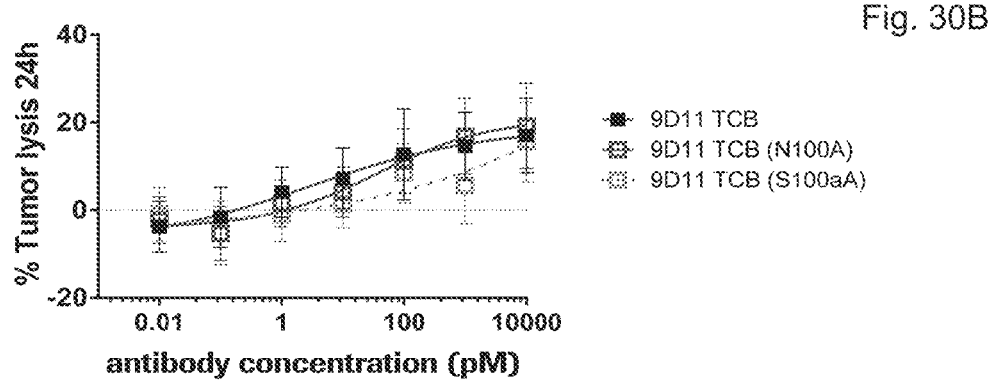

The results show that on SKov-3 cells the killing induced by the CD3 deamidation variants 16D5 TCB N100A and 16D5 S100aA is comparable to the one induced by 16D5 TCB (FIG. 29A). The same is true for 9D11 TCB and its variants 9D11 TCB N100A and 9D11 TCB S100aA (FIG. 29B). On FolR1 low expressing HT-29 cells the S100aA variant shows an impaired killing efficiency which is the case for 16D5 TCB (FIG. 30A) as well as for 9D11 TCB (FIG. 30B). The EC50 values related to killing assays, calculated using GraphPadPrism6 are given in Table 35.

TABLE 35

EC50 values (pM) for T-cell mediated killing of FoIR1-expressing SKov-3 and HT-29 cells induced by 16D5 TCB and 9D11 TCB and their deamidation variants N100A and A100aA.

| Antibody | EC50 [pM] | |
|---|---|---|
| | SKov-3 | HT-29 |
| 16D5 TCB | 1.283 | 56.67 |
| 16D5 TCB N100A | 1.886 | 91.95 |
| 16D5 TCB S100aA | 1.939 | 165.6 |
| 9D11 TCB | 1.283 | 2.827 |
| 9D11 TCB N100A | 1.886 | 37.72 |
| 9D11 TCB S100aA | 1.939 | n.d.* |

*not determined

Example 39

Generation of Mucin-1 T Cell Bi-Specific Constructs that Contain a Common Light Chain Gene Synthesis Desired gene segments were synthesized at Geneart AG (Regensburg, Germany) from synthetic oligonucleotides and PCR products by automated gene synthesis.

Production and Purification of MUC1 Antigen

For the generation of common light chain (CLC) antibodies against the "sea urchin sperm protein, enterokinase and agrin" (SEA) domain of human Mucin-1 (MUC1), a DNA fragment encoding SEA domain was synthesized (Uniprot P15941, amino acids 1041-1151). In order to prevent autoproteolysis of the SEA between positions G1097 and S1098, a process described previously, by Ligtenber et al. (1992). Cell-associated episialin is a complex containing two proteins derived from a common precursor. J Biol Chem 267, 6171-7. Parry et al., Identification of MUC1 Proteolytic Cleavage Sites in Vivo. Biochem Biophys Res Commun 283, 715-20, four additional glycine residues were inserted between G1097 and S1098. This insertion results in the relief of the conformational stress and the protein remains intact. The DNA fragment was inserted into pETXX, an inducible bacterial expression vector. The resulting plasmid expresses the SEA domain with a C-terminal avi tag and a His6 tag (SEQ ID NO: 47). While the avi tag was used for BirA-mediated in vivo biotinylation, the His6 tag (SEQ ID NO: 47) was used for purification.

A 500 ml culture was inoculated with the bacterial strain BL21 D3, transformed with the corresponding plasmid and a plasmid expressing BirA, and induced with 1 mM IPTG at an $OD_{600}$ 0.8. Afterwards, the cultures were incubated at 25° C. overnight and harvested by centrifugation. The bacterial pellet was resuspended with 25 ml BugBuster® Protein Extraction Reagent (Millipore) and incubated for 20 min at room temperature as described in the protocol. After centrifugation for 20 min at 16000×g, the supernatant was filtered and loaded on an IMAC column (His gravitrap, GE Healthcare). The column was washed with 40 ml washing buffer (500 mM NaCl, 20 mM Imidazole, 20 mM $NaH_2PO_4$ pH 7.4). After the elution from the column (500 mM NaCl, 500 mM Imidazole, 20 mM $NaH_2PO_4$ pH 7.4), the eluate was re-buffered using PD10 columns (GE Healthcare).

Selection of Anti-Human MUC1 SEA Domain Binders from the CLC Fab Libraries

Figure 31:
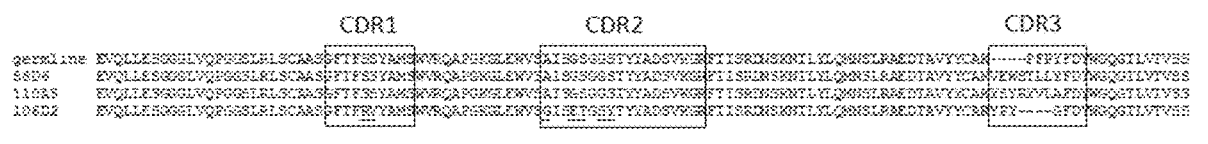

Selections against the SEA domain of human MUC1 were carried out using *E. coli*-derived and in vivo biotinylated MUC1. The antigens were enzymatically biotinylated by co-expression of the biotin ligase Bir A via an C-terminal avi-tag. Panning rounds were performed in solution according to the following pattern: 1. Binding of the phagemid particles of the CLC libraries to 100 nM biotinylated antigen protein for 0.5 h in a total volume of 1 ml, 2. capture of biotinylated antigen and attached specifically binding phage by addition of $5.4 \times 10^7$ streptavidin-coated magnetic beads for 10 min, 3. washing of beads using 5×1 ml PBS/Tween20 and 5×1 ml PBS, 4. elution of phage particles by addition of 1 ml 100 mM triethylamine (TEA) for 10 min and neutralization by addition of 500 ul 1 M Tris/HCl pH 7.4, 5. Re-infection of log-phase *E. coli* TG1 cells with the phage particles in the supernatant, infection with helperphage VCSM13 and subsequent PEG/NaCl precipitation of phagemid particles to be used in subsequent selection rounds. Selections were carried out over 3 rounds using either constant or decreasing (from $10^{-7}$M to $2 \times 10^{-9}$M) antigen concentrations. In round 2, capture of antigen:phage complexes was performed using neutravidin plates instead of streptavidin beads. Specific binders were identified by ELISA as follows: 100 ul of 50 nM biotinylated antigen per well were coated on neutravidin plates. Fab-containing bacterial supernatants were added and binding Fabs were detected via their Flag-tags by using an anti-Flag/HRP secondary antibody. The VH domains of clones exhibiting significant signals over background were short-listed for sequencing (58D6 VH, 106D2 VH, 110A5 VH) and further analyses. All clones derive from the IGHV3-23 germline sequence (FIG. 31). Of note, clone 58D6 and 110A5 originate from a library that was randomized only in CDR3, while clone 106D2 was identified from a library randomized in all 3 CDRs. Positions in CDR1 and 2 that deviate from the germline sequence are printed italic. All VH variants were expressed in combination with the same common light chain (common light chain VL).

Purification of Fabs

Fabs from bacterial cultures (protein sequence of variable heavy chains domains for 58D6 VH, 106D2 VH, 110A5 VH, all clones expressed the same CLC variable domain listed as SEQ ID NO: 31) were purified for the exact analysis of the kinetic parameters. For each clone, a 500 ml culture was inoculated with bacteria harboring the corresponding phagemid and induced with 1 mM IPTG at an $OD_{600}$ 0.9. Afterwards, the cultures were incubated at 25° C. overnight and harvested by centrifugation. After the incubation of the resuspended pellet for 20 min in 25 ml PPB buffer (30 mM Tris-HCl pH8, 1 mM EDTA, 20% sucrose), bacteria were centrifuged again and the supernatant was harvested. This incubation step was repeated once with 25 ml of a 5 mM $MgSO_4$ solution. The supernatants of both incubation steps were pooled, filtered and loaded on an IMAC column (His gravitrap, GE Healthcare). Subsequently, the column was washed with 40 ml washing buffer (500 mM NaCl, 20 mM Imidazole, 20 mM $NaH_2PO_4$ pH 7.4). After the elution (500 mM NaCl, 500 mM Imidazole, 20 mM $NaH_2PO_4$ pH 7.4) the eluate was re-buffered using PD10 columns (GE Healthcare). The kinetic parameters of the purified Fabs were then studied by SPR-analysis (Proteon XPR36, Biorad) in a dilution row that ranged from 100 nM to 6.25 nM.

Affinity-Determination by SPR Using BioRad's ProteOn XPR36 Biosensor

Figure 32A:
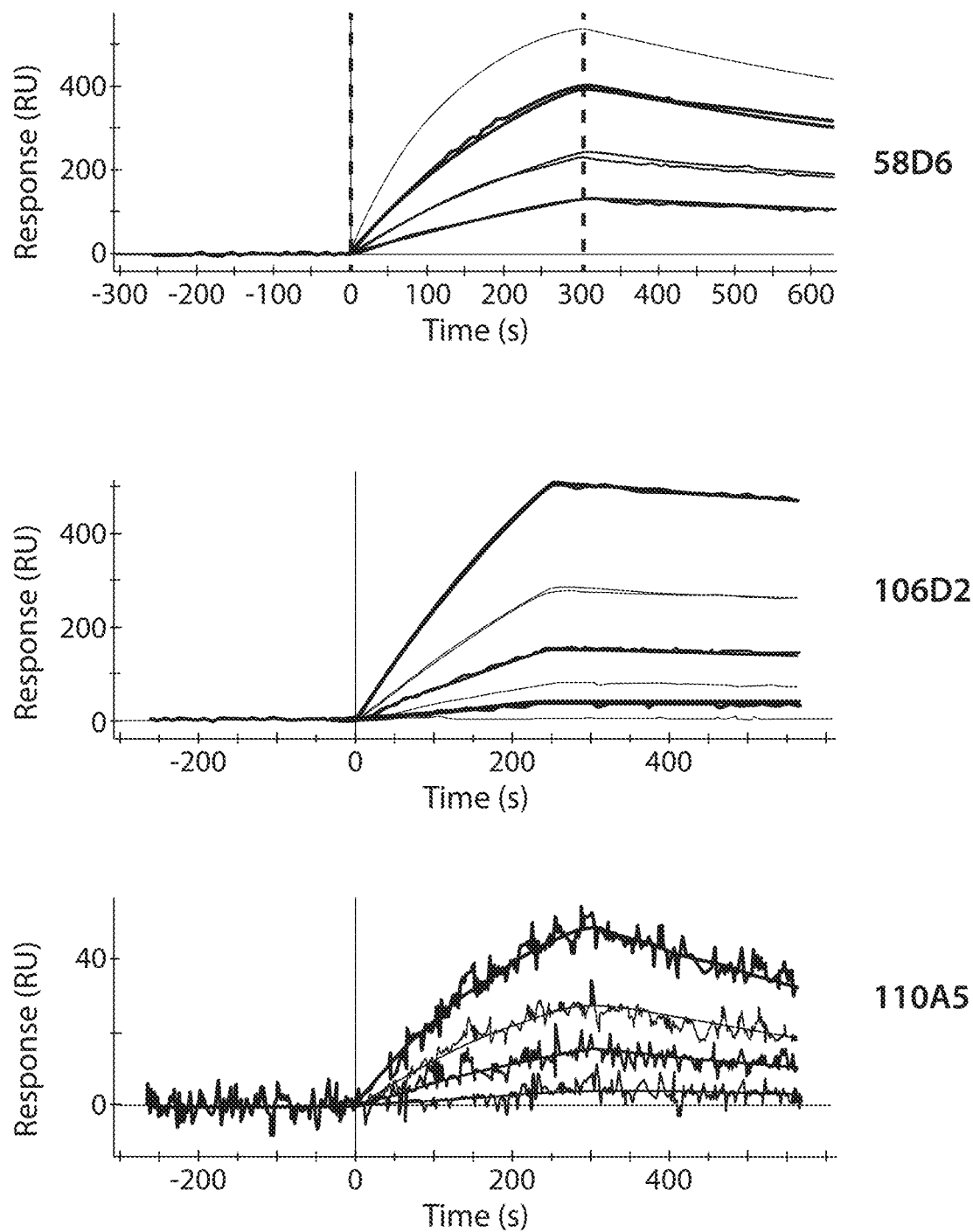

Affinity ($K_D$) of selected Fab clones was measured by surface plasmon resonance using a ProteOn XPR36 instrument (Biorad) at 25° C. with biotinylated MUC1 antigen immobilized on NLC chips by neutravidin capture. Immobilization of recombinant antigens (ligand): Antigens were diluted with PBST (10 mM phosphate, 150 mM sodium chloride pH 7.4, 0.005% Tween 20) to 10 μg/ml, then injected at 30 μl/minute at varying contact times, to achieve immobilization levels of about 200 response units (RU) in vertical orientation. Injection of analytes: For one-shot kinetics measurements, injection direction was changed to horizontal orientation, two-fold dilution series of purified Fab (varying concentration ranges between 100 and 6.25 nM) were injected simultaneously at 50 μl/min along separate channels 1-5, with association times of 250 or 300s, and dissociation times of 300s. Buffer (PBST) was injected along the sixth channel to provide an "in-line" blank for referencing. Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$. Regeneration was performed in horizontal orientation using 10 mM Glycine, pH 1.5 at a flow rate of 100 ul/min for a contact time of 30s. 3 clones bound specifically to MUC1 (FIG. 32A), but not to the "in-line" blank demonstrating the specificity of these binders. The kinetic and thermodynamic data of all measurements are summarized in FIG. 32B.

Cloning, Expression and Characterization of the MUC1-Based

Figure 33:
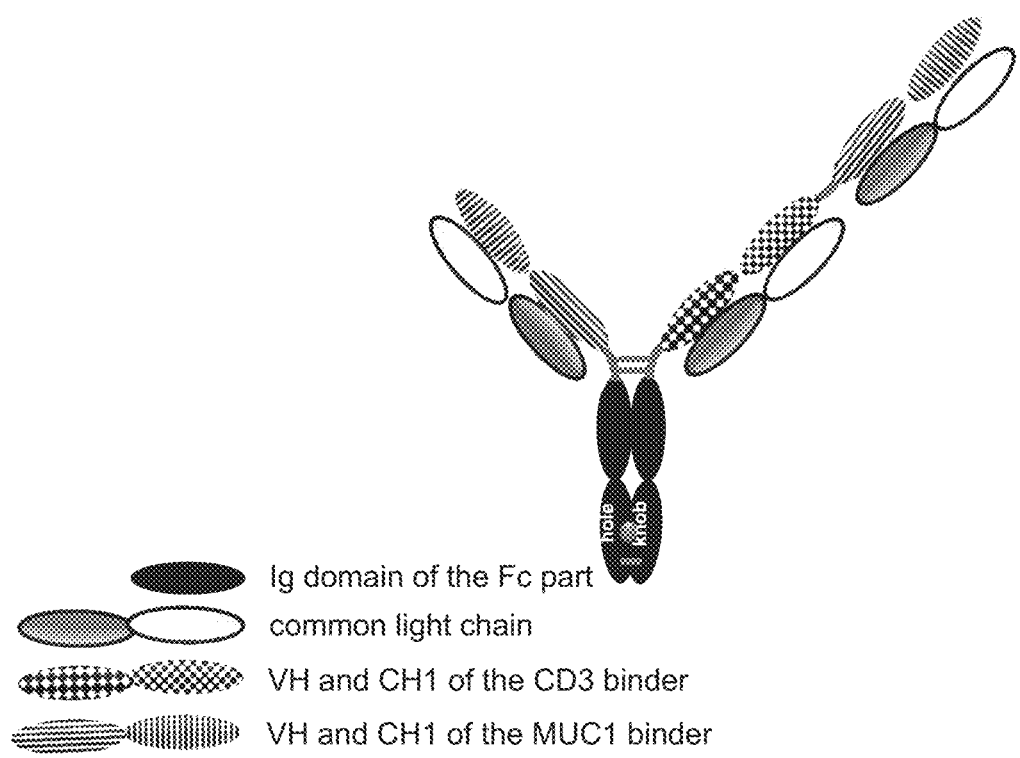
FIG. 33 depicts a schematic diagram of the generated TCB construct. The CLC TCB construct consists of 3 different immunoglobulin chains: 1) an IgG heavy chain harbouring the "hole mutations" in the Fc part and containing the target-specific VH domain; 2) an Ig chain consisting of the target-specific VH and a CH1 domain, followed by the CD3-specific VH domain and a CH1 domain, followed by the Fc part containing the "knob" mutations; and 3) the common light chain that anneals to both the MUC1-specific and the CD3-specific sequences.
Figure 34A:
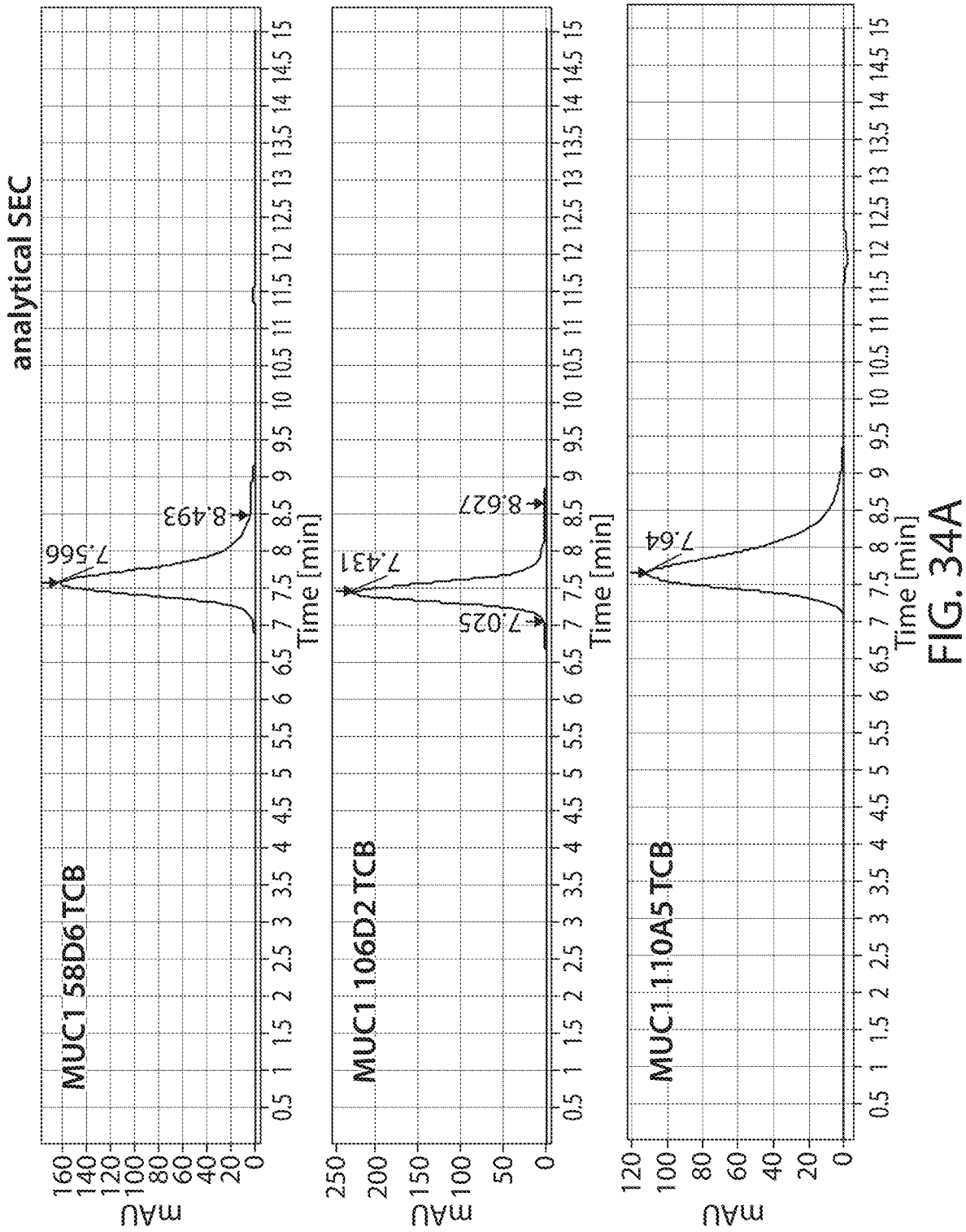
FIGS. 34A-B depicts purification and analytical characterization of the produced MUC1-specific TCBs (FIG. 34A and FIG. 34B). The purification method involved an affinity step (protein A) followed by size exclusion chromatography (Superdex 200, GE Healthcare). The final product was analyzed and characterized by analytical size exclusion chromatography (Superdex 200 column) and by capillary electrophoresis.
Figure 34B:
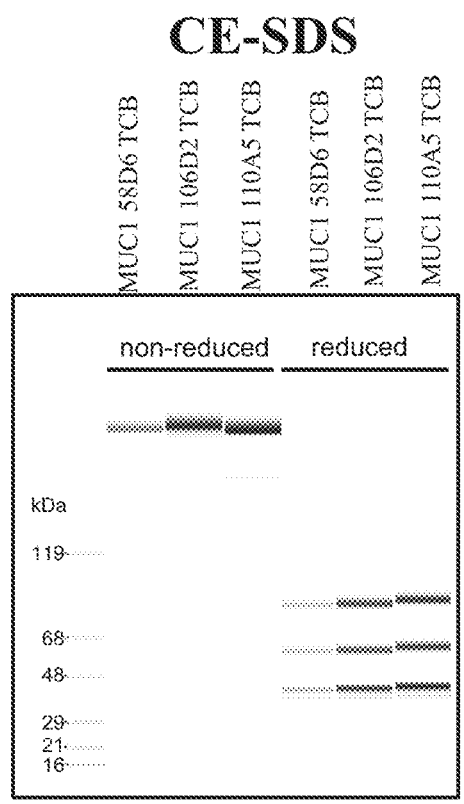
Figure 36A:
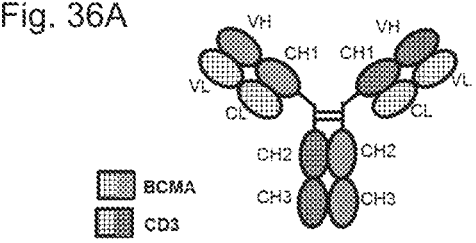
FIGS. 36A-G depict bispecific bivalent and trivalent antibodies comprising only the Fab fragments (specific to CD3 and BCMA) with or without an Fc part as specified: (A) Fab BCMA-Fc-Fab CD3; (B) Fab BCMA-Fc-Fab CD3-Fab BCMA; (C) Fab BCMA-Fc-Fab BCMA-Fab CD3; (D) Fc-Fab CD3-Fab BCMA; (E) Fc-Fab BCMA-Fab CD3; (F) Fab CD3-Fab BCMA-Fab BCMA; (G) Fab CD3-Fab BCMA. Preferably, the LC of Fab CD3 and Fab BCMA are identical (common LC) to avoid LC mispairing and reduce side-products. Fab CD3 and Fab BCMA are linked to each other with flexible linkers.
Figure 36B:
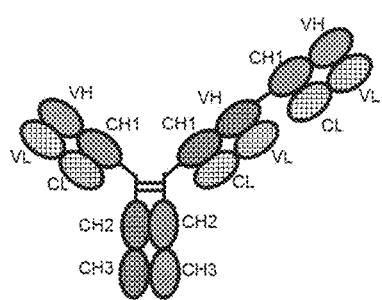
Figure 36C:
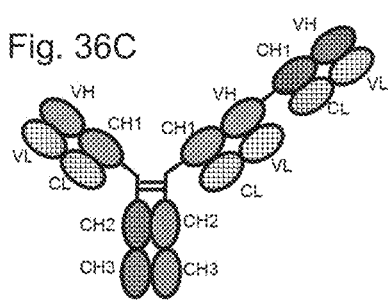
Figure 36D:
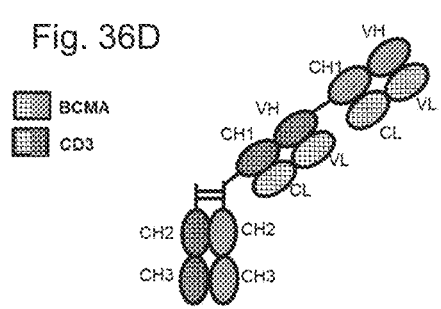
Figure 36E:
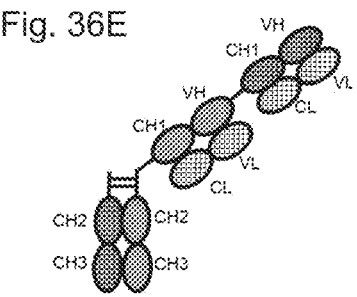
Figure 36F:
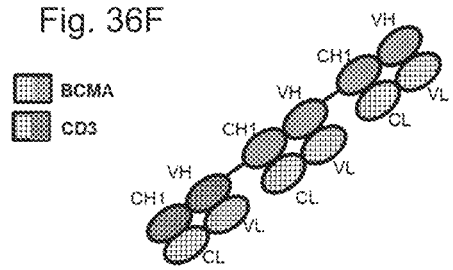
Figure 36G:
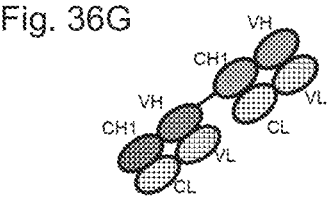

All Fabs demonstrating specific binding to MUC1 by SPR were converted into the T cell bi-specific (TCB) format. For this, the PCR-amplified DNA fragments of heavy and light chain VH-domains were inserted in frame into both Fc-containing Ig chains needed for the generation of a TCB (FIG. 33). The antibody chain expression is driven by an MPSV promoter and transcription is terminated by a synthetic polyA signal sequence located downstream of the CDS. In addition to the expression cassette, each vector contains an EBV oriP sequence for autonomous replication in EBV-EBNA expressing cell lines. The resulting DNA constructs were co-expressed in combination with the CLC (clone 58D6; clone 110A5) and purified from mammalian-derived cell culture supernatant (clone 58D6: clone 110A5). A summary of the analytical data for two bi-specific antibodies is shown clones in FIGS. 34A and B.

Binding Analysis of the MUC1-Specific TCBs Using Bio-Rad's ProteOn XPR36 Biosensor Binding of the produced MUC1-specific TCBs was measured by surface plasmon resonance using a ProteOn XPR36 instrument (Biorad) at 25° C. Biotinylated MUC1 antigen and an unrelated biotinylated antigen were immobilized on NLC chips by neutravidin capture. Immobilization of the antigens was performed as described before. For one-shot kinetics measurements, injection direction was changed to horizontal orientation, two-fold dilution series of the purified constructs (varying concentration ranges between 30 and 1.88 nM or between 100 and 6.25 nM) were injected simultaneously at 50 µl/min along separate channels 1-5, with association times of 120s, and dissociation times of up to 600s. Buffer (PBST) was injected along the sixth channel to provide an "in-line" blank for referencing.

Regeneration was performed in horizontal orientation using 10 mM Glycine, pH 1.5 at a flow rate of 100 ul/min for a contact time of 30s. 3 clones specifically bound to MUC1 (FIG. 35), but not to the "in-line" blank demonstrating the specificity of these binders. Due to the avidity effect of the bivalent TCB format, very strong binding to MUC1 was observed. In contrast, no binding to the unrelated antigen was detected indicating the specific binding of the TCB constructs.

Example 40

Generation of Anti-BCMA Antibodies 1.1: Production of Antigens and Tool Reagents
1.1.1: Recombinant, Soluble, Human BCMA Extracellular Domain The extracellular domains of human, cynomolgus and murine BCMA that were used as antigens for phage display selections were transiently expressed as N-terminal monomeric Fc-fusion in HEK EBNA cells and in vivo site-specifically biotinylated via co-expression of BirA biotin ligase at the avi-tag recognition sequence located at the C-terminus of the Fc portion carrying the receptor chain (Fc knob chain). The extracellular domains of human, cynomolgus and murine BCMA comprised methionine 4 to asparagine 53, methionine 4 to asparagine 52, and alanine 2 to threonine 49, respectively. These were N-terminally fused to the hinge of a human IgG1 enabling heterodimerization with an unfused human IgG1 Fc portion (hole chain) by knobs-into-holes technology.

For recovering of the extracellular domain of BCMA the following primers were used:
AAGCTTGGATCCATGTTGCA-GATGGCTGGGCAGTGCTCC-3 (SEQ ID NO: 48) incorporating a BamH1 site (bold, underlined) and reverse primer
(SEQ ID NO: 49)
5-GAATTCGCGGCCGCTCATCCTTTCACTGAATTGGTCACACTTGCATTA
C-3 primer
(SEQ ID NO: 50)
5-ACGTTAGATCTCCACTCAGTCCTGCATCTTGTTCCAGTTAAC-3
and reverse primer
(SEQ ID NO: 51)
5-AACGTTGCGGCCGCTAGTTTCACAAACCCCAGG-3

(SEQ ID NO: 52)
GAATTCAAGCTTGCCACCATGTTGCAGATGGCTGGGCAGTGCTCC-3 including a HindIII restriction site (bold, underlined) and Kozak consensus sequence and reverse primer
(SEQ ID NO: 53)
5-GAATTCTCTAGATTACCTAGCAGAAATTGATTTCTCTATCTCCGTAG
C-3

Gene synthesis can be also used to obtain the extracellular domain of BCMA.
1.2: BCMA-Expressing Cells as Tools
1.2.1: Human Myeloma Cell Line Expressing BCMA on their Surface BCMA expression was assessed on four human myeloma cell lines (NCI-H929, RPMI-8226, U266B1 and L-363) by flow cytometry. NCI-H929 cells ((H929) ATCC® CRL-9068™) were cultured in 80-90% RPMI 1640 with 10-20% heat-inactivated FCS and could contain 2 mM L-glutamine, 1 mM sodium pyruvate and 50 µM mercaptoethanol. RPMI-8226 cells ((RPMI) ATCC® CCL-155™) were cultured in a media containing 90% RPMI 1640 and 10% heat-inactivated FCS. U266B1 ((U266) ATCC® TIB-196™) cells were cultured in RPMI-1640 medium modified to contain 2 mM L-glutamine, 10 mM HEPES, 1 mM sodium pyruvate, 4500 mg/L glucose, and 1500 mg/L sodium bicarbonate and 15% heat-inactivated FCS. L-363 cell line (Leibniz Institute DSMZ—German collection of microorganisms and cell cultures; DSMZ No. ACC 49) was cultured in 85% RPMI 1640 and 15% heat-inactivated FCS. Briefly, cells were harvested, washed, counted for viability, resuspended at 50,000 cells/well of a 96-well round bottom plate and incubated with anti-human BCMA antibody (Abcam, #ab54834, mouse IgG1) at 10 µg/ml for 30 min at 4° C. (to prevent internalization). A mouse IgG1 was used as isotype control (BD Biosciences, #554121). Cells were then centrifuged (5 min at 350×g), washed twice and incubated with the FITC-conjugated anti mouse secondary antibody for 30 min at 4° C. At the end of incubation time, cells were centrifuged (5 min at 350×g), washed twice with FACS buffer, resuspended in 100 ul FACS buffer and analyzed on a Cantoll device running FACS Diva software. The relative quantification of BCMA receptor number on the surface membrane of H929, U266B1, RPMI-8226 and L-363 myeloma cell lines was assessed by QIFIKIT analysis (Dako, #K0078, following manufacturer's instructions). H929 cells expressed human BCMA with the highest density, up to 3.8 to 27-fold higher than other myeloma cell lines. H929 is considered as a BCMA$^{hi}$-expressing myeloma cell line as compared to U266 which is BCMA$^{med/lo}$-expressing myeloma cells and RPMI-8226 and L363 which are BCMA$^{lo}$-expressing myeloma cells. Table 36 summarizes the relative BCMA receptor number on the cell surface of human multiple myeloma cell lines.

TABLE 36

Quantification of BCMA receptor number on cell surface of NCI-H929, U266B1, RPMI-8226 and L-363 human myeloma cell lines

| Myeloma cell lines | Relative binding sites per cell |
| --- | --- |
| H929 | 50000 |
| U266 | 13000 |
| RPMI-8226 | 2000 |
| L363 | 1800 |

1.3: Obtaining BCMA Binders Out of an In Vitro, Recombinant Library 1.3.1: Construction of Common Light Chain Fab-Libraries Antibody libraries in the Fab-format are constructed on the basis of the humanized anti-CD3 antibody light chain were generated. Diversity was only introduced in the heavy chain. Six different heavy chain frameworks were used: VH1-46, VH1-69, VH3-15, VH3-23, VH4-59 and VH5-1. CDRs 1, 2 and 3 were randomized and each heavy chain library was combined with the non-randomized light chain. Libraries were generated as described by Nissim et al *EMBO J*. 1994 Feb. 1; 13(3):692-8, and Silacci et al. *Proteomics*. 2005 June; 5(9):2340-50.

1.3.2: Selection of Anti-BCMA Fab Clones

Anti-BCMA Fabs were established by phage display from synthetic Fab libraries consisting one constant VL and six different human VH sequences Selection rounds (biopanning) were performed in solution according to the following pattern: 1) pre-clearing of ~10$^{12}$ phagemid particles per library pool in immunotubes coated with 10 ug/ml of an unrelated human IgG to deplete the libraries of antibodies recognizing the Fc-portion of the antigens; 2) incubation of the non-Fc-binding phagemid particles with 100 nM biotinylated BCMA for 0.5 h in the presence of 100 nM unrelated non-biotinylated Fc knobs-into-holes construct for further depletion of Fc-binders in a total volume of 2 ml; 3) capture of biotinylated BCMA and specifically binding phage by splitting up and transferring the panning reaction into 16 wells on a neutravidin or streptavidin pre-coated microtiter plate for 20 min on a shaker; 4) washing of respective wells 10-30× with PBS/Tween20 and 10-30× with PBS using a plate washer; 5) optional competitive washing step by addition of 230 nM murine APRIL to displace Fab clones that recognize the binding site of the natural ligand thus selecting for APRIL-non-competing phage antibodies; 6) elution of phage particles by addition of 125 ul 100 mM TEA (triethylamine) per well for 5-10 min and neutralization by addition of an equal volume of 1 M Tris/HCl pH 7.4; 7) re-infection of log-phase *E. coli* TG1 cells with the eluted phage particles, infection with helperphage VCSM13, incubation on a shaker at 30° C. overnight and subsequent PEG/NaCl precipitation of phagemid particles to be used in the next selection round.

Selections were carried out over 3 to 5 rounds using constant antigen concentrations of 100 nM. Apart from selection campaigns during which only human BCMA was used as antigen, additional selection campaigns were carried out during which also cynomolgus or murine BCMA were used in an alternating fashion with human BCMA in order to select for cross-reactive antibodies. Moreover, as an alternative to streptavidin plate-based capture, capture of antigen:phage complexes was performed by addition of 5.4×10$^7$ streptavidin-coated magnetic beads to the panning reaction followed by washing steps using respective magnets under the conditions described above.

Specific binders were identified by surface plasmon resonance-screening of Fab-containing bacterial culture supernatants using BioRad's ProteOn XPR36 biosensor. In brief, after infection of log-phase *E. coli* TG1 cells with the eluted phage particles, single colony forming units (cfu) were plated and picked for inoculation of 1 ml expression cultures in 96-deep well plates. Fabs were captured from the supernatants on a ProteOn GLM chip that was derivatized with 8.000-10.000 RU of a goat anti-human IgG, F(ab')2 fragment specific polyclonal antibody (Jackson ImmunoRe

TABLE 37

Anti-BCMA clones and respective VL/VH pairings

| Fab clone | VL domain | VH domain |
| --- | --- | --- |
| pSCHLI372 | QAVVTQEPSLTVSPGGTVTLTCGS STGAVTTSNYANWVQEKPGQAFRG LIGGTNKRAPGTPARFSGSLLGGK AALTLSGAQPEDEAEYYCALWYSN LWVFGGGTKLTVL (SEQ ID NO: 31) | EVQLVESGGGLVKPGGSLRLSCAAS GFTFSNSGMIWVRQAPGKGLEWVGH IRSKTDGGTTDYAAPVKGRFTISRD DSKNTLYLQMNSLKTEDTAVYYCTT GGSGSFDYWGQGTLVTVSS (SEQ ID NO: 54) |
| pSCHLI373 | QAVVTQEPSLTVSPGGTVTLTCGS STGAVTTSNYANWVQEKPGQAFRG LIGGTNKRAPGTPARFSGSLLGGK AALTLSGAQPEDEAEYYCALWYSN LWVFGGGTKLTVL (SEQ ID NO: 31) | EVQLVESGGGLVKPGGSLRLSCAAS GFSFSNSWMNWVRQAPGKGLEWVGT IRQKTYGGTTDYAAPVKGRFTISRD DSKNTLYLQMNSLKTEDTAVYYCTT GGLFGYWDYWGQGTLVTVSS (SEQ ID NO: 55) | search, #109-005-006) in vertical orientation. Subsequently, human, cynomolgus and murine BCMA as well as an unrelated Fc knobs-into-holes construct were injected as analytes in horizontal orientation. Clones that exhibited significant binding responses to BCMA and did not bind the Fc-portion of the antigens, were bacterially expressed in a 0.5 liter culture volume, affinity purified and kinetically characterized by SPR-analysis using a one-shot-kinetics protocol on BioRad's ProteOn XPR36 biosensor.

Example 41

BCMA Binding Assays: Surface Plasmon Resonance

Assessment of binding of anti-BCMA antibodies to recombinant BCMA by surface plasmon resonance (SPR) as follow. All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany). The avidity of the interaction between anti-BCMA antibodies and recombinant BCMA Fc(kih) (human, cynomolgus and murine) was determined (Tables 38-40). Biotinylated recombinant human, cynomolgus and murine BCMA Fc(kih) were directly coupled on a SA chip following instructions (Biacore, Freiburg/Germany). The immobilization level ranged from 80 to 120 RU. The anti-BCMA antibodies were passed at a 4-fold concentration range (1.95 to 500 nM) with a flow of 30 μL/minutes through the flow cells over 120 seconds. The dissociation was monitored for 180 seconds. Bulk refractive index differences were corrected for by subtracting the response obtained on the reference flow cell. Here, the anti-BCMA antibodies were flown over an empty surface previously activated and deactivated as described in the standard amine coupling kit. Apparent kinetic constants were derived using the Biacore T200 Evaluation Software (v 1.0, Biacore AB, Uppsala/Sweden), to fit rate equations for 1:1 Langmuir binding by numerical integration, despite the bivalency of the interaction for comparison purposes.

TABLE 38

Avidity values for comparison purposes only (Experiment 1)

| Analyte | Ligand | Kon[1/Ms] | Koff[1/s] | KD[nM] |
|---|---|---|---|---|
| pSCHLI333 anti-BCMA IgG | huBCMA Fc(kih) | 4.55E+06 | 1.13E-02 | 2.5 |
| pSCHLI333 anti-BCMA IgG | cyBCMA Fc(kih) | 9.39E+06 | 1.24E-02 | 1.3 |
| pSCHLI333 anti-BCMA IgG | muBCMA Fc(kih) | 8.26E+06 | 1.62E-01 | 19.6 |

TABLE 39

Avidity values for comparison purposes only (Experiment 2)

| Analyte | Ligand | Kon[1/Ms] | Koff[1/s] | KD[nM] |
|---|---|---|---|---|
| pSCHLI372 anti-BCMA IgG | huBCMA Fc(kih) | 3.13E+05 | 2.66E-03 | 8.5 |
| pSCHLI372 anti-BCMA IgG | cyBCMA Fc(kih) | 7.85E+05 | 3.50E-03 | 4.5 |
| pSCHLI372 anti-BCMA IgG | muBCMA Fc(kih) | 1.30E+05 | 5.53E-01 | 42.7 |
| pSCHLI373 anti-BCMA IgG | huBCMA Fc(kih) | 1.40E+05 | 3.23E-03 | 23.0 |
| pSCHLI373 anti-BCMA IgG | cyBCMA Fc(kih) | 9.36E+04 | 9.28E-04 | 9.9 |

TABLE 40

Avidity values for comparison purposes only (Experiment 3)

| Analyte | Ligand | Kon[1/Ms] | Koff[1/s] | KD[nM] |
|---|---|---|---|---|
| pSCHLI372 anti-BCMA IgG | huBCMA Fc(kih) | 8.03E+05 | 2.84E-03 | 3.6 |
| pSCHLI372 anti-BCMA IgG | cyBCMA Fc(kih) | 1.63E+06 | 4.69E-03 | 2.9 |
| pSCHLI372 anti-BCMA IgG | muBCMA Fc(kih) | 4.69E+05 | 1.21E-02 | 25.7 |
| pSCHLI373 anti-BCMA IgG | huBCMA Fc(kih) | 9.78E+04 | 1.18E-03 | 12.1 |
| pSCHLI373 anti-BCMA IgG | cyBCMA Fc(kih) | 9.39E+04 | 7.98E-04 | 8.5 |

The affinity of the interaction between anti-BCMA antibodies or BCMA-TCB CLC antibodies and recombinant human BCMA Fc(kih) was also determined. Anti-human Fab antibody (GE Healthcare) was directly coupled on a CM5 chip at pH 5.0 using the standard amine coupling kit (Biacore, Freiburg/Germany). The immobilization level was about 6500 RU. Anti-BCMA antibody or BCMA-TCB CLC antibody was captured for 90 seconds at 25 nM. Recombinant human BCMA Fc(kih) was passed at a 4-fold concentration range (1.95 to 500 nM) with a flow of 30 μL/minutes through the flow cells over 120 or 180 seconds. The dissociation was monitored for 120 or 400 seconds. Bulk refractive index differences were corrected for by subtracting the response obtained on reference flow cell. Here, recombinant BCMA was flown over a surface with immobilized anti-human Fab antibody but on which HBS-EP has been injected rather than anti-BCMA antibody or BCMA-TCB CLC antibody. Kinetic constants were derived using the Biacore T200 Evaluation Software (v 1.0, Biacore AB, Uppsala/Sweden), to fit rate equations for 1:1 Langmuir binding by numerical integration (Table 41).

TABLE 41

Affinity constants determined by fitting rate equations for 1:1 Langmuir binding

| Ligand | Analyte | Kon[1/Ms] | Koff[1/s] | KD[nM] |
|---|---|---|---|---|
| pSCHLI372 anti-BCMA IgG | huBCMA Fc(kih) | 4.59E+04 | 5.23E-03 | 114 |
| pSCHLI372 anti-BCMA IgG | cyBCMA Fc(kih) | 2.68E+04 | 7.52E-03 | 281 |
| pSCHLI372 anti-BCMA IgG | muBCMA Fc(kih) | 9.92E+04 | 1.30E-01 | 1310 |
| pSCHLI373 anti-BCMA IgG | huBCMA Fc(kih) | 4.22E+04 | 5.70E-03 | 135 |
| pSCHLI373 anti-BCMA IgG | cyBCMA Fc(kih) | 2.10E+04 | 1.12E-02 | 535 |
| pSCHLI373 anti-BCMA IgG | muBCMA Fc(kih) | 1.27E+05 | 9.19E-02 | 724 |
| pSCHLI333 BCMAxCD3 TCB | huBCMA Fc(kih) | 9.10E+03 | 1.49E-03 | 164 |
| pSCHLI333 BCMAxCD3 TCB | cyBCMA Fc(kih) | 1.44E+04 | 2.63E-03 | 183 |
| pSCHLI333 BCMAxCD3 TCB | muBCMA Fc(kih) | 4.83E+02 | 3.47E-03 | 7190 |
| pSCHLI372 BCMAxCD3 TCB | huBCMA Fc(kih) | 5.59E+04 | 3.52E-03 | 63 |
| pSCHLI372 BCMAxCD3 TCB | cyBCMA Fc(kih) | 4.58E+04 | 7.57E-03 | 165 |
| pSCHLI372 BCMAxCD3 TCB | muBCMA Fc(kih) | 1.42E+04 | 4.87E-03 | 344 |

Example 42

Generation of Bivalent Anti-BCMA IgG Antibody with the Common Light Chain

To verify the hypothesis that the use of the common light chain could be applied to any BCMA antibodies, 83A10-CLC bivalent BCMA antibody was generated by substituting the native light chain of the bivalent BCMA antibody 83A10, previously described in WO/2014/122143, with the common light chain (CD3 LC (CLC)). The anti-BCMA antibody comprising two heavy chains of 83A10 and two common light chains were produced using the general techniques for generation of bivalent IgG antibodies as described in the Material and general methods section. Affinity of 83A10-CLC IgG antibody to human BCMA was measured by SPR with methods similar to the ones described in Example 41. Table 42 depicts the binding of recombinant human BCMA Fc(kih) to 83A10-CLC BCMA IgG antibody.

TABLE 42

Affinity constants determined by fitting rate equations for 1:1 Langmuir binding: Binding of recombinant BCMA Fc(kih) to 83A10-CLC anti-BCMA antibody

| Ligand | Analyte | Kon[1/Ms] | Koff[1/s] | KD[nM] |
|---|---|---|---|---|
| 83A10 CLC anti-BCMA IgG | huBCMA Fc(kih) | 8.78E+04 | 2.13E−3 | 24.3 |

Example 43

Specificity Test of Anti-BCMA IgG Antibodies to huTACI-R and huBAFF-R

Figure 37:
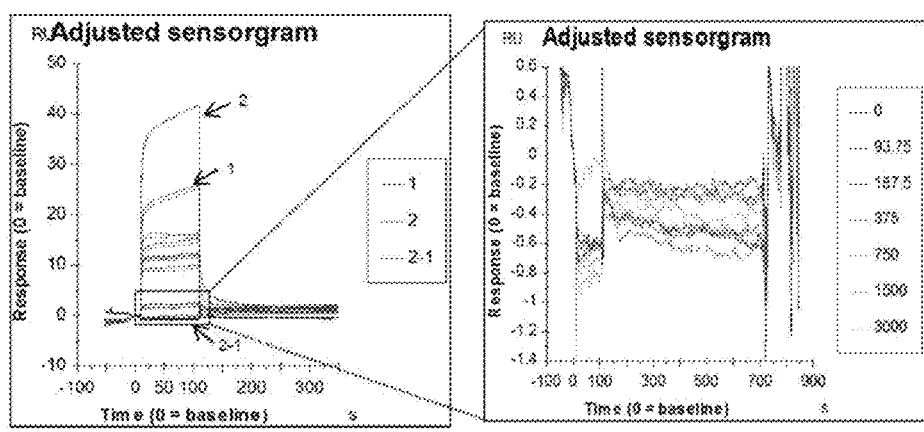
FIG. 37 depicts lack of binding of BCMA IgG antibody to TACI receptor as detected by surface plasmon resonance (SPR). Curve 1 corresponds to the signal on reference channel, curve 2 to the channel where the binding occurs (binding channel) and the curve 2-1 is the subtracted signal (binding channel—reference channel), meaning that this is the signal due to the binding event. SPR binding assay clearly demonstrated that pSCHLI372 IgG did not bind to human TACI receptor.

As members of the TNF-TNF-R superfamily, TACI and BAFF receptors are related to BCMA receptor with respectively 22% and 18.5% homology in the extracellular domain. Therefore, surface plasmon resonance (SPR) binding experiments were performed to examine the specificity of anti-BCMA IgG antibodies. All SPR experiments were performed on a Biacore T200 (GE Healthcare) at 25° C. with HBS-EP as running buffer (0.01 M HEPES pH 7.4, 0.15 M NaCl, 3 mM EDTA, 0.005% Surfactant P20). Fc fused huBCMA, huBAFF-R and huTACI-R were chemically immobilized with a high immobilization level (~5000 RU) on different flow channels of a Biacore CM5 sensor chip at pH 5.0 using the standard amine coupling kit (GE Healthcare). Initially high concentrated solutions (3 μM, dissolved in HBS-EP) of anti-BCMA IgG pSCHLI372 as well as a-huTACI-R IgG or a-huBAFF-R IgG as positive controls were injected (association time: 80s, dissociation time: 600s, flow: 30 μl/min) to check if binding occurs. A positive binding event of the a-huTACI-R IgG to huTACI-R as well as for a-huBAFF-R IgG to huBAFF-R and anti-BCMA IgG antibodies to huBCMA indicated that all receptors were still recognized after immobilization. For anti-BCMA IgG antibodies binding with fast kinetic rate constants to huBAFF-R and/or huTACI-R, a careful examination of kinetic parameter with low immobilization levels (300 RU) was performed on a new CM5 sensor chip. Anti-BCMA IgG antibody dilutions at concentrations of 3000-93.75 nM (2-fold dilution in HBS-EP) are injected (association time: 80s, dissociation time: 300s, flow: 30 μl/min), and sample(s) were tested in duplicate. Regeneration was also performed when applicable i.e no fast and complete dissociation. Kinetic evaluation of the interaction between anti-BCMA IgG antibodies and huBAFF-R or huTACI-R was performed by global fitting of the data to a 1:1 interaction model that includes a term for mass transport (Biacore T200 evaluation Version 1.0). A steady state analysis was also performed. As depicted in FIG. 37, curve 1 corresponds to the signal on reference channel, curve 2 to the channel where the binding occurs (binding channel) and the curve 2-1 is the subtracted signal (binding channel—reference channel), meaning that this is the signal due to the binding event. As shown in FIG. 37, the SPR binding assay clearly demonstrated that pSCHLI372 IgG did not bind to human TACI receptor. As positive control for binding, another BCMA IgG known to slightly bind to TACI receptor but with very fast on- and off-rate was used (data not shown).

Example 44

Production and Purification of BCMA-TCB CLC Fc-Containing (2+1) Antibodies

For the production of the bispecific antibodies, bispecific antibodies were expressed by transient polymer-based cotransfection of the respective mammalian expression vectors in HEK293-EBNA cells, which were cultivated in suspension. One day prior to transfection the HEK293-EBNA cells were seeded at 1.5 Mio viable cells/mL in Ex-Cell medium, supplemented with 6 mM of L-Glutamine. For every mL of final production volume 2.0 Mio viable cells were centrifuged (5 minutes at 210×g). The supernatant was aspirated and the cells resuspended in 100 μL of CD CHO medium. The DNA for every mL of final production volume was prepared by mixing 1 μg of DNA (Ratio Bispecific Antibody Production:heavy chain:modified heavy chain:light chain:modified light chain=1:1:2:1; Ratio standard antibody:heavy chain:light chain=1:1) in 100 μL of CD CHO medium. After addition of 0.27 μL of PEI solution (1 mg/mL) the mixture was vortexed for 15 seconds and left at room temperature for 10 minutes. After 10 minutes, the resuspended cells and DNA/PEI mixture were put together and then transferred into an appropriate container which was placed in a shaking device (37° C., 5% $CO_2$). After a 3 hours incubation time 800 μL of Ex-Cell Medium, supplemented with 6 mM L-Glutamine, 1.25 mM valproic acid and 12.5% Pepsoy (50 g/L), was added for every mL of final Production volume. After 24 hours, 70 μL of feed solution was added for every mL of final production volume. After 7 days or when the cell viability was equal or lower than 70%, the cells were separated from the supernatant by centrifugation and sterile filtration. The antibodies were purified by an affinity step and one polishing step size exclusion chromatography.

For the affinity step the supernatant was loaded on a protein A column (HiTrap Protein A FF, 5 mL, GE Healthcare) equilibrated with 6 CV 20 mM sodium phosphate, 20 mM sodium citrate, pH 7.5. After a washing step with the same buffer the antibody was eluted from the column by step elution with 20 mM sodium phosphate, 100 mM sodium chloride, 100 mM Glycine, pH 3.0. The fractions with the desired antibody were immediately neutralized by 0.5 M Sodium Phosphate, pH 8.0 (1:10), pooled and concentrated by centrifugation. The concentrate was sterile filtered and processed further by size exclusion chromatography.

For the size exclusion step the concentrated protein was injected in a XK16/60 HiLoad Superdex 200 column (GE Healthcare), and 20 mM Histidine, 140 mM Sodium Chloride, pH 6.0 with or without Tween20 as formulation buffer.

The fractions containing the monomers were pooled, concentrated by centrifugation and sterile filtered into a sterile vial.

Determination of the antibody concentration was done by measurement of the absorbance at 280 nm, using the theoretical value of the absorbance of a 0.1% solution of the antibody. This value was based on the amino acid sequence and calculated by GPMAW software (Lighthouse data).

Purity and monomer content of the final protein preparation was determined by CE-SDS (Caliper LabChip GXII system (Caliper Life Sciences)) resp. HPLC (TSKgel G3000 SW XL analytical size exclusion column (Tosoh)) in a 25 mM potassium phosphate, 125 mM Sodium chloride, 200 mM L-arginine monohydrochloride, 0.02% (w/v) Sodium azide, pH 6.7 buffer.

Figure 38A:
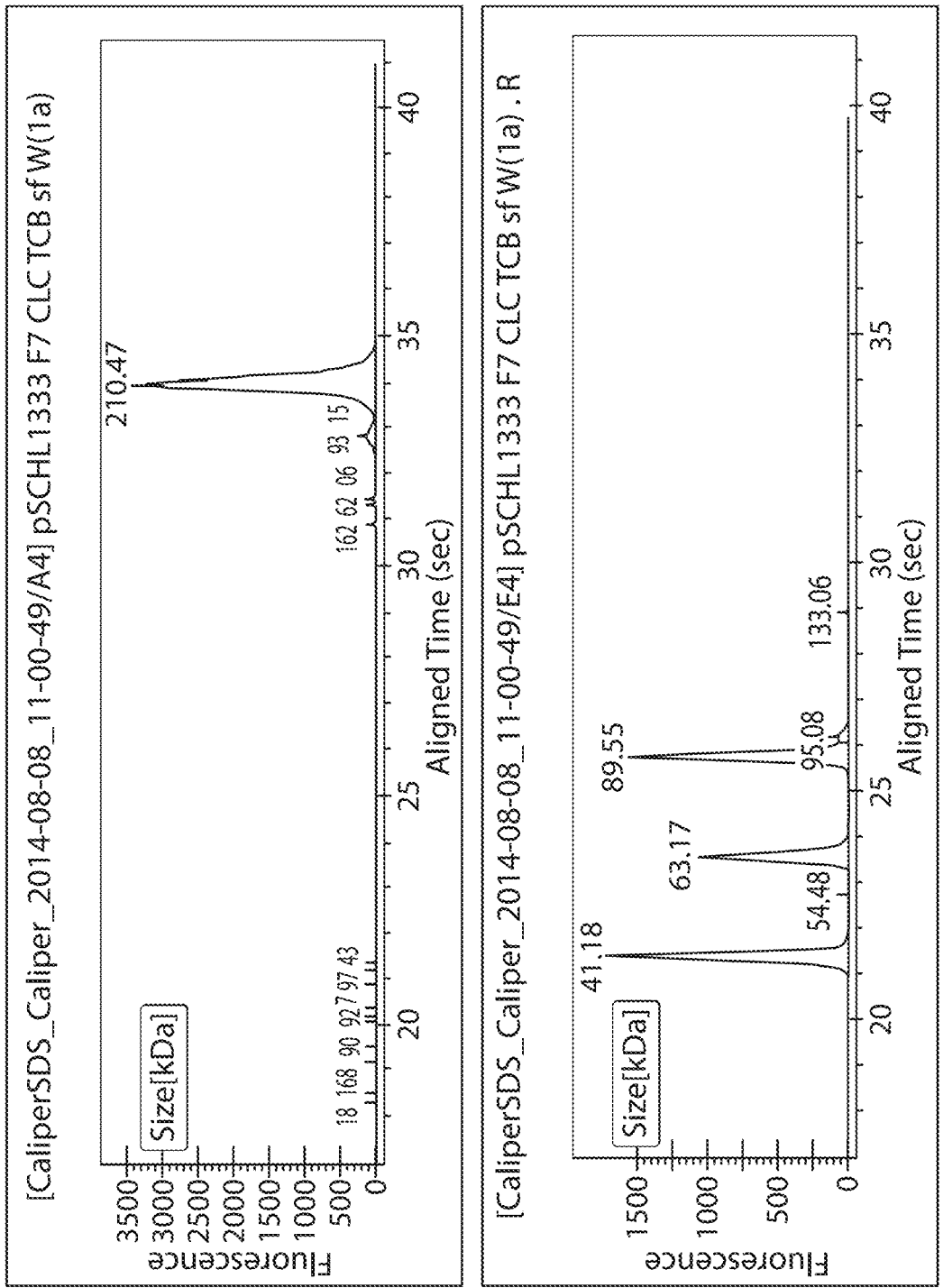
FIGS. 38A-C show production and purification of BCMA-TCB CLC. CE-SDS graphs (non-reduced (top) and reduced (bottom)) of the final protein preparations after Protein A (PA) affinity chromatography and size exclusion chromatographic (SEC) purification steps applied to (A) pSCHLI333-TCB CLC, (B) pSCHLI372-TCB CLC, (C) pSCHLI373-TCB CLC. All three molecules are of molecular format as described in FIG. 36B.
Figure 38B:
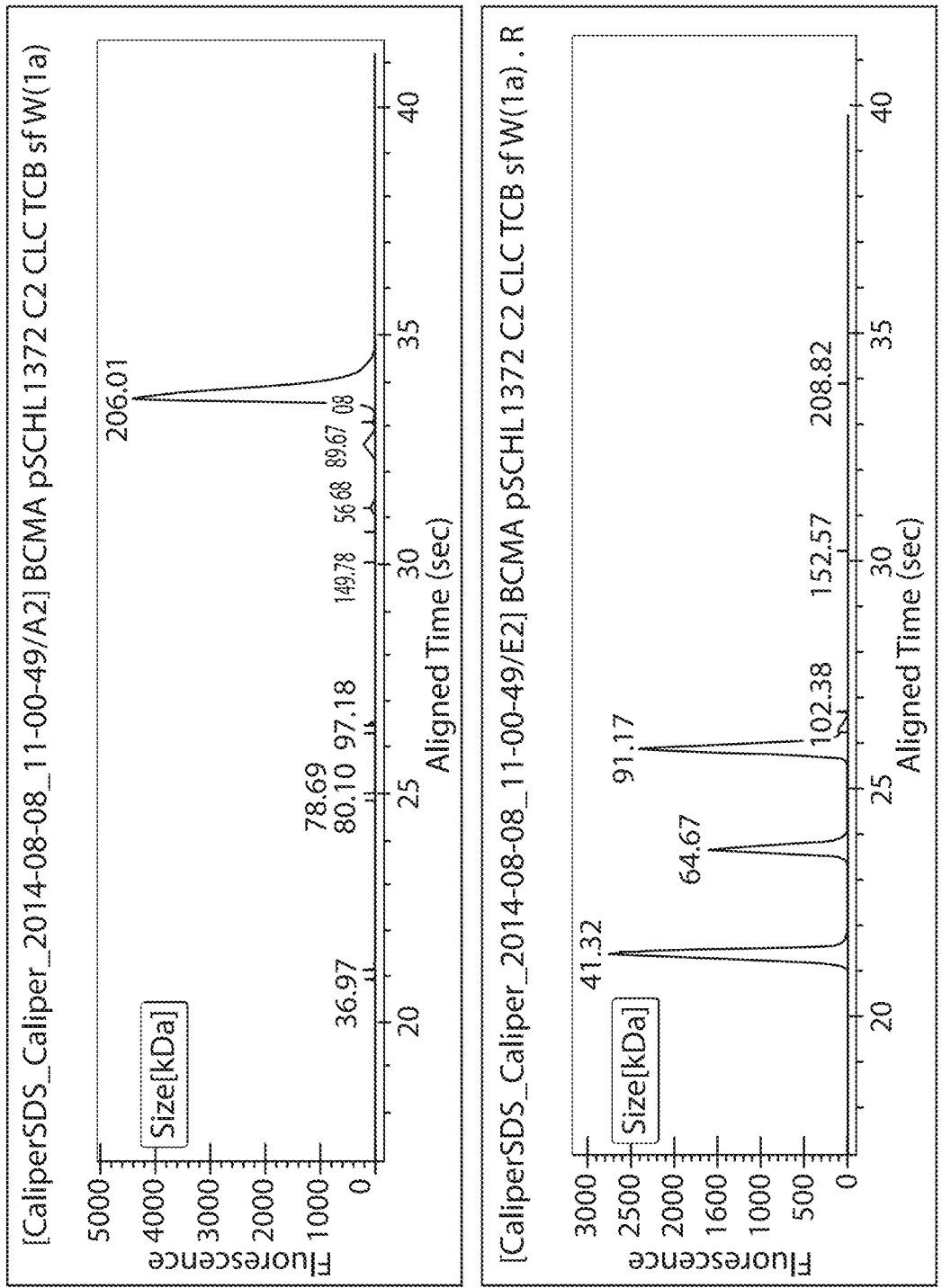
Figure 38C:
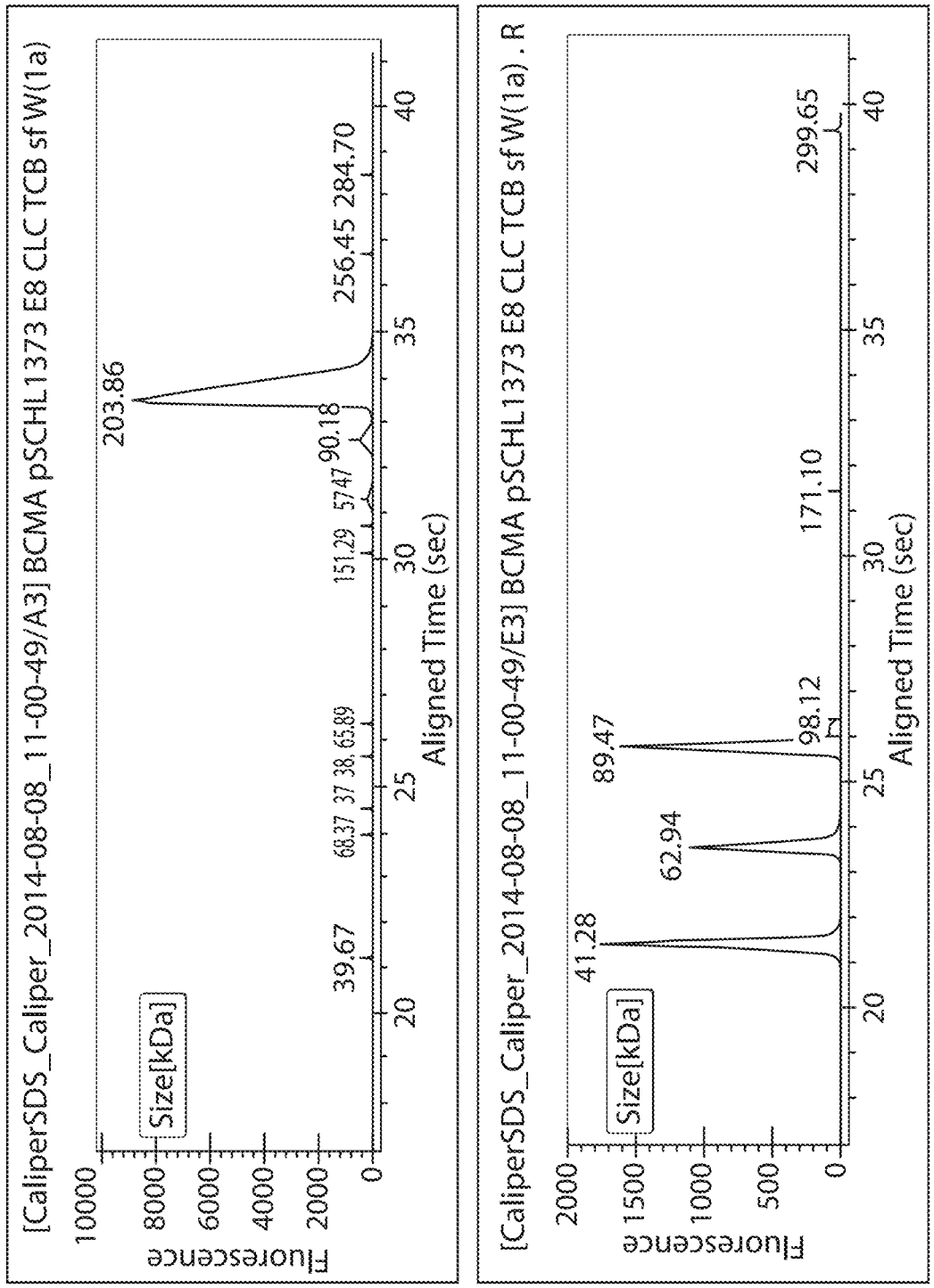

FIGS. 38A-C depicts the CE-SDS graphs (non-reduced (top panels) and reduced (bottom panels)) of the final protein preparations after Protein A (PA) affinity chromatography and size exclusion chromatographic (SEC) purification steps (FIG. 38A) pSCHLI333-TCB CLC, (FIG. 38B) pSCHLI372-TCB CLC, (FIG. 38C) pSCHLI373-TCB CLC. PA affinity chromatography and SEC purification steps applied to pSCHLI333-TCB CLC antibody resulted in a purity of 89.2% and 100% of monomer content (FIG. 38A), a purity of 88.5% and 100% of monomer content for pSCHLI372-TCB CLC antibody (FIG. 38B), and a purity of 91.8% and 100% of monomer content for pSCHLI372-TCB CLC antibody (FIG. 38C). Table 43 summarizes the properties of pSCHLI333-TCB CLC, pSCHLI372-TCB CLC, and pSCHLI373-TCB CLC antibodies following PA affinity chromatography and SEC purification steps. In all BCMA-TCB CLC antibodies, >88% purity and 100% monomer content were consistently reached. The overall results clearly demonstrate that advantages in production/purification features could be achieved with using a common light chain (CLC) to TCB antibodies and that only two purification steps (i.e PA affinity chromatography and SEC) were required to achieve already high quality protein preparations with very good developability properties.

TABLE 43

Production/purification profile of BCMA-TCB CLC antibodies following protein A affinity chromatography and size exclusion chromatography purification steps

|  | pSCHLI333-TCB CLC | pSCHLI372-TCB CLC | pSCHLI373-TCB CLC |
|---|---|---|---|
| Purity (%) | 89.2 | 88.5 | 91.8 |
| Yield (mg/L) | 4.2 | 4.1 | 2.73 |
| Titer (mg/L) | 26.9 | 21.2 | 37.1 |
| Monomer (%) | 100 | 100 | 100 |

Example 44

Binding of BCMA-TCB CLC Antibodies to BCMA-Positive Multiple Myeloma Cell Lines

BCMA-TCB CLC antibodies (pSCHLI333, pSCHLI372, pSCHLI373) were analyzed by flow cytometry for binding to human BCMA on BCMAhi-expressing H929 cells. MKN45 (human gastric adenocarcinoma cell line that does not express BCMA) was used as negative control. Briefly, cultured cells are harvested, counted and cell viability was evaluated using ViCell. Viable cells are then adjusted to $2\times10^6$ cells per ml in BSA-containing FACS Stain Buffer (BD Biosciences). 100 μl of this cell suspension were further aliquoted per well into a round-bottom 96-well plate and incubated with 30 μl of the BCMA-TCB CLC antibodies or corresponding TCB control for 30 min at 4° c. All BCMA-TCB CLC antibodies (and TCB controls) were titrated and analyzed in final concentration range between 0.12-500 nM. Cells were then centrifuged (5 min, 350×g), washed with 120 μl/well FACS Stain Buffer (BD Biosciences), resuspended and incubated for an additional 30 min at 4° C. with fluorochrome-conjugated PE-conjugated AffiniPure F(ab')2 Fragment goat anti-human IgG Fc Fragment Specific (Jackson Immuno Research Lab; 109-116-170). Cells were then washed twice with Stain Buffer (BD Biosciences), fixed using 100 ul BD Fixation buffer per well (#BD Biosciences, 554655) at 4° C. for 20 min, resuspended in 120 μl FACS buffer and analyzed using BD FACS Cantoll. As depicted in FIGS. 39A-B, the mean fluorescence intensity of BCMA-TCB CLC antibodies were plotted in function of antibody concentrations; (FIG. 39A) pSCHLI372-TCB CLC and pSCHLI373-TCB CLC on H929 cells; (FIG. 39B) pSCHLI372-TCB CLC and pSCHLI373-TCB CLC on MKN45 cells. BCMA-TCB CLC antibodies (pSCHLI333, pSCHLI372, pSCHLI373) antibodies did not bind to BCMA-negative and CD3-negative MKN45 cells at concentrations below 100 nM. When applicable, EC50 were calculated using Prism GraphPad (LaJolla, CA, USA) and EC50 values denoting the antibody concentration required to reach 50% of the maximal binding for the binding of anti-BCMA/anti-CD3 TCB antibodies to H929 cells are summarized in Table 44.

TABLE 44

EC50 values for binding of BCMA-TCB CLC antibodies to H929 cells

| Anti-BCMA/anti-CD3 TCB molecules | EC50 (nM) | EC50 (μg/ml) |
|---|---|---|
| pSCHLI372-TCB CLC | 344.8 | 65.9 |
| pSCHLI373-TCB CLC | no EC50 value | no EC50 value |

Example 45

Binding of BCMA-TCB CLC Antibodies to CD3-Positive Jurkat T Cell Line (Flow Cytometry)

BCMA-TCB CLC antibodies (pSCHLI333, pSCHLI372, pSCHLI373) were also analyzed by flow cytometry for their binding properties to human CD3 expressed on human leukemic T cells Jurkat (ATCC TIB-152). Jurkat T cells were cultured in RPMI supplemented with 10% heat-inactivated FCS. Briefly, cultured cells were harvested, counted and cell viability was evaluated using ViCell. Viable cells were then adjusted to $2\times10^6$ cells per ml in FACS Stain Buffer (BD Biosciences) containing 0.1% BSA. 100 μl of this cell suspension were further aliquoted per well into a round-bottom 96-well plate. 30 μl of BCMA-TCB CLC antibodies or corresponding TCB control were added to the cell-containing wells to obtain final concentrations of 0.12 nM to 500 nM. BCMA-TCB CLC antibodies and control IgG were used at the same molarity. After incubation for 30 min at 4° C., cells were centrifuged (5 min, 350×g), washed twice with 150 μl/well BSA-containing FACS Stain Buffer (BD Biosciences), then cells were fixed using 100 ul BD Fixation buffer per well (#BD Biosciences, 554655) at 4° C. for 20 min, resuspended in 120 μl FACS buffer and analyzed using BD FACS Cantoll. Binding of BCMA-TCB CLC antibodies to T cells were evaluated and the median fluorescence intensity was determined gated on CD3-expressing Jurkat T cells and plotted in histograms or dot plots. FIGS. 40A-B show the median fluorescence intensity for BCMA-TCB CLC antibodies (pSCHLI333, pSCHLI372, pSCHLI373) binding to Jurkat T cells (FIG. 40A) or MKN45 cells (FIG. 40B) and plotted in function of antibody concentration. EC50 values and maximal binding of anti-BCMA/anti-CD3 TCB antibodies to CD3-positive Jurkat T cells were not reached. Isotype control antibody did not bind to Jurkat T cells and BCMA-TCB CLC antibodies (pSCHL1333, pSCHL1372, pSCHL1373) antibodies did not bind to BCMA-negative and CD3-negative MKN45 cells at concentrations below 100 nM.

Example 46

Activation of Human T Cells Upon Binding of BCMA-TCB CLC Antibodies to CD3-Positive T Cells and BCMA-Positive Multiple Myeloma Cell Lines BCMA-TCB CLC antibodies (pSCHL1372, pSCHL1373) were analyzed by flow cytometry for their ability to induce T cell activation by evaluating the surface expression of the early activation marker CD69, or the late activation marker CD25 on $CD4^+$ and $CD8^+$ T cells in the presence or absence of human BCMA-expressing MM cells. Briefly, BCMA-positive H929 cells were harvested with Cell Dissociation buffer, counted and checked for viability. Cells were adjusted to $0.3 \times 10^6$ (viable) cells per ml in modified RPMI-1640 medium, 100 μl of this cell suspension were pipetted per well into a round-bottom 96-well plate (as indicated). 50 μl of the (diluted) BCMA-TCB CLC antibodies were added to the cell-containing wells to obtain a final concentration of 0.012 pM-100 nM. Human PBMC effector cells were isolated from fresh blood of a healthy donor and adjusted to $6 \times 10^6$ (viable) cells per ml in modified RPMI-1640 medium. 50 μl of this cell suspension was added per well of the assay plate to obtain a final E:T ratio of PBMC to myeloma tumor cells of 10:1. To analyze whether the BCMA-TCB CLC antibodies were able to activate T cells specifically in the presence of target cells expressing human BCMA, wells were included that contained 3 to 10 nM of the respective BCMA-TCB CLC antibodies molecules, as well as PBMCs, but no target cells. After 48 h incubation at 37° C., 5% $CO_2$, cells were centrifuged (5 min, 350×g) and washed twice with 150 μl/well PBS containing 0.1% BSA. Surface staining for CD4 (mouse IgGI,K; clone RPA-T4), CD8 (mouse IgGI,K; clone HIT8a; BD #555635), CD69 (mouse IgGI; clone L78; BD #340560) and CD25 (mouse IgGI,K; clone M-A251; BD #555434) was performed at 4° C. for 30 min, according to the supplier's suggestions. Cells were washed twice with 150 μl/well PBS containing 0.1% BSA and fixed for 15 min at 4° C., using 100 μl/well fixation buffer (BD #554655). After centrifugation, the samples were resuspended in 200 μl/well PBS with 0.1% BSA and analyzed using a FACS Cantoll machine (Software FACS Diva). FIG. 41 depicts the expression level of the early activation marker CD69 and the late activation marker CD25 on $CD4^+$ and $CD8^+$ T cells after 48 hours of incubation (representative results from two independent experiments). pSCHL1372-TCB CLC and pSCHL1373-TCB CLC antibodies induced an up-regulation of CD69 and CD25 activation markers in a concentration-dependent and specific manner in the presence of BCMA-positive target cells. No activation of $CD4^+$ and CD8+ T cells was observed when human PBMCs were treated with DP47-TCB control antibody, suggesting that despite binding to CD3 on the T cells T-cell activation does not occur when the TCB antibody does not bind to BCMA-positive target cells.

Example 47

Redirected T-Cell Cytotoxicity of $BCMA^{hi}$-Expressing H929 Myeloma Cells Induced by Anti-BCMA/Anti-CD3 T Cell Bispecific Antibodies (Colorimetric LDH Release Assay)

Figure 42A:
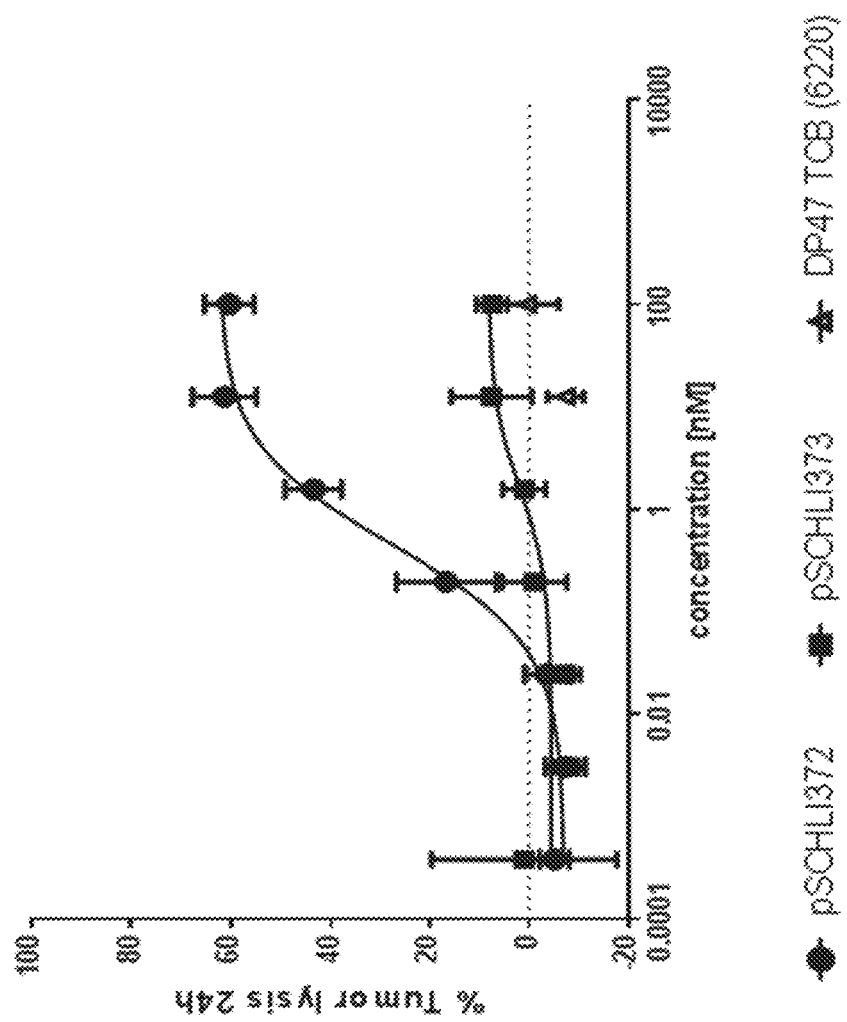
FIGS. 42A-B show BCMA-TCB CLC antibodies induce T-cell redirected killing of BCMAhi-positive H929 myeloma cells as detected by colorimetric LDH release assay. BCMA-TCB CLC antibodies pSCHLI372-TCB CLC (A, B) and pSCHLI373-TCB CLC (A) induced a concentration-dependent killing of BCMAhi-positive H929 myeloma cells as measured by LDH release. DP47-TCB which is a negative control TCB that does not bind to BCMA but only to CD3 did not induce H929 cell killing. E:T ratio used as 10 PBMCs:1 H929 cell; cells were incubated for 24 h before measurement of LDH release. Representative results are from three independent experiments.
Figure 42B:
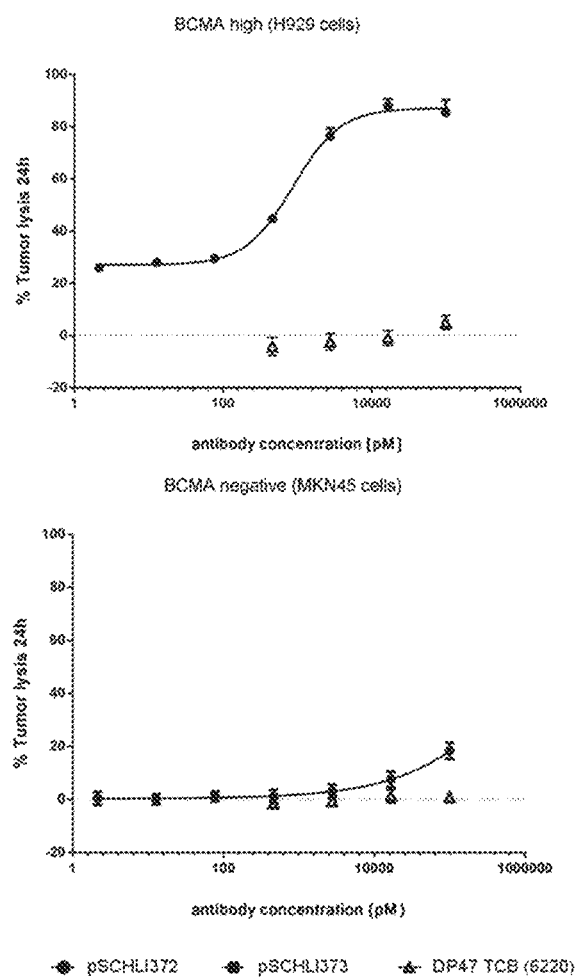
Figure 43:
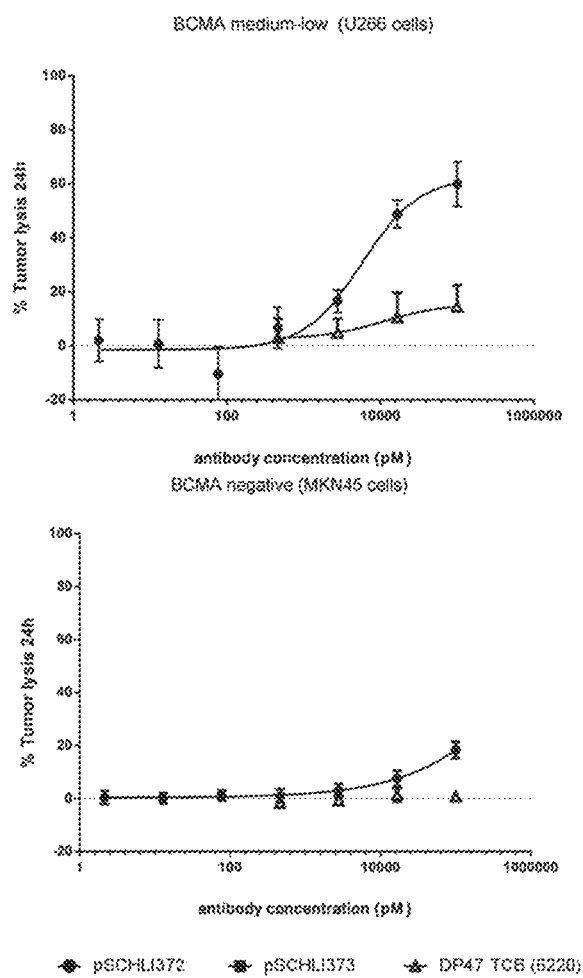
FIG. 43 shows BCMA-TCB CLC antibodies induce T-cell redirected killing of BCMAmed/lo-positive U266 myeloma cells as detected by colorimetric LDH release assay. BCMA-TCB CLC antibodies pSCHLI372-TCB CLC and pSCHLI373-TCB CLC induced a concentration-dependent killing of BCMAmed/lo-positive U266 myeloma cells as measured by LDH release. DP47-TCB which is a negative control TCB that does not bind to BCMA but only to CD3 did not induce H929 cell killing. E:T ratio used as 10 PBMCs:1 U266 cell; cells were incubated for 24 h before measurement of LDH release. Representative results are from two independent experiments.

BCMA-TCB CLC antibodies (pSCHLI372, pSCHLI373) were also analyzed for their potential to induce T cell-mediated apoptosis in BCMA-high expressing MM cells upon crosslinking of the construct via binding of the antigen binding moieties to BCMA on cells. Briefly, human BCMA-expressing H929 multiple myeloma target cells were harvested with Cell Dissociation Buffer, washed and resuspended in RPMI supplemented with 10% fetal bovine serum (Invitrogen). Approximately, 30,000 cells per well were plated in a round-bottom 96-well plate and the respective dilution of the construct was added for a desired final concentration (in triplicates); final concentrations ranging from 0.12 pM to 100 nM. For an appropriate comparison, all TCB constructs and controls were adjusted to the same molarity. Human total T cells (effector) were added into the wells to obtain a final E:T ratio of 5:1. When human PBMC were used as effector cells, a final E:T ratio of 10:1 was used. Negative control groups were represented by effector or target cells only. As a positive control for the activation of human pan T cells, 1 μg/ml PHA-M (Sigma #L8902) was used. For normalization, maximal lysis of the H929 MM target cells (=100%) was determined by incubation of the target cells with a final concentration of 1% Triton X-100, inducing cell death. Minimal lysis (=0%) was represented by target cells co-incubated with effector cells only, i.e. without any T cell bispecific antibody. After 20-24h or 48h incubation at 37° C., 5% $CO_2$, LDH release from the apoptotic/necrotic MM target cells into the supernatant was then measured with the LDH detection kit (Roche Applied Science), following the manufacturer's instructions. The percentage of LDH release was plotted against the concentrations of BCMA-TCB CLC antibodies in concentration-response curves. The EC50 values were measured using Prism software (GraphPad) and determined as the TCB antibody concentration that results in 50% of maximum LDH release. As shown in FIGS. 42A-B, BCMA-TCB CLC antibodies, pSCHLI372-TCB CLC (FIGS. 42A, B) and pSCHLI373-TCB CLC (FIG. 42B) induced a concentration-dependent killing of BCMA-positive H929 myeloma cells as measured by LDH release. The killing of H929 cells was specific since DP47-TCB control antibody which does not bind to BCMA-positive target cells did not induce LDH release, even at the highest concentration tested of 100 nM. Table 45 summarizes the EC50 values for redirected T-cell killing of BCMA-positive H929 cells induced by BCMA-TCB CLC antibodies.

TABLE 45

EC50 values for redirected T-cell killing of H929 cells induced by BCMA-TCB CLC antibodies

| Anti-BCMA/anti-CD3 TCB molecules | EC50 (pM) | EC50 (μg/ml) |
|---|---|---|
| pSCHLI333-TCB CLC | 980 | 0.19 |
| pSCHLI372-TCB CLC (Experiment 1) | 450 | 0.08 |
| pSCHLI373-TCB CLC | 1590 | 0.31 |
| pSCHLI372-TCB CLC (Experiment 2) | 900 | 0.17 |

Example 48

Redirected T-Cell Cytotoxicity of BCMA$^{med/lo}$-Expressing U266 Myeloma Cells Induced by BCMA-TCB CLC Antibodies (LDH Release Assay)

BCMA-TCB CLC antibodies (pSCHLI372, pSCHLI373) were analyzed for their ability to induce T cell-mediated apoptosis in BCMA$^{med/lo}$-expressing MM cells upon cross-linking of the construct via binding of the antigen binding moieties to BCMA on cells. Briefly, human BCMA$^{med/lo}$-expressing U266 multiple myeloma target cells were harvested with Cell Dissociation Buffer, washed and resuspended in RPMI supplemented with 10% fetal bovine serum (Invitrogen). Approximately, 30,000 cells per well are plated in a round-bottom 96-well plate and the respective dilution of the construct was added for a desired final concentration (in triplicates); final concentrations ranging from 0.12 pM to 100 nM. For an appropriate comparison, all TCB constructs and controls were adjusted to the same molarity. Human total T cells (effector) were added into the wells to obtain a final E:T ratio of 5:1. When human PBMC were used as effector cells, a final E:T ratio of 10:1 was used. Negative control groups were represented by effector or target cells only. As a positive control for the activation of human T cells, 1 µg/ml PHA-M (Sigma #L8902) was used. For normalization, maximal lysis of the MM target cells (=100%) was determined by incubation of the target cells with a final concentration of 1% Triton X-100, inducing cell death. Minimal lysis (=0%) was represented by target cells co-incubated with effector cells only, i.e. without any T cell bispecific antibody. After 20-24 h incubation at 37° C., 5% $CO_2$, LDH release from the apoptotic/necrotic MM target cells into the supernatant was then measured with the LDH detection kit (Roche Applied Science), following the manufacturer's instructions. The percentage of LDH release was plotted against the concentrations of BCMA-TCB CLC antibodies in concentration-response curves. The EC50 values were measured using Prism software (GraphPad) and determined as the TCB antibody concentration that results in 50% of maximum LDH release. Table 46 summarizes the EC50 values for redirected T-cell killing of BCMA-positive U266 cells induced by BCMA-TCB CLC antibodies.

TABLE 46

| EC50 values for redirected T-cell killing of U266 cells induced by BCMA-TCB CLC antibodies | | |
|---|---|---|
| Anti-BCMA/anti-CD3 TCB molecules | EC50 (pM) | EC50 (µg/ml) |
| pSCHLI372-TCB CLC | 5700 | 1.1 |

Amino Acid Sequences of Exemplary Embodiments

1) FcIR binders useful in common light chain format, variable heavy chain

| Description | Sequence | Seq ID No |
|---|---|---|
| 16A3 | QVQLVQSGAEVKKPGASVKVSCKASGYTFTSYYMHWVRQAPGQGLEWMGII NPSGGSTSYAQKFQGRVTMTRDTSTSTVYMELSSLRSEDTAVYYCARNYYA GVTPFDYWGQGTLVTVSS | 1 |
| 18D3 | QVQLVQSGAEVKKPGASVKVSCKASGYTFTSYYMHWVRQAPGQGLEWMGII NPSGGSTSYAQKFQGRVTMTRDTSTSTVYMELSSLRSEDTAVYYCARNYYT GGSSAFDYWGQGTLVTVS | 2 |
| 15H7 | QVQLVQSGAEVKKPGASVKVSCKASGYTFTSYYMHWVRQAPGQGLEWMGII NPSGGSTSYAQKFQGRVTMTRDTSTSTVYMELSSLRSEDTAVYYCARNYYL FSTSFDYWGQGTLVTVSS | 3 |
| 15E36 | QVQLVQSGAEVKKPGASVKVSCKASGYTFTSYYMHWVRQAPGQGLEWMGII NPSGGSTSYAQKFQGRVTMTRDTSTSTVYMELSSLRSEDTAVYYCARNYYI GIVPFDYWGQGTLVTVSS | 4 |
| 21D1 | QVQLVQSGAEVKKPGASVKVSCKASGYTFTSYYMHWVRQAPGQGLEWMGII NPSGGSTSYAQKFQGRVTMTRDTSTSTVYMELSSLRSEDTAVYYCARNYYV GVSPFDYWGQGTLVTVSS | 5 |
| 16F12 | QVQLVQSGAEVKKPGASVKVSCKASGYTFTSYYMHWVRQAPGQGLEWMGII NPSGGSTSYAQKFQGRVTMTRDTSTSTVYMELSSLRSEDTAVYYCARNFTV LRVPFDYWGQGTLVTVSS | 6 |
| 15A1 | QVQLVQSGAEVKKPGASVKVSCKASGYTFTSYYMHWVRQAPGQGLEWMGII NPSGGSTSYAQKFQGRVTMTRDTSTSTVYMELSSLRSEDTAVYYCARNYYI GVVTFDYWGQGTLVTVSS | 7 |
| 15A1_CDR1 | SYYMH | 8 |
| 15A1_CDR2 | IINPSGGSTSYAQKFQG | 9 |
| 15A1_CDR3 | NYYI GVVT FDY | 10 |
| 19E5 | QVQLVQSGAEVKKPGASVKVSCKASGYTFTSYYMHWVRQAPGQGLEWMGII NPSGGSTSYAQKFQGRVTMTRDTSTSTVYMELSSLRSEDTAVYYCARGEWR RYTSFDYWGQGTLVTVSS | 11 |
| 19E5_CDR1 | SYYMH | 8 |
| 19E5_CDR2 | IINPSGGSTSYAQKFQG | 9 |

1) FoIR binders useful in common light chain format, variable heavy chain

| Description | Sequence | Seq ID No |
|---|---|---|
| 19E5_CDR3 | GEWRRYTSFDY | 12 |
| 19A4 | QVQLVQSGAEVKKPGASVKVSCKASGYTFTSYYMHWVRQAPGQGLEWMGII NPSGGSTSYAQKFQGRVTMTRDTSTSTVYMELSSLRSEDTAVYYCARGGWI RWEHFDYWGQGTLVTVSS | 13 |
| 19A4_CDR1 | SYYMH | 8 |
| 19A4_CDR2 | IINPSGGSTSYAQKFQG | 9 |
| 19A4_CDR3 | GGWIRWEHFDY | 14 |
| 16D5 | EVQLVESGGGLVKPGGSLRLSCAASGETFSNAWMSWVRQAPGKGLEWVGRI KSKTDGGTTDYAAPVKGRFTISRDDSKNTLYLQMNSLKTEDTAVYYCTTPW EWSWYDYWGQGTLVTVSS | 15 |
| 16D5_CDR1 | NAWMS | 16 |
| 16D5_CDR2 | RIKSKTDGGTTDYAAPVKG | 17 |
| 16D5_CDR3 | PWEWSWYDY | 18 |
| 15E12 | EVQLVESGGGLVKPGGSLRLSCAASGETFSNAWMSWVRQAPGKGLEWVGRI KSKTDGGTTDYAAPVKGRFTISRDDSKNTLYLQMNSLKTEDTAVYYCTTPW EWSYFDYWGQGTLVTVSS | 19 |
| 15E12_CDR1 | NAWMS | 16 |
| 15E12_CDR2 | RIKSKTDGGTTDYAAPVKG | 17 |
| 15E12_CDR3 | PWEWSYFDY | 20 |
| 21A5 | EVQLVESGGGLVKPGGSLRLSCAASGETFSNAWMSWVRQAPGKGLEWVGRI KSKTDGGTTDYAAPVKGRFTISRDDSKNTLYLQMNSLKTEDTAVYYCTTPW EWAWFDYWGQGTLVTVSS | 21 |
| 21A5_CDR1 | NAWMS | 16 |
| 21A5_CDR2 | RIKSKTDGGTTDYAAPVKG | 17 |
| 21A5_CDR3 | PWEWAWFDY | 22 |
| 21G8 | EVQLVESGGGLVKPGGSLRLSCAASGETFSNAWMSWVRQAPGKGLEWVGRI KSKTDGGTTDYAAPVKGRFTISRDDSKNTLYLQMNSLKTEDTAVYYCTTPW EWAYFDYWGQGTLVTVSS | 23 |
| 21G8_CDR1 | NAWMS | 16 |
| 21G8_CDR2 | RIKSKTDGGTTDYAAPVKG | 17 |
| 21G8_CDR3 | PWEWAYFDY | 24 |
| 19H3 | QVQLVQSGAEVKKPGASVKVSCKASGYTFTSYYMHWVRQAPGQGLEWMGII NPSGGSTSYAQKFQGRVTMTRDTSTSTVYMELSSLRSEDTAVYYCARTGWS RWGYMDYWGQGTLVTVSS | 25 |
| 19H3_CDR1 | SYYMH | 8 |
| 19H3_CDR2 | IINPSGGSTSYAQKFQG | 9 |
| 19H3_CDR3 | TGWSRWGYMDY | 26 |
| 20G6 | QVQLVQSGAEVKKPGASVKVSCKASGYTFTSYYMHWVRQAPGQGLEWMGII NPSGGSTSYAQKFQGRVTMTRDTSTSTVYMELSSLRSEDTAVYYCARGEWI RYYHFDYWGQGTLVTVSS | 27 |
| 20G6_CDR1 | SYYMH | 8 |
| 20G6_CDR2 | IINPSGGSTSYAQKFQG | 9 |
| 20G6_CDR3 | GEWIRYYHFDY | 28 |

1) FoIR binders useful in common light chain format, variable heavy chain

| Description | Sequence | Seq ID No |
|---|---|---|
| 20H7 | QVQLVQSGAEVKKPGASVKVSCKASGYTFTSYYMHWVRQAPGQGLEWMGII<br>NPSGGSTSYAQKFQGRVTMTRDTSTSTVYMELSSLRSEDTAVYYCARVGWY<br>RWGYMDYWGQGTLVTSS | 29 |
| 20H7_CDR1 | SYYMH | 8 |
| 20H7_CDR2 | IINPSGGSTSYAQKFQG | 9 |
| 20H7_CDR3 | VGWYRWGYMDY | 30 |

2) CD3 binder common light chain (CLC)

| Description | Sequence | Seq ID No |
|---|---|---|
| common CD3 light chain (VL) | QAVVTQEPSLTVSPGGTVTLTCGSSTGAVTTSNYANWVQEKPGQAFRGLIG<br>GTNKRAPGTPARFSGSLLGGKAALTLSGAQPEDEAEYYCALWYSNLWVFGG<br>GTKLTVL | 31 |
| common CD3 light chain_CDR1 | GSSTGAVTTSNYAN | 32 |
| common CD3 light chain_CDR2 | GTNKRAP | 33 |
| common CD3 light chain_CDR3 | ALWYSNLWV | 34 |
| common CD3 light chain(VLCL) | QAVVTQEPSLTVSPGGTVTLTCGSSTGAVTTSNYANWVQEKPGQAFRGLIG<br>GTNKRAPGTPARFSGSLLGGKAALTLSGAQPEDEAEYYCALWYSNLWVFGG<br>GTKLTVLGQPKAAPSVTLFPPSSEELQANKATLVCLISDFYPGAVTVAWKA<br>DSSPVKAGVETTTPSKQSNNKYAASSYLSLTPEQWKSHRSYSCQVTHEGST<br>VEKTVAPTECS | 35 |

3) CD3 binder, heavy chain

| Description | Sequence | Seq ID No |
|---|---|---|
| CD3 variable heavy chain (VH) | EVQLLESGGGLVQPGGSLRLSCAASGFTFSTYAMNWVRQAPGKGLEWVSR<br>IRSKYNNYATYYADSVKGRFTISRDDSKNTLYLQMNSLRAEDTAVYYCVR<br>HGNFGNSYVSWFAYWGQGTLVTVSS | 36 |
| CD3 heavy chain (VH)_CDR1 | TYAMN | 37 |
| CD3 heavy chain (VH)_CDR2 | RIRSKYNNYATYYADSVKG | 38 |
| CD3 heavy chain (VH)_CDR3 | HGNFGNSYVSWFAY | 39 |
| CD3 full heavy chain (VHCH1)_ | EVQLLESGGGLVQPGGSLRLSCAASGFTFSTYAMNWVRQAPGKGLEWVSR<br>IRSKYNNYATYYADSVKGRFTISRDDSKNTLYLQMNSLRAEDTAVYYCVR<br>HGNFGNSYVSWFAYWGQGTLVTVSSASTKGPSVFPLAPSSKSTSGGTAAL<br>GCLVKDYFPEPVTVSWNSGALTSGVHTFPAVLQSSGLYSLSSVVTVPSSS<br>LGTQTYICNVNHKPSNTKVDKKVEPKSC | 40 |
| CD3 constant heavy chain CH1 | ASTKGPSVFPLAPSSKSTSGGTAALGCLVKDYFPEPVTVSWNSGALTSGV<br>HTFPAVLQSSGLYSLSSVVTVPSSSLGTQTYICNVNHKPSNTKVDKKVEP<br>KSC | 84 |

4) MUC1 binders useful in common light chain format, variable heavy chain

| SEQ ID NOS | Description | Nucleotide | Amino Acid Sequence |
|---|---|---|---|
| MUC1 Antigens | | | |
| 57 and 58 | MUC1 SEA-avi-His | ATGAGCTTTTTTTTCCTGAGCTTTCATATTAGCAACC TGCAGTTTAATAGCAGCCTGGAAGATCCGAGCACCGA TTATTATCAAGAACTGCAGCGTGATATCAGCGAAATG TTTCTGCAGATCTATAAACAGGGTGGTTTTCTGGGTC TGAGCAACATCAAATTTCGTCCGGGTGGTGGCGGTGG TTCAGTTGTTGTGCAGCTGACCCTGGCATTTCGTGAA GGCACCATTAATGTTCATGATGTGGAAACCCAGTTTA ACCAGTATAAAACCGAAGCAGCAAGCCGTTATAATCT GACCATTAGTGATGTTAGCGTTTCCGATGTTCCGTTT CCGTTTAGCGCACAGAGTGTCGACGGTCTGAATGATA TTTTTGAAGCCCAGAAAATCGAATGGCATGAACTCGA GCACCACCACCACCACCAC | MSFFFLSFHISNLQFN SSLEDPSTDYYQELQR DISEMFLQIYKQGGFL GLSNIKFRPGGGGSV VVQLTLAFREGTINVH DVETQFNQYKTEAASR YNLTISDVSVSDVPFP FSAQSVDGLNDIFEAQ KIEWHELEHHHHHH |
| MUC1 Binders | | | |
| 59 and 60 | 58D6 VH | GAGGTGCAATTGTTGGAGTCTGGGGGAGGCTTGGTAC AGCCTGGGGGGTCCCTGAGACTCTCCTGTGCAGCCTC CGGATTCACCTTTAGCAGTTATGCCATGAGCTGGGTC CGCCAGGCTCCAGGGAAGGGGCTGGAGTGGGTCTCAG CTATTAGTGGTAGTGGTGGTAGCACATACTACGCAGA CTCCGTGAAGGGCCGGTTCACCATCTCCAGAGACAAT TCCAAGAACACGCTGTATCTGCAGATGAACAGCCTGA GAGCCGAGGACACGGCCGTATATTACTGTGCGAAAGT TGAATGGTCTACTCTGCTGTACTTCGACTACTGGGGC CAAGGAACCCTGGTCACCGTCTCGAGT | EVQLLESGGGLVQPGG SLRLSCAASGFTFSSY AMSWVRQAPGKGLEWV SAISGSGGSTYYADSV KGRFTISRDNSKNTLY LQMNSLRAEDTAVYYC AKVEWSTLLYFDYWGQ GTLVTVSS |
| 61 and 62 | 106D2 VH | GAGGTGCAATTGTTGGAGTCTGGGGGAGGCTTGGTAC AGCCTGGGGGGTCCCTGAGACTCTCCTGTGCAGCCTC CGGATTCACCTTTCGGGTTTATGCAATGAGCTGGGTC CGCCAGGCTCCAGGGAAGGGGCTGGAGTGGGTCTCAG GTATTTCTGAAACTGGTTCTTACACATACTACGCAGA CTCCGTGAAGGGCCGGTTCACCATCTCCAGAGACAAT TCCAAGAACACGCTGTATCTGCAGATGAACAGCCTGA GAGCCGAGGACACGGCCGTATATTACTGTGCGCGTTA CCCGTACGGTTTCGACTACTGGGGCCAAGGAACCCTG GTCACCGTCTCGAGT | EVQLLESGGGLVQPGG SLRLSCAASGFTFRVY AMSWVRQAPGKGLEWV SGISETGSYTYYADSV KGRFTISRDNSKNTLY LQMNSLRAEDTAVYYC ARYPYGFDYWGQGTLV TVSS |
| 63 and 64 | 110A5 VH | GAGGTGCAATTGTTGGAGTCTGGGGGAGGCTTGGTAC AGCCTGGGGGGTCCCTGAGACTCTCCTGTGCAGCCTC CGGATTCACCTTTAGCTATGCCATGAGCTGGGTC CGCCAGGCTCCAGGGAAGGGGCTGGAGTGGGTCTCAG CTATTAGTGGTAGTGGTGGTAGCACATACTACGCAGA CTCCGTGAAGGGCCGGTTCACCATCTCCAGAGACAAT TCCAAGAACACGCTGTATCTGCAGATGAACAGCCTGA GAGCCGAGGACACGGCCGTATATTACTGTGCGAAATA CTCTTACCGTTACGTTCTGGCTTTCGACTACTGGGGC CAAGGAACCCTGGTCACCGTCTCGAGT | EVQLLESGGGLVQPGG SLRLSCAASGFTFSSY AMSWVRQAPGKGLEWV SAISGSGGSTYYADSV KGRFTISRDNSKNTLY LQMNSLRAEDTAVYYC AKYSYRYVLAFDYWGQ GTLVTVSS |
| 65 and 66 | Common light chain VL | CAGGCCGTCGTGACCCAGGAACCCAGCCTGACAGTGT CTCCTGGCGGCACCGTGACCCTGACATGTGGCAGTTC TACAGGCGCCGTGACCACCAGCAACTACGCCAACTGG GTGCAGGAAAAGCCCGGCCAGGCCTTCAGAGGACTGA TCGGCGGCACCAACAAGAGAGCCCCTGGCACCCCTGC CAGATTCAGCGGATCTCTGCTGGGAGGAAAGGCCGCC CTGACACTGTCTGGCGCCCAGCCAGAAGATGAGGCCG AGTACTACTGCGCCCTGTGGTACAGCAACCTGTGGGT GTTCGGCGGAGGCACCAAGCTGACAGTCCTA | QAVVTQEPSLTVSPGG TVTLTCGSSTGAVTTS NYANWVQEKPGQAFRG LIGGTNKRAPGTPARE SGSLLGGKAALTLSGA QPEDEAEYYCALWYSN LWVFGGGTKLTVL |
| 67 and 68 | Common light chain | CAGGCCGTCGTGACCCAGGAACCCAGCCTGACAGTGT CTCCTGGCGGCACCGTGACCCTGACATGTGGCAGTTC TACAGGCGCCGTGACCACCAGCAACTACGCCAACTGG GTGCAGGAAAAGCCCGGCCAGGCCTTCAGAGGACTGA TCGGCGGCACCAACAAGAGAGCCCCTGGCACCCCTGC CAGATTCAGCGGATCTCTGCTGGGAGGAAAGGCCGCC CTGACACTGTCTGGCGCCCAGCCAGAAGATGAGGCCG AGTACTACTGCGCCCTGTGGTACAGCAACCTGTGGGT GTTCGGCGGAGGCACCAAGCTGACAGTGCTGCGTACG CAACCCAAGGCTGCCCCCAGCGTGACCCTGTTCCCCC CCAGCAGCGAGGAACTGCAGGCCAACAAGGCCACCCT GGTCTGCCTGATCAGCGACTTCTACCCAGGCGCCGTG ACCGTGGCCTGGAAGGCCGACAGCAGCCCCGTGAAGG CCGGCGTGGAGACCACCACCCCCAGCAAGCAGAGCAA CAACAAGTACGCCGCCAGCAGCTACCTGAGCCTGACC CCCGAGCAGTGGAAGAGCCACAGGTCCTACAGCTGCC | QAVVTQEPSLTVSPGG TVTLTCGSSTGAVTTS NYANWVQEKPGQAFRG LIGGTNKRAPGTPARE SGSLLGGKAALTLSGA QPEDEAEYYCALWYSN LWVFGGGTKLTVLRTQ PKAAPSVTLFPPSSEE LQANKATLVCLISDFY PGAVTVAWKADSSPVK AGVETTTPSKQSNNKY AASSYLSLTPEQWKSH RSYSCQVTHEGSTVEK TVAPTECS |

4) MUC1 binders useful in common light chain format, variable heavy chain

| SEQ ID NOS | Description | Nucleotide | Amino Acid Sequence |
|---|---|---|---|
| | | AGGTGACCCACGAGGGCAGCACCGTGGAGAAAACCGT GGCCCCCACCGAGTGCTCC | |
| 69 and 70 | 58D6 knob heavy chain | GAGGTGCAATTGTTGGAGTCTGGGGGAGGCTTGGTAC AGCCTGGGGGGTCCCTGAGACTCTCCTGTGCAGCCTC CGGATTCACCTTTAGCAGTTATGCCATGAGCTGGGTC CGCCAGGCTCCAGGGAAGGGGCTGGAGTGGGTCTCAG CTATTAGTGGTAGTGGTGGTAGCACATACTACGCAGA CTCCGTGAAGGGCCGGTTCACCATCTCCAGAGACAAT TCCAAGAACACGCTGTATCTGCAGATGAACAGCCTGA GAGCCGAGGACACGGCCGTATATTACTGTGCGAAAGT TGAATGGTCTACTCTGCTGTACTTCGACTACTGGGGC CAAGGAACCCTGGTCACCGTCTCGAGTGCTAGCACAA AGGGCCCTAGCGTGTTCCCTCTGGCCCCCAGCAGCAA GAGCACAAGCGGCGGAACAGCCGCCCTGGGCTGCCTC GTGAAGGACTACTTCCCCGAGCCCGTGACAGTGTCTT GGAACAGCGGAGCCCTGACAAGCGGCGTGCACACTTT CCCTGCCGTGCTGCAGAGCAGCGGCCTGTACTCCCTG AGCAGCGTGGTCACCGTGCCTAGCAGCAGCCTGGGCA CCCAGACCTACATCTGCAACGTGAACCACAAGCCCAG CAACACCAAAGTGGACAAGAAGGTGGAGCCCAAGAGC TGTGATGGCGGAGGAGGGTCCGAGGCGGAGGATCCG AGGTGCAGCTGCTGGAATCTGGCGGCGGACTGGTGCA GCCTGGCGGATCTCTGAGACTGAGCTGTGCCGCCAGC GGCTTCACCTTCAGCACCTACGCCATGAACTGGGTGC GCCAGGCCCCTGGCAAAGGCCTGGAATGGGTGTCCCG GATCAGAAGCAAGTACAACAACTACGCCACCTACTAC GCCGACAGCGTGAAGGGCCGGTTCACCATCAGCCGGG ACGACAGCAAGAACACCCTGTACCTGCAGATGAACAG CCTGCGGGCCGAGGACACCGCCGTGTACTATTGTGTG CGGCACGGCAACTTCGGCAACAGCTATGTGTCTTGGT TTGCCTACTGGGGCCAGGGCACCCTCGTGACCGTGTC AAGCGCTAGTACCAAGGGCCCCAGCGTGTTCCCCCTG GCACCCAGCAGCAAGAGCACATCTGGCGGAACAGCCG CTCTGGGCTGTCTGGTGAAGACTACTTCCCCGAGCC CGTGACCGTGTCTTGGAACTCTGGCGCCCTGACCAGC GGCGTGCACACCTTTCCAGCCGTGCTGCAGAGCAGCG GCCTGTACTCCCTGTCCTCCGTGGTCACCGTGCCCTC TAGCTCCCTGGGAACACAGACATATATCTGTAATGTC AATCACAAGCCTTCCAACACCAAAGTCGATAAGAAAG TCGAGCCCAAGAGCTGCGACAAAACTCACACATGCCC ACCGTGCCCAGCACCTGAAGCTGCAGGGGGACCGTCA GTCTTCCTCTTCCCCCCAAAAACCCAAGGACACCCTCA TGATCTCCCGGACCCCTGAGGTCACATGCGTGGTGGT GGACGTGAGCCACGAAGACCCTGAGGTCAAGTTCAAC TGGTACGTGGACGGCGTGGAGGTGCATAATGCCAAGA CAAAGCCGCGGGAGGAGCAGTACAACAGCACGTACCG TGTGGTCAGCGTCCTCACCGTCCTGCACCAGGACTGG CTGAATGGCAAGGAGTACAAGTGCAAGGTCTCCAACA AAGCCCTCGGCGCCCCCATCGAGAAAACCATCTCCAA AGCCAAAGGCAGCCCCGAGAACCACAGGTGTACACC CTGCCCCCATGCCGGGATGAGCTGACCAAGAACCAGG TCAGCCTGTGGTGCCTGGTCAAAGGCTTCTATCCCAG CGACATCGCCGTGGAGTGGGAGAGCAATGGGCAGCCG GAGAACAACTACAAGACCACGCCTCCCGTGCTGGACT CCGACGGCTCCTTCTTCCTCTACAGCAAGCTCACCGT GGACAAGAGCAGGTGGCAGCAGGGGAACGTCTTCTCA TGCTCCGTGATGCATGAGGCTCTGCACAACCACTACA CGCAGAAGAGCCTCTCCCTGTCTCCGGGTAAA | EVQLLESGGGLVQPGG SLRLSCAASGFTFSSY AMSWVRQAPGKGLEWV SAISGSGGSTYYADSV KGRFTISRDNSKNTLY LQMNSLRAEDTAVYYC AKVEWSTLLYFDYWGQ GTLVTVSSASTKGPSV FPLAPSSKSTSGGTAA LGCLVKDYFPEPVTVS WNSGALTSGVHTFPAV LQSSGLYSLSSVVTVP SSSLGTQTYICNVNHK PSNTKVDKKVEPKSCD GGGGSGGGGSEVQLLE SGGGLVQPGGSLRLSC AASGFTFSTYAMNWVR QAPGKGLEWVSRIRSK YNNYATYYADSVKGRF TISRDDSKNTLYLQMN SLRAEDTAVYYCVRHG NFGNSYVSWFAYWGQG TLVTVSSASTKGPSVF PLAPSSKSTSGGTAAL GCLVKDYFPEPVTVSW NSGALTSGVHTFPAVL QSSGLYSLSSVVTVPS SSLGTQTYICNVNHKP SNTKVDKKVEPKSCDK THTCPPCPAPEAAGGP SVFLFPPKPKDTLMIS RTPEVTCVVVDVSHED PEVKFNWYVDGVEVHN AKTKPREEQYNSTYRV VSVLTVLHQDWLNGKE YKCKVSNKALGAPIEK TISKAKGQPREPQVYT LPPCRDELTKNQVSLW CLVKGFYPSDIAVEWE SNGQPENNYKTTPPVL DSDGSFFLYSKLTVDK SRWQQGNVFSCSVMHE ALHNHYTQKSLSLSPG K |
| 71 and 72 | 58D6 hole heavy chain | GAGGTGCAATTGTTGGAGTCTGGGGGAGGCTTGGTAC AGCCTGGGGGGTCCCTGAGACTCTCCTGTGCAGCCTC CGGATTCACCTTTAGCAGTTATGCCATGAGCTGGGTC CGCCAGGCTCCAGGGAAGGGGCTGGAGTGGGTCTCAG CTATTAGTGGTAGTGGTGGTAGCACATACTACGCAGA CTCCGTGAAGGGCCGGTTCACCATCTCCAGAGACAAT TCCAAGAACACGCTGTATCTGCAGATGAACAGCCTGA GAGCCGAGGACACGGCCGTATATTACTGTGCGAAAGT TGAATGGTCTACTCTGCTGTACTTCGACTACTGGGGC CAAGGAACCCTGGTCACCGTCTCGAGTGCTAGCACCA AGGGCCCCTCCGTGTTCCCCCTGGCCCCCAGCAGCAA GAGCACCAGCGGCGGCACAGCCGCTCTGGGCTGCCTG GTCAAGGACTACTTCCCCGAGCCCGTGACCGTGTCCT GGAACAGCGGAGCCCTGACCTCCGGCGTGCACACCTT | EVQLLESGGGLVQPGG SLRLSCAASGFTFSSY AMSWVRQAPGKGLEWV SAISGSGGSTYYADSV KGRFTISRDNSKNTLY LQMNSLRAEDTAVYYC AKVEWSTLLYFDYWGQ GTLVTVSSASTKGPSV FPLAPSSKSTSGGTAA LGCLVKDYFPEPVTVS WNSGALTSGVHTFPAV LQSSGLYSLSSVVTVP SSSLGTQTYICNVNHK PSNTKVDKKVEPKSCD |

4) MUC1 binders useful in common light chain format, variable heavy chain

| SEQ ID NOS | Description | Nucleotide | Amino Acid Sequence |
|---|---|---|---|
| | | CCCCGCCGTGCTGCAGAGTTCTGGCCTGTATAGCCTG<br>AGCAGCGTGGTCACCGTGCCTTCTAGCAGCCTGGGCA<br>CCCAGACCTACATCTGCAACGTGAACCACAAGCCCAG<br>CAACACCAAGGTGGACAAGAAGGTGGAGCCCAAGAGC<br>TGCGACAAAACTCACACATGCCCACCGTGCCCAGCAC<br>CTGAAGCTGCAGGGGACCGTCAGTCTTCCTCTTCCC<br>CCCAAAACCCAAGGACACCCTCATGATCTCCCGGACC<br>CCTGAGGTCACATGCGTGGTGGTGGACGTGAGCCACG<br>AAGACCCTGAGGTCAAGTTCAACTGGTACGTGGACGG<br>CGTGGAGGTGCATAATGCCAAGACAAAGCCGCGGGAG<br>GAGCAGTACAACAGCACGTACCGTGTGGTCAGCGTCC<br>TCACCGTCCTGCACCAGGACTGGCTGAATGGCAAGGA<br>GTACAAGTGCAAGGTCTCCAACAAAGCCCTCGGCGCC<br>CCCATCGAGAAAACCATCTCCAAAGCCAAAGGGCAGC<br>CCCGAGAACCACAGGTGTGCACCCTGCCCCCATCCCG<br>GGATGAGCTGACCAAGAACCAGGTCAGCCTCTCGTGC<br>GCAGTCAAAGGCTTCTATCCCAGCGACATCGCCGTGG<br>AGTGGGAGAGCAATGGGCAGCCGGAGAACAACTACAA<br>GACCACGCCTCCCGTGCTGGACTCCGACGGCTCCTTC<br>TTCCTCGTGAGCAAGCTCACCGTGGACAAGAGCAGGT<br>GGCAGCAGGGGAACGTCTTCTCATGCTCCGTGATGCA<br>TGAGGCTCTGCACAACCACTACACGCAGAAGAGCCTC<br>TCCCTGTCTCCGGGTAAA | KTHTCPPCPAPEAAGG<br>PSVFLFPPKPKDTLMI<br>SRTPEVTCVVVDVSHE<br>DPEVKFNWYVDGVEVH<br>NAKTKPREEQYNSTYR<br>VVSVLTVLHQDWLNGK<br>EYKCKVSNKALGAPIE<br>KTISKAKGQPREPQVC<br>TLPPSRDELTKNQVSL<br>SCAVKGFYPSDIAVEW<br>ESNGQPENNYKTTPPV<br>LDSDGSFFLVSKLTVD<br>KSRWQQGNVFSCSVMH<br>EALHNHYTQKSLSLSP<br>GK |
| 73 and 74 | 110A5 knob heavy chain | GAGGTGCAATTGTTGGAGTCTGGGGGAGGCTTGGTAC<br>AGCCTGGGGGGTCCCTGAGACTCTCCTGTGCAGCCTC<br>CGGATTCACCTTTAGCAGTTATGCCATGAGCTGGGTC<br>CGCCAGGCTCCAGGGAAGGGGCTGGAGTGGGTCTCAG<br>CTATTAGTGGTAGTGGTGGTAGCACATACTACGCAGA<br>CTCCGTGAAGGGCCGGTTCACCATCTCCAGAGACAAT<br>TCCAAGAACACGCTGTATCTGCAGATGAACAGCCTGA<br>GAGCCGAGGACACGGCCGTATATTACTGTGCGAAATA<br>CTCTTACCGTTACGTTCTGGCTTTCGACTACTGGGGC<br>CAAGGAACCCTGGTCACCGTCTCGAGTGCTAGCACAA<br>AGGGCCCAGCGTGTTCCCTCTGGCCCCCAGCAGCAA<br>GAGCACAAGCGGCGGAACAGCCGCCCTGGGCTGCCTC<br>GTGAAGGACTACTTCCCCGAGCCCGTGACAGTGTCTT<br>GGAACAGCGGAGCCCTGACAAGCGGCGTGCACACTTT<br>CCCTGCCGTGCTGCAGAGCAGCGGCCTGTACTCCCTG<br>AGCAGCGTGGTCACCGTGCCTAGCAGCAGCCTGGGCA<br>CCCAGACCTACATCTGCAACGTGAACCACAAGCCCAG<br>CAACACCAAAGTGGACAAGAAGGTGGAGCCCAAGAGC<br>TGTGATGGCGGAGGAGGGTCCGAGGCGGAGGATCCG<br>AGGTGCAGCTGCTGGAATCTGGCGGCGGACTGGTGCA<br>GCCTGGCGGATCTCTGAGACTGAGCTGTGCCGCCAGC<br>GGCTTCACCTTCAGCACCTACGCCATGAACTGGGTGC<br>GCCAGGCCCCTGGCAAAGGCCTGGAATGGGTGTCCCG<br>GATCAGAAGCAAGTACAACAACTACGCCACCTACTAC<br>GCCGACAGCGTGAAGGGCCGGTTCACCATCAGCCGGG<br>ACGACAGCAAGAACACCCTGTACCTGCAGATGAACAG<br>CCTGCGGGCCGAGGACACCGCCGTGTACTATTGTGTG<br>CGGCACGGCAACTTCGGCAACAGCTATGTGTCTTGGT<br>TTGCCTACTGGGGCCAGGGCACCCTCGTGACCGTGTC<br>AAGCGCTAGTACCAAGGGCCCCAGCGTGTTCCCCCTG<br>GCACCCAGCAGCAAGAGCACATCTGGCGGAACAGCCG<br>CTCTGGGCTGTCTGGTGAAAGACTACTTCCCCGAGCC<br>CGTGACCGTGTCTTGGAACTCTGGCGCCCTGACCAGC<br>GGCGTGCACACCTTTCCAGCCGTGCTGCAGAGCAGCG<br>GCCTGTACTCCCTGTCCTCCGTGGTCACCGTGCCCTC<br>TAGCTCCCTGGGAACACAGACATATATCTGTAATGTC<br>AATCACAAGCCTTCCAACACCAAAGTCGATAAGAAAG<br>TCGAGCCCAAGAGCTGCGACAAAACTCACACATGCCC<br>ACCGTGCCCAGCACCTGAAGCTGCAGGGGGACCGTCA<br>GTCTTCCTCTTCCCCCCAAAACCCAAGGACACCCTCA<br>TGATCTCCCGGACCCCTGAGGTCACATGCGTGGTGGT<br>GGACGTGAGCCACGAAGACCCTGAGGTCAAGTTCAAC<br>TGGTACGTGGACGGCGTGGAGGTGCATAATGCCAAGA<br>CAAAGCCGCGGGAGGAGCAGTACAACAGCACGTACCG<br>TGTGGTCAGCGTCCTCACCGTCCTGCACCAGGACTGG<br>CTGAATGGCAAGGAGTACAAGTGCAAGGTCTCCAACA<br>AAGCCCTCGGCGCCCCCATCGAGAAAACCATCTCCAA<br>AGCCAAAGGGCAGCCCCGAGAACCACAGGTGTACACC<br>CTGCCCCCATGCCGGGATGAGCTGACCAAGAACCAGG<br>TCAGCCTGTGGTGCCTGGTCAAAGGCTTCTATCCCAG | EVQLLESGGGLVQPGG<br>SLRLSCAASGFTFSSY<br>AMSWVRQAPGKGLEWV<br>SAISGSGGSTYYADSV<br>KGRFTISRDNSKNTLY<br>LQMNSLRAEDTAVYYC<br>AKYSYRYVLAFDYWGQ<br>GTLVTVSSASTKGPSV<br>FPLAPSSKSTSGGTAA<br>LGCLVKDYFPEPVTVS<br>WNSGALTSGVHTFPAV<br>LQSSGLYSLSSVVTVP<br>SSSLGTQTYICNVNHK<br>PSNTKVDKKVEPKSCD<br>GGGGSGGGGSEVQLLE<br>SGGGLVQPGGSLRLSC<br>AASGFTFSTYAMNWVR<br>QAPGKGLEWVSRIRSK<br>YNNYATYYADSVKGRF<br>TISRDDSKNTLYLQMN<br>SLRAEDTAVYYCVRHG<br>NFGNSYVSWFAYWGQG<br>TLVTVSSASTKGPSVF<br>PLAPSSKSTSGGTAAL<br>GCLVKDYFPEPVTVSW<br>NSGALTSGVHTFPAVL<br>QSSGLYSLSSVVTVPS<br>SSLGTQTYICNVNHKP<br>SNTKVDKKVEPKSCDK<br>THTCPPCPAPEAAGGP<br>SVFLFPPKPKDTLMIS<br>RTPEVTCVVVDVSHED<br>PEVKFNWYVDGVEVHN<br>AKTKPREEQYNSTYRV<br>VSVLTVLHQDWLNGKE<br>YKCKVSNKALGAPIEK<br>TISKAKGQPREPQVYT<br>LPPCRDELTKNQVSLW<br>CLVKGFYPSDIAVEWE<br>SNGQPENNYKTTPPVL<br>DSDGSFFLYSKLTVDK<br>SRWQQGNVFSCSVMHE<br>ALHNHYTQKSLSLSPG<br>K |

4) MUC1 binders useful in common light chain format, variable heavy chain

| SEQ ID NOS | Description | Nucleotide | Amino Acid Sequence |
|---|---|---|---|
| | | CGACATCGCCGTGGAGTGGGAGAGCAATGGGCAGCCG GAGAACAACTACAAGACCACGCCTCCCGTGCTGGACT CCGACGGCTCCTTCTTCCTCTACAGCAAGCTCACCGT GGACAAGAGCAGGTGGCAGCAGGGGAACGTCTTCTCA TGCTCCGTGATGCATGAGGCTCTGCACAACCACTACA CGCAGAAGAGCCTCTCCCTGTCTCCGGGTAAA | |
| 75 and 76 | 110A5 hole heavy chain | GAGGTGCAATTGTTGGAGTCTGGGGGAGGCTTGGTAC AGCCTGGGGGGTCCCTGAGACTCTCCTGTGCAGCCTC CGGATTCACCTTTAGCAGTTATGCCATGAGCTGGGTC CGCCAGGCTCCAGGGAAGGGGCTGGAGTGGGTCTCAG CTATTAGTGGTAGTGGTGGTAGCACATACTACGCAGA CTCCGTGAAGGGCCGGTTCACCATCTCCAGAGACAAT TCCAAGAACACGCTGTATCTGCAGATGAACAGCCTGA GAGCCGAGGACACGGCCGTATATTACTGTGCGAAATA CTCTTACCGTTACGTTCTGGCTTTCGACTACTGGGGC CAAGGAACCCTGGTCACCGTCTCGAGTGCTAGCACCA AGGGCCCCTCCGTGTTCCCCCTGGCCCCCAGCAGCAA GAGCACCAGCGGCGGCACAGCCGCTCTGGGCTGCCTG GTCAAGGACTACTTCCCCGAGCCCGTGACCGTGTCCT GGAACAGCGGAGCTCTGACCTCCGGCGTGCACACCTT CCCCGCCGTGCTGCAGAGTTCTGGCCTGTATAGCCTG AGCAGCGTGGTCACCGTGCCTTCTAGCAGCCTGGGCA CCCAGACCTACATCTGCAACGTGAACCACAAGCCCAG CAACACCAAGGTGGACAAGAAGGTGGAGCCCAAGAGC TGCGACAAAACTCACACATGCCCACCGTGCCCAGCAC CTGAAGCTGCAGGGGGACCGTCAGTCTTCCTCTTCCC CCCAAAACCCAAGGACACCCTCATGATCTCCCGGACC CCTGAGGTCACATGCGTGGTGGTGGACGTGAGCCACG AAGACCCTGAGGTCAAGTTCAACTGGTACGTGGACGG CGTGGAGGTGCATAATGCCAAGACAAAGCCGCGGGAG GAGCAGTACAACAGCACGTACCGTGTGGTCAGCGTCC TCACCGTCCTGCACCAGGACTGGCTGAATGGCAAGGA GTACAAGTGCAAGGTCTCCAACAAAGCCCTCGGCGCC CCCATCGAGAAAACCATCTCCAAAGCCAAAGGGCAGC CCCGAGAACCACAGGTGTGCACCCTGCCCCCATCCCG GGATGAGCTGACCAAGAACCAGGTCAGCCTCTCGTGC GCAGTCAAAGGCTTCTATCCCAGCGACATCGCCGTGG AGTGGGAGAGCAATGGGCAGCCGGAGAACAACTACAA GACCACGCCTCCCGTGCTGGACTCCGACGGCTCCTTC TTCCTCGTGAGCAAGCTCACCGTGGACAAGAGCAGGT GGCAGCAGGGGAACGTCTTCTCATGCTCCGTGATGCA TGAGGCTCTGCACAACCACTACACGCAGAAGAGCCTC TCCCTGTCTCCGGGTAAA | EVQLLESGGGLVQPGG SLRLSCAASGFTFSSY AMSWVRQAPGKGLEWV SAISGSGGSTYYADSV KGRFTISRDNSKNTLY LQMNSLRAEDTAVYYC AKYSYRYVLAFDYWGQ GTLVTVSSASTKGPSV FPLAPSSKSTSGGTAA LGCLVKDYFPEPVTVS WNSGALTSGVHTFPAV LQSSGLYSLSSVVTVP SSSLGTQTYICNVNHK PSNTKVDKKVEPKSCD KTHTCPPCPAPEAAGG PSVFLFPPKPKDTLMI SRTPEVTCVVVDVSHE DPEVKFNWYVDGVEVH NAKTKPREEQYNSTYR VVSVLTVLHQDWLNGK EYKCKVSNKALGAPIE KTISKAKGQPREPQVC TLPPSRDELTKNQVSL SCAVKGFYPSDIAVEW ESNGQPENNYKTTPPV LDSDGSFFLVSKLTVD KSRWQQGNVFSCSVMH EALHNHYTQKSLSLSP GK |

5) BCMA binders useful in common light chain format, variable heavy chain

| Amino Acid Sequences | pSCHLI333-TCB | pSCHLI372-TCB | pSCHLI373-TCB |
|---|---|---|---|
| BCMA VH | QVQLVQSGAEVKKPGASV KVSCKASGYMFSSFGMSW VRQAPGQGLEWMGWIYPV GQGTWYAQKFQGRVTMTR DTSTSTVYMELSSLRSED TAVYYCARVSYPPSHFDY WGQGTLVTVSS (SEQ ID NO: 77) | EVQLVESGGGLVKPGGSLRLS CAASGFTFSNSGMIWVRQAPG KGLEWVGHIRSKTDGGTTDYA APVKGRFTISRDDSKNTLYLQ MNSLKTEDTAVYYCTTGGSGS FDYWGQGTLVTVSS (SEQ ID NO: 78) | EVQLVESGGGLVKPGGSLRLSCAA SGFSFSNSWMNWVRQAPGKGLEWV GTIRQKTYGGTTDYAAPVKGRFTI SRDDSKNTLYLQMNSLKTEDTAVY YCTTGGLFGYWDYWGQGTLVTVSS (SEQ ID NO: 79) |
| BCMA CDR1 (VH) | GYMFSSFGMS (SEQ ID NO: 80) | GFTFSNSGMI (SEQ ID NO: 81) | GFSFSNSWMN (SEQ ID NO: 82) |
| BCMA CDR2 (VH) | WIYPVGQGTWYAQKFQG (SEQ ID NO: 83) | HIRSKTDGGTTDYAAPVKG (SEQ ID NO: 85) | TIRQKTYGGTTDYAAPVKG (SEQ ID NO: 86) |
| BCMA CDR3 (VH) | VSYPPSHFDY (SEQ ID NO: 87) | GGSGSFDY (SEQ ID NO: 88) | GGLFGYWDY (SEQ ID NO: 89) |
| CD3 VL | QAVVTQEPSLTVSPGGTV TLTCGSSTGAVTTSNYAN WVQEKPGQAFRGLIGGTN | QAVVTQEPSLTVSPGGTVTLT CGSSTGAVTTSNYANWVQEKP GQAFRGLIGGTNKRAPGTPAR | QAVVTQEPSLTVSPGGTVTLTCGS STGAVTTSNYANWVQEKPGQAFRG LIGGTNKRAPGTPARFSGSLLGGK |

5) BCMA binders useful in common light chain format, variable heavy chain

| Amino Acid Sequences | pSCHLI333-TCB | pSCHLI372-TCB | pSCHLI373-TCB |
|---|---|---|---|
| | KRAPGTPARFSGSLLGGK AALTLSGAQPEDEAEYYC ALWYSNLWVFGGGTKLTV L (SEQ ID NO: 90) | FSGSLLGGKAALTLSGAQPED EAEYYCALWYSNLWVFGGGTK LTVL (SEQ ID NO: 91) | AALTLSGAQPEDEAEYYCALWYSN LWVFGGGTKLTVL (SEQ ID NO: 92) |
| CD3 CDR1 (VL) | GSSTGAVTTSNYAN (SEQ ID NO: 93) | GSSTGAVTTSNYAN (SEQ ID NO: 93) | GSSTGAVTTSNYAN (SEQ ID NO: 93) |
| CD3CDR2 (VL) | GTNKRAP (SEQ ID NO: 94) | GTNKRAP (SEQ ID NO: 94) | GTNKRAP (SEQ ID NO: 94) |
| CD3CDR3 (VL) | ALWYSNLWV (SEQ ID NO: 95) | ALWYSNLWV (SEQ ID NO: 95) | ALWYSNLWV (SEQ ID NO: 95) |
| CD3 VH | EVQLLESGGGLVQPGGSL RLSCAASGFTFSTYAMNW VRQAPGKGLEWVSRIRSK YNNYATYYADSVKGRFTI SRDDSKNTLYLQMNSLRA EDTAVYYCVRHGNFGNSY VSWFAYWGQGTLVTVSS (SEQ ID NO: 96) | EVQLLESGGGLVQPGGSLRLS CAASGFTFSTYAMNWVRQAPG KGLEWVSRIRSKYNNYATYYA DSVKGRFTISRDDSKNTLYLQ MNSLRAEDTAVYYCVRHGNFG NSYVSWFAYWGQGTLVTVSS (SEQ ID NO: 96) | EVQLLESGGGLVQPGGSLRLSCAA SGFTFSTYAMNWVRQAPGKGLEWV SRIRSKYNNYATYYADSVKGRFTI SRDDSKNTLYLQMNSLRAEDTAVY YCVRHGNFGNSYVSWFAYWGQGTL VTVSS (SEQ ID NO: 96) |
| CD3 CDR1 (VH) | TYAMN (SEQ ID NO: 98) | TYAMN (SEQ ID NO: 98) | TYAMN (SEQ ID NO: 98) |
| CD3CDR2 (VH) | RIRSKYNNYATYYADSVK G (SEQ ID NO: 99) | RIRSKYNNYATYYADSVKG (SEQ ID NO: 99) | RIRSKYNNYATYYADSVKG (SEQ ID NO: 99) |
| CD3CDR3 (VH) | HGNFGNSYVSWFAY (SEQ ID NO: 100) | HGNFGNSYVSWFAY (SEQ ID NO: 100) | HGNFGNSYVSWFAY (SEQ ID NO: 100) |
| CD3 LC (CLC) | QAVVTQEPSLTVSPGGTV TLTCGSSTGAVTTSNYAN WVQEKPGQAFRGLIGGTN KRAPGTPARFSGSLLGGK AALTLSGAQPEDEAEYYC ALWYSNLWVFGGGTKLTV LGQPKAAPSVTLFPPSSE ELQANKATLVCLISDFYP GAVTVAWKADSSPVKAGV ETTTPSKQSNNKYAASSY LSLTPEQWKSHRSYSCQV THEGSTVEKTVAPTECS (SEQ ID NO: 101) | QAVVTQEPSLTVSPGGTVTLT CGSSTGAVTTSNYANWVQEKP GQAFRGLIGGTNKRAPGTPAR FSGSLLGGKAALTLSGAQPED EAEYYCALWYSNLWVEGGGTK LTVLGQPKAAPSVTLFPPSSE ELQANKATLVCLISDFYPGAV TVAWKADSSPVKAGVETTTPS KQSNNKYAASSYLSLTPEQWK SHRSYSCQVTHEGSTVEKTVA PTECS (SEQ ID NO: 101) | QAVVTQEPSLTVSPGGTVTLTCGS STGAVTTSNYANWVQEKPGQAFRG LIGGTNKRAPGTPARFSGSLLGGK AALTLSGAQPEDEAEYYCALWYSN LWVFGGGTKLTVLGQPKAAPSVTL FPPSSEELQANKATLVCLISDFYP GAVTVAWKADSSPVKAGVETTTPS KQSNNKYAASSYLSLTPEQWKSHR SYSCQVTHEGSTVEKTVAPTECS (SEQ ID NO: 101) |
| 2 + 1 Fc containing TCB (full molecule) | | | |
| BCMA pSCHLI333 VH_CH1 x CD3 VH_CH1 Fcknob LALAPG | QVQLVQSGAEVKKPGASV KVSCKASGYMFSSFGMSW VRQAPGQGLEWMGWIYPV GQGTWYAQKFQGRVTMTR DTSTSTVYMELSSLRSED TAVYYCARVSYPPSHFDY WGQGTLVTVSSASTKGPS VFPLAPSSKSTSGGTAAL GCLVKDYFPEPVTVSWNS GALTSGVHTFPAVLQSSG LYSLSSVVTVPSSSLGTQ TYICNVNHKPSNTKVDKK VEPKSCDGGGSGGGGSE VQLLESGGGLVQPGGSLR LSCAASGFTFSTYAMNWV RQAPGKGLEWVSRIRSKY NNYATYYADSVKGRFTIS RDDSKNTLYLQMNSLRAE DTAVYYCVRHGNFGNSYV SWFAYWGQGTLVTVSSAS TKGPSVFPLAPSSKSTSG GTAALGCLVKDYFPEPVT VSWNSGALTSGVHTFPAV | n/a | n/a |

5) BCMA binders useful in common light chain format, variable heavy chain

| Amino Acid Sequences | pSCHLI333-TCB | pSCHLI372-TCB | pSCHLI373-TCB |
|---|---|---|---|
| | LQSSGLYSLSSVVTVPSS SLGTQTYICNVNHKPSNT KVDKKVEPKSCDKTHTCP PCPAPEAAGGPSVFLFPP KPKDTLMISRTPEVTCVV VDVSHEDPEVKFNWYVDG VEVHNAKTKPREEQYNST YRVVSVLTVLHQDWLNGK EYKCKVSNKALGAPIEKT ISKAKGQPREPQVYTLPP CRDELTKNQVSLWCLVKG FYPSDIAVEWESNGQPEN NYKTTPPVLDSDGSFFLY SKLTVDKSRWQQGNVFSC SVMHEALHNHYTQKSLSL SPGK (SEQ ID NO: 102) | | |
| BCMA pSCHLI333 HC hole LALAPG | QVQLVQSGAEVKKPGASV KVSCKASGYMESSEGMSW VRQAPGQGLEWMGWIYPV GQGTWYAQKFQGRVTMTR DTSTSTVYMELSSLRSED TAVYYCARVSYPPSHFDY WGQGTLVTVSSASTKGPS VFPLAPSSKSTSGGTAAL GCLVKDYFPEPVTVSWNS GALTSGVHTFPAVLQSSG LYSLSSVVTVPSSSLGTQ TYICNVNHKPSNTKVDKK VEPKSCDKTHTCPPCPAP EAAGGPSVFLFPPKPKDT LMISRTPEVTCVVVDVSH EDPEVKFNWYVDGVEVHN AKTKPREEQYNSTYRVVS VLTVLHQDWLNGKEYKCK VSNKALGAPIEKTISKAK GQPREPQVCTLPPSRDEL TKNQVSLSCAVKGFYPSD IAVEWESNGQPENNYKTT PPVLDSDGSFFLVSKLTV DKSRWQQGNVFSCSVMHE ALHNHYTQKSLSLSPGK (SEQ ID NO: 103) | n/a | n/a |
| BCMA pSCHLI372 VH_CH1 x CD3 VH_CH1 Fcknob LALAPG | n/a | EVQLVESGGGLVKPGGSLRLS CAASGETESNSGMIWVRQAPG KGLEWVGHIRSKTDGGTTDYA APVKGRFTISRDDSKNTLYLQ MNSLKTEDTAVYYCTTGGSGS FDYWGQGTLVTVSSASTKGPS VFPLAPSSKSTSGGTAALGCL VKDYFPEPVTVSWNSGALTSG VHTFPAVLQSSGLYSLSSVVT VPSSSLGTQTYICNVNHKPSN TKVDKKVEPKSCDGGGSGGG GSEVQLLESGGGLVQPGGSLR LSCAASGFTESTYAMNWVRQA PGKGLEWVSRIRSKYNNYATY YADSVKGRFTISRDDSKNTLY LQMNSLRAEDTAVYYCVRHGN FGNSYVSWFAYWGQGTLVTVS SASTKGPSVFPLAPSSKSTSG GTAALGCLVKDYFPEPVTVSW NSGALTSGVHTFPAVLQSSGL YSLSSVVTVPSSSLGTQTYIC NVNHKPSNTKVDKKVEPKSCD KTHTCPPCPAPEAAGGPSVFL FPPKPKDTLMISRTPEVTCVV VDVSHEDPEVKFNWYVDGVEV HNAKTKPREEQYNSTYRVVSV LTVLHQDWLNGKEYKCKVSNK ALGAPIEKTISKAKGQPREPQ VYTLPPCRDELTKNQVSLWCL | n/a |

| 5) BCMA binders useful in common light chain format, variable heavy chain | | | |
|---|---|---|---|
| Amino Acid Sequences | pSCHLI333-TCB | pSCHLI372-TCB | pSCHLI373-TCB |
| | | VKGFYPSDIAVEWESNGQPEN NYKTTPPVLDSDGSFFLYSKL TVDKSRWQQGNVFSCSVMHEA LHNHYTQKSLSLSPGK (SEQ ID NO: 110) | |
| BCMA pSCHLI372 HC hole LALAPG | n/a | EVQLVESGGGLVKPGGSLRLS CAASGETESNSGMIWVRQAPG KGLEWVGHIRSKTDGGTTDYA APVKGRFTISRDDSKNTLYLQ MNSLKTEDTAVYYCTTGGSGS FDYWGQGTLVTVSSASTKGPS VFPLAPSSKSTSGGTAALGCL VKDYFPEPVTVSWNSGALTSG VHTFPAVLQSSGLYSLSSVVT VPSSSLGTQTYICNVNHKPSN TKVDKKVEPKSCDKTHTCPPC RAPEAAGGPSVFLFPPKPKDT LMISRTPEVTCVVVDVSHEDP EVKFNWYVDGVEVHNAKTKPR EEQYNSTYRVVSVLTVLHQDW LNGKEYKCKVSNKALGAPIEK TISKAKGQPREPQVCTLPPSR DELTKNQVSLSCAVKGFYPSD IAVEWESNGQPENNYKTTPPV LDSDGSFFLVSKLTVDKSRWQ QGNVFSCSVMHEALHNHYTQK SLSLSPGK (SEQ ID NO: 111) | n/a |
| BCMA pSCHLI373 VH_CH1 x CD3 VH_CH1 Fcknob LALAPG | n/a | n/a | EVQLVESGGGLVKPGGSLRLSCAA SGFSFSNSWMNWVRQAPGKGLEWV GTIRQKTYGGTTDYAAPVKGRFTI SRDDSKNTLYLQMNSLKTEDTAVY YCTTGGLFGYWDYWGQGTLVTVSS ASTKGPSVFPLAPSSKSTSGGTAA LGCLVKDYFPEPVTVSWNSGALTS GVHTFPAVLQSSGLYSLSSVVTVP SSSLGTQTYICNVNHKPSNTKVDK KVEPKSCDGGGGSGGGGSEVQLLE SGGGLVQPGGSLRLSCAASGFTFS TYAMNWVRQAPGKGLEWVSRIRSK YNNYATYYADSVKGRFTISRDDSK NTLYLQMNSLRAEDTAVYYCVRHG NFGNSYVSWFAYWGQGTLVTVSSA STKGPSVFPLAPSSKSTSGGTAAL GCLVKDYFPEPVTVSWNSGALTSG VHTFPAVLQSSGLYSLSSVVTVPS SSLGTQTYICNVNHKPSNTKVDKK VEPKSCDKTHTCPPCPAPEAAGGP SVFLFPPKPKDTLMISRTPEVTCV VVDVSHEDPEVKFNWYVDGVEVHN AKTKPREEQYNSTYRVVSVLTVLH QDWLNGKEYKCKVSNKALGAPIEK TISKAKGQPREPQVYTLPPCRDEL TKNQVSLWCLVKGFYPSDIAVEWE SNGQPENNYKTTPPVLDSDGSFFL YSKLTVDKSRWQQGNVFSCSVMHE ALHNHYTQKSLSLSPGK (SEQ ID NO: 113) |
| BCMA pSCHLI373 HC hole LALAPG | n/a | n/a | EVQLVESGGGLVKPGGSLRLSCAA SGFSFSNSWMNWVRQAPGKGLEWV GTIRQKTYGGTTDYAAPVKGRFTI SRDDSKNTLYLQMNSLKTEDTAVY YCTTGGLFGYWDYWGQGTLVTVSS ASTKGPSVFPLAPSSKSTSGGTAA LGCLVKDYFPEPVTVSWNSGALTS GVHTFPAVLQSSGLYSLSSVVTVP SSSLGTQTYICNVNHKPSNTKVDK KVEPKSCDKTHTCPPCPAPEAAGG PSVFLFPPKPKDTLMISRTPEVTC VVVDVSHEDPEVKFNWYVDGVEVH NAKTKPREEQYNSTYRVVSVLTVL |

| 5) BCMA binders useful in common light chain format, variable heavy chain | | | |
|---|---|---|---|
| Amino Acid Sequences | pSCHLI333-TCB | pSCHLI372-TCB | pSCHLI373-TCB |
| | | | HQDWLNGKEYKCKVSNKALGAPIE KTISKAKGQPREPQVCTLPPSRDE LTKNQVSLSCAVKGFYPSDIAVEW ESNGQPENNYKTTPPVLDSDGSFF LVSKLTVDKSRWQQGNVFSCSVMH EALHNHYTQKSLSLSPGK (SEQ ID NO: 114) |
| 83A10 VH | EVQLLESGGGLVQPGGSL RLSCAASGFTFSSYAMSW VRQAPGKGLEWVSAISGS GGSTYYADSVKGRFTISR DNSKNTLYLQMNSLRAED TAVYYCAKVLGWFDYWGQ GTLVTVSS (SEQ ID NO: 115) | | |
| 83A10 CDRH1 | SYAMS (SEQ ID NO: 116) | | |
| 83A10 CDRH2 | AISGSGGSTYYADSVKG (SEQ ID NO: 117) | | |
| 83A10 CDRH3 | VLGWFDY (SEQ ID NO: 118) | | |

| 6) Untargeted DP47 | | |
|---|---|---|
| Description | Sequence | Seq ID No |
| Light Chain DP47 GS | EIVLTQSPGTLSLSPGERATLSCRASQSVSSSYLAWYQQ KPGQAPRLLIYGASSRATGIPDRFSGSGSGTDFTLTISR LEPEDFAVYYCQQYGSSPLTFGQGTKVEIKRTVAAPSVF IFPPSDEQLKSGTASVVCLLNNFYPREAKVQWKVDNALQ SGNSQESVTEQDSKDSTYSLSSTLTLSKADYEKHKVYAC EVTHQGLSSPVTKSFNRGEC | 119 |
| Light Chain humanized CD3$_{CH2527}$ (Crossfab, VL-CH1) | QAVVTQEPSLTVSPGGTVTLTCGSSTGAVTTSNYANWVQ EKPGQAFRGLIGGTNKRAPGTPARFSGSLLGGKAALTLS GAQPEDEAEYYCALWYSNLWVFGGGTKLTVLSSASTKGP SVFPLAPSSKSTSGGTAALGCLVKDYFPEPVTVSWNSGA LTSGVHTFPAVLQSSGLYSLSSVVTVPSSSLGTQTYICN VNHKPSNTKVDKKVEPKSC | 120 |
| DP47 GS (VH-CH1)- humanized CD3$_{CH2527}$ (Crossfab VH-Ck)- Fc(knob) P329GLALA | EVQLLESGGGLVQPGGSLRLSCAASGFTFSSYAMSWVRQ APGKGLEWVSAISGSGGSTYYADSVKGRFTISRDNSKNT LYLQMNSLRAEDTAVYYCAKGSGFDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSCDGGGGSGGGGSEVQLL ESGGGLVQPGGSLRLSCAASGFTFSTYAMNWVRQAPGKG LEWVSRIRSKYNNYATYYADSVKGRFTISRDDSKNTLYL QMNSLRAEDTAVYYCVRHGNFGNSYVSWFAYWGQGTLVT VSSASVAAPSVFIFPPSDEQLKSGTASVVCLLNNFYPRE AKVQWKVDNALQSGNSQESVTEQDSKDSTYSLSSTLTLS KADYEKHKVYACEVTHQGLSSPVTKSFNRGECDKTHTCP PCPAPEAAGGPSVFLFPPKPKDTLMISRTPEVTCVVVDV SHEDPEVKFNWYVDGVEVHNAKTKPREEQYNSTYRVVSV LTVLHQDWLNGKEYKCKVSNKALGAPIEKTISKAKGQPR EPQVYTLPPCRDELTKNQVSLWCLVKGFYPSDIAVEWES NGQPENNYKTTPPVLDSDGSFFLYSKLTVDKSRWQQGNV FSCSVMHEALHNHYTQKSLSLSPGK | 121 |
| DP47GS (VH-CH1)- Fc(hole) P329GLALA | EVQLLESGGGLVQPGGSLRLSCAASGFTFSSYAMSWVRQ APGKGLEWVSAISGSGGSTYYADSVKGRFTISRDNSKNT LYLQMNSLRAEDTAVYYCAKGSGFDYWGQGTLVTVSSAS TKGPSVFPLAPSSKSTSGGTAALGCLVKDYFPEPVTVSW NSGALTSGVHTFPAVLQSSGLYSLSSVVTVPSSSLGTQT YICNVNHKPSNTKVDKKVEPKSCDKTHTCPPCPAPEAAG | 122 |

6) Untargeted DP47

| Description | Sequence | Seq ID No |
|---|---|---|
| | GPSVFLFPPKPKDTLMISRTPEVTCVVVDVSHEDPEVKF<br>NWYVDGVEVHNAKTKPREEQYNSTYRVVSVLTVLHQDWL<br>NGKEYKCKVSNKALGAPIEKTISKAKGQPREPQVCTLPP<br>SRDELTKNQVSLSCAVKGFYPSDIAVEWESNGQPENNYK<br>TTPPVLDSDGSFFLVSKLTVDKSRWQQGNVFSCSVMHEA<br>LHNHYTQKSLSLSPGK | |

7) Exemplary target sequences

| Description | Sequence | Seq ID No |
|---|---|---|
| Human CD3 | | |
| Human FoIR1 (ECD 25-234) | RIAWARTELLNVCMNAKHHKEKPGPEDKLHEQCRPWRKNA<br>CCSTNTSQEAHKDVSYLYRFNWNHCGEMAPACKRHFIQDT<br>CLYECSPNLGPWIQQVDQSWRKERVLNVPLCKEDCEQWWE<br>DCRTSYTCKSNWHKGWNWTSGFNKCAVGAACQPFHFYFPT<br>PTVLCNEIWTHSYKVSNYSRGSGRCIQMWFDPAQGNPNEE<br>VARFYAAAM | 227 |
| murine FoIR1 (ECD 25-232) | TRARTELLNVCMDAKHHKEKPGPEDNLHDQCSPWKTNSCC<br>STNTSQEAHKDISYLYRFNWNHCGTMTSECKRHFIQDTCL<br>YECSPNLGPWIQQVDQSWRKERILDVPLCKEDCQQWWEDC<br>QSSFTCKSNWHKGWNWSSGHNECPVGASCHPFTFYFPTSA<br>ALCEEIWSHSYKLSNYSRGSGRCIQMWFDPAQGNPNEEVA<br>RFYAEAMS | 230 |
| cynomolgus FoIR1 (ECD 25-234) | EAQTRTARARTELLNVCMNAKHHKEKPGPEDKLHEQCRPW<br>KKNACCSTNTSQEAHKDVSYLYRFNWNHCGEMAPACKRHF<br>IQDTCLYECSPNLGPWIQQVDQSWRKERVLNVPLCKEDCE<br>RWWEDCRTSYCKSNWHKGWNWTSGFNKCPVGAACQPFHFY<br>FPTPTVLCNEIWTYSYKVSNYSRGSGRCIQMWFDPAQGNP<br>NEEVARFYAAAMS | 231 |

8) Nucleotide sequences of exemplary embodiments

| Description | Sequence | Seq ID No |
|---|---|---|
| 16A3 | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCAACTAC<br>TACGCTGGTGTTACTCCGTTCGACTATTGGGGTCAAGGCACCCTCGTAAC<br>GGTTTCTTCT | 151 |
| 15A1 | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCAACTAC<br>TACATCGGTGTTGTTACTTTCGACTATTGGGGTCAAGGCACCCTCGTAAC<br>GGTTTCTTCT | 152 |
| 18D3 | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCAACTAC<br>TACACTGGTGGTTCTTCTGCTTTCGACTATTGGGGTCAAGGCACCCTCGT<br>AACGGTTTCTTCT | 153 |

8) Nucleotide sequences of exemplary embodiments

| | Sequence | Seq ID No |
|---|---|---|
| 19E5 | CAGGTGCAATTGGTTCAATCTGGTGCTGAAGTAAAAAAACCGGGCGNTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCGGTGAA<br>TGGCGTCGTTACACTTCTTTCGACTATTGGGGTCAAGGCACCCTCGTAAC<br>GGTTTCTTCT | 154 |
| 19A4 | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCGGTGGT<br>TGGATCCGTTGGGAACATTTCGACTATTGGGGTCAAGGCACCCTCGTAAC<br>GGTTTCTTCT | 155 |
| 15H7 | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCAACTAC<br>TACCTGTTCTCTACTTCTTTCGACTATTGGGGTCAAGGCACCCTCGTAAC<br>GGTTTCTTCT | 156 |
| 15B6 | CAGGTGCAATTGGTTCAATCTGGTGCTGAGGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCAACTAC<br>TACATCGGTATCGTTCCGTTCGACTATTGGGGTCAAGGCACCCTCGTAAC<br>GGTTTCTTCT | 157 |
| 16D5 | GAGGTGCAATTGGTTGAATCTGGTGGTGGTCTGGTAAAACCGGGCGGTTC<br>CCTGCGTCTGAGCTGCGCGGCTTCCGGATTCACCTTCTCCAACGCGTGGA<br>TGAGCTGGGTTCGCCAGGCCCCGGGCAAAGGCCTCGAGTGGGTTGGTCGT<br>ATCAAGTCTAAAACTGACGGTGGCACCACGGATTACGCGGCTCCAGTTAA<br>AGGTCGTTTTACCATTTCCCGCGACGATAGCAAAAACACTCTGTATCTGC<br>AGATGAACTCTCTGAAAACTGAAGACACCGCAGTCTACTACTGTACTACC<br>CCGTGGGAATGGTCTTGGTACGATTATTGGGGCCAGGGCACGCTGGTTAC<br>GGTGTCTTCC | 158 |
| 15E12 | GAGGTGCAATTGGTTGAATCTGGTGGTGGTCTGGTAAAACCGGGCGGTTC<br>CCNGCGTCTGAGCTGCGCGGCTTCCGGATTCACCTTCTCCAACGCGTGGA<br>TGAGCTGGGTTCGCCAGGCCCCGGGCAAAGGCCTCGAGTGGGTTGGTCGT<br>ATCAAGTCTAAAACTGACGGTGGCACCACGGATTACGCGGCTCCAGTTAA<br>AGGTCGTTTTACCATTTCCCGCGACGATAGCAAAAACACTCTGTATCTGC<br>AGATGAACTCTCTGAAAACCGAAGACACCGCAGTCTACTACTGTACTACC<br>CCGTGGGAATGGTCTTACTTCGATTATTGGGGCCAGGGCACGCTGGTTAC<br>GGTGTCTTCC | 159 |
| 21D1 | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCAACTAC<br>TACGTTGGTGTTTCTCCGTTCGACTATTGGGGTCAAGGCACCCTCGTAAC<br>GGTTTCTTCT | 160 |
| 16F12 | CAGGTGCAATTGGTTCAATCTGGTGCTGAAGTAAAAAAACCGGGCGNTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCNTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCAACTTC<br>ACTGTTCTGCGTGTTCCGTTCGACTATTGGGGTCAAGGCACCCTCGTAAC<br>GGTTTCTTCT | 161 |
| 21A5 | GAGGTGCAATTGGTTGAATCTGGTGGTGGTCTGGTAAAACCGGGCGGTTC<br>CCTGCGTCTGAGCTGCGCGGCTTCCGGATTCACCTTCTCCAACGCGTGGA<br>TGAGCTGGGTTCGCCAGGCCCCGGGCAAAGGCCTCGAGTGGGTTGGTCGT | 162 |

| | 8) Nucleotide sequences of exemplary embodiments | |
|---|---|---|
| | Sequence | Seq ID No |
| | ATCAAGTCTAAAACTGACGGTGGCACCACGGATTACGCGGCTCCAGTTAA<br>AGGTCGTTTTACCATTTCCCGCGACGATAGCAAAAACACTCTGTATCTGC<br>AGATGAACTCTCTGAAAACTGAAGACACCGCAGTCTACTACTGTACTACC<br>CCGTGGGAATGGGCTTGGTTCGATTATTGGGGCCAGGGCACGCTGGTTAC<br>GGTGTCTTCC | |
| 21G8 | GAGGTGCAATTGGTTGAATCTGGTGGTGGTCTGGTAAAACCGGGCGGTTC<br>CCTGCGTCTGAGCTGCGCGGCTTCCGGATTCACCTTCTCCAACGCGTGGA<br>TGAGCTGGGTTCGCCAGGCCCCGGGCAAAGGCCTCGAGTGGGTTGGTCGT<br>ATCAAGTCTAAAACTGACGGTGGCACCACGGATTACGCGGCTCCAGTTAA<br>AGGTCGTTTTACCATTTCCCGCGACGATAGCAAAAACACTCTGTATCTGC<br>AGATGAACTCTCTGAAAACCGAAGACACCGCAGTCTACTACTGTACTACC<br>CCTGGGAATGGGCTTACTTCGATTATTGGGGCCAGGGCACGCTGGTTAC<br>GGTGTCTTCC | 163 |
| 19H3 | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCACTGGT<br>TGGTCTCGTTGGGGTTACATGGACTATTGGGGCCAAGGCACCCTCGTAAC<br>GGTTTCTTCT | 164 |
| 20G6 | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCGGTGAA<br>TGGATCCGTTACTACCATTTCGACTATTGGGGTCAAGGCACCCTCGTAAC<br>GGTTTCTTCT | 165 |
| 20H7 | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCGTTGGT<br>TGGTACCGTTGGGGTTACATGGACTATTGGGGTCAAGGCACCCTCGTAAC<br>GGTTTCTTCT | 166 |
| 11F8_VH | CAGGTGCAATTGGTGCAGTCTGGGGCTGAGGTGAAGAAGCCTGGGTCCTC<br>GGTGAAGGTCTCCTGCAAGGCCTCCGGAGGCACATTCAGCAGCTACGCTA<br>TAAGCTGGGTGCGACAGGCCCCTGGACAAGGGCTCGAGTGGATGGGAGGG<br>ATCATCCCTATCTTTGGTACAGCAAACTACGCACAGAAGTTCCAGGGCAG<br>GGTAACCATTACTGCAGACAAATCCACGAGCACAGCCTACATGGAGCTGA<br>GCAGCCTGAGATCTGAGGACACCGCCGTGTATTACTGTGCGAGAGCTGTT<br>TTCTACCGTGCTTGGTACTCTTTCGACTACTGGGGCCAAGGGACCACCGT<br>GACCGTCTCCTCA | 167 |
| 11F8_VL | GACATCCAGATGACCCAGTCTCCTTCCACCCTGTCTGCATCTGTAGGAGA<br>CCGTGTCACCATCACTTGCCGTGCCAGTCAGAGTATTAGTAGCTGGTTGG<br>CCTGGTATCAGCAGAAACCAGGGAAAGCCCCTAAGCTCCTGATCTATGAT<br>GCCTCCAGTTTGGAAAGTGGGGTCCCATCACGTTTCAGCGGCAGTGGATC<br>CGGGACAGAATTCACTCTCACCATCAGCAGTTGCAGCCTGATGATTTTG<br>CAACTTATTACTGCCAACAGTATACCAGCCCACCACCAACGTTTGGCCAG<br>GGCACCAAAGTCGAGATCAAG | 168 |
| 36F2_VH | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCATGACACTAGCACCTCTACCGTTTATATGGAGCTGT<br>CCAGCCTGCGTTCTGAAGATACTGCAGTGTACTACTGTGCACGCTCTTTC<br>TTCACTGGTTTCCATCTGGACTATTGGGGTCAAGGCACCCTCGTAACGGT<br>TTCTTCT | 169 |
| 36F2_VL | GAAATCGTGTTAACGCAGTCTCCAGGCACCCTGTCTTTGTCTCCAGGGGA<br>AAGAGCCACCCTCTCTTGCAGGGCCAGTCAGAGTGTTAGCAGCAGCTACT<br>TAGCCTGGTACCAGCAGAAACCTGGCCAGGCTCCCAGGCTCCTCATCTAT<br>GGAGCATCCAGCAGGGCCACTGGCATCCCAGACAGGTTCAGTGGCAGTGG<br>ATCCGGGACAGACTTCACTCTCACCATCAGCAGACTGGAGCCTGAAGATT<br>TTGCAGTGTATTACTGTCAGCAGTATACCAACGAACATTATTATACGTTC<br>GGCCAGGGGACCAAAGTGGAAATCAAA | 170 |

8) Nucleotide sequences of exemplary embodiments

| | Sequence | Seq ID No |
|---|---|---|
| 9D11_VH | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCCCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCGGTGAC<br>TTCGCTTGGCTGGACTATTGGGGTCAAGGCACCCTCGTAACGGTTTCTTC<br>T | 171 |
| 9D11_VL | GATATTGTTATGACTCAATCTCCACTGTCTCTGCCGGTGACTCCAGGCGA<br>ACCGGCGAGCATTCTTGCCGTTCCAGCCAGTCTCTGCTGCACTCCAACG<br>GCTACAACTATCTCGATTGGTACCTGCAAAAACCGGGTCAGAGCCCTCAG<br>CTGCTGATCTACCTGGGCTCTAACCGCGCTTCCGGTGTACCGGACCGTTT<br>CAGCGGCTCTGGATCCGGCACCGATTTCACGTTGAAAATCAGCCGTGTTG<br>AAGCAGAAGACGTGGGCGTTTATTACTGTATGCAGGCAAGCATTATGAAC<br>CGGACTTTTGGTCAAGGCACCAAGGTCGAAATTAAA | 172 |
| 9D11_VL<br>N95S | GATATTGTTATGACTCAATCTCCACTGTCTCTGCCGGTGACTCCAGGCGA<br>ACCGGCGAGCATTCTTGCCGTTCCAGCCAGTCTCTGCTGCACTCCAACG<br>GCTACAACTATCTCGATTGGTACCTGCAAAAACCGGGTCAGAGCCCTCAG<br>CTGCTGATCTACCTGGGCTCTAACCGCGCTTCCGGTGTACCGGACCGTTT<br>CAGCGGCTCTGGATCCGGCACCGATTTCACGTTGAAAATCAGCCGTGTTG<br>AAGCAGAAGACGTGGGCGTTTATTACTGTATGCAGGCAAGCATTATGAGC<br>CGGACTTTTGGTCAAGGCACCAAGGTCGAAATTAAA | 173 |
| 9D11_VL<br>N95Q | GATATTGTTATGACTCAATCTCCACTGTCTCTGCCGGTGACTCCAGGCGA<br>ACCGGCGAGCATTCTTGCCGTTCCAGCCAGTCTCTGCTGCACTCCAACG<br>GCTACAACTATCTCGATTGGTACCTGCAAAAACCGGGTCAGAGCCCTCAG<br>CTGCTGATCTACCTGGGCTCTAACCGCGCTTCCGGTGTACCGGACCGTTT<br>CAGCGGCTCTGGATCCGGCACCGATTTCACGTTGAAAATCAGCCGTGTTG<br>AAGCAGAAGACGTGGGCGTTTATTACTGTATGCAGGCAAGCATTATGCAG<br>CGGACTTTTGGTCAAGGCACCAAGGTCGAAATTAAA | 174 |
| 9D11_VL<br>T97A | GATATTGTTATGACTCAATCTCCACTGTCTCTGCCGGTGACTCCAGGCGA<br>ACCGGCGAGCATTCTTGCCGTTCCAGCCAGTCTCTGCTGCACTCCAACG<br>GCTACAACTATCTCGATTGGTACCTGCAAAAACCGGGTCAGAGCCCTCAG<br>CTGCTGATCTACCTGGGCTCTAACCGCGCTTCCGGTGTACCGGACCGTTT<br>CAGCGGCTCTGGATCCGGCACCGATTTCACGTTGAAAATCAGCCGTGTTG<br>AAGCAGAAGACGTGGGCGTTTATTACTGTATGCAGGCAAGCATTATGAAC<br>CGGGCTTTTGGTCAAGGCACCAAGGTCGAAATTAAA | 175 |
| 9D11_VL<br>T97N | GATATTGTTATGACTCAATCTCCACTGTCTCTGCCGGTGACTCCAGGCGA<br>ACCGGCGAGCATTCTTGCCGTTCCAGCCAGTCTCTGCTGCACTCCAACG<br>GCTACAACTATCTCGATTGGTACCTGCAAAAACCGGGTCAGAGCCCTCAG<br>CTGCTGATCTACCTGGGCTCTAACCGCGCTTCCGGTGTACCGGACCGTTT<br>CAGCGGCTCTGGATCCGGCACCGATTTCACGTTGAAAATCAGCCGTGTTG<br>AAGCAGAAGACGTGGGCGTTTATTACTGTATGCAGGCAAGCATTATGAAC<br>CGGAATTTTGGTCAAGGCACCAAGGTCGAAATTAAA | 176 |
| 5D9_VH | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCTCTTAC<br>ATCGACATGGACTATTGGGGTCAAGGCACCCTCGTAACGGTTTCTTCT | 177 |
| 5D9_VL | GAAATCGTGTTAACGCAGTCTCCAGGCACCCTGTCTTTGTCTCCAGGGGA<br>AAGAGCCACCCTCTCTTGCAGGGCCAGTCAGAGTGTTAGCAGCAGCTACT<br>TAGCCTGGTACCAGCAGAAACCTGGCCAGGCTCCCAGGCTCCTCATCTAT<br>GGAGCATCCAGCAGGGCCACTGGCATCCCAGACAGGTTCAGTGGCAGTGG<br>ATCCGGGACAGACTTCACTCTCACCATCAGCAGACTGGAGCCTGAAGATT<br>TTGCAGTGTATTACTGTCAGCAGGATAACTGGAGCCCAACGTTCGGCCAG<br>GGGACCAAAGTGGAAATCAAA | 178 |
| 6B6_VH | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCTCTTAC<br>GTTGACATGGACTATTGGGGTCAAGGCACCCTCGTAACGGTTTCTTCT | 179 |

8) Nucleotide sequences of exemplary embodiments

| | Sequence | Seq ID No |
|---|---|---|
| 6B6_VL | GAAATCGTGTTAACGCAGTCTCCAGGCACCCTGTCTTTGTCTCCAGGGGA<br>AAGAGCCACCCTCTCTTGCAGGGCCAGTCAGAGTGTTAGCAGCAGCTACC<br>TAGCCTGGTACCAGCAGAAACCTGGCCAGGCTCCCAGGCTCCTCATCTAT<br>GGAGCATCCAGCAGGGCCACTGGCATCCCAGACAGGTTCAGTGGCAGTGG<br>ATCCGGGACAGACTTCACTCTCACCATCAGCAGACTGGAGCCTGAAGATT<br>TTGCAGTGTATTACTGTCAGCAGGATATTTGGAGCCCAACGTTCGGCCAG<br>GGGACCAAAGTGGAAATCAAA | 180 |
| 14E4_VH | GAGGTGCAATTGTTGGAGTCTGGGGGAGGCTTGGTACAGCCTGGGGGGTC<br>CCTGAGACTCTCCTGTGCAGCCTCCGGATTCACCTTTAGCAGTTATGCCA<br>TGAGCTGGGTCCGCCAGGCTCCAGGGAAGGGGCTGGAGTGGGTCTCAGCT<br>ATTAGTGGTAGTGGTGGTAGCACATACTACGCAGACTCCGTGAAGGGCCG<br>GTTCACCATCTCCAGAGACAATTCCAAGAACACGCTGTATCTGCAGATGA<br>ACAGCCTGAGAGCCGAGGACACGGCCGTATATTACTGTGCGAAAGACTCT<br>TCTTACGTTGAATGGTACGCTTTCGACTACTGGGGCCAAGGAACCCTGGT<br>CACCGTCTCGAGT | 181 |
| 14E4_VL | GAAATCGTGTTAACGCAGTCTCCAGGCACCCTGTCTTTGTCTCCAGGGGA<br>AAGAGCCACCCTCTCTTGCAGGGCCAGTCAGAGTGTTAGCAGCAGCTACT<br>TAGCCTGGTACCAGCAGAAACCTGGCCAGGCTCCCAGGCTCCTCATCTAT<br>GGAGCATCCAGCAGGGCCACTGGCATCCCAGACAGGTTCAGTGGCAGTGG<br>ATCCGGGACAGACTCCACTCTCACCATCAGCAGACTGGAGCCTGAAGATT<br>TTGCAGTGTATTACTGTCAGCAGCCAACCAGCAGCCCAATTACGTTCGGC<br>CAGGGGACCAAAGTGGAAATCAAA | 182 |
| CD3 heavy chain (VHCH1) | GAGGTGCAGCTGCTGGAATCTGGCGGCGGACTGGTGCAGCCTGGCGGATC<br>TCTGAGACTGAGCTGTGCCGCCAGCGGCTTCACCTTCAGCACCTACGCCA<br>TGAACTGGGTGCGCCAGGCCCCTGGCAAAGGCCTGGAATGGGTGTCCCGG<br>ATCAGAAGCAAGTACAACAACTACGCCACCTACTACGCCGACAGCGTGAA<br>GGGCCGGTTCACCATCAGCCGGGACGACAGCAAGAACACCCTGTACCTGC<br>AGATGAACAGCCTGCGGGCCGAGGACACCGCCGTGTACTATTGTGTGCGG<br>CACGGCAACTTCGGCAACAGCTATGTGTCTTGGTTTGCCTACTGGGGCCA<br>GGGCACCCTCGTGACCGTGTCAAGCGCTAGTACCAAGGGCCCCAGCGTGT<br>TCCCCCTGGCACCCAGCAGCAAGAGCACATCTGGCGGAACAGCCGCTCTG<br>GGCTGTCTGGTGAAAGACTACTTCCCCGAGCCCGTGACCGTGTCTTGGAA<br>CTCTGGCGCCCTGACCAGCGGCGTGCACACCTTTCCAGCCGTGCTGCAGA<br>GCAGCGGCCTGTACTCCCTGTCCTCCGTGGTCACCGTGCCCTCTAGCTCC<br>CTGGGAACACAGACATATATCTGTAATGTCAATCACAACGCCTTCCAACAC<br>CAAAGTCGATAAGAAAGTCGAGCCCAAGAGCTGC | 183 |
| Crossed CD3 heavy chain (VHCκ) | GAGGTGCAGCTGCTGGAATCTGGCGGCGGACTGGTGCAGCCTGGCGGATC<br>TCTGAGACTGAGCTGTGCCGCCAGCGGCTTCACCTTCAGCACCTACGCCA<br>TGAACTGGGTGCGCCAGGCCCCTGGCAAAGGCCTGGAATGGGTGTCCCGG<br>ATCAGAAGCAAGTACAACAACTACGCCACCTACTACGCCGACAGCGTGAA<br>GGGCCGGTTCACCATCAGCCGGGACGACAGCAAGAACACCCTGTACCTGC<br>AGATGAACAGCCTGCGGGCCGAGGACACCGCCGTGTACTATTGTGTGCGG<br>CACGGCAACTTCGGCAACAGCTATGTGTCTTGGTTTGCCTACTGGGGCCA<br>GGGCACCCTCGTGACCGTGTCAAGCGCTAGTGTGGCCGCTCCCTCCGTGT<br>TTATCTTTCCCCCATCCGATGAACAGCTGAAAAGCGGCACCGCCTCCGTC<br>GTGTGTGTCTGCTGAACAATTTTTACCCTAGGGAAGCTAAAGTGCAGTGGAA<br>AGTGGATAACGCACTGCAGTCCGGCAACTCCCAGGAATCTGTGACAGAAC<br>AGGACTCCAAGGACAGCACCTACTCCCTGTCCTCCACCCTGACACTGTCT<br>AAGGCTGATTATGAGAAACACAAAGTCTACGCCTGCGAAGTCACCCATCA<br>GGGCCTGAGCTCGCCCGTCACAAAGAGCTTCAACAGGGGAGAGTGT | 184 |
| Mutagenesis primer GAB7734 N95Q | GCAGGCAAGCATTATGCAGCGGACTTTTGGTCAAGG | 185 |
| Mutagenesis primer GAB7735 N95S | CAGGCAAGCATTATGAGCCGGACTTTTGGTCAAGG | 186 |
| Mutagenesis primer GAB7736 T97A | CATTATGAACCGGGCTTTTGGTCAAGGCACCAAGGTC | 187 |
| Mutagenesis primer GAB7737 T97N | CATTATGAACCGGAATTTTGGTCAAGGCACCAAGGTC | 188 |

8) Nucleotide sequences of exemplary embodiments

| Sequence | | Seq ID No |
|---|---|---|
| VHCH1[16D5]_<br>VHCH1[CD3]_<br>Fcknob_PGLALA<br>pCON999<br>(Inverted TCB<br>with 16D5<br>2 + 1:<br>pCON999 +<br>pCON983 +<br>pETR13197) | GAGGTGCAATTGGTTGAATCTGGTGGTGGTCTGGTAAAACCGGGCGGTTC<br>CCTGCGTCTGAGCTGCGCGGCTTCCGGATTCACCTTCTCCAACGCGTGGA<br>TGAGCTGGGTTCGCCAGGCCCCGGGCAAAGGCCTCGAGTGGGTTGGTCGT<br>ATCAAGTCTAAAACTGACGGTGGCACCACGGATTACGCGGCTCCAGTTAA<br>AGGTCGTTTTACCATTTCCCGCGACGATAGCAAAAACACTCTGTATCTGC<br>AGATGAACTCTCTGAAAACTGAAGACACCGCAGTCTACTACTGTACTACC<br>CCGTGGGAATGGTCTTGGTACGATTATTGGGGCCAGGGCACGCTGGTTAC<br>GGTGTCTTCCGCTAGCACAAAGGGCCCTAGCGTGTTCCCTCTGGCCCCCA<br>GCAGCAAGAGCACAAGCGGCGGAACAGCCGCCCTGGGCTGCCTCGTGAAG<br>GACTACTTCCCCGAGCCCGTGACAGTGTCTTGGAACAGCGGAGCCCTGAC<br>AAGCGGCGTGCACACTTTCCCTGCCGTGCTGCAGAGCAGCGGCCTGTACT<br>CCCTGAGCAGCGTGGTCACCGTGCCTAGCAGCAGCCTGGGCACCCAGACC<br>TACATCTGCAACGTGAACCACAAGCCCAGCAACACCAAAGTGGACAAGAA<br>GGTGGAGCCCAAGAGCTGTGATGGCGGAGGAGGGTCCGGAGGCGGAGGAT<br>CCGAGGTGCAGCTGCTGGAATCTGGCGGCGGACTGGTGCAGCCTGGCGGA<br>TCTCTGAGACTGAGCTGTGCCGCCAGCGGCTTCACCTTCAGCACCTACGC<br>CATGAACTGGGTGCGCCAGGCCCCTGGCAAAGGCCTGGAATGGGTGTCCC<br>GGATCAGAAGCAAGTACAACAACTACGCCACCTACTACGCCGACAGCGTG<br>AAGGGCCGGTTCACCATCAGCCGGGACGACAGCAAGAACACCCTGTACCT<br>GCAGATGAACAGCCTGCGGGCCGAGGACACCGCCGTGTACTATTGTGTGC<br>GGCACGGCAACTTCGGCAACAGCTATGTGTCTTGGTTTGCCTACTGGGGC<br>CAGGGCACCCTCGTGACCGTGTCAAGCGCTAGTACCAAGGGCCCCAGCGT<br>GTTCCCCCTGGCACCCAGCAGCAAGAGCACATCTGGCGGAACAGCCGCTC<br>TGGGCTGTCTGGTGAAAGACTACTTCCCCGAGCCCGTGACCGTGTCTTGG<br>AACTCTGGCGCCCTGACCAGCGGCGTGCACACCTTTCCAGCCGTGCTGCA<br>GAGCAGCGGCCTGTACTCCCTGTCCTCCGTGGTCACCGTGCCCTCTAGCT<br>CCCTGGGAACACAGACATATATCTGTAATGTCAATCACAAGCCTTCCAAC<br>ACCAAAGTCGATAAGAAAGTCGAGCCCAAGAGCTGCGACAAAACTCACAC<br>ATGCCCACCGTGCCCAGCACCTGAAGCTGCAGGGGGACCGTCAGTCTTCC<br>TCTTCCCCCCAAAACCCAAGGACACCCTCATGATCTCCCGGACCCCTGAG<br>GTCACATGCGTGGTGGTGGACGTGAGCCACGAAGACCCTGAGGTCAAGTT<br>CAACTGGTACGTGGACGGCGTGGAGGTGCATAATGCCAAGACAAAGCCGC<br>GGGAGGAGCAGTACAACAGCACGTACCGTGTGGTCAGCGTCCTCACCGTC<br>CTGCACCAGGACTGGCTGAATGGCAAGGAGTACAAGTGCAAGGTCTCCAA<br>CAAAGCCCTCGGCGCCCCCATCGAGAAAACCATCTCCAAAGCCAAAGGGC<br>AGCCCCGAGAACCACAGGTGTACACCCTGCCCCCATGCCGGGATGAGCTG<br>ACCAAGAACCAGGTCAGCCTGTGGTGCCTGGTCAAAGGCTTCTATCCCAG<br>CGACATCGCCGTGGAGTGGGAGAGCAATGGGCAGCCGGAGAACAACTACA<br>AGACCACGCCTCCCGTGCTGGACTCCGACGGCTCCTTCTTCCTCTACAGC<br>AAGCTCACCGTGGACAAGAGCAGGTGGCAGCAGGGGAACGTCTTCTCATG<br>CTCCGTGATGCATGAGGCTCTGCACAACCACTACACGCAGAAGAGCCTCT<br>CCCTGTCTCCGGGTAAA | 189 |
| VHCH1[16D5]_<br>Fchole_PGLALA_<br>HYRF<br>pCON983 | GAGGTGCAATTGGTTGAATCTGGTGGTGGTCTGGTAAAACCGGGCGGTTC<br>CCTGCGTCTGAGCTGCGCGGCTTCCGGATTCACCTTCTCCAACGCGTGGA<br>TGAGCTGGGTTCGCCAGGCCCCGGGCAAAGGCCTCGAGTGGGTTGGTCGT<br>ATCAAGTCTAAAACTGACGGTGGCACCACGGATTACGCGGCTCCAGTTAA<br>AGGTCGTTTTACCATTTCCCGCGACGATAGCAAAAACACTCTGTATCTGC<br>AGATGAACTCTCTGAAAACTGAAGACACCGCAGTCTACTACTGTACTACC<br>CCGTGGGAATGGTCTTGGTACGATTATTGGGGCCAGGGCACGCTGGTTAC<br>GGTGTCTTCCGCTAGCACCAAGGGCCCCTCCGTGTTCCCCCTGGCCCCCA<br>GCAGCAAGAGCACCAGCGGCGGCACAGCCGCTCTGGGCTGCCTGGTCAAG<br>GACTACTTCCCCGAGCCCGTGACCGTGTCCTGGAACAGCGGAGCCCTGAC<br>CTCCGGCGTGCACACCTTCCCCGCCGTGCTGCAGAGTTCTGGCCTGTATA<br>GCCTGAGCAGCGTGGTCACCGTGCCTTCTAGCAGCCTGGGCACCCAGACC<br>TACATCTGCAACGTGAACCACAAGCCCAGCAACACCAAGGTGGACAAGAA<br>GGTGGAGCCCAAGAGCTGCGACAAAACTCACACATGCCCACCGTGCCCAG<br>CACCTGAAGCTGCAGGGGGACCGTCAGTCTTCCTCTTCCCCCCAAAACCC<br>AAGGACACCCTCATGATCTCCCGGACCCCTGAGGTCACATGCGTGGTGGT<br>GGACGTGAGCCACGAAGACCCTGAGGTCAAGTTCAACTGGTACGTGGACG<br>GCGTGGAGGTGCATAATGCCAAGACAAAGCCGCGGGAGGAGCAGTACAAC<br>AGCACGTACCGTGTGGTCAGCGTCCTCACCGTCCTGCACCAGGACTGGCT<br>GAATGGCAAGGAGTACAAGTGCAAGGTCTCCAACAAAGCCCTCGGCGCCC<br>CCATCGAGAAAACCATCTCCAAAGCCAAAGGGCAGCCCCGAGAACCACAG<br>GTGTGCACCCTGCCCCCATCCCGGGATGAGCTGACCAAGAACCAGGTCAG<br>CCTCTCGTGCGCAGTCAAAGGCTTCTATCCCAGCGACATCGCCGTGGAGT<br>GGGAGAGCAATGGGCAGCCGGAGAACAACTACAAGACCACGCCTCCCGTG<br>CTGGACTCCGACGGCTCCTTCTTCCTCGTGAGCAAGCTCACCGTGGACAA<br>GAGCAGGTGGCAGCAGGGGAACGTCTTCTCATGCTCCGTGATGCATGAGG<br>CTCTGCACAACCGCTTCACGCAGAAGAGCCTCTCCCTGTCTCCGGGTAAA | 190 |

8) Nucleotide sequences of exemplary embodiments

| | Sequence | Seq ID No |
|---|---|---|
| CD3_common light chain pETR13197 | CAGGCCGTCGTGACCCAGGAACCCAGCCTGACAGTGTCTCCTGGCGGCAC CGTGACCCTGACATGTGGCAGTTCTACAGGCGCCGTGACCACCAGCAACT ACGCCAACTGGGTGCAGGAAAAGCCCGGCCAGGCCTTCAGAGGACTGATC GGCGGCACCAACAAGAGAGCCCCTGGCACCCCTGCCAGATTCAGCGGATC TCTGCTGGGAGGAAAGGCCGCCCTGACACTGTCTGGCGCCCAGCCAGAAG ATGAGGCCGAGTACTACTGCGCCCTGTGGTACAGCAACCTGTGGGTGTTC GGCGGAGGCACCAAGCTGACAGTCCTAGGTCAACCCAAGGCTGCCCCCAG CGTGACCCTGTTCCCCCCCAGCAGCGAGGAACTGCAGGCCAACAAGGCCA CCCTGGTCTGCCTGATCAGCGACTTCTACCCAGGCGCCGTGACCGTGGCC TGGAAGGCCGACAGCAGCCCCGTGAAGGCCGGCGTGGAGACCACCACCCC CAGCAAGCAGAGCAACAACAAGTACGCCGCCAGCAGCTACCTGAGCCTGA CCCCCGAGCAGTGGAAGAGCCACAGGTCCTACAGCTGCCAGGTGACCCAC GAGGGCAGCACCGTGGAGAAAACCGTGGCCCCCACCGAGTGCAGC | 191 |
| VHCH1[CD3]_ VHCH1[16D5]_ Fcknob_PGLALA pETR13932 (Classical TCB with 16D5; 2 + 1: pETR13932 + pCON983 + pETR13197) | GAGGTGCAGCTGCTGGAATCTGGCGGCGGACTGGTGCAGCCTGGCGGATC TCTGAGACTGAGCTGTGCCGCCAGCGGCTTCACCTTCAGCACCTACGCCA TGAACTGGGTGCGCCAGGCCCCTGGCAAGGCCTGGAATGGGTGTCCGG ATCAGAAGCAAGTACAACAACTACGCCACCTACTACGCCGACAGCGTGAA GGGCCGGTTCACCATCAGCCGGGACGACAGCAAGAACACCCTGTACCTGC AGATGAACAGCCTGCGGGCCGAGGACACCGCCGTGTACTATTGTGTGCGG CACGGCAACTTCGGCAACAGCTATGTGTCTTGGTTTGCCTACTGGGGCCA GGGCACCCTCGTGACCGTGTCATCTGCTAGCACAAAGGGCCCTAGCGTGT TCCCTCTGGCCCCCAGCAGCAAGAGCACAAGCGGCGGAACAGCCGCCCTG GGCTGCCTCGTGAAGGACTACTTCCCCGAGCCCGTGACAGTGTCTTGGAA CAGCGGAGCCCTGACAAGCGGCGTGCACACCTTCCCTGCCGTGCTGCAGA GCAGCGGCCTGTACTCCCTGAGCAGCGTGGTCACCGTGCCTAGCAGCAGC CTGGGCACCCAGACCTACATCTGCAACGTGAACCACAAGCCCAGCAACAC CAAAGTGGACAAGAAGGTGGAGCCCAAGAGCTGTGATGGCGGAGGAGGGT CCGGAGGCGGAGGATCCGAGGTGCAATTGGTTGAATCTGGTGGTGGTCTG GTAAAACCGGGCGGTTCCCTGCGTCTGAGCTGCGCGGCTTCCGGATTCAC CTTCTCCAACGCGTGGATGAGCTGGGTTCGCCAGGCCCCGGGCAAAGGCC TCGAGTGGGTTGGTCGTATCAAGTCTAAAACTGACGGTGGCACCACGGAT TACGCGGCTCCAGTTAAAGGTCGTTTTACCATTTCCCGCGACGATAGCAA AAACACTCTGTATCTGCAGATGAACTCTCTGAAAACTGAAGACACCGCAG TCTACTACTGTACTACCCCGTGGGAATGGTCTTGGTACGATTATTGGGGC CAGGGCACGCTGGTTACGGTGTCTAGCGCTAGTACCAAGGGCCCCAGCGT GTTCCCCCTGGCACCCAGCAGCAAGAGCACATCTGGCGGAACAGCCGCTC TGGGCTGTCTGGTGAAAGACTACTTCCCCGAGCCCGTGACCGTGTCTTGG AACTCTGGCGCCCTGACCAGCGGCGTGCACACCTTTCCAGCCGTGCTGCA GAGCAGCGGCCTGTACTCCCTGTCCTCCGTGGTCACCGTGCCCTCTAGCT CCCTGGGAACACAGACATATATCTGTAATGTCAATCACAAGCCCTTCCAAC ACCAAAGTCGATAAGAAAGTCGAGCCCAAGAGCTGCGACAAAACTCACAC ATGCCCACCGTGCCCAGCACCTGAAGCTGCAGGGGGACCGTCAGTCTTCC TCTTCCCCCCAAAAACCCAAGGACACCCTCATGATCTCCCGGACCCCTGAG GTCACATGCGTGGTGGTGGACGTGAGCCACGAAGACCCTGAGGTCAAGTT CAACTGGTACGTGGACGGCGTGGAGGTGCATAATGCCAAGACAAAGCCGC GGGAGGAGCAGTACAACAGCACGTACCGTGTGGTCAGCGTCCTCACCGTC CTGCACCAGGACTGGCTGAATGGCAAGGAGTACAAGTGCAAGGTCTCCAA CAAAGCCCTCGGCGCCCCCATCGAGAAAACCATCTCCAAAGCCAAAGGGC AGCCCCGAGAACCACAGGTGTACACCCTGCCCCCATGCCGGGATGAGCTG ACCAAGAACCAGGTCAGCCTGTGGTGCCTGGTCAAAGGCTTCTATCCCAG CGACATCGCCGTGGAGTGGGAGAGCAATGGGCAGCCGGAGAACAACTACA AGACCACGCCTCCCGTGCTGGACTCCGACGGCTCCTTCTTCCTCTACAGC AAGCTCACCGTGGACAAGAGCAGGTGGCAGCAGGGGAACGTCTTCTCATG CTCCGTGATGCATGAGGCTCTGCACAACCACTACACGCAGAAGAGCCTCT CCCTGTCTCCGGGTAAA | 192 |
| VHCH1[CD3]_ Fcknob_PGLALA pETR13719 (16D5 IgG format, 1 + 1: pETR13719 + pCON983 + pETR13197) | GAGGTGCAGCTGCTGGAATCTGGCGGCGGACTGGTGCAGCCTGGCGGATC TCTGAGACTGAGCTGTGCCGCCAGCGGCTTCACCTTCAGCACCTACGCCA TGAACTGGGTGCGCCAGGCCCCTGGCAAAGGCCTGGAATGGGTGTCCGG ATCAGAAGCAAGTACAACAACTACGCCACCTACTACGCCGACAGCGTGAA GGGCCGGTTCACCATCAGCCGGGACGACAGCAAGAACACCCTGTACCTGC AGATGAACAGCCTGCGGGCCGAGGACACCGCCGTGTACTATTGTGTGCGG CACGGCAACTTCGGCAACAGCTATGTGTCTTGGTTTGCCTACTGGGGCCA GGGCACCCTCGTGACCGTGTCATCTGCTAGCACCAAGGGCCCATCGGTCT TCCCCCTGGCACCCTCCTCCAAGAGCACCTCTGGGGGCACAGCGGCCCTG GGCTGCCTGGTCAAGGACTACTTCCCCGAACCGGTGACGGTGTCGTGGAA CTCAGGCGCCCTGACCAGCGGCGTGCACACCTTCCCGGCTGTCCTACAGT CCTCAGGACTCTACTCCCTCAGCAGCGTGGTGACCGTGCCCTCCAGCAGC TTGGGCACCCAGACCTACATCTGCAACGTGAATCACAAGCCCAGCAACAC CAAGGTGGACAAGAAAGTTGAGCCCAAATCTTGTGACAAAACTCACACAT GCCCACCGTGCCCAGCACCTGAAGCTGCAGGGGGACCGTCAGTCTTCCTC TTCCCCCCAAAACCCAAGGACACCCTCATGATCTCCCGGACCCCTGAGGT CACATGCGTGGTGGTGGACGTGAGCCACGAAGACCCTGAGGTCAAGTTCA | 193 |

| | 8) Nucleotide sequences of exemplary embodiments | |
|---|---|---|
| | Sequence | Seq ID No |
| | ACTGGTACGTGGACGGCGTGGAGGTGCATAATGCCAAGACAAAGCCGCGG<br>GAGGAGCAGTACAACAGCACGTACCGTGTGGTCAGCGTCCTCACCGTCCT<br>GCACCAGGACTGGCTGAATGGCAAGGAGTACAAGTGCAAGGTCTCCAACA<br>AAGCCCTCGGCGCCCCCATCGAGAAACCATCTCCAAAGCCAAAGGGCAG<br>CCCCGAGAACCACAGGTGTACACCCTGCCCCCATGCCGGGATGAGCTGAC<br>CAAGAACCAGGTCAGCCTGTGGTGCCTGGTCAAAGGCTTCTATCCCAGCG<br>ACATCGCCGTGGAGTGGGAGAGCAATGGGCAGCCGGAGAACAACTACAAG<br>ACCACGCCTCCCGTGCTGGACTCCGACGGCTCCTTCTTCCTCTACAGCAA<br>GCTCACCGTGGACAAGAGCAGGTGGCAGCAGGGGAACGTCTTCTCATGCT<br>CCGTGATGCATGAGGCTCTGCACAACCACTACACGCAGAAGAGCCTCTCC<br>CTGTCTCCGGGTAAA | |
| Fc_hole_PGLALA_<br>HYRF<br>pETR10755<br>(16D5 Head-<br>to-tail, 1 + 1:<br>pCON999 +<br>pETR10755 +<br>pETR13197) | GACAAAACTCACACATGCCCACCGTGCCCAGCACCTGAACTCCTGGGGGGG<br>ACCGTCAGTCTTCCTCTTCCCCCCAAAACCCAAGGACACCCTCATGATCT<br>CCCGGACCCCTGAGGTCACATGCGTGGTGGTGGACGTGAGCCACGAAGAC<br>CCTGAGGTCAAGTTCAACTGGTACGTGGACGGCGTGGAGGTGCATAATGC<br>CAAGACAAAGCCGCGGGAGGAGCAGTACAACAGCACGTACCGTGTGGTCA<br>GCGTCCTCACCGTCCTGCACCAGGACTGGCTGAATGGCAAGGAGTACAAG<br>TGCAAGGTCTCCAACAAAGCCCTCCCAGCCCCCATCGAGAAAACCATCTC<br>CAAAGCCAAAGGGCAGCCCCGAGAACCACAGGTGTGCACCCTGCCCCCAT<br>CCCGGGATGAGCTGACCAAGAACCAGGTCAGCCTCTCGTGCGCAGTCAAA<br>GGCTTCTATCCCAGCGACATCGCCGTGGAGTGGGAGAGCAATGGGCAGCC<br>GGAGAACAACTACAAGACCACGCCTCCCGTGCTGGACTCCGACGGCTCCT<br>TCTTCCTCGTGAGCAAGCTCACCGTGGACAAGAGCAGGTGGCAGCAGGGG<br>AACGTCTTCTCATGCTCCGTGATGCATGAGGCTCTGCACAACCGCTTCAC<br>GCAGAAGAGCCTCTCCCTGTCTCCGGGTAAA | 194 |
| VHCH1[9D11]_<br>VHCL[CD3]_<br>Fcknob_PGLALA<br>pCON1057<br>(9D11<br>inverted<br>format, 2 + 1:<br>pCON1057 +<br>pCON1051 +<br>pCON1063 +<br>pETR12940) | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCCCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCGGTGAC<br>TTCGCTTGGCTGGACTATTGGGGTCAAGGCACCCTCGTAACGGTTTCTTC<br>TGCTAGCACAAAGGGCCCCAGCGTGTTCCCTCTGGCCCCTAGCAGCAAGA<br>GCACATCGGCGGAACAGCCGCCCTGGGCTGCCTCGTGAAGGACTACTTT<br>CCCGAGCCTGTGACCGTGTCCTGGAACTCTGGCGCCCTGACAAGCGGCGT<br>GCACACCTTTCCAGCCGTGCTGCAGAGCAGCGGCCTGTACTCTCTGAGCA<br>GCGTGGTCACCGTGCCTAGCAGCAGCCTGGGCACCCAGACCTACATCTGC<br>AACGTGAACCACAAGCCCAGCAACACCAAAGTGGACAAGAAGGTGGAGCC<br>CAAGAGCTGTGATGGCGGAGGAGGGTCCGGAGGCGGAGGATCCGAGGTGC<br>AGCTGCTGGAATCTGGCGGCGGACTGGTGCAGCCTGGCGGATCTCTGAGA<br>CTGAGCTGTGCCGCCAGCGGCTTCACCTTCAGCACCTACGCCATGAACTG<br>GGTGCGCCAGGCCCCTGGCAAAGGCCTGGAATGGGTGTCCCGGATCAGAA<br>GCAAGTACAACAACTACGCCACCTACTACGCCGACAGCGTGAAGGGCCGG<br>TTCACCATCAGCCGGGACGACAGCAAGAACACCCTGTACCTGCAGATGAA<br>CAGCCTGCGGGCCGAGGACACCGCCGTGTACTATTGTGTGCGGCACGGCA<br>ACTTCGGCAACAGCTATGTGTCTTGGTTTGCCTACTGGGGCCAGGGCACC<br>CTCGTGACCGTGTCAAGCGCTAGTGTGGCCGCTCCCTCCGTGTTTATCTT<br>TCCCCCATCCGATGAACAGCTGAAAAGCGGCACCGCCTCCGTCGTGTGTC<br>TGCTGAACAATTTTTACCCTAGGGAAGCTAAAGTGCAGTGGAAAGTGGAT<br>AACGCACTGCAGTCCGGCAACTCCCAGGAATCTGTGACAGAACAGGACTC<br>CAAGGACAGCACCTACTCCCTGTCCTCCACCCTGACACTGTCTAAGGCTG<br>ATTATGAGAAACACAAAGTCTACGCCTGCGAAGTCACCCATCAGGGCCTG<br>AGCTCGCCCGTCACAAAGAGCTTCAACAGGGGAGAGTGTGACAAGACCCA<br>CACCTGTCCCCCTTGTCCTGCCCCTGAAGCTGCTGGCGGCCCTTCTGTGT<br>TCCTGTTCCCCCCAAAGCCCAAGGACACCCTGATGATCAGCCGGACCCCC<br>GAAGTGACCTGCGTGGTGGTGGATGTGTCCCACGAGGACCCTGAAGTGAA<br>GTTCAATTGGTACGTGGACGGCGTGGAAGTGCACAACGCCAAGACAAAGC<br>CGCGGGAGGAGCAGTACAACAGCACGTACCGTGTGGTCAGCGTCCTCACC<br>GTCCTGCACCAGGACTGGCTGAATGGCAAGGAGTACAAGTGCAAGGTCTC<br>CAACAAAGCCCTCGGCGCCCCCATCGAGAAAACCATCTCCAAAGCCAAAG<br>GGCAGCCCCGAGAACCACAGGTGTACACCCTGCCCCCATGCCGGGATGAG<br>CTGACCAAGAACCAGGTCAGCCTGTGGTGCCTGGTCAAAGGCTTCTATCC<br>CAGCGACATCGCCGTGGAGTGGGAGAGCAATGGGCAGCCGGAGAACAACT<br>ACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTC<br>ATGCTCCGTGATGCATGAGGCTCTGCACAACCACTACACGCAGAAGAGCC<br>TCTCCCTGTCTCCGGGTAAA | 195 |
| 9D11_Fchole_<br>PGLALA_HYRF<br>pCON1051 | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCCCTACCTCCTACGCGCAGAAATTCCAGGGTCG<br>CGTCACGATGACCCGTGACACTAGCACCTCTACCGTTTATATGGAGCTGT | 196 |

8) Nucleotide sequences of exemplary embodiments

| | Sequence | Seq ID No |
|---|---|---|
| | CCAGCCTGCGTTCTGAAGATACTGCAGTGTACTACTGTGCACGCGGTGAC<br>TTCGCTTGGCTGGACTATTGGGGTCAAGGCACCCTCGTAACGGTTTCTTC<br>TGCTAGCACCAAGGGCCCCTCCGTGTTCCCCCTGGCCCCCAGCAGCAAGA<br>GCACCAGCGGCGGCACAGCCGCTCTGGGCTGCCTGGTCAAGGACTACTTC<br>CCCGAGCCCGTGACCGTGTCCTGGAACAGCGGAGCCCTGACCTCCGGCGT<br>GCACACCTTCCCCGCCGTGCTGCAGAGTTCTGGCCTGTATAGCCTGAGCA<br>GCGTGGTCACCGTGCCTTCTAGCAGCCTGGGCACCCAGACCTACATCTGC<br>AACGTGAACCACAAGCCCAGCAACACCAAGGTGGACAAGAAGGTGGAGCC<br>CAAGAGCTGCGACAAAACTCACACATGCCCACCGTGCCCAGCACCTGAAG<br>CTGCAGGGGGACCGTCAGTCTTCCTCTTCCCCCCAAAACCCAAGGACACC<br>CTCATGATCTCCCGGACCCCTGAGGTCACATGCGTGGTGGTGGACGTGAG<br>CCACGAAGACCCTGAGGTCAAGTTCAACTGGTACGTGGACGGCGTGGAGG<br>TGCATAATGCCAAGACAAAGCCGCGGGAGGAGCAGTACAACAGCACGTAC<br>CGTGTGGTCAGCGTCCTCACCGTCCTGCACCAGGACTGGCTGAATGGCAA<br>GGAGTACAAGTGCAAGGTCTCCAACAAAGCCCTCGGCGCCCCCATCGAGA<br>AAACCATCTCCAAAGCCAAAGGGCAGCCCCGAGAACCACAGGTGTGCACC<br>CTGCCCCCATCCCGGGATGAGCTGACCAAGAACCAGGTCAGCCTCTCGTG<br>CGCAGTCAAAGGCTTCTATCCCAGCGACATCGCCGTGGAGTGGGAGAGCA<br>ATGGGCAGCCGGAGAACAACTACAAGACCACGCCTCCCGTGCTGGACTCC<br>GACGGCTCCTTCTTCCTCGTGAGCAAGCTCACCGTGGACAAGAGCAGGTG<br>GCAGCAGGGGAACGTCTTCTCATGCTCCGTGATGCATGAGGCTCTGCACA<br>ACCACTACACGCAGAAGAGCCTCTCCCTGTCTCCGGGTAAA | |
| 9D11_LC<br>pCON1063 | GATATTGTTATGACTCAATCTCCACTGTCTCTGCCGGTGACTCCAGGCGA<br>ACCGGCGAGCATTCTTGCCGTTCCAGCCAGTCTCTGCTGCACTCCAACG<br>GCTACAACTATCTCGATTGGTACCTGCAAAAACCGGGTCAGAGCCCTCAG<br>CTGCTGATCTACCTGGGCTCTAACCGCGCTTCCGGTGTACCGGACCGTTT<br>CAGCGGCTCTGGATCCGGCACCGATTTCACGTTGAAAATCAGCCGTGTTG<br>AAGCAGAAGACGTGGGCGTTTATTACTGTATGCAGGCAAGCATTATGAAC<br>CGGACTTTTGGTCAAGGCACCAAGGTCGAAATTAAACGTACGGTGGCTGC<br>ACCATCTGTCTTCATCTTCCCGCCATCTGATGAGCAGTTGAAATCTGGAA<br>CTGCCTCTGTTGTGTGCCTGCTGAATAACTTCTATCCCAGAGAGGCCAAA<br>GTACAGTGGAAGGTGGATAACGCCCTCCAATCGGGTAACTCCCAGGAGAG<br>TGTCACAGAGCAGGACAGCAAGGACAGCACCTACAGCCTCAGCAGCACCC<br>TGACGCTGAGCAAAGCAGACTACGAGAAACACAAAGTCTACGCCTGCGAA<br>GTCACCCATCAGGGCCTGAGCTCGCCCGTCACAAAGAGCTTCAACAGGGG<br>AGAGTGT | 197 |
| VLCH1[CD3]<br>pETR12940 | CAGGCCGTCGTGACCCAGGAACCCAGCCTGACAGTGTCTCCTGGCGGCAC<br>CGTGACCCTGACATGTGGCAGTTCTACAGGCGCCGTGACCACCAGCAACT<br>ACGCCAACTGGGTGCAGGAAAAGCCCGGCCAGGCCTTCAGAGGACTGATC<br>GGCGGCACCAACAAGAGAGCCCCTGGCACCCCTGCCAGATTCAGCGGATC<br>TCTGCTGGGAGGAAAGGCCGCCCTGACACTGTCTGGCGCCCAGCCAGAAG<br>ATGAGGCCGAGTACTACTGCGCCCTGTGGTACAGCAACCTGTGGGTGTTC<br>GGCGGAGGCACCAAGCTGACAGTGCTGAGCAGCGCTTCCACCAAAGGCCC<br>TTCCGTGTTTCCTCTGGCTCCTAGCTCCAAGTCCACCTCTGGAGGCACCG<br>CTGCTCTCGGATGCCTCGTGAAGGATTATTTTCCTGAGCCTGTGACAGTG<br>TCCTGGAATAGCGGAGCACTGACCTCTGGAGTGCATACTTTCCCCGCTGT<br>GCTGCAGTCCTCTGGACTGTACAGCCTGAGCAGCGTGGTGACAGTGCCCA<br>GCAGCAGCCTGGGCACCCAGACCTACATCTGCAACGTGAACCACAAGCCC<br>AGCAACACCAAGGTGGACAAGAAGGTGGAACCCAAGTCTTGT | 198 |
| VHCL[CD3]_<br>Fcknob_PGLALA<br>pETR13378<br>(9D11<br>CrossMab<br>format, 1 + 1:<br>pETR13378 +<br>pCON1051 +<br>pCON1063 +<br>pETR12940) | GAGGTGCAGCTGCTGGAATCTGGCGGCGGACTGGTGCAGCCTGGCGGATC<br>TCTGAGACTGAGCTGTGCCGCCAGCGGCTTCACCTTCAGCACCTACGCCA<br>TGAACTGGGTGCGCCAGGCCCCTGGCAAAGGCCTGGAATGGGTGTCCCGG<br>ATCAGAAGCAAGTACAACAACTACGCCACCTACTACGCCGACAGCGTGAA<br>GGGCCGGTTCACCATCAGCCGGGACGACAGCAAGAACACCCTGTACCTGC<br>AGATGAACAGCCTGCGGGCCGAGGACACCGCCGTGTACTATTGTGTGCGG<br>CACGGCAACTTCGGCAACAGCTATATGTTTGGTTTGCCTACTGGGGCCA<br>GGGCACCCTCGTGACCGTGTCATCTGCTAGCGTGGCCGCTCCCTCCGTGT<br>TTATCTTTCCCCCATCCGATGAACAGCTGAAAAGCGGCACCGCCTCCGTC<br>GTGTGTCTGCTGAACAATTTTTACCCTAGGGAAGCTAAAGTGCAGTGGAA<br>AGTGGATAACGCACTGCAGTCCGGCAACTCCCAGGAATCTGTGACAGAAC<br>AGGACTCCAAGGACAGCACCTACTCCCTGTCCTCCACCCTGACACTGTCT<br>AAGGCTGATTATGAGAAACACAAAGTCTACGCCTGCGAAGTCACCCATCA<br>GGGCCTGAGCTCGCCCGTCACAAAGAGCTTCAACAGGGGAGAGTGTGACA<br>AGACCCACACCTGTCCCCCTTGTCCTGCCCCTGAAGCTGCTGGCGGCCCT<br>TCTGTGTTCCTGTTCCCCCCAAAGCCCAAGGACACCCTGATGATCAGCCG<br>GACCCCCGAAGTGACCTGCGTGGTGGTGGATGTGTCCCACGAGGACCCTG<br>AAGTGAAGTTCAATTGGTACGTGGACGGCGTGGAAGTGCACAACGCCAAG<br>ACAAAGCCGCGGGAGGAGCAGTACAACAGCACGTACCGTGTGGTCAGCGT<br>CCTCACCGTCCTGCACCAGGACTGGCTGAATGGCAAGGAGTACAAGTGCA<br>AGGTCTCCAACAAAGCCCTCGGCGCCCCCATCGAGAAAACCATCTCCAAA<br>GCCAAAGGGCAGCCCCGAGAACCACAGGTGTACACCCTGCCCCCATGCCG<br>GGATGAGCTGACCAAGAACCAGGTCAGCCTGTGGTGCCTGGTCAAAGGCT | 199 |

8) Nucleotide sequences of exemplary embodiments

| | Sequence | Seq ID No |
|---|---|---|
| | TCTATCCCAGCGACATCGCCGTGGAGTGGGAGAGCAATGGGCAGCCGGAG<br>AACAACTACAAGACCACGCCTCCCGTGCTGGACTCCGACGGCTCCTTCTT<br>CCTCTACAGCAAGCTCACCGTGGACAAGAGCAGGTGGCAGCAGGGGAACG<br>TCTTCTCATGCTCCGTGATGCATGAGGCTCTGCACAACCACTACACGCAG<br>AAGAGCCTCTCCCTGTCTCCGGGTAAA | |
| 16D5 inverted<br>2 + 1 with<br>N100A in CDRH3<br>pETR14096<br>(pETR14096 +<br>pCON983 +<br>pETR13197) | GAGGTGCAATTGGTTGAATCTGGTGGTGGTCTGGTAAAACCGGGCGGTTC<br>CCTGCGTCTGAGCTGCGCGGCTTCCGGATTCACCTTCTCCAACGCGTGGA<br>TGAGCTGGGTTCGCCAGGCCCCGGGCAAAGGCCTCGAGTGGGTTGGTCGT<br>ATCAAGTCTAAAACTGACGGTGGCACCACGGATTACGCGGCTCCAGTTAA<br>AGGTCGTTTTACCATTTCCCGCGACGATAGCAAAAACACTCTGTATCTGC<br>AGATGAACTCTCTGAAAACTGAAGACACCGCAGTCTACTACTGTACTACC<br>CCGTGGGAATGGTCTTGGTACGATTATTGGGGCCAGGGCACGCTGGTTAC<br>GGTGTCTTCCGCTAGCACAAAGGGCCCTAGCGTGTTCCCTCTGGCCCCCA<br>GCAGCAAGAGCACAAGCGGCGGAACAGCCGCCCTGGGCTGCCTCGTGAAG<br>GACTACTTCCCCGAGCCCGTGACAGTGTCTTGGAACAGCGGAGCCCTGAC<br>AAGCGGCGTGCACACTTTCCCTGCCGTGCTGCAGAGCAGCGGCCTGTACT<br>CCCTGAGCAGCGTGGTCACCGTGCCTAGCAGCAGCCTGGGCACCCAGACC<br>TACATCTGCAACGTGAACCACAAGCCCAGCAACACCAAAGTGGACAAGAA<br>GGTGGAGCCCAAGAGCTGTGATGGCGGAGGAGGGTCCGGAGGCGGAGGAT<br>CCGAGGTGCAGCTGCTGGAATCTGGCGGCGGACTGGTGCAGCCTGGCGGA<br>TCTCTGAGACTGAGCTGTGCCGCCAGCGGCTTCACCTTCAGCACCTACGC<br>CATGAACTGGGTGCGCCAGGCCCCTGGCAAAGGCCTGGAATGGGTGTCCC<br>GGATCAGAAGCAAGTACAACAACTACGCCACCTACTACGCCGACAGCGTG<br>AAGGGCCGGTTCACCATCAGCCGGGACGACAGCAAGAACACCCTGTACCT<br>GCAGATGAACAGCCTGCGGGCCGAGGACACCGCCGTGTACTATTGTGTGC<br>GGCACGGCAACTTCGGCGCCAGCTATGTGTCTTGGTTTGCCTACTGGGGC<br>CAGGGCACCCTCGTGACCGTGTCAAGCGCTAGTACCAAGGGCCCCAGCGT<br>GTTCCCCCTGGCACCCAGCAGCAAGAGCACATCTGGCGGAACAGCCGCTC<br>TGGGCTGTCTGGTGAAAGACTACTTCCCCGAGCCCGTGACCGTGTCTTGG<br>AACTCTGGCGCCCTGACCAGCGGCGTGCACACCTTTCCAGCCGTGCTGCA<br>GAGCAGCGGCCTGTACTCCCTGTCCTCCGTGGTCACCGTGCCCTCTAGCT<br>CCCTGGGAACACAGACATATATCTGTAATGTCAATCACAAGCCTTCCAAC<br>ACCAAAGTCGATAAGAAAGTCGAGCCCAAGAGCTGCGACAAAACTCACAC<br>ATGCCCACCGTGCCCAGCACCTGAAGCTGCAGGGGGACCGTCAGTCTTCC<br>TCTTCCCCCCAAAACCCAAGGACACCCTCATGATCTCCCGGACCCCTGAG<br>GTCACATGCGTGGTGGTGGACGTGAGCCACGAAGACCCTGAGGTCAAGTT<br>CAACTGGTACGTGGACGGCGTGGAGGTGCATAATGCCAAGACAAAGCCGC<br>GGGAGGAGCAGTACAACAGCACGTACCGTGTGGTCAGCGTCCTCACCGTC<br>CTGCACCAGGACTGGCTGAATGGCAAGGAGTACAAGTGCAAGGTCTCCAA<br>CAAAGCCCTCGGCGCCCCCATCGAGAAAACCATCTCCAAAGCCAAAGGGC<br>AGCCCCGAGAACCACAGGTGTACACCCTGCCCCCATGCCGGGATGAGCTG<br>ACCAAGAACCAGGTCAGCCTGTGGTGCCTGGTCAAAGGCTTCTATCCCAG<br>CGACATCGCCGTGGAGTGGGAGAGCAATGGGCAGCCGGAGAACAACTACA<br>AGACCACGCCTCCCGTGCTGGACTCCGACGGCTCCTTCTTCCTCTACAGC<br>AAGCTCACCGTGGACAAGAGCAGGTGGCAGCAGGGGAACGTCTTCTCATG<br>CTCCGTGATGCATGAGGCTCTGCACAACCACTACACGCAGAAGAGCCTCT<br>CCCTGTCTCCGGGTAAA | 200 |
| 16D5 inverted<br>2 + 1 with<br>S100aA in<br>CDR H3<br>pETR14097<br>(pETR14097 +<br>pCON983 +<br>pETR13197) | GAGGTGCAATTGGTTGAATCTGGTGGTGGTCTGGTAAAACCGGGCGGTTC<br>CCTGCGTCTGAGCTGCGCGGCTTCCGGATTCACCTTCTCCAACGCGTGGA<br>TGAGCTGGGTTCGCCAGGCCCCGGGCAAAGGCCTCGAGTGGGTTGGTCGT<br>ATCAAGTCTAAAACTGACGGTGGCACCACGGATTACGCGGCTCCAGTTAA<br>AGGTCGTTTTACCATTTCCCGCGACGATAGCAAAAACACTCTGTATCTGC<br>AGATGAACTCTCTGAAAACTGAAGACACCGCAGTCTACTACTGTACTACC<br>CCGTGGGAATGGTCTTGGTACGATTATTGGGGCCAGGGCACGCTGGTTAC<br>GGTGTCTTCCGCTAGCACAAAGGGCCCTAGCGTGTTCCCTCTGGCCCCCA<br>GCAGCAAGAGCACAAGCGGCGGAACAGCCGCCCTGGGCTGCCTCGTGAAG<br>GACTACTTCCCCGAGCCCGTGACAGTGTCTTGGAACAGCGGAGCCCTGAC<br>AAGCGGCGTGCACACTTTCCCTGCCGTGCTGCAGAGCAGCGGCCTGTACT<br>CCCTGAGCAGCGTGGTCACCGTGCCTAGCAGCAGCCTGGGCACCCAGACC<br>TACATCTGCAACGTGAACCACAAGCCCAGCAACACCAAAGTGGACAAGAA<br>GGTGGAGCCCAAGAGCTGTGATGGCGGAGGAGGGTCCGGAGGCGGAGGAT<br>CCGAGGTGCAGCTGCTGGAATCTGGCGGCGGACTGGTGCAGCCTGGCGGA<br>TCTCTGAGACTGAGCTGTGCCGCCAGCGGCTTCACCTTCAGCACCTACGC<br>CATGAACTGGGTGCGCCAGGCCCCTGGCAAAGGCCTGGAATGGGTGTCCC<br>GGATCAGAAGCAAGTACAACAACTACGCCACCTACTACGCCGACAGCGTG<br>AAGGGCCGGTTCACCATCAGCCGGGACGACAGCAAGAACACCCTGTACCT<br>GCAGATGAACAGCCTGCGGGCCGAGGACACCGCCGTGTACTATTGTGTGC<br>GGCACGGCAACTTCGGCAACGCCTATGTGTCTTGGTTTGCCTACTGGGGC<br>CAGGGCACCCTCGTGACCGTGTCAAGCGCTAGTACCAAGGGCCCCAGCGT<br>GTTCCCCCTGGCACCCAGCAGCAAGAGCACATCTGGCGGAACAGCCGCTC<br>TGGGCTGTCTGGTGAAAGACTACTTCCCCGAGCCCGTGACCGTGTCTTGG<br>AACTCTGGCGCCCTGACCAGCGGCGTGCACACCTTTCCAGCCGTGCTGCA<br>GAGCAGCGGCCTGTACTCCCTGTCCTCCGTGGTCACCGTGCCCTCTAGCT | 201 |

8) Nucleotide sequences of exemplary embodiments

| | Sequence | Seq ID No |
|---|---|---|
| | CCCTGGGAACACAGACATATATCTGTAATGTCAATCACAAGCCTTCCAAC<br>ACCAAAGTCGATAAGAAAGTCGAGCCCAAGAGCTGCGACAAAACTCACAC<br>ATGCCCACCGTGCCCAGCACCTGAAGCTGCAGGGGGACCGTCAGTCTTCC<br>TCTTCCCCCCAAAACCCAAGGACACCCTCATGATCTCCCGGACCCCTGAG<br>GTCACATGCGTGGTGGTGGACGTGAGCCACGAAGACCCTGAGGTCAAGTT<br>CAACTGGTACGTGGACGGCGTGGAGGTGCATAATGCCAAGACAAAGCCGC<br>GGGAGGAGCAGTACAACAGCACGTACCGTGTGGTCAGCGTCCTCACCGTC<br>CTGCACCAGGACTGGCTGAATGGCAAGGAGTACAAGTGCAAGGTCTCCAA<br>CAAAGCCCTCGGCGCCCCCATCGAGAAAACCATCTCCAAAGCCAAAGGGC<br>AGCCCCGAGAACCACAGGTGTACACCCTGCCCCCATGCCGGGATGAGCTG<br>ACCAAGAACCAGGTCAGCCTGTGGTGCCTGGTCAAAGGCTTCTATCCCAG<br>CGACATCGCCGTGGAGTGGGAGAGCAATGGGCAGCCGGAGAACAACTACA<br>AGACCACGCCTCCCGTGCTGGACTCCGACGGCTCCTTCTTCCTCTACAGC<br>AAGCTCACCGTGGACAAGAGCAGGTGGCAGCAGGGGAACGTCTTCTCATG<br>CTCCGTGATGCATGAGGCTCTGCACAACCACTACACGCAGAAGAGCCTCT<br>CCCTGTCTCCGGGTAAA | |
| CD3 light<br>chain fused to<br>CH1;<br>Fc_PGLALA;<br>pETR13862<br>(Kappa-<br>lambda<br>antibody with<br>CD3 common<br>light chain<br>fused to CH1 +<br>Fc_PGLALA.<br>VHs fused to<br>kappa or<br>lambda<br>constant chain<br>pETR13859 +<br>pETR13860 +<br>pETR13862) | CAGGCCGTCGTGACCCAGGAACCCAGCCTGACAGTGTCTCCTGGCGGCAC<br>CGTGACCCTGACATGTGGCAGTTCTACAGGCGCCGTGACCACCAGCAACT<br>ACGCCAACTGGGTGCAGGAAAAGCCCGGCCAGGCCTTCAGAGGACTGATC<br>GGCGGCACCAACAAGAGAGCCCCTGGCACCCCTGCCAGATTCAGCGGATC<br>TCTGCTGGGAGGAAAGGCCGCCCTGACACTGTCTGGCGCCCAGCCAGAAG<br>ATGAGGCCGAGTACTACTGCGCCCTGTGGTACAGCAACCTGTGGGTGTTC<br>GGCGGAGGCACCAAGCTGACAGTGCTGAGCAGCGCTAGCACCAAGGGCCC<br>ATCGGTCTTCCCCCTGGCACCCTCCTCCAAGAGCACCTCTGGGGGCACAG<br>CGGCCCTGGGCTGCCTGGTCAAGGACTACTTCCCCGAACCGGTGACGGTG<br>TCGTGGAACTCAGGCGCCCTGACCAGCGGCGTGCACACCTTCCCGGCTGT<br>CCTACAGTCCTCAGGACTCTACTCCCTCAGCAGCGTGGTGACCGTGCCCT<br>CCAGCAGCTTGGGCACCCAGACCTACATCTGCAACGTGAATCACAAGCCC<br>AGCAACACCAAGGTGGACAAGAAAGTTGAGCCCAAATCTTGTGACAAAAC<br>TCACACATGCCCACCGTGCCCAGCACCTGAAGCTGCAGGGGGACCGTCAG<br>TCTTCCTCTTCCCCCCAAAACCCAAGGACACCCTCATGATCTCCCGGACC<br>CCTGAGGTCACATGCGTGGTGGTGGACGTGAGCCACGAAGACCCTGAGGT<br>CAAGTTCAACTGGTACGTGGACGGCGTGGAGGTGCATAATGCCAAGACAA<br>AGCCGCGGGAGGAGCAGTACAACAGCACGTACCGTGTGGTCAGCGTCCTC<br>ACCGTCCTGCACCAGGACTGGCTGAATGGCAAGGAGTACAAGTGCAAGGT<br>CTCCAACAAAGCCCTCGGCGCCCCCATCGAGAAAACCATCTCCAAAGCCA<br>AAGGGCAGCCCCGAGAACCACAGGTGTACACCCTGCCCCCATCCCGGGAT<br>GAGCTGACCAAGAACCAGGTCAGCCTGACCTGCCTGGTCAAAGGCTTCTA<br>TCCCAGCGACATCGCCGTGGAGTGGGAGAGCAATGGGCAGCCGGAGAACA<br>ACTACAAGACCACGCCTCCCGTGCTGGACTCCGACGGCTCCTTCTTCCTC<br>TACAGCAAGCTCACCGTGGACAAGAGCAGGTGGCAGCAGGGGAACGTCTT<br>CTCATGCTCCGTGATGCATGAGGCTCTGCACAACCACTACACGCAGAAGA<br>GCCTCTCCCTGTCTCCGGGTAAA | 202 |
| 16D5 VH<br>fused to<br>constant<br>kappa chain;<br>pETR13859 | GAGGTGCAATTGGTTGAATCTGGTGGTGGTCTGGTAAAACCGGGCGGTTC<br>CCTGCGTCTGAGCTGCGCGGCTTCCGGATTCACCTTCTCCAACGCGTGGA<br>TGAGCTGGGTTCGCCAGGCCCCGGGCAAAGGCCTCGAGTGGGTTGGTCGT<br>ATCAAGTCTAAAACTGACGGTGGCACCACGGATTACGCGGCTCCAGTTAA<br>AGGTCGTTTTACCATTTCCCGCGACGATAGCAAAAACACTCTGTATCTGC<br>AGATGAACTCTCTGAAAACTGAAGACACCGCAGTCTACTACTGTACTACC<br>CCGTGGGAATGGTCTTGGTACGATTATTGGGGCCAGGGCACGCTGGTTAC<br>GGTGTCTTCCGCTAGCGTGGCCGCTCCCTCCGTGTTCATCTTCCCACCTT<br>CCGACGAGCAGCTGAAGTCCGGCACCGCTTCTGTCGTGTGCCTGCTGAAC<br>AACTTCTACCCCGCGAGGCCAAGGTGCAGTGGAAGGTGGACAACGCCCT<br>GCAGTCCGGCAACAGCCAGGAATCCGTGACCGAGCAGGACTCCAAGGACA<br>GCACCTACTCCCTGTCCTCCACCCTGACCCTGTCCAAGGCCGACTACGAG<br>AAGCACAAGGTGTACGCCTGCGAAGTGACCCACCAGGGCCTGTCTAGCCC<br>CGTGACCAAGTCTTTCAACCGGGGCGAGTGC | 203 |
| CD3 VH fused<br>to constant<br>lambda chain;<br>pETR13860 | GAAGTGCAGCTGCTGGAATCCGGCGGAGGACTGGTGCAGCCTGGCGGATC<br>TCTGAGACTGTCTTGTGCCGCCTCCGGCTTCACCTTCTCCACCTACGCCA<br>TGAACTGGGTGCGACAGGCTCCTGGCAAGGGCCTGGAATGGGTGTCCCGG<br>ATCAGATCCAAGTACAACAACTACGCCACCTACTACGCCGACTCCGTGAA<br>GGGCCGGTTCACCATCTCTCGGGACGACTCCAAGAACACCCTGTACCTGC<br>AGATGAACTCCCTGCGGGCCGAGGACACCGCCGTGTACTATTGTGTGCGG<br>CACGGCAACTTCGGCAACTCCTATGTGTCTTGGTTTGCCTACTGGGGCCA<br>GGGCACCCTCGTGACCGTGTCATCTGCTAGCCCCAAGGCTGCCCCCAGCG<br>TGACCCTGTTTCCCCCCAGCAGCGAGGAACTGCAGGCCAACAAGGCCACC<br>CTGGTCTGCCTGATCAGCGACTTCTACCCAGGCGCCGTGACCGTGGCCTG<br>GAAGGCCGACAGCAGCCCCGTGAAGGCCGGCGTGGAGACCACCACCCCCA<br>GCAAGCAGAGCAACAACAAGTACGCCGCCAGCAGCTACCTGAGCCTGACC<br>CCCGAGCAGTGGAAGAGCCACAGGTCCTACAGCTGCCAGGTGACCCACGA<br>GGGCAGCACCGTGGAGAAAACCGTGGCCCCCACCGAGTGCAGC | 204 |

| | 8) Nucleotide sequences of exemplary embodiments | |
|---|---|---|
| | Sequence | Seq ID No |
| VHCH1[36F2]_<br>VHCL[CD3]_<br>Fcknob_PGLALA<br>pCON1056 | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCATGACACTAGCACCTCTACCGTTTATATGGAGCTGT<br>CCAGCCTGCGTTCTGAAGATACTGCAGTGTACTACTGTGCACGCTCTTTC<br>TTCACTGGTTTCCATCTGGACTATTGGGGTCAAGGCACCCTCGTAACGGT<br>TTCTTCTGCTAGCACAAAGGGCCCCAGCGTGTTCCCTCTGGCCCCTAGCA<br>GCAAGAGCACATCTGGCGGAACAGCCGCCCTGGGCTGCCTCGTGAAGGAC<br>TACTTTCCCGAGCCTGTGACCGTGTCCTGGAACTCTGGCGCCCTGACAAG<br>CGGCGTGCACACCTTTCCAGCCGTGCTGCAGAGCAGCGGCCTGTACTCTC<br>TGAGCAGCGTGGTCACCGTGCCTAGCAGCAGCCTGGGCACCCAGACCTAC<br>ATCTGCAACGTGAACCACAAGCCCAGCAACACCAAAGTGGACAAGAAGGT<br>GGAGCCCAAGAGCTGTGATGGCGGAGGAGGGTCCGGAGGCGGAGGATCCG<br>AGGTGCAGCTGCTGGAATCTGGCGGCGACTGGTGCAGCCTGGCGGATCT<br>CTGAGACTGAGCTGTGCCGCCAGCGGCTTCACCTTCAGCACCTACGCCAT<br>GAACTGGGTGCGCCAGGCCCCTGGCAAAGGCCTGGAATGGGTGTCCCGGA<br>TCAGAAGCAAGTACAACAACTACGCCACCTACTACGCCGACGCGTGAAG<br>GGCCGGTTCACCATCAGCCGGGACGACAGCAAGAACACCCTGTACCTGCA<br>GATGAACAGCCTGCGGGCCGAGGACACCGCCGTGTACTATTGTGTGCGGC<br>ACGGCAACTTCGGCAACAGCTATGTGTCTTGGTTTGCCTACTGGGGCCAG<br>GGCACCCTCGTGACCGTGTCAAGCGCTAGTGTGGCCGCTCCCTCCGTGTT<br>TATCTTTCCCCCATCCGATGAACAGCTGAAAAGCGGCACCGCCTCCGTCG<br>TGTGTCTGCTGAACAATTTTTACCCTAGGGAAGCTAAAGTGCAGTGGAAA<br>GTGGATAACGCACTGCAGTCCGGCAACTCCCAGGAATCTGTGACAGAACA<br>GGACTCCAAGGACAGCACCTACTCCCTGTCCTCCACCCTGACACTGTCTA<br>AGGCTGATTATGAGAAACACAAAGTCTACGCCTGCGAAGTCACCCATCAG<br>GGCCTGAGCTCGCCCGTCACAAAGAGCTTCAACAGGGGAGAGTGTGACAA<br>GACCCACACCTGTCCCCCTTGTCCTGCCCCTGAAGCTGCTGGCGGCCCTT<br>CTGTGTTCCTGTTCCCCCCAAAGCCCAAGGACACCCTGATGATCAGCCGG<br>ACCCCCGAAGTGACCTGCGTGGTGGTGGATGTGTCCCACGAGGACCCTGA<br>AGTGAAGTTCAATTGGTACGTGGACGGCGTGGAAGTGCACAACGCCAAGA<br>CAAAGCCGCGGGAGGAGCAGTACAACAGCACGTACCGTGTGGTCAGCGTC<br>CTCACCGTCCTGCACCAGGACTGGCTGAATGGCAAGGAGTACAAGTGCAA<br>GGTCTCCAACAAAGCCCTCGGCGCCCCCATCGAGAAAACCATCTCCAAAG<br>CCAAAGGGCAGCCCCGAGAACCACAGGTGTACACCCTGCCCCCATGCCGG<br>GATGAGCTGACCAAGAACCAGGTCAGCCTGTGGTGCCTGGTCAAAGGCTT<br>CTATCCCAGCGACATCGCCGTGGAGTGGGAGAGCAATGGGCAGCCGGAGA<br>ACAACTACAAGACCACGCCTCCCGTGCTGGACTCCGACGGCTCCTTCTTC<br>CTCTACAGCAAGCTCACCGTGGACAAGAGCAGGTGGCAGCAGGGGAACGT<br>CTTCTCATGCTCCGTGATGCATGAGGCTCTGCACAACCACTACACGCAGA<br>AGAGCCTCTCCCTGTCTCCGGGTAAA | 246 |
| 36F2-Fchole<br>PGLALA<br>pCON1050 | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCATGACACTAGCACCTCTACCGTTTATATGGAGCTGT<br>CCAGCCTGCGTTCTGAAGATACTGCAGTGTACTACTGTGCACGCTCTTTC<br>TTCACTGGTTTCCATCTGGACTATTGGGGTCAAGGCACCCTCGTAACGGT<br>TTCTTCTGCTAGCACCAAGGGCCCCTCCGTGTTCCCCCTGGCCCCCAGCA<br>GCAAGAGCACCAGCGGCGGCACAGCCGCTCTGGGCTGCCTGGTCAAGGAC<br>TACTTCCCCGAGCCCGTGACCGTGTCCTGGAACAGCGGAGCCCTGACCTC<br>CGGCGTGCACACCTTCCCCGCCGTGCTGCAGAGTTCTGGCCTGTATAGCC<br>TGAGCAGCGTGGTCACCGTGCCTTCTAGCAGCCTGGGCACCCAGACCTAC<br>ATCTGCAACGTGAACCACAAGCCCAGCAACACCAAGGTGGACAAGAAGGT<br>GGAGCCCAAGAGCTGCGACAAAACTCACACATGCCCACCGTGCCCAGCAC<br>CTGAAGCTGCAGGGGACCGTCAGTCTTCCTCTTCCCCCCAAAACCCAAG<br>GACACCCTCATGATCTCCCGGACCCCTGAGGTCACATGCGTGGTGGTGGA<br>CGTGAGCCACGAAGACCCTGAGGTCAAGTTCAACTGGTACGTGGACGGCG<br>TGGAGGTGCATAATGCCAAGACAAAGCCGCGGGAGGAGCAGTACAACAGC<br>ACGTACCGTGTGGTCAGCGTCCTCACCGTCCTGCACCAGGACTGGCTGAA<br>TGGCAAGGAGTACAAGTGCAAGGTCTCCAACAAAGCCCTCGGCGCCCCCA<br>TCGAGAAAACCATCTCCAAAGCCAAAGGGCAGCCCCGAGAACCACAGGTG<br>TGCACCCTGCCCCCATCCCGGGATGAGCTGACCAAGAACCAGGTCAGCCT<br>CTCGTGCGCAGTCAAAGGCTTCTATCCCAGCGACATCGCCGTGGAGTGGG<br>AGAGCAATGGGCAGCCGGAGAACAACTACAAGACCACGCCTCCCGTGCTG<br>GACTCCGACGGCTCCTTCTTCCTCGTGAGCAAGCTCACCGTGGACAAGAG<br>CAGGTGGCAGCAGGGGAACGTCTTCTCATGCTCCGTGATGCATGAGGCTC<br>TGCACAACCACTACACGCAGAAGAGCCTCTCCCTGTCTCCGGGTAAA | 247 |
| 36F2 LC<br>pCON1062 | GAAATCGTGTTAACGCAGTCTCCAGGCACCCTGTCTTTGTCTCCAGGGGA<br>AAGAGCCACCCTCTCTTGCAGGGCCAGTCAGAGTGTTAGCAGCAGCTACT<br>TAGCCTGGTACCAGCAGAAACCTGGCCAGGCTCCCAGGCTCCTCATCTAT<br>GGAGCATCCAGCAGGGCCACTGGCATCCCAGACAGGTTCAGTGGCAGTGG | 97 |

8) Nucleotide sequences of exemplary embodiments

| | Sequence | Seq ID No |
|---|---|---|
| | ATCCGGGACAGACTTCACTCTCACCATCAGCAGACTGGAGCCTGAAGATT<br>TTGCAGTGTATTACTGTCAGCAGTATACCAACGAACATTATTATACGTTC<br>GGCCAGGGGACCAAAGTGGAAATCAAACGTACGGTGGCTGCACCATCTGT<br>CTTCATCTTCCCGCCATCTGATGAGCAGTTGAAATCTGGAACTGCCTCTG<br>TTGTGTGCCTGCTGAATAACTTCTATCCCAGAGAGGCCAAAGTACAGTGG<br>AAGGTGGATAACGCCCTCCAATCGGGTAACTCCCAGGAGAGTGTCACAGA<br>GCAGGACAGCAAGGACAGCACCTACAGCCTCAGCAGCACCCTGACGCTGA<br>GCAAAGCAGACTACGAGAAACACAAAGTCTACGCCTGCGAAGTCACCCAT<br>CAGGGCCTGAGCTCGCCCGTCACAAAGAGCTTCAACAGGGGAGAGTGT | |
| CD3 VLCH1<br>pETR12940 | CAGGCCGTCGTGACCCAGGAACCCAGCCTGACAGTGTCTCCTGGCGGCAC<br>CGTGACCCTGACATGTGGCAGTTCTACAGGCGCCGTGACCACCAGCAACT<br>ACGCCAACTGGGTGCAGGAAAAGCCCGGCCAGGCCTTCAGAGGACTGATC<br>GGCGGCACCAACAAGAGAGCCCCTGGCACCCCTGCCAGATTCAGCGGATC<br>TCTGCTGGGAGGAAAGGCCGCCCTGACACTGTCTGGCGCCCAGCCAGAAG<br>ATGAGGCCGAGTACTACTGCGCCCTGTGGTACAGCAACCTGTGGGTGTTC<br>GGCGGAGGCACCAAGCTGACAGTGCTGAGCAGCGCTTCCACCAAAGGCCC<br>TTCCGTGTTTCCTCTGGCTCCTAGCTCCAAGTCCACCTCTGGAGGCACCG<br>CTGCTCTCGGATGCCTCGTGAAGGATTATTTTCCTGAGCCTGTGACAGTG<br>TCCTGGAATAGCGGAGCACTGACCTCTGGAGTGCATACTTTCCCCGCTGT<br>GCTGCAGTCCTCTGGACTGTACAGCCTGAGCAGCGTGGTGACAGTGCCCA<br>GCAGCAGCCTGGGCACCCAGACCTACATCTGCAACGTGAACCACAAGCCC<br>AGCAACACCAAGGTGGACAAGAAGGTGGAACCCAAGTCTTGT | 198 |

| Name | | |
|---|---|---|
| K53A<br>nt | CAGACCGTCGTGACCCAGGAACCCAGCCTGACAGTGTCTCCTGGCGGCAC<br>CGTGACCCTGACATGTGGCAGTTCTACAGGCGCCGTGACCACCAGCAACT<br>ACGCCAACTGGGTGCAGCAGAAGCCAGGCCAGGCTCCCAGAGGACTGATC<br>GGCGGCACCAACGCCAGAGCCCCTGGCACCCCTGCCAGATTCAGCGGATC<br>TCTGCTGGGAGGAAAGGCCGCCCTGACACTGTCTGGCGTGCAGCCTGAAG<br>ATGAGGCCGAGTACTACTGCGCCCTGTGGTACAGCAACCTGTGGGTGTTC<br>GGCGGAGGCACCAAGCTGACAGTCCTA | 205 |
| S93A<br>nt | CAGACCGTCGTGACCCAGGAACCCAGCCTGACAGTGTCTCCTGGCGGCAC<br>CGTGACCCTGACATGTGGCAGTTCTACAGGCGCCGTGACCACCAGCAACT<br>ACGCCAACTGGGTGCAGCAGAAGCCAGGCCAGGCTCCCAGAGGACTGATC<br>GGCGGCACCAACAAGAGAGCCCCTGGCACCCCTGCCAGATTCAGCGGATC<br>TCTGCTGGGAGGAAAGGCCGCCCTGACACTGTCTGGCGTGCAGCCTGAAG<br>ATGAGGCCGAGTACTACTGCGCCCTGTGGTACGCCAACCTGTGGGTGTTC<br>GGCGGAGGCACCAAGCTGACAGTCCTA | 206 |
| S35H<br>nt | GAGGTGCAATTGGTGGAAAGCGGAGGCGGCCTCGTGAAGCCTGGCGGATC<br>TCTGAGACTGAGCTGTGCCGCCAGCGGCTTCACCTTCAGCAACGCCTGGA<br>TGCACTGGGTGCGCCAGGCCCCTGGAAAAGGACTCGAGTGGGTGGGACGG<br>ATCAAGAGCAAGACCGATGGCGGCACCACCGACTATGCCGCCCCTGTGAA<br>GGGCCGGTTCACCATCAGCAGGGACGACAGCAAGAACACCCTGTACCTGC<br>AGATGAACAGCCTGAAAACCGAGGACACCGCCGTGTACTACTGCACCACC<br>CCCTGGGAGTGGTCTTGGTACGACTATTGGGGCCAGGGCACCCTCGTGAC<br>CGTGTCCTCTGCTAGC | 207 |
| G49S<br>nt | GAGGTGCAATTGGTGGAAAGCGGAGGCGGCCTCGTGAAGCCTGGCGGATC<br>TCTGAGACTGAGCTGTGCCGCCAGCGGCTTCACCTTCAGCAACGCCTGGA<br>TGAGCTGGGTGCGCCAGGCCCCTGGAAAAGGACTCGAGTGGGTGTCCCGG<br>ATCAAGAGCAAGACCGATGGCGGCACCACCGACTATGCCGCCCCTGTGAA<br>GGGCCGGTTCACCATCAGCAGGGACGACAGCAAGAACACCCTGTACCTGC<br>AGATGAACAGCCTGAAAACCGAGGACACCGCCGTGTACTACTGCACCACC<br>CCCTGGGAGTGGTCTTGGTACGACTATTGGGGCCAGGGCACCCTCGTGAC<br>CGTGTCCTCTGCTAGC | 208 |
| R50S<br>nt | GAGGTGCAATTGGTGGAAAGCGGAGGCGGCCTCGTGAAGCCTGGCGGATC<br>TCTGAGACTGAGCTGTGCCGCCAGCGGCTTCACCTTCAGCAACGCCTGGA<br>TGAGCTGGGTGCGCCAGGCCCCTGGAAAAGGACTCGAGTGGGTGGGATCT<br>ATCAAGAGCAAGACCGACGGCGGCACCACCGACTATGCCGCCCCTGTGAA<br>GGGCCGGTTCACCATCAGCAGGGACGACAGCAAGAACACCCTGTACCTGC<br>AGATGAACAGCCTGAAAACCGAGGACACCGCCGTGTACTACTGCACCACC<br>CCCTGGGAGTGGTCTTGGTACGACTATTGGGGCCAGGGCACCCTCGTGAC<br>CGTGTCCTCTGCTAGC | 209 |
| W96Y<br>nt | GAGGTGCAATTGGTGGAAAGCGGAGGCGGCCTCGTGAAGCCTGGCGGATC<br>TCTGAGACTGAGCTGTGCCGCCAGCGGCTTCACCTTCAGCAACGCCTGGA<br>TGAGCTGGGTGCGCCAGGCCCCTGGAAAAGGACTCGAGTGGGTGGGACGG<br>ATCAAGAGCAAGACCGATGGCGGCACCACCGACTATGCCGCCCCTGTGAA<br>GGGCCGGTTCACCATCAGCAGGGACGACAGCAAGAACACCCTGTACCTGC<br>AGATGAACAGCCTGAAAACCGAGGACACCGCCGTGTACTACTGCACCACC | 210 |

8) Nucleotide sequences of exemplary embodiments

| | Sequence | Seq ID No |
|---|---|---|
| | CCCTACGAGTGGTCTTGGTACGACTACTGGGGCCAGGGCACCCTCGTGAC<br>CGTGTCATCTGCTAGC | |
| W98Y<br>nt | GAGGTGCAATTGGTGGAAAGCGGAGGCGGCCTCGTGAAGCCTGGCGGATC<br>TCTGAGACTGAGCTGTGCCGCCAGCGGCTTCACCTTCAGCAACGCCTGGA<br>TGAGCTGGGTGCGCCAGGCCCCTGGAAAAGGACTCGAGTGGGTGGGACGG<br>ATCAAGAGCAAGACCGATGGCGGCACCACCGACTATGCCGCCCCTGTGAA<br>GGGCCGGTTCACCATCAGCAGGGACGACAGCAAGAACACCCTGTACCTGC<br>AGATGAACAGCCTGAAAACCGAGGACACCGCCGTGTACTACTGCACCACC<br>CCCTGGGAGTACTCTTGGTACGACTACTGGGGCCAGGGCACCCTCGTGAC<br>CGTGTCATCTGCTAGC | 211 |
| 90D7<br>nt | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCAACTAC<br>ACTATCGTTGTTTCTCCGTTCGACTATTGGGGTCAAGGCACCCTCGTAAC<br>GGTTTCTTCTGCTAGC | 212 |
| 90C1<br>nt | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCAACTAC<br>TTCATCGGTTCTGTTGCTATGGACTATTGGGGTCAAGGCACCCTCGTAAC<br>GGTTTCTTCTGCTAGC | 213 |
| 5E8 VH<br>nt | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCGGTCTG<br>ACTTACTCTATGGACTATTGGGGTCAAGGCACCCTCGTAACGGTTTCTTC<br>TGCTAGC | 214 |
| 5E8 VL<br>nt | GATATTGTTATGACTCAATCTCCACTGTCTCTGCCGGTGACTCCAGGCGA<br>ACCGGCGAGCATTTCTTGCCGTTCCAGCCAGTCTCTGCTGCACTCCAACG<br>GCTACAACTATCTCGATTGGTACCTGCAAAAACCGGGTCAGAGCCCTCAG<br>CTGCTGATCTACCTGGGCTCTAACCGCGCTTCCGGTGTACCGGACCGTTT<br>CAGCGGCTCTGGATCCGGCACCGATTTCACGTTGAAAATCAGCCGTGTTG<br>AAGCAGAAGACGTGGGCGTTTATTACTGTATGCAGGCACTGCAGATTCCA<br>AACACTTTTGGTCAAGGCACCAAGGTCGAAATTAAACGTACG | 215 |
| 12A4 VH<br>nt | GAGGTGCAATTGTTGGAGTCTGGGGGAGGCTTGGTACAGCCTGGGGGGTC<br>CCTGAGACTCTCCTGTGCAGCCTCCGGATTCACCTTTAGCAGTTATGCCA<br>TGAGCTGGGTCCGCCAGGCTCCAGGGAAGGGGCTGGAGTGGGTCTCAGCT<br>ATTAGTGGTAGTGGTGGTAGCACATACTACGCAGACTCCGTGAAGGGCCG<br>GTTCACCATCTCCAGAGACAATTCCAAGAACACGCTGTATCTGCAGATGA<br>ACAGCCTGAGAGCCGAGGACACGGCCGTATATTACTGTGCGAAATACGCT<br>TACGCTCTGGACTACTGGGGCCAAGGAACCCTGGTCACCGTCTCGAGTGC<br>TAGC | 216 |
| 12A4 VL<br>nt | GAAATCGTGTTAACGCAGTCTCCAGGCACCCTGTCTTTGTCTCCAGGGGA<br>AAGAGCCACCCTCTCTTGCAGGGCCAGTCAGAGTGTTAGCAGCAGCTACT<br>TAGCCTGGTACCAGCAGAAACCTGGCCAGGCTCCCAGGCTCCTCATCTAT<br>GGAGCATCCAGCAGGGCCACTGGCATCCCAGACAGGTTCAGTGGCAGTGG<br>ATCCGGGACAGACTTCACTCTCACCATCAGCAGACTGGAGCCTGAAGATT<br>TTGCAGTGTATTACTGTCAGCAGCATGGCAGCAGCAGCACGTTCGGCCAG<br>GGGACCAAAGTGGAAATCAAACGTACG | 217 |
| 7A3 VH<br>nt | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCTCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCGGTGAC<br>TTCTCTGCTGGTCGTCTGATGGACTATTGGGGTCAAGGCACCCTCGTAAC<br>GGTTTCTTCTGCTAGC | 218 |

| | 8) Nucleotide sequences of exemplary embodiments | |
|---|---|---|
| | Sequence | Seq ID No |
| 7A3 VL nt | GATATTGTTATGACTCAATCTCCACTGTCTCTGCCGGTGACTCCAGGCGA ACCGGCGAGCATTTCTTGCCGTTCCAGCCAGTCTCTGCTGCACTCCAACG GCTACAACTATCTCGATTGGTACCTGCAAAAACCGGGTCAGAGCCCTCAG CTGCTGATCTACCTGGGCTCTAACCGCGCTTCCGGTGTACCGGACCGTTT CAGCGGCTCTGGATCCGGCACCGATTTCACGTTGAAAATCAGCCGTGTTG AAGCAGAAGACGTGGGCGTTTATTACTGTATGCAGGCACTGCAGACCCCA CCAATTACCTTTGGTCAAGGCACCAAGGTCGAAATTAAACGTACG | 219 |
| 6E10 VH nt | CAGGTGCAATTGGTTCAATCTGGTGCTGAAGTAAAAAAACCGGGCGCTTC CGTTAAAGTGAGCTGCAAAGCATCCGGATACACCTTCACTTCCTATTACA TGCACTGGGTTCGTCAAGCCCCGGGCCAGGGTCTGGAATGGATGGGCATC ATTAACCCAAGCGGTGGCTCTACCTCCTACGCGCAGAAATTCCAGGGTCG CGTCACGATGACCCGTGACACTAGCACCTCTACCGTTTATATGGAGCTGT CCAGCCTGCGTTCTGAAGATACTGCAGTGTACTACTGTGCACGCGGTGAC TACAACGCTTTCGACTATTGGGGTCACGGCACCCTCGTAACGGTTTCTTC TGCTAGC | 220 |
| 6E10 VL nt | GATATTGTTATGACTCAATCTCCACTGTCTCTGCCGGTGACTCCAGGCGA ACCGGCGAGCATTTCTTGCCGTTCCAGCCAGTCTCTGCTGCACTCCAACG GCTACAACTATCTCGATTGGTACCTGCAAAAACCGGGTCAGAGCCCTCAG CTGCTGATCTACCTGGGCTCTAACCGCGCTTCCGGTGTACCGGACCGTTT CAGCGGCTCTGGATCCGGCACCGATTTCACGTTGAAAATCAGCCGTGTTG AAGCAGAAGACGTGGGCGTTTATTACTGTATGCAGGCATGGCATAGCCCA ACTTTTGGTCAAGGCACCAAGGTCGAAATTAAACGTACG | 221 |
| 12F9 VH nt | CAGGTGCAATTGGTTCAATCTGGTGCTGAAGTAAAAAAACCGGGCGCTTC CGTTAAAGTGAGCTGCAAAGCATCCGGATACACCTTCACTTCCTATTACA TGCACTGGGTTCGTCAAGCCCCGGGCCAGGGTCTGGAATGGATGGGCATC ATTAACCCAAGCGGTGGCTCTACCTCCTACGCGCAGAAATTCCAGGGTCG CGTCACGATGACCCGTGACACTAGCACCTCTACCGTTTATATGGAGCTGT CCAGCCTGCGTTCTGAAGATACTGCAGTGTACTACTGTGCACGCGGTGCT ACTTACACTATGGACTATTGGGGTCAAGGCACCCTCGTAACGGTTTCTTC TGCTAGC | 222 |
| 12F9 VL nt | GATATTGTTATGACTCAATCTCCACTGTCTCTGCCGGTGACTCCAGGCGA ACCGGCGAGCATTTCTTGCCGTTCCAGCCAGTCTCTGCTGCACTCCAACG GCTACAACTATCTCGATTGGTACCTGCAAAAACCGGGTCAGAGCCCTCAG CTGCTGATCTACCTGGGCTCTAACCGCGCTTCCGGTGTACCGGACCGTTT CAGCGGCTCTGGATCCGGCACCGATTTCACGTTGAAAATCAGCCGTGTTG AAGCAGAAGACGTGGGCGTTTATTACTGTATGCAGGCACTGCAGACCCCA ATTACTTTTGGTCAAGGCACCAAGGTCGAAATTAAACGTACG | 223 |
| pETR11646 Mov19 VH- CH1-Fchole PG/LALA | CAGGTGCAGCTGCAGCAGTCTGGCGCCGAGCTCGTGAAACCTGGCGCCTC CGTGAAGATCAGCTGCAAGGCCAGCGGCTACAGCTTCACCGGCTACTTCA TGAACTGGGTCAAGCAGAGCCACGGCAAGAGCCTGGAATGGATCGGCAGA ATCCACCCCTACGACGGCGACACCTTCTACAACCAGAACTTCAAGGACAA GGCCACCCTGACCGTGGACAAGAGCAGCAACACCGCCCACATGGAACTGC TGAGCCTGACCAGCGAGGACTTCGCCGTGTACTACTGCACCAGATACGAC GGCAGCCGGGCCATGGATTATTGGGCCAGGGCACCACCGTGACAGTGTC CAGCGCTAGCACCAAGGGCCCCTCCGTGTTCCCCCTGGCCCCCAGCAGCA AGAGCACCAGCGGCGGCACAGCCGCTCTGGGCTGCCTGGTCAAGGACTAC TTCCCCGAGCCCGTGACCGTGTCCTGGAACAGCGGAGCCCTGACCTCCGG CGTGCACACCTTCCCCGCCGTGCTGCAGAGTTCTGGCCTGTATAGCCTGA GCAGCGTGGTCACCGTGCCTTCTAGCAGCCTGGGCACCCAGACCTACATC TGCAACGTGAACCACAAGCCCAGCAACACCAAGGTGGACAAGAAGGTGGA GCCCAAGAGCTGCGACAAAACTCACACATGCCCACCGTGCCCAGCACCTG AAGCTGCAGGGGACCGTCAGTCTTCCTCTTCCCCCCAAAACCCAAGGAC ACCCTCATGATCTCCCGGACCCCTGAGGTCACATGCGTGGTGGTGGACGT GAGCCACGAAGACCCTGAGGTCAAGTTCAACTGGTACGTGGACGGCGTGG AGGTGCATAATGCCAAGACAAAGCCGCGGGAGGAGCAGTACAACAGCACG TACCGTGTGGTCAGCGTCCTCACCGTCCTGCACCAGGACTGGCTGAATGG CAAGGAGTACAAGTGCAAGGTCTCCAACAAAGCCCTCGGCGCCCCCATCG AGAAAACCATCTCCAAAGCCAAAGGGCAGCCCCGAGAACCACAGGTGTGC ACCCTGCCCCCATCCCGGGATGAGCTGACCAAGAACCAGGTCAGCCTCTC GTGCGCAGTCAAAGGCTTCTATCCCAGCGACATCGCCGTGGAGTGGGAGA GCAATGGGCAGCCGGAGAACAACTACAAGACCACGCCTCCCGTGCTGGAC TCCGACGGCTCCTTCTTCCTCGTGAGCAAGCTCACCGTGGACAAGAGCAG GTGGCAGCAGGGGAACGTCTTCTCATGCTCCGTGATGCATGAGGCTCTGC ACAACCACTACACGCAGAAGAGCCTCTCCCTGTCTCCGGGTAAA | 224 |

| | 8) Nucleotide sequences of exemplary embodiments | |
|---|---|---|
| | Sequence | Seq ID No |
| pETR11647 Mov19 VH-CH1-CD3 VH-CL-Fcknob PG/LALA | CAGGTGCAGCTGCAGCAGTCTGGCGCCGAGCTCGTGAAACCTGGCGCCTC CGTGAAGATCAGCTGCAAGGCCAGCGGCTACAGCTTCACCGGCTACTTCA TGAACTGGGTCAAGCAGAGCCACGGCAAGAGCCTGGAATGGATCGGCAGA ATCCACCCCTACGACGGCGACACCTTCTACAACCAGAACTTCAAGGACAA GGCCACCCTGACCGTGGACAAGAGCAGCAACACCGCCCACATGGAACTGC TGAGCCTGACCAGCGAGGACTTCGCCGTGTACTACTGCACCAGATACGAC GGCAGCCGGGCCATGGATTATTGGGGCCAGGGCACCACCGTGACAGTGTC CAGCGCTAGCACAAAGGGCCCCAGCGTGTTCCCTCTGGCCCCTAGCAGCA AGAGCACATCTGGCGGAACAGCCGCCCTGGGCTGCCTCGTGAAGGACTAC TTTCCCGAGCCTGTGACCGTGTCCTGGAACTCTGGCGCCCTGACAAGCGG CGTGCACACCTTTCCAGCCGTGCTGCAGAGCAGCGGCCTGTACTCTCTGA GCAGCGTGGTCACCGTGCCTAGCAGCAGCCTGGGCACCCAGACCTACATC TGCAACGTGAACCACAAGCCCAGCAACACCAAAGTGGACAAGAAGGTGGA GCCCAAGAGCTGTGATGGCGGAGGAGGGTCCGAGGCGGAGGATCCGAAG TGCAGCTGGTGGAAAGCGGCGGAGGCCTGGTGCAGCCTAAGGGCTCTCTG AAGCTGAGCTGTGCCGCCAGCGGCTTCACCTTCAACACCTACGCCATGAA CTGGGTGCGCAGGCCCCTGGCAAAGGCCTGGAATGGGTGGCCCGGATCA GAAGCAAGTACAACAATTACGCCACCTACTACGCCGACAGCGTGAAGGAC CGGTTCACCATCAGCCGGGACGACAGCCAGAGCATCCTGTACCTGCAGAT GAACAACCTGAAAACCGAGGACACCGCCATGTACTACTGCGTGCGGCACG GCAACTTCGGCAACAGCTATGTGTCTTGGTTTGCCTACTGGGGCCAGGGC ACCCTCGTGACAGTGTCTGCTGCTAGCGTGGCCGCTCCCTCCGTGTTTAT CTTTCCCCCATCCGATGAACAGCTGAAAAGCGGCACCGCCTCCGTCGTGT GTCTGCTGAACAATTTTTACCCTAGGGAAGCTAAAGTGCAGTGGAAAGTG GATAACGCACTGCAGTCCGGCAACTCCCAGGAATCTGTGACAGAACAGGA CTCCAAGGACAGCACCTACTCCCTGTCCTCCACCCTGACACTGTCTAAGG CTGATTATGAGAAACACAAAGTCTACGCCTGCGAAGTCACCCATCAGGGC CTGAGCTCGCCCGTCACAAAGAGCTTCAACAGGGGAGAGTGTGACAAGAC CCACACCTGTCCCCCTTGTCCTGCCCCTGAAGCTGCTGGCGGCCCTTCTG TGTTCCTGTTCCCCCCAAAGCCCAAGGACACCCTGATGATCAGCCGGACC CCCGAAGTGACCTGCGTGGTGGTGGATGTGTCCCACGAGGACCCTGAAGT GAAGTTCAATTGGTACGTGGACGGCGTGGAAGTGCACAACGCCAAGACAA AGCCGCGGGAGGAGCAGTACAACAGCACGTACCGTGTGGTCAGCGTCCTC ACCGTCCTGCACCAGGACTGGCTGAATGGCAAGGAGTACAAGTGCAAGGT CTCCAACAAAGCCCTCGGCGCCCCCATCGAGAAAACCATCTCCAAAGCCA AAGGGCAGCCCCGAGAACCACAGGTGTACACCCTGCCCCCATGCCGGGAT GAGCTGACCAAGAACCAGGTCAGCCTGTGTGGCCTGGTCAAAGGCTTCTA TCCCAGCGACATCGCCGTCGAGTGGGAGAGCAATGGGCAGCCGGAGAACA ACTACAAGACCACGCCTCCCGTGCTGGACTCCGACGGCTCCTTCTTCCTC TACAGCAAGCTCACCGTGGACAAGAGCAGGTGGCAGCAGGGGAACGTCTT CTCATGCTCCGTGATGCATGAGGCTCTGCACAACCACTACACGCAGAAGA GCCTCTCCCTGTCTCCGGGTAAA | 225 |
| pETR11644 Mov19 LC | GACATCGAGCTGACCCAGAGCCCTGCCTCTCTGGCCGTGTCTCTGGGACA GAGAGCCATCATCAGCTGCAAGGCCAGCCAGAGCGTGTCCTTTGCCGGCA CCTCTCTGATGCACTGGTATCACCAGAAGCCCGGCCAGCAGCCCAAGCTG CTGATCTACAGAGCCAGCAACCTGGAAGCCGGCGTGCCCACAAGATTTTC CGGCAGCGGCAGCAAGACCGACTTCACCCTGAACATCCACCCCGTGGAAG AAGAGGACGCCGCCACCTACTACTGCCAGCAGAGCAGAGAGTACCCCTAC ACCTTCGGCGGAGGCACCAAGCTGGAAATCAAGCGTACGGTGGCTGCACC ATCTGTCTTCATCTTCCCGCCATCTGATGAGCAGTTGAAATCTGGAACTG CCTCTGTTGTGTGCCTGCTGAATAACTTCTATCCCAGAGAGGCCAAAGTA CAGTGGAAGGTGGATAACGCCCTCCAATCGGGTAACTCCCAGGAGAGTGT CACAGAGCAGGACAGCAAGGACAGCACCTACAGCCTCAGCAGCACCCTGA CGCTGAGCAAAGCAGACTACGAGAAACACAAAGTCTACGCCTGCGAAGTC ACCCATCAGGGCCTGAGCTCGCCCGTCACAAAGAGCTTCAACAGGGGAGA GTGT | 226 |
| Variant | | |
| 16D5 VH_D52dE | GAGGTGCAATTGGTTGAATCTGGTGGTGGTCTGGTAAAACCGGGCGGTTC CCTGCGTCTGAGCTGCGCGGCTTCCGGATTCACCTTCTCCAACGCGTGGA TGAGCTGGGTTCGCCAGGCCCCGGGCAAAGGCCTCGAGTGGGTTGGTCGT ATCAAGTCTAAAACTGAGGGTGGCACCACCGGATTACGCGGCTCCAGTTAA AGGTCGTTTTACCATTTCCCGCGACGATAGCAAAAACACTCTGTATCTGC AGATGAACTCTCTGAAAACTGAAGACACCGCAGTCTACTACTGTACTACC CCGTGGGAATGGTCTTGGTACGATTATTGGGGCCAGGGCACGCTGGTTAC GGTGTCTTCC | 261 |
| 16D5 VH_D52dQ | GAGGTGCAATTGGTTGAATCTGGTGGTGGTCTGGTAAAACCGGGCGGTTC CCTGCGTCTGAGCTGCGCGGCTTCCGGATTCACCTTCTCCAACGCGTGGA TGAGCTGGGTTCGCCAGGCCCCGGGCAAAGGCCTCGAGTGGGTTGGTCGT ATCAAGTCTAAAACTCAGGGTGGCACCACCGGATTACGCGGCTCCAGTTAA AGGTCGTTTTACCATTTCCCGCGACGATAGCAAAAACACTCTGTATCTGC | 262 |

8) Nucleotide sequences of exemplary embodiments

| | Sequence | Seq ID No |
|---|---|---|
| | AGATGAACTCTCTGAAAACTGAAGACACCGCAGTCTACTACTGTACTACC CCGTGGGAATGGTCTTGGTACGATTATTGGGGCCAGGGCACGCTGGTTAC GGTGTCTTCC | |
| CD3_VH N100A | GAGGTGCAGCTGCTGGAATCTGGCGGCGGACTGGTGCAGCCTGGCGGATC TCTGAGACTGAGCTGTGCCGCCAGCGGCTTCACCTTCAGCACCTACGCCA TGAACTGGGTGCGCCAGGCCCCTGGCAAAGGCCTGGAATGGGTGTCCCGG ATCAGAAGCAAGTACAACAACTACGCCACCTACTACGCCGACAGCGTGAA GGGCCGGTTCACCATCAGCCGGGACGACAGCAAGAACACCCTGTACCTGC AGATGAACAGCCTGCGGGCCGAGGACACCGCCGTGTACTATTGTGTGCGG CACGGCAACTTCGGCGCCAGCTATGTGTCTTGGTTTGCCTACTGGGGCCA GGGCACCCTCGTGACCGTGTCAAGC | 263 |
| CD3_VH S100aA | GAGGTGCAGCTGCTGGAATCTGGCGGCGGACTGGTGCAGCCTGGCGGATC TCTGAGACTGAGCTGTGCCGCCAGCGGCTTCACCTTCAGCACCTACGCCA TGAACTGGGTGCGCCAGGCCCCTGGCAAAGGCCTGGAATGGGTGTCCCGG ATCAGAAGCAAGTACAACAACTACGCCACCTACTACGCCGACAGCGTGAA GGGCCGGTTCACCATCAGCCGGGACGACAGCAAGAACACCCTGTACCTGC AGATGAACAGCCTGCGGGCCGAGGACACCGCCGTGTACTATTGTGTGCGG CACGGCAACTTCGGCAACGCCTATGTGTCTTGGTTTGCCTACTGGGGCCA GGGCACCCTCGTGACCGTGTCAAGC | 264 |
| 16D5 [VHCH1]- CD3[VHCH1- N100A]- Fcknob_PGLALA | GAGGTGCAATTGGTTGAATCTGGTGGTGGTCTGGTAAAACCGGGCGGTTC CCTGCGTCTGAGCTGCGCGGCTTCCGGATTCACCTTCTCCAACGCGTGGA TGAGCTGGGTTCGCCAGGCCCCGGGCAAAGGCCTCGAGTGGGTTGGTCGT ATCAAGTCTAAAACTGACGGTGGCACCACGGATTACGCGGCTCCAGTTAA AGGTCGTTTTACCATTTCCCGCGACGATAGCAAAAACACTCTGTATCTGC AGATGAACTCTCTGAAAACTGAAGACACCGCAGTCTACTACTGTACTACC CCGTGGGAATGGTCTTGGTACGATTATTGGGGCCAGGGCACGCTGGTTAC GGTGTCTTCCGCTAGCACAAAGGGCCCTAGCGTGTTCCCTCTGGCCCCCA GCAGCAAGAGCACAAGCGGCGGAACAGCCGCCCTGGGCTGCCTCGTGAAG GACTACTTCCCCGAGCCCGTGACAGTGTCTTGGAACAGCGGAGCCCTGAC AAGCGGCGTGCACACTTTCCCTGCCGTGCTGCAGAGCAGCGGCCTGTACT CCCTGAGCAGCGTGGTCACCGTGCCTAGCAGCAGCCTGGGCACCCAGACC TACATCTGCAACGTGAACCACAAGCCCAGCAACACCAAAGTGGACAAGAA GGTGGAGCCCAAGAGCTGTGATGGCGGAGGAGGGTCCGGAGGCGGAGGAT CCGAGGTGCAGCTGCTGGAATCTGGCGGCGGACTGGTGCAGCCTGGCGGA TCTCTGAGACTGAGCTGTGCCGCCAGCGGCTTCACCTTCAGCACCTACGC CATGAACTGGGTGCGCCAGGCCCCTGGCAAAGGCCTGGAATGGGTGTCCC GGATCAGAAGCAAGTACAACAACTACGCCACCTACTACGCCGACAGCGTG AAGGGCCGGTTCACCATCAGCCGGGACGACAGCAAGAACACCCTGTACCT GCAGATGAACAGCCTGCGGGCCGAGGACACCGCCGTGTACTATTGTGTGC GGCACGGCAACTTCGGCGCCAGCTATGTGTCTTGGTTTGCCTACTGGGGC CAGGGCACCCTCGTGACCGTGTCAAGCGCTAGTACCAAGGGCCCCAGCGT GTTCCCCCTGGCACCCAGCAGCAAGAGCACATCTGGCGGAACAGCCGCTC TGGGCTGTCTGGTGAAAGACTACTTCCCCGAGCCCGTGACCGTGTCTTGG AACTCTGGCGCCCTGACCAGCGGCGTGCACACCTTCCCAGCCGTGCTGCA GAGCAGCGGCCTGTACTCCCTGTCCTCCGTGGTCACCGTGCCCTCTAGCT CCCTGGGAACACAGACATATATCTGTAATGTCAATCACAAGCCTTCCAAC ACCAAAGTCGATAAGAAAGTCGAGCCCAAGAGCTGCGACAAAACTCACAC ATGCCCACCGTGCCCAGCACCTGAAGCTGCAGGGGGACCGTCAGTCTTCC TCTTCCCCCCAAAACCCAAGGACACCCTCATGATCTCCCGGACCCCTGAG GTCACATGCGTGGTGGTGGACGTGAGCCACGAAGACCCTGAGGTCAAGTT CAACTGGTACGTGGACGGCGTGGAGGTGCATAATGCCAAGACAAAGCCGC GGGAGGAGCAGTACAACAGCACGTACCGTGTGGTCAGCGTCCTCACCGTC CTGCACCAGGACTGGCTGAATGGCAAGGAGTACAAGTGCAAGGTCTCCAA CAAAGCCCTCGGCGCCCCCATCGAGAAAACCATCTCCAAAGCCAAAGGGC AGCCCCGAGAACCACAGGTGTACACCCTGCCCCCATGCCGGGATGAGCTG ACCAAGAACCAGGTCAGCCTGTGGTGCCTGGTCAAAGGCTTCTATCCCAG CGACATCGCCGTGGAGTGGGAGAGCAATGGGCAGCCGGAGAACAACTACA AGACCACGCCTCCCGTGCTGGACTCCGACGGCTCCTTCTTCCTCTACAGC AAGCTCACCGTGGACAAGAGCAGGTGGCAGCAGGGGAACGTCTTCTCATG CTCCGTGATGCATGAGGCTCTGCACAACCACTACACGCAGAAGAGCCTCT CCCTGTCTCCGGGTAAA | 265 |
| 16D5- Fchole- PGLALA | GAGGTGCAATTGGTTGAATCTGGTGGTGGTCTGGTAAAACCGGGCGGTTC CCTGCGTCTGAGCTGCGCGGCTTCCGGATTCACCTTCTCCAACGCGTGGA TGAGCTGGGTTCGCCAGGCCCCGGGCAAAGGCCTCGAGTGGGTTGGTCGT ATCAAGTCTAAAACTGACGGTGGCACCACGGATTACGCGGCTCCAGTTAA AGGTCGTTTTACCATTTCCCGCGACGATAGCAAAAACACTCTGTATCTGC AGATGAACTCTCTGAAAACTGAAGACACCGCAGTCTACTACTGTACTACC CCGTGGGAATGGTCTTGGTACGATTATTGGGGCCAGGGCACGCTGGTTAC GGTGTCTTCCGCTAGCACCAAGGGCCCCTCCGTGTTCCCCCTGGCCCCCA GCAGCAAGAGCACCAGCGGCGGCACAGCCGCTCTGGGCTGCCTGGTCAAG GACTACTTCCCCGAGCCCGTGACCGTGTCCTGGAACAGCGGAGCCCTGAC | 266 |

| | 8) Nucleotide sequences of exemplary embodiments | |
|---|---|---|
| | Sequence | Seq ID No |
| | CTCCGGCGTGCACACCTTCCCCGCCGTGCTGCAGAGTTCTGGCCTGTATA<br>GCCTGAGCAGCGTGGTCACCGTGCCTTCTAGCAGCCTGGGCACCCAGACC<br>TACATCTGCAACGTGAACCACAAGCCCAGCAACACCAAGGTGGACAAGAA<br>GGTGGAGCCCAAGAGCTGCGACAAAACTCACACATGCCCACCGTGCCCAG<br>CACCTGAAGCTGCAGGGGGACCGTCAGTCTTCCTCTTCCCCCCAAAACCC<br>AAGGACACCCTCATGATCTCCCGGACCCCTGAGGTCACATGCGTGGTGGT<br>GGACGTGAGCCACGAAGACCCTGAGGTCAAGTTCAACTGGTACGTGGACG<br>GCGTGGAGGTGCATAATGCCAAGACAAAGCCGCGGGAGGAGCAGTACAAC<br>AGCACGTACCGTGTGGTCAGCGTCCTCACCGTCCTGCACCAGGACTGGCT<br>GAATGGCAAGGAGTACAAGTGCAAGGTCTCCAACAAAGCCCTCGGCGCCC<br>CCATCGAGAAACCATCTCCAAAGCCAAAGGGCAGCCCCGAGAACCACAG<br>GTGTGCACCCTGCCCCCATCCCGGGATGAGCTGACCAAGAACCAGGTCAG<br>CCTCTCGTGCGCAGTCAAAGGCTTCTATCCCAGCGACATCGCCGTGGAGT<br>GGGAGAGCAATGGGCAGCCGGAGAACAACTACAAGACCACGCCTCCCGTG<br>CTGGACTCCGACGGCTCCTTCTTCCTCGTGAGCAAGCTCACCGTGGACAA<br>GAGCAGGTGGCAGCAGGGGAACGTCTTCTCATGCTCCGTGATGCATGAGG<br>CTCTGCACAACCGCTTCACGCAGAAGAGCCTCTCCCTGTCTCCGGGTAAA | |
| CD3-CLC | CAGGCCGTCGTGACCCAGGAACCCAGCCTGACAGTGTCTCCTGGCGGCAC<br>CGTGACCCTGACATGTGGCAGTTCTACAGGCGCCGTGACCACCAGCAACT<br>ACGCCAACTGGGTGCAGGAAAAGCCCGGCCAGGCCTTCAGAGGACTGATC<br>GGCGGCACCAACAAGAGAGCCCCTGGCACCCCTGCCAGATTCAGCGGATC<br>TCTGCTGGGAGGAAAGGCCGCCCTGACACTGTCTGGCGCCCAGCCAGAAG<br>ATGAGGCCGAGTACTACTGCGCCCTGTGGTACAGCAACCTGTGGGTGTTC<br>GGCGGAGGCACCAAGCTGACAGTCCTAGGTCAACCCAAGGCTGCCCCCAG<br>CGTGACCCTGTTCCCCCCCAGCAGCGAGGAACTGCAGGCCAACAAGGCCA<br>CCCTGGTCTGCCTGATCAGCGACTTCTACCCAGGCGCCGTGACCGTGGCC<br>TGGAAGGCCGACAGCAGCCCCGTGAAGGCCGGCGTGGAGACCACCACCCC<br>CAGCAAGCAGAGCAACAACAAGTACGCCGCCAGCAGCTACCTGAGCCTGA<br>CCCCCGAGCAGTGGAAGAGCCACAGGTCCTACAGCTGCCAGGTGACCCAC<br>GAGGGGCAGCACCGTGGAGAAAACCGTGGCCCCCACCGAGTGCAGC | 267 |
| 16D5<br>[VHCH1]-<br>CD3[VHCH1-<br>S100aA]-<br>Fcknob_PGLALA | GAGGTGCAATTGGTTGAATCTGGTGGTGGTCTGGTAAAACCGGGCGGTTC<br>CCTGCGTCTGAGCTGCGCGGCTTCCGGATTCACCTTCTCCAACGCGTGGA<br>TGAGCTGGGTTCGCCAGGCCCCGGGCAAAGGCCTCGAGTGGGTTGGTCGT<br>ATCAAGTCTAAAACTGACGGTGGCACCACGGATTACGCGGCTCCAGTTAA<br>AGGTCGTTTTACCATTTCCCGCGACGATAGCAAAAACACTCTGTATCTGC<br>AGATGAACCTCTCTGAAAACTGAAGACACCGCAGTCTACTACTGTACTACC<br>CCGTGGGAATGGTCTTGGTACGATTATTGGGGCCAGGGCACGCTGGTTAC<br>GGTGTCTTCGCTAGCACAAAGGGCCCTAGCGTGTTCCCTCTGGCCCCCA<br>GCAGCAAGAGCACAAGCGGCGGAACAGCCGCCCTGGGCTGCCTCGTGAAG<br>GACTACTTCCCCGAGCCCGTGACAGTGTCTTGGAACAGCGGAGCCCTGAC<br>AAGCGGCGTGCACACTTTCCCTGCCGTGCTGCAGAGCAGCGGCCTGTACT<br>CCCTGAGCAGCGTGGTCACCGTGCCTAGCAGCAGCCTGGGCACCCAGACC<br>TACATCTGCAACGTGAACCACAAGCCCAGCAACACCAAGGTGGACAAGAA<br>GGTGGAGCCCAAGAGCTGTGATGGCGGAGGAGGGTCCGGAGGCGGAGGAT<br>CCGAGGTGCAGCTGCTGGAATCTGGCGGCGGACTGGTGCAGCCTGGCGGA<br>TCTCTGAGACTGAGCTGTGCCGCCAGCGGCTTCACCTTCAGCACCTACGC<br>CATGAACTGGGTGCGCCAGGCCCCTGGCAAAGGCCTGGAATGGGTGTCCC<br>GGATCAGAAGCAAGTACAACAACTACGCCACCTACTACGCCGACAGCGTG<br>AAGGGCCGGTTCACCATCAGCCGGGACGACAGCAAGAACACCCTGTACCT<br>GCAGATGAACAGCCTGCGGGCCGAGGACACCGCCGTGTACTATTGTGTGC<br>GGCACGGCAACTTCGGCAACGCCTATGTGTCTTGGTTTGCCTACTGGGGC<br>CAGGGCACCCTCGTGACCGTGTCAAGCGCTAGTACCAAGGGCCCCAGCGT<br>GTTCCCCCTGGCACCCAGCAGCAAGAGCACATCGGCGGAACAGCCGCTC<br>TGGGCTGTCTGGTGAAAGACTACTTCCCCGAGCCCGTGACCGTGTCTTGG<br>AACTCTGGCGCCCTGACCAGCGGCGTGCACACCTTTCCAGCCGTGCTGCA<br>GAGCAGCGGCCTGTACTCCCTGTCCTCCGTGGTCACCGTGCCCTCTAGCT<br>CCCTGGGAACACAGACATATATCTGTAATGTCAATCACAAGCCCTTCCAAC<br>ACCAAAGTCGATAAGAAAGTCGAGCCCAAGAGCTGCGACAAAACTCACAC<br>ATGCCCACCGTGCCCAGCACCTGAAGCTGCAGGGGGACCGTCAGTCTTCC<br>TCTTCCCCCCAAAACCCAAGGACACCCTCATGATCTCCCGGACCCCTGAG<br>GTCACATGCGTGGTGGTGGACGTGAGCCACGAAGACCCTGAGGTCAAGTT<br>CAACTGGTACGTGGACGGCGTGGAGGTGCATAATGCCAAGACAAAGCCGC<br>GGGAGGAGCAGTACAACAGCACGTACCGTGTGGTCAGCGTCCTCACCGTC<br>CTGCACCAGGACTGGCTGAATGGCAAGGAGTACAAGTGCAAGGTCTCCAA<br>CAAAGCCCTCGGCGCCCCCATCGAGAAACCATCTCCAAAGCCAAAGGGC<br>AGCCCCGAGAACCACAGGTGTACACCCTGCCCCCATGCGGGATGAGCTG<br>ACCAAGAACCAGGTCAGCCTGTGGTGCCTGGTCAAAGGCTTCTATCCCAG<br>CGACATCGCCGTGGAGTGGGAGAGCAATGGGCAGCCGGAGAACAACTACA<br>AGACCACGCCTCCCGTGCTGGACTCCGACGGCTCCTTCTTCCTCTACAGC<br>AAGCTCACCGTGGACAAGAGCAGGTGGCAGCAGGGGAACGTCTTCTCATG<br>CTCCGTGATGCATGAGGCTCTGCACAACCACTACACGCAGAAGAGCCTCT<br>CCCTGTCTCCGGGTAAA | 268 |

-continued

8) Nucleotide sequences of exemplary embodiments

| | Sequence | Seq ID No |
|---|---|---|
| 9D11<br>[VHCH1]-<br>CD3[VHCL-<br>N100A]-<br>Fcknob_PGLALA | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCCCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCGGTGAC<br>TTCGCTTGGCTGGACTATTGGGGTCAAGGCACCCTCGTAACGGTTTCTTC<br>TGCTAGCACAAAGGGCCCCAGCGTGTTCCCTCTGGCCCCTAGCAGCAAGA<br>GCACATCTGGCGGAACAGCCGCCCTGGGCTGCCTCGTGAAGGACTACTTT<br>CCCGAGCCTGTGACCGTGTCCTGGAACTCTGGCGCCCTGACAAGCGGCGT<br>GCACACCTTTCCAGCCGTGCTGCAGAGCAGCGGCCTGTACTCTCTGAGCA<br>GCGTGGTCACCGTGCCTAGCAGCAGCCTGGGCACCCAGACCTACATCTGC<br>AACGTGAACCACAAGCCCAGCAACACCAAAGTGGACAAGAAGGTGGAGCC<br>CAAGAGCTGTGATGGCGGAGGAGGGTCCGGAGGCGGAGGATCCGAGGTGC<br>AGCTGCTGGAATCTGGCGGCGGACTGGTGCAGCCTGGCGGATCTCTGAGA<br>CTGAGCTGTGCCGCCAGCGGCTTCACCTTCAGCACCTACGCCATGAACTG<br>GGTGCGCCAGGCCCCTGGCAAAGGCCTGGAATGGGTGTCCCGGATCAGAA<br>GCAAGTACAACAACTACGCCACCTACTACGCCGACAGCGTGAAGGGCCGG<br>TTCACCATCAGCCGGGACGACAGCAAGAACACCCTGTACCTGCAGATGAA<br>CAGCCTGCGGGCCGAGGACACCGCCGTGTACTATTGTGTGCGGCACGGCA<br>ACTTCGGCGCCAGCTATGTGTCTTGGTTTGCCTACTGGGGCCAGGGCACC<br>CTCGTGACCGTGTCAAGCGCTAGTGTGGCCGCTCCCTCCGTGTTTATCTT<br>TCCCCCATCCGATGAACAGCTGAAAAGCGGCACCGCCTCCGTCGTGTGTC<br>TGCTGAACAATTTTTACCCTAGGGAAGCTAAAGTGCAGTGGAAAGTGGAT<br>AACGCACTGCAGTCCGGCAACTCCCAGGAATCTGTGACAGAACAGGACTC<br>CAAGGACAGCACCTACTCCCTGTCCTCCACCCTGACACTGTCTAAGGCTG<br>ATTATGAGAAACACAAAGTCTACGCCTGCGAAGTCACCCATCAGGGCCTG<br>AGCTCGCCCGTCACAAAGAGCTTCAACAGGGGAGAGTGTGACAAGACCCA<br>CACCTGTCCCCCTTGTCCTGCCCCTGAAGCTGCTGGCGGCCCTTCTGTGT<br>TCCTGTTCCCCCCAAAGCCCAAGGACACCCTGATGATCAGCCGGACCCCC<br>GAAGTGACCTGCGTGGTGGTGGATGTGTCCCACGAGGACCCTGAAGTGAA<br>GTTCAATTGGTACGTGGACGGCGTGGAAGTGCACAACGCCAAGACAAAGC<br>CGCGGGAGGAGCAGTACAACAGCACGTACCGTGTGGTCAGCGTCCTCACC<br>GTCCTGCACCAGGACTGGCTGAATGGCAAGGAGTACAAGTGCAAGGTCTC<br>CAACAAAGCCCTCGGCGCCCCCATCGAGAAAACCATCTCCAAAGCCAAAG<br>GGCAGCCCCGAGAACCACAGGTGTACACCCTGCCCCCATGCCGGGATGAG<br>CTGACCAAGAACCAGGTCAGCCTGTGGTGCCTGGTCAAAGGCTTCTATCC<br>CAGCGACATCGCCGTGGAGTGGGAGAGCAATGGGCAGCCGGAGAACAACT<br>ACAAGACCACGCCTCCCGTGCTGGACTCCGACGGCTCCTTCTTCCTCTAC<br>AGCAAGCTCACCGTGGACAAGAGCAGGTGGCAGCAGGGGAACGTCTTCTC<br>ATGCTCCGTGATGCATGAGGCTCTGCACAACCACTACACGCAGAAGAGCC<br>TCTCCCTGTCTCCGGGTAAA | 269 |
| 9D11-<br>Fchole | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCCCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCGGTGAC<br>TTCGCTTGGCTGGACTATTGGGGTCAAGGCACCCTCGTAACGGTTTCTTC<br>TGCTAGCACCAAGGGCCCCTCCGTGTTCCCCCTGGCCCCCAGCAGCAAGA<br>GCACCAGCGGCGGCACAGCCGCTCTGGGCTGCCTGGTCAAGGACTACTTC<br>CCCGAGCCCGTGACCGTGTCCTGGAACAGCGGAGCCCTGACCTCCGGCGT<br>GCACACCTTCCCCGCCGTGCTGCAGAGTTCTGGCCTGTATAGCCTGAGCA<br>GCGTGGTCACCGTGCCTTCTAGCAGCCTGGGCACCCAGACCTACATCTGC<br>AACGTGAACCACAAGCCCAGCAACACCAAGGTGGACAAGAAGGTGGAGCC<br>CAAGAGCTGCGACAAAACTCACACATGCCCACCGTGCCCAGCACCTGAAG<br>CTGCAGGGGACCGTCAGTCTTCCTCTTCCCCCCAAAACCCAAGGACACC<br>CTCATGATCTCCCGGACCCCTGAGGTCACATGCGTGGTGGTGGACGTGAG<br>CCACGAAGACCCTGAGGTCAAGTTCAACTGGTACGTGGACGGCGTGGAGG<br>TGCATAATGCCAAGACAAAGCCGCGGGAGGAGCAGTACAACAGCACGTAC<br>CGTGTGGTCAGCGTCCTCACCGTCCTGCACCAGGACTGGCTGAATGGCAA<br>GGAGTACAAGTGCAAGGTCTCCAACAAAGCCCTCGGCGCCCCCATCGAGA<br>AAACCATCTCCAAAGCCAAAGGGCAGCCCCGAGAACCACAGGTGTGCACC<br>CTGCCCCCATCCCGGGATGAGCTGACCAAGAACCAGGTCAGCCTCTCGTG<br>CGCAGTCAAAGGCTTCTATCCCAGCGACATCGCCGTGGAGTGGGAGAGCA<br>ATGGGCAGCCGGAGAACAACTACAAGACCACGCCTCCCGTGCTGGACTCC<br>GACGGCTCCTTCTTCCTCGTGAGCAAGCTCACCGTGGACAAGAGCAGGTG<br>GCAGCAGGGGAACGTCTTCTCATGCTCCGTGATGCATGAGGCTCTGCACA<br>ACCACTACACGCAGAAGAGCCTCTCCCTGTCTCCGGGTAAA | 270 |
| 9D11_LC<br>[N95Q] | GATATTGTTATGACTCAATCTCCACTGTCTCTGCCGGTGACTCCAGGCGA<br>ACCGGCGAGCATTTCTTGCCGTTCCAGCCAGTCTCTGCTGCACTCCAACG<br>GCTACAACTATCTCGATTGGTACCTGCAAAAACCGGGTCAGAGCCCTCAG<br>CTGCTGATCTACCTGGGCTCTAACCGCGCTTCCGGTGTACCGGACCGTTT | 271 |

| | 8) Nucleotide sequences of exemplary embodiments | |
|---|---|---|
| | Sequence | Seq ID No |
| | CAGCGGCTCTGGATCCGGCACCGATTTCACGTTGAAAATCAGCCGTGTTG<br>AAGCAGAAGACGTGGGCGTTTATTACTGTATGCAGGCAAGCATTATGCAG<br>CGGACTTTTGGTCAAGGCACCAAGGTCGAAATTAAACGTACGGTGGCTGC<br>ACCATCTGTCTTCATCTTCCCGCCATCTGATGAGCAGTTGAAATCTGGAA<br>CTGCCTCTGTTGTGTGCCTGCTGAATAACTTCTATCCCAGAGAGGCCAAA<br>GTACAGTGGAAGGTGGATAACGCCCTCCAATCGGGTAACTCCCAGGAGAG<br>TGTCACAGAGCAGGACAGCAAGGACAGCACCTACAGCCTCAGCAGCACCC<br>TGACGCTGAGCAAAGCAGACTACGAGAAACACAAAGTCTACGCCTGCGAA<br>GTCACCCATCAGGGCCTGAGCTCGCCCGTCACAAAGAGCTTCAACAGGGG<br>AGAGTGT | |
| CD3_VLCH1 | CAGGCCGTCGTGACCCAGGAACCCAGCCTGACAGTGTCTCCTGGCGGCAC<br>CGTGACCCTGACATGTGGCAGTTCTACAGGCGCCGTGACCACCAGCAACT<br>ACGCCAACTGGGTGCAGGAAAAGCCCGGCCAGGCCTTCAGAGGACTGATC<br>GGCGGCACCAACAAGAGAGCCCCTGGCACCCCTGCCAGATTCAGCGGATC<br>TCTGCTGGGAGGAAAGGCCGCCCTGACACTGTCTGGCGCCCAGCCAGAAG<br>ATGAGGCCGAGTACTACTGCGCCCTGTGGTACAGCAACCTGTGGGTGTTC<br>GGCGGAGGCACCAAGCTGACAGTGCTGAGCAGCGCTTCCACCAAAGGCCC<br>TTCCGTGTTTCCTCTGGCTCCTAGCTCCAAGTCCACCTCTGGAGGCACCG<br>CTGCTCTCGGATGCCTCGTGAAGGATTATTTTCCTGAGCCTGTGACAGTG<br>TCCTGGAATAGCGGAGCACTGACCTCTGGAGTGCATACTTTCCCCGCTGT<br>GCTGCAGTCCTCTGGACTGTACAGCCTGAGCAGCGTGGTGACAGTGCCCA<br>GCAGCAGCCTGGGCACCCAGACCTACATCTGCAACGTGAACCACAAGCCC<br>AGCAACACCAAGGTGGACAAGAAGGTGGAACCCAAGTCTTGT | 272 |
| 9D11<br>[VHCH1]-<br>CD3[VHCH1-<br>S100aA]-<br>Fcknob_PGLALA | CAGGTGCAATTGGTTCAATCTGGTGCTGAAGTAAAAAAACCGGGCGCTTC<br>CGTTAAAGTGAGCTGCAAAGCATCCGGATACACCTTCACTTCCTATTACA<br>TGCACTGGGTTCGTCAAGCCCCGGGCCAGGGTCTGGAATGGATGGGCATC<br>ATTAACCCAAGCGGTGGCCCTACCTCCTACGCGCAGAAATTCCAGGGTCG<br>CGTCACGATGACCCGTGACACTAGCACCTCTACCGTTTATATGGAGCTGT<br>CCAGCCTGCGTTCTGAAGATACTGCAGTGTACTACTGTGCACGCGGTGAC<br>TTCGCTTGGCTGGACTATTGGGGTCAAGGCACCCTCGTAACGGTTTCTTC<br>TGCTAGCACAAAGGGCCCCAGCGTGTTCCCTCTGGCCCCTAGCAGCAAGA<br>GCACATCTGGCGGAACAGCCGCCCTGGGCTGCCTCGTGAAGGACTACTTT<br>CCCGAGCCTGTGACCGTGTCCTGGAACTCTGGCGCCCTGACAAGCGGCGT<br>GCACACCTTTCCAGCCGTGCTGCAGAGCAGCGGCCTGTACTCTCTGAGCA<br>GCGTGGTCACCGTGCCTAGCAGCAGCCTGGGCACCCAGACCTACATCTGC<br>AACGTGAACCACAAGCCCAGCAACACCAAAGTGGACAAGAAGGTGGAGCC<br>CAAGAGCTGTGATGGCGGAGGAGGGTCCGGAGGCGGAGGATCCGAGGTGC<br>AGCTGCTGGAATCTGGCGGCGGACTGGTGCAGCCTGGCGGATCTCTGAGA<br>CTGAGCTGTGCCGCCAGCGGCTTCACCTTCAGCACCTACGCCATGAACTG<br>GGTGCGCCAGGCCCCTGGCAAAGGCCTGGAATGGGTGTCCCGGATCAGAA<br>GCAAGTACAACAACTACGCCACCTACTACGCCGACAGCGTGAAGGGCCGG<br>TTCACCATCAGCCGGGACGACAGCAAGAACACCCTGTACCTGCAGATGAA<br>CAGCCTGCGGGCCGAGGACACCGCCGTGTACTATTGTGTGCGGCACGGCA<br>ACTTCGGCAACGCCTATGTGTCTTGGTTTGCCTACTGGGGCCAGGGCACC<br>CTCGTGACCGTGTCAAGCGCTAGTGTGGCCGCTCCCTCCGTGTTTATCTT<br>TCCCCCATCCGATGAACAGCTGAAAAGCGGCACCGCCTCCGTCGTGTGTC<br>TGCTGAACAATTTTTACCCTAGGGAAGCTAAAGTGCAGTGGAAAGTGGAT<br>AACGCACTGCAGTCCGGCAACTCCCAGGAATCTGTGACAGAACAGGACTC<br>CAAGGACAGCACCTACTCCCTGTCCTCCACCCTGACACTGTCTAAGGCTG<br>ATTATGAGAAACACAAAGTCTACGCCTGCGAAGTCACCCATCAGGGCCTG<br>AGCTCGCCCGTCACAAAGAGCTTCAACAGGGGAGAGTGTGACAAGACCCA<br>CACCTGTCCCCCTTGTCCTGCCCCTGAAGCTGCTGGCGGCCCTTCTGTGT | 273 |

| 8) Nucleotide sequences of exemplary embodiments | |
| --- | --- |
| Sequence | Seq ID No |
| TCCTGTTCCCCCCAAAGCCCAAGGACACCCTGATGATCAGCCGGACCCCC GAAGTGACCTGCGTGGTGGTGGATGTGTCCCACGAGGACCCTGAAGTGAA GTTCAATTGGTACGTGGACGGCGTGGAAGTGCACAACGCCAAGACAAAGC CGCGGGAGGAGCAGTACAACAGCACGTACCGTGTGGTCAGCGTCCTCACC GTCCTGCACCAGGACTGGCTGAATGGCAAGGAGTACAAGTGCAAGGTCTC CAACAAAGCCCTCGGCGCCCCCATCGAGAAAACCATCTCCAAAGCCAAAG GGCAGCCCCGAGAACCACAGGTGTACACCCTGCCCCCATGCCGGGATGAG CTGACCAAGAACCAGGTCAGCCTGTGGTGCCTGGTCAAAGGCTTCTATCC CAGCGACATCGCCGTGGAGTGGGAGAGCAATGGGCAGCCGGAGAACAACT ACAAGACCACGCCTCCCGTGCTGGACTCCGACGGCTCCTTCTTCCTCTAC AGCAAGCTCACCGTGGACAAGAGCAGGTGGCAGCAGGGGAACGTCTTCTC ATGCTCCGTGATGCATGAGGCTCTGCACAACCACTACACGCAGAAGAGCC TCTCCCTGTCTCCGGGTAAA | |

| 9) Additonal Common Light Chain Protein and Nucleotide Sequences | | |
| --- | --- | --- |
| CH2527 (VL_7-46(13)/VH_3-23(12)) | | SEQ ID NO. |
| Heavy chain "CH2527 (VH_3-23(12))" | EVQLLESGGGLVQPGGSLRLSCAASGFTFSTYAMNWVRQAPGK GLEWVSRIRSKYNNYATYYADSVKGRFTISRDDSKNTLYLQMN SLRAEDTAVYYCVRHGNFGNSYVSWFAYWGQGTLVTVSSASTK GPSVFPLAPSSKSTSGGTAALGCLVKDYFPEPVTVSWNSGALT SGVHTFPAVLQSSGLYSLSSVVTVPSSSLGTQTYICNVNHKPS NTKVDKKVEPKSCDKTHTCPPCPAPELLGGPSVFLFPPKPKDT LMISRTPEVTCVVVDVSHEDPEVKFNWYVDGVEVHNAKTKPRE EQYNSTYRVVSVLTVLHQDWLNGKEYKCKVSNKALPAPIEKTI SKAKGQPREPQVYTLPPSRDELTKNQVSLTCLVKGFYPSDIAV EWESNGQPENNYKTTPPVLDSDGSFFLYSKLTVDKSRWQQGNV FSCSVMHEALHNHYTQKSLSLSPGK | 123 |
| Light chain "CH2527 (VL_7-46(13))" | QTVVTQEPSLTVSPGGTVTLTCGSSTGAVTTSNYANWVQEKPG QAFRGLIGGTNKRAPGTPARFSGSLLGGKAALTLSGAQPEDEA EYYCALWYSNLWVFGGGTKLTVLGQPKAAPSVTLFPPSSEELQ ANKATLVCLISDFYPGAVTVAWKADSSPVKAGVETTTPSKQSN NKYAASSYLSLTPEQWKSHRSYSCQVTHEGSTVEKTVAPTECS | 124 |
| VH "CH2527 (VH_3-23(12))" | EVQLLESGGGLVQPGGSLRLSCAASGFTFSTYAMNWVRQAPGK GLEWVSRIRSKYNNYATYYADSVKGRFTISRDDSKNTLYLQMN SLRAEDTAVYYCVRHGNFGNSYVSWFAYWGQGTLVTVSS | 36 |
| VH CDR H1 "CH2527 (VH_3-23(12))" | TYAMN | 37 |
| VH CDR H2 "CH2527 (VH_3-23(12))" | RIRSKYNNYATYYADSVKG | 38 |
| VH CDR H3 "CH2527 (VH_3-23(12))" | HGNFGNSYVSWFAY | 39 |
| VL "CH2527 (VL_7-46(13))" | QTVVTQEPSLTVSPGGTVTLTCGSSTGAVTTSNYANWVQEKPG QAFRGLIGGTNKRAPGTPARFSGSLLGGKAALTLSGAQPEDEA EYYCALWYSNLWVFGGGTKLTVL | 125 |
| VL CDR L1 "CH2527 (VL_7-46(13))" | GSSTGAVTTSNYAN | 32 |
| VL CDR L2 "CH2527 (VL_7-46(13))" | GTNKRAP | 33 |
| VL CDR L3 "CH2527 (VL_7-46(13))" | ALWYSNLWV | 34 |

| 10) DNA sequences humanized CD3_CH2527 (CDR/VH/VL) | | |
|---|---|---|
| CH2527 (VL_7-46(13)/VH_3-23(12)) | | SEQ ID NO. |
| Heavy chain "CH2527 (VH_3-23(12))" | ATGGGATGGAGCTGTATCATCCTCTTCTTGGTAGCAACA GCTACCGGTGTGCATTCCGAGGTGCAGCTGCTGGAATCT GGCGGCGGACTGGTGCAGCCTGGCGGATCTCTGAGACTG AGCTGTGCCGCCAGCGGCTTCACCTTCAGCACCTACGCC ATGAACTGGGTGCGCCAGGCCCCTGGCAAAGGCCTGGAA TGGGTGTCCCGGATCAGAAGCAAGTACAACAACTACGCC ACCTACTACGCCGACAGCGTGAAGGGCCGGTTCACCATC AGCCGGGACGACAGCAAGAACACCCTGTACCTGCAGATG AACAGCCTGCGGGCCGAGGACACCGCCGTGTACTATTGT GTGCGGCACGGCAACTTCGGCAACAGCTATGTGTCTTGG TTTGCCTACTGGGGCCAGGGCACCCTCGTGACCGTGTCA TCTGCTAGCACCAAGGGCCCATCGGTCTTCCCCCTGGCA CCCTCCTCCAAGAGCACCTCTGGGGGCACAGCGGCCCTG GGCTGCCTGGTCAAGGACTACTTCCCCGAACCGGTGACG GTGTCGTGGAACTCAGGCGCCCTGACCAGCGGCGTGCAC ACCTTCCCGGCTGTCCTACAGTCCTCAGGACTCTACTCC CTCAGCAGCGTGGTGACCGTGCCCTCCAGCAGCTTGGGC ACCCAGACCTACATCTGCAACGTGAATCACAAGCCCAGC AACACCAAGGTGGAGAAGAAAGTTGAGCCCAAATCTTGT GACAAAACTCACACATGCCCACCGTGCCCAGCACCTGAA CTCCTGGGGGGACCGTCAGTCTTCCTCTTCCCCCCAAAA CCCAAGGACACCCTCATGATCTCCCGGACCCCTGAGGTC ACATGCGTGGTGGTGGACGTGAGCCACGAAGACCCTGAG GTCAAGTTCAACTGGTACGTGGACGGCGTGGAGGTGCAT AATGCCAAGACAAAGCCGCGGGAGGAGCAGTACAACAGC ACGTACCGTGTGGTCAGCGTCCTCACCGTCCTGCACCAG GACTGGCTGAATGGCAAGGAGTACAAGTGCAAGGTCTCC AACAAAGCCCTCCCAGCCCCCATCGAGAAAACCATCTCC AAAGCCAAAGGGCAGCCCCGAGAACCACAGGTGTACACC CTGCCCCCATCCCGGGATGAGCTGACCAAGAACCAGGTC AGCCTGACCTGCCTGGTCAAAGGCTTCTATCCCAGCGAC ATCGCCGTGGAGTGGGAGAGCAATGGGCAGCCGGAGAAC AACTACAAGACCACGCCTCCCGTGCTGGACTCCGACGGC TCCTTCTTCCTCTACAGCAAGCTCACCGTGGACAAGAGC AGGTGGCAGCAGGGGAACGTCTTCTCATGCTCCGTGATG CATGAGGCTCTGCACAACCACTACACGCAGAAGAGCCTC TCCCTGTCTCCGGGTAAATGA | 126 |
| Light chain "CH2527 (VL_7-46(13))" | ATGGGATGGAGCTGTATCATCCTCTTCTTGGTAGCAACA GCTACCGGTGTGCATTCTCAGGCCGTCGTGACCCAGGAA CCCAGCCTGACAGTGTCTCCTGGCGGCACCGTGACCCTG ACATGTGGCAGTTCTACAGGCGCCGTGACCACCAGCAAC TACGCCAACTGGGTGCAGGAAAAGCCCGGCCAGGCCTTC AGAGGACTGATCGGCGGCACCAACAAGAGAGCCCCTGGC ACCCCTGCCAGATTCAGCGGATCTCTGCTGGGAGGAAAG GCCGCCCTGACACTGTCTGGCGCCCAGCCAGAAGATGAG GCCGAGTACTACTGCGCCCTGTGGTACAGCAACCTGTGG GTGTTCGGCGGAGGCACCAAGCTGACAGTCCTAGGTCAA CCCAAGGCTGCCCCCAGCGTGACCCTGTTCCCCCCCAGC AGCGAGGAACTGCAGGCCAACAAGGCCACCCTGGTCTGC CTGATCAGCGACTTCTACCCAGGCGCCGTGACCGTGGCC TGGAAGGCCGACAGCAGCCCCGTGAAGGCCGGCGTGGAG ACCACCACCCCCAGCAAGCAGAGCAACAACAAGTACGCC GCCAGCAGCTACCTGAGCCTGACCCCCGAGCAGTGGAAG AGCCACAGGTCCTACAGCTGCCAGGTGACCCACGAGGGC AGCACCGTGGAGAAAACCGTGGCCCCCACCGAGTGCAGC TGA | 127 |
| VH "CH2527 (VH_3-23(12))" | ATGGGATGGAGCTGTATCATCCTCTTCTTGGTAGCAACA GCTACCGGTGTGCATTCCGAGGTGCAGCTGCTGGAATCT GGCGGCGGACTGGTGCAGCCTGGCGGATCTCTGAGACTG AGCTGTGCCGCCAGCGGCTTCACCTTCAGCACCTACGCC ATGAACTGGGTGCGCCAGGCCCCTGGCAAAGGCCTGGAA TGGGTGTCCCGGATCAGAAGCAAGTACAACAACTACGCC ACCTACTACGCCGACAGCGTGAAGGGCCGGTTCACCATC AGCCGGGACGACAGCAAGAACACCCTGTACCTGCAGATG AACAGCCTGCGGGCCGAGGACACCGCCGTGTACTATTGT GTGCGGCACGGCAACTTCGGCAACAGCTATGTGTCTTGG TTTGCCTACTGGGGCCAGGGCACCCTCGTGACCGTGTCA TCT | 128 |
| VH CDR H1 "CH2527 (VH_3-23(12))" | ACCTACGCCATGAAC | 129 |
| VH CDR H2 "CH2527 (VH_3-23(12))" | CGGATCAGAAGCAAGTACAACAACTACGCCACCTACTAC GCCGACAGCGTGAAGGGC | 130 |

| 10) DNA sequences humanized CD3$_{CH2527}$ (CDR/VH/VL) | | |
|---|---|---|
| CH2527 (VL_7-46(13)/VH_3-23(12)) | | SEQ ID NO. |
| VH CDR H3 "CH2527 (VH_3-23(12))" | CACGGCAACTTCGGCAACAGCTATGTGTCTTGGTTTGCC TAC | 131 |
| VL "CH2527 (VL_7-46(13))" | ATGGGATGGAGCTGTATCATCCTCTTCTTGGTAGCAACA GCTACCGGTGTGCATTCTCAGGCCGTCGTGACCCAGGAA CCCAGCCTGACAGTGTCTCCTGGCGGCACCGTGACCCTG ACATGTGGCAGTTCTACAGGCGCCGTGACCACCAGCAAC TACGCCAACTGGGTGCAGGAAAAGCCCGGCCAGGCCTTC AGAGGACTGATCGGCGGCACCAACAAGAGAGCCCCTGGC ACCCCTGCCAGATTCAGCGGATCTCTGCTGGGAGGAAAG GCCGCCCTGACACTGTCTGGCGCCCAGCCAGAAGATGAG GCCGAGTACTACTGCGCCCTGTGGTACAGCAACCTGTGG GTGTTCGGCGGAGGCACCAAGCTGACAGTCCTA | 132 |
| VL CDR L1 "CH2527 (VL_7-46(13))" | GGCAGTTCTACAGGCGCCGTGACCACCAGCAACTACGCC AAC | 133 |
| VL CDR L2 "CH2527 (VL_7-46(13))" | GGCACCAACAAGAGAGCCCCT | 134 |
| VL CDR L3 "CH2527 (VL_7-46(13))" | GCCCTGTGGTACAGCAACCTGTGGGTG | 135 |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A T cell activating bispecific antigen binding molecule comprising a first antigen binding moiety that binds to CD3 and a second antigen binding moiety that binds to Folate Receptor 1 (FolR1),
wherein the second antigen binding moiety comprises the heavy chain variable domain (VH) sequence of antibody 9D11 encoded by the sequence of SEQ ID NO: 171 and the light chain variable domain (VL) sequence of antibody 9D11 encoded by the sequence of SEQ ID NO: 172.

2. The T cell activating bispecific antigen binding molecule of claim 1, wherein the first antigen binding moiety is a Fab and/or wherein the second antigen binding moiety is a Fab.

3. The T cell activating bispecific antigen binding molecule of claim 1, further comprising a third antigen binding moiety that binds to FolR1.

4. The T cell activating bispecific antigen binding molecule of claim 3, wherein the third antigen binding moiety is a Fab, and wherein the third antigen binding moiety is fused at the C-terminus of the Fab heavy chain to the N-terminus of the first or second subunit of the Fc domain.

5. The T cell activating bispecific antigen binding molecule of claim 1, wherein the first and the second antigen binding moiety are fused to each other via a peptide linker.

6. The T cell activating bispecific antigen binding molecule of claim 1, wherein the first and second antigen binding moieties are Fabs, and wherein:
(a) the second antigen binding moiety is fused at the C-terminus of the Fab heavy chain to the N-terminus of the Fab heavy chain of the first antigen binding moiety; or
(b) the first antigen binding moiety is fused at the C-terminus of the Fab heavy chain to the N-terminus of the Fab heavy chain of the second antigen binding moiety.

7. The T cell activating bispecific antigen binding molecule of claim 1, further comprising an Fc domain composed of a first and a second subunit capable of stable association.

8. The T cell activating bispecific antigen binding molecule of claim 7, wherein the first and second antigen binding moieties are Fabs, and wherein:
(a) the second antigen binding moiety is fused at the C-terminus of the Fab heavy chain to the N-terminus of the first or the second subunit of the Fc domain;
(b) the first antigen binding moiety is fused at the C-terminus of the Fab heavy chain to the N-terminus of the first or second subunit of the Fc domain; or
(c) the first and the second antigen binding moiety are each fused at the C-terminus of the Fab heavy chain to the N-terminus of one of the subunits of the Fc domain.

9. The T cell activating bispecific antigen binding molecule of claim 7, wherein the T cell activating bispecific antigen binding molecule further comprises a third antigen binding moiety that binds to FolR1, wherein the first, second, and third antigen binding moieties are Fabs, and wherein:
(a) the second and the third antigen binding moiety are each fused at the C-terminus of the Fab heavy chain to the N-terminus of one of the subunits of the Fc domain, and the first antigen binding moiety is fused at the C-terminus of the Fab heavy chain to the N-terminus of the Fab heavy chain of the second antigen binding moiety; or
(b) the first and the third antigen binding moiety are each fused at the C-terminus of the Fab heavy chain to the N-terminus of one of the subunits of the Fc domain, and the second antigen binding moiety is fused at the C-terminus of the Fab heavy chain to the N-terminus of the Fab heavy chain of the first antigen binding moiety.

10. The T cell activating bispecific antigen binding molecule of claim 7, wherein the Fc domain:
(a) is an IgG Fc domain;
(b) is a human Fc domain;
(c) comprises a modification promoting the association of the first and the second subunit of the Fc domain; and/or
(d) comprises one or more amino acid substitution that reduces binding to an Fc receptor and/or effector function.

11. The T cell activating bispecific antigen binding molecule of claim 10, wherein the effector function is antibody-dependent cell-mediated cytotoxicity (ADCC).

12. The T cell activating bispecific antigen binding molecule of claim 7, wherein in the CH3 domain of the first subunit of the Fc domain an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

13. The T cell activating bispecific antigen binding molecule of claim 7, wherein each subunit of the Fc domain comprises three amino acid substitutions that reduce binding to an activating Fc receptor and/or effector function, and wherein said amino acid substitutions are L234A, L235A, and P329G, numbered according to Kabat numbering.

14. A pharmaceutical composition comprising the T cell activating bispecific antigen binding molecule of claim 1 and a pharmaceutically acceptable carrier.

* * * * *

SEQUENCE LISTING

<160> NUMBER OF SEQ ID NOS: 273

<210> SEQ ID NO 1
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Tyr Ala Gly Val Thr Pro Phe Asp Tyr Trp Gly Gln
            100                 105                 110

Gly Thr Leu Val Thr Val Ser Ser
        115                 120

<210> SEQ ID NO 2
<211> LENGTH: 120
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Tyr Thr Gly Gly Ser Ser Ala Phe Asp Tyr Trp Gly
                100                 105                 110

Gln Gly Thr Leu Val Thr Val Ser
            115                 120

<210> SEQ ID NO 3
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Tyr Leu Phe Ser Thr Ser Phe Asp Tyr Trp Gly Gln
                100                 105                 110

Gly Thr Leu Val Thr Val Ser Ser
            115                 120

<210> SEQ ID NO 4
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Tyr Ile Gly Ile Val Pro Phe Asp Tyr Trp Gly Gln
                100                 105                 110

Gly Thr Leu Val Thr Val Ser Ser
            115                 120

<210> SEQ ID NO 5
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asn Tyr Tyr Val Gly Val Ser Pro Phe Asp Tyr Trp Gly Gln
                100                 105                 110

Gly Thr Leu Val Thr Val Ser Ser
            115                 120

<210> SEQ ID NO 6
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

```
Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asn Phe Thr Val Leu Arg Val Pro Phe Asp Tyr Trp Gly Gln
             100                 105                 110

Gly Thr Leu Val Thr Val Ser Ser
         115                 120

<210> SEQ ID NO 7
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asn Tyr Tyr Ile Gly Val Val Thr Phe Asp Tyr Trp Gly Gln
             100                 105                 110

Gly Thr Leu Val Thr Val Ser Ser
         115                 120

<210> SEQ ID NO 8
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ser Tyr Tyr Met His
 1               5

<210> SEQ ID NO 9
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 9

Ile Ile Asn Pro Ser Gly Gly Ser Thr Ser Tyr Ala Gln Lys Phe Gln
1               5                   10                  15

Gly

<210> SEQ ID NO 10
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Asn Tyr Tyr Ile Gly Val Val Thr Phe Asp Tyr
1               5                   10

<210> SEQ ID NO 11
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Trp Arg Arg Tyr Thr Ser Phe Asp Tyr Trp Gly Gln
            100                 105                 110

Gly Thr Leu Val Thr Val Ser Ser
        115                 120

<210> SEQ ID NO 12
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Glu Trp Arg Arg Tyr Thr Ser Phe Asp Tyr
1               5                   10

<210> SEQ ID NO 13
<211> LENGTH: 120
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Trp Ile Arg Trp Glu His Phe Asp Tyr Trp Gly Gln
            100                 105                 110

Gly Thr Leu Val Thr Val Ser Ser
        115                 120

<210> SEQ ID NO 14
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Gly Trp Ile Arg Trp Glu His Phe Asp Tyr
1               5                   10

<210> SEQ ID NO 15
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ser Trp Tyr Asp Tyr Trp Gly Gln
            100                 105                 110

Gly Thr Leu Val Thr Val Ser Ser
```

```
                 115                 120

<210> SEQ ID NO 16
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Asn Ala Trp Met Ser
1               5

<210> SEQ ID NO 17
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Arg Ile Lys Ser Lys Thr Asp Gly Gly Thr Thr Asp Tyr Ala Ala Pro
1               5                  10                  15

Val Lys Gly

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Pro Trp Glu Trp Ser Trp Tyr Asp Tyr
1               5

<210> SEQ ID NO 19
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Glu Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Ser Asn Ala
                20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95
```

Tyr Cys Thr Thr Pro Trp Glu Trp Ser Tyr Phe Asp Tyr Trp Gly Gln
            100                 105                 110

Gly Thr Leu Val Thr Val Ser Ser
        115                 120

<210> SEQ ID NO 20
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Pro Trp Glu Trp Ser Tyr Phe Asp Tyr
1               5

<210> SEQ ID NO 21
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ala Trp Phe Asp Tyr Trp Gly Gln
            100                 105                 110

Gly Thr Leu Val Thr Val Ser Ser
        115                 120

<210> SEQ ID NO 22
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Pro Trp Glu Trp Ala Trp Phe Asp Tyr
1               5

<210> SEQ ID NO 23
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Pro Trp Glu Trp Ala Tyr Phe Asp Tyr Trp Gly Gln
            100                 105                 110

Gly Thr Leu Val Thr Val Ser Ser
        115                 120

<210> SEQ ID NO 24
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Pro Trp Glu Trp Ala Tyr Phe Asp Tyr
1               5

<210> SEQ ID NO 25
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Thr Gly Trp Ser Arg Trp Gly Tyr Met Asp Tyr Trp Gly Gln
            100                 105                 110

Gly Thr Leu Val Thr Val Ser Ser
        115                 120

```
<210> SEQ ID NO 26
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Thr Gly Trp Ser Arg Trp Gly Tyr Met Asp Tyr
1               5                   10

<210> SEQ ID NO 27
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Trp Ile Arg Tyr Tyr His Phe Asp Tyr Trp Gly Gln
            100                 105                 110

Gly Thr Leu Val Thr Val Ser Ser
        115                 120

<210> SEQ ID NO 28
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gly Glu Trp Ile Arg Tyr Tyr His Phe Asp Tyr
1               5                   10

<210> SEQ ID NO 29
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29
```

-continued

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Trp Tyr Arg Trp Gly Tyr Met Asp Tyr Trp Gly Gln
            100                 105                 110

Gly Thr Leu Val Thr Val Ser Ser
        115                 120

<210> SEQ ID NO 30
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Val Gly Trp Tyr Arg Trp Gly Tyr Met Asp Tyr
1               5                   10

<210> SEQ ID NO 31
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 32
<211> LENGTH: 14
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 32

Gly Ser Ser Thr Gly Ala Val Thr Thr Ser Asn Tyr Ala Asn
1               5                   10

<210> SEQ ID NO 33
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Gly Thr Asn Lys Arg Ala Pro
1               5

<210> SEQ ID NO 34
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ala Leu Trp Tyr Ser Asn Leu Trp Val
1               5

<210> SEQ ID NO 35
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160
```

```
Gly Val Glu Thr Thr Thr Pro Ser Lys Gln Ser Asn Asn Lys Tyr Ala
            165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 36
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 37
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

```
Thr Tyr Ala Met Asn
1               5
```

<210> SEQ ID NO 38
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

```
Arg Ile Arg Ser Lys Tyr Asn Asn Tyr Ala Thr Tyr Tyr Ala Asp Ser
1               5                   10                  15
```

Val Lys Gly

<210> SEQ ID NO 39
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

His Gly Asn Phe Gly Asn Ser Tyr Val Ser Trp Phe Ala Tyr
1               5                   10

<210> SEQ ID NO 40
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys
225

<210> SEQ ID NO 41
<211> LENGTH: 50
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(50)
<223> OTHER INFORMATION: /note="This sequence may encompass 1-10 'Gly
      Gly Gly Gly Ser' repeating units, wherein some positions may be
      absent"
<220> FEATURE:
<221> NAME/KEY: source
<223> OTHER INFORMATION: /note="See specification as filed for detailed
      description of substitutions and preferred embodiments"

<400> SEQUENCE: 41

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser Gly Gly Gly Ser Gly Gly Gly
        35                  40                  45

Gly Ser
    50

<210> SEQ ID NO 42
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(50)
<223> OTHER INFORMATION: /note="This sequence may encompass 1-10 'Ser
      Gly Gly Gly Gly' repeating units, wherein some positions may be
      absent"
<220> FEATURE:
<221> NAME/KEY: source
<223> OTHER INFORMATION: /note="See specification as filed for detailed
      description of substitutions and preferred embodiments"

<400> SEQUENCE: 42

Ser Gly Gly Gly Gly Ser Gly Gly Gly Ser Gly Gly Gly Gly Ser
1               5                   10                  15

Gly Gly Gly Gly Ser Gly Gly Gly Gly Ser Gly Gly Gly Ser Gly
            20                  25                  30

Gly Gly Gly Ser Gly Gly Gly Gly Ser Gly Gly Gly Ser Gly Gly
        35                  40                  45

Gly Gly
    50

<210> SEQ ID NO 43
<211> LENGTH: 54
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (5)..(54)
<223> OTHER INFORMATION: /note="This region may encompass 1-10 'Ser Gly
      Gly Gly Gly' repeating units, wherein some positions may be
      absent"
<220> FEATURE:
```

```
<221> NAME/KEY: source
<223> OTHER INFORMATION: /note="See specification as filed for detailed
      description of substitutions and preferred embodiments"

<400> SEQUENCE: 43

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Ser Gly Gly Gly Ser Gly Gly Gly
        35                  40                  45

Gly Ser Gly Gly Gly Gly
    50

<210> SEQ ID NO 44
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Gly Gly Gly Ser Gly Gly Gly Gly Ser
1               5                   10

<210> SEQ ID NO 45
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 5xHis tag"

<400> SEQUENCE: 45

His His His His His
1               5

<210> SEQ ID NO 46
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Met Gln Ala Ser Ile Met Asn Arg Thr
1               5

<210> SEQ ID NO 47
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 47

His His His His His His
1               5
```

```
<210> SEQ ID NO 48
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
aagcttggat ccatgttgca gatggctggg cagtgctcc                              39

<210> SEQ ID NO 49
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
gaattcgcgg ccgctcatcc tttcactgaa ttggtcacac ttgcattac                   49

<210> SEQ ID NO 50
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
acgttagatc tccactcagt cctgcatctt gttccagtta ac                          42

<210> SEQ ID NO 51
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
aacgttgcgg ccgctagttt cacaaacccc agg                                    33

<210> SEQ ID NO 52
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
gaattcaagc ttgccaccat gttgcagatg gctgggcagt gctcc                       45

<210> SEQ ID NO 53
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

<400> SEQUENCE: 53
gaattctcta gattacctag cagaaattga tttctctatc tccgtagc        48

<210> SEQ ID NO 54
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ser
            20                  25                  30

Gly Met Ile Trp Val Arg Gln Ala Pro Gly Lys Gly Leu Glu Trp Val
        35                  40                  45

Gly His Ile Arg Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Gly Gly Ser Gly Ser Phe Asp Tyr Trp Gly Gln Gly
            100                 105                 110

Thr Leu Val Thr Val Ser Ser
        115

<210> SEQ ID NO 55
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Ser
            20                  25                  30

Trp Met Asn Trp Val Arg Gln Ala Pro Gly Lys Gly Leu Glu Trp Val
        35                  40                  45

Gly Thr Ile Arg Gln Lys Thr Tyr Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Gly Gly Leu Phe Gly Tyr Trp Asp Tyr Trp Gly Gln
            100                 105                 110

Gly Thr Leu Val Thr Val Ser Ser
        115                 120

<210> SEQ ID NO 56
<211> LENGTH: 207

```
<212> TYPE: PRT
<213> ORGANISM: Homo sapiens

<400> SEQUENCE: 56

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                      45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65              70                  75                  80

His Leu Ser Leu Lys Glu Phe Ser Glu Leu Glu Gln Ser Gly Tyr Tyr
            85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 57
<211> LENGTH: 426
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 57
atgagctttt ttttcctgag ctttcatatt agcaacctgc agtttaatag cagcctggaa      60
gatccgagca ccgattatta tcaagaactg cagcgtgata tcagcgaaat gtttctgcag     120
atctataaac agggtggttt tctgggtctg agcaacatca aatttcgtcc gggtggtggc     180
ggtggttcag ttgttgtgca gctgaccctg gcatttcgtg aaggcaccat taatgttcat     240
gatgtggaaa cccagtttaa ccagtataaa accgaagcag caagccgtta taatctgacc     300
attagtgatg ttagcgtttc cgatgttccg tttccgttta gcgcacagag tgtcgacggt     360
ctgaatgata ttttttgaagc ccagaaaatc gaatggcatg aactcgagca ccaccaccac     420
caccac                                                                426

<210> SEQ ID NO 58
<211> LENGTH: 142
<212> TYPE: PRT
<213> ORGANISM: Artificial Sequence
<220> FEATURE:
<221> NAME/KEY: source
```

<223> OTHER INFORMATION: /note="Description of Artificial Sequence:
    Synthetic polypeptide"

<400> SEQUENCE: 58

Met Ser Phe Phe Phe Leu Ser Phe His Ile Ser Asn Leu Gln Phe Asn
1               5                   10                  15

Ser Ser Leu Glu Asp Pro Ser Thr Asp Tyr Tyr Gln Glu Leu Gln Arg
            20                  25                  30

Asp Ile Ser Glu Met Phe Leu Gln Ile Tyr Lys Gln Gly Gly Phe Leu
        35                  40                  45

Gly Leu Ser Asn Ile Lys Phe Arg Pro Gly Gly Gly Ser Val
    50                  55                  60

Val Val Gln Leu Thr Leu Ala Phe Arg Glu Gly Thr Ile Asn Val His
65              70                  75                  80

Asp Val Glu Thr Gln Phe Asn Gln Tyr Lys Thr Glu Ala Ala Ser Arg
            85                  90                  95

Tyr Asn Leu Thr Ile Ser Asp Val Ser Val Ser Asp Val Pro Phe Pro
            100                 105                 110

Phe Ser Ala Gln Ser Val Asp Gly Leu Asn Asp Ile Phe Glu Ala Gln
        115                 120                 125

Lys Ile Glu Trp His Glu Leu Glu His His His His His His
    130                 135                 140

<210> SEQ ID NO 59
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 59
gaggtgcaat tgttggagtc tgggggaggc ttggtacagc ctgggggggtc cctgagactc      60 tcctgtgcag cctccggatt cacctttagc agttatgcca tgagctgggt ccgccaggct     120
ccagggaagg gctggagtg gtctcagct attagtggta gtggtggtag cacatactac       180
gcagactccg tgaagggccg gttcaccatc tccagagaca attccaagaa cacgctgtat     240
ctgcagatga acagcctgag agccgaggac acggccgtat attactgtgc gaaagttgaa     300
tggtctactc tgctgtactt cgactactgg ggccaaggaa ccctggtcac cgtctcgagt     360

<210> SEQ ID NO 60
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Glu Trp Ser Thr Leu Leu Tyr Phe Asp Tyr Trp Gly Gln
            100                 105                 110

Gly Thr Leu Val Thr Val Ser Ser
        115                 120

<210> SEQ ID NO 61
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 61
gaggtgcaat tgttggagtc tgggggaggc ttggtacagc ctggggggtc cctgagactc     60
tcctgtgcag cctccggatt cacctttcgg gtttatgcaa tgagctgggt ccgccaggct    120
ccagggaagg ggctggagtg ggtctcaggt atttctgaaa ctggttctta cacatactac    180
gcagactccg tgaagggccg gttcaccatc tccagagaca attccaagaa cacgctgtat    240
ctgcagatga acagcctgag agccgaggac acggccgtat attactgtgc gcgttacccg    300
tacggtttcg actactgggg ccaaggaacc ctggtcaccg tctcgagt              348

<210> SEQ ID NO 62
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Val Tyr
            20                  25                  30

Ala Met Ser Trp Val Arg Gln Ala Pro Gly Lys Gly Leu Glu Trp Val
        35                  40                  45

Ser Gly Ile Ser Glu Thr Gly Ser Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Pro Tyr Gly Phe Asp Tyr Trp Gly Gln Gly Thr Leu Val
            100                 105                 110

Thr Val Ser Ser
        115

<210> SEQ ID NO 63
<211> LENGTH: 360
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 63

```
gaggtgcaat tgttggagtc tggggagggc ttggtacagc ctgggggtc cctgagactc    60
tcctgtgcag cctccggatt cacctttagc agttatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcagatga acagcctgag agccgaggac acggccgtat attactgtgc gaaatactct   300
taccgttacg ttctggcttt cgactactgg ggccaaggaa ccctggtcac cgtctcgagt   360
```

<210> SEQ ID NO 64
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Ser Tyr Arg Tyr Val Leu Ala Phe Asp Tyr Trp Gly Gln
            100                 105                 110

Gly Thr Leu Val Thr Val Ser Ser
        115                 120

<210> SEQ ID NO 65
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 65

```
caggccgtcg tgacccagga acccagcctg acagtgtctc tggcggcac cgtgaccctg     60
acatgtggca gttctacagg cgccgtgacc accagcaact acgccaactg ggtgcaggaa   120
aagcccggcc aggccttcag aggactgatc ggcggcacca caagagagc ccctggcacc    180
cctgccagat tcagcggatc tctgctggga ggaaaggccg ccctgacact gtctggcgcc   240
cagccagaag atgaggccga gtactactgc gccctgtggt acagcaacct gtgggtgttc   300
ggcggaggca ccaagctgac agtccta                                        327
```

```
<210> SEQ ID NO 66
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 67
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 67
caggccgtcg tgacccagga acccagcctg acagtgtctc ctggcggcac cgtgaccctg      60
acatgtggca gttctacagg cgccgtgacc accagcaact acgccaactg ggtgcaggaa     120
aagcccggcc aggccttcag aggactgatc ggcggcacca caagagagcc cctggcacc     180
cctgccagat tcagcggatc tctgctggga ggaaaggccg ccctgacact gtctggcgcc     240
cagccagaag atgaggccga gtactactgc gccctgtggt acagcaacct gtgggtgttc     300
ggcggaggca ccaagctgac agtgctgcgt acgcaaccca aggctgcccc cagcgtgacc     360
ctgttccccc ccagcagcga ggaactgcag gccaacaagg ccaccctggt ctgcctgatc     420
agcgacttct acccaggcgc cgtgaccgtg gcctggaagg ccgacagcag ccccgtgaag     480
gccggcgtgg agaccaccac ccccagcaag cagagcaaca caagtacgc cgccagcagc     540
tacctgagcc tgacccccga gcagtggaag agccacaggt cctacagctg ccaggtgacc     600
cacgagggca gcaccgtgga gaaaaccgtg gccccaccg agtgctcc                   648

<210> SEQ ID NO 68
<211> LENGTH: 216
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Gln Ala Val Val Thr Gln Glu Pro Ser Leu Thr Val Ser Pro Gly Gly
```

```
1               5                   10                  15
Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
                35                  40                  45

Leu Ile Gly Gly Thr Asn Lys Arg Ala Pro Gly Thr Pro Ala Arg Phe
            50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                    85                  90                  95

Leu Trp Val Phe Gly Gly Gly Thr Lys Leu Thr Val Leu Arg Thr Gln
                100                 105                 110

Pro Lys Ala Ala Pro Ser Val Thr Leu Phe Pro Ser Ser Glu Glu
                115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                    165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
                195                 200                 205

Thr Val Ala Pro Thr Glu Cys Ser
210                 215
```

<210> SEQ ID NO 69
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 69

```
gaggtgcaat tgttggagtc tgggggaggc ttggtacagc ctgggggtc cctgagactc    60
tcctgtgcag cctccggatt cacctttagc agttatgcca tgagctgggt ccgccaggct   120
ccagggaagg ggctggagtg gtctcagct attagtggta gtggtggtag cacatactac   180
gcagactccg tgaagggccg gttcaccatc tccagagaca attccaagaa cacgctgtat   240
ctgcagatga acagcctgag agccgaggac acggccgtat attactgtgc gaaagttgaa   300
tggtctactc tgctgtactt cgactactgg ggccaaggaa ccctggtcac cgtctcgagt   360
gctagcacaa agggcctag cgtgttccct ctggccccca gcagcaagag cacaagcggc   420
ggaacagccg ccctgggctg cctcgtgaag gactacttcc ccgagcccgt gacagtgtct   480
tggaacagcg gagccctgac aagcggcgtg cacactttcc ctgccgtgct gcagagcagc   540
ggcctgtact ccctgagcag cgtggtcacc gtgcctagca gcagcctggg cacccagacc   600
tacatctgca acgtgaacca caagcccagc aacaccaaag tggacaagaa ggtggagccc   660
aagagctgtg atggcggagg agggtccgga ggcggaggat ccgaggtgca gctgctggaa   720
tctggcggcg gactggtgca gcctggcgga tctctgagac tgagctgtgc cgccagcggc   780
```

```
ttcaccttca gcacctacgc catgaactgg gtgcgccagg ccctggcaa aggcctggaa      840
tgggtgtccc ggatcagaag caagtacaac aactacgcca cctactacgc cgacagcgtg      900
aagggccggt tcaccatcag ccgggacgac agcaagaaca ccctgtacct gcagatgaac      960
agcctgcggg ccgaggacac cgccgtgtac tattgtgtgc ggcacggcaa cttcggcaac     1020
agctatgtgt cttggtttgc ctactggggc cagggcaccc tcgtgaccgt gtcaagcgct     1080
agtaccaagg gcccagcgt gttccccctg gcacccagca gcaagagcac atctggcgga     1140
acagccgctc tgggctgtct ggtgaaagac tacttccccg agcccgtgac cgtgtcttgg     1200
aactctggcg ccctgaccag cggcgtgcac accttccagc cgtgctgca gagcagcggc     1260
ctgtactccc tgtcctccgt ggtcaccgtg ccctctagct ccctgggaac acagacatat     1320
atctgtaatg tcaatcacaa gccttccaac accaaagtcg ataagaaagt cgagcccaag     1380
agctgcgaca aaactcacac atgcccaccg tgcccagcac ctgaagctgc agggggaccg     1440
tcagtcttcc tcttcccccc aaaacccaag gacaccctca tgatctcccg gacccctgag     1500
gtcacatgcg tggtggtgga cgtgagccac gaagaccctg aggtcaagtt caactggtac     1560
gtggacggcg tggaggtgca taatgccaag acaaagccgc gggaggagca gtacaacagc     1620
acgtaccgtg tggtcagcgt cctcaccgtc ctgcaccagg actggctgaa tggcaaggag     1680
tacaagtgca aggtctccaa caaagccctc ggcgccccca tcgagaaaac catctccaaa     1740
gccaaagggc agccccgaga accacaggtg tacaccctgc ccccatgccg ggatgagctg     1800
accaagaacc aggtcagcct gtggtgcctg gtcaaaggct tctatcccag cgacatcgcc     1860
gtggagtggg agagcaatgg gcagccggag aacaactaca agaccacgcc tcccgtgctg     1920
gactccgacg gctccttctt cctctacagc aagctcaccg tggacaagag caggtggcag     1980
caggggaacg tcttctcatg ctccgtgatg catgaggctc tgcacaacca ctacacgcag     2040
aagagcctct ccctgtctcc gggtaaa                                          2067
```

<210> SEQ ID NO 70
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 70

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Glu Trp Ser Thr Leu Leu Tyr Phe Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Gly Gly Gly Gly Ser Gly Gly Gly Ser Glu Val Gln Leu Leu Glu
225                 230                 235                 240

Ser Gly Gly Gly Leu Val Gln Pro Gly Gly Ser Leu Arg Leu Ser Cys
                245                 250                 255

Ala Ala Ser Gly Phe Thr Phe Ser Thr Tyr Ala Met Asn Trp Val Arg
            260                 265                 270

Gln Ala Pro Gly Lys Gly Leu Glu Trp Val Ser Arg Ile Arg Ser Lys
        275                 280                 285

Tyr Asn Asn Tyr Ala Thr Tyr Tyr Ala Asp Ser Val Lys Gly Arg Phe
290                 295                 300

Thr Ile Ser Arg Asp Asp Ser Lys Asn Thr Leu Tyr Leu Gln Met Asn
305                 310                 315                 320

Ser Leu Arg Ala Glu Asp Thr Ala Val Tyr Tyr Cys Val Arg His Gly
                325                 330                 335

Asn Phe Gly Asn Ser Tyr Val Ser Trp Phe Ala Tyr Trp Gly Gln Gly
            340                 345                 350

Thr Leu Val Thr Val Ser Ser Ala Ser Thr Lys Gly Pro Ser Val Phe
        355                 360                 365

Pro Leu Ala Pro Ser Ser Lys Ser Thr Ser Gly Gly Thr Ala Ala Leu
370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
                405                 410                 415

Gln Ser Ser Gly Leu Tyr Ser Leu Ser Ser Val Val Thr Val Pro Ser
            420                 425                 430

Ser Ser Leu Gly Thr Gln Thr Tyr Ile Cys Asn Val Asn His Lys Pro
        435                 440                 445

Ser Asn Thr Lys Val Asp Lys Lys Val Glu Pro Lys Ser Cys Asp Lys
450                 455                 460

Thr His Thr Cys Pro Pro Cys Pro Ala Pro Glu Ala Ala Gly Gly Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
            500                 505                 510

Pro Glu Val Lys Phe Asn Trp Tyr Val Asp Gly Val Glu Val His Asn
        515                 520                 525

Ala Lys Thr Lys Pro Arg Glu Glu Gln Tyr Asn Ser Thr Tyr Arg Val
530                 535                 540
```

| Val | Ser | Val | Leu | Thr | Val | Leu | His | Gln | Asp | Trp | Leu | Asn | Gly | Lys | Glu |
| 545 | | | | | 550 | | | | | 555 | | | | | 560 |

| Tyr | Lys | Cys | Lys | Val | Ser | Asn | Lys | Ala | Leu | Gly | Ala | Pro | Ile | Glu | Lys |
| | | | | 565 | | | | | 570 | | | | | 575 | |

| Thr | Ile | Ser | Lys | Ala | Lys | Gly | Gln | Pro | Arg | Glu | Pro | Gln | Val | Tyr | Thr |
| | | | 580 | | | | | 585 | | | | | 590 | | |

| Leu | Pro | Pro | Cys | Arg | Asp | Glu | Leu | Thr | Lys | Asn | Gln | Val | Ser | Leu | Trp |
| | | 595 | | | | | 600 | | | | | 605 | | | |

| Cys | Leu | Val | Lys | Gly | Phe | Tyr | Pro | Ser | Asp | Ile | Ala | Val | Glu | Trp | Glu |
| | 610 | | | | | 615 | | | | | 620 | | | | |

| Ser | Asn | Gly | Gln | Pro | Glu | Asn | Asn | Tyr | Lys | Thr | Thr | Pro | Pro | Val | Leu |
| 625 | | | | | 630 | | | | | 635 | | | | | 640 |

| Asp | Ser | Asp | Gly | Ser | Phe | Phe | Leu | Tyr | Ser | Lys | Leu | Thr | Val | Asp | Lys |
| | | | | 645 | | | | | 650 | | | | | 655 | |

| Ser | Arg | Trp | Gln | Gln | Gly | Asn | Val | Phe | Ser | Cys | Ser | Val | Met | His | Glu |
| | | | 660 | | | | | 665 | | | | | 670 | | |

| Ala | Leu | His | Asn | His | Tyr | Thr | Gln | Lys | Ser | Leu | Ser | Leu | Ser | Pro | Gly |
| | | 675 | | | | | 680 | | | | | 685 | | | |

Lys

<210> SEQ ID NO 71
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71

```
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaagttgaa     300
tggtctactc tgctgtactt cgactactgg ggccaaggaa ccctggtcac cgtctcgagt     360
gctagcacca agggcccctc cgtgttcccc ctggccccca gcagcaagag caccagcggc     420
ggcacagccg ctctgggctg cctggtcaag gactacttcc ccgagcccgt gaccgtgtcc     480
tggaacagcg gagccctgac ctccggcgtg cacaccttcc ccgccgtgct gcagagttct     540
ggcctgtata gcctgagcag cgtggtcacc gtgccttcta gcagcctggg cacccagacc     600
tacatctgca acgtgaacca caagcccagc aacaccaagg tggacaagaa ggtggagccc     660
aagagctgcg acaaaactca cacatgccca ccgtgcccag cacctgaagc tgcaggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcggcgccc catcgagaa aaccatctcc    1020
aaagccaaag gcagccccg agaaccacag gtgtgcaccc tgcccccatc ccgggatgag    1080
ctgaccaaga accaggtcag cctctcgtgc gcagtcaaag gcttctatcc cagcgacatc    1140
```

```
gccgtggagt gggagagcaa tgggcagccg agaacaact acaagaccac gcctcccgtg   1200
ctggactccg acggctcctt cttcctcgtg agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                   1350
```

<210> SEQ ID NO 72
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 72

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Glu Trp Ser Thr Leu Leu Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Gly Ala Pro Ile Glu
                325                 330                 335
Lys Thr Ile Ser Lys Ala Lys Gly Gln Pro Arg Glu Pro Gln Val Cys
            340                 345                 350
Thr Leu Pro Pro Ser Arg Asp Glu Leu Thr Lys Asn Gln Val Ser Leu
        355                 360                 365
Ser Cys Ala Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Val Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 73
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73
gaggtgcaat tgttggagtc tgggggaggc ttggtacagc ctgggggtc cctgagactc         60 tcctgtgcag cctccggatt cacctttagc agttatgcca tgagctgggt ccgccaggct       120
ccagggaagg gctggagtg gtctcagct attagtggta gtggtggtag cacatactac         180
gcagactccg tgaagggccg gttcaccatc tccagagaca attccaagaa cacgctgtat       240
ctgcagatga acagcctgag agccgaggac acggccgtat attactgtgc gaaatactct       300
taccgttacg ttctggcttt cgactactgg ggccaaggaa ccctggtcac cgtctcgagt       360
gctagcacaa agggccctag cgtgttccct ctggccccca gcagcaagag cacaagcggc       420
ggaacagccg ccctgggctg cctcgtgaag gactacttcc ccgagcccgt gacagtgtct       480
tggaacagcg gagccctgac aagcggcgtg cacacttttcc ctgccgtgct gcagagcagc       540
ggcctgtact ccctgagcag cgtggtcacc gtgcctagca gcagcctggg cacccagacc       600
tacatctgca acgtgaacca caagcccagc aacaccaaag tggacaagaa ggtggagccc       660
aagagctgtg atggcggagg agggtccgga ggcggaggat ccgaggtgca gctgctggaa       720
tctggcggcg gactggtgca gcctggcgga tctctgagac tgagctgtgc cgccagcggc       780
ttcaccttca gcacctacgc catgaactgg gtgcgccagg cccctggcaa aggcctggaa       840
tgggtgtccc ggatcagaag caagtacaac aactacgcca cctactacgc cgacagcgtg       900
aagggccggt tcaccatcag ccgggacgac agcaagaaca ccctgtacct gcagatgaac       960
agcctgcggg ccgaggacac cgccgtgtac tattgtgtgc ggcacggcaa cttcggcaac      1020
agctatgtgt cttggtttgc ctactgggc cagggcaccc tcgtgaccgt gtcaagcgct       1080
agtaccaagg gcccagcgt gttccccctg gcacccagca gcaagagcac atctggcgga      1140
acagccgctc tgggctgtct ggtgaaagac tacttccccg agcccgtgac cgtgtcttgg      1200
```

```
aactctggcg ccctgaccag cggcgtgcac acctttccag ccgtgctgca gagcagcggc   1260
ctgtactccc tgtcctccgt ggtcaccgtg ccctctagct ccctgggaac acagacatat   1320
atctgtaatg tcaatcacaa gccttccaac accaaagtcg ataagaaagt cgagcccaag   1380
agctgcgaca aaactcacac atgcccaccg tgcccagcac ctgaagctgc aggggggaccg   1440 tcagtcttcc tcttcccccc aaaacccaag gacaccctca tgatctcccg gacccctgag   1500
gtcacatgcg tggtggtgga cgtgagccac gaagaccctg aggtcaagtt caactggtac   1560
gtggacggcg tggaggtgca taatgccaag acaaagccgc gggaggagca gtacaacagc   1620
acgtaccgtg tggtcagcgt cctcaccgtc ctgcaccagg actggctgaa tggcaaggag   1680
tacaagtgca aggtctccaa caaagccctc ggcgccccca tcgagaaaac catctccaaa   1740
gccaaagggc agccccgaga accacaggtg tacaccctgc ccccatgccg ggatgagctg   1800
accaagaacc aggtcagcct gtggtgcctg gtcaaaggct tctatcccag cgacatcgcc   1860
gtggagtggg agagcaatgg gcagccggag aacaactaca agaccacgcc tcccgtgctg   1920
gactccgacg gctccttctt cctctacagc aagctcaccg tggacaagag caggtggcag   1980
caggggaacg tcttctcatg ctccgtgatg catgaggctc tgcacaacca ctacacgcag   2040
aagagcctct ccctgtctcc gggtaaa                                       2067
```

<210> SEQ ID NO 74
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 74

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Ser Tyr Arg Tyr Val Leu Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
    210                 215                 220
Gly Gly Gly Gly Ser Gly Gly Gly Ser Glu Val Gln Leu Leu Glu
225             230             235                 240
Ser Gly Gly Gly Leu Val Gln Pro Gly Gly Ser Leu Arg Leu Ser Cys
            245                 250                 255
Ala Ala Ser Gly Phe Thr Phe Ser Tyr Ala Met Asn Trp Val Arg
            260             265                 270
Gln Ala Pro Gly Lys Gly Leu Glu Trp Val Ser Arg Ile Arg Ser Lys
        275                 280                 285
Tyr Asn Asn Tyr Ala Thr Tyr Tyr Ala Asp Ser Val Lys Gly Arg Phe
    290                 295                 300
Thr Ile Ser Arg Asp Asp Ser Lys Asn Thr Leu Tyr Leu Gln Met Asn
305                 310                 315                 320
Ser Leu Arg Ala Glu Asp Thr Ala Val Tyr Tyr Cys Val Arg His Gly
                325                 330                 335
Asn Phe Gly Asn Ser Tyr Val Ser Trp Phe Ala Tyr Trp Gly Gln Gly
            340                 345                 350
Thr Leu Val Thr Val Ser Ser Ala Ser Thr Lys Gly Pro Ser Val Phe
        355                 360                 365
Pro Leu Ala Pro Ser Ser Lys Ser Thr Ser Gly Gly Thr Ala Ala Leu
    370                 375                 380
Gly Cys Leu Val Lys Asp Tyr Phe Pro Glu Pro Val Thr Val Ser Trp
385                 390                 395                 400
Asn Ser Gly Ala Leu Thr Ser Gly Val His Thr Phe Pro Ala Val Leu
                405                 410                 415
Gln Ser Ser Gly Leu Tyr Ser Leu Ser Ser Val Val Thr Val Pro Ser
            420                 425                 430
Ser Ser Leu Gly Thr Gln Thr Tyr Ile Cys Asn Val Asn His Lys Pro
        435                 440                 445
Ser Asn Thr Lys Val Asp Lys Lys Val Glu Pro Lys Ser Cys Asp Lys
450                 455                 460
Thr His Thr Cys Pro Pro Cys Pro Ala Pro Glu Ala Ala Gly Gly Pro
465                 470                 475                 480
Ser Val Phe Leu Phe Pro Pro Lys Pro Lys Asp Thr Leu Met Ile Ser
                485                 490                 495
Arg Thr Pro Glu Val Thr Cys Val Val Val Asp Val Ser His Glu Asp
            500                 505                 510
Pro Glu Val Lys Phe Asn Trp Tyr Val Asp Gly Val Glu Val His Asn
        515                 520                 525
Ala Lys Thr Lys Pro Arg Glu Glu Gln Tyr Asn Ser Thr Tyr Arg Val
    530                 535                 540
Val Ser Val Leu Thr Val Leu His Gln Asp Trp Leu Asn Gly Lys Glu
545                 550                 555                 560
Tyr Lys Cys Lys Val Ser Asn Lys Ala Leu Gly Ala Pro Ile Glu Lys
                565                 570                 575
Thr Ile Ser Lys Ala Lys Gly Gln Pro Arg Glu Pro Gln Val Tyr Thr
            580                 585                 590
Leu Pro Pro Cys Arg Asp Glu Leu Thr Lys Asn Gln Val Ser Leu Trp
        595                 600                 605
Cys Leu Val Lys Gly Phe Tyr Pro Ser Asp Ile Ala Val Glu Trp Glu
```

```
                610               615               620
Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
                660                 665                 670

Ala Leu His Asn His Tyr Thr Gln Lys Ser Leu Ser Leu Ser Pro Gly
                675                 680                 685

Lys

<210> SEQ ID NO 75
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75
gaggtgcaat tgttggagtc tgggggaggc ttggtacagc ctggggggtc cctgagactc      60
tcctgtgcag cctccggatt cacctttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaatactct     300
taccgttacg ttctggcttt cgactactgg ggccaaggaa ccctggtcac cgtctcgagt     360
gctagcacca agggcccctc cgtgttcccc ctggccccca gcagcaagag caccagcggc     420
ggcacagccg ctctgggctg cctggtcaag gactacttcc ccgagcccgt gaccgtgtcc     480
tggaacagcg gagccctgac ctccggcgtg cacaccttcc cagccgtgct gcagagttct     540
ggcctgtata gcctgagcag cgtggtcacc gtgccttcta gcagcctggg cacccagacc     600
tacatctgca acgtgaacca caagcccagc aacaccaagg tggacaagaa ggtggagccc     660
aagagctgcg acaaaactca cacatgccca ccgtgcccag cacctgaagc tgcaggggga     720
ccgtcagtct tcctcttccc cccaaaaccc aaggacaccc tcatgatctc ccggaccccct     780 gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcggcgccc ccatcgagaa aaccatctcc    1020
aaagccaaag ggcagccccg agaaccacag gtgtgcaccc tgcccccatc ccgggatgag    1080
ctgaccaaga accaggtcag cctctcgtgc gcagtcaaag gcttctatcc cagcgacatc    1140
gccgtggagt gggagagcaa tgggcagccg gagaacaact acaagaccac gcctcccgtg    1200
ctggactccg acggctcctt cttcctcgtg agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa                                      1350

<210> SEQ ID NO 76
<211> LENGTH: 450
<212> TYPE: PRT
<213> ORGANISM: Artificial Sequence
```

-continued

```
<220> FEATURE:
<221> NAME/KEY: source
<223> OTHER INFORMATION: /note="Description of Artificial Sequence:
      Synthetic polypeptide"

<400> SEQUENCE: 76
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Ser Tyr Arg Tyr Val Leu Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 77
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Met Phe Ser Ser Phe
            20                  25                  30

Gly Met Ser Trp Val Arg Gln Ala Pro Gly Gln Gly Leu Glu Trp Met
        35                  40                  45

Gly Trp Ile Tyr Pro Val Gly Gln Gly Thr Trp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Ser Tyr Pro Pro Ser His Phe Asp Tyr Trp Gly Gln Gly
            100                 105                 110

Thr Leu Val Thr Val Ser Ser
        115

<210> SEQ ID NO 78
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ser
            20                  25                  30

Gly Met Ile Trp Val Arg Gln Ala Pro Gly Lys Gly Leu Glu Trp Val
        35                  40                  45

Gly His Ile Arg Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
```

```
                 85                  90                  95
Tyr Cys Thr Thr Gly Gly Ser Gly Ser Phe Asp Tyr Trp Gly Gln Gly
                100                 105                 110
Thr Leu Val Thr Val Ser Ser
            115

<210> SEQ ID NO 79
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Ser
            20                  25                  30

Trp Met Asn Trp Val Arg Gln Ala Pro Gly Lys Gly Leu Glu Trp Val
        35                  40                  45

Gly Thr Ile Arg Gln Lys Thr Tyr Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Gly Gly Leu Phe Gly Tyr Trp Asp Tyr Trp Gly Gln
                100                 105                 110

Gly Thr Leu Val Thr Val Ser Ser
            115                 120

<210> SEQ ID NO 80
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Gly Tyr Met Phe Ser Ser Phe Gly Met Ser
1               5                   10

<210> SEQ ID NO 81
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Gly Phe Thr Phe Ser Asn Ser Gly Met Ile
1               5                   10

<210> SEQ ID NO 82
<211> LENGTH: 10
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 82

Gly Phe Ser Phe Ser Asn Ser Trp Met Asn
1               5                   10

<210> SEQ ID NO 83
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Trp Ile Tyr Pro Val Gly Gln Gly Thr Trp Tyr Ala Gln Lys Phe Gln
1               5                   10                  15

Gly

<210> SEQ ID NO 84
<211> LENGTH: 103
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 85
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

His Ile Arg Ser Lys Thr Asp Gly Gly Thr Thr Asp Tyr Ala Ala Pro
1               5                   10                  15

Val Lys Gly

<210> SEQ ID NO 86
```

```
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Thr Ile Arg Gln Lys Thr Tyr Gly Gly Thr Thr Asp Tyr Ala Ala Pro
1               5                   10                  15

Val Lys Gly

<210> SEQ ID NO 87
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 87

Val Ser Tyr Pro Pro Ser His Phe Asp Tyr
1               5                   10

<210> SEQ ID NO 88
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Gly Gly Ser Gly Ser Phe Asp Tyr
1               5

<210> SEQ ID NO 89
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Gly Gly Leu Phe Gly Tyr Trp Asp Tyr
1               5

<210> SEQ ID NO 90
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
                20                  25                  30

Asn Tyr Ala Asn Trp Val Gln Glu Lys Pro Gly Gln Ala Phe Arg Gly
```

```
                35                  40                  45
Leu Ile Gly Gly Thr Asn Lys Arg Ala Pro Gly Thr Pro Ala Arg Phe
        50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 91
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
        50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 92
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
        50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 93
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Gly Ser Ser Thr Gly Ala Val Thr Thr Ser Asn Tyr Ala Asn
1               5                   10

<210> SEQ ID NO 94
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Gly Thr Asn Lys Arg Ala Pro
1               5

<210> SEQ ID NO 95
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Ala Leu Trp Tyr Ser Asn Leu Trp Val
1               5

<210> SEQ ID NO 96
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 97
<211> LENGTH: 648
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (603)..(603)
<223> OTHER INFORMATION: a, c, t, g, unknown or other

<400> SEQUENCE: 97
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagtatacca cgaacatta ttatacgttc      300 ggccagggga ccaaagtgga aatcaaacgt acggtggctg caccatctgt cttcatcttc     360
ccgccatctg atgagcagtt gaaatctgga actgcctctg ttgtgtgcct gctgaataac     420
ttctatccca gagaggccaa agtacagtgg aaggtggata acgcctcca atcgggtaac      480 tcccaggaga gtgtcacaga gcaggacagc aaggacagca cctacagcct cagcagcacc     540
ctgacgctga gcaaagcaga ctacgagaaa cacaaagtct acgcctgcga agtcacccat     600
canggcctga gctcgcccgt cacaaagagc ttcaacaggg gagagtgt                  648

<210> SEQ ID NO 98
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Thr Tyr Ala Met Asn
1               5

<210> SEQ ID NO 99
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Arg Ile Arg Ser Lys Tyr Asn Asn Tyr Ala Thr Tyr Tyr Ala Asp Ser
1               5                   10                  15

Val Lys Gly

<210> SEQ ID NO 100
<211> LENGTH: 14
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 100

His Gly Asn Phe Gly Asn Ser Tyr Val Ser Trp Phe Ala Tyr
1               5                   10

<210> SEQ ID NO 101
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 102
<211> LENGTH: 688
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Met Phe Ser Ser Phe
```

```
            20                  25                  30
Gly Met Ser Trp Val Arg Gln Ala Pro Gly Gln Gly Leu Glu Trp Met
        35                  40                  45
Gly Trp Ile Tyr Pro Val Gly Gln Gly Thr Trp Tyr Ala Gln Lys Phe
50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Val Ser Tyr Pro Pro Ser His Phe Asp Tyr Trp Gly Gln Gly
                100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
            130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Lys Val Glu Pro Lys Ser Cys Asp Gly
            210                 215                 220
Gly Gly Gly Ser Gly Gly Gly Ser Glu Val Gln Leu Leu Glu Ser
225                 230                 235                 240
Gly Gly Gly Leu Val Gln Pro Gly Gly Ser Leu Arg Leu Ser Cys Ala
                245                 250                 255
Ala Ser Gly Phe Thr Phe Ser Thr Tyr Ala Met Asn Trp Val Arg Gln
                260                 265                 270
Ala Pro Gly Lys Gly Leu Glu Trp Val Ser Arg Ile Arg Ser Lys Tyr
            275                 280                 285
Asn Asn Tyr Ala Thr Tyr Tyr Ala Asp Ser Val Lys Gly Arg Phe Thr
            290                 295                 300
Ile Ser Arg Asp Asp Ser Lys Asn Thr Leu Tyr Leu Gln Met Asn Ser
305                 310                 315                 320
Leu Arg Ala Glu Asp Thr Ala Val Tyr Tyr Cys Val Arg His Gly Asn
                325                 330                 335
Phe Gly Asn Ser Tyr Val Ser Trp Phe Ala Tyr Trp Gly Gln Gly Thr
                340                 345                 350
Leu Val Thr Val Ser Ser Ala Ser Thr Lys Gly Pro Ser Val Phe Pro
            355                 360                 365
Leu Ala Pro Ser Ser Lys Ser Thr Ser Gly Gly Thr Ala Ala Leu Gly
            370                 375                 380
Cys Leu Val Lys Asp Tyr Phe Pro Glu Pro Val Thr Val Ser Trp Asn
385                 390                 395                 400
Ser Gly Ala Leu Thr Ser Gly Val His Thr Phe Pro Ala Val Leu Gln
                405                 410                 415
Ser Ser Gly Leu Tyr Ser Leu Ser Ser Val Val Thr Val Pro Ser Ser
                420                 425                 430
Ser Leu Gly Thr Gln Thr Tyr Ile Cys Asn Val Asn His Lys Pro Ser
                435                 440                 445
```

Asn Thr Lys Val Asp Lys Lys Val Glu Pro Lys Ser Cys Asp Lys Thr
        450                 455                 460

His Thr Cys Pro Pro Cys Pro Ala Pro Glu Ala Ala Gly Gly Pro Ser
465                 470                 475                 480

Val Phe Leu Phe Pro Pro Lys Pro Lys Asp Thr Leu Met Ile Ser Arg
            485                 490                 495

Thr Pro Glu Val Thr Cys Val Val Val Asp Val Ser His Glu Asp Pro
        500                 505                 510

Glu Val Lys Phe Asn Trp Tyr Val Asp Gly Val Glu Val His Asn Ala
    515                 520                 525

Lys Thr Lys Pro Arg Glu Glu Gln Tyr Asn Ser Thr Tyr Arg Val Val
530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Gly Ala Pro Ile Glu Lys Thr
                565                 570                 575

Ile Ser Lys Ala Lys Gly Gln Pro Arg Glu Pro Gln Val Tyr Thr Leu
            580                 585                 590

Pro Pro Cys Arg Asp Glu Leu Thr Lys Asn Gln Val Ser Leu Trp Cys
        595                 600                 605

Leu Val Lys Gly Phe Tyr Pro Ser Asp Ile Ala Val Glu Trp Glu Ser
    610                 615                 620

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
                645                 650                 655

Arg Trp Gln Gln Gly Asn Val Phe Ser Cys Ser Val Met His Glu Ala
            660                 665                 670

Leu His Asn His Tyr Thr Gln Lys Ser Leu Ser Leu Ser Pro Gly Lys
        675                 680                 685

<210> SEQ ID NO 103
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Met Phe Ser Ser Phe
            20                  25                  30

Gly Met Ser Trp Val Arg Gln Ala Pro Gly Gln Gly Leu Glu Trp Met
        35                  40                  45

Gly Trp Ile Tyr Pro Val Gly Gln Gly Thr Trp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Ser Tyr Pro Pro Ser His Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
        355                 360                 365

Cys Ala Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 104
<211> LENGTH: 642
<212> TYPE: DNA
<213> ORGANISM: Homo sapiens

<400> SEQUENCE: 104
caaggcttga ggtatgaaat aatctgtctc aatgaatatg caaataacct tagatctact      60
gaggtaaata tggatacatc tgggccctga agcatcatc caacaaccac atcccttctc     120
tacagaagcc tctgagagga aagttcttca ccatggactg gacctggagg gtcttctgct    180

```
tgctggctgt agctccaggt aaagggccaa ctggttccag ggctgaggaa gggattttt      240 ccagtttaga ggactgtcat tctctactgt gtcctctccg caggtgctca ctcccaggtg    300
cagctggtgc agtctggggc tgaggtgaag aagcctgggg cctcagtgaa ggtttcctgc    360
aaggcatctg gatacacctt caccagctac tatatgcact gggtgcgaca ggcccctgga    420
caagggcttg agtggatggg aataatcaac cctagtggtg gtagcacaag ctacgcacag    480
aagttccagg gcagagtcac catgaccagg gacacgtcca cgagcacagt ctacatggag    540
ctgagcagcc tgagatctga ggacacggcc gtgtattact gtgcgagaga cacagtgtga    600
gaaaccacat cctcagagtg tcagaaaccc tgagggagga gt                       642
```

<210> SEQ ID NO 105
<211> LENGTH: 869
<212> TYPE: DNA
<213> ORGANISM: Homo sapiens

<400> SEQUENCE: 105

```
gcaggattta gggcttggtc tctcagcatc ccacacttgt acagctgatg tggcatctgt     60
gttttctttc tcatcctaga tcaggctttg agctgtgaaa taccctgcct catgcatatg    120
caaataacct gaggtcttct gagataaata tagatatatt ggtgccctga gagcatcaca    180
taacaaccac attcctcctc tgaagaagcc cctgggagca cagctcatca ccatggactg    240
gacctggagg ttcctctttg tggtggcagc agctacaggt aaggggcttc ctagtcctaa    300
ggctgaggaa gggatcctgg tttagttaaa gaggatttta ttcaccctg tgtcctctcc    360 acaggtgtcc agtcccaggt gcagctggtg cagtctgggg ctgaggtgaa gaagcctggg    420
tcctcggtga aggtctcctg caaggcttct ggaggcacct tcagcagcta tgctatcagc    480
tgggtgcgac aggcccctgg acaagggctt agtggatggg agggatcat ccctatcttt     540 ggtacagcaa actacgcaca gaagttccag gcagagtca cgattaccgc ggacaaatcc     600
acgagcacag cctacatgga gctgagcagc ctgagatctg aggacacggc cgtgtattac    660
tgtgcgagag acacagtgtg aaaacccaca tcctgagagt gtcagaaacc ctgagggaga    720
aggcagctgt gccgggctga ggagatgaca ggggttatta ggtttaaggc tgtttacaaa    780
atgggttata tatttgagaa aaaaagaaca gtagaaacaa gtacatactc taattttaag    840
ataaatattc cattcaagag tcgtaatat                                      869
```

<210> SEQ ID NO 106
<211> LENGTH: 502
<212> TYPE: DNA
<213> ORGANISM: Homo sapiens
<220> FEATURE:
<221> NAME/KEY: modified_base
<222> LOCATION: (128)..(128)
<223> OTHER INFORMATION: a, c, t, g, unknown or other

<400> SEQUENCE: 106

```
catggagttt gggctgagct ggattttcct tgctgctatt ttaaaggtg atttatggag       60 aactagagag attaagtgtg agtggacgtg agtgagagaa acagtggata tgtgtggcag    120
tttctganct tagtgtctct gtgtttgcag gtgtccagtg tgaggtgcag ctggtggagt    180
ctgggggagg cttggtaaag cctgggggggt cccttagact ctcctgtgca gcctctggat    240
tcactttcag taacgcctgg atgagctggg tccgccaggc tccagggaag gggctggagt    300
gggttggccg tattaaaagc aaaactgatg gtgggacaac agactacgct gcaccccgtga   360 aaggcagatt caccatctca agagatgatt caaaaacac gctgtatctg caaatgaaca    420
```

```
gcctgaaaac cgaggacaca gccgtgtatt actgtaccac agacacagtg aggggaggtc      480
agtgtgagcc cggacacaaa cc                                              502

<210> SEQ ID NO 107
<211> LENGTH: 514
<212> TYPE: DNA
<213> ORGANISM: Homo sapiens

<400> SEQUENCE: 107
gaactcacca tggagtttgg gctgagctgg cttttcttg tggctaaaat aaaaggtaat       60
tcatggagaa atagaaaaat tgagtgtgaa tggataagag tgagagaaac agtggatacg     120
tgtggcagtt tctgaccagg gtttcttttt gtttgcaggt gtccagtgtg aggtgcagct     180
gttggagtct gggggaggct tggtacagcc tgggggggtcc ctgagactct cctgtgcagc    240
ctctggattc acctttagca gctatgccat gagctgggtc cgccaggctc agggaaggg      300 gctggagtgg gtctcagcta ttagtggtag tggtggtagc acatactacg cagactccgt    360
gaagggccgg ttcaccatct ccagagacaa ttccaagaac acgctgtatc tgcaaatgaa    420
cagcctgaga gccgaggaca cggccgtata ttactgtgcg aaagacacag tgaggggaag    480
tcattgtgag cccagacaca aacctccctg cagg                                514

<210> SEQ ID NO 108
<211> LENGTH: 200000
<212> TYPE: DNA
<213> ORGANISM: Homo sapiens

<400> SEQUENCE: 108
tgttcttgcc tcttcccctg gggtagagtc ctcctgtttt ccccagttgt tccctcccac      60
agctctcaca atctctgttg gtgtccccat cttccagatc tgctgccatg acctgcagat     120
taaggctctg attccataag aaactgaggg gagctgcttc tcaatagatc tttgatgggg     180
acctctgttc ccatatcagt tcatgagggg ctgctccagt gccctaggat gctgattttc     240
atggcttgct cctgcagggt aatatctgag tttcatagtg ggaatcagag agttgggtct    300
ggatgcattt cagaagtgtg ggctctcatt ctctcccaga cagtcacttt gggaaggata    360
gattcttgtg actgtaaagg ttcttcaaga gaatagcaca actcttcagt atgttgtccc     420
ttagaatttc tcactacaac acgcttaaca cactcgactt caagcaatgc aatgtgtatt    480
tgtgctccat cttgtaatgg cctacgttga atacgacaga ctgtgcctca ggtaatttca    540
tatcttgact ttattactct gtacaagaac ttgcctctcc ctagatttca attttttttg     600
ttttaaacct tcagttatct gaagcattta ataaaatttg cgaacttcca tcttttctgt    660
ttatctgtta ttgctgatgt tattgtttta aaaataaata tatatttctc attcatgtac    720
atttttaagc tgagcagcat attttttaagt aaaacctgga ataataaaag aatccaaaca    780
tttttcagct gccccaaaaa aaccaaatta tggtaaatgt gttcactgga acactactca    840
tcacttataa taaatatatt tctggtacac agagcaacaa agaaaaatat ctaagtgttt    900
atgctgagta aaatacgcca gacaaataag aatatgtacc atattactcc atttatgcaa    960 tttctttta gtgaaaaaga atctaaagca atatccagaa gatcagtagt tacctggaaa    1020
aagggtagac caaaggaagg ggaaaggagg aaacttacag aagaacaaga gaaaatgttg    1080
aggggagttc acttgtccag cttggaaatg atgggttaca tcatgttgat caattgcaca    1140 cttttaaatat gtgaagtcta ttatctgcca attaacactc gcaaaattta ttgcaagcag   1200
```

```
acaaatgaaa aattagacag agagaggatg gtataaagat agaaaatata tattaaatgt    1260
cagaaatgtc tgagaattta actcctgacc ctagttccgt ccttatttt aggtgaatgg     1320
tagcgtgcac caaaatcaca cacattctca gtacaggaag tgggttccac aaagcacacg    1380
aggtatgtcc aattcttacc aagatttggt tcagggagta acagtgatga ggaatcacag    1440
gcccagatac cggggctcac tcatctcaga catgacctcg tggacacaca cttagcccct    1500
cctccatgtg taggttgact tccacatatg taaatggaga aaccattgac tcctacagaa    1560
cataatttac agaaatatac aaaagataaa atagtgcaaa tacttatcac aacaaaattt    1620
cctaataaga cagtgtattt tccaaatacc gtaattgtca cccaactcct gtggggccgt    1680
gtcattttat ctggggtctg ccgtctcctc aggattccca ccccagagct ctctatgtag    1740
taggagacaa gcaaataggg ccctccctct gctgctgaaa atcagccaaa tcctgaccct    1800
gcagctctgg gagaggagcc cccgccccgg gattcccagc tgtctccact tggtcatgaa    1860
cactgaacac agaagacaca ccatggagtc tgggctgagc tggattttcc ttgttgcagt    1920
tttaaaaggt gatttatgga gaatgagaca cactgagtgt gactggacat aagtgagaga    1980
aacagtggat ttgtgtggca gtttctgacc agggtgtctc cgtgtttgca ggtgtccagt    2040
gtgaggtgca gctggtggag tctggggag gcttagtaaa gactggaggg gtctctgaga     2100
ctctcctgtg cagcctctgg attcaccttc agtagctctg ctatgcactg ggtccaccag    2160
gctccaggaa agggtttgga gtgggtctca gttattagta caagtggtga taccgtactc    2220
tacacagact ctgtgaaggg ctgattcacc atctctagag acaatgccca gaattcactg    2280
tatctgcaaa tgaacagcct gagagccgac gacatggctg tgtattactg tgtgaaagac    2340
gcagtgagaa gtcagtgtga gcccagacac aaacctcctg cagggtacct gggacaacca    2400
gggaaagcct gggacactgt atactgggct gtccccaggg gcaagtccag gtggtataag    2460
gctgggtttc ctgtcatggt ctagggttgc cttgttagca aattacccca gggaccatct    2520
ctagatttcc aattctgtaa taacatttga tgtcgtctct gactgcacaa tgtcccctca    2580
actttgtatc tttttttttt ttgtaacagg aggacacatc ctcaccctgc agaagcctga    2640
gtgtcacttt gggggcagaa atgacctgcc ttgatcacat tgatcactgt cctgaggaaa    2700
atacccccaca ggggacccccg atgactccag caaaggctct gcctcaaaac cattgaagag   2760
tccttccttt cattagaatt gaccacagca cctgggcttc agcacaagcc ataccacaga    2820
cgtcacaaag cagcagcttg acacctgatc caggtgcatt ttctcacctt tagaagctga    2880
gagaggggtg tactctcaag gtcaacacac tctttgtggg ttttttacaca gaaaacctgg    2940
ttttacttta tttcatttga agataaatga acaaatgtgc atctataaat gattgtaatt    3000
ttcacattta ttccaattcc aatatttctg aattctgcat aatgtcctgg cacaaggttg    3060
tgttttctat aggtattttt caacagacca agaaaatgca ttttccaatt tccctgtttt    3120
tcctccatgt gcagagacct tgagtagagc acgtctgact gtgtttgtct gttttcacgc    3180
tgctgatgaa gacataccag agacgaggaa acttacaaca gaaagagttt tattggactt    3240
acagttccac gtggctggaa aggcctcaca atcatggtgg aaggtgaaag gcacatctga    3300
catggcggca gacaagagaa gagagcttgt gctgggtctc cccttttaa aaccatcaga     3360
tctcatgaga ctcattcact attaagagaa cagtgcagga gagacacaac acccataact    3420
cagtcacctc ccactggtcc ctcccacaac attgagaatt atgggagtta cacataaaaa    3480
tgagatttga gtgaggacac atccgaccca tatcattcca ccgcaggttc cctcccaaat    3540
ctcacgtcct cacatttcaa aaccaatcat gccttcccaa cagctcccca aaggctaaac    3600
```

```
tcatttcatc attaacacag aagtccacag tacaacattt cacctgagac aaggcaagtc    3660
cttcccactt ataagcctgt aaattcaaaa gcaagttaca agcattgggt aaacacaccc    3720
attggaaatg acagaaattg cccataacaa aaagacccca tgcaagtcca aaatccagca    3780
gggcagtcaa atcataaagc tccacaatga tcacctgtaa ctcccttct cacatccggg     3840 acatgttgat gcaacaggtg agttcccatg gtcttgggca gctccacccc tgtggctttg    3900
cagggtacag cctccctcct ggctgctttc acaggctggt gttcagtgtc tgtggatttt    3960
ccaggcacaa agtgcaaact gtcagtggat ctaccattcc agggtctgga ggatagcagc    4020
cctcttctca cagctccact aggcagtgcc ccagtaggga ctctgtgtgg gagctcgggc    4080
cctatatttc ctttcctcac tgccgtagca gaggttcccc atgaatgagc caccactgca    4140
gccaacttgt gactggacat ccaggtgttt tcatacacct tctgaaatct aggcagaggt    4200
tctcaaaccc caattcttag cactctttcc ataatggttc attttttgg cctgttcatt     4260 actggtattt ttcaaaggaa tctcacttga atctttactc ttttgcaatt tgtctccatg    4320
acaatgttgg gaagttttat ctccaccatc ataacatgat ctagtgatct cacacatttg    4380
tggcaaacaa tacctacaaa ttcagaagct ctttgctttt ctttccatga aatataattc    4440
tttctgttct gtgtataagc atatcttagc aaccctgcac acacccacat agatgtccac    4500
aagcctatga attattctct gtaaataaaa acttatatca atttccctca atgttcataa    4560
ttctcctgag tgtgaggaag ctccttctcg atctgttcaa acaaaatgcc cagagaccat    4620
ccggtaggta aggagttcac ctggctctgg tgtggggtct gtctctttcc ctctgttgtc    4680
ccacaggtca gcccagttgt tcaggtccta agaagaaagc ccaggtttgt cctgatttta    4740
aaacacttca aacttctgat gactctcctg ttacccacat ccatggagat agattattta    4800
ttatataatt caccaaacta atgtcaaatg tccaagttgc aataccgcac atcctagggt    4860
atgttcatgc aattcaatgg aggagaaagt ctttcagaga cagatggatc tgaaatgata    4920
aatatgtggg taaggactct ggacttgagt gtcattgtcc agccatgttg cacaagtgtg    4980
tcctgtcagg gaaggatcag agttccttgt gctctcagag ggaagggtc acagagttcc     5040 tctctggttc ccaggaaagg taatcgcact aatcttcatg atcttcatga gactatcctc    5100
cagtgctgac ctgttataga gttttttgtct gaagttctca ctgcaatccc caatctacat   5160
attttcaatc agaagtgttt agaggccagg acacatcttc aaggtcacac attgagaagg    5220
atgtagatat gtcccactac cttctcctga gatctcagac agaatccag atttcaaaag     5280 gacacagaag gacagctctc aggtgctttt aaaaaatgac ccacttccag ggacagggag    5340
cttccctata accatggtgg atgttctgaa ctacaataaa cattggatgg atccaggatt    5400
gtttgaagtc actgtcatta ttacattcag ctgctgtttc aatgtgtctg aagtagtaaa    5460
tgacaattta gatgacaatt tatatgaatc ttcaagggta gaacaatatt gaccatattc    5520
caaaatctgt ccttgatcca tgatcacact catctcccag accaggtcct tcagcacgtc    5580
tctttacctg aaagaagagg actctgggct tggagagggg agaccccaag aagacaactg    5640
agttctcaaa gggcacagcc agcatcctac tcccagggcg agcccaaaag actgggcct    5700 cctcctcct ttttcacctc tccatacaaa ggcaccaccc acatgcaaat cctcacttaa    5760
gcacccacag gaaaccacca cacatttcct taaattcagg ttccagctca catgggaaat    5820
actttctgag agtcctggac ctcctgtgca agaacatgaa acatctgtgg ttcttccttc    5880
tcctggtggc agctcccaga tgtgagtatc tcagggatcc agacatgggg atatgggagg    5940
```

```
tgcctctgat cccagggctc actgtgggtc tctctgttca caggggtcct gtcccaggtg    6000
cagctgcagg agtcgggccc aggactggtg aagccttcgg agaccctgtc cctcacctgc    6060
actgtctctg gtggctccat cagtagttac tactggagct ggatccggca gcccccaggg    6120
aagggactgg agtggattgg gtatatctat tacagtggga gcaccaacta caaccccctcc   6180 ctcaagagtc gagtcaccat atcagtagac acgtccaaga accagttctc cctgaagctg    6240
agctctgtga ccgctgcgga cacggccgtg tattactgtg cgagagacac agtgagggga    6300
ggtgagtgtg agcccagaca aaaacctccg tgcagggagg cggaggggac cggcgcaggt    6360
gctgctcagc gccagcaggg ggcgcgcggg gcccacagag caggaggccc ggtcaggagc    6420
aggtgcaggg agggcggggc ttcctcatct gctcagtggt ctccctcctc gccagcacct    6480
cagctgtccc caggggtcct cttttcttat tatctgtggt tctgcttcct cacattcttg    6540
tgccaagaaa gaaatgagga agacaaattt tcgtctgtag ttgaagtttc accaattact    6600
aggaactttc ctagaagttc ctgcatggcc cattatagct tacagattaa atatatatca    6660
agcttctcat ctcttgattt gtgtcatcaa ctgaattgtg ccctctttga aattcatatg    6720
cagaaacctt aaattcaatt gatgtatatt ggaattttaa tgaaataatt aaggttaaat    6780
gtggtcataa gtgtaagact ctaattcaac agacgtgtcg tctttataag aagaggaaga    6840
gacaccagag acctctcact tttcacgtgc aggcagagaa gaggccatgt ggagacgtaa    6900
tgcactagaa ggtggcccag tgcaagccag gaagaagcct caccaagaac caaccctgcc    6960
agaacattga tcttcaacat tcagactgca gaattttaag aaaatcaata tttgttgttt    7020
aagccaccca ctcctgttgt cttcttatga agatccagac agactaatac cacataactc    7080
tgttagcgct gtcccctgga tgcagaatca gcccgctggg gctgggcaca tctctcagat    7140
ttccacataa agtaggcaaa aaatagtagt tctgatataa aaatttgtca tgtccctgtt    7200
ggccaatttc tgggcaaggt cttttaaaga agccctgggg gctttgtcac aaaagttgcc    7260
ttttatcatt tattaggaca taactgatga acaatgagta ccagttggat ggagactgac    7320
cactgaccat cttctgctgt ctcctaagta tgccacagaa aaccacacca acattactct    7380
atgtcttcaa ctttctaaat ttgcactgat tggtatttaa ggcaggccca gcgttgaata    7440
actcctttag ttttttgcttc tctgggaaag gtcttatcta tcctggcctt ggtcttcaag    7500
tttcagcaat tctgggaagc caaggacgcc tctatctcct cctccatgct ctgcaactca    7560
cctgagaaca gctttctcat tggaatgtct tctgtttaag gaataagagt ccctgtttca    7620
ggcttgggtg cctgagtaca cctactggat ccagcccagg attggagaaa cttcccagaa    7680
cacatcacct gagaaatgac cagtcacact gttacacttt cacaatttcc gcttcctcat    7740
gagaaaatta aaattgcaga gacttttca taagcgttgt gccatgtcct ttcttgtttt    7800
cttgcctgtt catttatgtc agaccaggtg ccacatctat gtaatcaggt tagaatcctg    7860
cctccagtaa cacatgaaaa ggacctatgg ttgtactttt ggtctttgct ccaaagtgta    7920
aagattacaa aagtcatcac cctcattctt atgccaagag tcatctgcac aatctgatct    7980
tcaatacatt ttagaatcca tcaaatgaat gaaattccat tttttaaatt accaccccaa    8040
aaactagaga gatgggcatg tccagaatag cagttgatgg ttgcttaact ggaagagaag    8100
tttcagaagc cacaagctgt tgaaggcact tacgtggtta gcactataga cgtctgcaag    8160
acagatgtgg actagggtga aatgacagtt ccagagggcc gcactctcct cagtcttctg    8220
gaatttccct ctagaaatct ccagaatcta aaaaatacaa tccaaatatg tttcctatgg    8280
gtcataactg gggaagttta attactgaaa aatataccag gagccttctc caaaagatcc    8340
```

```
tacagggaag aacttttcca gaacctcata ctatgtgaag ggaagaaaaa tctgcccatt   8400
ccagatccct ccccacttcc tccattatta tacaaatgag taaggttagc caatagggta   8460
agatgtaagc aaatagtcca gggaaactga agccacaaaa aggagtaaag atgaaaattc   8520
agcttttccc ctggagatgc ctggtcaagg tcacagccca gaaaaggaat ctgattgagt   8580
ctctaggttt ccatggtcag aacaagcagt gctgacccgc actgcacaat cctttctaac   8640
caggatgatg gctctggatt aaatatgaga gtgtgccaat gcacagtctc tgaggagaac   8700
atagggacac taaaaaagca atggcaggga gttagacaag gacagtagag caatatgaag   8760
cctctgacgt gaacattttt aaaaacaaga tcttggaaac tccctcattc acctcagctt   8820
cttttatcat gaagactttc caagattctt aactgagaca agaaaataa caacctgcat    8880
gcacttccga agtctccgct tgtatcctgt ttgctttaga tctctaggag aaaaatgtca   8940
gacacctggg cctagtgtca atgtgggagg cactttctac agatgaggcg caagaaggaa   9000
gggaaaacgt gtgttattgg aatagtggat atgaagtgtg ctctcatctg aaagcatctg   9060
cacctgctgg aaatctcaga tgcaacattc aactgcaaga accaaggcac acccaaatct   9120
cctgtaagat tttggattca ttatccactg attcagtgca actggagctt cagagaaggg   9180
gctccctcct gtgtcatagc atccttgctt tgagttcatt agatttagta aggctaatca   9240
attgttgaa gagatggtgt cagcagcgta tgctgtcact gaaggagtat tctaaaccag    9300
gacaaagcca tttcatgtta ggcgagggaa gctggcggaa aatgctttat gagccccaca   9360
ggaacttcct tgcaaggcaa gggctgggct ggaggggcg cgcaggaacc gcccagcaca    9420
ggttccatcc ccggaggggt gcacaggagg ctggggacga ggttccctct cagcgcctgt   9480
gtcttccttt ggcaacaaaa aaaatcctaa gtgttcaaga agttgctgat gtgtctttaa   9540
gtatcctgtt ccgtcagagc cttcctata actgaaggca accagaactg tgttttaaag    9600
tcggttccga ggactgcaag tatcttaata gtgaggatat aaaggatagg aatggtttta   9660
ctaattgaaa ggatacagaa ttgtgggtt ccgaggactg caagtatctt aatagtgagg    9720
atataaagga taggaatggt ttcactaatt gaaaggatac agaattgtgg gagtcactat   9780
gttcctatga ataaaaatt cagatttcag tgttaagtaa tgttgcctac attgtgtgag    9840
tgacagggca gtggtggatc tgagagtgtg gcaggtgcac agacctagtg agtcagaaat   9900
caatatgaa agatgaggat ctatggatat gaactgaaag taagtaaaca gttcatgaaa    9960
ttctattaaa tggagtagga aataaaaccc aaacttatcc aaaacacaaa ttccttggcg  10020
attattttgg gagcagtgag ttcatcagga accccaaact tctcttacgt cttctgattc  10080
ctgttgtcca tgagatgaga aattcagctc taattgtgca tcacagggca aatctgtaaa  10140
ccaggagtgt ttctattgag gatcatggtg gatcaggatt ccaggcaggt gctggagaca  10200
ctgtctcagg agcgcccaga tgatctcagg gggacctgct ggacactcac gtggaacatc  10260
agcagtcact ttctcagagt aaccagtgag ctgtgctggt gcctgatggg actaggatgg  10320
ggtcaaggca cctttctcagt gtcatggaga gtgattgttc cagaaatcat ccaggtggtc  10380
tctacgctaa tcaaatatgg gttcacaggg aggaacatgt gctctgggtg cttggtcttc  10440
agtgaaagga cgtctggcca ccaaaagttt gtaaatggag cagggcatgc atttcctcaa  10500
ggaggattag ggcttggagc atcagcatcc cactcttgta aggctgatgt gtcatttacc  10560
ttccctttct tatcccaaat cagggtcttc agctatgaaa tgctctgact catgaatatg  10620
caaataacct gagatgcact gaggtaaata tggatatttg tcagccctga gagcatcatc  10680
```

```
cagaaaccac atccctccgc tagagaagcc cctgacggca cagttcctca ctatggactg    10740
gatttggagg gtcctcttct tggtgggagc agcgacaggc aaggagatgc caagtcccag    10800
tgatgaggag gggattgagt ccagtcaagg tggctttcat ccactcctgt gttctctcca    10860
caggtgccca ctcccaaatg cagctggtgc agtctgggcc tgaggtgaag aagcctggga    10920
cctcagtgaa ggtctcctgc aaggcttctg gattcacctt tactagctct gctatgcagt    10980
gggtgcgaca ggctcgtgga caacgccttg agtggatagg atggatcgtc gttggcagtg    11040
gtaacacaaa ctacgcacag aagttccagg aaagagtcac cattaccagg acatgtcca    11100 caagcacagc ctacatggag ctgagcagcc tgagatccga ggacacggcc gtgtattact    11160
gtgcggcaga cacagtgtga aacccacat cctgagagtg tcagaaacgc caggaaggag    11220
gcagctgtac tggcatggag gggatgacaa aggttattag attgaagatt ttcttagaaa    11280
acgacttcaa gtcattaaag aagaggaaca acataaatgt gtatttgtga aattttaatt    11340
gagagatttt tcatacaaca tttattctgt aagctatttc agggattgga atatgaatca    11400
aattaataaa gctgatatag acatcctctg aaggcatctt cgtaaacatc aatttctgaa    11460
tcagtgttgt aaatattttg gaacacagac acaagatcac attttactc tacttttatc    11520 tctatttta aaaaatgcca aaaagaatct tattttgtgc atgccccatt ttgaattccc    11580
accgtcaatg catgatagtt cttggttttc ctcattcaag ttgtcatttg tcattaagag    11640
tgttgtgtgt tttaaccatt ctaataggtg agtaacggta tctaattttt atttaaatgc    11700
acatgtccct aaaaaattca tatttaacaa ttttttatata attttggtg agatgcctct    11760 cgtgatattt ggttcatttt ttaaatgcat tttttatcag ttgtaagtat gcttgcatat    11820
tgattataaa agtcatttaa caaattaaaa taattcattt aacaaatatg catcttggaa    11880 ttttttctc caagtctgca gttgtctttt actcccttat ccctgtgtat tgcagaaaaa    11940
tgtttgtgtg tgtgtgtgcc tgtgtatgta caaatttaga ttttaaaaat gtacatttt    12000 attcatttaa agatcatgtc tttggcagta tatctgaaat ctcattgtaa aagacacaat    12060
agtcattatt ttttccatgt ctctaatctt aggacacaat caactcatga gtgtttaacc    12120
ttccctacct gattggagga ctatccacct gagacatttg gaatacttct gtaaggagat    12180
gtgtccttcc cattatttct ttatttagtc atctattgat gttcctattg gtttatggat    12240
gtctatttca tactccgaag aagatccttg ttacattact tgtttattg ttcaaaacac    12300 cacagcttta ttaggtgctg ggagctcatt tagtttggat cctgcatcct tacagcacac    12360 ctcatcttt tgttttaga catttccctg tttccaagta ttacaataaa ttctaagctt    12420
gttctctacg ttacctttt tgtacataga atcagccatt tttctaaaga ctgctcgttt    12480
ttcatgttaa agaacagtat tgaaatttaa aaatgtgatc ctgggtatgt gtgttgttaa    12540
tgtggtatca gtacttcttc taggatatct ccaccaattg gcctagtaaa tgggcatgtt    12600
tataggaacc caagtttatg gacacatcga aactatttat gtatctaatc ctctgtaatg    12660
tgattacatt aaaaatgaga acacactggt gtctccatcc aactatgcta ccatatggat    12720
gtttccagcc ttccttccct cactgtccat aaccacccac tgcaaagtga ggaaccccat    12780
cccaccatat gccattttat tacttagctg cacaatttca ggacacatgc atagcagtat    12840
cagaaatgta aagctcgttg gaaacatgtt tatctactag aacagactgc ttatgtgcag    12900
tttctttaca ctgtaaactt atagaatttc ttcattttca aagttgctta ggtcagcaac    12960 ttcatttcc actctcctca gtgaagtcat ttcaatgaca atgtataatg tcattttatt    13020
gaaattcttt caaagccaaa actatagtcc ggtaaacata tagaggatat tcaaggaatt    13080
```

```
tagagagtgg gtataaaata agtaaaaatg gcactgttta agaagagtaa aattgttttt    13140
agtgatatac aatggttgag acacaacaca attaatttgg ctaagctcat acttttgtga    13200
cagaaaatat aaacctaaat atatacaatt tttgtaaaaa aactttagca gttcattaac    13260
cccagggtta aacaagactg tgtaaaatta tctaataact tatttgatga gggtggggat    13320
atcatgagac atatgcaaca aagaatgaag gcattttcct catttgcatg taagatgtta    13380
ccattcacta aagaccttta ataaaaaaaa atttctacgt gatccagtat ttttttcctt    13440
ctgtcaagca ataactcat aggattcttt tctttccttg gttgagaaag attttcctac    13500
aagcttcagc acacgtcagg catacactgt ccctgaatgg gcatttaccc tcagatgggt    13560
acacacacct gtcaacatgg gggctcttct gtcagacaaa cacaccttta ctcatgtgga    13620
ttcttccctc agacaaacac acatgtcccc acgtggactc tttcctcaga ttacaacatt    13680
tgtccttaca tttactattt cctcagaaaa cagacattgc atcatgtggt ctcttgtctc    13740
agacaagcaa acatgtcttc agtcagataa gtctgtggat ttccacattg actgtttcct    13800
tacacaagca cctatatcca atatttaact gttttgtgag aaatttatcc cttttctctg    13860
gaaatgtatt tttatgttct tactggacat attttttaat aatgtttggt actatgaaga    13920
tacccgaaca ctgtccatac gagagaataa gaaagagtaa taagcagatt aaccctgtgc    13980
atccagaccc aggagtcctt tgatcctgcc cttccgaaat ggagacacag aggaaggatg    14040
agcaatgctg agcagtgcac ccatgaccac aaaaggaaag acatggcaat gtgtcccctc    14100
ccctcctcat gaaaggcagc tcatcccctg ttccttcagg ccctggtgag gagccacccc    14160
atgtatattc ccttgatcag tgtccacacc atggggtctg cactgatctg ggcttccctt    14220
ctcatcaccc tcaatattag tgtcccttgt gaatcaggtc cagctgcggc tgttccacat    14280
ggggccgttc ttccatttcc tcagtgtttg cagaagtcct gtgtgaagtt tattgatgga    14340
gtcagaggca gaaattgta cagcccagtg gttcactgag actctcctgc aaagcctctg    14400
atttcacctt tactggctac agcatgagct tggtccagca ggcttcatga cagggattgg    14460
tgtgggtgga aacagtgagt gatcaagtgg gagttctcag agttactctc catgagtaca    14520
aataaattaa cagtcccaag cgacaccttt tcatgtgcag tctaccttac aatgaccaac    14580
ctgaaagcca aggacaaggc tgtgtattac tgtgagggac acaggagagg gaatatctgt    14640
gtgagcccag acacaaaaat ctctgcagag agacaggagg gaactgcatg gtagatgctc    14700
ctcataacca caaggggca gtcaggacca tcaggaggag ctcaggacac ctgggggtgc    14760
tcagaaccat gagggggtgct caggacatcg ggggctctca gaaccatgag gggtgctcag    14820
gacatcaggg ggctctcaga accaccaggg ggcgctcagg acacctgggg gcgctcagaa    14880
gcatcagggg tgctcaggat atcagagtgc cctcagtacc acgaggggc gctcatgaca    14940 ccaggggcac tcagaaccac cagggggggc tcagtacacg ggggttctct taggaagcag    15000
ctccacatca ggagcctgag aggctgtgat tgcgttttaa acctgggtga ttcccgacct    15060
ggtcaagaaa aagtctcccc caggatctct caccatttct tcttggtaat tccatgattt    15120
ttttttacct acaaaacatt aagttagaac agggatttaa ttcaacttt aattctgcag    15180 attttccgag taatagtagc aatgttccct caggacaatt tttaaaattg gctatttata    15240 tattttatt atgtaaaatg atactatctt gaaaatagta aaattttaa aatcataccct    15300 ctaatcccag cactttagga ggttcgggca ggcagatcag ttgcgctcag gagttttaga    15360
acagcctggc aacacattta gatctttcc atacaaaaag aaaagaaaa agaaaatagc    15420
```

```
taggtgtggt gctacctctg gtaccagcta tttgaaagtc tgaggtggga ggatccctta    15480
agcctgggag gttgatgctg cagtgagctg tgattgtgcc actacactcc ggcctggttg    15540
acagagtgag acccttctt aaaaatacaa actgtttcaa taagtagagc tttgtgtctt     15600
tgtgctgtaa taatcagttg tatatatttt ctaactgtaa ctcagcatat gcatggtgtt    15660
ctgtttcttt ttctttcatt tgctgttggt ggaaattaaa cacctcttta aacgctcttg    15720 ttctccctt tggttcgctt cgggtgtcct gtttaacaga ctatttcttc atcttccctt     15780
tttctttgaa agtcttttc tttctcagtt tccatgcagg ataaagaaag tccctttact    15840
ttctgtcctc caagtctggt gaacagctcc cttctcttca taaccactga agccaaccaa    15900
gtttaggagg ataacagctc tccttagaat atgctcgtct acctggagac tctctgccct    15960 cctcacccctt ttctagggtc ctgcacacat cacactcatc ccatcccctc ccttccctaa   16020
gtaccacaga gtgggctctg cagttcctgc ttccctgtgt gtgctcagcc ctggggctca    16080
ctagtgcttt gatgatgacg ttcaaatccc catgtgctta gactctctaa gaccaccctc    16140
taggaagatg ccattgtgag tgagtcctgg aaatcatggg ctgtgttcag tttcatattg    16200
ctggatcttc tctattttaa aggaatactg gcaattaaga ttagagtttg tattgaatat    16260
tcatgccaaa aaagttttct ttcaaaactt ttcaaataaa acaattttc ctgcctagtt    16320 tgaaaactac aatgtaaatt caacaaataa tataatacaa ttttaaaggt gacgtttgtc    16380
ttattggtta ttcaatttat taaaaacaga agatatttaa aataaattcc attgcacatt    16440
taagtgatgt atttgacaag aatggcattt acatacattt ttaccaaaac acgtatttaa    16500
atatatttgt ctttttaata ttggtagagg cagacataca cgtagaaaag catcatttttg   16560 tactacaatc tcaaactgta aacacaattt aaattcagtt aaataattag aataatatga    16620
aacaggccgg gcgtggtggc tcatgcctgt aatcccagca ctttgggagg ccgaggcggg    16680
cggatcacga ggtcaggaga tcaagaccat tctggctaaa acggtgaaac cccgtctcta    16740
ctaaaaatac aaaaaattag ccgggcgcag tggcgggcgc ctgtagtccc agctacttgg    16800
gaggctgagg caggagaatg gcgtgaaccc gggaggcgga gcttgcagtg agccgagatc    16860
ccgccactgc actccagcct gggcgacaga gcgagactcc gtctcaaaaa aaaaaaaaa    16920 aaaaaaatg aaacaaatag gtgcgttgtt ttggtgttta gatatacatt cacttttgca    16980
tgggcacatg tatgtgtctt tgctgggctg ttgtgtatgt atgtgtgctt gtatgaccat    17040
caagttttca aatacatcat taaatttcat agttacattc gtcttggcca ggcacggagg    17100
ctcaggcctg taatcccagc attttgggag gcttaggcaa gcagatgact tggagttaag    17160
agttcaagac cagccttgtc aacatgccaa aaccccatct ctacgaaaaa tacaaaaatt    17220
agccaggtgt tgtggcacgt gcctttagtc ccagtcgac agggaaatgc tgggtcagaa     17280
atcccacaca aagtctctac ttggttacca cctaatggaa ctgtaggaag aaagccacca    17340
tccttcagaa cccagaatgg tagatccact gacagcttgc acagtgtgcc tggaagagcc    17400
agaaacactc agtgacagcc catgagtgta gccagaaggg agattgtgcc ctgcaaagcc    17460
acaagggcag aactgtccaa gaccatggga acccaccagt tgcatccggt aacctggatt    17520
tgagacatgg agtcaaagaa gactattttg gaacgttaag atttgactgc ccagctggat    17580
ttcagacttg cacgtggcct gcagtttgga ccaatttctc ccatttgcaa tggctgtatt    17640
tacacaatgc ctgaaccccc attgtaccta ggaagtaact tgcttgtttt ttatttaca     17700 ggctcataga tggaagggag ttgccttgtc tcagaaaaga ccatgggctg tggacttttg    17760
agttggggct caaatgagtt aagacttcag gggcctgttg gaaagtcatg aatggttttg    17820
```

```
aaacgtaagg acattagatt taagaggcgc cagtgttgga atcatatggt ttggctgtgt   17880
ccctgcacaa atctcatctt gaattgtatc tcccacaatt cccacgtgtc gtgggagaaa   17940
cccagtggga ggtgattaaa tcatggaggg agttcttctt tgtgcgttat tgtgatagtg   18000
gatgactctc atgagatctg atggttttaa aaaacgggag ttccctgccc tctctttgtc   18060
tgctgccatc tccatgtaag ataaaacttg ctcctccttg ccttccacca tgatgtggag   18120
gcctcccaag ccatgtgtaa ctgtaagtcc attaaacttt ttcctctata aattactcag   18180
tctcatgtat gtctttatta gcagtgtgaa aacagactaa tacagcaaat atcaatctct   18240
taaaatattt tgttgttctg catgtaatat agcacagtct aatatgggag gtaaaataaa   18300
tcatccatgg accttcagat ataagtcata gggtaattat gcctgtgtcc ctgaaggagt   18360
gaactagagg ttatacacac tagtggcact accttttggca aagggtgttc aggggtttct   18420
gaaagttctg ataattttaa ttttaaaatt gaatttacta tgtatttctt catcaacctt   18480
tccagaagat ttttggcagt aagaacagcc tagtattgga gtaatactga tgaattagag   18540
agttattttg taattattct cctgagattt gcatgaatca attgatatag aagttcgtat   18600
gtcccaagtt gaaacatcag aatcaagaag gcttcatcac ccttaatggc tgtggttttt   18660
ggcaaggcag tacttcaatt cagccagaaa gagagacaac aataaaactt tcaaatgcag   18720
gggagtctga cctcagtctc tctctcttat aaaggcaaag gcaaagctgt gccacatcaa   18780
gatttttctt caagccttca gagtcaacat tgggaatgga aaagccaatc actttgtcct   18840
tagagaaggc gaagatctga gaggaatgca gagttgtgtt catgaaggtg atgacattgt   18900
tatttcttct cctttgccca gtgactgctt tcaagttgag tgtttcagat gtcagacctg   18960
acttatagggg atggttgtga ctgcacgtgt ctgacagggg ctgagactct atatctctaa   19020
gtgtcctgtc ctaggagcag ctacaggagt cagccctaga ctggaagtgc cctcactgac   19080
cctctgcctc acctgtgcag cctctggcca gttgaagaaa gttttatccc tggaacatct   19140
tttgtcaaaa ccactccaac tagtattcat gacctatggt ccacaccctc aagtacacag   19200
acatgatcat gctatgactt ggtgtctaga agatccctgc acttttaatt ttacctctaa   19260
tattagactc cactttatca catgcggaca cagcagaata ttttaagact ttcatatgtt   19320
atgctgaaaa attcaatagt tcataaaagt ctacttccca tcactgccag tgtttactac   19380
tgagtaagga tctgccatcc cctagggagg aactataatg gatggtgtgc cctgttagtg   19440
gttatgggaa tgaatccatc ttgtggcaaa tggcagcatc ttcttgtttt gcaagattaa   19500
atagttttct atggtgtata aatacaacat tgtctttatc catttgtcta tctactgaca   19560
ctcagattgt ttccatatat tggctaagat taatagtgtt tcaataaaca taggattcaa   19620
ctatcttaac aaggtggtaa tttcatctgc tttgggtata tttctaaaag cagaatttct   19680
ggtcatataa catttccagt tttaattcat ttggtgcctt tatattgctt tccataattg   19740
tgaaaatata gagtggtata gccattatga aaaacagttt cagttttgag gtatgatcca   19800
taaacaaata atgtttgatt atggctctcc atgagaattt ctaataaata tgatagaagt   19860
caagaaagcg tctcacatta aagcaaggat taatttatc ccttactccc tcaaaagcaa   19920
aagattggaa gcatgcatga tggaggctgt tagcagggtt cagaatgata tcataaaagg   19980
aaactcagtt ggataaaaat gttgggcttt cagtcatagg tatgtcgata ctcaatatga   20040
aaccgcgaag tcaaatgagg atctagaatg tgttcacttg aaccaacagc acattctcag   20100
acgcacctat tgctgcatca caagggtgat gaactttttga aacaagtaaa gtgtgagtgc   20160
```

```
acagtaagtg ataaagttat cacctttaca tgaagtttgt tcaatatgcc aaaggcttgt   20220
acagattaat catacacaaa tatacacaat gtattttttgc atacacagat gtctagagga   20280
tgattctttt agggaaaatt cttcaggtca cagaaatctg tgtaagttgg aggtcccatg   20340
aaaaagtatc tctttataaa tactggtcta ttgctcaatt agggaaaatg atctctgttg   20400
gagaaagctt ccaatttggg agatttcttc attgcttctt gagttgtaag acatgaacca   20460
aaaaattgac tggagttttt tggagtttca tggctggagt ttcatggctg tgttgttaaa   20520
aatttcttat acggtttctt tcaattattt gagatcagtt tttctgattt ttttctccag   20580
tagataaatt ttcacaagat ctcaggaaac catgtctctg gtgctttagt ttgaaaaact   20640
aacttcctag gtaaagaagc ttctgtctaa ccatgatgag ctcatttctt ctgcatacca   20700
tgaagtttga gaccccattg tccagaatca tgaaaatttt acactccagt ttactgaaaa   20760
tcttgacttt gaatttaata ttgattggca ttgacaaaaa tggttcattc ttggatgtgt   20820
cctaagttgc tcacccaaca tatcagtgga ctgagaatct tccattagct ccctctgtcc   20880
atagcactga gtctattgac aatctttgca gtcctctatg aaggagagtc ctgaggttca   20940
tcagattctt gtagacactc agatgaacca aaggaattaa cggaattgag gactgccagc   21000
catttccaca acactaggaa taattaccat ctaagtgtaa aggtctacat cattcagaat   21060
accctgcatg acaggctgat gcaaaaaaaa atccaaccct gcagaggctt cacagcaacc   21120
ctcacagttc cttcagggaa gaaataatct ccaagttcag tgagtcagta aagctgttct   21180
gagctacagt aaacattgga ttgggcccag ttttgtctga gttcaatgtg attgttatac   21240
tcagctgctg atcctatatg gactgagtat ggataaattta aatgagcctg gctgcgtggt   21300
ttgttatatg aaaacctgaa ctaaatataa ataagggca tgtctggact agcatgaggg   21360
tgagagattc tgggagctcc acccccctta ctcttattgc cctttcctcc aggaacctcc   21420
aggtcctcag ggtgagaatc cacacagatc ccttcatggc tctattgcca ggagaccaaa   21480
tctctgataa aatcactcag accttcttca gacagacaac ccagggaaag gcattttta   21540 caccccttatg tatgtgggga aggtaatcc atacccatta gaagcccctg ccagcagcct   21600
aactttatca tgaaaatggg taaaattagc caataggggt acatttaaga aaatttttcct   21660 gtgatgttcc atccagaaaa gagcaaaaat cagcttcaca cctggagact tcctgtatcg   21720
ggcacagctc agagaaagaa gatcaccaca gaattaaaat gcaactgtaa gaacatgtaa   21780
tgcttccgtg ttccacacat tatgtctcac cagtttagtc aatatggatt aaatatgaga   21840
gcgtggcaat gcacaaactc tatctgagga ggaaagtcag agaaaaaatg ttaaagaaaa   21900
tatggcaatt tgaagcctct gacaccagca acttcagcac caaggaaatg atttcaccct   21960
cattggcctc aaatttactt ttcatggagc attttcaggg ttccaaagtg agaccaggtg   22020
aattcaatgt gcatgcactt ctcaggtgtc cacgtgtatt ttgtttattt tatttctatt   22080
tgcagaaagt aaacacatat tcagccttag tgtcagtgta gggagtgctt tccatgacat   22140
gaataccaga aaaaaggaa aaacatgggg ccaattaatg taaaaattag ccactgtgtg   22200
tgtgtgtgtg tgtgtgtgta ggtgtgattt gaatactaga gttggagtgg gcttctatcc   22260
acatgcacct gcacctgcag gtagtctcag gtgcaataat caactgcctg acctaaagg   22320 aaacaagaat ctccccaaac ccctgaagag tgtttgggtt taccgtgtgt ccagtgattc   22380
agtgcctcta gagctccagg aaggggctcc cccggtgatg cctgagatct tttcttcagg   22440
tctcccctgc agagttcctc tgggtttcct aagggcaatt cactatttca aaagatggtg   22500
tgagaagcac atgctgtcac taaaggagaa ttctgagcca cggcacagcc actttatact   22560
```

```
gggctagaga cactggtatg aatatactct gtaagtttag acagaaagcc tcgtgcatgg   22620
taggggctgg gctgcagggg gtgctcagga taaacgcagc acagtctccc gccccagagc   22680
aggtgcacag gaggctgggg aggggttcct ctcagggcct gggacttcct ttgaaaatat   22740
ctaaaataag tatttcacaa gggctgctgt tgtttgtata aatatcctat tcaattgtga   22800
gcatttatca aactggatgt tgtaatgaca accactttta caatggggat ttcaaactcc   22860
cctagatatc ttaatagtaa gcagctggag gtcaagaaga gatcctttct tttaaataag   22920 tgcaatttt  ggagaaacat actcattccc aaaataacgc attcacatat taaggtctag   22980
aaatggctca agttgtccct ggtgcattcg aatgtgggtt caaagtgagg tgcgtgtcct   23040
gagggagctt gttctccagt ggaggaagct ctgtcaacac agagttcagg gatgtgtagg   23100
ggtcgtatcg cctctaacag gattacggct tgaaccctca gcatgtacaa ttgtgtcgtc   23160
catctgtcat gtatttgctc tatctcatcc tggctcagga attgggctat tcaatagcat   23220
ccttcgtgaa tatgcaaatc actaaggtta atacagatat ctctgtgccg tgagagcatc   23280
acccaacaac cacacccctc cttgggagaa tccctagat cacagctcct caccatggac    23340
tggacctgga gcatcctctt cttggtggca gcagcaacag gtaagggact ccccagtccc   23400
agggctgagg gagaaaccag gccagtcatg tgagacttca cccactgctg tctcctctcc   23460
acaggtgccc actcccgagt gcagctggtg cagtctgggc ctgaggtgaa gcagcctggg   23520
gcctcggcga aggtctcctg caaggtgtct ggttaaactg tcatcaccta tggtatgaat   23580
tggatacgac agaccccagg acaggggctt gagtggatgg gatggatcat cctaccctgg   23640
tgaacccaat gtatgcccac agattcacac acggtttgtc ttctccatgg acacctctgt   23700
cagcacggcg gatctgcaga ctagctgcct aaagactgag gatgcagcca tttattactg   23760
tgtgaggtac accgtgtgga aacccacatc ccgagagttt tagaaaccct gaggaaggag   23820
gcagctgtga tgagctgagg cagtggtgca gcatgtctct aaacttccat tttatctaag   23880
tttgcattga gttccgcttt aatattagcc aggaatgtgg gatagacggg tgctcctaag   23940
aggtccttaa tttgcccatt ttgatgggtt ttccagaaga cgtgagaagc cactttgtta   24000
acaaagcatc ccaaagccat gccctgctcc agaaacacgt gtacccattt cctggtcttt   24060
ggttaactga caagctctca tcagcgcacc tgggctaatt tctcatcagg tagaaaaatg   24120
tgttgtaaag caaggctaac gttgtgatag caattcctgc tcaataacct tcagcatcgt   24180
tgttgttgtg ttctatcaac taattacgtg acttcaaggt tctcattggg agtgtcttat   24240
aaatttaagg gatatataga agttccccta attaaaataa aacaattgtg agcacaacct   24300
cagtgttcaa ccatgtctcc acccttccca ccattcaccc caaagaaatg ttcacctctc   24360
ctggaagtcg ggttcatttt caaattagtt attttttatt ttactatatc aagattattg   24420
tatgtgacta ctgtagcaga aagtgaatta tgggaacttg aagtaaccaa cgaaagataa   24480
attcagaact aattaaacaa gatgtcagaa cgtgattggc tctagtcttt taaaattcag   24540
caggttatgt aaccaggctt taaatttaca catcttcctg ttaccttcac ggcacagtca   24600
actcccatta tgtaagaaat ggcaactgca ttcccaagcg tcatccaaaa ttgtaaaaat   24660
agactgggtg aggtgaggag ttgattgttt aaattccgct ctgaagaagc agcatcaact   24720
caacaaacca ccgcttttcc ctcagtgact agagctatgt cgcaggccac atggacctaa   24780
atatccttga tagagataat aggactacat aaattgggct gatcatttt atgctgtaaa    24840 attaataggt gagtctgcac tccagcctgg gcaacaaaac aagtcttgcc tgtaaataca   24900
```

```
aaagaaagat aaattaatag gtactgactt tgacatttcg gataataata tttcataaa    24960
ccgaatttaa ttatacccac attgttacct acaccttcac tgaaaagttc ctagttatca    25020
tgagttccat caacactcca cgtgttcaaa tctggacatc caagagagtc tggagaataa    25080
aatgcaatga gggcagtgaa acttgcatat attcagcacc tcttaactca ggaggactca    25140
atacaccctg gaacactctg cttttctgaa tggctcacaa tgactccagc tcactctcca    25200
acctcctcaa acatctggct tctgtttgcc ctaagttcac gctctgctct tagtctgtgc    25260
tctgaagtct ttgcaaaggt gaaaatgagc tgtcagatgg aacttccttc tcacctcagc    25320
atggaattta ctgtttcatt taatgaccac tctttccata atggttgatt tctttcagcc    25380
tgttcattac tggtgatttt caagggaatc tctattgaat ttttacattt ttgcattttt    25440
gtctcggtga caatgttgag aagtttttac ctctagcatc ataacatgat ctagtgacct    25500
gacacatttg tggcaagcaa tacctacaaa ttcagaagtt ctttggttac tttccacaaa    25560
atataattat ttctggtctg tgtatgagca tatcctagca accttgtact ccacacaggt    25620
agatgtctac aagcctatga attaatctct gtaaataaaa atttatctca atttctttca    25680
atgttcataa ttcttctgag gatgaggaag atctttctgg atctattcag acaataggcc    25740
cagagaccac ctggtatgta aggagctcac ctggctcacc tggttccccc tgttgtctca    25800
cataaggtca agcccacttg ttcaggtcct aagaagagag ctcagtttta tctgatttta    25860
caacactccc aatttctgct gactctcctg ttacccacat ccatggagat acattattta    25920
ttatacaatt aaccaaagta atgtcaaagg cccaatgtgc aatattgcac atcctagggt    25980
atgttcatgc aattgaatcg aggagaaagt ctttcagaga cagatggatc tgaactggta    26040
aatatgtgtg taaggactct gggcttaagt gtcattgtcc agccatgttt cacaggtgtg    26100
acctgtcagg gaagaaccag agttccttgt gttctcagag ggagggggtc ccagaagtcc    26160
tctctggttc ccaggaaagg taattgcatt aatcttggtg atgagactat catccagtga    26220
tgatgtacta tagagtttat gtttgaagtt gacactctat cgcaatctac atcttttcac    26280
acagaagtgt ttagaggtca ggccacatct tcaggatccc acattgagaa ggacagagat    26340
atattccact accttctcct gagatctcag gcagaaaccc aaatttcaaa aggtctcaga    26400
agggcagctc tcagggcta tttaaaaata acccacttcg tgggacaggg agcatccttc    26460
taaccatgat ggatgttctg aactacaata aacattgcat ggaaccaggg tctgaattca    26520
ctgtgattat tacactccac tgctgtttca atgtgtctga aggggtaaat gacaatttag    26580
atgacctggg tgtgtggttt gttttacata aatcttcaag gatagaacag cattgaacct    26640
attccaaaat ctgtccctga tccaagatca cactgatctc ccagagcagc atcttcagca    26700
catttcccta cctggaagaa gaggactatg ggcttggtaa ggggaggcca caggaagaga    26760
actgagttct cagagggcac agccagcttc ctactcccag ggcaagccca aaagactggg    26820
gcctccctcc tccctttttca cctgtccata caaagtcacc gcccacatgc aaatcctcac    26880
ttaggcacct acaggaaacc agcacacatt tccttaaatt tgggatccag ctcacatggg    26940
aaatactttc tgagactcat gggcctcctg cacaagaaca tgaaacacct gtggttcttc    27000
ctcctgctgg tggcagctcc cagatgtgag tgcctcaggg atccgacct gaagatatga    27060
gatgctgcct ctcatcccag ggctcaccgt ggttctctct gttcacaggg gtcctgtccc    27120
aggtgcagct gcaggagtcg ggcccaggac tggtgaagcc ttcggagacc ctgtccctca    27180
tctgcgctgt ctctggtgac tccatcagca gtggtaactg gtgaatctgg gtccgccagc    27240
ccccagggaa ggggctggag tggattgggg aaatccatca tagtgggagc acctactaca    27300
```

```
acccgtccct caagagtcga atcaccatgt ccgtagacac gtccaagaac cagttctacc   27360
tgaagctgag ctctgtgacc gccgcggaca cggccgtgta ttactgtgcg agatacacag   27420 tgagggagg tgagtgtgag cccagacaca aacctcccta cagataggca gaggggcgg    27480 gcacaggtgc tgctcaggac caacagggg cgcgcgaggc cacagagccc gaggccgggt   27540
caggagcagg tgcagggagg gcggggcttc ctcatcagct cagtgatctc cctcctcgcc   27600
agcactcaga tgtccccagg gctcctgttt ctttattgtc tgtggttctg cttcctcaca   27660
tccttgtggc agacaagaaa ggaggaagac aattttctg tttactgttg aggtttcacc    27720
aattactagg aactttccta caagttcctg cgtgactcat tttaccgtat atgtgtgtgt   27780
gtataaatat atacacatac acacacacac catatatata caccatatat attatataga   27840
tacacaccat atatattata tatatacaca ccatatatat tatatatata cacaccatat   27900
atattatata tatacacacg atatatataa tatatatata cacaccatat gtatattata   27960
tataaacaca ccgtatatat atatggtttc tcaccatctc ttgatttgtg tcatcaatgg   28020
aattgtgccc tatttgaaat tcatttaccc aaaccttaaa tccaatggat ctataccgga   28080 atttttaatga tgcaattaag gttaaatgtg gtcaaagtgt gagaccctaa ttcaataaac   28140
cagttgtctt tataagaaga ggaagagaca cccgagacct ctcacttttc gcgtgcacac   28200
agagaagaag ccgtgaggag acgtagtgca ctagaaggtg gccctgtgca agccaggaag   28260
aagccgcgct aagaaccaat ttttacagct ccttgatctt ccacattcag actgcagaat   28320
tgtaagaaaa tcaatatttg ttgtttaacc cacccactcc tgttgtcttc ttatgaagat   28380
ccaaacagac tgataccacg taattctgtt agctctggtt cgtggaggga ggagcagccc   28440
cctgaggctg gacacttctc tcagatttcc acgtgaagta ggtaaaaata gtagctctca   28500
tataaaaatg tgtcatgacc ctgttggcca tttttgagca aggtctctga aaccagccct   28560
tgtgtgtgtg tcacaaatgt tttcttttat cttttatttg gacataacac atagacaagg   28620
cgtaccagct ggatggagac tggtcactgc ccatcttctg ttgtctcctt aggatgtcac   28680
agaaaaccac accaacatca ccaacgtcac tgttttttctt caaccacctc aaaccgacta   28740
tagaaatgat ccctgcagta taagtctatt tcttcaaact ttctaaattt gcactggaat   28800
ctcttcctaa atgggagct acatggggtc tgagttttgt tcctttcttc ccagtcttcc    28860
ccaagtgcca aggacagaat agacttaaaa taaaatttgg ccgtcagtgg ccccaacccc   28920
acatcacttt ctaaaaccca catcctgcat ccatccttct ctggacaccc ctcatcgggc   28980
tacctacgaa tggccagaag ctgccatcac cttctgggct gaggccacga gttatacaca   29040
cgtgtgattt cagtcacaca cactctactg caggacacac ctgtgttctt gaggcactca   29100
ggcaccctgc tgatctcagt cattctctaa taaattacac atctcttatt aataaaggtc   29160
cagatggtcc catcagctgc agagcagtgg agtaaagctc atgggtgggt ccgtcaggta   29220
gaagtcagac aatggatggg atggctggtc acttcccttt tcactgatgt ccccagtgaa   29280
tattaatgga ataaaaccat attaactaca gagggacaga aaagaagact agctcatcaa   29340
ggtatttaag gaccaggaac tttatttggg gggaaagtga agacactttt aaatggaaag   29400
ccctaaagca catacaacag ctgacagagt ggccactgtg cacatgaagg ctgaggagac   29460
ggatggcagc gtccgttcct ccaagatgtc cctgggtgtg tgatggttgg actccttatg   29520
catatgaata taagagctgg actcagggag aaaaaagggc catatctcat aggaaaggaa   29580
gcccaaaaaa gcagatgggc atccctggag agagctcatt agatttggtg tgtttaagac   29640
```

```
aaaaatttct tccaaaaatt gtaatgttct aagctaaata tgaacctctt caataaactg    29700
agaattaaca ggagaataga gctatgagtt gagagaagaa acaaatcatg agagagcaga    29760
aagcaaatcc acaaaaaact gtcatatgac agaagtcaga atggagctgg ggcagctact    29820
tcattattct gaagacttgt tgaccatgtg gagaaggggc ttgaacaaat ggggacgttc    29880
tccaaccttc tgaatcagcc tccttcttat gcatgagtaa aaatcatagt tctgggtgtg    29940
accttcccaa atttcctgtc tgtacctctt cccccagggg tagagtgtct tcccaccaca    30000
atggtttctc accagtgtcc tcagcttctc ctccattgaa cttaccctgc agattaagaa    30060
tttcttctag atgtagttct ttgggaattt tctgttttct ttagtttctg ttgactccac    30120 cacacccat aggtcacagg tttgattgat ttccctgga gacagtggag gtggatccag     30180
gcgttcaaca gtcctcgctg ttcctccctt cctgtcagca ccacaggaca gcagataagg    30240
gagttgactg tagattttc gaattcttgg gaaaatcctg caaggactag tagattcaca    30300
ctccaatacc attagcacat gcatccaaaa aaaatactca cgaaatattt ccaggttagc    30360
ctgttcctct ctcaatgcca tccagtggca cctgccctgg gttcaccaac atgtgggccc    30420
cactcctctc tgctggcatc tctctcctca catttcagtc ttctcgttag ctctgtgaaa    30480
gcaactcaga tatgttaaaa ggttttcttc ttcatttatt cagttttca ggtttgttgt     30540 taatgaggtc agaataagac catagttttc tcattttca cattcccaca ctgagtagcc     30600
actttctata taaaagccag aaactaaggg aacaaatcaa atatccatat ccactacagg    30660
tgaacgttaa acaatttgac atatgattat gaactaaagt acaatgcaga attagaatca    30720
aggcatcctc attctcataa aagcatgtct acattctcaa ataactctgc tgagtgaaag    30780
tagctgaaga attaagagtg caattcataa acttctaatt gtataaactg caaaaggtcc    30840
aactattcta aagtaacaga gcagatttga aatttgtgag aaacgggtgt tgaaagtaat    30900
tggctggtga gatgaaatta cagagaagtg acagaaagat ttaggggtta acttaattgt    30960
acacaacctg attaaagttt gcacacatac gttaccattt tccaaattgt gcagtgtaga    31020
tttgaattaa ttattaattg tacttaaaaa aagcagtaac aaataaacac atgaatatgt    31080
ttactgagga ggaacaaaaa atagatgggt atgaacactg gaaacatctc agactcttga    31140
aagtacacag gcttgaacac tggttctctc cgtatacttc cggtaaacgg ctgaatacac    31200
taaaagaaaa cagagatgtc ctggcagggg tggaatcctg cagacctcac taggtgtgtc    31260
ccacactgcc ctggagttgt ctcaggggag cagtctcctc tagtggtcag aggcacaggc    31320
tgagataatg gggttaactc tgtccagctg tgtgactttg aatgcattgt ataaacactc    31380
tgttctgtat gtaatttatc ttccttaaaa tgcaacattg acacttacat taaatgtatt    31440
ctacaaatat gtcaaaaaga agatgatgac tgctaaatga ttatcaaggc acaatcacat    31500
aatataatga tattttcctg agtgataaga tgactaccaa tctcgggggc actttgtctg    31560
ctctgagccc tgcccctcct caggattccc atcccagagc ttgctataca gtaggagaca    31620
tgcaaatagg tttctccctc tgctgatgac cagtcctgac cccatagctc tgggagagaa    31680
gcgccagccc tgggattccc aggggtttcc atttggtgat caggactaaa gacagaggac    31740
ccaccatgga gcttgggctg agctgggttt tcactgttgc tgttttaaaa ggtgaactag    31800
agagattgag tgtgaatgga tacacttgag agaaacagtg gatatgtctg gaactttctg    31860
accaggacac ctacaagttt gcaggtgtcc agtgtgaggt acagctggtg gagtctgaag    31920
aaaaccaaag acaacttggg ggatccctga gactctcctg tgcagactct ggattaacct    31980
tcagtagcta ctgaatgagc tcagattccc aggctccagg gaaggggctg gagtgagtag    32040
```

```
tagatatata gtaggataga agtcagctat gttatgcaca atctgtgaag agcagattca   32100
ccatctccaa agaaaatgcc aagaactcac tctgtttgca aatgaacagt ctgagagcag   32160
agggcacggc cgtgtattac tgtatgtgag tcaccaggta agaagacatc agtgtgaaca   32220
cagacacaga atttcctgaa ataagggagg agtctgggct aaaagggcac tcaggaccca   32280
cagaaaacag gggaagctct agggcaggtg cagatggtca tcatgggctg ctttccttga   32340
gggtctgagg cttcctctgc atctaacagt ttccctggga gcctctggac atttatgctt   32400
ctgtggccac ccctgaggtc tctggacatt ctcatttgtt gcaaaggcag atgtaagtat   32460
tggaggcata aaaatgcaca ggaggccagg gagtctgtag acattgttac cccagaaggt   32520
caatctcacc actagtgctg gaggagggtg ggagtttgat gaagctgccc taagtatcct   32580
gtggtctaag ctaagtccaa cgaggccatt tgtgcctccc tgagcacagt tatccatcag   32640
agatgtccca tgtgtcccag cagcagccat gtctcagtgt cttcactgtg cacagccagt   32700
gtctgggagg agctcccagg atgggtgtct ttggcacaca ccaggtggcg ggtgttagag   32760
tgcggtgcag cagctggctg cctgttctat tgggctccct gatgctggag agatgggagg   32820
tgcattctca ggtccagcac cctgtttgtg aattttttata taaaaccat gattttactt   32880 cattttctca gatgacatag ataattagga acagaacctg caaagaaatt gtaattttca   32940
actttacccc aaatttattg tttcttaatt ctgtgtaaga tccagacata ttattgcctt   33000
cctcatgaga aattgttcta tttaaaatga aattagtttt ttctcacatt ctttgtttct   33060
gttcaagtac agagatcttg attaaagtaa gttgggttct ttccacacac taaccctcac   33120
ctcccccaga gaaagagcag agattttcct cactctgagt ctaagggagg agctgttcct   33180
gcacgattca gagcctgcag agaccccccc cgccaggtgc agcttcagtg agtcaggtat   33240
ttctccttgt gggtgacctc caccgccagt gattgctgct caggtctaat tgtgggttaa   33300
gcattaggac acccttcagg tgatcacatc tcagtcttat tctgaaaatc accatgaaca   33360
gggatagttc aatgcctatt ctcctgacat tagtttctct ttattatttg gttccaagta   33420
tggagaaaaa tgtgacaata aatttgtcag aatctaacct cagaatccac tgcattactc   33480
taggatactc acaaattgaa cacaaatgag ctctttattc tcataaaagt atacgtattt   33540
gggaatttca atgtgttctc cagaacctgt gcatgccaac aactgtgttt ctcagtgccc   33600
acttggcctg gtgaagccct cacagaccct ctccctcacc tgtgctgtct ctggattccc   33660
catcacaacc agtgcttcct gctgtagctg cattcataaa ccccccagga agggactgga   33720
gtgaatccag tgcacaggtc atgagggagt gcacattcca acccactcct caagagtcca   33780
gtcaccatct ccagatccat gtccaaaaag cagttcttcc tacagccgag ctaagtgagt   33840
cacaagcaca cagccatgta ttttaacaa aagacacagt aaggtaacca cagtgggaac   33900
tcacacccaa acctccctgt gggggtgcac aggacagcca cagttactca ggaccccagg   33960
attcctcagg acaccaaggg gcactcaagg ccattgtaga tgccctcagg tagccaaggg   34020
ttctcaggaa acatggagga aaaccaggac cccaaaaggt gctccgtaca gcagggact   34080 caggacaatt gcggggactc agagcaggct caaagctcag cttcagggca ggtgcagctg   34140
gggttgaaag gggctggatg aggggtttg tgacaccatc atatttcacc actagacaca   34200
ctccactttg tctattctaa cgcatgtgag tgtatgatta gaaaatgata tttatataaa   34260
tacataacca tagttagctg tgtcaagttg tcctcttgct aggtgtccat agctaggtgc   34320
atcagccttg tccataagga ctaattcccc gcaattactg gagaatctca taaattgtgg   34380
```

```
tcaattatgt cagattcctc tcttttcctg ccttcctttc tcccttcttc tctctctctc    34440
acacagaaac ttacatacac ccaccccaca acacaccaaa atctataact tttattacct    34500
gatatattca ataaacctga ttaatgtgca gcttttccag cttcgttatt tatgctgttg    34560
taacaataag aacaatgtgt ttcctagctg tgtacttctc taagctgagt agcatctttg    34620
tttataatac ctagaattaa aaacaaccca aatgtcaatc accagcttaa ttggtaaaca    34680
aattgaggaa aagtcattca ttgacatact atccactact accatcaact aatgttgggt    34740
acactcaaca gcatggttaa attcacaagt acttgtgatg agtaaaatga gccaaagtaa    34800
caaaagtgca tacataagat acaactttca taaattctat agaacaaaaa gtaatcttaa    34860
gttacataaa aatcagtagt tccactgtga gtattgtagg agaggggaag gactaggaag    34920
gaggaattat agtacaagac aaaattttga gggaattgac ttgttatcta tgttgctcgc    34980
gatgatgtct atgacccatt tgtaaaattg aacacttcat atggagatta ttattttaa     35040
tttaactcca ttaatgatag tactaattat agcaggtata atttggtatc aaaagaatta    35100
gacagagata aataaaatac atgaaaagtc agagactctt gaatatacac ataaatgagc    35160
cctgggcatc tctgtatttt tagagaaatg ctagaatata gaaaataat ggcataattt     35220
tatgtcacta aaaagtttta tcgaactcca ccagtcatgt ggtattagtt cattttcaca    35280
ctggtataaa gaactacctg cgactgggta gtttacaagg aaaagagatt tagttggctc    35340
accgttcttc atggctgggg aggccacagg aaacttacaa tcatggtgga aggtgaaggg    35400
gaaacaaggc acatctccca gggcagcagg agagagagag aggggggaag tgacacatac    35460
ttttaaacaa tcagtggttg ttagaactca ctcactacca tgagaacaac atggggaaac    35520
tggacccatg atccaatcac ctctcacctg gtccctcccc tgacatgtgg ggattacaat    35580
ttgagatgat actttgatgg ggatacgaaa tcaatctata tcacatgtcc agctctgtcc    35640
tggagttgtt tcagggatcc agggtgtccg gctgatagaa ccagtgacac caagctcaca    35700
ccctcagctg tagttgacac cacgcaaagc caagagatta caactaagat ttagtttgaa    35760
tgtcgtgtct gatgaagtca cacactcaga gaaagtgaat atggaaaagt ttattatttg    35820
cactctatag gtgtctggtg agtgcagggc aggtctccca ggaaaatctg aaacagcttg    35880
aaagaagagg aaaggagact ggctcagcat ttttatgatg gtttggtcct gggggcagag    35940
tgaggcttcc cactcacaga aaggggtttg caggggttga aactccccct ggcatcgaat    36000
gaagaagctc ctgtgatttc aaactagagc caccttgtgt ggcaaaaaag gagatgatgg    36060
aggaatatgc tttaaatcat cagcagtcac gcacccaaaa atagtgtgac aacttattct    36120
atgcagcagg aataaaaata attaataaga aagaagataa gggttcagtg tgggtggaca    36180
acacgcaggt ctacagaaat gagatgactt tagaaatata agcaaaggat aatgaaaaaa    36240
aggaggggaa ggggaattaa acagggtcct ggtctgatgt cttgggtaga agcttctcac    36300
aatcaaggac taccagctca ttctgcaggt cttaggtcag ccatctgctt aaaaacatca    36360
gaaacgccag agaatctatg aacatggtca gtttaacatt tcctatttga gtagctttac    36420
agttgtgtgg aattcttaac tggttcttgt tttttctttt agatacaggc tctcaccctg    36480
tcacacagtt taaagtgcag tggtgtgatc atagctcgct gtaattttga actcctgact    36540
catattcttc ccatcttagc ctcttgaata tctagaacta gaggggcatg ccactcatcc    36600
cctccttatt ttttatttta tttttttcata taaataaggt ctctttgtgt tgcccaggct    36660
ggttttgatt gcctggtctc atgggatttc cctcacttcc cttctgaaag tggtgtgatt    36720
atacagatga tccagtgcat ctggcctgaa ttgattcttt aattgtaaaa tacgaaccca    36780
```

```
ataattaact tcctgaatgt tttctgcagt gagttagtta aaaggatctg acaagattcc    36840
ttccaatatg attcaagagc agtattgtcc actgatgttc cttccagttt ccttgttgaa    36900
gatcacaaga gtctgtggaa aagaggtagt aaaaaggccg cctcaaactc ttcgtggttg    36960
gagtgggtac cacacatgca agcagtagga caaggatgat ctctggggta aagtctataa    37020
acatataggc cttttagctg ccaagtcata gggtaataac tgatgcagcc tgaggagtgg    37080
accatggttt catagtgcta gtgggagaac ccttggccaa gcaagtttta cattttatta    37140
cattttatta aagatttgat aattttaatg taaagatgac attttttaaa cattcccaga    37200
agattgtgag tggtattgat tctgtctcgt atgaacaatg acagtgccct ccacggttag    37260
attatgttat aaactagaat gaggtagagt gtttggtgtg ttaaatcact attttttag     37320
cttctatgtt agtttttgt ttgtgtgtta gcatttgctt taaaattcta ttaatcagat     37380
ctctagttgg tagaaattca tctgaaagtt tcttccattg ttgtccattt tgataggatt    37440
tccagaagat gtaagaaccc tctctgtttg caaaaatatt ccaaagttgt gcaccatcta    37500
gaaacatagt tacttaattc taattttaa tttattaaaa agttgtgata agtgcaaagt     37560
tttctgcctt ctgaattgat ttcataacac acagaataat atatactaaa tggaagtttg    37620
tactagtaat acaaattact gattaataac ctctacttt attattgagg tattatccat     37680
caatatataa tcttaaatca atgatctcag tgggaatctt acctaagtaa tatacaaaat    37740
attttcctga tctcgacaca aaatagatgt gaacacattc ttcatattca gccatgtctc    37800
ctgtctatca cattatgaac cacatgctaa ctttgattta cttgggactt gctctaaatt    37860
caaactagtt atctttatc ttcacgcagc tggattatta tgtgtggcta ttttatcaga     37920
gtgataagat acaatactaa caattttcac tgcaggcatg tctaggcaag cccctgtgc     37980
acaatgacct tggtgggttg acattctat ggggactctc ccctgtctgc ctaggagagt     38040
tatctgcctc ctccctctat cattttcctc tttgaataag tgcatctaac tgccgttaga    38100
atacagacaa aggccaacct taactgcttc cagctgacag gggatgctgt ttcgggaaga    38160
tctcccttga ggtctgtcta agggacccag taaaagggag ccattatccc aggcttcact    38220
tggatgacca tttggagttg atgcctgaag gtgagaagag acaaaccggg ttattagaag    38280
acatgtatca aaaccaaaca aggtggtaag gacagtttga aaaaaaattc caaggctgct    38340
gacacaccca gatatctggt ggctgtagtt atgcctgcta agatttgggt gcatgggct     38400
tggctttcgt tagctccctt ggacttattt tcccaaacaa agaaacctcc gggttagggg    38460
gaccctattt attccagtca cctggcatga tttgccggat aattgctcag aattaaaata    38520
ttcgtccaga tgtttatata gcccatgcct gtgtttcttc tgagctgcag ccagagatca    38580
ttggttggtt cacagcgata agcagagtta gtctaaaatg gaggcaaata cttaaaactt    38640
atttcttctc tcagttaatg gattctatag agaaagtag ctactcagca tgggaatgta     38700
aaaaaatgag taaactatga tcttattctg aactcattaa caacaaacct gaaaaaccaa    38760
ttgaagagac tgtaatttaa agacaagtgt atgatatgtt ttgaaacata attttctct    38820
ctccagttct gattttgtc agaaactaat cattatagga ctgagttgtt tgcaaaataa     38880
actttagtct tatggttggt ctgatcattt gcataaagtg aagccataat aattaataat    38940
aattctgtag gaaaagcctg caagcatgag gagcttcaca gtctaacact atgagcacat    39000
gcatcctcca gcaactcact gaatattttc aagtcagccg gttcttagct taaataacat    39060
ccagttggta tctgtcccag gaacactaat atatggttct ctctgcaggc ccctttctcc    39120
```

```
acagattaag ggttttttttt ttttctctgt aatatcaact cagatatgtt gaatgctttt    39180
tccttattag tggttttttca ggtttgttgt taatgatttc agaataagat cattgtttac    39240
tcattttttt taaattcccg tgccgagtag ctacttttct ctatagaatc cattaactgg    39300
gagaaaaaat aacattttct tatgggtgaa caattaaata gtttgacata tatttatgta    39360
ctggtatata atgcagcttg aaatcaaggc atgcctcaat cataaaaatc atggctaaat    39420
tctcaaagaa ttgtgctgag tgaaagaagc taaggaatta agagtaaatt ttatataatt    39480
cattgtagaa atattagaag atgccactac cataaattaa aatgaagaag acttaaattt    39540
ttctgagaaa atggtgttgg gaatgatgcg gatgtgattt aagtttcaga ggaataagaa    39600
aaaagattta gggattaatt taattattca aaacttgatt gaagtgccga gtgaatggct    39660
ccaaacatag tctacatttt tcaaatcatt ccctataaat ttgaattaat tatttatttt    39720
tatacttgaa taaagcaata acaaagaaat aaatgaatat ttttgctaaa atggagcaat    39780
aaaaagactg atattgacag aagaaatatg actgacttct gaaaatacac acacatgagc    39840
cgtggttctc tctacatatt tagataaaatt acagaaagtt gtcataactg atggggaatc    39900
ctgcagactt cactaggcat agtccacact gccctggagt tgtctcaggg gagctgcctc    39960
ctccagtggt tagagcacag gcccaggtaa taggactcat ttttttagat gtgtaatttt    40020
agacacactg cacaactgct gtgttctctg tgcaaattat ctcctgtaaa atgtaacatt    40080
gaaacctgcc ttaaatatat tgtgtaaata tgtaaaaata aaatcagatt gtgagagcta    40140
aatgctaatc aaggcgcaat cacgtaatat acaattatat tttcctgaat gatggaatta    40200
ataccaatct ccccccaggac acttcatctg cacggagccc ggcctctcct cagatgtccc    40260
accccagagc ttgctatata gtcggggaca tccaaatagg gccctccctc tgctgatgaa    40320
aaccagccca gctgaccctg cagctctggg agaggagccc agcactggga ttccgaggtg    40380
tttccattcg gtgatcagca ctgaacacag aggactcacc atggagtttt ggctgagctg    40440
ggttttcctt gttgctattt taaaggtga ttcatggaga actagagata ttgagtgtga    40500
gtgaacacga gtgagagaaa cagtggatat gtgtggcagt ttctaaccaa tgtctctgtg    40560
tttgcaggtg tccagtgtga ggtgcagctg gtggagtctg gaggaggctt gatccagcct    40620 gggggggtccc tgagactctc ctgtgcagcc tctgggttca ccgtcagtag caactacatg    40680
agctgggtcc gccaggctcc agggaagggg ctggagtggg tctcagttat ttatagcggt    40740
ggtagcacat actacgcaga ctccgtgaag ggccgattca ccatctccag agacaattcc    40800
aagaacacgc tgtatcttca aatgaacagc ctgagaccgg aggacacggc cgtgtattac    40860
tgtgcgagag acacagtgag gggaagtcat tgtgcgccca gacacaaacc tccctgcagg    40920
aacgctgggg ggaaatcagc ggcagggggc gctcaggagc cactgatcag agtcagcccc    40980
ggaggcaggt gcagatggag gctgatttcc tgtcaggatg tgggactttg tcttcttctg    41040
acggttcccc agggaacctc tctaagttta gcattctgtg cctatgaacg tcttctctaa    41100
gtatttgaaa gagattattt taatatgaag agcagttctc actcgcccaa aatgtggatt    41160
gatgcttact gggatgaaaa gtccccaaac atggtcaccc cgataagagt ctgagtgagc    41220
tcagggcttc ctgctgagtc tcctcctatc agaccaagga cagggacctc agtgaggttc    41280
ccccgtcaag aacagtcttt atggatactg attgtgggcg gcaacccacc caggtgccga    41340
cgcaagagac cgaggacacg agctgttcca gtacaataaa atataaaaca agaatagtta    41400
taccagatat agatcttaga tatgattata tatgaatatc attaatcatt agttggtagc    41460
aattactctt tattccaata ttataataat cctcactcta caatcataac ctaggaaaag    41520
```

```
ccaggccata cagagatagg agctgagggg acatagtgag aagtgaccag aagacaagag   41580
tgcgagcctt ctgttatgcc tggacagggc gaccagaggg ctccttggtc tagcagtaat   41640
gccagcatct gggaagacgc ctgttgccaa gcggaccatg gtctagtggt agactcagtg   41700
tcaaggaaaa acacctgcta cttagcagac caggaaaggg agtctcccett tccccgggga   41760 gtttagagaa gactctgctc ctccacctcc tgtggagggc ctgatatcag tcagacccgc   41820
ccgcacttat ccggaggcct aacagtctcc ctgtgatgct gtgcttcagt ggccacactc   41880
ctagtccgcc ttcgtgttcc atcctgtaca cctggctctg ccttctagat agcagtagca   41940
aatcagtgaa agtactaaca gtctctgata agcagaaata atattgtaag ctgtttctct   42000
ccttctcctc tctctctctg cctcagctgc caggcaggaa agggccccct gtccagtgga   42060
cacgtgaccc atgtgacctt acctatcatt ggagatggct cacactcctt accctgtccc   42120
tttgtcttat atccaattaa tatcagcgca gcctggcatt cagggccact actagtctcc   42180
gcatcttggt ggtagtggtc ccccgggccc agctgtcttt tcttttatct ctttgtcttg   42240
tgtctttatt tctatgctct ctcgtctccg cacacgggga gaaacccact gaccctgtgg   42300
ggctggtccc tacactgatc acagacaata gagggtaggc caggatcagt gtcatgtagg   42360
acatcacagg tttcacctct gaaccttttc ctgacactaa atatgcaaat cagcatcagc   42420
actgatctgg tgattctttt gttcctaatc catttacttc cttttcagt cgttgttttc   42480 attttttccat ttgcttttcc tgctttctgc aaaaggaaga ttttttccctg tggtcaaaat   42540 tccggacctc aagcccttcc ctggcgctca ggtgggtctc aggctgtggc tgctgcagtc   42600
acgcgggaga ggctggtggg actttcttca ctcctcgtca ctcagggccc tccactgtgt   42660
tgcatggaga cttatctgga aatgcaagtt gcgactgaga actgaagggg acaagcttgt   42720
ttggttaaca tgggatgtgg atgtgtttct aattttgttc tgataaactt tcacagagta   42780
actttctgca ctagtcatgt gaggaagagg atgtgaacgt agtcagaata aaaatagaac   42840
aacttgtgtt ataatctta caggtgaagc tggagaaggt catgaataga gggttctcat   42900
gcacacatcc ctgataacaa gaactaccat aaaattactc tgcacaacca caactttcaa   42960
caaaggctac cacaacaata agagaattaa tattgtgagg atatctgccc tgcaactccc   43020
agtacaatct taaactgatt ccaccccttgt tattaattct tctaccccca ggataattgc   43080
ctcagaacag ctcatgtaag tcctctcatt tatcccttaa aacaaccttt accaccttt   43140 actaacctga cttcctttac ctacctaaat atgcccaggg ataatccac tggaatgctc   43200 attttcaaat acatattatt tgattttgga gaatttcttt ctgtctgata ttcaggtgtg   43260
acaagctgta gagggtcaca ccactttcct gtgagatgta ggggatgaca atttgggggg   43320
atggctggaa acatccaata tcctcagggt cggccatcag taagcgcagg ctggaagtct   43380
cagaacgagt tgaagttgct taaccacgga attttacctt ctccagatca gctttgatgg   43440
aatcagggcc aaactggtta tcaatgataa tctacctaac attgagtcaa ctgatcacag   43500
ttttaataac ctctattaaa aattcacacc aacacttgga ttagtgtctg atcaaataac   43560
tacaaagtat tttccagcca agtataccat aaaacagacc attacccatg gagaaaaaca   43620
tttaacatga gttctaggtc cttacattgt taaaggtgta aaactgatta ttttttaaatt   43680 atgctttta tttttgctat tgagttgtag aagtttcatt tacattttgg atattaacgc   43740 tttttttcaga tacatgatat attatccaat tctgtgagtt ggaattattt cattgctttg   43800
cagaatattt ttttaatcta gtccaacttg ttcaattctg cttttttta aatgtgcttt   43860
```

```
gaatgtaaaa tccagaaaaa gattgctaat ttttgaggat tgggagtttt acagttgcag    43920
gaatttcatt gaaatattta atgcatttaa agtaattttt tgtgtttatt ctaacctaaa    43980
attcttaatt cttcacatgt gaaaatccag ttttcataac atgctctttg aagacacca     44040 taatttagcc attgtatgtt gatggttctc atgctgaaaa tcagttcgcc atcaaaatgt    44100
gggtttatat ctaagctctc tatatgcatt tatgctgaaa ccattcggat ttattactct    44160
gtgtttgtaa caaatgttga ggactggaag tgaaatgcct caagctttat tcttgcctta    44220
ttacagatat tagacccaaa tattctaacc ttctactagt gagtataata atagctgtcg    44280
cttttttttt ttttttttga ttcagagttt cactcttgtt gtgtaggctg gagtgcagtg    44340
gtgtgatctc agctcaccgc aacctctgcc tcccgggttc aagcgattct cctgcctcgg    44400
cctcccgagt agctgggatt acaggcatgc accaccacac ccggctaatt ttgtattttc    44460
agtaaagatg gggtttctcc atgttggtca ggctggtcgc gaactccaga cctcaggtga    44520
tcctcccgcc tcagcctccc aaagtgctgg gattacaagc atgagccact gcacccagcc    44580
tcttcatttt ttttttattc atatgttcat tcagcagcca ctatgtcttc ccattgattt    44640
ctttggtttc ctctttacta tcttttttctt tttagtaaag ctgttactcc taagggaaga    44700
tgggaggtgg gcctggacag ggatttggtg cattcctctc ttcactcaca gttcttattg    44760
atctctccag tgtctctaga acactggttt tcctggcatt accgctgcag ataatttctc    44820
ttgcaatgta gtgctgatga ggaggtgtgt ctggatgcat ttcagctata gttgctgttt    44880
tgctttccct gacacaaccg tcccaagggg tagaggctgg agcattttgt gatgtgtccc    44940
cagtactgaa gaaaaagcct tcaatagcag gaggaattcc tcaactgtat acactctgag    45000
aatttaaaca ataacttctc tatcacactc aaatttaaac catccaatga atatgtctac    45060
tttaatcgtg tgttaactta aatgatattt ggcagcctct gtcccagaaa agattatcat    45120
ctgctcctgt ttatttccct gcaagtcttt atctctcttc agatttcaga tatcttgttt    45180
gtcttataac atcaaaaatc tgatgaattt aagaaaatgt gctaatttgc agatcagtaa    45240
gctttagtag ttgtgagaat aataacaaat ttttatggga tgcctgcatc tccaagctga    45300
gtagcatctt tatttctaac actcagaaac tagaaacaat gcaaatatca agaagatata    45360
tagataaaga gtaatggcat gctaatttac ggtaatcata gccatcacta gaatcaatac    45420
actgttgatg ctcaatgtgg ttgaatcaca agtagttata atgagtgaga agccacacac    45480
ataaaacaca tactatataa ttcctgtata ataaattctt gaaactcaaa accaaagtat    45540
tcaatatgaa ggattgactc agaatatggc aagggaaaaa aataattggg aaggaggaat    45600
tgtagagtaa cacaaggaaa cttttaagtg taatttatttt gtttgttatc tggatggttt    45660
ttggggatgc acaggtgagc acgagtggaa ttacattttg ttgtgtttgt tttttctga    45720 agagatgtgg tcctactctg tgacccaggc aggactgcag tggtgggatc atagttcaat    45780
gtagcttcca acttctggtc accaacaatc ctcctgcatc tgccatctaa gtagctgaaa    45840
ctacagttgt gtgccaccag gctcagcttg agtacttatt aaatcaaaca ctttatgcaa    45900
tatttaatgt atggcaataa tgtctcattg agagtattac aaataaatga atggataatt    45960
tgttcagtac agattgatgg aaaatagaca ctaacatgag gaatgtctga catttatgaa    46020
catacaactg cataaaatgt gttctcttac attcattagg taaacacaat agtgcataca    46080
catcaaacca tgctttcatt acaggaagga agttctgaaa atgtcactgg gggtgaccca    46140
cgctgtgctg ggcttggttc gggggcagtc aggcccggtg gtgagaagca caggcccaga    46200
tacccaggct tactctgcaa atgtgagctc tggggacatt gtaccaccca tctgtgcttc    46260
```

```
tgctggtaat tttccatctg taacgtggaa ataacattga tactacatac cgtgatttct    46320
ccacatatgt aaaaataaaa taagatgatt gctgctaagt ttaaataagg gcagttttca    46380
taggtccatt gtacctcaat aaaattactt taaaataaaa attacaaata cagttgtagg    46440
tttaaagagt ttatcacaga acaaacttat aataagaaac tatattttca aaaattgtat    46500
caatatctct aaactccccc aggacacact cacctgctct gggctctcca ctctcctcag    46560
gattcccacc ccagagcttg ctatatagta ggagacatgc aaacagagcc aaacctctgc    46620
tgatgaaaag cagcccagcc ctgaccctgc agctctggga gaggagcccc agctccagga    46680
ttcccaggtc ttttccattta gtcttcaggg ctgagcacag aggactcacc atggagtctg    46740
ggctgagctg ggttttcctt gttgctattt tgaaggtga ttcatgggga atgagttgaa    46800
tgtaagtgaa tatgagtgag agaaacagtg gatgtgtgcg gcagtttctg accagggtgt    46860
ctctgtgttt gcaggtgtcc agtgtgaggt gcagctggtg gagtctgggt gaggcttggt    46920
acagcctgga gggtccctga gactctcctg tgcagcctct ggattcacct tcagtagctc    46980
ctggatgcac tgggtctgcc aggctccgga gaaggggctg gagtgggtgg ccgacataaa    47040
gtgtgacgga agtgagaaat actatgtaga ctctgtgaag ggccgattga ccatctccag    47100
agacaatgcc aagaactccc tctatctgca agtgaacagc ctgagagctg aggacatgac    47160
cgtgtattac tgtgtgagag gcacagtgag gggaggtcag tgtgagccca gacacaaacc    47220
tcctgcaggg gcatctggag ccacaagggg gcgctcagga tacacagagg acaggggcag    47280
ccccagggca ggtgcaggtg gaggtcaagg gctgctctcc ttcagggtct gtggcttcct    47340
ctcatctaac agttccgcag ggagcctctt gtatttacag tgatgtgcta ctgaggtttc    47400
taagtttgta aagtttatta ctacaggagg aaccactatc aaacgccctt aaggcaggtg    47460
tcactaatgg agaaaggaaa gtgcacagga ggctgggtga ggctgtggac actgtctgcc    47520
tatgattcaa gtttcacaag cagtgacgga gaaatgggag tttgatggag ctccctaact    47580
accatgtggt ctaaactaag tccaactaag tccctgagct ctgggtgccc atcagggatc    47640
cgccatgtgc ccggcagccg cgtgcctttt tgtctcctct gcgcccaatc actgtctgtg    47700
atgagcttcc aggatgtgtg tgtttggcac aaaccaggtg atggacgtca gacagcagca    47760
gctggtgccc ggatcatggg ctccctaatg ctggaggaat gagaggtgca ttctcaggga    47820
caagacattg ttgatggatt tttatgtaga aaccacgatt ttacttgctt ctctcaggag    47880
acatagaaga agcaaccatg cagtcagcaa ataattataa tttccacaat tacccccaaat   47940 ggttaatcct taattctgcg cagggtccca ccgtagagtc acctttctca tgaggaatgg    48000
ttgaatctag aatgagtcca catgattttc atatttttgg cttctgtcca tgttcagaga    48060
gttagagtag agtaagtttg gacctttcca cacactaagc ctcacctccc ccacagaaag    48120
agcagagact tcaactattc ctgagtgtgg ggtagggggct ggtcctgcac acctcagagc   48180
ctgcagagac tgccacgtgc agtgttatag acttgggtgt tttctcattc aggagggggtg   48240 acctccacgg cctccgattt ctgctaagat ataactgtga gtgcagaatt aggacactat    48300
taggctatca tgcctcactt ctattctgaa aatcaccctc tttatagtaa aagaaaacaa    48360
ttcaatgtcc atgcccctga aagtcatttc tttttaattt ggttgcgagt ttaccacata    48420
gtgcctgaat ttattctcag aatctactga attgtttata aatctcacaa attgaacaaa    48480
agtgaattct tcattcttac taaaatgtgt gtatgtagga atttcagtgt gttttccaga    48540
agccatgcac accaaccact gtgtttcatg gtcatttatt ggcctggtga ggccctcaca    48600
```

```
gacccctcc ctcacctgtg ctgtctctgg attctccatc acaactagtg cttcctgctg    48660
gagctggatc cgccagtcct cagtcaaggg agtggatcag ggcataggtc acgagggagc    48720
acaaattcta acccactcct catgagctca gtcaccatct ccagatccac gtccaagaac    48780
caaattttct tttagctgag ttctgtgacc aacaatgcca caaccttgta ttactgtgag    48840
aggaacagaa gagatgtcag tgtgatccca gacacaaact tccctggaga ggggcccagg    48900
accaccaaag agcactcagg cccatgaaaa cagggcccaa gctggagaac gggtttcctg    48960
tcaccctcac ctttcaccat tagatactct acactatgcc tatgctgagg tgtgtgttta    49020
atataattag aaaatggtat ttatatacgt gtataatcat atctagtgta agaatttgta    49080
gtttccacct tatgtgacca ttaaagacaa catctctcac gttattcaag gaccttataa    49140
agtataatac ttttacataa gatttatctc cttttgtgtg tttctccttc tgtctatatt    49200
ctctctctct cttcctccct cttctctct ctctctccat ctctctctct ctgtctctct    49260
ctcacacaca aatacacaca catgcaatcg gtgacagtat ataggctaat taagaatata    49320
ttcccatatg atttaaaaat aacagtttta caaatatttg cctttaattt ttcaaagaaa    49380
attaaatcca aatgccagtg attttttatg tgacttttaa aatttaaatt gttaatttgt    49440
gttttcatca atgcttgtat gtgtgcttgt gtattctcac agattatgtg gtgccttcac    49500
agaattaaac atgtgaaact ctccacttga atttctgtga ctcaggactg gtgagcaaaa    49560
agttagaagt cactctcctg atccttccct acagctgcag attcctgaag gtaatgacct    49620
cacagtagac caaggccctc aaaggtgacc ttgagttcca gcacatcttg ggaggccaag    49680
cggatgtttg tgaaagaaat agtggctatg tgacagtttc taaccagaat atctctgtgt    49740
tttcaggtat ccagggtgag gcccagctta cagagtctgg gggagacttg gtacactgag    49800
aggggcccct gaggctctcc tgtgcagcct cttggttcac cttcagtatc tatgagattc    49860
actgggtttg ccaggcctca gggaaggggc tggaatgggt tgcagttata tggcgtagtg    49920
aaagtcatca atacaatgca gactatgtta ggggcagact caccacttcc agagacaaca    49980
ccaagtacat gctgtacatg caaatgaaca gcctgagaac ccagaacatg cagcattta    50040 actgtgcagg aaacatcgtg atgggaagtc cacgtgggct cagagacaga ctgccatgca    50100
ggacacaggg ggtggcttgg ctgaaggggg cactcagcac ccacagaaga caggagcagc    50160
ccagggcagg ggcaggtgga gttcaagggc tgctttcctg tcaggttctg tggcttcttc    50220
tgcatcaaat gcgttctcct gggagcctct ctatatttat ggttctctgc ctaccactga    50280
ggcctctgga ttggaaaaga ttactactag aaaaaaaaat tctcatatac ccctgaagaa    50340
tacatcatta attgaggcag aagatgtcac aggaggccag ggaggctgtg gaaactgtgc    50400
gacgtggatg cacatctgac aacaaagaca tgaaaaatca gggaacactg ataaaacctc    50460
ctaattatgc catggccctc tctaagccta gtaaagccat tgatgccttc ctgggccaaa    50520
cccacccatc aggggatcac tcctgtgtcc cagcagcaga catgccttag aatctccact    50580
gtatgtaatc actgtctggg aggagctccc agggcatgtg tctttgcatt aaccaggtga    50640
tgggtgtcag agaacagcag ctggatgcct ggtctatggg ttccctgatg ttgaagaaat    50700
gggaggtgca gtctcagagc caatacactg tttatgcatt tttatataga aaccatgatt    50760
tttcttgctt ctctcagatg acatagagga tcaagaaaac agtctgtaaa caattgtaat    50820
gtccccattt cttctgaata aatgcattat ttcttaattc tgagtggggg tttgtcagac    50880
catgcccttc tcctaagcaa ttgttcaatc caggctgaaa ccacatgggg atcacatact    50940
ttggtttggt tcaggtgcag aggtcttcag tagagcaaat ttggtccttc ccacacagta    51000
```

```
agcctcacct tcctcagaga aagagctgag attgatccaa ctttgtctga ggtgggagct   51060
gcttctccac accttggagc ttgcagagac ccctaaatgc agctttattg agtcaggtgt   51120
gtctccatgt gggggacttc tgctgctagt gatctctgct cagttctaaa tgtgggttca   51180
gaattaggac acttaggtta tcacgcctca aaaattacca tcattgtaga tagaaataat   51240
agtacaatgc caattgttgt cacttgtttc ttattattat tggagtataa gtttgaagag   51300
acaaattgtt accatatatt tgcataaatc taatgtcaga atctcttgaa ttgctcttga   51360
acacttacaa actggttaga agcagattct tattttttttc tatactagtg tattttggga   51420
tgtcaacatt ttgtccagaa catgtgagta ccaataactg tgtgtttcag aaatgactgt   51480
gagattcagt catttctatc gagtgggaaa accagttaac tttgtctttg atatatggat   51540
ggaagcccaa gatagaggct tgtcagtcat tgtttctgtg ccttctccct tgggaatgtc   51600 tgtattttt tatgctctgt cctgggtcta taccccaatg gttcccctac tccatggcac   51660
ctgcctgtgc ctgtgcatgc ccctgccac actctccgtg aaacatctgc tttggctcag   51720
gaagaacccc tcctctgcct ttttttcctcc tgcccctggt ccacattctt ctccatccac   51780
aggctctcag cagcacctcc catccacact aaccctacat ggggtcatac cttgtccacc   51840
acttcctctc tcttttcttc tgagctttgc cttttattcc aacagcctgt ttccatctca   51900
cctggacttg tgtacaggaa aggatttacc gagcagtctt gggttgtgca aaccctgaac   51960
attcctgaaa aagtgctttc tcaagctagg cccatattca gctcctggga gatgatatct   52020 gccttttgg catactcctc ctggtagtat tattaaacca cttgattaag ataaggttta   52080
catctgtaaa actacacatt atttaacata cttaactcat tgagtttgga gtaagtatac   52140
atctgcaaag ttatccccat catcaaggtc ataaccatag aaatcacttc caaaacattc   52200
ctcttatctc tcttaatatt gtgattattt tattagttaa aatgtatttt tgtttgtgtt   52260
tgtctgtgtc tctgtgtgtg tagcctgggt gcacgctata ctacctgttt tcataatgac   52320
ttatggtgaa tgcctattag tgctcaagag gccggcgtct gagcactgga ggtcaattgt   52380
gcaggtgtca cacacatctg tgatgggccc aataaacagc cctgggcaca agcactcagg   52440
tgagcttccc tggtggacaa tgcttcacac atgttgtcat gcatcactgc tgggagaact   52500
ggggacaaga gactcctcag ggaaagaaca cctgggagct catgcctgga ttctcagggc   52560
cttctccctg gtgcctttgc tcattttaat tcatattcat tcgctataat aaagctgcac   52620
ccatgagaat aacagctttt cttgtgtcct ttatttgtac tgattaaggg gcctgaggat   52680
ggtcttggga cactcaacac aattacatca gagttggaga atgctagaaa gttcctgatt   52740
gctgacgcat ggctagagga ttttttataa catcaaagga tgagaaagtg cgggataaaa   52800
gacattcaat gcccagatgg ctacagaatc atatggcatg agatggcatg tacactccaa   52860
taaggagcag gaagtgaaag taatccatgg aatttagaaa caacagatac agcttcctag   52920
gagttgttcc ctgaaaaagg aaaagtaaaa ataatgagga acaacccgaa tatgcaattc   52980
atatctgtga tagctaaaat aatagtaaaa agatgcacat ccagccctgc agtgtgccct   53040
gtgagccgag gctgctagac tcccattcac caccaaaggg tacagttgtc cagaaacaac   53100
acacaacaca taagagtgac acagaaggta gcccagagtt tgggctgggg agaggaatcc   53160
actagacaac tataacaagg aggacagcat ggaaagtggc atcatttgt gatatgattg   53220 atatcattaa tttatatcat cggattgtga acaaagttag ccaatggact atgagagtga   53280
ctgacgtagc agcttctctg gcttcgtgtg ctgcagatga gaggagaatg tttggggagga   53340
```

```
tgctggaccc acagctcaca acagacatat gacagacgta gctgatccca acctcaagta   53400
ggatgttctt gatgagacag cttccctggt gcactggata tcagatcctg tatagtttca   53460
gaacttgtgt agtttgtgtt gctttggctt tttctctgga tcttttaggt gctaatgaaa   53520
tgagagtgct tcacaaaaaa atggggcaga caaaggggat agttaagggc ctcctccaag   53580
caatgtggat atcataaaat aaatgttaaa aaatgaaaga actaaacaag aaggtgctgg   53640
ggttgacaca aaggacttaa aacagcacta ccaggagttg ggtgcagcaa tgggcatccc   53700
ttcaggtcca tcagcaagtc agagacctaa acaaatattc cctattcatg ttgaattggc   53760
agagtgtaaa aatctagaag acaaaatggc caggaaaaat gtgcgatttt gcatgggtga   53820
aggtctggca agttaatcat cttgaggact gttgaggtcc tgaggtggtc ctgcccttgc   53880
ttgatgccca ggccgtagtc caactcacac gaaattgcca gggaatagac agtagttttt   53940
ttagtagttc ttgttatcag gcataagtgc atttgaattt tctcttcatg gcctttcctg   54000
gcactatttc tcattttttt taacacacat agtttcaact agatttatca ccttcacagg   54060
gtcacagaga agggtggaag aagggaggcc ctggtatggg tctcgaagaa acatggaaaa   54120
gagtggagag ggacaatagc agggtgtaag gaattattga gaccttactc tgcccctccc   54180
aggaggctca ggccagcctt tttctgcatt tgaggttctg ggttataaac gctgtagact   54240
cctcccttca gggcagggtg acaactatgc aaatgcaagt gggggcctcc ccacttaaac   54300
ccagggctcc cctccacagt gagtctccct cactgcccag ctgggatctc agggcttcat   54360
tttctgtcct ccaccatcat ggggtcaacc gccatcctcg ccctcctcct ggctgttctc   54420
caaggtcagt cctgccgagg gcttgaggtc acagaggaga acgggtggaa aggagcccct   54480
gattcaaatt ttgtgtctcc cccacaggag tctgtgccga ggtgcagctg gtgcagtctg   54540
gagcagaggt gaaaaagccc ggggagtctc tgaagatctc ctgtaagggt tctggataca   54600
gctttaccag ctactggatc ggctgggtgc gccagatgcc cgggaaaggc ctggagtgga   54660
tggggatcat ctatcctggt gactctgata ccagatacag cccgtccttc caaggccagg   54720
tcaccatctc agccgacaag tccatcagca ccgcctacct gcagtggagc agcctgaagg   54780
cctcggacac cgccatgtat tactgtgcga gacacacagt gagagaaacc agccccgagc   54840
ccgtctaaaa ccctccacac cgcaggtgca gaatgagctg ctagagactc actccccagg   54900
ggcctctcta ttcatctggg gaggaaacac tggctgtttg tgtcctcagg agcaagaacc   54960
agagaacaat gtgggagggt tcccagcccc taaggcaact gtataggga cctgaccatg   55020
ggaggtggat tctctgacgg ggctcttgtg tgttctacaa ggttgttcat ggtgtatatt   55080
agatggttaa catcaaaagg ctgcctaaca ggcacctctc caatatgaca gtattttaat   55140
tagtgaaaat tttacacagt tcatcattgc ttgcttgcct tcctccctcc tgtccactct   55200
cactcactcc ttcttttatt ttctacttaa ttttacaaaa tcatttaacc ccttttttgaa   55260
ctattaatag gttatctttg tttggtgatt gttttccttt caataatatg tactgaataa   55320
ttcatctttg tgccaattca taagtattct ggtgtaataa agacttcttt cataaaaatt   55380
ggataaatta aaataaagat aaatttttaa aaacatacga tctatcaaaa ctgaaccata   55440
aagaaataaa aactctgggt tgggtgtgtt tgctcattcc tgtaatccca gcactttggg   55500
aggccatggc cggtggatca cctgaggtca ggagttcgat atcggtctgg caaacgtgga   55560
gaaacgctgt ctccactaaa aatacaaaaa ttagctggac atggtggtgc tcgcctgtag   55620
tcccagatac ttgggagcct aaggccagag aagagattga acccgggagg cagaggttga   55680
aataagccga aatctagcca ctgcattcca gactgggcaa cagagtgaga ctccatcccg   55740
```

```
aaaaaaaaaa actgaacaga cctatgagta aagagattga gtcagtgatt tttcaaacat   55800
ctcaaatcaa agaaaagtca agaacttcat ggcttcacta ctgaatttta tcaaaaattt   55860
aaaaaaaaac tagaatctct atacaaattt ccaacaaaat aaagaggaaa aaatacatgc   55920
aagcttattt tggaaggtcc tatttccaaa gcaaggaaaa gacactccaa ataaataaaa   55980
ttacaggcta atatccctga ttatctagtt tcaaaaactc tcaagggtgg tgagaaacca   56040
aattcaacag cacattaaca acagaattca ccatgatcag gtgtggttta tctctaggaa   56100
gcaatgaagt ttcaacctgc agaaataaat gtgatatatc aaatgaaaat attgaaggac   56160
taaaaccata tgcaccatat gtccatgtca atagatgcag aaagagcctc tgtcgaaatc   56220
cactacactc taatttttaa aaatctgaac atattatgca taaaacatat atacctcaac   56280
ataataaaga ccacatatca caagcccaca tctaacatca tacacagtga tgaaaatttt   56340
attttcctct aagactagaa actagacaag atgcttcact atcaccaata ttattaaaca   56400
cagcactggg tggtctagac aaaacaggcc agaagaaaaa aatagaagtc atccatatag   56460
taatgaataa atataaaata tattttttaca tattacatgc tcttatttat acaaagcctt   56520
aaacactcca ccaaaaaaga ttgaaactaa tgaagaaatt caataaagtt gcagaatcca   56580
aaatcaaact tacatttcaa gatggcaggt tagaggcatt gctagtattc ctcttccact   56640
tggaaggaca aactgatgtg gagagatgaa catcgcggac ttattttcaa gaagcaatgc   56700
aggaactgaa cagaaacact gaaataatct acaaactttc tgaaaaagca ggaagctgca   56760
gcctacactg tgagtcaggt gaagggctgg gagtccccag catttgaggg agaacagcca   56820
aaaatttcag ccagtggtcc caagttgaaa gtagctctca acagggtgt gtaatataac   56880 ctagggttgg gacgaactcc cttggccagg gcctgggtag ggaagtgtta aaagtggtct   56940
ctgcaagttt aggagccatg ggtgcaggag ctggtgccct gctttgcagc agacaggaag   57000
gggcatggca tgaaacccat ggctgcagtc tccatgggga cagcctatga ctcctggcat   57060
ttggaggtat tgatcacaga ttgactgaaa ctcatctcac tgctgccagt ggaacaccac   57120
gggagtggat cagcctcacc aagtatgtgg gaactgtgtg gggcctacca ccacctgcca   57180
ctccccaccc cctgcccaaa cttctgtgga ggagaggcag ccatggtccc atctggaaca   57240
tcatcccagt ggcctgagaa ccaccctgt cccccacacc cacagggct gctgcttgcc   57300 ctgcatacag agactcagag gggaaaccca cctggcccaa ccctcacctt gctttgtgca   57360
gccacctgcc ctggcagctt aacacaaaag acagcatctt ttgggagcta catagccaca   57420
cccactgcct aagaatccat agtagccccc atacctgggc aacacaaggc ttgcaaaaat   57480
cccaccgcta ataatgcagc tggtgctctt ttgcaagcac cacctcttag ctggaggcca   57540
accaactatg cattacagca tctccctagta gactaacact gcatcctgga aggagaaaat   57600
gactgtgcga tctcagttat caccatggcc tgcaccactt tggatgacca ggagatcctg   57660
agtctctcca tgtgaccagt tcattgctac tatacccatc attcaagaaa gccagtacac   57720
aaaggctatc aatatccatg gaatttcaca gagtctcctt cactctcctg cctgccactc   57780
ccatcagacc cggttctgct gttcactgtt gaaaaatatg aggacagttc acatcactgg   57840
atcacttaga gacatttgcc cacaccagcc tgaagtgtgt caacgtcact gggcagctag   57900
acctagagaa gaaacataac tcacagtacc atggctccca ggttctcctc ctcttagggg   57960
aagggagtgc accacattga gggaacacct catgggacaa gagaatctgg atggcaggcc   58020
ttggacacca gatccctcca ctggtgggaa acttcttcta gcagaagtac agttgcagca   58080
```

| | |
|---|---|
| ctgggctcag ctgggaaagt cttcagctct ttctcaacag acagccctgt tgcttgtgaa | 58140 |
| gaatcttgaa gaagaggaag cctttccccc ttgtacacca ctgtaggcac acttggggtc | 58200 |
| tctcccacaa gacctcagca tgggtgcaac tatagacagc ctttctggaa cacatcattg | 58260 |
| tgactgcatc ccccagaaac agcactttct ggattcaggc ttgcatgaga cagagagtca | 58320 |
| cagttcctct ctatttggca catgaacatt tgtacagatg aaaaaacatg cctgtcttat | 58380 |
| ctgaatagcc ggaatactgg gacagcagta tgtctgagag gtggataaat ttcctactga | 58440 |
| cttgacaaga gagctgaggt ggttccaacc cttcccaccg ataagacctc agtgggactc | 58500 |
| actaaaacct ctttcagcca actctgtcaa ggctgggact taatttaccc acctgcttta | 58560 |
| gccacaacta gtttctaccc aaggaaaagt cctccactga tgtgaagctt gagccatcaa | 58620 |
| gcaaataaat aaatcactgg ggacaaataa aataaacatg tgcatgccac agaggaatga | 58680 |
| gataaggttt aagagacctc taccattcta accccataga agacagtgaa cttgctcaca | 58740 |
| gaccgagcag atttctactg caatcaacac ataggaaagc catcatacaa agattctcca | 58800 |
| taaccccgga actcttacag agtcttcacc cctctaagga ccaaaaacca aatcaggttg | 58860 |
| taattaatta taagcattaa agtctcattc ttaagggaaa aaaatccatt taaaaacaaa | 58920 |
| cacaagaaac agtcaaatca aacataaatt caataataat tagaaaatct accaaaatga | 58980 |
| gaggaaatga gaaaaataac tggggaaaaa tgagaaaaca gggtgctgtg ccagtgccaa | 59040 |
| aaggtcacaa ggtcacacta cctctccagc aataaaccat aacaaaatg gagtctttga | 59100 |
| aatatcagaa aagaaaatca gaatgttgat tgataagcta ctcaagaaga tatcagaaaa | 59160 |
| aggcaaaaat cataataaat aaatttataa aactgttgag aatatgaata caaatttta | 59220 |
| cagagagata gacatcctaa agagaaacca atcagaactc ctgaaaattt aaaaaaatgc | 59280 |
| agggaattgg aaagggaatt acaaaatgcc atggaaagtt tgaaaaatag actgaaaaaa | 59340 |
| agtagcagaa ataacaatag actagaaaca gtacaaaata aagtagaag taaaatattc | 59400 |
| gaggaaaaag aaaaaggaaa cagttaaaga aaaaagtaga aagaccagac tattattgaa | 59460 |
| ataaccaaat cagagaaaaa taaatttaaa aagagccaaa agaagtgaaa aaagtctcca | 59520 |
| ggaaatatgg gattatgtaa aacaaacaaa tttaagaata attggtgctc ctgaagaaga | 59580 |
| aaaaataata ataagtttgg gaaaacttct ctgaaggaat aattgagaac tacttctctg | 59640 |
| gcctgactaa agacctagat atccaaatcc aaaaagttca aggaactcct ggggaattca | 59700 |
| ttgcaaaaat accttcacca agcatacagt catcaggcta cctaaagtct acatgaagga | 59760 |
| aataattcta agagcagtaa aacgaagaaa cccatcagaa taatggcaga cgtctcagca | 59820 |
| gaaacttgac aagcaagaca gattagggtt ctattttcaa actccttaaa cagaaaaact | 59880 |
| ttcaaccaag aattcttttt tatcccgcca aactgtttta taataaaaa agaaataaag | 59940 |
| tcattttcag aaaaacaaat gctgagggaa ttcatcacta tcaaaccagc actacaagaa | 60000 |
| atgctagaat aagttctaaa ccttgaaaca aaaggccaat atgcacaaaa atggaacctc | 60060 |
| ttaaaaatta aaaactcacg gggcctataa aacaataaca caatatcaaa gaataaacaa | 60120 |
| aattaggtaa cgacatgaca aagagaatag caactcatat ctaaatattc acattgaatg | 60180 |
| taaatcataa aaggcatgga agaaggaatt tcacaaaaat agaaaccagg agtgagcagg | 60240 |
| actagctatt tttgatctca gacaaaacag gacttcaaag caaaaacaat ttaaaaagac | 60300 |
| atagatgatc actatacaat gataaaagga tcaattcaac aaaaaattac aattacatat | 60360 |
| ttatatgcac caaacactgg aggaactaga ttcattaaac aagtactgct agacctaaaa | 60420 |
| aactgagaga gttagcaaaa caatcataat gggagatttt agtacaatca tgacagtact | 60480 |

```
aaacagatct tcgagacaaa aagtcaacag ataaacaatg cacttaaatg actcactgga   60540
acaaatggat gcagcagata tttacagaac attctatcca agatctgcag aatatacatt   60600
cttctaatca gcacatgcaa cattctccaa ggtagagcat atactaggcc acaaaacaag   60660
tctcaataaa tttttaaaac aatgaaatca tatcaagtat cttctcagac cacagcagaa   60720
taaaactaaa aatcatctcg ctaaagaact gtcgaaaatg aacaaataca tagaaattaa   60780
gaaatttgct tctgaataat atctgggtta acagttacat caagatgaaa atttaaaaat   60840
tatcttaatt aaattataat aatgagacaa gttattgaaa cctcaaaaat aaaggaaaag   60900
cagtgataag aggaaagttt atagtgccag ctgcctgcat caaaaagtct gaagagcac    60960 aaattcacaa cctaatgtca caccttgaga aattggagaa acaagaacaa actaaacata   61020
gagccagaag aagaaaagaa ataacaaaga tcagagcaga actaaatgca atccaaacaa   61080
aaaaaagcaa tgaaacaaac agttggttat ttgaaaaaat aaacaaattc atgggtcatt   61140
agctagatta acaagaaaaa gaatatcaaa gatccaaata agctcagaaa tgaaacgaga   61200
cattacaatc tacaccacta atataaaaaa taatttgaga ctactaagtt caccttcatg   61260
tgcacaatgt agaagactta gaggaaatgg aaaaatttct agaaacatac aacactccta   61320
gattaaataa aaaagaaaca gttactttga atagacaaat aacaaacagt gagattgaat   61380
cagtaattca agaattgcca acaataacaa caatgaaata gggccaggtg aattcacagc   61440
tgaattctat caaaaaattt aagaagaat tgctgccaat tttgctgcaa ctattttta    61500 aatttagata aaaaagaatc ctccctaaat tattctatga agctagtata accaagatac   61560
caaaaccagg aaaacacaca cacacagaca cacacacact ctacagatga atttccctga   61620
taaatataga tgcaaaaata gcaaaaaaaa aaatagctag ttgagttcaa cagcacatca   61680 aaagataat tcctcatgat caagcgtgtt tcatctcaga attgcaggga ttatttgaac    61740
atactcaagt caataaatgt aatacatcac ataaacagaa ttacaaataa aaaccttacg   61800
attgtctcaa tagatgcaga aaaagcattc aacaaaattc agcatttttt aatgataaaa   61860
actgtaaata aatgaggcat agaagaaacc tgcctcaaac taataaaagt tacatatgaa   61920
aaatccacag ctaatatcat gctgaatgtg aaaaagttaa agcatttac cctgagaaca    61980 caaacaatac aaggatgccc aagttcacca attctattca acatagttct ggaagttcta   62040
gccagagcaa ttagtcagga gaaaaaaat aagggtatcc aaatttaaaa agagaacgtc    62100
agactatcac tgtttacaga tcaagggatt atatatatta aaaccctaga ctcctccaaa   62160
atactaatag ttttagtaaa tgaattcagt taagtctcag attacaaaat acatgtacac   62220
aaattagtag cacggctata tcaacaac agcaatgctg agagttaaat caagaactcc     62280
atccctttta cagaagctgc gaaaagatag tatatttacc aatatactta accaaaaggg   62340
taaaagatct caacaaggag aactacacaa cactgctgaa agaaatcata gatgatacaa   62400
acaaatgcaa atgcatcccc tgatcatgga ttgcaagaat cgctattgtg aaaatgacca   62460
taatgcctaa agcaatctac agaatcaatg aaattcttat taaaatacca acattatttt   62520
cttcagaatt caaaaataat aacgctgaaa tttatttgaa accaaaaaaa agccaaaata   62580 cccaagaaa tcctaataag ataagaaaa ttggagccat cacattactg aacttcatat      62640
tacaccacaa ggctgcagtt accaaaacaa catggcactg acataatagt aggctcatag   62700
accactggaa caaaatagag aacccagaaa taaagccaca tatgtaaatc caactgatgc   62760
tttgcaaaat gtaccaaatt ttaaattgaa aaatagacac cacatttaac aaatggtaca   62820
```

-continued

| | | | | |
|---|---|---|---|---|
| agaaaaacta | gcaagccaca | tgtaaaagaa | taaaactgga | tttctatctg | tcaccatata | 62880 |
| aaagaccaac | tcaagatgaa | tcaggtactg | aaatataaga | cattaaactc | aaaaattcta | 62940 |
| gaaaacaata | ttggaaaaac | acttttagac | atcagggtag | gcaaagaatt | tataactaag | 63000 |
| accccaaaag | caaatgcagc | aaaaacaaaa | ctaaatttat | ggaacccatt | taaactaaag | 63060 |
| tgtttcttca | cagcacaact | aagagtcaat | ggagtaaaaa | gacaactcac | agaacgggag | 63120 |
| aaaatatgtg | caaacttcac | atctgacaaa | aaattggtat | attcagaatc | tacaaaatac | 63180 |
| taaaacaagt | cgccaagaaa | aaacaaacga | tcccatttga | aagtggacaa | gggacataaa | 63240 |
| tagatagttc | tcagaagaag | atatacaaat | ggccaacaaa | catatgaaaa | actgtgtaac | 63300 |
| atcactaatc | atcaggaaaa | tacaaattaa | aaccacaatc | taataacacc | taatcctgca | 63360 |
| agaatggcca | ctataaaaag | tcaaaaaaca | aagggaatg | cttatacact | gttgatgaaa | 63420 |
| atgtaattta | gtataaccac | tatggaaaac | actattgaga | tttcttgaaa | agcagaaagg | 63480 |
| tagatctact | attttttttt | tctttttttga | gatggagtct | ctctcagtca | cccaggctgg | 63540 |
| agtgcagtgg | tgcaatctca | tctcattgca | acctccgcct | cccgtgtcaa | gtgatgctcc | 63600 |
| cacctcagcc | tccggagtat | ctgggattac | aggcacccac | catcatgcct | ggctaattgt | 63660 |
| tttttgaatt | tttgtagaga | cggggtttcc | ccatgttggc | caggctggtc | tccaactcct | 63720 |
| gacctcagct | gatcctcccc | gctcggcagc | ccaaattact | gaaattacag | gcgtgcagca | 63780 |
| tcacacctgg | ccagatctac | tgtttgatcc | agcaatctca | ttactggaga | gctacccaaa | 63840 |
| ggaaataaag | tcattatatg | aaaagacgt | gtatatgtat | gtttatagca | gcagaattca | 63900 |
| aaattgaaaa | tatgtgaaac | caatttaaat | gcccattggc | caatgagttc | agaaagaaaa | 63960 |
| tgtgacatcg | cctgtaatcc | cagcatttcg | ggaggccgaa | gagggcggat | cacgaggtca | 64020 |
| ggagatcgac | accatcctgg | ccaacatggt | gaaatcccgt | ctctactaaa | aatacaaaaa | 64080 |
| atttgccgga | cctgttggcg | tgcacctgga | gtcccagcta | ctcgggaggc | tgaggcagga | 64140 |
| gaattgcttg | aacccgggag | gcagaggctg | cagtgaaccg | agattgcagc | actgcactcc | 64200 |
| agcctgggtg | acagagcaag | actctgcctc | aaaaaaaaaa | aaaaaaaaag | aaaagaaaag | 64260 |
| aaaaagaaaa | tttgacatat | atacatcatg | gaatactacc | aagccgttaa | agggaatggc | 64320 |
| ataatgtcct | ttgcagcaac | ttggatgaag | ctggaggtaa | tgagtataag | tgaagttaca | 64380 |
| caggagtaga | aaagcaaaaa | ctgtgtttgc | acacttacaa | gtgggagatg | ggctatgaac | 64440 |
| ttgcaaaggc | atacagagtg | atataaggga | cttttggagac | tcagaaggga | aagaatagga | 64500 |
| tggatactag | agagaaaata | actacacttt | aggtagagtg | tacactattc | aggtgatgaa | 64560 |
| tgtactaaaa | tctcagaatt | tattgctata | taattcctcc | atctaacaaa | aaaatattta | 64620 |
| ccccaaagc | tattgaaatt | aaacaaaaat | caacctacaa | aaataagcat | cttctgtata | 64680 |
| cactaaaaaa | tgattattca | aaattaaaat | caagaaaata | aatctaaata | caacagctta | 64740 |
| aaattcataa | aataaatttt | accaaaataa | atttaacaag | gatacaaaat | atctgcacat | 64800 |
| tgaaaattat | aatatattga | ttaaaatgta | agaaaacaca | aataaatgga | aggctatctt | 64860 |
| gtgttcttgt | gttactggaa | catacattgt | taatatgtcc | atcctaacct | aagcatttac | 64920 |
| agattcaatg | caatcccatt | caaaatttca | aagatatgca | tttacataaa | ttgaaaaaaa | 64980 |
| aaacctctct | catttgaatg | gctggggtga | ttgacccgga | ctatcaattt | gaaatcagac | 65040 |
| tactactcca | caatggaggt | gagacagagt | atgtctggaa | tacaggagat | ttcttaggac | 65100 |
| atctcttagt | attactttgc | catgggatta | agatcaatgg | gaaaaacaa | cctaattcag | 65160 |
| gcaggaatac | aaatggccca | gatacttcag | aaataaaagt | ttgggtcttc | acccagatta | 65220 |

```
aaaatcctga ccagccaagg tacttgctga aggcaaaaca aatacagaat gggtagtgga  65280
agaaggtagt tgtcaatacc aggaatgacc acacgaccag aagtggggac cgtaattgtc  65340
gtgagtatct ccttaagctg ataagcaact tcagcaaagt ctcaggatat tttctccata  65400
tcttgttagg aatatatttc tgcatgtgta taactgtact aagaaaatat cttcattgtg  65460
ccggacacgg tggctcacac ctgtaatccc agcaatttag gaagccaagg tgggtggatt  65520
acctgaggtc tagaggtcga gaccagcttg accagtatgg tgaaacgccg tctctaccaa  65580
aaatacaaaa attagcctgg catggtggca ggtgcctgta atcccaggct tctcagaagg  65640
ctgagacagg agaatagctt gaaccctgaa cccgcgaggc agaggtggca gtgagccaag  65700
attgcaccac tgcactccag cctgggcaac agactgagac tccatctaaa aacaaacaa  65760 acaaacaaaa atatattaat tgttttcatt gaatttgttt tcttttatc atgtgtcaca  65820 agatttattg acttcctatc agcatttaaa tgttgttaac tatatgtagt ggtatgtatg  65880
taggttaagg attagtgcac tttcagttgt atgaaggata gctgtattat gttaggcata  65940
attatgacct tattattgtc tttatttgga gttcaagcat gattgcagct agatgtgtag  66000
gggtgctaag ttgacaagag gtgggctttt gatgcttgat actaggtgtc aacttgattg  66060
gattaaagga tgcctacgtg gctgggaagt attgtttctt ggtgtgtctc tgggggtttt  66120
gccagaggag gctgacattt gagtcaatgg actggaaatt tgagtttgtc atgttgcatg  66180
atccttttaa agtcttatag aacttagttg actattattt tggtgtagtt catttgtata  66240
aatatttctt tgaagtttaa ttttcttcct ttgcgtttgt ctgtcactgg caacacggta  66300
attgtagcct tttagaaata gcttagaagg ttggcgactc atcattttt aaaaaagtta  66360 gagaacagtt ggcatgactt ttttaaattc tgagagccat tttttatcta acatataggc  66420
tatcatgaag aatatttata gtgtgcttga gaagcatgcg tattcactg cgcttggttg  66480 gaatgttctg tagatgtcta ttaggtcagt ttgttcaata gtgttgttta agtccatggg  66540
cttcctaaga attttttttat gggtgttcta tacattattg agggtgaggt gttgaagtct  66600 cctccttttct tattgttttc tatttctcac ttcatatctc ttaaactctt gttaatgcgg  66660
ttatatttct atttttataa ctatgtaaaa tagaaataaa ataataattg cttagtaatt  66720
ttaatgggaa aatcacataa taagaaatta tattttccca aatgctgcca tcaccactaa  66780
actcctccag gagtctcaca tctgctctgg gctctgctct ctcctaaggg gtcccacatc  66840
agagtttgct acagaggagg agacaagaaa atagggccct ccctctcctg atgaaaacca  66900
gccctgccct gaccctgcaa ctctgggaga agatctctag tccagaatta ccaggagttt  66960
ggatttgatg atcagctctg tacaaacatg gctcaccata gagttagggc tgagctgggt  67020
ttcccttgtc attattttaa aaggcgaata atggagaact tgagatatgg agtgtgagtg  67080
gatatgagtg aaaaaacagt gattctgtgt ggcaggttct gactcagatg tctctgtgct  67140
tgtaggtgtc tagtgtgggg tgcagatggt ggagtcttgg ggagagttgg cacaagctga  67200
atgtgcctga gactctgccg tgcatcctct gaatccacct tctgtagcta ctagatcagc  67260
tgaatctgcc aggctccagg aaaggggctg cagtgagtag tagatataat gtacgatgga  67320
agtcagacat aatatgcaga ctctgtgaag gtcagattca ccatctccaa agacaatgcc  67380
aagcacaggt tgtatctgca aatgaacagt ctgagagctg agaatatggc tctgtattat  67440
tgagtcaaag gtaccaaatg aagggacatc agtgtgaacc cagacacaaa atttcctgca  67500
gggaggaggg aggaggctgg gctgcagtgg gcactcagca cacacaaaag gcagggacag  67560
```

```
ttccaggggc aggtacaggt gcaggtgaag gcaaaggtct actttccttc cagatctgtg   67620
gattcctctg catccaacag ttcgcctggg cctctgtctt tatggatctg cgcctaccac   67680
tgatgtctct gggttagtaa agtttgctac tataggagga acattgtca tttgtcagaa    67740
aggcgaataa tggagaacaa agatattga gtgtgagtgg atatgagtga aaaaacagtg    67800
attatgtgtg gcaggttctg accaaaatgt ctctgtgttt gtaagtgtct agtgtgaggt   67860
gcaggtggtg gagtgtaggg gagaggcaag aggcagaaaa gcgcgcagga ggccgggtga   67920
ggctgtagac attgtcagct cactatgcca atctcacaac agtgctggag aaggtgggag   67980
tctgatggag cttcccaaca accctgtggt ctaagctaag tccattaagg ccgctggttc   68040
ctcctggaac atagctgtcc atcaggaatc ccccatgtgc ccagcagcag ccacgcgtta   68100
gcatcttcac tgtgcacagt cattgtttgg gaggagctcc aggatgggtc tctttgtcaa   68160
aaaccgggtg atggtgtcag agagctgtgc cgggtgcctg gtccagggc tccctgacgt    68220
tggaggtata ggaggtgcgt tctcagggtg ggaacacctt ttatggaaat gtacagaaga   68280
aaacatgatt ttccttggtc ctctcagatg acatggagaa gaaagcgcgc agcttgcaaa   68340
caattgtaat gtccttgtaa tttcctactt tatcccaagt tcattgattc ttgtaaacct   68400
tggtttctgt ccaagtacag agatattgat tagagtgagt ttggttcttt ccacacacta   68460
accctcacct cccccagata aagagcacat tgtccttact ctgagtctga gggaggagct   68520
gttcctgtac aactaagggc ctgcagagac ccccatgtac agctttgcag agtcagatct   68580
ttccacatgt gaggcgacct ccacggccca tgattgctgc tcaggtctaa ttgtggattc   68640
aggattagga catcctttag gctatcacag gtcaatcaga ttctgaaaaa tcactgttat   68700
catagacaga ggtaataatt caatacccac tcccctgaca gcagattctc tttcttattt   68760
ggttgaaagt ttgaagaaaa taagtgacca tttattattc ttattctaac tttagtatcc   68820
actatttgtt ctagggggatt cacaaatttc aaaacactga gctcttcatt ctcatgaaaa   68880
tgtgcatatt tgtgaatttc aacgtgttgt tcagaacctg tgcatgccga catctgtatt   68940
tctcgtgcgt tcttggcctg gcgaagccct cacagaccct ctccctcatc tgtgctgtct   69000
ctgcttctcc atcacaacca gtgcttcctg ctggagctgg atccctcagc tccccaggga   69060
agggactgga gtgaatcagg tgcacaggtc atgagggaga acacaacgca acccacgcct   69120
caagagtcca gtcaccatct ccagatccac atccaaaaca cagtttcttc tacagctgag   69180
ctacctgagc aacgagtaca caaccatgaa tttttacaca aaagatacag caaggggaag   69240
tcattgtgag cccagaaaca aacctccctg cagggaagct caggaactgc gggaggccct   69300
cgggacacca gggggcgctc aggacacaca tcaaggcagg tgcaagagga aaaggtgctg   69360
gagatggggt ttggcatcat catcatattt cactgacacc cgccactgtg tttattctca   69420
tgtacgtgat tctttgtatt attagaaaat ggcgtttatg taaataaata accatatgta   69480
ggtgcatcaa gtcgtcctct ccctttttt ttttttttt ttttggagt cctgctctgt     69540
cacccaggtt ggagtgcagt ggcgcgatct cggttcactc caacctccgc ctcccgagtt   69600
caagcgattc tcctgactca gcctcccgag tagctggaat tacaggtgtg caccaccgcg   69660
cccggctaag ttttgtattt ttagtagaga ccggatttcg ccatattggc caggctggcc   69720
tcaaactcat gatctcagtt gatccgcccg ccttggcctc ccacagtgct gggattacag   69780
gtgtgagcca ccgcgcccgg cccgtcctct ccatcttatg tggaactttt ccattaagac   69840
tctgagtccc tggattttatt tgagaacctc ataaatcatg gtcaattatg tctctttctc   69900
ctctttctcc cttcttcact cctctctagc tcacaaactg aaacacacac agaattttct   69960
```

```
aacttcaatt acctgatgtg ttgaagacaa ttgattaaag cgcagctttt ccagttcagc    70020
cactgttcat attgttgtaa gaataagaac gttgtgtttc tcagctgcgt gcttctctaa    70080
gatgagtagc agctttttta aataataccc agaggctgaa agcaatctga ataccaatca    70140
tcagcttaat cagtaaacac aaggtggtaa attcgctcac tggaaaaaca ccgattgtta    70200
caatcaggta aggctggata ctctcaacag caagtgtaaa ttcacaagta tatatgctga    70260
ttaaaataag acaaacaaat acaagtacat acatactgtt ccacttttac aaattctata    70320
aaatgaatgc taatctaaag ttacataaag aaaaccagta gctgactctg gacctggtgt    70380
gaggagggaa gggttaggaa ccagaaattg taggaaatga agaagaaatg ctgaaggtag    70440
tggagttttt tctatgttga tgaaggtaat agttatgtca ctattaatca aatcgtacac    70500
attatgggat gcctattatt tgtgaatttc accctattaa aatattacaa gttaaaacaa    70560
gtataatttt gtagaaaatt agttagacat agatgaataa aatgtatgat aaataaaaaa    70620
agaaaatcac agaacaatag cataaggact tcactcatca aactgaagaa attttaaatt    70680
tctcaacaca gaattaaaga tttaattaga tatacataag aaatcaaaga ctcctggata    70740
tacacacaaa taaaccctaa gtccacctgt attttaggg aaacgctaga atacaagaaa    70800
ataatgtcat gatttcatta cataacgggg gttaatgaaa ccacatcagg catgtccagc    70860
tgtgtcctgg ggttggttca gggaacgggt gtgtcctgtg gttaggagac gtggcaacaa    70920
gctcacagca tcagttctag ctgacaccat aaaaaggcca agagatcaca attaaaatgt    70980
catgcggatg tcacatctgt gggtgcggca cactccccca tgtgaatacg gaaaggttaa    71040
ctacactctt caggtgtctg ctgagagtag agctgtctct caggaatgtc caaaatggct    71100
caatagagca agaaaggaga ctggctcagg gttcctgtag tgccttggtg gtgtgggcag    71160
agtgagggtt ctcactcaag aaaggagttt gtggcgtttg aacatctaca tggcttcaaa    71220
tagggtaact cctgtgattc ctaactagat tcacctcgtg tgggaaagaa aggagatgat    71280
gaaggaatga gccttaagtt atcagcagtc agacatcaaa acaatagtct gatgacttat    71340
tctatgtagc acctataaaa atcgttccgg gcgcggtggc ccaaacctgt catcccagcc    71400 tttttgggagg ctgaggcggg tggatcatga ggtcaggagt tcaagaccag cctgaccaat    71460
atggtgaaac cccgtctcta ctaaaaatat ttaagaaaaa aaatagttgg gttatggtgg    71520
tgggcgcctg taatcccagc tactcaggag gctgaggcag gagaatagct tgatcccagg    71580
gggcgtaggt tgtagtgagc tgagatcaca ccactgcact gcagcctggg tgacagagca    71640
agactccgtc tcaaaaaaaa aaaagagta aaaaatatc agcccaagat gggtggacaa    71700
caaccaggcc tacaaaaaag gagaagactc cttataagaa taagcaaatc ataatgaaaa    71760
ttaggaggaa aacaaggaga gtgaggtgaa aggcatgggg cagggatta acaagggtc     71820 ctgttccaat gtcttgtgtg gagacttttc actatctaaa atcatccacc tattctgaat    71880
gtcttaggtg aactgtctgc tccaaaacat cagaaccacc agaggatttt tgaggatact    71940
cagtttaata tcttatattt gaggtgcctt acaactgtgt aaaatgctta gttattatca    72000
gtgtaattag agatagggcc tcactgtgtc acacaggttg gggttcagtg gcacaatcat    72060
agctcactgt taccttgaac ttctggccca cataatcctt ctgtctcagc ctcctgagta    72120
gcatggacta gagaggtgca ccaccacaca cagctgattt aaaaaaaatt gtttcataga    72180 aatgggtct ctctatgttg cccaggctgg tcttgaactc ctggtctcac gtgattcccc    72240
ctggttttgt ttctcaaagt ggtggaatta aaggcatgag ccaccgtatc tgctcagaaa    72300
```

```
tgattatttt gttgcaaaat actaacccaa gaattgactc cctgaatttt ctctgcagca   72360
ttttggttaa tagtgtctga taagatttat ttcaatagtt tcaacagcag agtgttctcc   72420
tgatgtttcc tccaatagtg ataatttcat ggttgaagat cacaaactac tattaaaaga   72480
tgacataaaa aggcaacctt aaacttttgg tgatggagtg agtataataa aaaattactt   72540
tcaatattgt gtaacacacg cctgcagtag gaggaaggtg agcaatgagg gtaaaatttc   72600
taaacgtatg aatcttccag ctccccagtc atagggcagt aactgatgag tcctgagaga   72660
gggaacgtaa tgccgtagtg cttgtgggat aactcttggc caagagagtt tccatatttt   72720
attaaagtgg ttataatttt taaatttaaa gatgccattt tttcaacata tccagaatat   72780
tgtgagcggg attgattctg tatgatacga gcaatggcga tgccttctgt ttggataata   72840
ttacaaacca ggttaagact gagtggtgta acgatgcacc agaacattat tctagcttcc   72900
atactagatt ttgttttttct ctttgtttgc attagtttca aatttatatg taaggtctct   72960
agaatgtagg agtttatttg aaagtgtctt ttcttgttgg ccattttgat ggggcttcca   73020
ggagatttaa aaacctcctc tgcctgcagc acagttaaaa attctgcgtt acagtagaac   73080
atctgtattt aatcctggtc tttggttgat tgacaagctc taatacatgc aataacttct   73140
gccttctggg ctggttttac atcaggtaga ggaatatata ctaagtgaaa atttgcacta   73200
gtaatatata ttattaataa ccaccacttg tattatttaa gtgttattaa tcaagaatta   73260
atgttaaatc aagggtctca atggcaatat tacctaaggg atatacaaga tattttgcta   73320
atctaggtaa aatagatgtg aacacactct tagtatccag ccatgtctcc tgtctatcac   73380
attattaacc acacagtaaa ttcacttggg acttgttcta attatctaat tagtcactta   73440
cttatctcaa agcctctgga ttattatgtg tgactatttt agcagagagt gaagaaagac   73500
aacccaggct gaccaaacaa tgaggaaaat cacaacctga tgaaaccaga aacctggatg   73560
tgagtggctc caggattgaa taatttgaca gctcatgtgc ccaggctgtt tcttgtctca   73620
gttttccaca ctgatacatc cagaaaggca gcttcacccc ccagaggact cccatcatgc   73680
tgtgacatgg tgacaacatt cccaaagctc acacacatat gttaaatatt ggctggaaaa   73740
ggggcagaga catttctgga attctcttct gaaggaccat gaatgcctca accaaccatc   73800 tccctgcct ccatgactag aaatgcacca cgtgcccaca cggatattca tccctcatgg   73860
ggataagact ccattgatga ggctgactat tttatcatat aaaattacta aagactgatt   73920
taagggtttc aaaaactaat tgaactctgt tgttctatgt ccaccagaga ttacaaatct   73980
tccaatgatg ccttctttgt ttttttgtctg cttgactttg tctcttcaac ttgttctgta   74040
ccccagagaa tctctttcag ctccctcagg tgcattcaat tgttttatttt aactgacaat   74100 ttctaaatca gttaaagaca ttacgctaaa gactccatat tcctaggtcc atattccttt   74160
ttccatattc ctaggaaggc attgtgaccc agagtctggg catgaccttg tgagtgttcc   74220
tgaccctcct ccatatgaga tgctggtctg ggtgttcttg cccctttccc tggggtagag   74280
tcctcctgtt ttccccaggt gctccctccc acagctctag tgttctcaat cagtgtcatc   74340
accttccaga tcttctgccc tgccctgcag actaaggctc tgattccata agcaagatag   74400
gggagctgct cctcaataga tctttggtga ggatctctgt tcccatctca attcctgtag   74460
ggtggaacca gtgttcctag gattctggtt tcagtagctt gtccctgcag agtaaattct   74520
tagttctgta gggggattaa gggagttggg tctgaataca ttttagatgt cgaggatctt   74580
gttctctccc agaaagacac ttcgggaaag taagactttg gtaactgtcc cctttcttgg   74640
ggaaagggat tcaagaggat aggttgcttt tgggcatgtg gtcccttaaa atttcacact   74700
```

```
aaaaagcgtt tcccacactc aatttcaagc agcccaatat atatttgtat tttttcttgg   74760
aacagacaat attttatatt ccagactctg ccttaggtaa tttcaaaccc tggctttgtt   74820
actctctaca agaaattgct tctccataag cttcagattt gttgtgtgtt ttgaaatttt   74880
atcagaaata ttaagaaaaa ttggcaaaat tccatcctcc atgtttatct gttattgttg   74940
atgcagttgt aaaaaataag aaaaatatat tcctttttc tgtacatttc caagcttagt    75000
agcaattttt tagtaacacc cagaataata aaaaattcaa atattgttta gctgcttaat   75060
aggaaaacaa attatagtaa atttgtttgc tagaatgcta cccagcattt ataataagta   75120
aacatttgat atcccaact acaaggtaaa atatccattt atgctaacta aaataagcca    75180
aacaaatgag aatatatact gttatttcat ttttataaat tctgaaaaat taaaatgaat   75240
ttgcagcaat gtaaagatca gtagttgcca gggaaatggt agaagaaaga aaggaaaagg   75300
agaaagaata cagaagaaca aaaggaaatg ttaagaattc tcttgtccaa cttgataagg   75360
atgacggtta catcattttt atcaactgta atctttaaat atgtgaaagt ttattatctg   75420
taaactaaac gttataaact ttattacaag caaaaattga agttagaca agaaggagtg    75480 atagaaagag aaaatgtata ttaaatttca gaaatattta agaatgtatc tgcctgaacc   75540
ctagttctca ccatatcttt aggtgaatgc taaaatgcag caaaatcacg catgttctca   75600
ctacagaaag tgggttctac aaaccacact cggcacattt agctttgtcc tggagttggt   75660
gcagggagtt attggggcca gtgatgagga gcacaggcca agataccagc gattacttat   75720
cccaaacatg agctctaaca tacacactta gtcccttttc cgtgtgtggt ttacttccac   75780
atctgtacat ggagagacca ctgactgaca aaatataatt tatacaaata tgtaaaatta   75840
aatagggtga tcagttcaag gtgtttatca cagcataatt ttacaataag acagcatatt   75900
tcccaaatac catcattgtc accaaactcc ttcaaggcac agtcatctta tctgggcccc   75960
gtcctctcct caggtgtccc accccagagc ttggtatata gtaggagaca tgcaaataag   76020
gccctccctc tgctgatgaa aatgagccca gccctgaccc tgcagctctg ggagaggagc   76080
cccagccgtg agattcccag gagtttccac ttggtgatca gcactgaaca cagaccacca   76140
accatggagt ttgggcttag ctgggttttc cttgttgcta ttttaaaagg taattcatgg   76200
tgtactagag atactgagtg tgagggggaca tgagtggtag aaacagtgga tatgtgtggc   76260
agtttctgac cttggtgttt ctgtgtttgc aggtgtccaa tgtgaggtgc agctggtgga   76320
gtctggggga ggcttggtac agccagggcg gtccctgaga ctctcctgta cagcttctgg   76380
attcaccttt ggtgattatg ctatgagctg gttccgccag gctccaggga aggggctgga   76440
gtgggtaggt ttcattagaa gcaaagctta tggtgggaca acagaatacg ccgcgtctgt   76500
gaaaggcaga ttcaccatct caagagatga ttccaaaagc atcgcctatc tgcaaatgaa   76560
cagcctgaaa accgaggaca cagccgtgta ttactgtact agagacacag tgaggggagg   76620
tcaatgtgag cccagacaca aacctccctg caggggcgca cagagccacc aggggcgct    76680 agggaccgcc tgagtacggg acaggtccca ggagcaggtg caggggagg tttccttttt    76740 ccttggctgg aaaagtcacc tttatcttcc cagggctcga gccttctagg ctgtgatatt   76800
ttattacttg tatttactgt tcattattta tcattagttt ttaaattttg gtaattttta   76860
caactctatg gatatatttt taagtgtata ctttcaagaa ataaacattc ctaattattt   76920
gcactgattc tcccagagtt ttattaacat ttgttgacat cagcaactac atagctatag   76980
ggacaaacac ttttaacgat agacagttgt ttaggcctga aaccccgttt atactaaaaa   77040
```

```
tttacaaaaa ttagcctggc gtggtgaagg gcgcctgtaa tcccagctac tcgggaggct      77100
gagcaaggag aattgcttga atccgggaag cggaagtcac agtgagtgga gtggactgcc      77160
actacactcc agcctggcga cagagcgaga ctttgtatga aagaaagaaa agaaaaggaa      77220
gaaaggaaga aaggaaggaa ggaaggaagg aaggaaggaa ggaaggaagg aaggaaggaa      77280
ggaaagagag gaaagagaga ggaaggaagg aaggaaggaa ggaaggaagg aaggaaggaa      77340
ggaaagagag gaaagaaaga gaggaaggaa ggaaggaaaga gaaaggaagg aaggaagaaa      77400
agaaggaaag aaagaaaaaa gatatataaa cacgcagacc tatgcatata accataggga      77460
tttatattaa acattacaat aaaataattc taaaaatgtg tcctaaggaa tcaaacataa      77520
tgatgaagta aatataaatg ttagagtaat ttataattga tttgttattt ttaatcgttt      77580
acatgaattt atttctattt gttcatttaa aagtagtata ttggtcattt caagagagct      77640
aacagtaaat ttcagatgtt gttgttacga tatatgataa gaatttgagg tggtgaatga      77700
taattatctt atttctcaat tatcttagtt attccatatt gtattcacaa atcataacat      77760
tgcttcttac cttataaata taaacaacca taatttgtga aattacaata attttcttta      77820
ttttaatttt ttaatttatc ccagatcatt atctttttct tcgcttccag atctcactgg      77880
atcatctcga gggcccatcc tcacccctgt ctcccgaaga cttctggaga ggctgcagga      77940
cgggcagaag gaggagcccc gtgtgagtcc acacgacctg gagcctccct ctccttggat      78000
taggccatct cctcgggatc acagggctct tcattatcct tacccgctg ttgtaccaaa      78060 caagcaacat cacacttcaa ttcatcaggg tttgctttaa ttttctaaat catcgtgaag      78120
gtgataattt taacagtaac gtatcacaac caaataggaa aagccctttt ccatggaaca      78180
gggtttctta tcaggatata catgtattat ggattctcaa tttatttgta gatgagatgc      78240
tattatctcc atattgtaga tgattctgct aagtcatctc ttaaaattaa ttttttccaaa      78300 gactcaaaca aataaatgat ataattacaa atttcaggtg taatagctga gccaacattg      78360
agattatatt aacatttaga acatgaactt gcaaatattg ttattttcct gtcggctgtc      78420
cccaattgtg attttataca gaatattaga aatttatcct gataaatcag gttaaaatat      78480
tatatcacta gttattaac ttttataact aataatataa aatgttccac atatttttta      78540
gccatgtttt acttacccgt gatatgtgta tttattaatt tttcatttta agatgccacc      78600
tttatctttc ttatttctgg gattttattc tagtagatag agctgaatgc attttaataa      78660
ttatcataat aatcacattt acattttgca ttttaatttt catatacatt ttattaatat      78720
tttaatttca atataaaata ttttcctaca aatgtcaatt tttgattttt atgagataaa      78780
attaacctat acaaaataca tatattttca atgtacagtt tgagggtttc tggcaaatgt      78840
gcacacattt gtctccagca tctaagttat gatgaggagc aggtccatct ccacaacaag      78900
tgtcctcttc ggtgcttcca gtcagctctc acataaggaa tttttttttca aatttaatat      78960 agatacagag ggtaaatgtt tggatttgtc acggggggatt attgagtgat gctgaggttt      79020
ggaatacaga ttcccaccga cctctccctc ccactctcca gcagtccaca gtgtctatca      79080
ttctcataat tatgtccatg tgtgctcaat gctgaggtct tacttaggag aatatgtggt      79140
attcagtttt ctgctcctac attaatttgt ttaggattaa gggccccagc ttctttcatt      79200
ttactgcaaa ggacatgatt tcattctttt tcatggctgt gtagtattat acattgtaga      79260
tgtaccgcat tttgtatatt cagtctacca atgatgtgca tctggtttga tctatgtcgt      79320
tgccactgtg aatagcacag caatgaacat agatgtggat gtgtcttttt ggtagaatta      79380
tttgcttact tttcagtgta taccccgtgg tgggattgct gtgtaaaatg atatctctgt      79440
```

```
tttaagttct ttgagaaatc tccagtctga tttccaaagt ggaaacacca atttatattc   79500
ccctcatcag tgtatgtgtt ctcttttctc cacagtccca gcagcatcca ttgttttttg   79560 acttttagt  gataaccatt ctgagtggtg cgtggctgca cacctacagt catctcatct   79620
ttgataaggc tgatgaaaac aagcaatgag gaagggactc cctgttcaat aaatggtgct   79680
gggacaactg gctaggcata tgatgaagat tgaagctgga tatctactt  caacatgtat   79740 aaaattaaca caaaattcat taaagtttta aatgtaagac ctcaaaccat aaaaatcctt   79800
gaagacaacc taggaaatac tcttcttgac atcaggtttg acaaaaaaat gttggctgag   79860
tatccaaaac caattgcaac aaaaagaaaa atagacaagt ggggcctaat taactgagga   79920
gctcctgctc agcaaaacaa acaaagaagc aaacaaaact aacagcacag tactcagaca   79980
acctacagaa tgtggaaaga tattcacaaa cgttccatcc aacaaagccg taatatccag   80040
aatctatagg gaaattaaac aaatcaagaa gcaaaaaata ataataataa taacccatt    80100 aaaaatgggc tgatatggtt tgctgtgtcc ccacccaaat atcaacttga attgtatctc   80160
ccagaattcc catgtgttgt gagacggacc caggggagg  taattgaacc atgggggcct   80220
gtctttcccg tgctattctc ttggtagtga ataagtctca ccagatctaa tgagacttat   80280
caggggttta tctgatgggt ttatcagggg tttccgcttt tgcttcttcc tcttttctc    80340 ttgccatcac caggtaagga gtgccttta  cctgccaccg tgttttggag gccttcacag   80400
ccatgtggaa ctgtaattcc aattaaacct cttttgttc  ccagttttgg gtgtgtcttt   80460
gttagcagtt tgaaaatgga ctaatgcgtg ggcaaatgac acagacactt ctcaaaggaa   80520
tacatacaag tgaccagcaa atatatttt  aaaatgttta acatcactaa tcatcagaga   80580
aatgtaaata gaaaaatgtt ctgatttctg tcactatagg tccatttct  tgtttgaat    80640 ttcatataca tggaataaaa tattatagct catttttgta agaagctttt actatctgtg   80700
aggttcattc atgtgatagc atctatcaag gttttgtcaa catatgtata aatatgtatg   80760
tactcataca catatagata tttcatatct gaatcagtcc attgcattaa taaatgacag   80820
attattaaat aaatcagttc attaagtgaa taagtgacaa tatgtatatc tatttcctg    80880 ttgatggaat ttaaatttgt ttccaatata aatatcataa acaaaactgt catacatatc   80940
tttgtacaag ttcttctgtt tatattcaca tattttatt  gataaaatat gttgaaatat   81000
aagtatgcat tataccttt  cagctttatg gagctatcac tgacaaataa aattttctgt   81060
atttaaggta caccaattga tgtattgata ttcttgggga aatgctcata atgatcaagg   81120
taattggcat gcctatcatc tcagagagtt aacattttat gcctttaatt tattgtgtat   81180
gtgtgatgaa atcacctaat atctacttgt ctggcaaaag atatgtttat aatgcaacat   81240
tcattagtat agtcacattg ctgtaggttt gatctccaga actatttcaa cctgtgtatt   81300
agtccattct caccctaatg taaggaacta cctgagactg ggaaatttat ggagaaaagt   81360
ggtttagttg actcacagtt ctgcaggctt aacagcaagt attactagga ggtatcagga   81420
aacttacagt catcacagaa agtgaagggg aagcaaggac cgcttcacat gctggcagga   81480
gagagagaaa gagcaagggg agatgcacca ccctttaaa  ccttgagatc ttgtgagaac   81540
tctgtcacaa gaacagcaaa agggaagacc gcccgcatga tccaatcact ccccatcaga   81600
cacctgctac aacacttggg gattaaaatt tgacatgaga tgtgggtgaa aacacagagc   81660
caaaccatat cattccaccc atggtctatc agaaatctca tgtccttctc acattgcaaa   81720
atatcattat gccttctcaa cagtcttcca ggcttaactc atttcagcat tatcacaaaa   81780
```

```
atctatagtc taaagtcacc tctgagacaa ggtaaatttc ttcccccta  aaacctgtaa    81840 aattaaaaag aagttagtta tttccaagac acaatggaga tgcatgtact gggtaaatgc    81900
tcccattcca aatgggtgtc attggccaca gaaaaggggc tacaggcccc atgcaagtcc    81960
aaacaccagt agggcagcca ttaaatgtta aagctacagc ataatttcct tttaccccaa    82020
gtctcacatc caggacacac tgatacaagg gttgggctcc caaggcctta ggaagctcca    82080
ccctgtggct caacgtggta cagtccccat gactgctttg ataagctggc attgagtttc    82140
tatggcttta caggcacacc atgcaagctg ttggtggatc taccattccg gggtctggag    82200
gaaggtgccc ctcttctcac agatccacta ggcatctagt gcctagtgcc cagtgggtac    82260
tctgtgtggg agatccaaca ccacatttc cttccacact ggcctagtag aggtactcca    82320
ttagggctca gccctgcata agacttctgc ctgaataccc agacattttc atacgtcatc    82380
tgaaatctaa aggaagctc ccaaacctca actcttgcct tatgtgcacc cgcagactca    82440
acaccacgtg gaagcaacca aagcttaggg cttgcaccct ctgaagcaat ggcctgagct    82500
ggaccttggc cccttagcc atggctggca ggagagggac agggatgtcc caaggctgca    82560
cagagcagtc gggtcctggg cccggaccat gaaaccattt ttctctactg ggcttctggg    82620
cctgtgacgg gagggaccgc agcaaagatc tctgaaatgc tctcaagatg ttttttcccat  82680 cgggttcctc attacttatg caaatttctg cagcccgctt gaatttcttc ccaggaaatg    82740
gattcttctt gtctaccaca tggtcaggct gcaattttt tcaacctttt atgatctgct     82800
tcccttttaa acataagttc aaatttcaga ccatctctta atgaatgcat atgacttaca    82860
ttttcagaaa cagccagggc aaacattgaa tgctttgcta cttagaaatt ttttctgcta    82920
gataccttaa gtcatctctc cctagttcaa cattgcacag atctctaggg caggggcaaa    82980
atgccactag tccttttgct aaagcatagc aagtgtgagc tttactccag ttcacaagaa    83040
gttcttcatc ttagcatctg agaccacctc agcctggact ttattgtcca tatcactatc    83100
tgcattttgt tcaaaaccat tcagtaagcc tctagaaagt ttcaaacttt tccacagctt    83160
cctgtcttct tgtgagccct ccaagcttta ccagcctctg tccattaccc agttacaaag    83220
tcacttccac agttttaggt atcttaatag cagtgcccac tcctagtgca aattttctgt    83280
attagttgat tctcacactg ctgtaaagaa ctacctgaga ctgggtaatt tatgaagaaa    83340
agagtttagt agactcacag ttcttccaggc taaacaggaa gcattactgg gaggcatcag    83400
gacacacaat gatggccgaa ggtgaagggg attcaaaaat cttctttgca agatggcagg    83460
agagagacag caagggagac gggaggtgcc acacttttaa accatcagat ctcttgagaa    83520
ctttatcagg agaacagcaa agaggaaggc caccccatta cccaatcact ttatattagg    83580
cccttccttc aacatgtagg gattacaatt tggcatgaga tttgagtggg aacacagagc    83640
caaactgtat caacctgcat aactgaaagt tataacctct gaccaacatc acccaatttt    83700
ttcctcctcc cagcccctgg gaactactat tctactttgc ttccaagaac atgaatattt    83760
tagattctac atataaatgt gttcatgcaa catttgactc tctgtgtctc actccactta    83820
gcaaagtgtc ctctatgtgt tgtaaatgtt agaatttcct cgttttaaa ggcagaataa     83880 tattcacttt taggtaggaa taagccacat tttatctgtt gattcataga tggacattga    83940 cctatttct atatctaggc tattatgaat aatctcacaa taaacatata tttgtcacac     84000
tcactttatt ttctctagat gtatactcag aagtgggtat attctatgtt caattcattg    84060
agtaatcttc atgctgtttt ttcataatgg ctgtactaat ttgcatttg ttccaaacca     84120 tacatggata actttgtacc acatattcag gtctttgttt aagtcttaaa tccatttta    84180
```

```
gctgatttat atgtattgtg tgagataagg tcaattttt  ttcttccgca tatggatgcc   84240
cagttttcac agcacttgtt gaagagactg tttcttctct attgtgtgtt cttggcagtt   84300
catcaaagat cagtttattg ggaagaaatt ggtggacttc cagattgtct gtaatgttct   84360
gttggattct atgtctgttt aaatgtcagc attatactgt tttgatttac atagatttga   84420
ttttgaaatt atagaatatg atatattcag ttatatttta cccaaaatta ttttggctat   84480
ttaaagcttt tgtattttta cataaattgg agaacttttt aatattttg taaaaccatg    84540
ccatggagat tatatattta ttttataggc ataataga   tatacctaat ttatgggaac   84600
atgtaatata ttgatgcatt tataaacgtg taaagatcag atcaggattg gtatatctat   84660
cacattaaac gtgtatattt tctttatgct aggcacattt gaacgactct cttctggcca   84720
ttttaacgta tacattagat tatcgttaac tatagtcacc ttactcatct gtcaaacatt   84780
taggttgtat ttctcctata taactgtata tctgtcttca gtaatcatct tctctttatc   84840
ctcttctctc ttgtatccaa ccaggcttct ggtaaacaac aatctactct ctgtcttcag   84900
gaaatccaat gttttagttg tgacataaaa gtaagaagat gcaatatttg tctttctgtg   84960
tttggtttat ttaacttaac attatggctt ccacttccat tcatattgtt gcaaatgaca   85020
agatatcaac atttatggct gaataatatt ctattgccta catcgattat attttatat    85080
ccatttctcc acctacagac actgaggttg ctttcatatc tgggctattg tgaatagagc   85140
tgcaagaact tggagtgcac atgcctttat gaggcagtga ttttatcttc tttagaacat   85200
actcagaata ggatttgctg agtcatcagt tatttctatt tttctttat tttggagtct    85260
tcatacaact ttgcacaata gtggaaatac aaacggaaaa accattataa aaagcagttt   85320
cagttttgag gtatgatcca aaaacacaca acatttcatc atgattctca ttgggagtct   85380
ctaatgaatc tggtggaaag gcaggaagtt ttctaaccttt gttaagaaaa ttatgagttt   85440
gcacctttt cttttttgagg ctggaaattg gcatgattca agatgcgtaa tgttagcagg   85500
tttcagaatg atacagcgaa aatcataatg agaaggcaag agagagaata agagaaagac   85560
aggaaaacaa agaaacaaat aaatttcaca agagaagaaa ctgctggatg tcagtgttgg   85620
gttttgttcc tagacatatc tgtactgagt gagaaaccat gaagccaagg gaagagtcta   85680
gaacttgttc aagtgaagca tcagcatatt tctccaaggc acctattgtc accccatcac   85740
aagggtgatg agttttgaa  taccattaaa tatgagttcc tagtaagtaa tcatgtttcc   85800
atgaaattca gttaaaatgc aaagggtgtg tccagatcac tcacgcacaa aaatacaaaa   85860
tttgcctttg catttatggc tgcatagagg taaagtccat tgagacttca gcaggttaca   85920
gagatctgtt aagttttgga ttcccatagg agagtgcctc ttagtgaagg ttggactatt   85980
aattaagtat gtacaaattc cctctatggg agtagtgttc catttgtgtg gaatttttaa   86040
ttccttattg aattgcaaaa caaatcccaa ggactgactc catggagttt tactgtagtg   86100
ttcataaaaa tatttaataa gattccttcc agtgtttcaa ggaaagtttt tctctaaaat   86160
tttttctaat acataaattt tcctgcctaa aattgaaaca ggctgttgtt aaaaagacat   86220
actggaatgg cagctttaat ctattggtga taggaatgag cataatacat gaatctcttt   86280
gagtgttctg cctcatccaa atactgtatg gcaaaggcta gtactggagg taaaatctct   86340
aaatgtatt  gttccagcca tcaagtcatg gggcaataac agatacatcc ttgaggcaga   86400
ggaccataat gccacagtgc tagtaggagt acatgtcgcc aagggagttc aagggttcct   86460
taaaattgtg ataatttaa  tgtaagaaca ccttattaga gacagggttt cagcatgttg   86520
```

-continued

```
accaggcttg gtctagaact cttgacctct tgatctgccc gccttggcct cccaaactgc    86580
tgatattaca ggagtgagtc actgtgtcta gccagtccat ttattttctt ctgcacatgg    86640
atacccataa acttatgtgg aagattgtgg gaggttataa cagtgtcata ctttagtatc    86700
agccatacct cacagaatca ttttataata gttcctttca tgggtgtact tcactcagtt    86760
catgcaaaac ctggcaggtg acaggctaaa acacaaaat accgaagcgt ttaaccaact     86820
gaaagggctg tagccttttg tcaatgaatt atttcaagac acggagaaca catatagatt    86880
ataaataaaa tactttcaca tccccttaaa ggtggaaatt gaggaaattt tacctaaatg    86940
tgtccaaagg gccctgtggc ttggtttctg tctaggtccc aatgataggg ttctcccagg    87000
attttgtggc tgtcttgtta cacttcatca agaattaacc tctgctgttt cctcaaagtg    87060
tttaattgga taatgaattt gtctataaat tgaagagttg aaatacatca aatattaatt    87120
tgtaataatc tggcacaaat tatctaagca aattcaataa ctagatgttt tttcatttat    87180
ttttatttaa aatcaggatc taagcactga tatgctttaa taacatctgt gaccctctca    87240
gcagttttct cttctgagta tatgatctgc tgtggcagtt ttcttagctt caatgttacc    87300
tcttttggca atgactaccg tctttatatt tgccaggaat ctgggataaa ggagtgcttc    87360
taagagttcc ctaacttgcc cattttggtg ggtgttccag aacatatgag atgctctgtt    87420
gttaacaaag catcccaaag ccatgcactg ccctaaaatg tgtttgtttc ctagtttgac    87480
aaattggaag ttctaataaa tacaatcact tctgccatct gggctgattt tacatcagat    87540
agagggctgt attccaaaga aaagcttaca ttagtaatag caattctagt cagaaaccta    87600
gagttttatc attgaggtgc aattcataac aaataatatt aggtcgaggt tctcagtggc    87660
agtgtctaaa tctcttaggt gtacagggtc ttccctgtta acatgaagca tttataagca    87720
cagtcatagt ttccagctat gcttctccct gtctcattat caccacaaac tatggcctca    87780
cctggaactt gggttaattt ccaaataagt aatttttag tgtttatgcc tctagattat      87840
tatgtgagaa agttaacatt cagtagaaag ttaaaagaa catttgaact gactaaacaa     87900
cacagacaat caagaataaa attcaaagcc tagatgtgag aggctccagg cctggataat    87960
gcaatagttc atgtatgcag gcagtttctt tgcccagttc tacactgata cacccagaat    88020
gtcagcttca tgccagattt gactcctatt atgtagagac atggcaatac attctcaagg    88080
gtcacatgaa ataatatgaa aattggtggg aatagggag gagacaactc tgcaattctc     88140
atctgaagga ccaggaaagc ctggacagac catctcccca gcctccgtga ctgcaccacg    88200
tgcccacatg gacactcatc cctgataggg taagaagact ccattgatgg ggctgagcat    88260
tttatgatag aaattactag agactgacgt ggaggtttca acaactaata tttataacca    88320
aaatttaatt acccccacat tgttaccatt ttcttcagtg aaaaattgct tgccatgatt    88380 aagtttaag tagatttcca atgttcacaa ctgagcttcc aagagagtct tgagaacaaa     88440
aacaatgagg gcagagaaat ctaccttttc tgtattcacc actaaactca agtggactca    88500
gcactgcctt tgatcactgc tacttctctg cagagttcag gtttctactt ctcacaattc    88560
tgacacacat tctacctctc ctcaaatgtt tggcctctgc ttcttgtaag gtcaccctct    88620
gttcttaact tcttctctga gtcattttgt gaggtggtca tgagccatta aatggatatt    88680
ttatattttc ccaacatgaa tcacatgagt ggtcatgaat tatacttctg attatggcag    88740 ttgattttc ttggcatgtt catgactagt aatatttgaa gccatttcat tcaaatcttc      88800
ggggcttcgt ttttgttgct atgacatttt ttcttctatt gagtctttcc actagtatta    88860
taacatgacc tagtatccag gctcagttgt cattaataat aaccacatat gtcaaaaatc    88920
```

```
atgcattctt ttcacagcag acataatttc ctcttttctg cagatgaaga cacactgctg   88980
agctaccccc acttacaaga atatatgcac aattatgata tcttcattta tttgactaat   89040
aagctatatc attctccctt caaattcttt acccccccaga agtcctggac aaatttctgc   89100
atctgctcaa acgataaact cagaactaca tggtgagtaa aagtcacctg gttctggata   89160
ttgggtccat ctcttcccct ccaatgtccc agagcacctc agcacacctg tccaggttct   89220
atcaagaaag agtagctcct gcacactgaa ggaaacaatt gagttaagag aggacctgca   89280
gatgatagac aatattgaaa actattaata tgacaaagga ttactaccaa gcatgtgaaa   89340
taagctcaac gggtgcggtg gttcatgtct gtagtaccag caatttggga ggcaagttgc   89400
gcagatcacc tgaggttagg agctcgacac cagcctgacc aacataaaga cacccctgtc   89460
tctactaaaa gtacaaaatt agccgggcat ggtggcatgc gcctgtaatc ccagctactc   89520
gggaggctga ggcaggagca tcacttgaac ctgggaagtg gaggttgcgg tgagctgaga   89580
tggcaccatt gcactccagc ctgggcaaca agagggaaac tccatctcaa aaaaaaaatt   89640
acaaaaaatt agctgagcgt ggtggtgggc gcctgtatac ccagctgcta gggagactga   89700
ggcaggagaa tggcttgaac ccaggaggtg aaggttgcag tgagctgaga ttgcgccatt   89760
gcactccatc ctgggcaaca agagtgaaac tccatctcaa aaaaaaaaaa agagacttgc   89820
aaagggcaaa tagatcatag acagacagat agatagatag acctattagt atacatacat   89880
acatatatat acactaatat tcaggaaaat gcaaattcat aatgagatgt cttttcaccc   89940
ttcatctctg ctagaaagtt tgttatctga aaaacaaata catacataca tacttattaa   90000
aagctggcca ggatgcctag aaagtaaaac tcatagacca ctggtggaaa tgtaaattag   90060
tgcagccatc aagggaaaaa aatagaacta ccatatattc cagcaatcca actgctaagt   90120
atatatctat ttaaatattt aaaagaaaaa actaatattg aagagatacc tgtacaccca   90180
tgtttattgc agcactaatc acaatttcta agatatgaaa tcaacatatg tgtccatcaa   90240
cagatgaatg gatacataaa atgtgatata tttacacaat ggaatattat tcagccttaa   90300
caatgaaatt ctgccgtttg aagcaacatg gatggaatgg gacaccacta tgttgagtga   90360
aatgagtcag acacagaaaa ataaataccg catttctcag cgttacttct agaagtaaat   90420
agtagagtag tggtgatgag atgccaggaa tgagagaagg ctgagataag aagaggtttg   90480
ttaacaaaca cacaattaca ggtagacagg agggatgtgc tctagtgttc tacagcacag   90540
tagggtgact acagttaaca atatattgta cgttttctgt ttacaagaag ccagaagaga   90600
gaattttcta tgctaccaac acaaataaat gttagtgtct gaactgacga atttgctcat   90660
tgttctgatt ttggtcatac caagtggcac acatgtattc aaatatcaca ctgtatccca   90720
taaacataag cagttattat gtgccaaatt tgaaaaatcc tttaattaaa aagaattata   90780
ttggcgtaca ttcaaaatga ttcaacacag agacaggaat aaataccatt tttctttgaa   90840
atagttaatt aactaacaat gtagttacat tcatttgcac caaatcgtgt atttgataat   90900
ggtatgcata gacagattta tgcataggat aatatctttt aattttagac tactacttaa   90960
tactataaat ataaataatt ttaaaacaac taagtaaaaa gaataaagct gagaaaatgt   91020
gtgtgtggtg tgtgatgtgt gagctttttc ttgtgcacca ctgtgtcctt ggtggatgtg   91080
tggttcatgt gtttgttttt atttactctg tttggggttc tctttgcttc taggatctgt   91140
agttcagttt ctttcacaaa attgggaaca ttcttcgcta ttatcttttt caaatagttt   91200
ctgtgtattt ataatttctc cttctcagat ttaaaatata cacatactat aattttgata   91260
```

-continued

```
ttaatgttta gtttctttct tcactctctt ttcgtttgca atttactttg tgaaatttct    91320
agtgacatac taatcacatg gttttattga aaagctgagc cagctctact gaggtgtgtg    91380
ccaaaagatt gctcgatgtt tatacagcat tgcttttgat ttcttatgca tttccatttg    91440
atttattctt agtattttca tatttcagtt ccctatctat gtccacgatt tctttaagag    91500
attcttgcgt gtgaattata gttactttac atatcttgtt taattagata tttataatat    91560
ctgtttcatc tacaaatctc atgctgatca tttgtttatt acaactttgg tacttctcat    91620
taatgtatgt aataattgtt gatagccaca gatactggga tggacagtgg atactggcct    91680
tattatttca ttttatgcat ttctgcctgt atttgaccac actttacctt tgccaggcct    91740
ttactgtgga agtatctgtg aatcttctca gaactatatt tgacattcac ttttgcagtg    91800
gacatcaaag ttgaagtctg ttcttctgtg tccaccagag acttcagttc ctccagtgat    91860
accttgtttt tctttcctgc ttggcttgt ctcttcacct gttccctcct ccagagaatc    91920
atgttcagct ccctcaggtg gattaaaatg ttatttaact gacaattgtg aaattggtgg    91980
aaagcaatag aataaaggga gattttctga cctttcttgg gttcatattg tgaacatgag    92040
tctgggtgtg accttcccaa tgtttctgaa cttcctccag atgagatgtt ggtctgtgtg    92100
ttcttgctct tttccctgct gtggagtcct cttgttttcc ccagttgttc cctcccgcag    92160
ctccaatgtt ctctttttgt gttatcacct tacagatttg ctgactagaa ctgcagatta    92220
aggctctgat taaataagaa ggaggggaga tacttctcaa tggaacttag gtgaagacct    92280 ctttttcccat ctcagttcct aagggattgc ccagtgccct aagatactgg tttggtggct    92340
tgcccctcca gaataattct tgttctcca gtggggatat ggaaggtggg tctgaacact    92400
tttcagaagg gtgggcactt tttctctcct agacagacac aatgggacag aacaattttg    92460
gtgactgtcc ccatttgggg gaaaaaggat tcaataggat aggaaaactc ttcagtctgt    92520
ggtcccttag aaattcaccc tacaacacat ttaccacact tgacttcaag aaatccaata    92580
tatatgtgtg ttttcatctt gtaatagcct acatttaca tgccatactc tgcctcagtt    92640
cagctcatac cccagctttg ttactcttta caagaacttg cctctcccta gatttcacat    92700
ttgctgttta tcttaaaact tcaagtatct aaagtattat ttttaaaaaa tggccagttg    92760
tggtggctca cacctgtaat cccaacgctt tgggaggctg aggtatgtgg atcacctgag    92820
gtcaggagtt tgagaccacc ctggccaaca tggtaaaacc tgtctctact aaaaatacaa    92880 aaaaaaaaa atagcttggc atggtggcag gcacctgtaa tcccagctac tcgggaggct    92940
gatactggag aatagcttga acccacgagg cagagtttgc aagtcgtacc attgcactcc    93000
agcctgggcg acagagtgag actctgtctc aaaaaaaaaa attccaaaat tccagctcct    93060
ctgtttatct atttttgttg atactgttgt tgtaaaacat aagtaaaata tattattcat    93120
ctatgtacat ttccaagctg tgtagaagaa ttttaataa gacccagagt aaaaaagaa    93180 tgcaaatatg taggggccag ccctacaggg tctgtggatc tttctcccca tgtgcagaga    93240
tgagagatca tagaaataaa ggcacaagac aaagagatag aagaaaaaac agccgggccc    93300
aggggaccac taccaccaag acacagacta gaagtggccc caaatgcctg gctctgctgt    93360
tatttattgg atacaaggca aaaggggaag ggtaaggagt gtgagtcatc tgcaatgatt    93420
gataaggtca tgtgggtcac gtgtccacca gacagagggc acttccctgt ttggcagccg    93480
aggcggagag agagagagga cagcttaggt cattatttct tccattctct tctcagaaag    93540
atcaaagact ttaatacttt cactaattct gctactgcta tctagagggc ggagcaggtg    93600
tacagagtgg aacatgaaag tgaaacagga gtgtgaccgc tgaagcacag catcacagag    93660
```

```
agacgtttag gcctctggag ggctgcgggc aggtttgact gatgtcaggc cttccacaag   93720
aggtggtgga gcagagtctt ctctaactcc cccggggaaa gggagactcc ctttccaggt   93780
cttctaagta atgggtgcct tcccaggcac tggcgctacc actagactga ggagccctct   93840
agtggccctg tccgggcgtg acagaggctc acactcctgt cttctggtca cttctcaccg   93900
tgtcccttca gctcctattg ctgtatggcc tggttttttcc taggttataa ttgtagagca   93960
aggattatta taatgttgga ataaagagta atgctacaga ctgatgatta atgatattca   94020
tatataaaca tatctataac ctattactag tacaactatt cttattttac atattctctt   94080
cattacacta gaacagcttg tgccctcagt ctcttgcctc agcacctggg tggcttgccg   94140
cccagacaaa tattgttaag cttcttaata gaaaaacaaa ttatggtaaa tgtgttcact   94200
ggaatactac ccgtcattta taataaatta atgcctgata cacagagcaa caaggtaaaa   94260
tatctaagta tttatgttga gtaaaataag ctaaacaaat aagaatatat actatgtaat   94320
ttcattttta taaattctga taaataaaaa tgcatctgaa gtaaaataat gaagataagt   94380
agttgcctgg ggaaatggta gaagaaggga gggggagagg aggaggaata cagcagaaca   94440
aggggcaaat gttgagaaga attcacttgt ccactttctt gataatgata gcagttacat   94500
cattttattt agttgtacat tttaaatatg tgaagtttat catctttcaa ttaagcctca   94560
taaaatgtct tacaagcaaa caaatggaaa cttagacaag gaaagagtaa tagaaagata   94620
gaaaaaataa gttcaatgtc agaagtacct gaaaattaat gtgcctggat cctagttctc   94680
tccatatttt cagaagagtg ctggagggca gcaaaaccac acatgctctt attacggaaa   94740
gtgggttctg ataaaaacac tagacacatc cagctttgtc ctggagttgg tttagggga   94800 tgtcagagac agtgatgaag agcacagggc cagataccgg ggttcactca tcccagacat   94860
gagctcctag atgcatacag agccccccca tgtgtgggtt tacttccact tctgtaaatg   94920
gagaaaatat tgtctcctac agaacatagt ttacatgaat attttaaaatg aaataggg tg   94980 attagtgcaa agtgtttatc acagcacaat ttcataataa gacagcatat tttccaaatg   95040
caatcattgc cagcaaactt ctacagggca ccgtcgtctt atctgggtac agcctactcc   95100
tcaagggtcc caccctagag cttgctatat agtaggagat atgcaaatag ggccctccct   95160
ctactgatga aaaccaaccc aaccctgacc ctgcagctct cagagaggtg ccttagccct   95220
ggattccaag gcatttccac ttggtgatca gcactgaaca cagaggactc accatggagt   95280
tggggctgtg ctgggttttc cttgttgcta ttttagaagg tgattcatgg aaaactagag   95340
agatttagtg tgtgtggata tgagtgagag aaacagtgga tatgtgtggc agtttctgac   95400
cttggtgtct ctttgtttgc aggtgtccag tgtgaggtgc agctggtgga gtctggggga   95460
ggcttggtac agcctgggg gtccctgaga ctctcctgtg cagcctctgg attcaccttc   95520
agtagctata gcatgaactg ggtccgccag gctccaggga aggggctgga gtgggtttca   95580
tacattagta gtagtagtag taccatatac tacgcagact ctgtgaaggg ccgattcacc   95640
atctccagag acaatgccaa gaactcactg tatctgcaaa tgaacagcct gagagacgag   95700
gacacggctg tgtattactg tgcgagagac acagtgaggg gaggtcagtg tgagcccaga   95760
cacaaacctc cctgcagggg tccgcaggac caccagggga cgacaggaca ctgagcacag   95820
ggctgtctcc agggcaggtg caggtgctgc tgagggctgg cttcctgtca tggcctgggg   95880
cggcctcatt gtcaaatttc cccagggaac ttctccagat ttacaatcct gtactaatat   95940
ttgatgtctc taaatgcaac ctttttttttc cttttttgtgt ctgtttttttt tttttttaaaa   96000
```

```
acaggaggac acatcctcac ctccacagaa gccacagtgt cactttgggg gcagaaataa   96060
tcctttcgtg gtcaacaggg tgagagtttt gaggaatccc agggaaacct ggggaatgtt   96120
ttccaattag actcagggca gagacctcca tgggaatctc tgattagaac aggctttgag   96180
ttctgatggg agccaaaaga gaggctcacc cagggtcagg gttcttaaaa cctgatggtt   96240
ttcacagcaa tcccccttca tcttgtgaaa ctgggcacat ctgactcaga ctgattcagt   96300
tgaccctctt tctgctaatc catttccctt cccagtagac ttgattctca cagatccctt   96360
tcttcttctc tttcctgaaa acagaggatg tgttttctgt agtctaaatt ccaaggctca   96420
ggtctgcagg agctgggtag gctgaggggt cttcctcact cactattgcc tggaaaatcc   96480
tgctgtcttc tgtgcatgga ggcatttgga aaatgaagca ggcattagtc atgaagggaa   96540
taatactagt tttctccaat gggatgttga tgtagagctg atcttatgct tctcacactg   96600
tcacaaagtt tggactctca cctgtgactt tgaggagagc ttgtgatacc ttatcttgtt   96660
ttaatatgaa tagactctcc cttagctcag gaagctggaa cagactccat ttggctcctt   96720
catttgtaag acatcaaggg ctcctcaccc acccccttcc tcaaggactt aacttgttta   96780
agctgactcc cagcatctca aagagtgcga ttaactgata aggtactgtg gcaagctgtg   96840
tccgtagttc ccaggaattt ggccaggtga tggtacccta aagcccctgc atttctgtct   96900
ggcagataac acccagagcc cccacaccta tcatcttgtg atgaatttaa agcccctgca   96960
cctggaactg tttgcctgta accatttgtc ctttcaactt ttttgcctgt tttacttctg   97020
ttagaatgct acagttaggc tccccctccc ctctctaaac caaagtataa aagaaaatct   97080
agcaccttct tcggggctga gagaatttcc agcgttagcc atctctcagt tgccagctaa   97140
taaaggactc ctgaattcat ctcaaagtgc ggcgtttctc tctaactcgc tcggttacaa   97200
caagctgagg atggacactc cattgtgcag tgagctctgg gtgacagtaa tcgtagggtc   97260
tccccgggca gcctaaggtc aatactgctg gccgtcggga agacaggct ggaattcctg   97320 ggaagacctg catctgccat ctaccacgga gtccctatggt cttctgttac actctctttg   97380
aatcagcacc acctagatta tctaaaacac tctttgtgac ttcatgactg ggaaaaaata   97440
atggcagtct ctactaacac ctgtgttaag ccatgggagc aacacctagg ctagtgtgtg   97500
attgagtagt tgagactgtg gtctagtcaa ggtgacacat aaaattgatt gttgccatta   97560
tgatatttta ttttatattt gacaatataa tcatgctcat attataaata tttctgttac   97620
attatttgtg tcagaggctt tggaaccaga acaacttcat cttgaataag gggtaggaaa   97680
aataagactg agacctgctg ggctacattc ccagtaagct aaggcgttct tagtcacagg   97740
atgagatagg aggtctgcac aagatccagg tcataaagac cttgctaata aagtttacag   97800
taaagaaact ggctgaagcc caccaaaacc aagatggtga caaaagtgac ctctgtttgt   97860
cctcattgct cattatatgc taagtattat gctttaacat tctaaaagac actccccaca   97920
gagccatgac agtttacaaa tgccatagca acatcaggaa gtttccctag aaactaaaga   97980
gtggaggaaa cctcagcttt gggaattgcc cggggaattc atgaataatc cttctttgt   98040 ttaacgtata atcaagaaat aaccataaaa atggacaacc agcagcccat accacttctc   98100
tgcctatata gtagccattc tttattctct tactttccta ataaacttgc tttccttta   98160 ttctgtagat ttgccccaat tgggatccct ttccagtaac atttgtgtta ttattggttt   98220
tctaagcaga aaactctgag aggaggtgtc agccgggctt cctgggttga gtagaggctc   98280
agaaagcagt gaaactcact catttcctgc atcaggactt actttggtcc tggatgaata   98340
atattgaaga tatatgctta aaatattcct aacatcacaa tttgtgcatg tgttttcttc   98400
```

```
cctaagaaag ctataaacag tgaaaatttt gctgtaagct tccctgtgtc ttctctccct   98460
ctctccattc cccctcccct gaaactaaaa ggaatgtttt aacattatgg gcttttaagt   98520
ctgtatttct gtgaccagca gaccttatct atgctcccaa ttcaaattcc ttgtaaacac   98580
aatttgtaaa atcctgcgag atcctgtctc cttggccacg ccactgcaag gtcataaagt   98640
agatcaaact taagttacaa ttctgatttt cctcaagatc tgagacatgt taattgtctt   98700
tgtttcttgc tcaggtaaca tctcttttg ctcttttta tctcttttg cacttaaatc      98760
taagtttaca ttagtcatgt atctagaatg tagaaatatg tcttaaagtt acttaacttt   98820
ttaaaaatt tatggggttt ccagaagatg tgagaacctc ctttatttat aaaatagctg    98880
attgcacgtt gctcaataat ttcctcttta atttatctct ctcctgtcac attatactat   98940
gataagcaaa aagaaatgaa ggcataccat caacagttta cttagatatc tcctcagcta   99000
aatttctaag gtataattta ctaattctaa ttttatccaa tttaacataa ttaagataaa   99060
ttatataaca aggtacacat atgttccagt tctaacacca tgtttgtgac agaaataaaa   99120
cagagcttct ctctgtaatg tggtcatctg agccctgagg tgatgggtca cataggtatt   99180
tttatgatat ttaagggttt ggtcaagaac agtgataaca agtctgaaca agactggtca   99240
tacttgaaag gttacaggta aagttactgc tgttatttta tattaacgcc ttattagaat   99300
aaagctcaga ggaagaggcc acatcctagg tcacagtagg aggaggaatg gagctgtgct   99360
ctgctctcca cactactttt cacatcccag gcacaagccc aggttccatg acgcacggca   99420
tctagagggc agttctcagg ggatgatctc agggcacctg cttcctcggg cagggcgctt   99480
ccttctctca attgcagact tgctccttct gcaaggtctg aagtcagcac ttgtattccc   99540
atgattttta caggttctct tccctaatat ggcaaaaatc ttttattaa attttcaatt    99600
ttatttctc tgaagcacac tgcattagca gaaacgaata tatcacattc cttatccgcc    99660
cacacagcca aagattcctg aagacagagc tgatgtgacg tactcatagg tggatctctg   99720
cccctcagag gtggccttgg tcttcaagtt tcagcaattt ctaggaagcc aaagacacct   99780
ccatctactc ctccctgctc gacagctcac ctgagaacag cttctcatt ggaatgtctt    99840
gtgtttaaga aataaaagtt gctgtttgag gttagggagc ccaggtgcac ctaccagatc   99900
cagcccagga ttggagatac ttttcagaag acaacatcac ctgagacacg accagtccca   99960
ctgtttcact ttcacaattt cagcttcttc agaagaaaat taaaattgtt gagacttgtt   100020
cataagcgtt gtgccatgtc cttttctctgt tttcttgcct gttcattgat gtcatgccag  100080
gtgccacttc tatgtaatag gatcagaatt ctgcctctag taacacatca gaggtgaggt   100140
ttgattgtac ttttggttta tgctccaaaa cgtagattat aaaattcatc accctcattt   100200
ttatgtcaaa agtaatctgc ataatctgga tgtcaatact ttttggaatc tatgaaataa   100260
cagaaattgc aagaaatatt acccactcca aacctggaga gacaggcatg tgcagaatgg   100320
caattgacac ctgcttaact ggagcagaag ctgcagaagc cacaagctgt tgagggcact   100380
tacatggtaa gcactacaga cgtctgaaga cagatgtgga ctcagtaaat gtaacagttc   100440
cagagggtct tatacttcta agttttctgg aatttctttc cagaaacctc aagattctaa   100500
aatgtacatt ccaaagacat ttcctataga tcaaaattgc agatattaat tactgagaaa   100560
cataccacga gccttcttca aaagcttcta caggaaagga cttttccaga accttatcct   100620
atgtgaagga agacaaatct cccactgcag atttctctcc cattcttcca taattgtaga   100680
aatgagtaaa gttagccaat agaggtaaga tataagtaaa taatccaggg atgctgaaaa   100740
```

```
caaaaaaggg agtaatcgcc caaaatgagc ttttccctg gagacgcctg gtcaagatca   100800
taggccagaa gaggaagctg actgtgtctc taggtttcca ctgtcagaac aggcagtgct   100860
tacctgcact gcacaatcca ttctaaccag gatgatggct ctggattaaa ggtgaaagtg   100920
tggcaatgca cagactctat ctgaggagaa cacaggaaaa ctaaaggaca acggcagagg   100980
gtgagacaag aacagtagag caatctgaag cctctgacat catgattttt aagaccaatg   101040
tcttaaacac tccttcattg acctcagctt ctttcatcat gaagcctttg cagtgactct   101100
atctgagaaa aagaaaataa cctcctgcat gcacttctca agtctctgct tgtatcctgt   101160
ttgctttagg tctctagggg aaaaagtcag atacctggac ctagtgtcag tgtaggaggc   101220
acatcctaaa agctacaaac taggaagaag ggaagatggg tgttattgga atagtggata   101280
tggagtgggc tttcttctga aagtatatgc acctgctggt attctcagat gcaacattca   101340
actgcaagag cccattgaag aaacaaggca ctcccaaatc tcctgtaaga ttctgtattc   101400
atttcagata agcccacatg tccccgcatt aacttttct tcagacaagc acatacatct   101460
gaaactgaac agctatgtgg caaaataagc tcaggataga agtaattgtg gactccagct   101520
ctgacaattt gtagatctgc attttaaaaa ttctaactga agactttgct ttattgtaga   101580
ggacagtggt ttacagctcg aattgcacag cctacaggca gatgtccatt tcctctgggc   101640
aaggtttatt tttatttgtt tactgtactt atttgttgac aaacattgat actataaaga   101700
taccctaaca gcgtccacat gaaagaaaaa gaaagagcaa tggacacatc aaccctgaac   101760
atccagtccc aggaatcctt tgaccctgcc ctccttgcaa cccagagata tagattggat   101820
gagccctgct gagcagaaca cacatgtccc caggagaaag acatggaaat gaggcccctc   101880
cctgctaatg aaaagcagct cttcccctct tctcctgcag gtcctggtga ggagccaccc   101940
aatatctgtg cccttcctca gtgtccacac catcgggtct atgatgatct gggcttcact   102000
tgtcatcact ctcaatattg aggttccccg ttaaacagac tgagtgaact gtggctgctc   102060
cacgtggggg ctgttctcag tctgttgctt ctgtgcttgc agaggtcccc tgtgaagtta   102120
attactggag tctctcagag aaatactaca gaccaagaat tctcagactt ttctggaaac   102180
cctgtggatt cactttcact gaaaacagca taagcttggt ccagcaggct tcatgacagg   102240
ggtgggtgta ggtgataaca tcagtaattc aagtggaagt tctcagtggg actctccttg   102300
agtacaaaga agattaacag tcctcagaga cacgcttttc agatgattct ctcttaagat   102360
gattaacctg agagctcagg aaaattccgt ttattactgt gagggacacg gtgaggggac   102420
atctgtgtga gctcagacac aaacctgcct gcagggagac acaaacctcc ctgcatggta   102480
gatgcttctc agaaccacca gggggtgcac aggaaaccag aaggtgctca ggacaccagg   102540
gggtgctcag aaccaccatg actcactcaa gacgccaggg gcgctcagaa ccaccgtggg   102600
gcactcagga caccagggga cattcagagc caccaggggt ggctcaggaa acctaggggg   102660
gtgctcagga caccagggg actcaggaaa ctaggggta ctcagaacca ccaggtggtg   102720
ctcaggacac cagggagctc tcagaaccat ctgggggcac tgaggaaacc aggggactca   102780
aacactaggg tgtgctctga agcaccagcg gaccctcagg actgcagggg gcgctcagga   102840
cactagggaa cactcagaac caccaggaag cgctcagaac caccagggg ccctcaggac   102900
atcagagcgt gctgaggacc tccgggggcg ctcaggacct tcagagagtg atcagaacac   102960
cagagggcgc tcagaacacc aggaggtgct caggacagca aggggctctc aggacactag   103020
ggtgtgctca gtaaaccagg ggtccctcac aaccaccagg gggcactcag gacaccaggg   103080
gatgctcagg acaccagggg ccactgagga caccaccgct cccttagcag gcagctccac   103140
```

```
atcaggcccc tgggttgggg caggaagggt gttttccttt tggatcttgc cactaaactc 103200
ttgggagttt ttctccttcc tttgtggttt caagaaacat tggtagattc ttctcaggta 103260
taaagctctg cttttcttgta ttatgtaatg ttttttggttt cggatgttac cagaattaca 103320
ctgcactgtg agaggattca ttcctcgtgt gtgcaatagt gaatgaaagc tgcaatgtta 103380
ggggtggctt tgaaagctac gttaggggtg gctaagggca gttagcagga aatgatcatc 103440
actatagaag gctactcatt tctttgcaca tttccataaa taattgtagt ttatgcccta 103500
aaaactgcat gctttcttgg ccctttttct aaatgcctc caatccaaga ccagtcatct 103560
aattaagctg tatgtcaaag accaccaatc aagttaagtc tgtttaatga aacactttgt 103620
aaacaaaaaa gtacatctgt gtttgtatag tcagctttaa attttacatt gctttacaaa 103680
tattaatttt gtaaatttag tctcataatt atcgtcagta tttaaaatct aaagtcatg 103740 ctatgttaaa ttaagtaatc ttagctttct cactatgaat tagagttact aagaattaga 103800
atagtaagag catgtaataa gcttttggtg aagtttataa agaaagatga agatacgttt 103860
tttgctttaa aatattttgt tttccagttt acaggacctt tctactggtt ttaagataac 103920
aatcactgtt tacatctaac cctttttttta aacacctgct gtttaagatt ataaaattat 103980
aaaattaaaa acctagttaa aaccagattg atctttgtaa tttaacaaga tgttcagtat 104040
tgttgtttta ataaaaaaaa ataggtaaat acttagctac tagaaaaata atcatctact 104100
taatcataag gttttactta ggtaaacacc taaatttcat gggttataaa catggttaat 104160
aggtgaaaaa ctttaatgga caagtattac agttttcata atattctag gtaagctatt 104220 taaaaaataa attaggtaaa tgaaataaaa taaaccattt aaataaactt gttctacaat 104280
ttaaaaatct aaagttttaat taataatat atattatata aatgtttatg cattactaat 104340
tgtttaaaat atatatacta taaggaaaac ttttttaaaaa tacatattat aagaaaatat 104400
tttttgaaaa catttgtttt tagaaaaata atttattttaa ttcaaaggtt aattataaaa 104460
tgtcgtaaac atacccagtt agtaagagag gtttaaagaa agttctagac atagagaagt 104520
acttttggta agaaaggtta aaataaaaaa aaattatatg agaaggaatt ttgtaggata 104580
actttttata tataaaagtg actatttatg aaagaataat gtttagaata aaacaagatg 104640
ttcaagtatg ccataaatgg ttcgtgtaag tcaaaataag gtttatagaa agctaactta 104700
ttaaaaaaac ttcatgttat cgagttgact ataattgaaa gggaagaatt tattatagtc 104760
tttataggga tctggcttc atatgaaaat atactaacac actgaagatt ggttagaatg 104820
acaaaattgt cttaaagtat tgattattc aataaaatta taaggtatta taattttta 104880 acccaaaatt ttaactttttg ttgcatcttg ccatttttat ttttttccat tgagaaggc 104940 ttgagaggat ctcaacttt tcatcagctc ctttaacatt gtttcttact tacagcagtt 105000
agcctctgag ttaacttcta actgttgtta gttctgact gctattattt cctgatgtta 105060
aaatcctcta tcttaaagtt ctaaataaaa tgttttcttt caatataata ttcagtgtcc 105120
ttggcttttc tttaactgtc taaattttc tatgaaacca aaatcttcac ttgtaaagac 105180
acattcttcc taggtctgat taattcaaat acttttttca ttagagttga cttgcaggtt 105240
atgtacatgg agttccccat agggaaaac agtcacagtg cagaaggctt tatttttgct 105300
atttggtaac tgggcatgag acaaattttta aatttcattg aaataattcc tatgtaagtg 105360
ttattaagtt tttcaactac ttagtaatac tgagagttta agacaataga aattaatgtt 105420
atgacattca tgtaactatc tgtataactt ttaaagtcct tgtgctgcta ctttactgag 105480
```

```
ctttgaatcc taggtctaaa aaggacacac aacactttgg gaggctaagg tgggcaaatc  105540
acctgaggtc agaagttaga gaccagcctg gccaccatga caaaacccg tctttactaa   105600
aaaatacaaa aattagctgg gcatggtggc aggtgcctgt aatcccagct acttgggagc  105660
ctgaggcaga gagaattgct tgaactcagg gaggtggacg ttgcagtgag cagatattgc  105720
actactgcac tccagcctgg gtgacagagt gagactccat ctcagaaaaa ataaataaat  105780
aaaataaaaa ataaaaagga caccaagtcc agctaaatct taaacaccga cagcaattaa  105840
agccccatct acagacctgg aagaaaatga caagaaaaat tgatcacact ctcaagacac  105900
aagcccagaa attgaaacta cttaaccacc ccagccccag ggactattac agaagaagtg  105960
gctttgtaag attgtaaaag ctaattttga gagatgaaat cagttcagag tttctttata  106020
aattaaacat taatgcaagg ctagcatctg ggcccctgtg ccagattgac cagggttcct   106080
tgaagaatta atccacattt aaatttaaaa aacagataaa actgtataaa agatctatgc  106140
aaattatttt tatggtaaaa gtaattataa tttaatagat ttattttca gaattgatag   106200
ttttaacttt tctcatgctg ttcttctaag gggttatatt ttagaaaatc aattctactc  106260
tttcaaaaat atttttttc ttttttttag aaatcactga gttttcatgt ggctaaataa    106320
ataacttatt ttacaataat ctgtaatcct attttgtaat atcaagtgtt gtaaacttt    106380
gatatttgac aaagttcaca aaataaaatt ctaaattcag tcatttgaac accctgaaaa   106440
gaaacacatt tagcttattt ggtacagtta aattatacag gaagtaatgt caaatttgca   106500
atggttatta actttggact atatttatat aaatgtggac tatataattt gaatatactt  106560
atgtaaagag tatatgttcc aaaattctat tagattcaag tgattttat atgtcttagt    106620
atcagtagta cttatgatta taatttaaaa ttttttgttta tcacagaaat aaccaaattt  106680
tctcctcaat tctgtcttta accaggggta ttctaaaagg tcggtcattc acaattgttg   106740
ttttactttg attctttatc aggtggctta taataatcta tagaactttg agtagtactc   106800
ttaaatatac aatatacaat tttgacaatt ttataaattg tgccattggt atagagagaa   106860
aaacttccat gagtctcatg agacctgaag catttatgat gattgttaat ctaatatcaa   106920
gcaggacagg atgtaattgc atgaactgaa tgaaaggag actgaaataa tttttataac   106980
ttattcttta aagcatttgc tatttactta tgttttattg ttcagaatca agaaaacttt  107040
gtcttttaag ctattcacag ttttaacaa ttttaactat actctattga gaaaaattga   107100
aaatataatt tcttcttctc tacataattt ctccaaaatt tggaaactgt aggtattctt  107160
atatcaaaat agttatttgc ataggttcga taaaaatctg ctttcttcca taacagagca  107220
caattagaga caatggtcac tttaccaagg ctttaacttg aatgacatat tttctgattt   107280
actttataaa atgaagagct gtacagctga tataagcccc tttggaaaac tgcatttta   107340
cctttttttt ttttttaac agggccctga gctgtagtaa gtaaataatt ttgctttctg   107400
acaggcccag gaacccaag ttttcttgga tacttgaaaa ataaaaagt aaaccaatcc    107460
atatagctat ctgatggcac agataaaata ttggctgggc ttgaggcttt taaagatctt  107520
acccttagat tccttataaa aaatagcaaa agcaatgtat gaataaaaca gcctatgtac  107580
aacaaacaac aacaaaaaca aaaacaataa aaagagagct aatatgttaa gtgattattt  107640
ttgctgcatc ttatacaaaa aaatcaggcc aagtataata agcctaaaat ttattttaca  107700
aataaattag tcctatatg attttgtctc caataaaatt ggggaattat agggagaaat    107760
attctttcaa aataaactat agtgcatctg ttattaggtt ctaaccttgt ccacttgttt   107820
ttcaatttac aatattttcc acaatttgga ctcaattta aaatattct ttccacaagt     107880
```

```
ctccaaaata acattttcag tgattttctt tttaaatatt tttttcctat ttgaaatctc 107940
cagaaggtaa actgtgcttt cttacagcta gtcaacttaa actctaaaat aaaataaaat 108000
caatgatatg gtttgtctct gtgttcccac caaaatctca gtttgtatag taataatttc 108060
cacatgtcaa gggtggaagg aggtgaagat aattgaatca cgggacgtgt tttctccatg 108120
cttttatcct attagtgagt gagttctcac aagacctgat ggttatataa agggcctccc 108180
tcttcacatg acacttctct ctcctgcagc catgtgaaga ggtacgtgtt tgctgccctt 108240
tccatcatga ctgtaagttt cttggggcct ccccagccat gtagatctgt gagacaatta 108300 aaccttttt taaataaatt atccagcatc aggtatgtcc ttatagcagc atgaaaattg 108360
tctaatacca gcaacttaat tatatacaaa aattccttt ataccctcct actgtgaagg 108420
gaaaataaat cttgagaccc caaaattact aagctaaaga aagagtcaa tgtggtgtta 108480 caggagatag aaagaaatta tttaggtaga tagttgggat gagagagtct ctggcaaaat 108540
aacttttctt ctaacaaaaa tcagctcaga ataacttct tctctaatta cacacagttc 108600
aaagaaatca cttctaacaa aaagcagact aaataatcag gctgtgaaat atagataagc 108660
aactctgcca cagagagggt gtttctgggt gtaatcacca aacctcacat atataggatg 108720
ggtcccagta aaaacagtga gccttaataa gcacattcct tttcttttct gggagtacac 108780
taagatagaa aagctggaag cttgcacggg gtttgcgacg ccggcacctg tgaggaagta 108840
cctgggacca ggcaagaaaa cccttctggc ctttcttagc acatgcacgg tggaagaaga 108900
taagcagtgt ggaggagatc aagcaaagtg cccgcctgcc caatgaaagc atgaggtggg 108960
gttgccagag actttgctct atgcagatgg cacacattgt cctaactgtt tttgcaccct 109020
atgctgataa gacaccgtct ccccacgagc acatttataa aaatccttac atttttactgc 109080 agcacgataa cccatttggg accctctct gtgacagaca gctttttttt tattttacct 109140
attaaacttg tgctctaacc tcacccttag catgtctgcg accttgatat tcacggccgt 109200
gagacaaaga agttcgggtg gtattccaga caacgaggct gccatactgg aaagtgcttt 109260
gggcaaatct gcctcccctt ctgtttaaag tgattcctct gaggctaacc tgagaccaat 109320
acacagctga ttgcttcctc ttcactatca tttatgtaaa aacgaagatc cactgagtca 109380
gactaaattg tgcattcagt ggtaggctaa taaagtactc aaaagaacgc aacctattgt 109440
ctcttatcta cttctaaact gcagtccgtg cttttgattc gtcctgcctt acaggaaaaa 109500
tccaaagtac atttacata tattgattga tgtctcatgt ctctctaaaa tgtataaaag 109560
caagctgtac ttcaatcgcc ttgggcacat gtctcaggac ttcctgagga tggtcatggg 109620
tgagttccta actttggcaa gataaacgta ttagtctgtt ctcctgctgc taataaaaca 109680
taacaaagac cgggtaattg ataaaggaaa gaggtttaat tgactcacag tttcacatgg 109740
ctggggacac ttcacaatct tgtcagaaaa gcaagcgaca tcttacacgg tggcagacta 109800
gagagagctt gctcagggca actcctcttt acagaaccat cagatctaat gagaagtatt 109860
tactatcatg agaacagcat gggaaagacc tgcccctgtg attcaattat ctctcattgg 109920
gtccttccca tgacacatgg gaactgcagg actagaattc aaggttagat ttggatggcg 109980
acacagacaa accacattag taaacttcct aaattgactg agacctgtct cagatatttg 110040
tcgtttacct aattcatgtt cagccttcag agttccaagg cctatatcag ttttccagga 110100
ttgtttcccc ttttgttgt ttgttatttc ctcctttatt tatatgtttt acttctcttt 110160
tttctcccac tattttctta ttaatggatg tgaaacttca caacatttga aatataggta 110220
```

```
acaatgaact ataataacaa cttgggacct atttatctag aaataatccg tcctacccat    110280
gaaagaaaaa aacaaaaaca aaaacagaag cccagaaact tattttgtgg taaaatgctt    110340
cctctgaaat attttggaaa ggaaaaagtt gggaagatat gaaatgaaaa taaaaacttc    110400
tgatgtcaat tcattatgtc atgaggggga aaaaaactaa acgatgatcc acgcaagaaa    110460
ctgattttcc tttcattcct gagaaaatag ccacagacag ataaaatgtt agatatcttc    110520
acagatagct acaatttgtt catctttgaa atacttagtg caggagaacc acttgatatt    110580
ctatttccct atgtgcttct ttttcattac tacatgtaag ttttcatgca attcctcctt    110640
cccctctagc cagcttttcc cctttatata ttgaaagccc taaaaatgt cttttgggaa     110700 tggcactaac cacgcattgt ttctgtgatt acttttcttc caagcatgcc ataactttga    110760
aaaattaatt ttaatttgat tgagagctct ctcagaaacc tttggttaca ctaggcaaaa    110820
tccaaaatca ggagccaatt attgtaaaaa tcagccatag tacactgtgc gtctgtgtgt    110880
gtgtgtgtgt gtgtgtgtgt gtgtgtgtgt gtacatgtgt gttttaattt ttgtgagctt    110940
tgagccatgt agttctctct gtggagatac tatttggcgt gactttgaat agagaattct    111000
aaaagaaata agaagctcct atgagttctc tgaaagtttc tggactcacc atggatcttg    111060
actgtgtcat tgcatcagac agtcccaggg aacagactct ctggtggttt catagaatct    111120
atgcttgggc tctccctgca gtttactggg tatagtaatg acaaatcact gtttcaagag    111180
acaatttcaa aagcattaga tgctgctgag agaggattgt gaaccagggg actgcccctt    111240
tcttcttgga gagcgacatt gggagaatat gctctgtgag cccaaacagc atcctcccct    111300
gcagggtgag ggcagagttg cagggcaggc ccagaaccca ctccacacag atgtcagccc    111360
tggagctgct gcagaggagt ctgaggagaa aattttttcca gcacctgaat tacacttatt    111420
tcaaaacaaa aatgcaatta aaagttaaa acaagtaatt aatgtccagg cacagtggct     111480
tacacctata atcccagaaa tttgagaagc tgaggtggga agatttattg aacccaggag    111540
tttgagatca gtctgtgaaa aatagtgagg cttcatcttt attttttgaaa ataaaaataa    111600 aataaaacat aaaaaattta gcaaaaacta cgatgcgtct ttacatacc catcatactt      111660 gaagcattta cctaacccaa tgaggtgatg aggacccaat ttgaaggag aaaatttag       111720 acttttcata tatcttaata gttggaagat gtagaagaaa tatatttata tcaattaaat    111780
gtgtgcaaat attgacagac acaccatacc aggagttcaa cttgcaaagg gtaaaaccaa    111840
aaaagtttga gattgttaat gtgccatttg aaggtgagat cgttttgagg accatgtcct    111900
gtgagagttt gtttctctat tagaggagtt ctgtactcat aaagtctgg acatgccagg     111960 agacaagtat cagtaaacaa atatcagaac ttgaacttca gcttcccact cttgcattct    112020
ccatgtgtca tctctctact atttctcatt ctagatcagg tctttagcta tgaaatattc    112080
cacctaatta acatgtaaat agattgaagt ccacagagtt aaatatgtat attttctcct    112140 gttttttccca attgttccct cccacagctc caatattctc cactgttacc atcaccttct   112200
agatctgctg ccatgccctg cagattaagg atttgattcc atgacagaga ggaggtgcat    112260
ttcaatggaa ctttggtgag aacctcggtt tttatcccat ttcctctggg gctccaccag    112320
tgcatctgga ataatgggtt cagtggctgg cccctgcagg gtgattcctt agttctgtag    112380
tgaagatgag ggaggtgggt ctgaatgcat ttcagaagta tgggctctcc tctctcagac    112440
agacactttg ggaaaataag attttttctga ctgcacccat tctagaacaa aggaattcaa   112500
ttggataaga atgctgataa aaaaaacctc aaaccaaatt aaatttaaag gagtttaatt    112560
gagcaatgga tgattcatga attgggcagc ccccggaatc acagcagatt gaaagagact    112620
```

```
tcagtgcagc catgtggttg aagaagattt atacattttt ttaaattatg tacagaaatc  112680
agaagtgagg tacagaaaca gctggattgg ttacaggctg atgtttgtct tatttaaaca  112740
cagtttgcac actcaagagt gtatgagtgg ttgaggtatg gctgctgaaa ttggccaacg  112800
ctcagctgtt ggtgaggtgc tcaggtacat actcctgagt taggttttca atctcgtcca  112860
cctattcagg taggttaccg tttgtccaca aggactcaaa catagaagta cggagtcctc  112920
ctcaggccat atttaattca ctttatcagt gcccttcagc atatggttcc tgagaatttc  112980
acacggcaac atgtttacca ccctagaatt taagcaatcc aatacatgta ataggctgta  113040
tttcacatgg caacttctgc ctcagtttag ctaacactat ggctttgttt ctctctacaa  113100
gaactcattt ctcccaagat ttccattttc ctgaaaggaa ataaatctt tgggaccccc  113160 atatcactaa gccaaaggga aaagccaagc tgaaaactgt ttggggcaaa cccaccttcc  113220
attctttccc taaaatgata gctgttaagg tgtttacaag ctacatatct ccttcaaaat  113280
ttgaccgcac agaaaatcct tgtagaccaa ggacattgta gaccaagcag agagtcactt  113340
ctctgctcac gtaagtcaaa tgcatatctg attgctccct ttgctctatt gtttcactaa  113400
gccagactaa ggcctatgtg actattcctg taaactgtgc attcagttaa aggctaatcg  113460
gaaactcaaa taatgcaacc atttctctca tacctaccta tgatctggta gctctccccc  113520
caacttcaat ttgtcctgcc tttttgaact aaataaatat accttacata tattaattaa  113580
tgtctcatgt ctccctaaat tgtataaaac caagctgtgt cccaccacac tgggcacgta  113640
tcatcaggac tccctgaggc tgtgtcacag gcatgtcctt agtcctggaa aaatgaactt  113700
cctaaatcta ttgagattag tctcagatac tctttggttt ataagtatgt tttctatctc  113760
ataacttcaa ttatctgaaa tactaaagga aatctgccaa ataacacatt atcttgttta  113820
tctgttattg ttgttgcaaa aataaatata tttatataat ttatgtataa ttgatcatct  113880
ttgtacatta ccaaactgag tagcagattt gttagtaaga cccaatgtaa taaaaaattc  113940
aaatatcaat taacaactta atagaaaaac aaattacgct acatttgttt gccgaaatgc  114000
taccaatttt tataaaaaaa taaacacata taacataaat ggtttaattc tcagtatttc  114060
tattgagaaa ataagccaa atacataagc gaatatacta tattatttca ttcttataaa  114120
ttctaccaaa taaatactag tctaaagaaa tatgaaaaca tcagtagttt ataagaaat  114180 ggtagaaaaa gggaagggga aaaaacaaat aatataaaag atcaagagga atgctgaggg  114240
gagttgactt gttacctcat tgaaaataga gattattttt tcaaagttta ctattgcaca  114300
tgttaaatat gtgaattta tcatctgtca gttaaaactc ataaaattta ttacaagtaa  114360
acagccgaca ttttatacaa aaaagggatg ataggaagaa acaaataaat acattaaatg  114420
tcagatacgc caaaaactta tctgcctgac ccctagttgt ctccgtaatt tttggatgaa  114480
aaccagccca cccctgaccc tgctgctctg ggagaggagc cccagccttg ggattcccaa  114540
gtgtttgcat tcagtgatca ggactgaaca cacaggactc accagggagt ttgtgctaag  114600
ctgggttttc cttgttgcta tattaaaatg tgattcatgg agaactagag agattgagtg  114660
tgagttacat gagtgagaga aacagtggat atgtttggca atttctgact tttgtgtctc  114720
tgtgtttgca ggtgtccagt gtgaggatca gctggtggga tctgggggag gcttggtaca  114780
gcctgggggg tccctgagac cctcctgtgc agcctctgga ttcgccttca gtagctatgt  114840
tctgcactgg gttcgccggg ctccagggaa gggtccggag tgggtatcag ctattggtac  114900
tggtggtgat acatactatg cagactccgt gatgggccga ttcaccatct ccagagacaa  114960
```

```
cgccaagaag tccttgtatc ttcaaatgaa cagcctgata gctgaggaca tggctgtgta   115020
ttattgtgca agagacacag tgaggggaag tcaatgtgag cccagataca aacttccctg   115080
caggaacgct ggaggaaatc agctgcaggg ggcgctcagg agccactgat cagagtcagc   115140
ccaagaggca ggtgcacaca gaggctgatt tcctgtcagg gtgtgggact tcgtcttttt   115200
accatttctc tagggaacct ctctaagttc agaattctgt gcttaccaat gtcatctcta   115260
catgtttttt aatgattatt ttgagaacct attcttacat gcacaaaatg cagatggatg   115320
cttacagaga tgaaaagtcc tcaaccatgg tcaccaggat cagccttgag gaaactcagg   115380
ggtgcctggt gaatcttctc cagtcagact caggacagaa acctctgtga gattccctga   115440
ctagatcagt cttcaggaat tttgatacca gccaatagag aggctgggcc agggtcagtg   115500
tcatgtagaa cctcacaggt ttcacgtctg acccttctcc ttctcctgac actaaagtat   115560
gcaaatcagt atcagcactg atctgggtcc ccttttgctc ttaaaccatt ctatttcttt   115620
ttatttgttg ttgttcttgc ttttcctcgt acttctcttg ctccctgtaa aatggggagg   115680
tgtttcttgc tgcaaaagcc ccaagcctca agcccattcc ctgcagctca ggcggggctc   115740
aggctgtggc tcctgcagcc acatgggagt ggctgttggg gctttctctt ctcccattgc   115800
tcagcaccct ccagtgtgtt gtgtggagac tatctgggaa cgaatgtgga caacaggagt   115860 gaagggatg agcttgcgtg acagaatgg gatgtggatg tgaaatttat cctgtgctgt   115920
acaaacaacc acagattcaa cttcctcacc agtagtatta gaaagagggt gtgaaagttg   115980
tcagaataaa aatggaaaca cttgtgttaa caccctgaca aatggaacta ggaatgacca   116040
tgaagaagtt tctcatgcat atactccaga aaacaagaac taccgtaaat ggattctgct   116100
taaccacagc cttggataga agaaaccaca accttacaaa aatcacttct acaaggatat   116160
cttcccagca actccctgtt taaccctaca gtgatgccac ccttagtcct acaaaaatca   116220
cttctacaag aatatcttcc cagcaactcc ctgtttaacc ctacagtgat gccacccttaa   116280 gtcctgattc taggagcaca ggataatcct ctcaaaacga cttatgtaac ccacctcatt   116340
ttcactgtgt aaacctatgg attcacatcc tggagtcact gctgcatttg ttcttaatgg   116400
tcattagccc ctttcacaat atttgaggct gttttttctct gatgtctctt ctaaaataaa   116460
gaatttccaa gtggacagca gtaaagaagc tatttaggaa gatgtaatgg gaaggcatct   116520
ttaacattct gttgaatgtt tccacatggc acttcaatcc cctaaaatac tttgctgtat   116580
cagcatgtga tgaatcggag tataatattg aaggtaaaat gggaaataca tgggcttttg   116640
atgaatcaag tcataggatg agaatgtctg tgtccttgag gaaggagacc atgggttgta   116700
agttctagtg gaggtacctt tggcaaaggg agttcatgag tttctgaacc ttatgctact   116760 tttaattta ggacgcaatt tatgatgtat gtttacttaa atctttccag agacatttgt   116820
cagtaaggac agggtagcat tgtgtaata gtgatgactt agagagttat tttgtaattg   116880
ctcctgtaag gtatgcacat tgctcacttg atacagaagt tcaaatgtca caggtggaaa   116940
aacaggaata aaggtgggca gatcacaagg taaggagatg gagaccatcc tggctaacac   117000
ggtgaaaccc catcgctact aaaaaataca aaaaattagc caggcatggt ggcgggcacc   117060
tgtagtccca gctactcagg aggctgaggc gggagaatag cgtgaacccg ggaggcgag   117120 cttgcagtga gccgagatcg caccactgaa cttcagcctg gcaacagag ggagactcca   117180 tctcaaaaaa aaaaaaaaa agaaaacagg aataaagcaa attttatgaa ctgtcatgac   117240
tgtagttttt ggcaaggaca ttatcatgtc aacctgtaaa taaacagaca acaataaaac   117300
atatcaaatc catggggagt ctgacctatg tccctctgtc ttataagcac aaggctttgc   117360
```

```
cacatccaaa atattattca ggctccaggg tataaaatgc ttttggactg tggaaggtaa   117420
cagctctccc ctcaggcagg ggtaaggtat ctggggaatg cagagttgtg ttcataagga   117480
agatgtcatt atcgtgtctt ctcctgtgcc tggtagcagg tcctgaaggt gaacgtctca   117540
gatgtcagac atgggtctat cgggttagga taggtacatg tgactgacag ggactgattc   117600
tccatgtaat cacatgccct gtcccaggag cagctgcagg agtcagccct ggacctgaat   117660
agcacacact taccctctgc ctcacctaca ctgttactgg ccactccgtc acaaccagtc   117720
cttactagtg gacctggatc tgccggctct cagggagggg ctgcaatgga taaaatccat   117780
tgctagtggt ggtgggagtc catttgtctt gtggaaaatg gcagcatttc cttattttat   117840
aaggcataat aatgctatgt tgtgtacaca taccacattg tctttatcca tttgcccatt   117900
gacagacact tagtttccat atcttggctg ttgtgaatac agctgcaata atcacaggag   117960
cgcaggtatc ttcacaaggc ggtaatttca tctctttggg tatatttcca taagctgcat   118020
cactggtcat atggtatttc tgttttaatt catttaggag ccaccacact gttttgccta   118080
atggtaatga tgagaataca gaatgtcata gccgctacga agaacagttt tagatttgag   118140
gtataatcca aaagcaaata atgtttgatc agggttctca tatgaggctc taataaataa   118200
gtccagaaag ttttcccatc ttgggcaagg atgagtttgc ccctaattgt ctttgaggaa   118260
gaagattggc agaacgtgag atggagtctg ttggcaggat tcaggattca gtaataacta   118320
gtaatggcac agaaaaatag agagatagag acatacagag aaagagagag agaatatgaa   118380
tctcataaga ggaaaatttg ctaaatatca gcattgggtt ttcagtcata gacacatttg   118440
tatgagccag gaaccatgga gtcaagtgag gagtggagaa tatgttcagt ccaaaaatca   118500
gcatattctc agaggcaccc attgccccat cacacaggtg gagaattttg gaaaccagtg   118560
aagtgcgagt tcacattagg tgattaagct accatgtttc gataaacttt cattaacatg   118620
caaagtactt ccatagataa ctgatgcaca aatatacgag atgcctttt gcgtttatgg   118680 atgtctagag aaaaataagt gagaaaattt ttccaggttg cagagatctg tttaagttgc   118740
agattccata ggagagtgtc tttgaatgaa tactgttcta ttaattaaat aggtcaaaat   118800
tccctctgtt ggagcagcct tccaattata tagatttctt tatagcttct tgagttgtga   118860
aacataaacc caaggattga cttactggaa tatgactgct gtgttgatta aatttctgat   118920
aaggtttctt ccaatgattt gagaatagct ttcctgtttt tttactcaag gaaatgaatt   118980
ttcacaaggt ctcaggacat cacgtttcag gtgctttagt taaagagact cttcttgggg   119040
gcagtcagct ttcttccaac catgagctca tttcttcagc aaaccattcg ctttgtgcct   119100
ctattaagaa ttatgaagct tttgtacttc aatgcactga aaatcatgcc ccttgaatta   119160
aatgttgatt ggcactgaca tgaattggcc actcttgtat atgtgtccta tgttatgggc   119220
tcaacataac agtggactga gaatcgtcca ttagctgcct ctgattgtgg cactgaccag   119280
attgagaatc ctcagagtca tccatgaaaa agagagtcct taggttcatg aggttcttgg   119340
agacattcag gtaagtggag gagagaaaca ggattggggg ctgccagcca tttcaacaag   119400
actgggaaca attatcatct atgtttaaag gtctacatca ttccaaacac cctccaggtt   119460
tctctgagtt cattgtgatg attacattca gctgcttctc cagtgagttt aaatgagcat   119520
gtggcaattc agatgagcct ggctgtgggg tttattatat gtaaatctga actacataaa   119580
caaagagggc atgtctgacc gtatgagggt gcaaaatcct ggagacccca caccccacac   119640
tcttgtgctt tcttttctcc agcaacctcc aggtttttttt gtatgagaat tgtaatagat   119700
```

```
tatctcatgg ctaagtcatc aagagacgta aactctgaga aatacaagca gaaaattctc    119760
cagatagaag atccagggga agaacatttc tagcaccta tctatgtagg ggaaggcagt    119820
ccatctccat tacagacccc tcacagcagc cttcctttat aaggaaaatg ggtcaaatta   119880
gccaataggg taagaatcct ataatgttcc agccagaaaa gggaaagcat caatttgact    119940
tctggagact ctgtatatag gtcacattcc atagaaagaa gagcactaaa ttattaagat    120000
tcaattgtaa ctacatatga tacttccggg atgcacaaat taaagatgaa agtgtgacaa    120060
tgcacaggct ctgtcagaga aggagaacgt agggaaactg aaagagaatg gcagagagta    120120
agacaaggac agaagagcaa tatgaagcct ctgacatcaa ctctgtaagg acaaggtctt    120180
ggcaactccc gcattgacca cagattctgt taccatgggc catttgcagg gttcctagct    120240
aaggaaaaag aaaaaaaaaa ctgcatgcac ttcccaagtc tccacttgta tcctgttttt    120300
cttagatctc taggacaaaa aaaatggcat aaacctagac ctagtgtcag tgtaggaggt    120360
actttcttta taggcaagac actaggaaga agggaaaatg tgtgttattg gactaggaga    120420
tacagagatg gctttaatct gaatagatct acacccgcag gtattctcga atgcaacatt    120480
caactacaag agcctaatga agaaacacga ccctccccaa accctgcaa gctcttgtat    120540 tcactgtgtc tccactgatt tagtgcacct ggagcttcag agcactggct ccctcctgtg    120600
tcctagaatc ttttctttgg gtctttctgc agaattcaat aggattagtt aggctaatca    120660
attgtttcaa gagatggtgt tggcagcata tattgtcgct ggaagagtat tctaagccag    120720
gacacaggca ctttatgccg gactaaagac tctggagaaa atgttttgtg agccctgaca    120780
gaaacctcct tgaaaggtaa gggctgggca ggaggggca ctgaggagcc acgcagcaca    120840
cggtccagcc ctagaacagg aggctgggga ggaggtttcc tctcagggcc tcggttttcc    120900
ttcgtcagaa aaaaaaaat ctaaaataac cgttcaacaa gttgctgata tgccttcaaa    120960
tatcctgcta caatggaaca attcatataa cttcaggcaa tgagaactat ttttaaatt    121020 gggcttctag gattataagt atcttaatag tgaaaatgtg aagaataggt atgatttac    121080 tatttcaatg gatacagaat tgtgggagtc actatattcc tatgaacaaa aaattcagat    121140
ttcagtgtta agtaatgttg cctacattgt gtgagtgacg gggcagtggt ggatccgaga    121200
gtgtggtggg tgcacggaca taatgattca gaaagcaata tggaaagatg agtatctatg    121260
gatacgaact gaaagtatgt aaatacttca caaaatacta ataaacggag ttgaatataa    121320
aacccataat tatccaaaac acaaatttct tggaagttat tttgggaaca tgatttctta    121380
aagaactcca aactcttgtt tcaacttctg actcctcgtt tctgtgatat aagaaaacca    121440
tttccaatta tgcatctcag ggcaattctg taaacccaga gcgtttctgc tgaagatcct    121500
ggggaatcaa gacaccgggc aggtgatgga gacactgtct caggtgcgcc caacgaatct    121560
cagaggaacc tgctggagag tcacgtggaa catctacagt cagtttctca gagtcaacag    121620
tgagctgtgt tggtgcctga ggggaccatg atgggccaa ggcacgtgcc cagtgtcgtg    121680
gacagtgatg gtccagaaat gatctagatg gtcttgacgc taatgaaata tgggttcaga    121740
gtgaggagca taatctgtgg ggacttgttc ttcagtgaaa ggatcctgtc cgcaaacaga    121800
aatggagcag gacatgcatt tcttcaagca ggattagggc ttggaccatc agcatcccac    121860
tcctgtgtgg cagatgggac atctatcttc tttctcaacc tcgatcaggc tttgaggtat    121920
gaaataatct gtctcatgaa tatgcaaata accttagatc tactgaggta aatatggata    121980
catctgggcc ctgaaagcat catccaacaa ccacatccct tctctacaga agcctctgag    122040
aggaaagttc ttcaccatgg actggacctg gagggtcttc tgcttgctgg ctgtagctcc    122100
```

```
aggtaaaggg ccaactggtt ccagggctga ggaagggatt tttccagtt tagaggactg   122160 tcattctcta ctgtgtcctc tccgcaggtg ctcactccca ggtgcagctg gtgcagtctg   122220
gggctgaggt gaagaagcct ggggcctcag tgaaggtttc ctgcaaggca tctggataca   122280
ccttcaccag ctactatatg cactgggtgc gacaggcccc tggacaaggg cttgagtgga   122340
tgggaataat caaccctagt ggtggtagca caagctacgc acagaagttc cagggcagag   122400
tcaccatgac cagggacacg tccacgagca cagtctacat ggagctgagc agcctgagat   122460
ctgaggacac ggccgtgtat tactgtgcga gagacacagt gtgagaaacc acatcctcag   122520
agtgtcagaa accctgaggg aggagtcagc tgtgctgagc tgaaaaatg acaggggtta   122580 ttcagtttaa gactgtttag aaaacggggtt atatatttga gaacaaagaa caatagaaac   122640
acaatctaat tgtaagagaa atattccatt caagagccac cacataagcc aaactgacag   122700
agtgggaaag gccacactca gtaaagttga tacaaacata ccataaaggt gctactatga   122760
acaagttttt gaattagatg aataaatcat ttggagcaag gttatttggt catatgttaa   122820
gagtaagcat gattcttaca aagtgggaaa attgtctttc aaatgtttct gtcacttctt   122880
accataaagt tcattttaga ggttttagga ttacagtgaa attgcacaga aggtgtgaga   122940
attcccatga atccctgccc cgcacggaca ccgcctcctc cactacagcc atcctgcccc   123000
acagtcacaa ataagtcaca atggatgaat ctacaagaac tcttggttct ttctttttct   123060
ggtgatcccc taatataaca agcctaaatt atcttggaac acccaggtat tttcaatggc   123120
tttctagaag tgatattagt cagagggaaa gtgagtgagg ctattactat ttgagcactt   123180
tcttccaaaa tccacaaaat atatgttaat ttggagtttt tctaacttct ggtttacaat   123240
gtcccttccc agagagtaag attttttaagc ttttagtgag gctggaaaaa aaaatttta   123300 aaaagagaa ataagctttc ctgtattagg ctgacttatc ccagcggcag caacaagcac   123360
agcccagacc caggaaaagt cttaataata ttatctaatg tgctctggag actcttcag   123420 cactccctca acataggag aagaaaaca aatttccctt tgtcttatga tatgagttta   123480
tagagtcttg ttctctgtaa ctagtaactt caagtattct gttttatcta agaagcacaa   123540
cgaaggtcat gagaagccta gcaggccaga actacagctg tctaggtacc ggagtgagtg   123600
ttatgagatc aaccagtgca aggctcttta gaacaaaacc tagataacag acatctgggt   123660
tgcatagcaa tggtcatgtg taatcctgag ttatgaacct gttacaattt gattaactgt   123720
ctctgtcctg cctccgtatc cctgcttttg tgcactctaa gcttgcttca agctagccca   123780
cccccatttg ggaagtgtgt ataaaagtca agcgctctct ttgttctgtg cccagtcttt   123840
ggtcattgag tctgctgggt ctgggtgtac tcagtaataa aaatatcctc ctgtatacac   123900
cccaagatct ctctctggtc ctccggattc tgcaacattt caggcagatt cacatctcta   123960
aaaggccagc aagttctggt caatcccata atgaaaatcc tttaatgaga cttggcacac   124020
gtgacaataa gagactcctt gtataatgcc ctagagttgg attagacaca ctgtgagctc   124080
ttgggtggtg gttctgaata aggcagtttg tgcagcaaat gcaaacacat gcatgggatc   124140
caggcaggaa caaagcttc cctttacaaa gtgggtgggc atctggaggg agccctcaga   124200
ggtgggcagt ggtcgtcctt gctgactgca cattagccag aggcgtgacc ataattggtc   124260
ttgcagggaa agagcaccac tgaggtcata ggttatgaaa atgtttgtca tcctccagtg   124320
agcaagtcca tcctgcttgc ttgtgggtgt caactccatg gtggatacac tctgggagat   124380
gacaagatgc acacaaacct cctctcacta attatccact accacacact caagaccaac   124440
```

```
ctttgctcca gaaaggaata cgtgtctgtg gaaatagaca gagcttaagt attttgtaac 124500
ctggtgaaca tactgtgcaa aaccaaacgt ttcaggaaga ttagctcaga aatgtttatc 124560
aagtgactga agggcagtgg cgggtgaggt gatgggacag cctcagggct gcacatgagg 124620
agggctccct cccccatgca ggcttttcct ccaggagctg caccaggaac tcaaggaaga 124680
tcagggagaa ttctgagaac accctgctgt ggagctgcct agagaagaag aataaatgat 124740
gaaaaataca actctgagta atgcatgggt ttttgttcat gaaaactctc tctctgaaag 124800
cttgtgaagg tcttgaaata cccctgatta gctgaagaca aacatttaaa ccctccttcc 124860
acagggagtt caagcaggct ggatgtgtcc ttctatggat gatcttcctc agccccttcc 124920
tcttcccagc tcatccctgg ctctctgtgt aaaaagttct catcagcgga atgtggttga 124980
tgaagtgacg tcttcaattt cctcatcttc tatgtggtca tgttattttc ctcatctgaa 125040
gtttaaaaac tcacctgcat gcagcacatg acaggctaaa atctcttgtg acaaaacag 125100 taacaaaggc acccaccatg gttgagcacc cgtgttgctg acaacgacca ccagggtca 125160 acgtcctctt cacaatcctg tgtcagagca gcacttgagt gatttcaata acaacttccc 125220
aggagaatca gctgaaaact acttgtccca ttttccatac agatataacc cctctatttt 125280
cctgaagaaa tagaaagagc tgaatgctga atacactgaa tgtctgctgg ttttgcaagt 125340
ttgtgactat atcactttct aatttctgac ctgtgcagac cactgtacag acttttctca 125400
ctggtgggac caggcttcca gatgtcaaat ataaatgagc ttcttcatat aaaagtcaac 125460
acaagctcct catggtttca gtgctcactg aatggagttg gaaataaaac ccacaattat 125520
ccataacaca aattccttgg aagttatttt gggataatga gttcataacc tgtagaccaa 125580
gagtccaaga gtgtttctat tgaagagcct gggggatcaa gacaccaggc aggtgatgca 125640
gacactgtct aaagagtgcc cagcggctct cagagggacc tactggatac tcacgtggga 125700
catcagcaat cactttctca gagtcaccag tgagctgtgc tggttcctga agggtccagg 125760
atagggccaa ggcacctgct ctgtgtcggg gagagtgatt gttccagaaa tcatagaggt 125820
ggtctctatg cttataaaat ctatgttcac agtgagaagt ctgttctgag agggcttatt 125880
cttcagtgaa aggacctctg cccacaaatg ttcataaatg gagcagggca ttcatttcct 125940
caagcaggat cagggcttga gtcatcagca tctcactctt gcaaggctga tgtgtcgttt 126000
gtcttccctt tcttatcatc gaccaggctt tgagctatga aatgcccgtt ctcatcaata 126060
tgcaaataac ctgagatcga ctgaggtaaa tatggatatg tctgtgccct gagagcatca 126120
cccaacaacc acatccctcc tctagagaat cccctgaaag cacagctcct caccatggac 126180
tggacctgga gaatcctctt cttggtggca gcagccacag gtaaggggct cccaagtccc 126240
agtgatgagg aggggattga gtccagtcaa ggtggctttt atccactcct gtgtcccctc 126300
cacagatgcc tactcccaga tgcagctggt gcagtctggg gctgaggtga agaagactgg 126360
gtcctcagtg aaggtttcct gcaaggcttc cggatacacc ttcacctacc gctacctgca 126420
ctgggtgcga caggcccccg acaagcgct tgagtggatg gatggatca cacctttcaa 126480 tggtaacacc aactacgcac agaaattcca ggacagagtc accattacca gggacaggtc 126540
tatgagcaca gcctacatgg agctgagcag cctgagatct gaggacacag ccatgtatta 126600
ctgtgcaaga tacacagtgt gaaaacccac atcctgagac cgtcagaaac cccaaggagg 126660
aggcagcttc actgaatgag gaggttacag ggcttacgat gtttaaagtt gttcagaaaa 126720
taggctaagc aattgaggaa tatgagtaat agaaatatgt acgcactcta tacaggaaat 126780
atttctaata actgtcaccc tatatgcaaa attcgcagag aggtaaaagc agaaatcagt 126840
```

```
caagctgatg caaagttccc cacgtaggct ttgtgcagat gtaagttcta aaatcagata  126900
gataaataat ttggagcaag attgcttgat aacatggcta atgctgaata tgattcctaa  126960
aaactggcca aaatatattc caatttgtct ctgccacctc tcttacataa aatgtattaa  127020
aaagtagttt taagaccaca gcaaaattga acagaaggtg cagagatttc ctatgtgccc  127080
ctgcttcaca catgcacagc cttccccact gtcaccatcc tgccccagag tcatcaataa  127140
gttacaatgg atgaacttac atggatggat tggttctttc ctcttccggc ggtcccttgg  127200
cataccaagt ctaaactatc ttgaagcaca acaggttctt cgagtgggtt cctgggaatg  127260
aagccagtta gaggaaaagt gggtggggct attcctatta ggagtctttt ttagaagact  127320
cataaaatgt atatgttcct atagattctg tgactcctga cttagtatcc cttcccagac  127380
ggtaagcttc ctaaatgttt agaggcagat ccatatctat ggaaagaaag caagttctag  127440
tgaatcccat aaggaatgtc ctttaatgag aagtggagac cttggtcatg aggcacatca  127500
tgtatgattt tctataattc ctttagattc actgtaagct tttgagggtg tttctggatg  127560
aggccctttg tacagaaaat gaaaactcag gcatgagttc caggcacaac caaccaactt  127620
ccttccaaag tgggagggaa tagaagaaac cctctcctgt gtgggcgctg gtcccccctcc  127680 attgctggct gcacattagc cagaggcatg agcccaatta gtcttggagg gtgacagccc  127740
cactggggtt gctggctata gaaatgcctg tcctcttcca gctgagtgag tcaacctgct  127800
cgcttgttgg agtcaactgc atggcaggtg cactctggaa gatgacaaga tgcacacaaa  127860
ccttctgtaa agtatcaatt actacacact caaaaccaaa ctgtattcca gagacaggtg  127920
tctgcaggga taaacagaat ttaagcattt tttgaatagg gaagacactg ccaaatgcca  127980
tatgtttcag gaagtttaac tcagaaatgt tgatgacata actcagaaac gtgaggtgac  128040
atgacagctt caggggctgc acatgaggag ggctcacttc cccatgcagg cttttcttcc  128100
aggaactcta ccaggaactc acagaagatg agggagattc tgaaaacatc attctgtggt  128160
gctgcccagg gaggaaaaat aagatatggg aaaaaaaact atataaatta ttagatttgt  128220
taatacaaac tatttctgaa gccttgtgga ggtcctgaca taagccatca ttagctgtga  128280
acaaatatct acaccctcct ttcctgggga gttcagttag gttgcgtctc ttcttttatg  128340
gacagtatcc cccaacccct ttatttcctg cacacctgct gctctccatg ggacgagttc  128400
tcatcagtga aatgtggttg atgtagtgag gtcttcactt ttctcattgt attagtcagg  128460
attatctaga gggagaacta acaggataga ggtctgtatt tgacggggag tttttaagga  128520
ggactgactc acacgatcac aagatgaagt ctcatgatag gccgtctgca agctgaggag  128580
caaggaagcc agtccaagtc ccaaaacctc gaaagtcagg aagacgacgg tgcagccttc  128640
ggtctgtcgc caaaggacag agagccctg gcaacccgct ggcttaagtc caagagtgaa  128700
aaagctgaag aacttggcgt ctgatgttcg agggcaggaa gcatccagca tgggagaaag  128760
atggaggctg gaagactcaa caagtctagt ctctccaatt tctcctacct gcttcattct  128820
agccatgctg gcagctcatt agatggtgcc cagggaggtt gaggttgggt ctgcctcacc  128880
cagtctactg actcaaatgt taatcttctt tggcaatacc ctcacagaca cactcaggaa  128940
caattctttg catctttcag tgcaatcaag ctgacactca gtattaaaca tcacactcat  129000
cttctgtgtt gtcatgttcc tctcttcatc tgaggttaag gaactcacca gcatgtagca  129060
catcgtagct taatgtctct catggacaaa atagtggcaa ggcacccact agggttaagc  129120
atcctgtgtc gccgacagca accaccacag gaccaagtct ctctaccatc ctgtgtcagg  129180
```

```
gcatcgcctc agtgattgta ttggcaactt ccctcgagag tcatcttaaa aacggcttgt   129240
ctcatttccc acgaaggtat agcccatcca ttttctcttc ctagcaaaat ggaaaaggat   129300
gaatacacgg aatgtctcct ggtcttgcaa cttggtgact ttattccttt ctaatttctg   129360
atcaatgcag cccactctac aattttttt ttcactgaaa tgacccacat tctggatgtt   129420
aaatataatt gaacttcctc atttataatt cagaacaagt acctcagagt ttctgtcctc   129480
atgcaccact ctaaacttac acaagttgtt tatttatttg tttcatttc tggcatctct    129540 actggggtc ttcatcatac ccattttatg ttatttctac aaatgatttt taaaatttat    129600
aggtacttaa ttaaatattc aggaaacaag agaataaaat gaatgtaaaa taaaataaaa   129660
gtaaataaat taatatttaa aataaagaag ccagcagctg aaagcaagga aaatctatta   129720
tgctgggtca gagagtatgg agaactcata gtacaatatc ttctgcacgt taatcattac   129780
ttctactcaa gttacagggt cctctctctt tatatcagag ctttccctaa catgtgcaat   129840
gaagactgaa cacagattcc tccctcaaga ctgacctagc atctctcact gagcctgagc   129900
tgacaagtca tagatatcac atttgtctaa gaaaataatg acaccctgta aagttaccta   129960
ccagcgatat ggagacaatt tgaataatat aaataaagcc taaacttgat aggtagtcat   130020
ttatccttag aaggattgac tgctgtctct acatgtgttt tttatcacag agaagctact   130080
agtgccacag tccaagttgc tgaatatttt atttcctagc atgagttact acagaatgtg   130140
ttcaacatga aagaatgcag ctgttgttaa gggagaggag atgtgattat ggaacacgag   130200
cagggatcca gcagacattc ctctttcacg tttgccccc aacagagaca ccagtaaaac    130260
gatgaaatga ttgactttag tctccacagt ctaatgtgag atttatacca gatgttttct   130320
gccactgttt tatagtagaa aatataatct ctaaagaaat tccattttta gagacaatac   130380
catcctccag gaagctgcaa atgcccataa cagagagtat tatagtgcct tgtggccagg   130440
agctacaaca cctgggtttg gaaactaatg gacagaaata tcaggttttc ttgccaaatc   130500
tatgatgaaa atttggagaa tgtttctttc catctccata acaatatgtt gtgatggagt   130560
ggaggtcctg gtacataaga aggtatgtgt tcgcagtggg tacagaatta gacccataaa   130620
atgattgttc tactggggtt cccttgttgt tggaccagct gaccaagaaa gtgttgtaag   130680
aggtgtagta tttagtgaat actgtcatat ttttgaaggt accatatttg aagctaccag   130740
gagaaacaga gatacatcaa tctagcctag ggagactcta tgaatttatt ttatttcctt   130800
caaaatgagg taaaaaattg catcagttga aatgccgatg ataatcaagt gatgaaagac   130860
aacatccact cagtgtttta ggtgtggttt aacccaaaag ttatacaata tgtgagaacc   130920
tgaactctgg agccctggcc atctctcaga agaatctaga aggtagactg acctctccca   130980
cagtgtgatg tccatggaga ctggggatgg ctactgtctc aatcttggga tcccggaata   131040
gtcttaatat gattctgtgt gtatgtggat cattgtgtgt aagtgggagg attccaataa   131100
ctgtgtctgt gtgtttgtga gtgtctatgt ttctgtgtgt gagcttgtgt gtctttgttt   131160
tatattaaaa tgagtaattt agtttctgat cattagactg tgtctttgag ggagtgtgtg   131220
ggagaatgtg catgcctgtg tctgtgagtt agtttgtaaa agggtatgtt atattgaatg   131280
tgtgtgtctg ggtccttcag tatttgagcc tattaattta catgaacatg aattttttga   131340
aggtgtgtaa gtataaaact tttgtaaatg taattgtttg aatgctagtg tgtgcagagc   131400
tatttgagtg tgaatgtgtt acttgtatta cttagtgagt gtgtgcccct atgtgagttt   131460
gtttgggtga gtcattacct atgactctac atatgaaggt gttgagggtg tgtgtgagtc   131520
tgtgagcatg ttttcattac ctatgactct acatatgaag gtgttgaggg tgtgtgtgag   131580
```

```
tctgtgagca tgtttatgtg catgtgaaat gttgttatgt atgctttgaa agacttgtct  131640
cttgacctca atatcatttg tctgaaaata ccaggtatgt ttaagccctt agaatctaag  131700
gaatagtttg ttgtttagga taaatcctca ataagattaa caactgattt ctcaccaaaa  131760
atcaggaagg ccaaagctca ctggagtggc atatcaaaag tgctaaaata cactatcaat  131820
caaaaattcc atactagcaa gaacaccttc aaaagtgaag gagaaatcaa gataatagaa  131880
ataaacaaaa gctatggagt ccatcaaaac cacaaattcc taatgagaaa tactaaatag  131940
agtcctgcag gctccaatga aaacagagtg gagaatattt aaaaatctta cacctaaaag  132000
aacaacaaca acaagtatcc cagtaatcac atttgtgtaa tgaaaaccaa tattgtttta  132060
tttttgcctt gagtctcatg ttctattcct ttttttaaaa aaaaatagat ataatagtaa  132120
tgacaaattt gaataatgtg cctataattt atggttataa aattcattat aaatttgaat  132180
aatgtgcata taatttataa tgtatgaata tgtaacaaca caataagtga aaatggatac  132240
agctgtagag aagcagagtt gtatgcacta ttgaactaag gcaatcataa tttaaactac  132300
tctgttataa atctgaatta ccaattgtaa tatccaggtt agctataaaa acttaagtaa  132360
aagtaaaaaa aaaaaaaaat tagcaggaca gctgactaaa cgtgcctgac actcttcaac  132420
cccacatgaa ataaccacag aaatgaataa acagctgaga ctagagaaat tcaacagagt  132480
tagatatcat actaaataat aaagcaaaaa gcttacagct gaagaattta atgaataaaa  132540
taaaaatgca gtttacagat tcaataacag aaaataacga gcaaaataa gaatttctga   132600 gcttgaagac aagtctttca aaataattcc agcagaccaa aaagaaaaaa aaagagaatg  132660
aaagagagaa ggaaggaagg aaggaaggaa ggaaggaagg aaggaaggaa ggaaggaaga  132720
taaaatttta aaacatagaa accctatag ttttcaaaac acaatttgaa aacaagtttt    132780
tgagttatgg aaaatccagg ggaaaattcc agagggaaaa aaatgaaaat gatgtaggaa  132840
acatatttaa taaacaaga gcagaaaacg tcccatatca tgggagatag atggttattc   132900
agatccagga aactcaaata ttccaaacag actgaaacta aacagatcct ctctgaagaa  132960
tgctttcctc aaattatcaa aagacaaaga tagagcatga tagagtagga tagtatattc  133020
aaaatattga ataaaaaag tatccagcca ataatataat acctagaaac attattattc    133080
acaaactaac aaatatataa tgtttatcgg actaacatga acaggaaatc catcacctcc  133140
aggctggcct tacaagaaat gctcaagatt cttacatctg gaagagaaaa cataatagcc  133200
acaattatga aaaattttta aaaaccata aacccacta gtaaagccaa tacacaaaaa     133260
agaaaataaa tgaatcaaat cttatcacta caaaaattac aaaactacaa aaataaccaa  133320
taggttaaga ataagaaaca agagatacac aaaacaatga gaaagaatc aatgaaagtg    133380 aaagaagtaa gacctcttct atctattatt agcttgaaag taagtggatt aaattttaca  133440
tttaaaatac atagactgag ttgaagagaa aagaaaagaa aaaagaaac aaacaaacaa    133500 aagtgccaac tataggctgc tatgttaagc ccattttgca ttgttataaa gaagtacctg   133560
agtctggaca atttacttta aaaacaaaaa cagtctacaa attcaatgca attcccatca   133620
aaatatcacc atcattcttc acagaactag aattcatatg gaaccaaaaa agacttggat  133680
aggcaaagca agactaagca aaaagaacaa atccggaggc atcacattac ctgaattcaa  133740
actatactat agggccacag tcaccaaaac agcatggtac tggtataaaa ataagcacat  133800
agatcagtgg aaaagaatag agaacccaga aataatgcca aatattatat caatgaatct  133860
ttaacaatgc aaacaaaaac ataaggtggg gtatggagac catattcaac aaatggtgct  133920
```

```
gggataattg gcaagccata tgtagaagaa ctatatcctc atctctcacc ttatacaaaa    133980
atcaactcga gatggattaa ggacttaaat ctgagagatg aaaacataaa aattctagaa    134040
gataacatct gaaaaactct tctcaatatt ggcttaagca aagtcttcat aaccaagaac    134100
caaaagcaaa tgcaacaaaa acaatgataa ataggtagga cttgattaaa ctaaaaagtt    134160
tctgcacagc aaaataaaca atcagcagtg taaaaagaca atctatagag tgggagaaaa    134220
tcttcacaat ctatacatcc aacaaaggac taatatctag aatctacgag gaactcaaac    134280
aaattagcca caaccaccaa aaccaccacc aaaaacaatt ccataaaaca ataagctaac    134340
gacataaaca gaccatcctc aaaataagat atacaaatgg caaataaaca tgaaaaaaat    134400
gctcaacatc actaatgatt agggaaatgc aaatcaaaac cacaatggag atgcaagtca    134460
ataccacatt actcctgcaa gaatagtcat aatcaaaaaa taaaaaaata gatgttggtg    134520
atgatgcagt gaaaagggaa cactggcggg aatgtaatct agtacaaaca ccatggaaaa    134580
cagtgtggag attccttaaa gaaaaaaagg agaacaaata tttcatccag gagtcccatt    134640
actgggatct acccagagga agtcaccata caaaaaagat acttgcacat gcacatgaat    134700
gttcacagga gcacaattcg caggtgcaat aatatggaac gggcccaaat gccatcagt     134760 caatgggtgg ataagaaat tgtgatacac acacacacac gcacaccatt atatatat       134820 ataattttt ttttttttt tttttttgg ggagacggag tctcgctctg tcgcccaggc       134880
cggactgcgg actgcagtgg cgcaatctcg gctcactgaa agctctgctt cccgggttca    134940
cgccattctc ctgcctcagc ctcccgagta gctgggacta caggcgcccg ccaccgcgcc    135000
cggctaattt tttgtatttt tagtagagac ggggtttcac cttgttagcc aggatggtct    135060
cgatctcctg acctcgtgat ccacccgcct cggcctccca aagtgctggg attacaggcg    135120
tgagccaccg cgcccggcca tatatatata attttatatt ttctatatat acatattttt    135180
tatatatgta catatatacg tgtatatgtg tatatatgta tatatttacc atggaatatt    135240
aagccataaa aaggaacaaa ataatgacag tcacagcaac ctggagggaa ttggagacca    135300
ttattctaag tgaagtagct cagaagtggg aaactaaaca ttatatgttc tcactcatac    135360
gtgggaaata agctatgagg atgcaaaggc ataagaatga tacaatagac tttgggggact   135420 tggaatagat gagggggggct gagggataaa agactacaaa ttgggtacag tgtatactgt    135480
tggggtgatg ggtgcgccaa aatctcataa atcatcacca aagaaattac tcatgtaacc    135540
aaaccctacc tcttccccca aaacctatgg aaataaaaat aaaattatgt aaagtaaaat    135600
aaaataaagg tatatttggc tgacagttct gcaggctgta caagaagcat agtactggca    135660
tctgcttctg tcgatggcct caggaagttt tcaattgtgg cagaaggtga aaaaggagca    135720
cgtatgtcaa tggcgataga agagaagaaa aggcagaaaa ttaaggttgt tgggtgggtg    135780
ccatgctcct taaacagcca ggtatcatgt gaacgaatag aatgagaaca cactcattac    135840
cacgtgaagg gcatcaaggc ttttatgaga gatccgtgtt cacgacccaa aaacctccct    135900
ctaggtccta cctccaacac cggagataac attgcaacat gagatctgaa gtgaacagc    135960 atccaaacta tatcagttac ctacaaaaaa ctcactccaa ttgtaatgat gcacttacgt    136020
tgaatatgaa ggtatggaaa aagttatgta atgcaaataa aaactaactt cacctggagt    136080
agctatactt gtagtggata aaccagactt taagttaaaa gctgtaaaga cagacaaaga    136140
aggacactat gtataaataa agagttcaac ccaggaagaa ggcataagaa ttttaaagat    136200
atatacccaa cgatacagta cccaggtatg cagagcaaat gttatcagat ctaaaaggat    136260
agacaccaat acaataattg ctggcgactt caatccctca ctgaaagcat tgcacagttt    136320
```

```
atccaaagag aaaatgaaca gaaaatttca gattaaaatt gcaccagagg ccaggcacaa   136380
taactcacat ctgtaattcc cgcactttgg gaggctaagg caggtggatt ggtagagagc   136440
tcaggagttt gagactagcc tgggtagcat ggcaaaaccc tgtctctaca aaaaaaataa   136500
ataaataaaa aataaaaaac agccagtgtg gtagcatgtg cctaaagatc cagctaccca   136560
ggaggctgag gtgggaaaat caccagaacc cagggagata gaggctccat agagccctga   136620
tggcacccat gcacgccctc ctgggcaaca gagcgagact gtatctcaaa acaataatt   136680 gcaccacaga ctgaacggac tcaacagaca cttacagaac acttcgccaa acagcagcag   136740
attgcacatt cttttaaca gcacaatgaa catcctccag aatttaatat atttggacac   136800
aaaaaagtct cgaaattata aaatatcaa agccatatca agtatcattt ccaaacacaa   136860
tgaaataaac tagaaaccct agaggatgga atatttgaaa caatgcaaat atatgaaaat   136920
taaacaacat gcttctgtgt gaccattgga taaggaata acttaaaatg aaactttaaa   136980
aatttattga aataaataaa aatagaaata caatatagca aaagctactg gttacagcta   137040
aagcaatatt aagagaaaag tttctagcaa taaacaccta aatcaaaaaa gtagaacgat   137100
ttctcaaaaa ccacccacct atgtgtctta agaactagag aagcaagaac aaacagaatt   137160
cataattgta gaaaaaatag acagtaaata tcagagcaga attttaaaat acagaaaaaa   137220
aattctataa aggatcagca aggccgggcg cggtgactca tgactgtaat cccagctttt   137280
tgggaggccg aggggggcgg atcatgaggt caggtgattg agaccatctt ggccaacatg   137340
gtgaaacccc gtctctacca aaatacaaaa aattagccag gcgtggtggc acacgcctat   137400
attcccagct acttgggagg ctgaggcagg ggaatccctc gaatctggga ggcgaggtt   137460 gcagtgagcc gagatcgcgc cactgtactc cagcctggca acagaacaag actccatctc   137520
caaaaataaa taagtaataa caaagggat cagcaaaaca gttgttttct tgaaaatgta   137580
aaaaagcaag aaggcattat ctagattaac tacaaatgaa aagagaaaat gcccatatac   137640
atacaatcag aaatgaaaaa agagacatca caatgatacc acaaaaatac aaaagatcat   137700
tagagggtat tatgaacaac tatatgctag agaaaattca agaacctaga ggaaatggat   137760
aaattcatga acacatgcaa actaccaaga ctgaaccaag aagaagtaga aagcctaaac   137820
agaacaatga ataacaggag ataataataa tgaaaagtct cccatcacag aaatgttcag   137880
gacctgatgg tttcacagtt gtgttctact taacttaaaa aaaaatcatg aaaacagatt   137940
attgttaaac tattcaaaaa attgaagaaa aattatttaa ttataatttt aatattattt   138000
ttaaaatttc aacttttatt tcaggtacag ggggtacata tgcaagtttt tttacatggg   138060
catattgtgt gatgctgagg tttggggtat ggatcccctc acccagggag ttagcataat   138120
acccaatagt cagtctttca acccatgcac ctctctctcc ctccccactc cagcagttca   138180
cagtgcctat tgtttccatg gtcatgtcca catgtgctca acctttagca ctcactttca   138240
agtgagaaca tgtgatattt tgtttccttt ttctgtgtta acttgtttac gactatgacc   138300
tccagctgca tccatgttgc tgcaaaggac atgatttgt ttcttttgtg acagagtctc   138360
actctctcac caggcaggag tgcagtgacg cgatctcagc ttactgcaac ctctaagtcc   138420
ctggttcaag tgattctcct gcctcagcct cccgggtagc tgggattaca ggcatgtgcc   138480
actatgccca gctaaatttt gtattttag cagagagggg gtttcactat attggccagg   138540
atgatcttga tctcctgacc tcatgatctg tctgcctcag cctcccaaag tgctgggatt   138600
ataggtgtga gccaccacac tttttttat gaatgtgtgg tattttatga ttttatattg   138660
```

```
catacatacc attttattca tctaatacat cattgattgg cacctagatt gattccatat    138720
ctttgcggtt gtgaatagtg tggcaagagg catgagtgca tgtgcatttt ttggtagaat    138780
gatttatttt actttggcta tatacctaat gatgggattg ctgggtcaaa cagtagctct    138840
gtttcaagtt ctttgagaat tctctaaact gctttgcaca gtgctgaact aatttacatt    138900
tccaccaccc atgtatgtgt tcccttttct tcacttccca cccagcagct gttttttgtt    138960 taacttttt catattagct attatgactg gtctgagatg gtatttcatt gttgtttta     139020 tttgcatttc tctgataatt aatgatgttg gaaatttttt tcatgtctgt tggccactga    139080
gattgacagg cttacaagtg tcttagtcca gcagttttcg gtaacaggct atccactttc    139140
attttctctt cctcacatgc cccatttctg ggttgtccat cccaaccaac agttactgct    139200
ggagctgaat ccactagccc gcttccatgg gctgtcagga acacattgca agggtgacac    139260
acacgatgat ccatctctgc agagccaact ctccttctcc agagattcat ccaagaaaca    139320
attttgacta tacctgagct ctgtgacatc tgaggacatg gtttgtatta ctgtgcaaga    139380
caaacagtga gaggaagtca atgtgagtcc agacataaac cttcctgctg agaacaatgg    139440
aaagcttttc ttctaagata aggaataaga aagaatgcc cagtcttaat aattctaatc    139500
agcatattga tgatagtttt aaccatagaa atttgagaaa gaaaaaaata gtaaaggca    139560 tacaaattga ggggaataag ttaaattgtt tctgtttaca gacaatataa ctttataaat    139620
tccaaaaaaa taaaaaattc tgaaaaaaca gccactgaaa actaacaaac aaatttagta    139680
acattgcagt atacaaaatt tatatggaaa actcagtagt gttactaaaa actaaaaatt    139740
aactatttaa aaatcataag acaatgtcag ttgcatttac aataatatta ataacttac     139800 ttagtggcca tgcacagtag tttacacctg taattcttgt actttgggag tagggggaga    139860
atcacttgag gctaggagtt tgagaccagc ctgggcaaca cagcaagacc aatatctatt    139920
tctaaaaatc acttagaaaa aatgttggtc aaataagtga aaatctgtgc attgaagact    139980
atatgacatt gatgaaataa ataaatctat atgcaaatat atgggaaact attccatatt    140040
cacagattga agataataat actgttaaca tgtctatact acccaaagca atctacagat    140100
ccaaagcaat ttctatacaa atgacatttt caacaaacta cttttaaat gataaaattg      140160 aatcacaaaa gaccccagat gtccaaagta accttgaata caaacatcaa agcgggggga    140220
ggtttcctag tacctgaact gcaaatatgc tatgaaacta caataataaa actgcatgct    140280
gctgactttc taaataaact ttaatattct gaattgaagt tatttgacaa ttttcttctat    140340 cattttatct ttactaaagt gttgcatgag tgtttatcta gacagataat gtgcaaagag    140400
tcttcctggg tggtaaaatc ccataagcgt ctccaggagc tccgagctct ctctaggctt    140460
ctcagtatgt tcaggttcaa gagacagaaa gaattctctc agcccttcac tgcttttgc     140520 cctcttgacg gtcagaagtc cagaacatgc tttgtgggga cataatagag gggaccaaaa    140580
tagacacttt cagcaaaccc actataacaa gttctgctgc ccatgggcat cttctccagg    140640
tacatgttgg tcgccagacc ctcaggctca cctacaccat gtggaggagg acctctaccc    140700
acactcattt cagcacaact accgtgtagc tcagcatcag taggtcacac tacaatacat    140760
taaacatcac tcagctaatt acttattgag gttttcattt gtccatatgc tatcaatatt    140820
gggcagtttc aaatgacaac ctagaggact taatgatagt taaatttatg tcttctatta    140880
cggaaaaaca tcccttacct aatgacaggt tcagctgttt tgccaagat ggtgctcttc      140940 cctggcctgc tagtctccta catgagaagc atcaatgaac tgggcagcac cacacacttg    141000
tcaagtgatc actgggaatg atgtcagcta cagaggatgg ggtagggttg ctcataccta    141060
```

```
tgctccttac ttctaggaca catcaggtgt ctatggattt agagcatgtc tgcaccctgg 141120
tggactgcac actttaccca gggagaaagg tctctgagtg tgggtggcaa gccacctagg 141180
tgccaaggta agagaccgag ggcacaagct gttccagtat aataaaatat ataaaataag 141240
aatagttata ctagatatag atcatagata tgattatata tgaatatcat taatcattag 141300
tttatagcaa ttactcttta tcccaatgtt attaataatc ctcgctctat aatcataacc 141360
taggaaaaac caagccatac agagatagga gtggaaggga catggtgaga agtgaccaga 141420
agacaagact gcgagccttc tgttatgccc ggacatggcc accagagggc tccttggtct 141480
agcggtaaca ccagcttctg ggaagatgcc cgttgccaag cagaccgtgg tctagcggta 141540
gcgtcagtgt caaggaaaaa cacccgctac ttagcagacc aggacaggga gtctcccttt 141600
ccccagggga gtttagagaa gactctcctc ctccacctct tgtgtagggg atcagtcagg 141660
cccacccgag ttatctggag gcctaatcat ctccctctga tgctgtgctt cagtggtcac 141720
tctcctagtc tgctatcatg ttccatcctg tatacctggc tctgccttttt agataacagt 141780 agcaaaatta gtgacagtac taaaagtctc tgatatgcag aaataatggc gtaagctgtc 141840
tgtctctctc cctctctctc tctctctgcc tcagctgtca ggcaggaaag gacccctgtc 141900
cagtggacac gtgacccact tgaccttacc tatctcattg gagatgactc acactcttta 141960
ccctgcccct tttggtttgt gtccaataaa tatcagtgca gccagacatt cggggccact 142020
accggtctcc atgtcttggt ggtagtggtc ccctgggccc agctgtcttt tatctctttg 142080
tcttgtgtct ttatttctac aatctctcat ctccacacac agggagaaaa acccaccgac 142140 cctgtgggc tcgtccctac atctgagctt ctcaatggag gtctacttct ctatgagact 142200
agcaccttct gtggagtctc atgctgaatg tctccttctt gattatggtc atcggttatg 142260
cagtgctgta attagaaacc cttacagaat aacctacaaa acaagaatga tactaccttc 142320
tacagacatg acaattctac ctaatgtgca caactggacc tattgacatc ttagccagga 142380
gaggatgcag gcataaagca gatgattttc cgattgttcc accctaccgg gttatattga 142440
acagtggaca caggattcaa caggtaccga ttattaatcc agtgaggaaa ttatagaata 142500
gtcccaagtc taggcagaga agagtagctg aagacagtac tttccctgca gctctgagat 142560
tcactaaaat gtccagctct gtccctcact cgtgaatatc acagactaaa ggacacccctt 142620 cccacagcat tggctctcca tgaagatttg aaattgatgc ccaggcctca gggtctgctg 142680
acagagctgt gacagtggga gtggaactca cacagagcaa acagagtgt gttgcataat 142740 aaggctgtac aacattttca taatggaggg aatctcttgg tcccaggaag atgacaattt 142800
aatatgtctc aggcctgtgg cgctctcttt aggagctttg tgtgtggctt ctttgtatac 142860
tctggctcca ggaactccag tgagggaaga gattcgtcac ctcctgtgcg aaggggggctg 142920 aagcgaggaa gacaagtggc ctggcttcca cagaacccat aagctaaaac actccgagtt 142980
cccttgactg caagaaatgc agctgtcatc acggtttcaa gtgccagagt ctttaatgat 143040
tatgtttcaa ctcatgagag tgccaggaaa attccaccag tatgaactac tcaaatatgt 143100
cattttgtaa cattacttca ttgcttgctc tcatatcctc catgtttctg aaaaagcaaa 143160
gtttccatgc tttatcatct gcaccaatga ggccatattt aagctatatt ttcatatgaa 143220
cgtctcttga agattttaaa atagcaacaa atgttgcaac aatatgctta accagaaaaa 143280
aaataaagca aagcagtcta tgttgactca tgtgacattg ataatgtata ttagattata 143340
ttggttgctt attcagttgg tcatgggaga agagccttct ttccagccaa agaatactaa 143400
```

```
gaactccctc ttctaatgac gaatttcagc tgatcttgct gagaatattt agcaagaaga 143460
cagaaacaga gactcctaaa gggagctcca gagtcctgag atacatttaa gttttcattt 143520
tcctggaacc cagagattcc ccactgttct acaagacaag accccattct atgaccctgt 143580
ctgaggagag ctcaggggca gtgagctccc cctcacatta ccccttcacc ctatgccctt 143640
ggggctctgt ccatgcaaat aagtcccggg ttcaagaacg aatagaggca gggctgtgag 143700
tgttatgctg tgtgctggct ctgagctggg gtctctagta gcactctcca catccataga 143760
tacatggccc ctccgctact ccttctctgc ctgctggctg ccctctgtgg tgagttactc 143820
atgatttcat acgtggggag acacgggatg aggcaaatgt gtctgtgact cacagatgtt 143880
ctctattctc aggggttcac agtgaggacc accttgtgca atgggaggaa gaagtagtgg 143940
tccccttggt catgctcagc ctcacctatg ccgccatgc acattcaatt tctgaacatt 144000
ctgtttcctg gatccaccat ctcccatcaa aaggtcttca gtgtgttggt gtgatatggg 144060
ttaagggaaa cactaagccc caaccttcag ggcagagcta gcatctccag aaacacatag 144120
taaaaaacaa gaaaacttac agctgagaag tgtgatggct ggggatgcag gcgtgtatta 144180
ctgtgctcaa ggcactgtga ctcgaatcca gagtgaactc agacacaaac ctgccctgca 144240
ggggttcttg ggaccacaag gggaaggatc aggtcaccag ggtgtactta ggaaccactg 144300
aactgggtca ggcacaggag gtgggggtca gggctcctcc ccagggaagg gcttttaatc 144360
tccatgcctt gtaaacctct gacaagccag gcagacacag acatattttt aagctatgga 144420
aaaagatgta cctttcattt tggaggaaaa agatcataag tgtgaaagca aaacttacca 144480
agggccaggt actggaataa ctgtaatcta cataatcact ctaagaattc taagaattta 144540
caagtgcaat catcctcatt tcataaactc accttaaata agagctttct aactgatccc 144600
atatattctg attttgttta tttcttcaac actttattat cttcaaggca tttcactgat 144660 gtcaattta gaagaatcat atgcaaacag cctctcgtgg tggttgaaag cccacagcct 144720
cgccagtcct gtggatattt ctggatgttc tcagagtctc cattgtctgt agagaagaat 144780
tgtcccaata gttatttcac ttttgtcttc cacaaagttg gaaagatggg gatcactcag 144840
gggaatcgag atcaacaaac agaaagcctg aacccaccat atacaagata ggatgtattt 144900
ttttaggaat atattaattc ccagaccctc aggctcacat accccatgtg gaggggaaca 144960
cacatccact ccttcactca agccaagctg gccatgcagc tcagcttctg caggctcagg 145020
actgcaagct ctccagtgtg ggagtggagc taatgggagg tgaggccaag tctctgccct 145080
cacagagtct catgatgaag atctgatgaa atatttccac agtaacattt ctttggatat 145140
ataaatgtag aatatatttt gaaataatga atgatgtatc ttctgatgga ttcatgttgg 145200
ggaggcaata gaggaaaaat aaaggtaatt ttaaatttct gctcccagct acagcacttg 145260
attttgattt agtgcatgac tgtttgaaat tttttgatgc agtcaacttc agcagcccag 145320
acctggaagc ccagccaata aatgctccag attgggaaat ttaaactgat gggagctgtt 145380
tcatggagga ggaaaaatgc tgagccagtt gtgcgatcat aactattgac tggataatag 145440
aagcctgtgc cctttctgcc agtacctctg gtccgaaacc tgagctaatc accctcacca 145500
agttgagtaa acattgacac ctatactaag tacaccttca tggtggtgca tgctcatggg 145560
gccatctgga aagaaagagg ccttgtctca tcaggaaata aggacattaa acacccaata 145620
gaaatggtgt taaactacta gaggtgtgtt ctcatcctc tcatcctcca ttatgcattg 145680
ccctgagcac ccaaaagatg actcattggc acctaaagga aatcagactg cagaaaaggc 145740
tgagaagtga gcagtgcagg atgcacacct gctatgagct ttgattccac atctggagtt 145800
```

-continued

```
tccatagttc aaactccatt atactaaata gacaagaagc atgcctgcga ctggggattt   145860
ggtaaaacag atccagattt attctgaaaa actaatgctt atggattatt cttactctcc   145920
gaggccctgg tctacaattt taaaacattt acatgagggc acacactcca aatgatattc   145980
ccttgcagac tttgtatgac catgtgtcag aatggtcaga aaactgttca gaaagtcaca   146040
tacgagtgtg ttttgtgtgc caaaaatatc tttgagactg aacaaaatct tgcaacgaa    146100
gaggtacaac acagagaact gtgactcttg gaagattggc aagtggattc actcacatgc   146160
ctgtggccag tggcaactat aaattcctcc tgattgttct agatattgtt tcaagatggg   146220
tagaagcata tctcaccaag tcccaaagag ccacatgact ggctaaggca taattcaagg   146280
aaatcgttgc caggtttgga ctcccatgca ctatacacag tgacaatgat ctttctttta   146340
tttcagagtt tactcaaaag gtaagtcaag cactgcaaat cgaatggaaa ccacagtcat   146400
catggagacc acagtcagca gtaaagaaat aaaagataac accttgaaga agacaatagc   146460
caaactcagg caggaaattg acctgcgttg ggatagattt tttcttattg ccttgttctg   146520
gggcagaacg gtgccctgaa gtgggcttgg gaaaagtctc tttgaaatta tatataggag   146580
gcccttccag acctcttgcc agtaacagca cctttagagc tggtaaaaga gcccagagtt   146640
aaacaatatg tgcagattgg tgcagacctt gctaactgca catcagcttg ctatttccag   146700
gcctgtttat tccacagtga gcctcttcac cccttccatc caagagacaa gatgccacta   146760
cagtcttgta aaagtcaaaa acaagatcag cagctgactg aaaggtggaa cagacccat    146820
gatgtgctac tgattaacct tgttcagtt aagttatcca atgtaaagcc atgggtgcat    146880
cgctgttgga gaaaacctgt cccacctcaa tttgacccca gataacagac tacctggtca   146940
cataagccta aggaaaacct gaagttgctg ataaagagga gacaagaaga cagataggta   147000
ataccttct gttaatataa aattcttaat gagttctata gttataagta cattatttct    147060
ccttattaaa actaatcttt tttgctgaat gggtggaaga tggtggcttc cctgcaaaag   147120
aaaacatagt tggttctgta aagagtttgc ccatttcttc cactataggc ctgccctggc   147180
ataatacaag ctcccaacgt aagaatttat gattttccat ccattggaga agccatcttt   147240
tccatctatt ataaaaacag aagacacttc attaatatca ctcccactat aggctatgcc   147300
atatccagtg aggtaggatg gctgacagtg gtgcgaatcc aagtaattgg tcaagcactg   147360
ctatgtgtga agaaacacca cagcatactc tacactgtca ctcatgatat ggaattgttg   147420
cctccttagc aatgtaactg agcccttaat atgtggctgg gatgacaagg caatgccagc   147480
ctgcagagtg gaatctgttc ttccctctgg ggttagctac agcctgtggc actcatggct   147540
ggccctactt tccttacaac tggactaaaa gaagcaactg gatatgacct tatatcccag   147600
gatgtaactg tccaaagtgc attctctta tgtcaactgg aaaagtgtga aagacagaca    147660
ctactgacat aaacagacat cctagttgtt ctgcccacta gccagctctt cccccccaggt 147720
ggcagtcata gatttagaat tgcaagtaga ggccctggct aagcaaacca ccagtccctt   147780
taacaacacc taccatgcca tcatcattct tactgaagaa acctcacaga tttgacaagt   147840
gacactatga agctatatga ccctaggtat tgcaactaca gccaaaggta acacttgtgt   147900
attaatgaac actgaatgtt gcatatatat acaagattag tcccacaata taactcaagc   147960
tatgcaagca ttagataccc atatttctgc tagagatgga tgccctctct cagaacccca   148020
tgacagcatg gttagttga cttcctaaca catggaagag tttcatatat agtgagctg    148080
gtattctgtt cattgctatc ttcaattgct atggatttta ttgctatctt gcactttaag   148140
```

```
tgagaatgta atactgacct tctcaaaaac tcctaggtcc ttgcaccata atgctccaac  148200
aaacacctac tgtaattccg gagactccag aatatttcca actccagttt aatggattcc  148260
cttccaatac atacaaccta tgccctttct aaagaagtag ccagaatgac tatgacacat  148320
gttttccata gaaacgaaat ggaatttgac agtggggaat gatatacagg cagcttaatt  148380
tcaaaatgca ttttaaactt agtatttgag gtttttaatat tatttttttat actccctgaa  148440 acctgaaatt tcacacttac attttaattc agacttaata gcaacaaata accagaaacac  148500 atgaattgcc tgtaatctct ataccttgca ttgtaagcca catttcaagt gtaaccttac  148560
ttgtcagcac agtatgttta ccacaggcat aattgcttgt cctgactgtc cagaaggcag  148620
ggtggtatta agtatgcggc ctctggagct gggaagtctg gctttgtata ccgtctctgc  148680
cactgctaac tggaggacaa tgggccagtt acttcctgta ccccagtttt ctcatatgta  148740
aagtagggtt gttgtaagaa tgaaattagt taatatttag tacctaacaa ctaataggca  148800
ttacatggta gctattggta ttgctatcgt cagagaacac acaggagtcc attgttattt  148860
ttaccctccc cctccaaaca aaatgtgtaa gacactagac atggtagctc tgtaacgggg  148920
ttcgtcatgt attaaactgt gtacccaaat gatatgtcaa agtcctgaca accagcactt  148980
cagaacacgt ccttatttgg aaatatggta gctggagatg ttattagtga agatgaggtc  149040
ttacttgagc agggcaggcc tcaatgtgg gaagatgggt gtctttctaa gtacaaggaa  149100
atttggacac agagacagag acatacagtg tgccatatga cagcagaggc aaagatcaga  149160
gtggtgcagc agtaaaccaa tgcatgtccg ggattaccag tcacctccac aagtgaggaa  149220
agggcaagga agaattctcc tgagtctcag agggagtgca gcccagctca cacttgattt  149280
tggacttcta gtctctagaa ctgtgagaga atacagtcct gtcattttta agccacccag  149340
tttgtagtat ttcattttgg cagccctagg atattcatac agaattcttc acccaaaagg  149400
aagcactctt tcacacaaac agtcaaagtc ctggatgaca acaacctgg agactgcaaa  149460 cctccaagga atcaaaggaa gttctataaa ttctaggggc cccatctttc aaaggctgct  149520
cctcaagtcc acacccacac tttggaagga gaatcctgct cttggacatg ggatccttag  149580
tgagccaact gccaataatc caacatcgtc atgaattaaa gatctctgac atttcctctt  149640
caccaagggg aattctgtca agtagtaagt aaaacccttc ttcagtaatc tccacaccaa  149700
acagttctgc atggcttggg acgcctcagg aaacttataa tcatggcaga agaaaaacgg  149760
gaagcaaggc agtcatacat ggtggcagaa gagaggttaa acttttctgt ctctcttggg  149820
tgtaaagata taatcttgag gcaaacagca gaatcaattt tcttacgcct tgaaatagac  149880
tccacctttc tcccttcac cataaatatt cccttcacat taatctaact ttatgtttgc  149940
atcgaactat gtgccttttt ggaagttccg gaagctaatt tgagacagat agacaaagtc  150000
gggagaccct gatgcagaat tccagaggtg acttcaatgt tgctagttaa caacccaggc  150060
attgcccaga tgatgccagc ccaagatcta ggtggactgg gatgccagag agccgccaga  150120
acaagacgca cagacctggt tctcagccca aatcttgcat gcctttctta ccaacttttc  150180
cttttttaaa cccctgcctt tccttcaaaa ttcaagtggt tgcttgggat gggaatgcgg  150240
tcacttcccc tttaccatta tggttaatac aataatcttt gtaccagatc tctctcttgt  150300
taattggatc ctgcaggtgg cagattccgg accagagtga ggttagaaac tgaatgcaca  150360
tactgggtgg ttcacagaca cggtgttctg tgaagtttat gggtggattc ctggggaagc  150420
ctgcaagcct gttagtgatt agcagaaccg catccagcta ctgggatctg cacgccaggt  150480
gccgtgagcc cctcaccatg ttccctggtc ccagctgccc gcggatggtt cagccttgac  150540
```

```
aacgggctcg gtgttctggg tggtgggaga gcaaggggc cccttgggca gcgtgctaca 150600
gggctgtgaa tccaggggcc cacccggtgt tccctgtgga gtcactgagg gaatgagggg 150660
cttctcaggg cacagagctg taacgccttt gtgcagtggt ggctgaatac agtgacactg 150720
ggcgcgtggt gagaagcggg gcaaggtcag ttcactggac cctccgccct gagcctcaga 150780
tgagtcgggg gtccccagac aggcccggcc tctgccctgc ggcggacact ggagcctttg 150840
ctgtggccgc caccgaggag ccttgacctc aaagcagcgg gaacctctct acccacctcg 150900
gaaacctgaa ggcagcggcg gcctctccca gccaggacct cgccggcatc cgggtctcca 150960
ggcccaaccc tgtaccacat aaaggaagtc cccgctgagc tacccggggg acacagcgcc 151020
gttgggtggg cggcgcggc ggggcgggaa gcaccggggc agctgccaca gagatgcgcg 151080
ggggctgtcg ggaagtgggc ggtccggag acgcggggct gatgggacgt gggcggtccg 151140
gggacgcgcg ggggatggcg ggacgtcggc gatcggagat gccaggggc agctgggacg 151200 tgggcggtct ggagaggcgc ggggggcagct gagatgcagg tggtccggga cgcgcggggg 151260
ctggcgggtt gtgggcggtc cagggatgcg aggggcagc tgggacgtgg gagttccggg 151320
gacgcgtggg gtcgccagga agcggggtct aggacttaga tccgccttct cttcaggcca 151380
tgcagccccg aagctccgaa tcctgggatg actcctgtcc atgttggaag ggaccctgcc 151440
agtcctggca aggttcaaag gccttagggc aagaaatgtt agtagagtcc tggaagacga 151500
tgtgggaacg ggtagcggac accggatggt gatcgttctc ctacaagacc ttgacatgga 151560
tggggagaaa cagagaagaa ccttccaagt ttgtcccact ggacatgccc accacacttt 151620
accagccctt ttctagaagg cctgtgcgta acacatgaaa aagctccgct cgacctttcc 151680
ctgacctttt aaaagaaaac atttgctgca tctaatccgc ctagatataa ggaggttccc 151740
aaatgtatga cagagtcaga aaattacatg tcttgtaagt taccatgtgc ttgtcttttg 151800
ttttccgttt ttttttcgttt ttttgttttt tgttttgag acggagtctc actctgtcgc 151860
ccaggctgga gtgcagtggc aggatcttgg ctcactgcaa cctctgcttc ctgagtttca 151920
acaattgtgc tgcctcagcc tcccgagtag cttggattac aagtgtgcac caccacgcct 151980
ggctaatttt tgtagttttt agtagagatg gggttttgcc acgttggcca ggctggtctt 152040
gaactcctga cctcaggtga gccacccacc ttgcctctca aagtgctggg attacaggtg 152100
tgagccaccg tgcctggccg taagttacca tgtgcttttt aaaaaaatca tagcaaaggg 152160
gtgtcttctg gaaatgacat tttgaaatgg tgttattaga ccacccctgg aagggacaca 152220
gtaaccacac gtccacgttc gttcagtggg tgagaggaca tggagggag acctgggcag 152280 gaagggaaga gggttccatg ccaggctgct catatttaga agacatttc atatcattgt 152340 cattgttttc ttgtgtgcgt tttattcctc gctattgtat acatcattgg aaattctaag 152400
tattcttttg aaatatctag tctttctaga tgttctgaag tgcctgatgt atgttaaaat 152460
tacaggtggt aaaataataa attttgtaaa tatctttttg ttaaaattca tatgcagtgt 152520 tttatttat tttgatgttg gtggggggtg gggaggatga ccaaatccct gcttgatcaa 152580
cacacattgc gtttgtgctc tggttcaggg gaggagagag gaggagaaag tgcagacttc 152640
caggcctctg tgcgcaccgg gaggagagat taatgatcat ctcttctgtc tgtgtgtttg 152700
ttttatttat ctatggatat cctgtgtata aaggatgaac aagtcctatt tataacatct 152760
aatcttttca ggtgttaagt tgccagtgta tgacggaagc agcgttatta aacgaacgca 152820
gcttgtacat attgtgttaa aattcataaa aagccagtct tctgaaaaga accctgggc 152880
```

-continued

```
cctccctccg cagcctccgg cgccagctgc aggaagacct ggccagggga aggtgggtgg   152940
aacaagctgc tgctggctgt ggggaaggcg gtggagccca ggcctccaca ggttccccac   153000
aggctcccca caggctcgcg cggatctggt cgctgggttc cgcacgggcc gcgtgggggc   153060
gcctgctggg agcgaggagg cgccatcctg gctcgcctgc tccaggagga cgctctgggc   153120
ctgcgcagat gcagttctcc aggatgggcg cgggcgctgg gggccgcgct ccttgggctg   153180
ctgcgcctcc actgagccgc ctgggtgtga ggacctcacg ccggcgcctc cgggaaggac   153240
gcggagccgc cgcggccgag cccagggctg cagctgctgc ccgacgcccg cgagaaggcc   153300
cttccgccac cgcccgcggg ttcgaacttg agcagctgc tgccagctga ggcgccagcg     153360
gcgtcgggag ctcctcagag tcagtgtttt gtgctggatt cggcatgtcc tctgaaaact   153420
cgggaatttg tcactgaaat ggtgacagga ggtgagaagt ttttttagac gttgccttcg   153480
ctgaccgggc gccgggctca ggcctggaat cccagcactt gggaggccg aggcgggcgg    153540 atcgcttgag ctccggaggt ggagaagctg ccttcgtggt aactgtggtc ttaagttcag   153600
ctgagaacga taaatggctt ttccttgaat tggctgcttt tgtgatttct ctcaggctca   153660
tctttcgtca gttaaaaatc cagtggtagg tgtagcttag agacgggaaa ttttttggttt  153720 tgttttggct acacgtaagt cttggaaatt attttctttt acgttccaat gtgagcaaat   153780
ccagaaggat gtcagattaa acaccgaatt taacaaattc agccgggcac ggtggctcac   153840
gcctgtaatc ccagcacttt gagagaccga ggcgggtgga tgatgagttc aggagtttga   153900
gaacagcctg accaacatag tgaaactccg tctctactaa aaaacaaaa attagccggg    153960 cgtggttgtg cgcgcctgta atcccagcta ctcaggaggc tgaggcagga gaatcgccga   154020
gattgcgcca ctgcactcag cctgggcgac agagcgagac ttcgtctcaa aaaaacaaaa   154080
aaaaaaatca atcattggaa tactgttgtt cattacaatt aatgaacgtt tgatacacgc   154140
ataaacgcac taaattcacg agtacatata agtaaaataa gccaaaaaaa aaaaaactac   154200
atcctgtatg atgacacttt tatacattct acagaataga aactgaagtg acatgaaggt   154260
cgggagttga atggagaaaa ggtgagagaa agagggagg aaggcgttgc aagagaataa    154320
gagaaaatgt tgagggtaat tgatttgttt tctatcttaa taatggtgat ggttacatca   154380
ataatttcca aattgtacat tttgtgtgtt aattagaatt ttatattatt caagctatta   154440
caaataaata cctgtataaa tttcttaggg acggtgtaag ggagatggat aaatcacata   154500
aaaagtcaga tatttctgaa tgtacaatga ataaccctta gctctatctc tattttttgg   154560
taattctaaa atgcagcagt tttttttaat gttttatta caagaagggt ttcttcaaac    154620
cacaccaggt atgcgtaact ctgggataaa gttggctaag ggagctgtgg gatccggtgg   154680
agaggagcac aggtcccgat cctggagccc attcttgtca catgtgagct ccaggacaca   154740
tctcatagct ccctcatgct tctgggttta cattcacatc tgtaaatgga ggaccaatgg   154800
gcatctgcct ctaacaatgt attttcgtgt gttaagataa tgtatgctaa atgtttacca   154860
cagcacaatc ttttactaag aaattacatt ttttccaaat attatcattg tcttcaagcc   154920
ccaccaccca ctagaaaact tcatctgctc tgtgccttgc cctgtcctca gacatcctgc   154980
ccaagagact tctatatagt aggagacatg caaatagttc cctccctctg ctgatgaaaa   155040
ccagcccagc cttgaccctg cagctctggg agaggagctc aagtgccagg attcccaggt   155100
gttttcactt ggtgatcaga acttaacaca gaggactcac catgttgttt gggctgagct   155160
gggctttcct tgttactatt ttaagaggtg attcatgaag aactacagat attgtttgtg   155220
agtggatatt agagaaacag tggatatgtg tggcagttgc tgaccaggat ttctctgtgt   155280
```

```
ttgcaggtgt gcagtatgag gtgcagctgg tagagtcttt ttttttttttt tttttttcact  155340
ttttagcgaa catccatggg ttacaaaata atgggttggc ttttcttcca acactttaca  155400
gacaccatca attttcctct tgcttataag gttttaacca gaagaatgct gtcatcatct  155460
ttcctgttct tttagaaaga atgccccctc aactcatctc cacttgtctg catgtatttc  155520
tatttgtctt tggttttcag cagttttaat aagattcacc taaatgtgtg tgtgtgtgtc  155580
gagggtgtt atgctattgt tctgtgttct ctgagatgca tggattcacc gtttactctg  155640
tctccatttt tgtgaaaaca attagaaaaa aagtcagtgt gagcctagaa acaagcctcc  155700
ctgaagtggg cactggacca cctgggggcg ctcaggaccc actgagcaca agagccagcc  155760
ccagggcagg tgcagagggg tgttaaggtc tggtttcctg tcagccctgt ggcttcctct  155820
ccataaaaca gttccttttg tggcacatct ctggattcct tatccttttt ttcctgtgaa  155880
gtctgaagaa gaaacatttg tcgtaacaag agaaaaactt tctcatatgc accaaaggca  155940
gagtcaccta cagtcattta ctcctgtttc tgaatgtcaa taaggtgtca atgcttctga  156000
agttaatcag ctaaatctat aaaaggtgcg gtgtttaact cagcatggca gcccagctca  156060
acagaactcc aagggccagt gagcaagcag gcaggataaa gtgcatgctg ggcattgggg  156120
cagagggagt tagcatccag tgcaagagaa gaaagccccc gtggtggtca ttgtcaggac  156180
tccaagccca cagttccaat tgtaggtgat actgggcaaa ggaagagaga ccccaccaat  156240
ggttagtgtg gatttcgagt ctgatggttc cacactcaca ctccaggtga atatgaaaac  156300
atttattaac tctattttg aggtgtctgc tgagagcagc acaggcctct caagaaattt  156360
caaactggaa tttcctcagt agacaggaaa ggaggctggc tcagggcttt ataatgattt  156420
ggtggtgggg ttggggggtgc gtttctactc aggagaagga gattgtgtga tttaaacctc  156480
acagggcat cagataaggg agcttctgtg atttcttact agatttacca catgcagggg  156540
ataaggagga ggaagaataa accttaattc gtcagcaacg aggcaccaaa ataggacct  156600
gacgctttat tctccctagc agcttaagaa aatgagtgaa aaagagagag aagagtccac  156660
tatgtgtgaa aagcaaacag gtctaaagaa aataaaaatt ttattactgt aagcacataa  156720
taaaaagaaa gagaagaatg aatgagacag gcaggggtgc tgaatcaatg tcctgagtgg  156780
ggccttttca ttatccacag ttatcagtta attctgaagg tctcaggtca gcttcctgct  156840
tcaaaatatc acaggccctt acagtatatg tgaaaatcct cggtttgtcg ttcttcacta  156900
aagtagcctt ataattagat gtacttctga atttaatctt cagttgtgtt aaataaaaaa  156960
aaacacaatc tacaatttag gaaagtgaga gtttattttt atcaaggttt acagccatcc  157020
catatgctgg aaagcatagc ttttggtaaa gacgagagaa aggcactccc aggaagaagg  157080
ggttgggcag aagctttatg ctgaagggtt tggctaaaca gacataatca acaggttaca  157140
ggaggggcta ctgatgttca tggaggtggt cctcacacat gcatactgaa caaacatgtc  157200
tgtaacgtat gaccccctgtt cacttaccag tggagactta gcatttaaat tcattacagt  157260
caggccctat gtgccaatag cagaagcaga aacacaaagg cactcagggt gcagcctctg  157320
taaacggcca gagccaggcc atggtgagtg gtctctgatc aggagaaagg tcctgatatc  157380
actctagtgt tcaatcaaag ctggggttat ggcttgtgga acaggggtca gttcatcagg  157440
ggatgggctg caattgtctt catagtgctt gtctcagtgc cggtgcttac tgagccgcta  157500
gagaaaacga ataacctatt ggcagttaga agacagttta ccttttaagt gtgggagtga  157560
gtggcagaac ccttgcctga catggcttta ggtcttgttt ataatttgac atcttattgc  157620
```

```
cacagagatt ctgttctgtc attcttttgg atctctattt taacattagt gttggtcatt 157680
gttgtgtcta aaccgcaaag gggagtgagt gtaagaggcg cgtctgatct tgtcatggct 157740
gggatctcag tttttaggct tttctggagt cccttagatg aacagatgga ctatttagtc 157800
agttggggca cttaggattt tattttgtt ttacagttca taaatatgaa ccctagtatt 157860
gacattgtgc atattcactg ctgtgttgtg gttaaaatta cctggtaaga ttcccttcaa 157920
agccgttcaa gagcaatatc ctaccctgat gtttcttcca gtaaatacca ttccctgttt 157980
taatgtcatt agaggctatt gaaagatgt aggaaaatga tagcttaatc tgtcgatgac 158040
tggagtgggt aagatacagt catcactttc aatgctttgt catgcgtgca tgtaatagga 158100
agaggtgagc tctgggggaa aatctctaaa tgtatgggcc ttccagccac caaatcataa 158160
ggtgatgact gatgtctcac tgagggactt gactataatg ctctagtgct agggagagaa 158220
actttggcca aggaagttca agattttctt aaggtttgga caagtttagt tcaagtatga 158280
caattttctt caacattttc agaagattgt ggatgggaat gatgctgagt tatataagta 158340
attctaatgc cttctgtgtt tagataatat tataaacaag actgtttggg tataatgacc 158400
cactacaata tatatacttt tagttgttac accatttcat tttcctttag gattttactt 158460
tctaagttac atgaatcagg tccctaaaat ataggcgtgc atctaaaatt tattctttgg 158520
tgagaatttt tacgtgttcc agaagatatg agaaacttct ttgcgtgaag agcatcccaa 158580
agtcaggcac tcctgtaaaa catgtactta atccttgtct ttggcttatt gatgagctct 158640
gttgaccaca ataaaacttc tgtcatgcgg gctgacttga catcaggtag aggaacagat 158700
tctgaatgta ctactgaatt gagtgcataa cctccagttt cgttactgat gtatgattca 158760
tcagagatga tactagatca aggatttcaa tcggaatcta atctaaaaga tgtgaataaa 158820
ctttcctaat ttagatagta ttacttgtga gcacactgct agtattccag ccatgtctcc 158880
tgtctgtcac actgaattca cgctaacttt gatctaaaag ttaacacttg ttctaatgtt 158940
caaatatgtt attttattc taatgtctct agattattat ctgtggctat tttaggcaag 159000
agtgaaggaa agcaaggtta actgactaaa aatgagaaaa agcacaacct aatgtaatgg 159060
aagtcaggac atcagcatct ccaggcttgt ctatttctag agttcatgca accagggat 159120 ttctttctc attttacac aaagaaacac ccaaattgtc catttcatct cccattgact 159180
cttatcatct gtctctgtca gtttgcttag aattttggcc tccagcttaa tccaagttgc 159240
tgcaaaaaca tgatttcatt cattttaca gctgcatggt attccactgt gtataagtac 159300
cacgttttct ttttttcagtc tgtaactgat cggcatttag tttcattata tgtctttggt 159360
actgtgaata gcacagtgat acacacgtga gttgatgtgt cttttttgttc caatgattgg 159420 tttttctcttg gacatatacc cagcaatgag attgctgagg ggaatggtag ctctgtttta 159480
aattctttga gaaatctcca gattgatttc atcagtctct tgggccaaat tatatttcca 159540
ccaaaagtgt gtaagtggtc cgttatctct atagccttgc ctgcatctgt taatttctga 159600
tctttcagtg atagcaattc tgacatatgt gagaaagtat atcatttggt tttgattcgc 159660
acttatctga tgactgaata tgctgagcat ttttataggt tagttggcca cttctatgtg 159720
tgtatttgag aagtttctgt gcatgtcctt tctccatttc taatgggggtt atttggttta 159780 tgctggtgat taagttccct atgaattacc accttacaca cactaagata atcagcattc 159840
aaaaaagaaa aatgaataga aaacataac cacttgtagg tatagacata ctgaatttgg 159900
aatggtcatg gcttgcatgt tggtattgaa atggacagc aactttggaa aatggtcttc 159960
acagaaaacc tcataaatgt agctagtgtc accactcaca gaagtagatg gagaatacaa 160020
```

```
ctcaagtgtc catcgactgc cagagggatg aagacgccgc ggtgcgtctg taacccacag  160080
ggatgaagac gccgcggtgc gtctgtgcat ctgtaaccca cagggatgaa gacgccgcgg  160140
tgcgtctgta acccacaggg atgaagacgc cgcggtgcgt ctgtaaccca cagggatgaa  160200
gacgctgtgg tgctttaaaa aggagtgaag cactgacata ggctgcaact cggatgggcc  160260
ttgtaaacat tgggtgagtg aactgaggga gacacggaag tctacatcct gaattgtcct  160320
attgacatga agtatgcaga ggaggaaaat ccctagagac agatcacagg gggtgagtgg  160380
aggggaaatg gagagtgacg cttaatggag ctgaggtttt cttttctgtg atgaaaatgt  160440
tcccaaacca aatactggtg atatttgcac aacattgcaa atgtgtaaag tatcactgac  160500
ccgtacactt aatcgtggct aaaattgtaa attttatgtc atgtgtatct caacacaata  160560
gaaatgagca ccacttttg tttagtgact caacaacaat aacatttagg tttaaattct  160620
ggattcccca acagaaccag tgcttcctgc tggagctgga tccatcagcc cccagggaag  160680
ggatggagtg ggtcaggtgc acaggtcatg aagggagcac aaattctaac ccactcctca  160740
agagtccagt caccacctcc agatctatgt ccaaaaacag ctcttcgtat ggctgagtga  160800
cattagcaac aagcacacag ccatgtttgt ttttttgttt tgtttggtg tgtgtgtgtg  160860 tgttttgat agagtcttgt gtcacccagg ctggagtgca gtggggcaat caatcttggc  160920
tcactacgag ctccacctcc tgggttcaag tgattctcca gcctcagcct caagtagct  160980 tggactgcag gcactcacca ccacacctgg ctaatttttg tattttagt agagacaggg  161040 tttcactatg ttggccaggc tggtcttgaa ctcctgacct tctgatccac ccgactcggc  161100
ctccaaaagt gctgggatta caggtataag ccactgtgcc cagccacaaa caagtatttt  161160
taagcaaaag acacagtgaa gagacttcag tatgagccca cacacaaacc ttcctgtggg  161220
agtttacaga acagcagtgg gtgctgagga cagaagccag cacccaggaa ccagcaggga  161280
aacccagggg gcatttggca ccgcctgaag gctcaggacc attgtggggc tcagtggtca  161340
ggcaggctca aggttcagcc tcagagcagg tgtagcaggg ggcgaaaggc tctgaagacg  161400
gagtttagtg tcaccttctc atttccacta ctaaacaccc tccagcacat ctattctaat  161460
gtgtatgggt gttcatgtgt ttagagaata ttatttatgt tatgaatcta tagccatctt  161520
gtgggtgcat caagttaacc tcttcaacct atgtggaccc tgttcattag gaataagtcc  161580
ctgtatttga ggacctcaca aattaataat tatgtagaat cactttcttt ttcagtctcc  161640
tttccttcct ctttctttct ttctcactca cacactgaca aacacacggg gtgccataac  161700
attaattacc tgatgtatta aagaatattg attcatttgc aacttgacca gtttagctgt  161760
tgttcatgtt gttgtaagat caggaacatg tttctcagct gtgtactcct ctaagctgag  161820
cagcagcttt atttgaaata cacagaaact gaaaacaatc caaatattaa tcagcacctt  161880
cataagtaaa caaattgtgg aaaagtcgtt tattgggata gtacccacta ctacaatcag  161940
taaatgttgg atacgatcaa cagcatggtt caattcacaa gtacatatga tgagtatagt  162000
gagccaaagc acatacatat gattccgttt tataaactgt acaaagtgaa tactcattgg  162060
aaattacata acaaagatca ctaactgact tctccatagt aagagaagcg aaggtatagg  162120
agggagaaat tgtgagagac aaagagaaaa ttgagaggcg aattgatttg ttttctctgt  162180
gaatggtcat taggtcaatg tttgtcaaat ggtgaacata ttgtgtgaag attatatgtc  162240
tgtattactt cattaaagct attataaata aaagtctaat gtggtagaaa aagatgaaga  162300
gagaaataaa aataatacaa gaaaagtcat gaactcctga atgaattaac ccttagtttt  162360
```

```
tctctattac ttataaaaac accaagatac agccaaataa tatcacgata tcattataag 162420
aagagtgttt tgtaaacctc actgggaatt tatagctctt tcctagagtt aattttggga 162480
acagttggat ccaattgtga gaaatgcagg ctggacactg agactggctc ttatgagatg 162540
tgagctcttg tctatgtcac atggtccttc catacttggg ggtttacatt cacatctgta 162600
aatgaaggaa acattgactc tcaaagaaca tatttcatgt gcatgtaaaa gtatgaatgc 162660
tagtgagaat taattactta tgaagtataa tcacccacat ccactcttgg acacagccca 162720
ctctgaggca tctgttacag aactcattat atagtaggag acatgcaaat agggtcctcc 162780
ctctgctgat gaaaaccagc ccagccctga ccctgcagct ctgggagagg agccccagcc 162840
ctgagattcc caggtgtttc cattcggtga tcagcactga acacagagaa cgcaccatgg 162900
agtttggact gagctgggtt tccttgttg ctattttaaa aggtgattca tggataaata 162960
gagatgttga gtgtgagtga acatgagtga gagaaacagt ggatatgtgt ggcagtgtct 163020
gaccagggtg tctctgtgtt tgcaggtgtc cagtgtgaag tgcagctggt ggagtctggg 163080
ggagtcgtgg tacagcctgg ggggtccctg agactctcct gtgcagcctc tggattcacc 163140
tttgatgatt ataccatgca ctgggtccgt caagctccgg ggaagggtct ggagtgggtc 163200
tctcttatta gttgggatgg tggtagcaca tactatgcag actctgtgaa gggccgattc 163260
accatctcca gagacaacag caaaaactcc ctgtatctgc aaatgaacag tctgagaact 163320
gaggacaccg ccttgtatta ctgtgcaaaa gatacacagt gaggggaagt cagcgagagc 163380
ccagacaaaa acctcgctgc aggaagacag gaggggcctg ggctgcagag gccactcaag 163440
acacactgag catagggtta actctgggac aagttgctca ggaaggttaa gagctggttt 163500
cctttcagag tcttcacaat ttctccatct aacagtttcc ccaggaaccc tgtctagatc 163560
tgtgatctgg atctgctgaa actgcctgtg tcaccttcct cacctgtgac tattggggga 163620
gctgattgtg gacactccag tgtgtgggat ttcttggtga cagcaattgt gtcttctgtc 163680
tagccatgtc tagggctgcc catcaggaag gtcaggctgg aatttttgga aagaggcgca 163740
cctgccatcc accaggaaat tttgttgtct tttgttctgc tagaactaaa tcagacacac 163800
caaggttaac tagcactatc ttcctagctt gagaaacttg atggcaggct tgaataacac 163860
ctgtatgaag ccatcagagc aacaactaga ttaatgtctg ctagaattaa atcaggcaca 163920
ccaaggttaa ctagcactat cttcctagct cgagaaactt gatagcaggc ttgaataaca 163980
cttgtatgaa accatcagag caacacctag aatagtgtct gatttaataa ttgagactat 164040
ggtctagcca aggagacaca taaaacatga tttccatggt tggttcatat tttatattta 164100
ttaatagaat ctggctggta ttataaacag cttttgccaaa atatatgtgt tagtgttggt 164160
cttcggagaa gcaaactctg tgactggatt agcttcgtgt acagtttcct tcgtgtacag 164220
tttccctgtc cactcttctg agaggaaatg cagaggtggt ggaagggtc tggggtagct 164280 gaatgcatat gagggaagtc ggtccctgag tgaaggagaa agggaggagg actgggtgga 164340
actttcctaa acttctttgt tgttctatga aggtccagca aggtcactga atcagagtcg 164400
tgtcacagtt cccatcaggg acccagtgac tcccagcagt ggctctgctc agatcagcgc 164460
agagcttgtt cgtctcctga gagtggagca caggacgtgg ctccaacacc agccatggca 164520
tggaagacag agagcagccc tgggtgcctg ggtcaggtgc attgtgctcc ctgcaggtgg 164580
agggagggaa gtgctgactc agggcccaga gactgtgggt tctatacaga acatacactt 164640
ttacttcatt tctgtggatg acatagaaac aaacatgcag tctgtaaaca atggtgattc 164700
ctacatttgc cccaattgct ttattcctta attctgcaga atgtcctggc acagaattgc 164760
```

```
ctttctcatg tggaattgtg tcgtgtgttg tggatgtgtg agccctactt tcattgtttt   164820
cccccatgta cagagctcct aaatagagaa cagctgaccc tccttctaca ctgttgctct   164880
cctccccaca gagagagcac ataattacct gaggctgaat ctgaggtggg atctgtcctc   164940
tgaacctcag agcctgcaga gaccccagc  tgcagattca tggagtcagg tgtttgtaca   165000
tgtgggaacc ttgagctgtt cttttgtcag tgaacactcc ttaaaactaa ttgtgggttc   165060
agaattagga cacccattga tctatcacac ctcagctcat tctgccactc agaatctcca   165120
gaaattcagg aaatggttga atgtacattt ttgtgacaaa ttttctcat  ttcacttagt   165180 tgtgagtttg gttagcagaa agtgctacca tttatgggtc ccaaactgat gaagctcatt   165240
tgcttcaaca gaagttagga ggctcctaaa acttctcatc agcccttctc tctgcacttc   165300
atgtgaaatt cagttttacc tggaattctg gtgtgttggt ttagccagag ttccccatcc   165360
tccatgtctg atttcctgg  gtatctgatc agtttccttg cccttcacca tacctcggtg   165420
acgtctaatc accctggccc aacatcaaga attctggcag gttggtttaa gcaagatttg   165480
ctgtgcccct gatgtttcct ctcagtaatt ttccatcttc cggacccac  cctgctgctt   165540 ggctttaaat cccccatgtt tccattctgc atttggagtt cagctgaatc tctctcctca   165600
ctgcaaaaca ccattgccct gatcccgaca cctaccatga ggaccctgga taaagtcttc   165660
cttactgtgc tggaacaagt gtctttactt gatattttt  ctttaataaa tctacccttta  165720 gtgcttccta aattgctcaa ggaacctcga aaaataagat aagtgcgatt atccatttta   165780
ctgtgtgtgt atgtgtgaat ttcaatttcc atgtgtggtg tccagaagtc ctgagcacaa   165840
acagttttgc ttctctgtcc aattctttgc ttctgaaagc caggagtcat cccaacattg   165900
gtaaattggc gatttgtttt tactatttag tgactgacat atttcactta acctgaagct   165960
tcatgaacac attgatgaaa agtagataga agacttgttt ggaaatgcca gatttagggt   166020
agactttacc acccacgtgt gtctggagat ctccttagga ttccaagaac agggtggttt   166080
ttttccacca caggacaagg atgagaacct ccaagctgtg atgataaagg acaggcaggg   166140
ccatgtgtgg acaaggatgg gctgctgcca cgtccagagt gttctctcct agcaacgccg   166200
ccatctcctt cctcacactg tggtatttgt cagatgggaa acatgcctag aatttatctt   166260
tgacatatgg atggaagccc aggctagagg catttgacag cttatttctg aacctacttc   166320
tttaaggaat gcccagatcc cttgctctgc ttcctggttc ttaacccctt tagctcccttt  166380 ccgctcctgc acccatgcac tgcctctta  cggccacttc cccacaccct tcactgtagc   166440
accattttct tgggctcctt ggaaatatca cagctttggt ttaactcaca gatcaggcac   166500
actcatgggc ccctccagag gttctcgatt tccctccctc aggctcctcc ctggggtcct   166560
aacttggcca tctctatcct ctcttctgag cctggccatc cacaatccat cccatctgga   166620
cttgtgtata gcactgggtt aactcagcag gtatgaattg ttcaaaccct gcacattcct   166680
aaaaaataac taaaaaaaaa aaacttttg  ttcatttatt gctgttacct actgtgatga   166740
gatctccgag tccataaaat attgcacctg ataacagtgt ctgtggatgt ctgtagcctt   166800
gggacatgcg gtacaagttt aatcagtgat ttatagtgaa tgtctacttt tgttttgctg   166860
gagagggctg tcgtctgagt attgtggtca gttcccagg  tgttccatag tctatgattc   166920
attccccaaa cacagccctg gacaagagag ctcagcggca ctcccttgt  tgtcaacact   166980 tcacacaagc catcttacct cacagctgaa caattacaca tgtgtagaag gctccactgt   167040
gagaggacac ctgagagctt gtgcctggat tctccagggc ttcactcctt gtgccttttg   167100
```

```
tctttactta ttttaaattg tatcattttt ctgtaataaa ctgttcctgt gaatagaaca    167160
gttatgagtc ctgtgttttt actgatttt cagcctacag gtggcagatg agaactctca    167220
acacagttgt gttagaagaa ggatttccta gagagaccct gactcaatga tgatacatgg    167280
ctgaagcatt gcatggaaaa cgtaagtgtt caggtatgga atggcaaaat ttgatacctg    167340
gggagtgaca gaatactaca gtctattaca gcagctgagc tgaaatcggt ttctggaggt    167400
aaatgggatt tagaaattat aaatccaact cccaaggagc tggctcaatc aatacataat    167460
gaaatgtgaa atgattagaa atagcctaaa tatgcaattt ccatctgtga gagctaagtg    167520
aaaatccagg agagagttgg cagggagagg gatactgcac caacctcaga ttttgaccat    167580
tttcatttag ggctgatggg ctcatgacca ctagagttag caattacact gtgataaaag    167640
ataaaagctt cacaaactct acccacccag aaggggctc aggtggtgaa atagggaggg    167700
taaggcatga aacgactgaa atatgggagg atagtgagat gggttctctc ttttgagtt    167760 ttatcttttg cttctttact aattttgtt aatctggatt tggagaatga ctagtgtaaa    167820
agtggattct gttttgagtc ccttagaatg gaggagaatg tgtgggccaa tgttgtgccc    167880
agagactact acagaacaat agtagatgaa tgtacatgac ccaaacacaa agctttgtgg    167940
ttgctgatgg gagagctgca ctgccctggc ctactgaata cagcttctc caaagtgtat    168000 ttaccctgac aatggagatt gcctttctct tttaagtgaa aaaatggaa cactacaata    168060 aagtagtggt aatgctgtgt gtgtatgtat aagcattct ggagtgggtt tgtgataatt    168120
gggatatgta tcacttatcc ttttatttgt ataaattat ggggtgaaag tgccgttttg    168180
ttacatggat atattgttga gggataaaat ctgggctttg agtatagcca tcatctggat    168240
ggtgtatatt gtacccatta agtaacttct catcccacat gccactccca ccctcccaac    168300
cttccaagtc tccaatattt cttattccac actctgtatc catgtgtaca tattatttag    168360
ctctcactta tatatgacat gtggtattca actttattct tctgagttct ttaacttaag    168420
atagtggcct acagtttcat ccatgctact ggaaaataca taatttcatt ccttgtctat    168480
tattgagtag taattaaatg tgtatatgta catacacatg tatagtgtgt gtatgtgtgg    168540
ggatgtgtgt gtacatatat gtatatgtat gaacatatac gactgtttcc tttatctaat    168600
catttactaa tagaaactta gtttggtacc atgtatttgc tattgtgaat agagcagcaa    168660
taaacatata aatgcaggca tctatctgat ataataattt atcttccctt gggtagatac    168720
ccagtagtgg gactgctgaa tgaaatatta gttccaatat taattatttg caaaatctcc    168780
atactgtttt ccatagagct tatagtaatt tacatttcca ctagcagtgt ataagcactc    168840
ctgcttctct gcatccttac tagcatctgt tttttgtttt gttccatttt tcttttgac    168900 tgttttaata gtagcttttc tgactggtat aagatggtat ctcactgtgt ctttaaattg    168960
catttttctg atgattaatg tcattgatta tttttcata tgctggttga tgattttttt    169020
gtcttttgaa aaataaacat tgtagtaatt tgctcatttt taatgtggtt atttgtgggt    169080
ttttgtgttg cttttgttc ttgtagtttg taaatattag ctctttgtca gatacagagt    169140
ttaaaaatag tttatcccat tctgtacgct ttcggttaag ttttttgatt atttgttttg    169200
ctgttcagat gctttgcttc ttatttgtat aagtccaaa tggtctattt cggttttat    169260 tgtttacttt taaggttgta gtcatgaatt ctttgcctag acaatctcc agaacaatat    169320 ttcctagaat agcatctgca actttcgac tctcaggtct cccagttaag tcttttatcc    169380
atattggctt aattttggat atagtgagag atacgggtcc agtttattc tgctgcaaat    169440 ggctgttcag ttttcctgc acaatttata taacaaggtg acctgttccc agtgtatgct    169500
```

-continued

```
tcttgtctag ttttccacag tcagtttggc tgcaggcatt tgactttatt tatgaaatgt    169560
ctattctgtt ccactcatct atggctttct gctagattgt tacttgattg ttacttgtgt    169620
ataataatgc tactgggtttt tgtatgcttt tttcatttat tctaaaactt tactgaatta    169680
actcatcaat tctaggagta ttttgaaaga atattagttt ttttaagtac aaaatcatat    169740
tatcagcaaa cacaaagagt ttgacttcct cttttccaat ttgagtgcct ttatttcttt    169800
ctcttgccta atttctctgg ctaggatttc aagttccata ttgattaaga gtggtgaaag    169860
tgggcatcct tgacgtgttc tgagtcttag gaggaatact ttcaacatat tcctattcag    169920
tataatgttg tttcggagtt tgaaggtgat ttatggagaa tgagagatgt tgagtgcgag    169980
tggacatgag tgagagaaac agtagatatg tgtggccgtt tctgaccagg gtgtctctgt    170040
gtttgcaggc gtccagcgtg aggcgcagct ggtggagtct ggggagggct tggtacagcc    170100
tgggtgggtc cccgagactc tcatttgcag cttctagatt caccttcagt gacttctgaa    170160
tgcactggat ccgccaggct tctgggaaag ggctggagtg ggttggccgt attagaacca    170220
aacgtaacag ttacacgaca gaatgcgctg catctgtgaa aggcaggttc accatctcaa    170280
gagatgattc aaagaacaca ctgtatctgc aagtgaatac cctgaaaacc gagtacacgg    170340
ccatctatta ctgtactaga gacagtgagg gggaggttaa cgtaggccca tacacaaatc    170400
tccctgcagg ggcgcgcagg gccaactggg ggcgctcggg acccactgag gatgggacag    170460
gtcccagggg cgggtgcagg gggaggtttc cttctcagc tgcaggaggc gggtttgttt    170520
ttgcaggaat atggagtctt atgaggtttt gatattttac tatggttatt tatcatgatt    170580
ttttaaaatt gggatttgtg ttttagtaat ttttaaattt atatgtaggg gtatttttaa    170640
aaattaagtt ttagggtaca tgtgcacaac gtgcaggttt gttacatatg tatacatgtg    170700
ccatgttggt gtgctgcacc cattaactcg tcacttaaca ttaggtatat ctcctaatgc    170760
tatccctccc ccctcccccc acctcacaac aggcccggt gtgtgttccc cttcctgtgt    170820
ccatgtgttc tcattgttca attcccacct atgagtgaga gcatgcggtg tttagttttt    170880
tgtgattgca atagtttgct gagaatgatg gtttccagct tcatccatgt ccctacaaag    170940
gacatgaact tatcattttt tatggctgca tagtattcca tggtgtatat gtgccacatt    171000
ttcttagtcc agtctatcat tgttggacat ttgggttggt tccaagtttt tgctattgtg    171060
aatagtgcca caataaacat atgtgtgcat gtgtctttat agcagcatga tttataatcc    171120
tttgggtata tacccagtaa tgggattgct gggtcaaatg gttatttcta gttcaagatc    171180
cctgtggaat cgccacactg acttccacaa tggttgaact agtttatagt cccaccaaca    171240
gtgtaaaagt gttccctatt tctccacatc ctctccagca cctgttgttt cctgacctt    171300
taatgattgc cattctaact ggtgtgagat ggtatctcat tgtggttttg atttgcattt    171360
ctctgtaccc taaaacttaa agaataaaaa aaatccttca aaataattc ttcctaataa    171420
tatgcactta ttctcctagg ttgtattaac atctgttgat atcttcaact acatagctat    171480
ggcgacatta atttacatct gtagacatat gtgtaaatac acaaacttat gcatacatgt    171540
ctagtctttt atatttaata taataaaatc attataaaat atgtcctaat gaatgaaact    171600
taatgattaa ctaaatataa attatagtaa tccattattc attgcaatga ttctctatag    171660
tttacataaa ttggtatcta tttgtaagct taaatatagt gtattggtca ttttaaaatg    171720
gccaagaaca aatttcaaat gtccctgtca cacaaacaca cacaataagg atttgaggat    171780
ttgagttgat atatatgtca attagctaga ttcagttatt ccatattgca ttcataaatc    171840
```

```
ataacatagc tttgcactct ataaatacat agtcaaaatt tctcaatttt caatgaaatt 171900
ttaattatac atttttttaat ccgtcctagg tcatgatttt tttctccctg tcaggatatg 171960
attagattgt cctgagaaac tcattcagcc tcctgcctcc tgaaggcttc aaaggcttca 172020
ggaagtaagc tcctggatgg gcagaagcag gcaaatcttt catgtgcaca ggacctggag 172080
catctctctt tggattaagc cccctcctca ggattacagg gctcttcatt tttctcaaca 172140
ggctgttgta ccagataagc acaaaaactt aatttcatta tgctttgctt ttttttaaaaa 172200 aaaaaatga aggtaataat tttaacaata aacatattac aacctgctac acatgagacc 172260
cttcttgtgc ttcgaccttt cttctcagga gtttatatgt attacatata ttcagttttt 172320
ttctgagttg gaatgcttat tacagattat tccccttatt acagattact cttttaatttt 172380 atctcttaga atgattttttc gagagcccct gcctgcccgc gcctggtgga atggagcaga 172440
gcctgggctg agccaggcgc gcaggggcct ccgcacgtgc cgcgccggta gcagacgcca 172500
agcgggcgga cagtgagcgt gagaggccgg ctcggagtgg ccgccggagc agtgccgggg 172560
atggaagaac agcccatctt caccaccgga gcacaggtct tccagattga ccccaacacc 172620
aaaaagcact ggatgcctgc gagcaacagg cggccaccgt ttcttacttc tatgatgtca 172680
caaggaacat ctatgggatc gtcagtgtgg acggagccaa ggtgaccata aacagcacaa 172740
tcacaccgaa tatgaccttc accaatgtgt cacagacgtc tgggcagtgg gccgacagca 172800
gagccaacac ggtgtttggt ttggggttttt cctctgagca gcagctgaca aagttttcag 172860
agaaattcca ggaggtggag gaagcggcca agacagccaa agacaagacc caggagaaca 172920
tggagccctc gagtaataat cccgagaatc cgggcatgga gccccatctt ctactccggc 172980
atccagtgtc aacgggacgg acgatgaaag gcctctcagg ccgctgcagc tgacacgcac 173040
ctgcagtctg ggaaccacaa gctgaaggcg gcctcgacgc aaagagctgc ccacgggaag 173100
aggtgggaga tggagctgca gacccggcgg gagagcgacg cccggctgcc cacggcgctg 173160
caggagtcgg tggccagcgt ggagcagagg aagaggccgt gagatccaca gagaggagaa 173220
gaacacgcag ctgaagagga agatagagga gctggaggcg gagctccgag aaaacgagaa 173280
agagtggaag tccccaaaag caaagtaaaa ctactcctca gctcaggtga gtgcaactgt 173340
gtctctgaga agatggaggc ggcagagaga ggatcaaacc ctggaagaca aagtgcgttc 173400
cctgaagaga gacactgagg agagcaaatc cagacagcgc cacctggggg tggaggtgaa 173460
gagtttcccg gaggtgctgg accggaagat ccacaacctg cctgacttcc gcccaggcct 173520
tgcatactgt gcaccaataa ctagggctgg ccgaggccca ggcccctcct gtgagtccca 173580
agcgtgtgtg cgagaccaga tggcgctagg acgttccctg tgtgcgttgc ttctgtaaat 173640
gcaggcgcag tttcttgtat ttccaaacca actgtgccgt ctactcaccc cttcccagaa 173700
tagaaatctc ttgtccaggc acagtgtctc acgcctgtaa tcccagcact tgggaggtc 173760 gaagcgcggg aggatcacga ggtcaggaga ccgagagcat cttggccaac atggtgaaac 173820
cctccctgtc tgtactaaaa aaccaaaaat tagccaggct tggtggcaag cacctgtagt 173880
cccacctact tgggaggctg gtgcagggga atcgcttgaa ccaggagaga gagtttgctg 173940
tgagccgaga tcgcaccact gtcctccagc ctgggcaaca gagcgagact ccatctccaa 174000
aaaaaaaaaa aaaaaggaa aagaaaattt cctctcgctt ctctggcctt gtgaggttgt 174060
ggacaactgg aagattttga ctcaggaatc cagaactagg tctaccttca acatttacac 174120
agtcaggcca gggatgttta tattttttcat aagggctgtt gaaaccatat gaactgaaaa 174180
aaagcacttt ctaatccaaa tattgatatt ctttacacca ggtcatcggg ctccttttat 174240
```

```
cgaatagcat tcagggtatt tgaatgtcca tcaggcgcca ggcccagggg gcacagggag   174300
aacaacattc ctctccgtca ataacgagag gctttaaaac aactgtttag tggagactta   174360
tcgagatgcc aaacaggttt ctggtgggta cattttctgg cctggggatc acctgcatcc   174420
acgatattgc cctctgcccc ccagtttgta tggttgcgac aatgttcctt ttcttggttt   174480
taatttctga gcggatgatt gtggtgcggg aacagcacac agtgagggtg cctagcacaa   174540
tgcctggtgc aaagtaggtt ttttataaac gtttgtgcgg ctcacacctg taatcccagc   174600
aatttgggag gctgaagcag gcggatcacc tggggtcggg agttcgagac cagcctgacc   174660
aacatggaga aacctcatct ttactaaaaa tatgaaaaaa aaaatagccg ggagtggtgc   174720
atgcctttaa tctcagctac tcgggaggct gaggcaggag aatcacttga taccgggagg   174780
cagaggttgc agtgagtgga gatcgtgcca ttgcactcca gcctgggcaa caaaagtgaa   174840
attccgtctc aaaaaaattt ttttctaaag ccccactcaa aaccagggta ttattagcag   174900
tgtaatagtt gggccacagt tgaaaataca ttcaattcag ttcatgtgct ctcaaatatc   174960 cttttttcctt ttaaagttgt tctcagttgt aatattactc aaaatattag taatttatac   175020
taatgacaca ggttacaata ttgtatacat aatttagtga catttgattg gaaaaaatac   175080
atgttcccca tgtcttgagt atttttttcct tctctataaa atgtatgctt ataattattt   175140
aagtttcaga tgctagcatt atcttttttga tatctgggat ttaatttttag taggtatact   175200 ggaatgcctt ttattaattc atataataat gttcatattt tagataggat tttaatatta   175260
attttactat ttactgaatt tcaaactttt ctactttttt tgttttttatg agataaaatt   175320 cacacataag aaaaaatgca tagatctgaa atgtgtcact agagagtttc tggcaaatgt   175380
gaataccttt gtccccagca cctaaggtag cctgaagagc aagtctctcc ccaaaacatg   175440 cgtcttttc tatgcctgtg gtcaaatcct gcatgggggaa aggtttcgat ttctgacact   175500
atagatgtat tttattctgc tttgaacttt atataaatgg aatcaaacat tatagactttt   175560 ttttggtaag gggctacttt tctatttttg aggttaattc atgctagcta atgtataaaa   175620
ttagatcaac atattgtcgt ttattcaatt catagacaga ctgtgatatg aaccaccaaa   175680
attttcatgt acatggagag agagagagag aaagagagga agcagagata ttttatatct   175740
gagtcagtcc attaagtaaa taatgacaa tattttcatt tattttatg tcagtggact   175800 ttaaatttgt gtccagttta tgaatattat atgcagagct gttacaaata tcttagtgta   175860
agttttctga tgttctattt ttattgagaa aatatgaagt atgtatttct ttattctaag   175920
agtaagttta attttttttca gtggtattga ggcataattg aaatattttt ataatatata   175980
tgtttaaggt gcaccaattg atgttttgat attgtattag tccattctaa cactgctata   176040
aagaaatgcc tgaggctgag gtgggcggat cacgaggtca ggagatcgag accatcctgg   176100
ctaacacggt gaaaccccgt ctctactaaa aaaaccaaaa gttaactggg cgtggtggca   176160
ggtgcctgta gtcccagtac tccggaggct gaggcaggag aatggcgtga acctgggagg   176220
tggagctttc agtgagctga gattgcacca ctgcactcca ctccagcctg ggcgacagag   176280
cgaaactctg tcaaaaaaaa aaaaaaaaaa aaaaaaaaaa aaaaaaaaaa aaaaaaagct   176340
tgacactgag taatttggaa aaaaaaaaag atgtaagatg tttaattgac ttgtgagaac   176400
tcaactcatg cattgtcatg aaaacagcac caggagtcag ttctaaacca ttcatgaagg   176460
acccacgcca tgacccagtc acctccaacc aggtcacact tccacaattg aggattataa   176520
tacgacgtga gatttgggt aggacacaga tccaaagcat atcagatata cattgtaaaa   176580
```

```
tgctcatcat agtcaaggta atttgcatat ccatcttctc acagagctac cgtttaatttt  176640
tttttaaatg tagagcttgt gtgtgtatgt gtgtctgata acaacaccta agacctactc  176700
ttagcaaaaa tcacttttac aatatagtat taaatacagg aacattgctg tgcattagat  176760
ctccagaaat gattcagctt gcacaactga aactctgtgc cctttgaccg atatcaccca  176820
atttccctct cctcccaggt cgtgggaccc agtactctac tcgctgctat caagaacttg  176880
gatattttag atcctacatg cagatgacat cgtgaagcat ttgtctttcg gcatctggct  176940
tattccactt agcaccatgt cctctagctc catccgtgtt gttgcaaatg tcagaatttc  177000
cttttttttt ttgaaagcca aatgaaattc agtttatata tatacatttt ctttatacag  177060
tcatcaatct atggtcatta aattctttca caaatctaca ctattataaa taatcttgca  177120
attaacatgt atttgacatc ataatttat ttcctttgac gatataacaa gaagtgggat  177180
caccaggtca tatgatagct ttattttca atttattgac taaccaatct taccatacga  177240
tataaggata ccctcttcac cacattcttg ccaacatttg ttatcttttg tcttgctgat  177300
aataaccatt ttaagtggtg tgaggtgata tctcattggg cttttatttt gaattcccct  177360
gataattagg aatgttgagt acctttttag gatctgtttt tcatctgtgg gtcttctgaa  177420
aaaaaatcta accaggtttt tgccctctgt attaggtcag ttgatatttg ctgttgagtt  177480
gtatggttaa tttatatatt tgggtggaac ttcttgttag atatataatt gcacatagtt  177540
ttttttactg tgcttgcttt tggtattaaa ttcaaataat ttctgaatca atgacgaata  177600
tttttccatg ttgtctatga tttatggttt caggttatgt tcattttag ttgattttg  177660
tatatggtgt tagagaaggt ctagtttcat ttcattttt ttttgcacat gcatgaccat  177720
tttctacacc attgattgag gagactgtcc tttcttcact gtgtgttctt ggcatacaaa  177780
attaggaaga cacataatta aaaaagaaaa catcagatga atattcctgg tgaacataga  177840
cctaaaagtt ctgagcaaaa tactagcaaa tagaatccag aagcacttta aatgtgata  177900
catcatgatc aagtaggctt taccctgga aggcaagttt cattcaacat ccaaaaatca  177960
gtaactgatt cactatgtaa gcaaaataaa agcgaaaaac atagattatc tcaatagatg  178020
ctgagaaagc tttaatagc atccaacatc cactcataat aaaaaccctc aacagactag  178080
gcatcagaaa aatataccctc gaaattataa gagctatcta tgacaaacca cagtcaacat  178140
catactgaat aagcaaaagt tcaaacccct tgagaattga aaaagacaa ggatgccgtc  178200
tcaccactcc tattgaacat agtattagaa atcctagtcc gaggaaccag gcaataacaa  178260
aaataaaagg cagctgatat ggtttggatt tgtgtcccca cccaaatagc atgtcgaatt  178320
gtaaccacca atgttggagg tggcgtctgg tgaaggatga ttagatcatg gggatgtgtt  178380
ttcctctctc atgctgttct cctgacagag ctctcaggag atctggtttc aaagtgtgtg  178440
gtacctctcc cttatctctt cctcctgctg cagccatgta agacatgatg tttcccattc  178500
tgtcatgatt gtcaggttcc ccaggcctcc ccagccatgc ttcctgtaca gcctgcagaa  178560
ccatgaatta aattaaatta aagaattaaa tatctttata aattactcac tcctgtgtgt  178620
ttctttgtag tgtgagaatg gactaatgca gcatccaaat gggaaaagaa tgcaatgtat  178680
ctgtccaaac tgatgataaa attctatacc tataaaattc taaagactct gacaaaataa  178740
ttcaagagag ataaacaact ttggtaaagt ctcaggatac aaaaatcaat gtacaaaagt  178800
ctccagcatt tctatatccc aaccacatcc aagctgagag tgaaatcaag aacacaatcc  178860
tgtcccactt acaatgctca caaaaaatga agtgcctgaa aatacaggta aaaaacaagg  178920
tgaaagaact gtataaggag aactaccaaa cacagcagaa agaaatcaca aatgacagaa  178980
```

```
ataaatgtga aaacatttca tactcatgga ttggaagaat tgatattgta aaaattgtca 179040
tactgcccaa agcaatttac agattcaatg ctatttacat aaaactctca ccagcattct 179100
tcagataaat agaaaaaaaa ttctaaaatt tatatggaat aaaaaaaaga ccctgaatag 179160
ccacagcaat cctaagcaaa aagaacaatg ccagaggcat catggtactg aatttaaact 179220
acaccataaa gtcatggtaa caaaaacagc ttggtactgg taaaagggca gacatgcaga 179280
aaaagtggaa caaagagaa agcagaaata aagctgcatg cttgcaacca tctgatattt 179340
gataaggctg acaaaacaag caatggggaa aaaactctat tcaataaatg gattctggca 179400
gatatgcaga atgcaagagt gaaggaggtt gggcagcttc tacctagatt tcagaagatg 179460
tgcatggaga accctatatg ccaaggaaga agcctgctgc aggagtggag ccaccacaga 179520
cagtgtctat taggacaata ccaaagatgg ggaaagatgg ggtcggaacc cccattcaga 179580
gtccccacta gggcacttca tagtaaagct gtgggaatgt ggccacaacc ctcaagatcc 179640
cagaatggta gagtcaaagg cagcttgtcc tctcagcctg gaaaaccttc tggcacttga 179700
ctctaacctg tgaaagcagc accatgggct gtgcccagct acagggatga tattcctgag 179760
gtttttggga ccccctttgt cctagtgtgc cctggtggaa gtacataaag tcaagagaga 179820
ctattttgta gctttaagat ttaatatctg ccttactagg ctttaggtgt gtctagagca 179880
tgttggcagt tccttttggcc aatttattcc ttttgtattg acaatattta cccaattcct 179940
gtggcactat tgcaccttgg aagtaaacaa ctgtttaaaa cttttttttt tttttttga 180000 gacggagtct tgctctgtcg cccaggctgg agtgcagtgg cgcgatctcg gctcaccgca 180060 accctgtct cctggcttca ctgcctcagc ctcccgagta gctgggatta caggcgctca 180120
tcaccacgcc cgactaattt ttgtattttt agtagagaca gggtttcact gtattagcca 180180
ggatggtctt gatctcctga cttcgtgatc cacccgcctc ggcctcccaa agtgctggga 180240
ttacaggcgt gagctgccac gcccagcctg tttaaaacat tttgcaagct catagctgca 180300
gagaaattgc cttaagactc agaggagact ttggtatttt cagtcggagg ttgaccaagt 180360
gaagagtttg gtcactatta aaaaaactat taaaaaaaag atgactttgc aatctaagaa 180420
ggacatgaga tcaggacaca agagtaaaat ggtatagttt agatgatggt ccctgctaaa 180480
tctcaaggtg aaatgtgatt cacagcattt gcggtggggc cgactgggag gttttgagac 180540
atggggaaag atccttcagg aatggcttgg tatccacccc atggtaatta gtgaattatt 180600
tctgtattat ctactgtgag atctgatttt caaaataatc tagcaaccat cctcccctt 180660 catgtcctcc ctctcaccat gtaacacagc ctgtttcccc tttgccttcc accatgactg 180720
taagctttct gaggccatca catgatgcag atgctgatgc catgcttctc acttagcctg 180780
cagaactatc agccaaataa gccaaataga ctagtacact gtccaaagca atatacagat 180840
tcaatgcaat ttctattaag taaccaatat aattgattac atattttaaa aaaccataaa 180900
atttatatgg aatcaaaaaa gagcttgaac atcaaaagca acccctaagga aaagtaacaa 180960 agctggaagc accacattgc cggacttcaa attatactac acagatataa taagaatgac 181020
atcatcgtag tgacaaaaaa taaaaattga tgtaacacaa cagacagccc agaaataaag 181080
ccaaatatct acgaccacct gttatttgac aaaactgaca aaaatatac actggagaaa 181140 caaccctta ttcaataagt ggtgcttgga aaattgggca gccacacaaa gaagaataaa 181200
accagacttc tatctcacaa tagacaaaaa ttaagtgaat atggattcaa cacttaaaaa 181260
tataaactga atctacaaaa atacttgaag aaaatgcaaa aaaaaagttc tctggacatt 181320
```

```
ggcctaggca aataaaacat gactaagatt tcaaaagcaa atgcaatgaa aacacagaca   181380
aacaggactt aagtaaaaat cttctgcaca gaaaaagaaa taatcaacat ggtgagtaaa   181440
caacctgcag gatggtagaa ggtatcatct cacctcagtt aacatggctc atattaaaca   181500
cacacacaca cacacacaca cacacacaaa caaaacacta accaatgctc gtaaggatac   181560
agagaaaaga aaactcttat gcattgttga ggagaatgta aactagtaca gtcactatgg   181620
agagcagtgt ggaggtacct caaaaaacta caaatagaac taccgtatga tccagcaatt   181680
ccactactgc aaatttatcc aaaggaatga aaatcattgt atcagagaat tctgcacccc   181740
agtgtatgtg gcaggacctt tcacaatagc caagatatgg aatcaacaca ggtgttgaac   181800
acaagagaat aatggttaaa gatgatgtgg tgcatataca tgacgaagta ctcatcagcc   181860
ataagaaatg aaatcatgtt atttgtggca atgaggatgg aactggagga cattatgtta   181920
aatgaactaa gccagggaca gaaagtaata caccttgttt tctcactcat aggtggatac   181980
ttaaaaaaaa atggtctcct agaagtaaag aatagaacag aggataccag acgctgggaa   182040
gggtagggta aaggacgaga taggcagaga tttgttaaat aatacaaaat tagagctagg   182100
gaggaggaat agattataat gatctttacc actgtaggat gatacggtta acaataatat   182160
gtagttttaa atagttagaa gaaggatact gagtgttcct aacaaaaaga aatggtttga   182220
gatgatggat gtgctaatta ccctaatctg accccctatgc attatatgta tcaaaacatc   182280
actatgtacc tcatgaatag ttacaattat tgtctattaa aattatattt taaaataaca   182340
caaaattcat tggcagtgac ataaatggag gctctgggat aggtgtgggg ataaagggag   182400
gctctgggat acattacagg cctaacatgt cagtgggcag aggagcttcc attagctttt   182460
tctatttgta gcactgagta gatgtgacat ttctcaaagt ttgccctaca atagagacct   182520
gagttccagg gaggtcttgc aggcagctgt gcagatggaa gaagcaggag tagagggttg   182580
ctggcccatt caacaatagt aggatgatta ttgtgcatgt agagaagtca acattgtttt   182640
aagtagttgc atcactggat gacatgaaaa acaaatccag tggaaatcct taaatattat   182700
tggtagtgaa actgttttgg gtgaggaaat gttcactgaa gttaagtgag ccagtaaagc   182760
tgttaagaac tataaaaaca ttggattgga ttcagctttg tctgaattta atgtgattat   182820
tactggctca ggcagggggtc acaaatcaag atggataggt ggtaccaacc agaaaaagcc   182880
atggaccaga aagattcaca gctgaattta ttcggatgta taagaagag ttgctaccaa    182940 tcctagtgaa actattcccc aaaaattagg ataagggact cctccctaaa ttattctgtg   183000
agaccagcat tattctgata acaaaacctg gcagagacta aaaaaaaaga taactttggg   183060
ccaatattca tgatgcaaaa atgctcaatg aaatactagc aaactgacca cagcagcaca   183120
tcaaaaagct aatccaccat gatcaagtag actttgttcc taggatgcaa ggttggttca   183180
tatacgcaaa tcagtaagtg tgattcgtct cataaacaga actaaaaaca aaaccatgct   183240
atcaatggac atagaaaagg tattcaatga aatttaacat tgtttcatat ccaaaaccct   183300
caactaggca tgaagaaaca tacctcaaaa taataaccat ctatcatgaa cccacagcca   183360
aaatcatact gaatgggcaa aagctggaag cagttttccc tgaaaactgg aacaagaaaa   183420
gcattcccac tctaaccact cctgttcatc atagtcatgg aggtcccagc cagagcgtgc   183480
aggcaagaga aagaaaagca tcagaaccgg aagagaggat gtcaaaccat ctctgtagat   183540
gaaatgatca taatcccgag tctgtagttt ggtgattgac attaatttgg aaaaattgtc   183600
agtcatcatt gctttaaata tttcttctta acctttctct gttccttctc tttcccatgt   183660 aatacctaa taattgtctc acaattcttg gataagctgt tctggtttct tatgggtgtg    183720
```

```
tatttgtgta cttgtatgtt tgtgtgtgta tttgtgtgtt tacttttta aaaaaatatt  183780
tctccatttt cagtttggga cattgctact gagatatttt taatttcaga tttttttcct  183840
cagccatgct gcgtctacat ataagtccat tgaaagcatt gcttaattct gttacaatat  183900
tcttgatatc tacattttt tgcttttaa gagtttgcat atttcgactt gcataacaca  183960
actgttcctg gatgccctct gcttaactca tcacagccct tagcatatga gttatagcgg  184020
ggtcttaaat tccttgtttg gtaattccaa cttacatgac gtagctgagt ctcattctaa  184080
tgcttgttct gtctcattac actgtgatat ttttctttta gtatgtctcg tgattttttt  184140
agccagaaat tatgtaccag gtaaaagaaa ctgctgtaaa gaggccttta gcgatgtcat  184200
tgtaagatgt ggagagaaat gtgttccata atcctacggc catggcttac tctagcaagc  184260
ttaggccttt gaaaataaac ccttacatga aagtgaaaac ataagtctta gatttggaga  184320
atttgcttgc aaatcaaata tttggaaaat gactttatc acaaatgtac aaattacctt  184380
acaattgaac aacaacaaaa ccacacaaat taattttaaa atgggcaaag atctgaatag  184440
aaatcgcatc taaaaataaa tataaagaga tcaacttcat tttcattagg tatatgcatg  184500
tttaatattc aaaaaatact actatcttat gaggatgggt aaaatacaca atatagataa  184560
taccaaatgg tgatgaggaa gttgaaaaac aggaacattc actctttgct ggtggtaatg  184620
ctgaaatggc acatagacat gtacagttaa taatttagtg tatattacaa acagctaga  184680
agagaagatt tagaattgtt aacacaaaga aataatcaat gatggagatg aaagatatac  184740
cagttatcca gatttaatca ctgcatataa taatctttta tcaaaatata tacccccataa  184800
agattttgaa ctcatgtatc tatataaatt aggtattaaa aaacagcaat gcagggaat  184860
ccagctaatt gcacattccc tgaatgtacc ctttcttgtc aaaaaggagt tccagagact  184920
cttgaaaacg tagtgcagtt catgtgagaa atagaggttc agaaatgcct cattataccc  184980
tcctcctttt ggaattcaag cacaactaac cagtattttt cattaaaaca gatcttaaga  185040
ctcagaaaac agattctttg cagcagtaag ataccaaatt ctaacctgac tcaagaatag  185100
gatcacatga cagagagcag accttgaaaa gaatcaaaga cttttacct aaaatatatt  185160
tatttgacat atttttaaaat caccctgcac agttatcttt tgagagagaa atttacgttc  185220
tgtagcgaat ctccttccct ttccaggtct agttgttaga ttagctgaga gtctagcatc  185280
ttttaaatgt catagtagaa aacatttgct atctactgcc tctaacgtg gccacataag  185340
agaattcatc tacataataa gaatcttgtt ctccaaaacc cgttatccta acctatgtag  185400
ggaaaagaga gatcagactg ttactctatg tagaaaagga agacgtaaga aactccattt  185460
tgatctgtac cctgaagaat tgttttgcct tgagatgctg ttaatctgta acttttgccc  185520
caaccttgtg ctcacagaaa catatgttgt atggaatcaa agtttaaggg atctagggct  185580
gtgcaggatg tgccttgtta acaatatgtt tacaggcagt atgcttggta aaagtcatca  185640
ccattctcca ttcttgatta ccaagggta caatgcagt gcagaaagcc acgggacct  185700
ctgcccaggg aagccgggta ttgtccaaca tttctcccca ctgagacagc ctaagatatg  185760
gcctcgtggg atggaaaaga cctgaccgtc ccccagcctg acaaccgtga agggtctatg  185820
ctgaggagga ttagtaaaag aggaaggcct ctgtctcctg catgtccctg gaatggaat  185880
gtctcggtat aaaacccaat tgtacatttg ttctattctg agataggaga aaaccacct  185940
gtggctggag gtgagacatg ttggcagcaa tgctcctctg ttactcttta ctacactgag  186000
atgttagggt ggagagaagc ataaatctgg cctatgtgca catccagcga tagtaccttc  186060
```

```
ccttgaactt atttgtgaca cagattcctt tgctcacacg ttttcttgct gcccttctcc    186120
ccactatcac cctgttctgc cacattcccc ttgctgagat agtgaaaata ataatcaata    186180
aatactgagg gaactcagag accggtgccg gtgtgggtcc tccgtatgct gagcaacggt    186240
cccctgtgcc tactgttctt tctctatact tggtctctgt gtcttatttc ttttctcagt    186300
ctctcatccc acctgacgag aaatacccac agttgtggag ggggtgggcc ccttcaaaca    186360
cagaaacgtt tttctactga tttcagctct ttaaataaaa agttaagtct ttcaatcaga    186420
aaatctttga attcacctgt aagctgtaat cccctcccca cactgcctca cttgtagctc    186480
ttttatcttt atgaaacaaa tcgacacatg tctcatatgt attgactgat gtctttctct    186540
ctaagacatt aaatttaagc tgcaatcaag ccactttggg cacacgttct caagatcttc    186600
tggggctgtg tcacagggca tggtcctcac atttggctcg aataaatcta aatattttgc    186660
aaagttgact ttttcattaa tagttcttac agaacctact ctgtgctctt tgttacaagc    186720
ataaaatcaa tatagtatta gttataatag tattgggtat accacatatt ggcaatttct    186780
tatgaagtta ggcatagact aacaatggga tcaagtgtaa atgttttaat gtatttatgc    186840
aagttatttt gatatttatg ttctgcagat acttctatca gatttattat atcagctaat    186900
tatttgtttt atgattgggt gcatttttta tagatgataa caccatatct tttctaggcc    186960
tttattggag aaaattgtgt gaaactactc aggactacat gtgaaagtcc ttattggagt    187020
ggctgacaga attgaagtac atttcctctg tagccaccag acacccagat tcctccagta    187080
acaccttaat tttgtttcct gcttggcttt ggtcttcagt cttgtgctat ccagagagac    187140
tctgtcttac aaatccccca ggtcattcta aagccacatg gaccggacaa ttgtcaatgt    187200
ggtgggaagg gtcgcactga acggtcactc tctgtccttc tgagggagcc atactgcagg    187260
cagacatggc agtcctggct caggttgtgt ccttccaagt atccctgccc tcctgcaggt    187320
gtgatgctga tccatgcatc ttcctcccat tcctgggtag agggtctcct tgttttttcc    187380
cagatcttct tccagcagcc actatgtctt cccactgatg tcttcagctt cctcttttct    187440
gcccttccca gcaggatgag gcttttattc ctgaagaaag agagaggagg tgggagatga    187500
ggctgttatt cctgagagaa tgaacagggc tttggagctt ttctttcttc tatcccagtt    187560
tctatgagtt cctccagtac cagtaacaca aaggtgttac tggctttgcc cctgcatgtt    187620
aattctctag caatgtagtg gtgacagtgg aggtgggtct ggatgcattt cagctgcagt    187680
tgctgttttt cttccagca cagaaccaac ttgggagcta cagggcaaga gcttttgta    187740
atgtgtcctc aatcctggga gaaagttttt caatagcaat aggaatctct cagttgtatg    187800
ttctctgaga atttaaacaa taacttattt attatactca atttttaaaca atgtaataaa    187860
tatgtctaat ttaatcttgc attagcttat gtgacatttg ctggccattg ccccagataa    187920
ggccattttc tcttcctgtt tatccctgca agtgactgac ttttgcaaga tgtaaggttt    187980
cttgtttgcc ctataacatc aataatctga aatattaaag aaaatgtgct aatttgcaga    188040
tcagtaaggt tagttgtttc tgtaaaaata tatatgttttt tttgagatgg agtcttgctc    188100
tgtcaccatg ctggagtgca gtcgtgtgaa cttggctcac tgcaacctcc gccccttgg    188160
ttcaagcgat tctcctgcat cagcctccat agtagctggg actacaggag tcttggcctc    188220
caaaagtgct gggatttctg gcataagcca tcacacccag ccaaaaataa tatattttaa    188280
ggggtgcata catctccagg ctgagtagga gctttatttg tagtactcag taactggaat    188340
taacacaact attaaggagc attataaata aatagtaagg gtgcactcat taactggaat    188400
actgttcctc attagaatca acacatcctt tagttcatgt cctttgcagg gacatggatg    188460
```

```
aagctggaaa ccatcatagt cagaaaacta tcacagggac aggaaaccaa acaccgcatg   188520
ttctcactca taagtgggat cttaacagtg agaacacatg acacaggga ggggaatgtc   188580 acacaccagg gcctgtcggg gtggggagca aggggaggga cagcattagg agaaatacct   188640
aatgtagatg acaggttgat gagtgcagca aaccagcatg gcacatgtat atctatgtaa   188700
caaacctgca tgttctccac atgcatctca gaacttaaag tataatttta aaaacacatt   188760
atttatatag aaccaaatta ctggctcaca agtaattata ctgtgcaaaa aaccacacaa   188820
atgaaattga gactataaga tttcacttga acaaaatctt gaaaaataga tctaaagtaa   188880
caaagatgac tgactcaata tggtgagagg aaaatgactg ggaggcagga atgagaggaa   188940
cacagggaaa cttttaagtg taattcattg gtatcttgat tgttatttgg gatgcacagg   189000
tgagcacatg tgtaattaca ttttttttcct ttggagacat tttcttgctt tgtcatccag   189060
gctggagctc cgtggtgaca tcatagctct ctgcagcctc agaccctggg tctccagcaa   189120
tcctcctccc tctgccctat ctagctggga ctacagctgt gcaccaccat gctcggcttc   189180
agtgtgtatt caaccagaca ctttaattat gcagtattta ttacgtggca ataatgcctc   189240
aataagggta ttgcaaataa gtggatggat aatttgttca attaagattg atggaaatat   189300
agacacttac atgacaaatg tatgacaatc aagaaaataa aactgtagga aacatacttt   189360 acttttgtt aggtaatcgc aacagtgcat acacatcaca ccatgttctc attacagaga   189420
aaaggttctg caaacctcac ttggtgtgac ctcctgtatg ctgggcttgg ctcagggaga   189480
agtcaggacc agtggtgaga agcacaggcc cagataacca gactcactct gaccaaatgt   189540
gagtgctggg gacattgtac aatccatctg tgttttgctg atattttttc atctgtaacg   189600
tggaaataac attgatacta cataccatgg tttctgtgca tatggaaaaa taaaagatga   189660
ttggtgcaaa ctttaaatac acacagttta tgtagatcaa ttgtacctca ataaaactgt   189720
tttaaaataa aaattacaaa actataagtt ttataggttt taagggttta tcatagaaca   189780
aacttacaat aagaaacaag aatttccaaa tgctatcaat atcacaaatc tcccccagga   189840
cgctctgaca tgctctgagc cccactctct cctcaggcgt cccatcccag agcttggcat   189900
gtagtaggag acatgcaaat agagccctcc ctctgcttat gaaaaccagc ccagccctga   189960
ccctgcagct gtgggagagg agccccagcc ctgggatttt caggtgcttt cattttgtga   190020
tcaggactga acacagagga ttcaccatgg agtcatggct gagctgggtt tttcttgccg   190080
ctatttaaaa aggtaattca ttgagaacta ttgaaattga gtgtgagtgg ataagagtga   190140
gataaacagt ggatacgtgt ggcagtttct gaccagggtt tctttgtgtt tgcaggtgtc   190200
cagtgtgagg tgcagctggt ggagtctggg ggaggcttgg tccagcctgg ggggtccctg   190260
agactctcct gtgcagcctc aggattctcc tttagtagct atggcatgag ctgggtccgc   190320
caggctccag ggaaggggct ggagtgagtg gcacatatct ggaatgatgg aagtcagaaa   190380
tactatgcag actctgtgaa gggccgattc acaatctccg agacaattct aagagcatgc   190440
tctatctgca aatggacagt ctgaaagcta aggacacggc catgtattac tgtaccagac   190500
acagtgagag gaagtccgtg tgagcccaga cacaaacctc cctgcagggg cacgcggggc   190560
caccagaggg tgcccaggat cccctgaaga cagggacagc ccaaaggcag gtgcagatgg   190620
atgtcaagag ggtctgtggc ttcgtctaca tctaactgtt tcctggtgag cctctgtata   190680
tttatttttc tgtgcccact aatgaggttg gtaagtttaa acacttttt ttttgagatg   190740 aagtctcgtg cttgtgcccc aggctggagt gcaatggcat gatctcagct cactgcaaca   190800
```

```
tccgcctcat gaattcaagc gattttcctg cctcagcctc ccaagtagct gggattccag   190860
acaactgcca ccacgcccgg ctaattttttg tattttttagt agagacaggc tttcaccatg   190920
ttggccaggc tagtctcgaa ctcctgacct caggagaccc tcccaccttg gctcccaaa    190980 gtgctgggat tacaggcatg agccactgtg cctagccaaa aaagacttca ttattatagg   191040
aggaaaaatt ctcatctgca agtgtcactg atggaagcag aaaaaatgcc caggaagtca   191100
ggtgaggctg tagacactgt caacccagga tgcaaatctc accacaagtg caggagaaag   191160
ggcagggggt tgatggatca tcctaactaa cgtatggttt aagctgagcc cagcaagacc   191220
ctcagtgcct ccctaaccac agttgcccctt cagggataac ccatgtgctc aacagcagcc   191280
acaccttagt atctccactg tgcagtcatt gtctaggaca agctcccagg atgtggggct   191340
ttggcacaaa ccaggtcatg gatgtcgag aggggcagct gggtgtctgg tccataggct    191400
ccctgatgtt ggagggttga gaggtgcatt ctctgggcca acatatactc tagggatatt   191460
tacttcagaa cacataattt tatttgttgg tttatggtta atggggtatt catcccttca    191520
atcatttgtc ctttgattta caaaaacatt ccaatttcac tttggaagta attttattat    191580
gtgcaattaa gtcattattg attatagtca cactattttg ctactaaata gtaggtgtta    191640
ttcattcttt ctaactctgt attttgtacc cattaaccat atccacctgt tctctggccc    191700
ccactagcct cccagactcc agttaccatc cttctaccat ccgtgttcct gagtttaatt   191760
ctgttgattt ttagagcaca cacataagta agaacctgca atgcttttttt tttcagtgcc    191820 tggtcttttt cacttaacat agtgacctcc agttccatcc atgttgttgc aaatgactgg   191880
atctcatgga atacctaatt ttattcggtt ctttcatatg acatagagaa gcaagcatgc   191940
agtctacaaa caactgtaat tttcacattt accccaaatg aattattact tatttctgtg   192000
cagggtccag gcacatagta gcctttctct tgagggactg ttaaatttag agtgagatca   192060
cttgtttctc atattatatg attcctgtcc atgtgcagag atcttaagta atctgcttct   192120
ttctgcacac taactctgac cttctcgaca aaaagagtag agatttttcat gtttcctgag   192180 tctggggtag gagttagtcc tacacaactc agagcctgca gagacctccc agtgcagttt   192240
tatagacaca ggtgctttct catgggggggt gagacctcca cttcctgtga ttgctgctca   192300
gatctaactg tgatttcaga tttaggacac cattaggctc tcaaaccatt tctattctaa    192360
aaatcagcct catcatagaa aatggaaata attcaatatc catttccctg accgtatttc    192420
atccttgttt ttaatttggt gcaagtttat tacatatttg cctgaatcta acttcagaat    192480
caactgaatt ggtctagaaa tctcaaaaat tgaacagaag tgggttttat tatttttacc    192540
aaaatgtgtg taggtagggt ttccaatgta tcatccagaa cttgtgcatg ctaacaactg    192600
tttttctcag tcaattatca gcctggtgaa gcccttgcaa acccctcac tcacctgtgc    192660 tgcctctgga ttctctgtca caatcagtgc ttcctgtagg cactggatgg aaagcacagg   192720
agtgggtcag gtgcatacgt gatgagtgga ggatgaattc cagcccactt atcatgaatt    192780
cagacaagcc cacatgttcc cacatgcact atatcttcag acaagcagat gtgtctgcac   192840
atgaattctt ctttcagaca aacacgtctg tcccctcatg gactcttgcc acacacaagc   192900
acacgtggct tcttgtggac tgtactttca gacaagcaca cattgtttca tgtgacatc     192960 ttcctcccac aaatgcattt tccctgagt agactcttct cccacaagcc catatgtcct    193020
cacatggaca tttctcacag gcaaacaccc atttcccccat gtagtccctt ccctcagaca   193080
agcacacgta ttcccaggta gactcttccc ttagacaagc acagctgttc ccatatgaac   193140
ccttccatat gacaagcaca catgttccca tgtgaactcc cgtataacaa gcacacatat   193200
```

```
ttcctcacgg gctcatcact cagataggtc tgcatgtcca catgtggact ctactctcag   193260
acaagcccac aggtcctcac atggactctt ctctcaaaca cccgttctcc attgtagact   193320
cttcccttag acaagcacgc attttcccat gtgaactctt ctgcatggga agcacacata   193380
ttcccacagg gactcttctc tgaaacaccc attctccatt gtagactctt cccttagaca   193440
agcacgcatt ttcccatgtg aactcttccg catggaaagc acacatattc cacagggat    193500 tcttcactaa gacaagcatg attgtctcca ctgtgaccct tccctcagag aagtacactt   193560
gtctacatat ggactcttct ctcagacaag caaacatgtc ccacgtgga ctctttcttc    193620 tgacaagcac acgtgtcccc atgttgttat aatcattttc tcacctctgt ctcacaaagt   193680
tgccctgtcc tccaagaata attttgacct ctcacttctc attcacacta tggtgattgg   193740
tgcgcagcat tttcacccaa gagaaatgca ggcagctctc agaatttatt gtgatggagg   193800
caggaagaca aacacaaaga taaaacttgt cgctaccttg ctgggctgtg ttctgtgcag   193860
agtctctgaa ggctgccctg gggctgtgtc ctaagctgta tctctctgat tccactagga   193920
gaatgcacat agagaaattc aagctgaatg gtgtcctgat ccctgcctca ttctgctatt   193980
cttccctatt cctcagaaat tcacccaaca ttgccctctg tcttgtattg tctacattct   194040
cacagactct ctcatagaac ttcagcttca atggtcagag ccctggtcac ttcttcccaa   194100
ctctccgcac atgccaagtg cacattagag actcaataat gaggctcacc aggggcagta   194160
gtagtttcat ctatcacagt ggagatgaaa atccatgatt taaaataggt ttctaaaaaa   194220
gaaaatatgt ctcacatcaa acacaaatga gagaatgcaa cggcataatt cattttcagg   194280
tttttcatat gtaaatctcc taaagtacat aatttagttt ttagtgtggt tcctgatcca   194340
tgaatccttt tgccttcttc attatctttc attcaaacaa acagagacca tacccactgt   194400
tcacagtgta gcctcatgga gaacatcttc accagtcagc ccagtcagtg agtgaggcct   194460
ttaaatcctt catgctaatt caaatttctg gctttattct tagtagaccc caggttttcg   194520
gggatgttgg gttgtgccag cactcctaaa taagggagat agaaattatt tcctcaggca   194580
tcctcttgca acatttggac aattgcccat agtttgatta ttgaggtgtg atgcatcaaa   194640
ataatgttag ttcaatcttc tctcaaccag tcattgaaca ttgaaatttt gtaattattt   194700
atttggatat ctctgaagtt tacctcttga atatttaggt catattataa atagtttaag   194760
ctgcctacta ggtaaaatga tctgctgcag aattttgact tccttgctgt gcattttgc    194820 atttaaattg aagtttctat tactcgtgtg tctagaatgt aaaaatacgt cttacatttt   194880 ctcgaattt tcatttcact ggagtttcca gaagatgaga aaacctccct tgtgtataaa    194940
atacctggta acacattgct caatagtttc gttgctgaga ccagctcagt cgggagaccc   195000
taacccagcg gtgctagagg aattaaagac acacacagaa atatagaggt gtgaagtggg   195060
aaatcagggg tctcacagcc ttcagagctg agagccctga agaaagattt acccacgtat   195120
ttattaacag caagccagcc attaatattg tttctataga tattaaatta actaaaagta   195180
tcccttatgg gaaatgaagg gatggaccga attaaagggg gtgggtctgg ctagttatct   195240
gcagcaggaa catgccctaa ggcacagatc actcatgcta ttgtttgtgg tttaagaacg   195300
cctttaagcg gttttctgcc ctgggggggc caggtgttcc ttgccctcat tccggtaaac   195360
ccacaacctt ccagcgtggg cattatggcc atcatgaaca tgtcacagtg ctgcagatat   195420
tttgtttgtg gccagttttg gggccagttt atggccagat tttgggggc ctgttcccaa    195480 catttcctct ttaatttttt tctcctctca tattgtactg ttataagcaa tgagatatca   195540
```

-continued

```
ggacacatca tcaacactttt gctaagaaat atcttcagct aaattcccag agtatcatat   195600
actaatccta atttaacta aggtaacata attaagatac attctataac aagtcacaca     195660
tattatccag tatccagtaa catgtttgtg acagaaacaa agcaggtgct tcctctgcaa    195720
agggtcatct gaggtctgag ttgagggtca cacaggtatt tttctggttt acaagggtgg    195780
gaacgacaac agtaataacg actctgaaca gcactggccc ttccttgaaa ggttgcaggt    195840
aaagctactg ctgctatatc aaattaacac cttactagaa taaagcccag agggagggtc    195900
cacatgctag gtcacagagt gaggagaaat ggagctgtgc tctgctctcc acactaccta   195960
caagatccca gacacacgcc caggttccac tgatgcaagg catctacagt gcagttctaa    196020
ggcacctgct tcctgggca gggagcatcc tcctgtcaat tgcgcacctg ctccttctgc     196080
aagctattaa gtgagcactt ctattgccat gaattataca tgttctctct cttaacatgt    196140
atattgaaca tgcttactta cattgcattt tattttctc tgaaatacac tggatgagca     196200
gaagaaaata aatcacaccc ctgatgcttt ccacacatac aaagattcct gaaggcagag    196260
ctgactgata tcctcaccag tagaccactg cctttcagag atgatcttgg tattcaagtt    196320
ccagcaattc ttgaagttaa agggcaccct tatctcctct ccactgcttt gcacctcacc    196380
tgatatcagc tttctcatta gaatgccttg tgtttaagga atgagagttc ctgtcacagg    196440
tgcaaaggcc caggttctcc cactggctcc agtccagggc tagggacacc tgtaagacca    196500
tgatatcatc tgatacataa cctttacatc ataagcttta cataaccttt acatacataa    196560
catcacacat agcattcatg atacacacat cagatcacct ttacatgctc taacatgtaa    196620
agattaggaa agtcatcaag ctcattctta tgtcaaaaaa catctgcaca atttgaacat    196680
caacaattt tgaaatctat caaggaattg aaattgcaag ggaaattacc cattccaaat     196740
actgaagata cagacatgtc caggatcaga gttgacactg gctgaactgg aaaagaactt    196800
gaagaaagca cgagttggtg agagcacaca catggtaaat gctatgaaag cctaaacggc    196860
agatgtggac tagggtgaga ttcctgggga cctacactcc atagtcttct gaactttcct    196920
tcaaaatctt ccagattctc aggtatacaa tccaaataat tttttatgg gtctgaattg     196980
gggaggatta attactgaga aatgtaccaa gagccttcta aaaaaaaaaa atcctatagg    197040
aaatgagatt ttccagaacc tggaggaacc tacagttccc taaagacaga cactgaggag   197100
aataaatctc gacagcgccg cctggaggtg gaggtgaaga gcttcctgga ggagctggac    197160
cggaagatcc acgacctgaa tgactcccgc ccaggcctcc caagctgggc accgacaact    197220
agggctggtg gaggcccggg atccccaccg tgagtcccaa gcatgtgtgc gagaccagat    197280
ggcgctagga cgttccctgt gtgcgttgct tctgtaaatg cagacgcagt ttgtcgtgtt    197340
tccaaaccag ttgtgctgtc cactcgctcc tttccagagt agaaatctcc tctccgccgg    197400
gcgcggtggc tcacgcctgt aatcccagca ttttgggagg tcgaggcggg cggatcacga    197460
gatcaggaga tcgagaccat cctggctaac acggtgaaac cctgtctcta ctaaaaatac    197520
aaaaaattag ccaggcgtgg tggcaggtgc ctacagtccc agctactccg aggctatggc    197580
agtagaatcg cttgaacccg ggaggcggag gttgcagtga ccgagatca ttccactgca     197640
ctccagcctg ggcgacagaa caagattctg tctcattaaa aaaaaaaaa aataggcttc    197700
aggaagtagc tcctagatgg gcagaatcgg tttaaccctc tgtgtccaca ggatctggag    197760
cctctctctc cttagattag gccacctcct caggattaca gggctcttca gttttctcaa    197820
catgctgttt ttgcccccaaa taaacacaaa agcactttat tttcttatgc ttacctttaa   197880
tttttcaaaa caacataaag gtgataattt taacaataaa catattacaa cctactatac    197940
```

```
atgataccct tcctgtagtt cgaggtttat tctcaggaat ttatatgtat tacttatttt   198000
caattgcttt ctgatatggg atgtcaatgc cactttacta cagtctttat tcttttaagt   198060
tatctctaaa atctctaaaa attaatcttt ccaaagcacc actcaaaacc agtgtattat   198120
tagaacttgt gggtgtaatc gttggaccaa tattaagaat aaattcttaa tggactaact   198180
cagatataaa atttctgtcc ttcctctctc tctacatata tacataacga ctttgaggtt   198240
tcagttgaat cagtccattc attgaatgta tgacaatagg ttgatctaat tgtatacgtt   198300
aaatagcatg aagaaacctc aacaatagca aaagtagccc cttaccaaaa acagctctat   198360
tatgttagat tccacttatg agaagttcaa agagaaaaa catggatctg tattgtcaga   198420
aatctaaaca tttccccaca caggagctga ccacaggcac aggaagacct gtgttggggg   198480
atggactgct cttcagtcta ccttaggtgc cggggacaag agtattcacg tttggcagaa   198540
actctctagt gagaaattcc agatctatgc atttcctctt atatgtaaat tttctcataa   198600
aaacaaaaaa taatgtataa aataatttaa aattcagaac ataataaaaa tgacattaca   198660
tgcctatcca aaacattcag taatgaacat tattatatga attaataaaa tccattcaaa   198720
tatacctact gaaattaact tctggaaaat aaaaagacaa gggtaacatc cgtaacttaa   198780
aaattaataa gcatatattt catagagaag aaaaaggtag tcaagacata tgtggaatgt   198840
gtattctttt ttccaatcaa atgtcattaa actatttaaa caatttttta acctgtgtca   198900
taagtataga ttactaatat ttgtctgata ttacaactgt gaacaagttt taagaaaaa   198960 aggatatttg acagcatgtg aactaaattg aatttattct taatattgag tccaacgatt   199020
acacccacaa gttctaataa taccctggtt ttgagtggtg ctttggaaaa attaattttt   199080
agagatttta gagataactt aaaagaataa agaatgtaat aaagtgacat tgacatccca   199140
tacataacaa catattgatc tatttttgt tgatggactt taaatttgtt tctagtttat    199200
gaatattata agcaaagctg ttacaaatac cttagtgtaa gttttcctat gttgtctcat   199260
ttttattgcg aaaacatgac gtatgcattt cttcttgta agagtaattt taactttttt   199320
cagtttcatt gaggtatatt tgaaaaaatt ttttaaaagt atatggttga ggaacaatgc   199380
accacttgat gctttgtctt aggccattct cacattgcta taaagaaatg cctgagacta   199440
atttgaaaaa aagaaaaaga tgtttaattg gctcatgatt ctgcaggctc tataggaaat   199500
gtagttgttt attcttctgg ggagactcag gaaagttaga atcatggcag aagacaaaga   199560
ggagcagggc aatcacatgg ccagagcagg agccacagga ggcgtgcggt gggggggtgc   199620
ggggcgggtc tacacaccgt tagacaccag atccttgtgag aactcacgca ctgtcatgag   199680
aacagcagca ggagttgttg ctaaaccatt catgaaagac gtaccccatg acccagtcat   199740
gtcccaacag gtcctacttt caggaatgag gattataata taacatgaga tttgggtcaa   199800
gatacggatc caaaccatat cagatacaca ttgtaaaatg atcatcgtag tcaaggtaat   199860
ttgtgtgtat atcatctcac agagctacaa ttttattttt ttaagtttac tgcatgtgtg   199920
tgtgtgtctg atgagaacaa ctaaaatcta ccctgttagc aaaaatcgtt tttacagtaa   199980
agtattaact ataggaacat                                               200000
```

<210> SEQ ID NO 109
<211> LENGTH: 700
<212> TYPE: DNA
<213> ORGANISM: Homo sapiens
<220> FEATURE:
<221> NAME/KEY: modified_base
<222> LOCATION: (19)..(19)

<223> OTHER INFORMATION: a, c, t, g, unknown or other
<220> FEATURE:
<221> NAME/KEY: modified_base
<222> LOCATION: (46)..(46)
<223> OTHER INFORMATION: a, c, t, g, unknown or other

<400> SEQUENCE: 109

```
aggttctggg ttataaacnc tgtagactcc tcccttcagg gcaggntgac caactatgca      60
aatgcaagtg ggggcctccc cacttaaacc cagggctccc ctccacagtg agtctccctc     120
actgcccagc tgggatctca gggcttcatt ttctgtcctc caccatcatg gggtcaaccg     180
ccatcctcgc cctcctcctg gctgttctcc aaggtcagtc ctgccgaggg cttgaggtca     240
cagaggagaa cgggtggaaa ggagccctg attcaaattt tgtgtctccc ccacaggagt      300
ctgttccgag gtgcagctgg tgcagtctgg agcagaggtg aaaaagcccg ggagtctct      360
gaagatctcc tgtaagggtt ctggatacag ctttaccagc tactggatcg gctgggtgcg     420
ccagatgccc gggaaaggcc tggagtggat ggggatcatc tatcctggtg actctgatac     480
cagatacagc ccgtccttcc aaggccaggt caccatctca gccgacaagt ccatcagcac     540
cgcctacctg cagtggagca gcctgaaggc ctcggacacc gccatgtatt actgtgcgag     600
acacacagtg agagaaacca gccccgagcc cgtctaaaac cctccacacc gcaggtgcag     660
aatgagctgc tagagactca ctccccaggg gcctctctat                           700
```

<210> SEQ ID NO 110
<211> LENGTH: 688
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 110

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ser
            20                  25                  30

Gly Met Ile Trp Val Arg Gln Ala Pro Gly Lys Gly Leu Glu Trp Val
        35                  40                  45

Gly His Ile Arg Ser Lys Thr Asp Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Gly Gly Ser Gly Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Gly
        210                 215                 220
Gly Gly Gly Ser Gly Gly Gly Ser Glu Val Gln Leu Leu Glu Ser
225                 230                 235                 240
Gly Gly Gly Leu Val Gln Pro Gly Gly Ser Leu Arg Leu Ser Cys Ala
                245                 250                 255
Ala Ser Gly Phe Thr Phe Ser Thr Tyr Ala Met Asn Trp Val Arg Gln
                260                 265                 270
Ala Pro Gly Lys Gly Leu Glu Trp Val Ser Arg Ile Arg Ser Lys Tyr
                275                 280                 285
Asn Asn Tyr Ala Thr Tyr Tyr Ala Asp Ser Val Lys Gly Arg Phe Thr
        290                 295                 300
Ile Ser Arg Asp Asp Ser Lys Asn Thr Leu Tyr Leu Gln Met Asn Ser
305                 310                 315                 320
Leu Arg Ala Glu Asp Thr Ala Val Tyr Tyr Cys Val Arg His Gly Asn
                325                 330                 335
Phe Gly Asn Ser Tyr Val Ser Trp Phe Ala Tyr Trp Gly Gln Gly Thr
                340                 345                 350
Leu Val Thr Val Ser Ser Ala Ser Thr Lys Gly Pro Ser Val Phe Pro
                355                 360                 365
Leu Ala Pro Ser Ser Lys Ser Thr Ser Gly Gly Thr Ala Ala Leu Gly
        370                 375                 380
Cys Leu Val Lys Asp Tyr Phe Pro Glu Pro Val Thr Val Ser Trp Asn
385                 390                 395                 400
Ser Gly Ala Leu Thr Ser Gly Val His Thr Phe Pro Ala Val Leu Gln
                405                 410                 415
Ser Ser Gly Leu Tyr Ser Leu Ser Ser Val Val Thr Val Pro Ser Ser
                420                 425                 430
Ser Leu Gly Thr Gln Thr Tyr Ile Cys Asn Val Asn His Lys Pro Ser
        435                 440                 445
Asn Thr Lys Val Asp Lys Lys Val Glu Pro Lys Ser Cys Asp Lys Thr
        450                 455                 460
His Thr Cys Pro Pro Cys Pro Ala Pro Glu Ala Ala Gly Gly Pro Ser
465                 470                 475                 480
Val Phe Leu Phe Pro Pro Lys Pro Lys Asp Thr Leu Met Ile Ser Arg
                485                 490                 495
Thr Pro Glu Val Thr Cys Val Val Val Asp Val Ser His Glu Asp Pro
                500                 505                 510
Glu Val Lys Phe Asn Trp Tyr Val Asp Gly Val Glu Val His Asn Ala
        515                 520                 525
Lys Thr Lys Pro Arg Glu Glu Gln Tyr Asn Ser Thr Tyr Arg Val Val
        530                 535                 540
Ser Val Leu Thr Val Leu His Gln Asp Trp Leu Asn Gly Lys Glu Tyr
545                 550                 555                 560
Lys Cys Lys Val Ser Asn Lys Ala Leu Gly Ala Pro Ile Glu Lys Thr
                565                 570                 575
Ile Ser Lys Ala Lys Gly Gln Pro Arg Glu Pro Gln Val Tyr Thr Leu
                580                 585                 590
Pro Pro Cys Arg Asp Glu Leu Thr Lys Asn Gln Val Ser Leu Trp Cys
                595                 600                 605
```

```
Leu Val Lys Gly Phe Tyr Pro Ser Asp Ile Ala Val Glu Trp Glu Ser
    610                 615                 620

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
                645                 650                 655

Arg Trp Gln Gln Gly Asn Val Phe Ser Cys Ser Val Met His Glu Ala
                660                 665                 670

Leu His Asn His Tyr Thr Gln Lys Ser Leu Ser Leu Ser Pro Gly Lys
                675                 680                 685

<210> SEQ ID NO 111
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ser
            20                  25                  30

Gly Met Ile Trp Val Arg Gln Ala Pro Gly Lys Gly Leu Glu Trp Val
        35                  40                  45

Gly His Ile Arg Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Gly Gly Ser Gly Ser Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
```

```
                275                 280                 285
Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
            340                 345                 350

Leu Pro Pro Ser Arg Asp Glu Leu Thr Lys Asn Gln Val Ser Leu Ser
                355                 360                 365

Cys Ala Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
                435                 440                 445

Lys

<210> SEQ ID NO 112
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 113
<211> LENGTH: 689
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113
```

-continued

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Asn Ser
            20                  25                  30

Trp Met Asn Trp Val Arg Gln Ala Pro Gly Lys Gly Leu Glu Trp Val
        35                  40                  45

Gly Thr Ile Arg Gln Lys Thr Tyr Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Gly Leu Phe Gly Tyr Trp Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
    210                 215                 220

Gly Gly Gly Gly Ser Gly Gly Gly Ser Glu Val Gln Leu Leu Glu
225                 230                 235                 240

Ser Gly Gly Gly Leu Val Gln Pro Gly Gly Ser Leu Arg Leu Ser Cys
            245                 250                 255

Ala Ala Ser Gly Phe Thr Phe Ser Thr Tyr Ala Met Asn Trp Val Arg
            260                 265                 270

Gln Ala Pro Gly Lys Gly Leu Glu Trp Val Ser Arg Ile Arg Ser Lys
        275                 280                 285

Tyr Asn Asn Tyr Ala Thr Tyr Tyr Ala Asp Ser Val Lys Gly Arg Phe
    290                 295                 300

Thr Ile Ser Arg Asp Asp Ser Lys Asn Thr Leu Tyr Leu Gln Met Asn
305                 310                 315                 320

Ser Leu Arg Ala Glu Asp Thr Ala Val Tyr Tyr Cys Val Arg His Gly
            325                 330                 335

Asn Phe Gly Asn Ser Tyr Val Ser Trp Phe Ala Tyr Trp Gly Gln Gly
            340                 345                 350

Thr Leu Val Thr Val Ser Ser Ala Ser Thr Lys Gly Pro Ser Val Phe
        355                 360                 365

Pro Leu Ala Pro Ser Ser Lys Ser Thr Ser Gly Gly Thr Ala Ala Leu
    370                 375                 380

Gly Cys Leu Val Lys Asp Tyr Phe Pro Glu Pro Val Thr Val Ser Trp
385                 390                 395                 400

Asn Ser Gly Ala Leu Thr Ser Gly Val His Thr Phe Pro Ala Val Leu
            405                 410                 415

Gln Ser Ser Gly Leu Tyr Ser Leu Ser Ser Val Val Thr Val Pro Ser
```

```
                    420                 425                 430
Ser Ser Leu Gly Thr Gln Thr Tyr Ile Cys Asn Val Asn His Lys Pro
        435                 440                 445
Ser Asn Thr Lys Val Asp Lys Lys Val Glu Pro Lys Ser Cys Asp Lys
    450                 455                 460
Thr His Thr Cys Pro Pro Cys Pro Ala Pro Glu Ala Ala Gly Gly Pro
465                 470                 475                 480
Ser Val Phe Leu Phe Pro Pro Lys Pro Lys Asp Thr Leu Met Ile Ser
                485                 490                 495
Arg Thr Pro Glu Val Thr Cys Val Val Val Asp Val Ser His Glu Asp
            500                 505                 510
Pro Glu Val Lys Phe Asn Trp Tyr Val Asp Gly Val Glu Val His Asn
        515                 520                 525
Ala Lys Thr Lys Pro Arg Glu Glu Gln Tyr Asn Ser Thr Tyr Arg Val
    530                 535                 540
Val Ser Val Leu Thr Val Leu His Gln Asp Trp Leu Asn Gly Lys Glu
545                 550                 555                 560
Tyr Lys Cys Lys Val Ser Asn Lys Ala Leu Gly Ala Pro Ile Glu Lys
                565                 570                 575
Thr Ile Ser Lys Ala Lys Gly Gln Pro Arg Glu Pro Gln Val Tyr Thr
            580                 585                 590
Leu Pro Pro Cys Arg Asp Glu Leu Thr Lys Asn Gln Val Ser Leu Trp
        595                 600                 605
Cys Leu Val Lys Gly Phe Tyr Pro Ser Asp Ile Ala Val Glu Trp Glu
    610                 615                 620
Ser Asn Gly Gln Pro Glu Asn Asn Tyr Lys Thr Thr Pro Pro Val Leu
625                 630                 635                 640
Asp Ser Asp Gly Ser Phe Phe Leu Tyr Ser Lys Leu Thr Val Asp Lys
                645                 650                 655
Ser Arg Trp Gln Gln Gly Asn Val Phe Ser Cys Ser Val Met His Glu
            660                 665                 670
Ala Leu His Asn His Tyr Thr Gln Lys Ser Leu Ser Leu Ser Pro Gly
        675                 680                 685
Lys

<210> SEQ ID NO 114
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Ser Phe Ser Asn Ser
            20                  25                  30
Trp Met Asn Trp Val Arg Gln Ala Pro Gly Lys Gly Leu Glu Trp Val
        35                  40                  45
Gly Thr Ile Arg Gln Lys Thr Tyr Gly Gly Thr Thr Asp Tyr Ala Ala
    50                  55                  60
Pro Val Lys Gly Arg Phe Thr Ile Ser Arg Asp Asp Ser Lys Asn Thr
65                  70                  75                  80
```

-continued

Leu Tyr Leu Gln Met Asn Ser Leu Lys Thr Glu Asp Thr Ala Val Tyr
                    85                  90                  95

Tyr Cys Thr Thr Gly Gly Leu Phe Gly Tyr Trp Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
            355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450

<210> SEQ ID NO 115
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Gly Trp Phe Asp Tyr Trp Gly Gln Gly Thr Leu Val
            100                 105                 110

Thr Val Ser Ser
        115

<210> SEQ ID NO 116
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 116

Ser Tyr Ala Met Ser
1               5

<210> SEQ ID NO 117
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 117

Ala Ile Ser Gly Ser Gly Gly Ser Thr Tyr Tyr Ala Asp Ser Val Lys
1               5                   10                  15

Gly

<210> SEQ ID NO 118
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 118

Val Leu Gly Trp Phe Asp Tyr
1               5

<210> SEQ ID NO 119
<211> LENGTH: 215

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 120
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
```

```
                    85                  90                  95
Leu Trp Val Phe Gly Gly Gly Thr Lys Leu Thr Val Leu Ser Ser Ala
                100                 105                 110

Ser Thr Lys Gly Pro Ser Val Phe Pro Leu Ala Pro Ser Ser Lys Ser
            115                 120                 125

Thr Ser Gly Gly Thr Ala Ala Leu Gly Cys Leu Val Lys Asp Tyr Phe
        130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
    210

<210> SEQ ID NO 121
<211> LENGTH: 688
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Gly Gly Gly Gly Ser
210                 215                 220
```

-continued

Gly Gly Gly Gly Ser Glu Val Gln Leu Leu Glu Ser Gly Gly Gly Leu
225                 230                 235                 240

Val Gln Pro Gly Gly Ser Leu Arg Leu Ser Cys Ala Ala Ser Gly Phe
            245                 250                 255

Thr Phe Ser Thr Tyr Ala Met Asn Trp Val Arg Gln Ala Pro Gly Lys
        260                 265                 270

Gly Leu Glu Trp Val Ser Arg Ile Arg Ser Lys Tyr Asn Asn Tyr Ala
    275                 280                 285

Thr Tyr Tyr Ala Asp Ser Val Lys Gly Arg Phe Thr Ile Ser Arg Asp
290                 295                 300

Asp Ser Lys Asn Thr Leu Tyr Leu Gln Met Asn Ser Leu Arg Ala Glu
305                 310                 315                 320

Asp Thr Ala Val Tyr Tyr Cys Val Arg His Gly Asn Phe Gly Asn Ser
            325                 330                 335

Tyr Val Ser Trp Phe Ala Tyr Trp Gly Gln Gly Thr Leu Val Thr Val
        340                 345                 350

Ser Ser Ala Ser Val Ala Ala Pro Ser Val Phe Ile Phe Pro Pro Ser
    355                 360                 365

Asp Glu Gln Leu Lys Ser Gly Thr Ala Ser Val Val Cys Leu Leu Asn
370                 375                 380

Asn Phe Tyr Pro Arg Glu Ala Lys Val Gln Trp Lys Val Asp Asn Ala
385                 390                 395                 400

Leu Gln Ser Gly Asn Ser Gln Glu Ser Val Thr Glu Gln Asp Ser Lys
            405                 410                 415

Asp Ser Thr Tyr Ser Leu Ser Ser Thr Leu Thr Leu Ser Lys Ala Asp
        420                 425                 430

Tyr Glu Lys His Lys Val Tyr Ala Cys Glu Val Thr His Gln Gly Leu
    435                 440                 445

Ser Ser Pro Val Thr Lys Ser Phe Asn Arg Gly Glu Cys Asp Lys Thr
450                 455                 460

His Thr Cys Pro Pro Cys Pro Ala Pro Glu Ala Ala Gly Gly Pro Ser
465                 470                 475                 480

Val Phe Leu Phe Pro Pro Lys Pro Lys Asp Thr Leu Met Ile Ser Arg
            485                 490                 495

Thr Pro Glu Val Thr Cys Val Val Val Asp Val Ser His Glu Asp Pro
        500                 505                 510

Glu Val Lys Phe Asn Trp Tyr Val Asp Gly Val Glu Val His Asn Ala
    515                 520                 525

Lys Thr Lys Pro Arg Glu Glu Gln Tyr Asn Ser Thr Tyr Arg Val Val
530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Gly Ala Pro Ile Glu Lys Thr
            565                 570                 575

Ile Ser Lys Ala Lys Gly Gln Pro Arg Glu Pro Gln Val Tyr Thr Leu
        580                 585                 590

Pro Pro Cys Arg Asp Glu Leu Thr Lys Asn Gln Val Ser Leu Trp Cys
    595                 600                 605

Leu Val Lys Gly Phe Tyr Pro Ser Asp Ile Ala Val Glu Trp Glu Ser
610                 615                 620

Asn Gly Gln Pro Glu Asn Asn Tyr Lys Thr Thr Pro Pro Val Leu Asp
625                 630                 635                 640

```
Ser Asp Gly Ser Phe Phe Leu Tyr Ser Lys Leu Thr Val Asp Lys Ser
            645                 650                 655

Arg Trp Gln Gln Gly Asn Val Phe Ser Cys Ser Val Met His Glu Ala
        660                 665                 670

Leu His Asn His Tyr Thr Gln Lys Ser Leu Ser Leu Ser Pro Gly Lys
            675                 680                 685

<210> SEQ ID NO 122
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
```

```
              305                 310                 315                 320
Val Ser Asn Lys Ala Leu Gly Ala Pro Ile Glu Lys Thr Ile Ser Lys
                325                 330                 335

Ala Lys Gly Gln Pro Arg Glu Pro Gln Val Cys Thr Leu Pro Pro Ser
                340                 345                 350

Arg Asp Glu Leu Thr Lys Asn Gln Val Ser Leu Ser Cys Ala Val Lys
                355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 123
<211> LENGTH: 455
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
                20                  25                  30

Ala Met Asn Trp Val Arg Gln Ala Pro Gly Lys Gly Leu Glu Trp Val
            35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220
```

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
        260                 265                 270

Asp Val Ser His Glu Asp Pro Glu Val Lys Phe Asn Trp Tyr Val Asp
    275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 124
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Gly Gln Pro
            100                 105                 110

```
Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
        130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 125
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 126
<211> LENGTH: 1425
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 126
atgggatgga gctgtatcat cctcttcttg gtagcaacag ctaccggtgt gcattccgag      60
gtgcagctgc tggaatctgg cggcggactg gtgcagcctg gcggatctct gagactgagc     120
tgtgccgcca gcggcttcac cttcagcacc tacgccatga actgggtgcg ccaggcccct     180
ggcaaaggcc tggaatgggt gtcccggatc agaagcaagt acaacaacta cgccacctac     240
tacgccgaca gcgtgaaggg ccggttcacc atcagccggg acgacagcaa gaacaccctg     300
tacctgcaga tgaacagcct gcgggccgag gacaccgccg tgtactattg tgcggcac      360 ggcaacttcg gcaacagcta tgtgtcttgg tttgcctact ggggccaggg caccctcgtg     420
```

```
accgtgtcat ctgctagcac caagggccca tcggtcttcc ccctggcacc ctcctccaag      480
agcacctctg ggggcacagc ggccctgggc tgcctggtca aggactactt ccccgaaccg      540
gtgacggtgt cgtggaactc aggcgccctg accagcggcg tgcacacctt cccggctgtc      600
ctacagtcct caggactcta ctccctcagc agcgtggtga ccgtgccctc agcagcttg       660 ggcacccaga cctacatctg caacgtgaat cacaagccca gcaacaccaa ggtggacaag      720
aaagttgagc ccaaatcttg tgacaaaact cacacatgcc caccgtgccc agcacctgaa      780
ctcctggggg gaccgtcagt cttcctcttc cccccaaaac ccaaggacac cctcatgatc      840
tcccggaccc ctgaggtcac atgcgtggtg gtggacgtga gccacgaaga ccctgaggtc      900
aagttcaact ggtacgtgga cggcgtggag gtgcataatg ccaagacaaa gccgcgggag      960
gagcagtaca acagcacgta ccgtgtggtc agcgtcctca ccgtcctgca ccaggactgg     1020
ctgaatggca aggagtacaa gtgcaaggtc tccaacaaag ccctcccagc ccccatcgag     1080
aaaaccatct ccaaagccaa agggcagccc cgagaaccac aggtgtacac cctgccccca     1140
tcccgggatg agctgaccaa gaaccaggtc agcctgacct gcctggtcaa aggcttctat     1200
cccagcgaca tcgccgtgga gtgggagagc aatgggcagc cggagaacaa ctacaagacc     1260
acgcctcccg tgctggactc cgacggctcc ttcttcctct acagcaagct caccgtggac     1320
aagagcaggt ggcagcaggg gaacgtcttc tcatgctccg tgatgcatga ggctctgcac     1380
aaccactaca cgcagaagag cctctccctg tctccgggta aatga                     1425

<210> SEQ ID NO 127
<211> LENGTH: 705
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 127
atgggatgga gctgtatcat cctcttcttg gtagcaacag ctaccggtgt gcattctcag       60
gccgtcgtga cccaggaacc cagcctgaca gtgtctcctg gcggcaccgt gaccctgaca      120
tgtggcagtt ctacaggcgc cgtgaccacc agcaactacg ccaactgggt gcaggaaaag      180
cccggccagg ccttcagagg actgatcggc ggcaccaaca gagagcccc tggcacccct       240 gccagattca gcggatctct gctgggagga aaggccgccc tgacactgtc tggcgcccag      300
ccagaagatg aggccgagta ctactgcgcc ctgtggtaca gcaacctgtg ggtgttcggc      360
ggaggcacca agctgacagt cctaggtcaa cccaaggctg ccccagcgt gaccctgttc       420 ccccccagca gcgaggaact gcaggccaac aaggccaccc tggtctgcct gatcagcgac      480
ttctacccag gcgccgtgac cgtggcctgg aaggccgaca gcagcccgt gaaggccggc       540 gtggagacca ccacccccag caagcagagc aacaacaagt acgccgccag cagctacctg      600
agcctgaccc ccgagcagtg gaagagccac aggtcctaca gctgccaggt gacccacgag      660
ggcagcaccg tggagaaaac cgtggccccc accgagtgca gctga                     705

<210> SEQ ID NO 128
<211> LENGTH: 432
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 128

```
atgggatgga gctgtatcat cctcttcttg gtagcaacag ctaccggtgt gcattccgag      60
gtgcagctgc tggaatctgg cggcggactg gtgcagcctg gcggatctct gagactgagc     120
tgtgccgcca gcggcttcac cttcagcacc tacgccatga actgggtgcg ccaggcccct     180
ggcaaaggcc tggaatgggt gtcccggatc agaagcaagt acaacaacta cgccacctac     240
tacgccgaca gcgtgaaggg ccggttcacc atcagccggg acgacagcaa gaacaccctg     300
tacctgcaga tgaacagcct gcgggccgag gacaccgccg tgtactattg tgtgcggcac     360
ggcaacttcg gcaacagcta tgtgtcttgg tttgcctact ggggccaggg caccctcgtg     420
accgtgtcat ct                                                         432
```

<210> SEQ ID NO 129
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129

```
acctacgcca tgaac                                                       15
```

<210> SEQ ID NO 130
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130

```
cggatcagaa gcaagtacaa caactacgcc acctactacg ccgacagcgt gaagggc         57
```

<210> SEQ ID NO 131
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131

```
cacggcaact tcggcaacag ctatgtgtct tggtttgcct ac                         42
```

<210> SEQ ID NO 132
<211> LENGTH: 384
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 132

```
atgggatgga gctgtatcat cctcttcttg gtagcaacag ctaccggtgt gcattctcag      60
gccgtcgtga cccaggaacc cagcctgaca gtgtctcctg gcggcaccgt gaccctgaca     120
tgtggcagtt ctacaggcgc cgtgaccacc agcaactacg ccaactgggt gcaggaaaag     180
```

```
cccggccagg ccttcagagg actgatcggc ggcaccaaca agagagcccc tggcacccct    240
gccagattca gcggatctct gctgggagga aaggccgccc tgacactgtc tggcgcccag    300
ccagaagatg aggccgagta ctactgcgcc ctgtggtaca gcaacctgtg ggtgttcggc    360
ggaggcacca agctgacagt ccta                                           384
```

<210> SEQ ID NO 133
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 133

```
ggcagttcta caggcgccgt gaccaccagc aactacgcca ac                        42
```

<210> SEQ ID NO 134
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 134

```
ggcaccaaca agagagcccc t                                               21
```

<210> SEQ ID NO 135
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 135

```
gccctgtggt acagcaacct gtgggtg                                         27
```

<210> SEQ ID NO 136
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 136

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

|   |   | 85 |   |   |   | 90 |   |   |   | 95 |   |
|---|---|---|---|---|---|---|---|---|---|---|---|

Ala Lys Pro Phe Pro Tyr Phe Asp Tyr Trp Gly Gln Gly Thr Leu Val
              100                     105                 110

Thr Val Ser Ser
         115

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147
<400> SEQUENCE: 147

000

<210> SEQ ID NO 148
<400> SEQUENCE: 148

000

<210> SEQ ID NO 149
<400> SEQUENCE: 149

000

<210> SEQ ID NO 150
<400> SEQUENCE: 150

000

<210> SEQ ID NO 151
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 151

```
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg acccgtgaca ctagcacctc taccgtttat   240
atggagctgt ccagcctgcg ttctgaagat actgcagtgt actactgtgc acgcaactac   300
tacgctggtg ttactccgtt cgactattgg ggtcaaggca ccctcgtaac ggtttcttct   360
```

<210> SEQ ID NO 152
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 152

```
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg acccgtgaca ctagcacctc taccgtttat   240
atggagctgt ccagcctgcg ttctgaagat actgcagtgt actactgtgc acgcaactac   300
tacatcggtg ttgttacttt cgactattgg ggtcaaggca ccctcgtaac ggtttcttct   360
```

<210> SEQ ID NO 153
<211> LENGTH: 363
<212> TYPE: DNA

<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 153

```
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg acccgtgaca ctagcacctc taccgtttat   240
atggagctgt ccagcctgcg ttctgaagat actgcagtgt actactgtgc acgcaactac   300
tacactggtg gttcttctgc tttcgactat tggggtcaag gcaccctcgt aacggtttct   360
tct                                                                 363
```

<210> SEQ ID NO 154
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"
<220> FEATURE:
<221> NAME/KEY: modified_base
<222> LOCATION: (47)..(47)
<223> OTHER INFORMATION: a, c, t, g, unknown or other

<400> SEQUENCE: 154

```
caggtgcaat tggttcaatc tggtgctgaa gtaaaaaaac cgggcgnttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg acccgtgaca ctagcacctc taccgtttat   240
atggagctgt ccagcctgcg ttctgaagat actgcagtgt actactgtgc acgcggtgaa   300
tggcgtcgtt acacttcttt cgactattgg ggtcaaggca ccctcgtaac ggtttcttct   360
```

<210> SEQ ID NO 155
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 155

```
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg acccgtgaca ctagcacctc taccgtttat   240
atggagctgt ccagcctgcg ttctgaagat actgcagtgt actactgtgc acgcggtggt   300
tggatccgtt gggaacattt cgactattgg ggtcaaggca ccctcgtaac ggtttcttct   360
```

<210> SEQ ID NO 156
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 156
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg acccgtgaca ctagcacctc taccgtttat   240
atggagctgt ccagcctgcg ttctgaagat actgcagtgt actactgtgc acgcaactac   300
tacctgttct ctacttcttt cgactattgg ggtcaaggca ccctcgtaac ggtttcttct   360

<210> SEQ ID NO 157
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 157
caggtgcaat tggttcaatc tggtgctgag gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg acccgtgaca ctagcacctc taccgtttat   240
atggagctgt ccagcctgcg ttctgaagat actgcagtgt actactgtgc acgcaactac   300
tacatcggta tcgttccgtt cgactattgg ggtcaaggca ccctcgtaac ggtttcttct   360

<210> SEQ ID NO 158
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 158
gaggtgcaat tggttgaatc tggtggtggt ctggtaaaac cgggcggttc cctgcgtctg    60
agctgcgcgg cttccggatt caccttctcc aacgcgtgga tgagctgggt tcgccaggcc   120
ccgggcaaag gcctcgagtg ggttggtcgt atcaagtcta aaactgacgg tggcaccacg   180
gattacgcgc ctccagttaa aggtcgtttt accatttccc gcgacgatag caaaaacact   240
ctgtatctgc agatgaactc tctgaaaact gaagacaccg cagtctacta ctgtactacc   300
ccgtgggaat ggtcttggta cgattattgg ggccaggca cgctggttac ggtgtcttcc   360

<210> SEQ ID NO 159
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (53)..(53)

<223> OTHER INFORMATION: a, c, t, g, unknown or other

<400> SEQUENCE: 159

```
gaggtgcaat tggttgaatc tggtggtggt ctggtaaaac cgggcggttc ccngcgtctg    60
agctgcgcgg cttccggatt caccttctcc aacgcgtgga tgagctgggt tcgccaggcc   120
ccgggcaaag gcctcgagtg ggttggtcgt atcaagtcta aaactgacgg tggcaccacg   180
gattacgcgg ctccagttaa aggtcgtttt accatttccc gcgacgatag caaaaacact   240
ctgtatctgc agatgaactc tctgaaaacc gaagacaccg cagtctacta ctgtactacc   300
ccgtgggaat ggtcttactt cgattattgg ggccagggca cgctggttac ggtgtcttcc   360
```

<210> SEQ ID NO 160
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 160

```
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg acccgtgaca ctagcacctc taccgtttat   240
atggagctgt ccagcctgcg ttctgaagat actgcagtgt actactgtgc acgcaactac   300
tacgttggtg tttctccgtt cgactattgg ggtcaaggca ccctcgtaac ggtttcttct   360
```

<210> SEQ ID NO 161
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (47)..(47)
<223> OTHER INFORMATION: a, c, t, g, unknown or other
<220> FEATURE:
<221> NAME/KEY: modified_base
<222> LOCATION: (177)..(177)
<223> OTHER INFORMATION: a, c, t, g, unknown or other

<400> SEQUENCE: 161

```
caggtgcaat tggttcaatc tggtgctgaa gtaaaaaaac cgggcgnttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcntac   180
gcgcagaaat tccagggtcg cgtcacgatg acccgtgaca ctagcacctc taccgtttat   240
atggagctgt ccagcctgcg ttctgaagat actgcagtgt actactgtgc acgcaacttc   300
actgttctgc gtgttccgtt cgactattgg ggtcaaggca ccctcgtaac ggtttcttct   360
```

<210> SEQ ID NO 162
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 162

| gaggtgcaat tggttgaatc tggtggtggt ctggtaaaac cgggcggttc cctgcgtctg | 60 |
| agctgcgcgg cttccggatt caccttctcc aacgcgtgga tgagctgggt tcgccaggcc | 120 |
| ccgggcaaag gcctcgagtg ggttggtcgt atcaagtcta aaactgacgg tggcaccacg | 180 |
| gattacgcgg ctccagttaa aggtcgtttt accatttccc gcgacgatag caaaaacact | 240 |
| ctgtatctgc agatgaactc tctgaaaact gaagacaccg cagtctacta ctgtactacc | 300 |
| ccgtgggaat gggcttggtt cgattattgg ggccagggca cgctggttac ggtgtcttcc | 360 |

<210> SEQ ID NO 163
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 163

| gaggtgcaat tggttgaatc tggtggtggt ctggtaaaac cgggcggttc cctgcgtctg | 60 |
| agctgcgcgg cttccggatt caccttctcc aacgcgtgga tgagctgggt tcgccaggcc | 120 |
| ccgggcaaag gcctcgagtg ggttggtcgt atcaagtcta aaactgacgg tggcaccacg | 180 |
| gattacgcgg ctccagttaa aggtcgtttt accatttccc gcgacgatag caaaaacact | 240 |
| ctgtatctgc agatgaactc tctgaaaacc gaagacaccg cagtctacta ctgtactacc | 300 |
| ccttgggaat gggcttactt cgattattgg ggccagggca cgctggttac ggtgtcttcc | 360 |

<210> SEQ ID NO 164
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 164

| caggtgcaat tggttcaatc tggtgctgaa gtaaaaaaac cgggcgcttc cgttaaagtg | 60 |
| agctgcaaag catccggata caccttcact tcctattaca tgcactgggt tcgtcaagcc | 120 |
| ccgggccagg gtctggaatg gatgggcatc attaacccaa gcggtggctc tacctcctac | 180 |
| gcgcagaaat tccagggtcg cgtcacgatg acccgtgaca ctagcacctc taccgtttat | 240 |
| atggagctgt ccagcctgcg ttctgaagat actgcagtgt actactgtgc acgcactggt | 300 |
| tggtctcgtt ggggttacat ggactattgg ggccaaggca ccctcgtaac ggtttcttct | 360 |

<210> SEQ ID NO 165
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 165

| caggtgcaat tggttcaatc tggtgctgaa gtaaaaaaac cgggcgcttc cgttaaagtg | 60 |

| | |
|---|---|
| agctgcaaag catccggata caccttcact tcctattaca tgcactgggt tcgtcaagcc | 120 |
| ccgggccagg gtctggaatg gatgggcatc attaacccaa gcggtggctc tacctcctac | 180 |
| gcgcagaaat tccagggtcg cgtcacgatg acccgtgaca ctagcacctc taccgtttat | 240 |
| atggagctgt ccagcctgcg ttctgaagat actgcagtgt actactgtgc acgcggtgaa | 300 |
| tggatccgtt actaccattt cgactattgg ggtcaaggca ccctcgtaac ggtttcttct | 360 |

<210> SEQ ID NO 166
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 166

| | |
|---|---|
| caggtgcaat tggttcaatc tggtgctgaa gtaaaaaaac cgggcgcttc cgttaaagtg | 60 |
| agctgcaaag catccggata caccttcact tcctattaca tgcactgggt tcgtcaagcc | 120 |
| ccgggccagg gtctggaatg gatgggcatc attaacccaa gcggtggctc tacctcctac | 180 |
| gcgcagaaat tccagggtcg cgtcacgatg acccgtgaca ctagcacctc taccgtttat | 240 |
| atggagctgt ccagcctgcg ttctgaagat actgcagtgt actactgtgc acgcgttggt | 300 |
| tggtaccgtt ggggttacat ggactattgg ggtcaaggca ccctcgtaac ggtttcttct | 360 |

<210> SEQ ID NO 167
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 167

| | |
|---|---|
| caggtgcaat tggtgcagtc tggggctgag gtgaagaagc ctgggtcctc ggtgaaggtc | 60 |
| tcctgcaagg cctccggagg cacattcagc agctacgcta taagctgggt gcgacaggcc | 120 |
| cctggacaag ggctcgagtg gatgggaggg atcatcccta tctttggtac agcaaactac | 180 |
| gcacagaagt tccagggcag ggtaaccatt actgcagaca atccacgaga cacagcctac | 240 |
| atggagctga gcagcctgag atctgaggac accgccgtgt attactgtgc gagagctgtt | 300 |
| ttctaccgtg cttggtactc tttcgactac tggggccaag gaccaccgt gaccgtctcc | 360 |
| tca | 363 |

<210> SEQ ID NO 168
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 168

| | |
|---|---|
| gacatccaga tgacccagtc tccttccacc ctgtctgcat ctgtaggaga ccgtgtcacc | 60 |
| atcacttgcc gtgccagtca gagtattagt agctggttgg cctggtatca gcagaaacca | 120 |
| gggaaagccc ctaagctcct gatctatgat gcctccagtt tggaaagtgg ggtcccatca | 180 |
| cgtttcagcg gcagtggatc cgggacagaa ttcactctca ccatcagcag cttgcagcct | 240 |

```
gatgattttg caacttatta ctgccaacag tataccagcc caccaccaac gtttggccag    300
ggcaccaaag tcgagatcaa g                                              321
```

<210> SEQ ID NO 169
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 169

```
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctggaatg gatgggcatc attaacccaa gcggtggctc tacctcctac    180
gcgcagaaat tccagggtcg cgtcacgatg acccatgaca ctagcacctc taccgtttat    240
atggagctgt ccagcctgcg ttctgaagat actgcagtgt actactgtgc acgctctttc    300
ttcactggtt tccatctgga ctattggggt caaggcaccc tcgtaacggt ttcttct      357
```

<210> SEQ ID NO 170
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 170

```
gaaatcgtgt taacgcagtc tccaggcacc ctgtctttgt ctccagggga aagagccacc     60
ctctcttgca gggccagtca gagtgttagc agcagctact tagcctggta ccagcagaaa    120
cctggccagg ctcccaggct cctcatctat ggagcatcca gcagggccac tggcatccca    180
gacaggttca gtggcagtgg atccgggaca gacttcactc tcaccatcag cagactggag    240
cctgaagatt ttgcagtgta ttactgtcag cagtatacca cgaacatta ttatacgttc     300 ggccagggga ccaaagtgga aatcaaa                                        327
```

<210> SEQ ID NO 171
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 171

```
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctggaatg gatgggcatc attaacccaa gcggtggccc tacctcctac    180
gcgcagaaat tccagggtcg cgtcacgatg acccgtgaca ctagcacctc taccgtttat    240
atggagctgt ccagcctgcg ttctgaagat actgcagtgt actactgtgc acgcggtgac    300
ttcgcttggc tggactattg gggtcaaggc accctcgtaa cggtttcttc t             351
```

<210> SEQ ID NO 172

```
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 172
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcaag cattatgaac   300
cggacttttg gtcaaggcac caaggtcgaa attaaa                             336

<210> SEQ ID NO 173
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 173
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcaag cattatgagc   300
cggacttttg gtcaaggcac caaggtcgaa attaaa                             336

<210> SEQ ID NO 174
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 174
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcaag cattatgcag   300
cggacttttg gtcaaggcac caaggtcgaa attaaa                             336

<210> SEQ ID NO 175
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 175

```
gatattgtta tgactcaatc tccactgtct ctgccggtga ctccaggcga accggcgagc     60
atttcttgcc gttccagcca gtctctgctg cactccaacg gctacaacta tctcgattgg    120
tacctgcaaa aaccgggtca gagccctcag ctgctgatct acctgggctc taaccgcgct    180
tccggtgtac cggaccgttt cagcggctct ggatccggca ccgatttcac gttgaaaatc    240
agccgtgttg aagcagaaga cgtgggcgtt tattactgta tgcaggcaag cattatgaac    300
cgggcttttg gtcaaggcac caaggtcgaa attaaa                              336
```

<210> SEQ ID NO 176
<211> LENGTH: 336
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 176

```
gatattgtta tgactcaatc tccactgtct ctgccggtga ctccaggcga accggcgagc     60
atttcttgcc gttccagcca gtctctgctg cactccaacg gctacaacta tctcgattgg    120
tacctgcaaa aaccgggtca gagccctcag ctgctgatct acctgggctc taaccgcgct    180
tccggtgtac cggaccgttt cagcggctct ggatccggca ccgatttcac gttgaaaatc    240
agccgtgttg aagcagaaga cgtgggcgtt tattactgta tgcaggcaag cattatgaac    300
cggaattttg gtcaaggcac caaggtcgaa attaaa                              336
```

<210> SEQ ID NO 177
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 177

```
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctggaatg gatgggcatc attaacccaa gcggtggctc tacctcctac    180
gcgcagaaat tccagggtcg cgtcacgatg accgtgaca ctagcacctc taccgtttat    240
atggagctgt ccagcctgcg ttctgaagat actgcagtgt actactgtgc acgctcttac    300
atcgacatgg actattgggg tcaaggcacc ctcgtaacgg tttcttct                 348
```

<210> SEQ ID NO 178
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 178

```
gaaatcgtgt taacgcagtc tccaggcacc ctgtctttgt ctccagggga aagagccacc     60
ctctcttgca gggccagtca gagtgttagc agcagctact tagcctggta ccagcagaaa    120
```

```
cctggccagg ctcccaggct cctcatctat ggagcatcca gcagggccac tggcatccca    180
gacaggttca gtggcagtgg atccgggaca gacttcactc tcaccatcag cagactggag    240
cctgaagatt ttgcagtgta ttactgtcag caggataact ggagcccaac gttcggccag    300
gggaccaaag tggaaatcaa a                                              321
```

<210> SEQ ID NO 179
<211> LENGTH: 348
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 179

```
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctggaatg gatgggcatc attaacccaa gcggtggctc tacctcctac    180
gcgcagaaat tccagggtcg cgtcacgatg acccgtgaca ctagcacctc taccgtttat    240
atggagctgt ccagcctgcg ttctgaagat actgcagtgt actactgtgc acgtcttac    300 gttgacatgg actattgggg tcaaggcacc ctcgtaacgg tttcttct               348
```

<210> SEQ ID NO 180
<211> LENGTH: 321
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 180

```
gaaatcgtgt taacgcagtc tccaggcacc ctgtctttgt ctccagggga aagagccacc     60
ctctcttgca gggccagtca gagtgttagc agcagctacc tagcctggta ccagcagaaa    120
cctggccagg ctcccaggct cctcatctat ggagcatcca gcagggccac tggcatccca    180
gacaggttca gtggcagtgg atccgggaca gacttcactc tcaccatcag cagactggag    240
cctgaagatt ttgcagtgta ttactgtcag caggatattt ggagcccaac gttcggccag    300
gggaccaaag tggaaatcaa a                                              321
```

<210> SEQ ID NO 181
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 181

```
gaggtgcaat tgttggagtc tgggggaggc ttggtacagc ctggggggtc cctgagactc     60
tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaagactct    300
tcttacgttg aatggtacgc tttcgactac tggggccaag gaaccctggt caccgtctcg    360
``` agt                                                                    363

<210> SEQ ID NO 182
<211> LENGTH: 324
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 182
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gactccactc tcaccatcag cagactggag     240
cctgaagatt ttgcagtgta ttactgtcag cagccaacca gcagcccaat tacgttcggc     300
caggggacca aagtggaaat caaa                                            324

<210> SEQ ID NO 183
<211> LENGTH: 684
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 183
gaggtgcagc tgctggaatc tggcggcgga ctggtgcagc ctggcggatc tctgagactg      60
agctgtgccg ccagcggctt caccttcagc acctacgcca tgaactgggt gcgccaggcc     120
cctggcaaag gcctggaatg ggtgtcccgg atcagaagca agtacaacaa ctacgccacc     180
tactacgccg acagcgtgaa gggccggttc accatcagcc gggacgacag caagaacacc     240
ctgtacctgc agatgaacag cctgcgggcc gaggacaccg ccgtgtacta ttgtgtgcgg     300
cacggcaact tcggcaacag ctatgtgtct tggtttgcct actggggcca gggcaccctc     360
gtgaccgtgt caagcgctag taccaagggc ccagcgtgt tccccctggc acccagcagc      420
aagagcacat ctgcggaac agccgctctg gctgtctgg tgaaagacta cttccccgag      480
cccgtgaccg tgtcttggaa ctctggcgcc ctgaccagcg gcgtgcacac ctttccagcc     540
gtgctgcaga gcagcggcct gtactccctg tcctccgtgg tcaccgtgcc ctctagctcc     600
ctgggaacac agacatatat ctgtaatgtc aatcacaagc cttccaacac caaagtcgat     660
aagaaagtcg agcccaagag ctgc                                            684

<210> SEQ ID NO 184
<211> LENGTH: 696
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 184
gaggtgcagc tgctggaatc tggcggcgga ctggtgcagc ctggcggatc tctgagactg      60
agctgtgccg ccagcggctt caccttcagc acctacgcca tgaactgggt gcgccaggcc     120

```
cctggcaaag gcctggaatg ggtgtcccgg atcagaagca agtacaacaa ctacgccacc    180
tactacgccg acagcgtgaa gggccggttc accatcagcc gggacgacag caagaacacc    240
ctgtacctgc agatgaacag cctgcgggcc gaggacaccg ccgtgtacta ttgtgtgcgg    300
cacggcaact tcggcaacag ctatgtgtct tggtttgcct actggggcca gggcaccctc    360
gtgaccgtgt caagcgctag tgtggccgct ccctccgtgt ttatctttcc cccatccgat    420
gaacagctga aaagcggcac cgcctccgtc gtgtgtctgc tgaacaattt ttaccctagg    480
gaagctaaag tgcagtggaa agtggataac gcactgcagt ccggcaactc ccaggaatct    540
gtgacagaac aggactccaa ggacagcacc tactccctgt cctccaccct gacactgtct    600
aaggctgatt atgagaaaca caaagtctac gcctgcgaag tcacccatca gggcctgagc    660
tcgcccgtca caaagagctt caacagggga gagtgt                              696
```

<210> SEQ ID NO 185
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 185

```
gcaggcaagc attatgcagc ggacttttgg tcaagg                              36
```

<210> SEQ ID NO 186
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 186

```
caggcaagca ttatgagccg gactttggt caagg                                35
```

<210> SEQ ID NO 187
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 187

```
cattatgaac cgggcttttg gtcaaggcac caaggtc                             37
```

<210> SEQ ID NO 188
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 188

```
cattatgaac cggaattttg gtcaaggcac caaggtc                             37
```

<210> SEQ ID NO 189
<211> LENGTH: 2067

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 189

| | |
|---|---:|
| gaggtgcaat tggttgaatc tggtggtggt ctggtaaaac cgggcggttc cctgcgtctg | 60 |
| agctgcgcgg cttccggatt caccttctcc aacgcgtgga tgagctgggt tcgccaggcc | 120 |
| ccgggcaaag gcctcgagtg ggttggtcgt atcaagtcta aaactgacgg tggcaccacg | 180 |
| gattacgcgg ctccagttaa aggtcgtttt accatttccc gcgacgatag caaaaacact | 240 |
| ctgtatctgc agatgaactc tctgaaaact gaagacaccg cagtctacta ctgtactacc | 300 |
| ccgtgggaat ggtcttggta cgattattgg ggccagggca cgctggttac ggtgtcttcc | 360 |
| gctagcacaa agggccctag cgtgttccct ctggccccca gcagcaagag cacaagcggc | 420 |
| ggaacagccg ccctgggctg cctcgtgaag gactacttcc ccgagcccgt gacagtgtct | 480 |
| tggaacagcg gagccctgac aagcggcgtg cacactttcc ctgccgtgct gcagagcagc | 540 |
| ggcctgtact ccctgagcag cgtggtcacc gtgcctagca gcagcctggg cacccagacc | 600 |
| tacatctgca acgtgaacca caagcccagc aacaccaaag tggacaagaa ggtggagccc | 660 |
| aagagctgtg atggcggagg agggtccgga ggcggaggat ccgaggtgca gctgctggaa | 720 |
| tctggcggcg gactggtgca gcctggcgga tctctgagac tgagctgtgc cgccagcggc | 780 |
| ttcaccttca gcacctacgc catgaactgg gtgcgccagg cccctggcaa aggcctggaa | 840 |
| tgggtgtccc ggatcagaag caagtacaac aactacgcca cctactacgc cgacagcgtg | 900 |
| aagggccggt tcaccatcag ccgggacgac agcaagaaca ccctgtacct gcagatgaac | 960 |
| agcctgcggg ccgaggacac cgccgtgtac tattgtgtgc ggcacggcaa cttcggcaac | 1020 |
| agctatgtgt cttggtttgc ctactggggc cagggcaccc tcgtgaccgt gtcaagcgct | 1080 |
| agtaccaagg gcccagcgt gttcccctg gcacccagca gcaagagcac atctggcgga | 1140 |
| acagccgctc tgggctgtct ggtgaaagac tactttcccg agcccgtgac cgtgtcttgg | 1200 |
| aactctggcg ccctgaccag cggcgtgcac acctttccag ccgtgctgca gagcagcggc | 1260 |
| ctgtactccc tgtcctccgt ggtcaccgtg ccctctagct ccctgggaac acagacatat | 1320 |
| atctgtaatg tcaatcacaa gccttccaac accaaagtcg ataagaaagt cgagcccaag | 1380 |
| agctgcgaca aaactcacac atgcccaccg tgcccagcac ctgaagctgc aggggaccg | 1440 |
| tcagtcttcc tcttcccccc aaaacccaag gacaccctca tgatctcccg gacccctgag | 1500 |
| gtcacatgcg tggtggtgga cgtgagccac gaagaccctg aggtcaagtt caactggtac | 1560 |
| gtggacggcg tggaggtgca taatgccaag acaaagccgc gggaggagca gtacaacagc | 1620 |
| acgtaccgtg tggtcagcgt cctcaccgtc ctgcaccagg actggctgaa tggcaaggag | 1680 |
| tacaagtgca aggtctccaa caaagccctc ggcgccccca tcgagaaaac catctccaaa | 1740 |
| gccaaagggc agccccgaga accacaggtg tacaccctgc cccatgccg ggatgagctg | 1800 |
| accaagaacc aggtcagcct gtggtgcctg gtcaaaggct tctatcccag cgacatcgcc | 1860 |
| gtggagtggg agagcaatgg gcagccggag aacaactaca agaccacgcc tcccgtgctg | 1920 |
| gactccgacg gctccttctt cctctacagc aagctcaccg tggacaagag caggtggcag | 1980 |
| caggggaacg tcttctcatg ctccgtgatg catgaggctc tgcacaacca ctacacgcag | 2040 |
| aagagcctct ccctgtctcc gggtaaa | 2067 |

<210> SEQ ID NO 190
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 190

```
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc     120
ccgggcaaag gcctcgagtg ggttggtcgt atcaagtcta aaactgacgg tggcaccacg     180
gattacgcgg ctccagttaa aggtcgtttt accatttccc gcgacgatag caaaaacact     240
ctgtatctgc agatgaactc tctgaaaact gaagacaccg cagtctacta ctgtactacc     300
ccgtgggaat ggtcttggta cgattattgg ggccagggca cgctggttac ggtgtcttcc     360
gctagcacca agggcccctc cgtgttcccc ctggccccca gcagcaagag caccagcggc     420
ggcacagccg ctctgggctg cctggtcaag gactacttcc ccgagcccgt gaccgtgtcc     480
tggaacagcg gagccctgac ctccggcgtg cacaccttcc ccgccgtgct gcagagttct     540
ggcctgtata gcctgagcag cgtggtcacc gtgccttcta gcagcctggg cacccagacc     600
tacatctgca acgtgaacca caagcccagc aacaccaagg tggacaagaa ggtggagccc     660
aagagctgcg acaaaactca cacatgccca ccgtgcccag cacctgaagc tgcaggggga     720
ccgtcagtct tcctcttccc cccaaaaccc aaggacaccc tcatgatctc ccggacccct     780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcggcgccc ccatcgagaa aaccatctcc    1020
aaagccaaag gcagccccg agaaccacag gtgtgcaccc tgcccccatc ccgggatgag    1080
ctgaccaaga accaggtcag cctctcgtgc gcagtcaaag gcttctatcc cagcgacatc    1140
gccgtggagt gggagagcaa tgggcagccg gagaacaact acaagaccac gcctcccgtg    1200
ctggactccg acggctcctt cttcctcgta gcaagctca ccgtggacaa gagcaggtgg     1260
cagcagggga acgtcttctc atgctccgtg atgcatgagg ctctgcacaa ccgcttcacg    1320
cagaagagcc tctccctgtc tccgggtaaa                                    1350
```

<210> SEQ ID NO 191
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 191

```
caggccgtcg tgacccagga acccagcctg acagtgtctc ctggcggcac cgtgaccctg      60
acatgtggca gttctacagg cgccgtgacc accagcaact acgccaactg ggtgcaggaa     120
aagcccggcc aggccttcag aggactgatc ggcggcacca acaagagagc ccctggcacc     180
cctgccagat tcagcggatc tctgctggga ggaaaggccg ccctgacact gtctggcgcc     240
cagccagaag atgaggccga gtactactgc gccctgtggt acagcaacct gtgggtgttc     300
```

```
ggcggaggca ccaagctgac agtcctaggt caacccaagg ctgccccag cgtgaccctg      360 ttccccccca gcagcgagga actgcaggcc aacaaggcca ccctggtctg cctgatcagc      420
gacttctacc caggcgccgt gaccgtggcc tggaaggccg acagcagccc cgtgaaggcc      480
ggcgtggaga ccaccacccc cagcaagcag agcaacaaca agtacgccgc cagcagctac      540
ctgagcctga cccccgagca gtggaagagc acaggtcct acagctgcca ggtgacccac      600
gagggcagca ccgtggagaa aaccgtggcc cccaccgagt gcagc                      645
```

<210> SEQ ID NO 192
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 192

```
gaggtgcagc tgctggaatc tggcggcgga ctggtgcagc ctggcggatc tctgagactg       60
agctgtgccg ccagcggctt caccttcagc acctacgcca tgaactgggt gcgccaggcc      120
cctggcaaag gcctggaatg ggtgtcccgg atcagaagca agtacaacaa ctacgccacc      180
tactacgccg acagcgtgaa gggccggttc accatcagcc gggacgacag caagaacacc      240
ctgtacctgc agatgaacag cctgcgggcc gaggacaccg ccgtgtacta ttgtgtgcgg      300
cacggcaact cggcaacag ctatgtgtct tggtttgcct actggggcca gggcacccctc      360 gtgaccgtgt catctgctag cacaaagggc cctagcgtgt tccctctggc ccccagcagc      420
aagagcacaa gcggcggaac agccgccctg ggctgcctcg tgaaggacta cttccccgag      480
cccgtgacag tgtcttggaa cagcggagcc ctgacaagcg gcgtgcacac cttccctgcc      540
gtgctgcaga gcagcggcct gtactccctg agcagcgtgg tcaccgtgcc tagcagcagc      600
ctgggcaccc agacctacat ctgcaacgtg aaccacaagc ccagcaacac caaagtggac      660
aagaaggtgg agcccaagag ctgtgatggc ggaggagggt ccggaggcgg aggatccgag      720
gtgcaattgg ttgaatctgg tggtggtctg gtaaaaccgg cggttccct gcgtctgagc      780 tgcgcggctt ccggattcac cttctccaac gcgtggatga gctgggttcg ccaggccccg      840
ggcaaaggcc tcgagtgggt tggtcgtatc aagtctaaaa ctgacggtgg caccacggat      900
tacgcggctc cagttaaagg tcgttttacc atttcccgcg acgatagcaa aaacactctg      960
tatctgcaga tgaactctct gaaaactgaa gacaccgcag tctactactg tactaccccg     1020
tgggaatggt cttggtacga ttattgggc cagggcacgc tggttacggt gtctagcgct     1080
agtaccaagg gcccagcgt gttccccctg gcacccagca gcagagcac atctggcgga     1140 acagccgctc tgggctgtct ggtgaaagac tacttccccg agcccgtgac cgtgtcttgg     1200
aactctggcg ccctgaccag cggcgtgcac accttccag ccgtgctgca gagcagcggc     1260
ctgtactccc tgtcctccgt ggtcaccgtg ccctctagct ccctgggaac acagacatat     1320
atctgtaatg tcaatcacaa gccttccaac accaaagtcg ataagaaagt cgagcccaag     1380
agctgcgaca aaactcacac atgcccaccg tgcccagcac ctgaagctgc aggggaccg     1440 tcagtcttcc tcttcccccc aaaacccaag gacaccctca tgatctcccg gaccctgag     1500 gtcacatgcg tggtggtgga cgtgagccac gaagaccctg aggtcaagtt caactggtac     1560
gtggacggcg tggaggtgca taatgccaag acaaagccgc gggaggagca gtacaacagc     1620
```

| | |
|---|---|
| acgtaccgtg tggtcagcgt cctcaccgtc ctgcaccagg actggctgaa tggcaaggag | 1680 |
| tacaagtgca aggtctccaa caaagccctc ggcgccccca tcgagaaaac catctccaaa | 1740 |
| gccaaagggc agccccgaga ccacaggtg tacaccctgc ccccatgccg ggatgagctg | 1800 |
| accaagaacc aggtcagcct gtggtgcctg gtcaaaggct tctatcccag cgacatcgcc | 1860 |
| gtggagtggg agagcaatgg gcagccggag aacaactaca agaccacgcc tcccgtgctg | 1920 |
| gactccgacg gctccttctt cctctacagc aagctcaccg tggacaagag caggtggcag | 1980 |
| caggggaacg tcttctcatg ctccgtgatg catgaggctc tgcacaacca ctacacgcag | 2040 |
| aagagcctct ccctgtctcc gggtaaa | 2067 |

<210> SEQ ID NO 193
<211> LENGTH: 1365
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 193

| | |
|---|---|
| gaggtgcagc tgctggaatc tggcggcgga ctggtgcagc ctggcggatc tctgagactg | 60 |
| agctgtgccg ccagcggctt caccttcagc acctacgcca tgaactgggt gcgccaggcc | 120 |
| cctggcaaag gcctggaatg ggtgtcccgg atcagaagca agtacaacaa ctacgccacc | 180 |
| tactacgccg acagcgtgaa gggccggttc accatcagcc gggacgacag caagaacacc | 240 |
| ctgtacctgc agatgaacag cctgcgggcc gaggacaccg ccgtgtacta ttgtgtgcgg | 300 |
| cacggcaact tcggcaacag ctatgtgtct tggtttgcct actggggcca gggcaccctc | 360 |
| gtgaccgtgt catctgctag caccaagggc ccatcggtct tccccctggc accctcctcc | 420 |
| aagagcacct ctgggggcac agcggccctg ggctgcctgg tcaaggacta cttccccgaa | 480 |
| ccggtgacgg tgtcgtggaa ctcaggcgcc ctgaccagcg gcgtgcacac cttcccggct | 540 |
| gtcctacagt cctcaggact ctactccctc agcagcgtgg tgaccgtgcc ctccagcagc | 600 |
| ttgggcaccc agacctacat ctgcaacgtg aatcacaagc ccagcaacac caaggtggac | 660 |
| aagaaagttg agcccaaatc ttgtgacaaa actcacacat gcccaccgtg cccagcacct | 720 |
| gaagctgcag gggaccgtc agtcttcctc ttccccccaa aacccaagga caccctcatg | 780 |
| atctcccgga cccctgaggt cacatgcgtg gtggtggacg tgagccacga agaccctgag | 840 |
| gtcaagttca actggtacgt ggacggcgtg gaggtgcata atgccaagac aaagccgcgg | 900 |
| gaggagcagt acaacagcac gtaccgtgtg gtcagcgtcc tcaccgtcct gcaccaggac | 960 |
| tggctgaatg gcaaggagta caagtgcaag gtctccaaca agccctcgg cgcccccatc | 1020 |
| gagaaaacca tctccaaagc caagggcag ccccgagaac cacaggtgta caccctgccc | 1080 |
| ccatgccggg atgagctgac caagaaccag gtcagcctgt ggtgcctggt caaaggcttc | 1140 |
| tatcccagcg acatcgccgt ggagtgggag agcaatgggc agccggagaa caactacaag | 1200 |
| accacgcctc ccgtgctgga ctccgacggc tccttcttcc tctacagcaa gctcaccgtg | 1260 |
| gacaagagca ggtggcagca ggggaacgtc ttctcatgct ccgtgatgca tgaggctctg | 1320 |
| cacaaccact acacgcagaa gagcctctcc ctgtctccgg gtaaa | 1365 |

<210> SEQ ID NO 194
<211> LENGTH: 681
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 194

| gacaaaactc acacatgccc accgtgccca gcacctgaac tcctgggggg accgtcagtc | 60 |
| ttcctcttcc ccccaaaacc caaggacacc ctcatgatct cccggacccc tgaggtcaca | 120 |
| tgcgtggtgg tggacgtgag ccacgaagac cctgaggtca agttcaactg gtacgtggac | 180 |
| ggcgtggagg tgcataatgc caagacaaag ccgcgggagg agcagtacaa cagcacgtac | 240 |
| cgtgtggtca gcgtcctcac cgtcctgcac caggactggc tgaatggcaa ggagtacaag | 300 |
| tgcaaggtct ccaacaaagc cctcccagcc cccatcgaga aaaccatctc caaagccaaa | 360 |
| gggcagcccc gagaaccaca ggtgtgcacc ctgcccccat cccgggatga gctgaccaag | 420 |
| aaccaggtca gcctctcgtg cgcagtcaaa ggcttctatc ccagcgacat cgccgtggag | 480 |
| tgggagagca atgggcagcc ggagaacaac tacaagacca cgcctcccgt gctggactcc | 540 |
| gacggctcct tcttcctcgt gagcaagctc accgtggaca agagcaggtg gcagcagggg | 600 |
| aacgtcttct catgctccgt gatgcatgag gctctgcaca accgcttcac gcagaagagc | 660 |
| ctctccctgt ctccgggtaa a | 681 |

<210> SEQ ID NO 195
<211> LENGTH: 2070
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 195

| caggtgcaat tggttcaatc tggtgctgaa gtaaaaaaac cgggcgcttc cgttaaagtg | 60 |
| agctgcaaag catccggata caccttcact tcctattaca tgcactgggt tcgtcaagcc | 120 |
| ccgggccagg gtctggaatg gatgggcatc attaacccaa gcggtggccc tacctcctac | 180 |
| gcgcagaaat tccagggtcg cgtcacgatg accggtgaca ctagcacctc taccgtttat | 240 |
| atggagctgt ccagcctgcg ttctgaagat actgcagtgt actactgtgc acgcggtgac | 300 |
| ttcgcttggc tggactattg gggtcaaggc accctcgtaa cggtttcttc tgctagcaca | 360 |
| aagggcccca gcgtgttccc tctggcccct agcagcaaga gcacatctgg cggaacagcc | 420 |
| gccctgggct gcctcgtgaa ggactacttt cccgagcctg tgaccgtgtc ctggaactct | 480 |
| ggcgccctga caagcggcgt gcacaccttt ccagccgtgc tgcagagcag cggcctgtac | 540 |
| tctctgagca gcgtggtcac cgtgcctagc agcagcctgg gcacccagac ctacatctgc | 600 |
| aacgtgaacc acaagcccag caacaccaaa gtggacaaga aggtggagcc caagagctgt | 660 |
| gatggcggag gagggtccgg aggcggagga tccgaggtgc agctgctgga atctggcggc | 720 |
| ggactggtgc agcctggcgg atctctgaga ctgagctgtg ccgccagcgg cttcaccttc | 780 |
| agcacctacg ccatgaactg ggtgcgccag gcccctggca aaggcctgga atgggtgtcc | 840 |
| cggatcagaa gcaagtacaa caactacgcc acctactacg ccgacagcgt gaagggccgg | 900 |
| ttcaccatca gccgggacga cagcaagaac accctgtacc tgcagatgaa cagcctgcgg | 960 |
| gccgaggaca ccgccgtgta ctattgtgtg cggcacggca acttcggcaa cagctatgtg | 1020 |
| tcttggtttg cctactgggg ccagggcacc ctcgtgaccg tgtcaagcgc tagtgtggcc | 1080 |

| gctccctccg tgtttatctt tcccccatcc gatgaacagc tgaaaagcgg caccgcctcc | 1140 |
| gtcgtgtgtc tgctgaacaa ttttacccct agggaagcta aagtgcagtg gaaagtggat | 1200 |
| aacgcactgc agtccggcaa ctcccaggaa tctgtgacag aacaggactc caaggacagc | 1260 |
| acctactccc tgtcctccac cctgacactg tctaaggctg attatgagaa acacaaagtc | 1320 |
| tacgcctgcg aagtcaccca tcagggcctg agctcgcccg tcacaaagag cttcaacagg | 1380 |
| ggagagtgtg acaagaccca cacctgtccc ccttgtcctg cccctgaagc tgctggcggc | 1440 |
| ccttctgtgt tcctgttccc cccaaagccc aaggacaccc tgatgatcag ccggaccccc | 1500 |
| gaagtgacct gcgtggtggt ggatgtgtcc cacgaggacc ctgaagtgaa gttcaattgg | 1560 |
| tacgtggacg gcgtggaagt gcacaacgcc aagacaaagc cgcgggagga gcagtacaac | 1620 |
| agcacgtacc gtgtggtcag cgtcctcacc gtcctgcacc aggactggct gaatggcaag | 1680 |
| gagtacaagt gcaaggtctc caacaaagcc ctcggcgccc ccatcgagaa aaccatctcc | 1740 |
| aaagccaaag gcagccccg agaaccacag gtgtacaccc tgcccccatg ccgggatgag | 1800 |
| ctgaccaaga accaggtcag cctgtggtgc ctggtcaaag cttctatcc cagcgacatc | 1860 |
| gccgtggagt gggagagcaa tgggcagccg gagaacaact acaagaccac gcctcccgtg | 1920 |
| ctggactccg acggctcctt cttcctctac agcaagctca ccgtggacaa gagcaggtgg | 1980 |
| cagcagggga acgtcttctc atgctccgtg atgcatgagg ctctgcacaa ccactacacg | 2040 |
| cagaagagcc tctccctgtc tccgggtaaa | 2070 |

<210> SEQ ID NO 196
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 196

| caggtgcaat tggttcaatc tggtgctgaa gtaaaaaaac cgggcgcttc cgttaaagtg | 60 |
| agctgcaaag catccggata caccttcact tcctattaca tgcactgggt tcgtcaagcc | 120 |
| ccgggccagg gtctggaatg gatgggcatc attaacccaa gcggtggccc tacctcctac | 180 |
| gcgcagaaat tccagggtcg cgtcacgatg acccgtgaca ctagcacctc taccgtttat | 240 |
| atggagctgt ccagcctgcg ttctgaagat actgcagtgt actactgtgc acgcggtgac | 300 |
| ttcgcttggc tggactattg gggtcaaggc accctcgtaa cggtttcttc tgctagcacc | 360 |
| aagggcccct ccgtgttccc cctggccccc agcagcaaga gcaccagcgg cggcacagcc | 420 |
| gctctgggct gcctggtcaa ggactacttc cccgagcccg tgaccgtgtc ctggaacagc | 480 |
| ggagccctga cctccggcgt gcacaccttc cccgccgtgc tgcagagttc tggcctgtat | 540 |
| agcctgagca gcgtggtcac cgtgccttct agcagcctgg gcacccagac ctacatctgc | 600 |
| aacgtgaacc acaagcccag caacaccaag gtggacaaga aggtggagcc caagagctgc | 660 |
| gacaaaactc acacatgccc accgtgccca gcacctgaag ctgcagggg accgtcagtc | 720 |
| ttcctcttcc cccaaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcggcgcc cccatcgaga aaaccatctc caaagccaaa | 1020 |

```
gggcagcccc gagaaccaca ggtgtgcacc ctgcccccat cccgggatga gctgaccaag    1080
aaccaggtca gcctctcgtg cgcagtcaaa ggcttctatc ccagcgacat cgccgtggag    1140
tgggagagca atgggcagcc ggagaacaac tacaagacca cgcctcccgt gctggactcc    1200
gacggctcct tcttcctcgt gagcaagctc accgtggaca gagcaggtg gcagcagggg     1260 aacgtcttct catgctccgt gatgcatgag gctctgcaca accactacac gcagaagagc    1320 ctctcccctgt ctccgggtaa a                                              1341
```

<210> SEQ ID NO 197
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 197

```
gatattgtta tgactcaatc tccactgtct ctgccggtga ctccaggcga accggcgagc      60
atttcttgcc gttccagcca gtctctgctg cactccaacg gctacaacta tctcgattgg    120
tacctgcaaa aaccgggtca gagccctcag ctgctgatct acctgggctc taaccgcgct    180
tccggtgtac cggaccgttt cagcggctct ggatccggca ccgatttcac gttgaaaatc    240
agccgtgttg aagcagaaga cgtgggcgtt tattactgta tgcaggcaag cattatgaac    300
cggacttttg gtcaaggcac caaggtcgaa attaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt       657
```

<210> SEQ ID NO 198
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 198

```
caggccgtcg tgacccagga acccagcctg acagtgtctc ctggcggcac cgtgaccctg      60
acatgtggca gttctacagg cgccgtgacc accagcaact acgccaactg ggtgcaggaa    120
aagcccggcc aggccttcag aggactgatc ggcggcacca acaagagagc ccctggcacc    180
cctgccagat tcagcggatc tctgctggga ggaaaggccg ccctgacact gtctggcgcc    240
cagccagaag atgaggccga gtactactgc gccctgtggt acagcaacct gtgggtgttc    300
ggcggaggca ccaagctgac agtgctgagc agcgcttcca ccaaaggccc ttccgtgttt    360
cctctggctc ctagctccaa gtccacctct ggaggcaccg ctgctctcgg atgcctcgtg    420
aaggattatt ttcctgagcc tgtgacagtg tcctggaata gcggagcact gacctctgga    480
gtgcatactt tcccgctgt gctgcagtcc tctggactgt acagcctgag cagcgtggtg    540
acagtgccca gcagcagcct gggcacccag acctacatct gcaacgtgaa ccacaagccc    600
```
agcaacacca aggtggacaa gaaggtggaa cccaagtctt gt        642

<210> SEQ ID NO 199
<211> LENGTH: 1377
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 199
gaggtgcagc tgctggaatc tggcggcgga ctggtgcagc ctggcggatc tctgagactg        60
agctgtgccg ccagcggctt caccttcagc acctacgcca tgaactgggt gcgccaggcc       120
cctggcaaag gcctggaatg ggtgtcccgg atcagaagca agtacaacaa ctacgccacc       180
tactacgccg acagcgtgaa gggccggttc accatcagcc gggacgacag caagaacacc       240
ctgtacctgc agatgaacag cctgcgggcc gaggacaccg ccgtgtacta ttgtgtgcgg       300
cacggcaact tcggcaacag ctatgtgtct tggtttgcct actggggcca gggcaccctc       360
gtgaccgtgt catctgctag cgtggccgct ccctccgtgt ttatctttcc cccatccgat       420
gaacagctga aaagcggcac cgcctccgtc gtgtgtctgc tgaacaattt ttaccctagg       480
gaagctaaag tgcagtggaa agtggataac gcactgcagt ccggcaactc ccaggaatct       540
gtgacagaac aggactccaa ggacagcacc tactccctgt cctccaccct gacactgtct       600
aaggctgatt atgagaaaca caaagtctac gcctgcgaag tcacccatca gggcctgagc       660
tcgcccgtca caaagagctt caacagggga gagtgtgaca agacccacac ctgtcccccct       720 tgtcctgccc ctgaagctgc tggcggccct tctgtgttcc tgttcccccc aaagcccaag       780
gacaccctga tgatcagccg gacccccgaa gtgacctgcg tggtggtgga tgtgtcccac       840
gaggaccctg aagtgaagtt caattggtac gtggacggcg tggaagtgca caacgccaag       900
acaaagccgc gggaggagca gtacaacagc acgtaccgtg tggtcagcgt cctcaccgtc       960
ctgcaccagg actggctgaa tggcaaggag tacaagtgca aggtctccaa caaagccctc      1020
ggcgccccca tcgagaaaac catctccaaa gccaaagggc agccccgaga accacaggtg      1080
tacaccctgc cccatgccg ggatgagctg accaagaacc aggtcagcct gtggtgcctg      1140
gtcaaaggct tctatcccag cgacatcgcc gtggagtggg agagcaatgg gcagccggag      1200
aacaactaca agaccacgcc tcccgtgctg gactccgacg gctccttctt cctctacagc      1260
aagctcaccg tggacaagag caggtggcag caggggaacg tcttctcatg ctccgtgatg      1320
catgaggctc tgcacaacca ctacacgcag aagagcctct ccctgtctcc gggtaaa        1377

<210> SEQ ID NO 200
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 200
gaggtgcaat tggttgaatc tggtggtggt ctggtaaaac cgggcggttc cctgcgtctg        60
agctgcgcgg cttccggatt caccttctcc aacgcgtgga tgagctgggt tcgccaggcc       120
ccgggcaaag gcctcgagtg ggttggtcgt atcaagtcta aaactgacgg tggcaccacg       180
gattacgcgg ctccagttaa aggtcgtttt accatttccc gcgacgatag caaaaacact       240

```
ctgtatctgc agatgaactc tctgaaaact gaagacaccg cagtctacta ctgtactacc    300
ccgtgggaat ggtcttggta cgattattgg ggccagggca cgctggttac ggtgtcttcc    360
gctagcacaa agggccctag cgtgttccct ctggccccca gcagcaagag cacaagcggc    420
ggaacagccg ccctgggctg cctcgtgaag gactacttcc ccgagcccgt gacagtgtct    480
tggaacagcg gagccctgac aagcggcgtg cacactttcc ctgccgtgct gcagagcagc    540
ggcctgtact ccctgagcag cgtggtcacc gtgcctagca gcagcctggg cacccagacc    600
tacatctgca acgtgaacca caagcccagc aacaccaaag tggacaagaa ggtggagccc    660
aagagctgtg atggcggagg agggtccgga ggcggaggat ccgaggtgca gctgctggaa    720
tctggcggcg gactggtgca gcctggcgga tctctgagac tgagctgtgc cgccagcggc    780
ttcaccttca gcacctacgc catgaactgg gtgcgccagg cccctggcaa aggcctggaa    840
tgggtgtccc ggatcagaag caagtacaac aactacgcca cctactacgc cgacagcgtg    900
aagggccggt tcaccatcag ccgggacgac agcaagaaca ccctgtacct gcagatgaac    960
agcctgcggg ccgaggacac cgccgtgtac tattgtgtgc ggcacggcaa cttcggcgcc   1020
agctatgtgt cttggtttgc ctactggggc cagggcaccc tcgtgaccgt gtcaagcgct   1080
agtaccaagg gcccagcgt gttcccctg gcacccagca gcaagagcac atctggcgga   1140
acagccgctc tgggctgtct ggtgaaagac tacttcccg agcccgtgac cgtgtcttgg   1200
aactctggcg ccctgaccag cggcgtgcac acctttccag ccgtgctgca gagcagcggc   1260
ctgtactccc tgtcctccgt ggtcaccgtg ccctctagct ccctgggaac acagacatat   1320
atctgtaatg tcaatcacaa gccttccaac accaaagtcg ataagaaagt cgagcccaag   1380
agctgcgaca aaactcacac atgcccaccg tgcccagcac ctgaagctgc aggggaccg   1440 tcagtcttcc tcttcccccc aaaacccaag gacaccctca tgatctcccg gacccctgag   1500
gtcacatgcg tggtggtgga cgtgagccac gaagaccctg aggtcaagtt caactggtac   1560
gtggacggcg tggaggtgca taatgccaag acaaagccgc gggaggagca gtacaacagc   1620
acgtaccgtg tggtcagcgt cctcaccgtc ctgcaccagg actggctgaa tggcaaggag   1680
tacaagtgca aggtctccaa caaagccctc ggcgccccca tcgagaaaac catctccaaa   1740
gccaaagggc agccccgaga accacaggtg tacaccctgc ccccatgccg ggatgagctg   1800
accaagaacc aggtcagcct gtggtgcctg gtcaaaggct tctatcccag cgacatcgcc   1860
gtggagtggg agagcaatgg gcagccggag aacaactaca agaccacgcc tcccgtgctg   1920
gactccgacg gctccttctt cctctacagc aagctcaccg tggacaagag caggtggcag   1980
caggggaacg tcttctcatg ctccgtgatg catgaggctc tgcacaacca ctacacgcag   2040
aagagcctct ccctgtctcc gggtaaa                                        2067
```

<210> SEQ ID NO 201
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 201

```
gaggtgcaat tggttgaatc tggtggtggt ctggtaaaac cggcggttc cctgcgtctg     60 agctgcgcgg cttccggatt caccttctcc aacgcgtgga tgagctgggt tcgccaggcc    120
```

| | |
|---|---|
| ccgggcaaag gcctcgagtg ggttggtcgt atcaagtcta aaactgacgg tggcaccacg | 180 |
| gattacgcgg ctccagttaa aggtcgtttt accatttccc gcgacgatag caaaaacact | 240 |
| ctgtatctgc agatgaactc tctgaaaact gaagacaccg cagtctacta ctgtactacc | 300 |
| ccgtgggaat ggtcttggta cgattattgg ggccagggca cgctggttac ggtgtcttcc | 360 |
| gctagcacaa agggcsctag cgtgttccct ctggcccca gcagcaagag cacaagcggc | 420 |
| ggaacagccg ccctgggctg cctcgtgaag gactacttcc ccgagcccgt gacagtgtct | 480 |
| tggaacagcg gagccctgac aagcggcgtg cacacttcc ctgccgtgct gcagagcagc | 540 |
| ggcctgtact ccctgagcag cgtggtcacc gtgcctagca gcagcctggg cacccagacc | 600 |
| tacatctgca acgtgaacca caagcccagc aacaccaaag tggacaagaa ggtggagccc | 660 |
| aagagctgtg atggcggagg agggtccgga ggcggaggat ccgaggtgca gctgctggaa | 720 |
| tctggcggcg gactggtgca gcctggcgga tctctgagac tgagctgtgc cgccagcggc | 780 |
| ttcaccttca gcacctacgc catgaactgg gtgcgccagg ccctggcaa aggcctggaa | 840 |
| tgggtgtccc ggatcagaag caagtacaac aactacgcca cctactacgc cgacagcgtg | 900 |
| aagggccggt tcaccatcag ccgggacgac agcaagaaca ccctgtacct gcagatgaac | 960 |
| agcctgcggg ccgaggacac cgccgtgtac tattgtgtgc ggcacggcaa cttcggcaac | 1020 |
| gcctatgtgt cttggtttgc ctactggggc cagggcaccc tcgtgaccgt gtcaagcgct | 1080 |
| agtaccaagg gcccagcgt gttccccctg cacccagca gcaagagcac atctggcgga | 1140 |
| acagccgctc tgggctgtct ggtgaaagac tacttccccg agccgtgac cgtgtcttgg | 1200 |
| aactctggcg ccctgaccag cggcgtgcac acctttccag ccgtgctgca gagcagcggc | 1260 |
| ctgtactccc tgtcctccgt ggtcaccgtg ccctctagct ccctgggaac acagacatat | 1320 |
| atctgtaatg tcaatcacaa gccttccaac accaaagtcg ataagaaagt cgagcccaag | 1380 |
| agctgcgaca aaactcacac atgcccaccg tgcccagcac ctgaagctgc aggggaccg | 1440 |
| tcagtcttcc tcttcccccc aaaacccaag gacaccctca tgatctcccg gaccccctgag | 1500 |
| gtcacatgcg tggtggtgga cgtgagccac gaagaccctg aggtcaagtt caactggtac | 1560 |
| gtggacggcg tggaggtgca taatgccaag acaaagccgc gggaggagca gtacaacagc | 1620 |
| acgtaccgtg tggtcagcgt cctcaccgtc ctgcaccagg actggctgaa tggcaaggag | 1680 |
| tacaagtgca aggtctccaa caaagccctc ggcgccccca tcgagaaaac catctccaaa | 1740 |
| gccaaagggc agccccgaga accacaggtg tacaccctgc cccatgccg ggatgagctg | 1800 |
| accaagaacc aggtcagcct gtggtgcctg gtcaaaggct tctatcccag cgacatcgcc | 1860 |
| gtggagtggg agagcaatgg gcagccggag aacaactaca agaccacgcc tcccgtgctg | 1920 |
| gactccgacg gctccttctt cctctacagc aagctcaccg tggacaagag caggtggcag | 1980 |
| caggggaacg tcttctcatg ctccgtgatg catgaggctc tgcacaacca ctacacgcag | 2040 |
| aagagcctct ccctgtctcc gggtaaa | 2067 |

<210> SEQ ID NO 202
<211> LENGTH: 1323
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 202
caggccgtcg tgacccagga acccagcctg acagtgtctc ctggcggcac cgtgaccctg     60

```
acatgtggca gttctacagg cgccgtgacc accagcaact acgccaactg ggtgcaggaa    120
aagcccggcc aggccttcag aggactgatc ggcggcacca caagagagc ccctggcacc     180 cctgccagat tcagcggatc tctgctggga ggaaaggccg ccctgacact gtctggcgcc    240
cagccagaag atgaggccga gtactactgc gccctgtggt acagcaacct gtgggtgttc    300
ggcggaggca ccaagctgac agtgctgagc agcgctagca ccaagggccc atcggtcttc    360
cccctggcac cctcctccaa gagcacctct gggggcacag cggccctggg ctgcctggtc    420
aaggactact ccccgaacc ggtgacggtg tcgtggaact caggcgccct gaccagcggc     480
gtgcacacct tccggctgt cctacagtcc tcaggactct actccctcag cagcgtggtg     540
accgtgccct ccagcagctt gggcacccag acctacatct gcaacgtgaa tcacaagccc    600
agcaacacca aggtggacaa gaaagttgag cccaaatctt gtgacaaaac tcacacatgc    660
ccaccgtgcc cagcacctga agctgcaggg ggaccgtcag tcttcctctt ccccccaaaa    720
cccaaggaca ccctcatgat ctcccggacc cctgaggtca catgcgtggt ggtggacgtg    780
agccacgaag accctgaggt caagttcaac tggtacgtgg acggcgtgga ggtgcataat    840
gccaagacaa agccgcggga ggagcagtac aacagcacgt accgtgtggt cagcgtcctc    900
accgtcctgc accaggactg gctgaatggc aaggagtaca agtgcaaggt ctccaacaaa    960
gccctcggcg cccccatcga gaaaaccatc tccaaagcca aagggcagcc ccgagaacca   1020
caggtgtaca ccctgccccc atcccgggat gagctgacca agaaccaggt cagcctgacc   1080
tgcctggtca aaggcttcta tcccagcgac atcgccgtgg agtgggagag caatgggcag   1140
ccggagaaca actacaagac cacgcctccc gtgctggact ccgacggctc cttcttcctc   1200
tacagcaagc tcaccgtgga caagagcagg tggcagcagg ggaacgtctt ctcatgctcc   1260
gtgatgcatg aggctctgca caaccactac acgcagaaga gcctctccct gtctccgggt   1320
aaa                                                                  1323
```

<210> SEQ ID NO 203
<211> LENGTH: 681
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 203

```
gaggtgcaat tggttgaatc tggtggtggt ctggtaaaac cgggcggttc cctgcgtctg     60
agctgcgcgg cttccggatt caccttctcc aacgcgtgga tgagctgggt tcgccaggcc    120
ccgggcaaag gctcgagtg ggttggtcgt atcaagtcta aaactgacgg tggcaccacg     180
gattacgcgg ctccagttaa aggtcgtttt accatttccc gcgacgatag caaaaacact    240
ctgtatctgc agatgaactc tctgaaaact gaagacaccg cagtctacta ctgtactacc    300
ccgtgggaat ggtcttggta cgattattgg ggccagggca cgctggttac ggtgtcttcc    360
gctagcgtgg ccgctccctc cgtgttcatc ttcccacctt ccgacgagca gctgaagtcc    420
ggcaccgctt ctgtcgtgtg cctgctgaac aacttctacc ccgcgaggc caaggtgcag    480 tggaaggtgg acaacgccct gcagtccggc aacagccagg aatccgtgac cgagcaggac    540
tccaaggaca gcacctactc cctgtcctcc accctgaccc tgtccaaggc cgactacgag    600
aagcacaagg tgtacgcctg cgaagtgacc caccagggcc tgtctagccc cgtgaccaag    660
```

```
tctttcaacc ggggcgagtg c                                              681
```

<210> SEQ ID NO 204
<211> LENGTH: 693
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 204

```
gaagtgcagc tgctggaatc cggcggagga ctggtgcagc ctggcggatc tctgagactg     60
tcttgtgccg cctccggctt caccttctcc acctacgcca tgaactgggt gcgacaggct    120
cctggcaagg gcctggaatg ggtgtcccgg atcagatcca agtacaacaa ctacgccacc    180
tactacgccg actccgtgaa gggccggttc accatctctc gggacgactc caagaacacc    240
ctgtacctgc agatgaactc cctgcgggcc gaggacaccg ccgtgtacta ttgtgtgcgg    300
cacggcaact tcggcaactc ctatgtgtct tggtttgcct actggggcca gggcaccctc    360
gtgaccgtgt catctgctag ccccaaggct gccccagcg tgaccctgtt tccccccagc    420
agcgaggaac tgcaggccaa caaggccacc ctggtctgcc tgatcagcga cttctaccca    480
ggcgccgtga ccgtggcctg gaaggccgac agcagccccg tgaaggccgg cgtggagacc    540 accacccca gcaagcagag caacaacaag tacgccgcca gcagctacct gagcctgacc    600
cccgagcagt ggaagagcca caggtcctac agctgccagg tgacccacga gggcagcacc    660
gtggagaaaa ccgtggcccc caccgagtgc agc                                 693
```

<210> SEQ ID NO 205
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 205

```
cagaccgtcg tgacccagga acccagcctg acagtgtctc ctggcggcac cgtgaccctg     60
acatgtggca gttctacagg cgccgtgacc accagcaact acgccaactg ggtgcagcag    120
aagccaggcc aggctcccag aggactgatc ggcggcacca cgccagagc ccctggcacc    180 cctgccagat tcagcggatc tctgctggga ggaaaggccg ccctgacact gtctggcgtg    240
cagcctgaag atgaggccga gtactactgc gccctgtggt acagcaacct gtgggtgttc    300
ggcggaggca ccaagctgac agtccta                                        327
```

<210> SEQ ID NO 206
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 206

```
cagaccgtcg tgacccagga acccagcctg acagtgtctc ctggcggcac cgtgaccctg     60
acatgtggca gttctacagg cgccgtgacc accagcaact acgccaactg ggtgcagcag    120
aagccaggcc aggctcccag aggactgatc ggcggcacca acaagagagc ccctggcacc    180
```
cctgccagat tcagcggatc tctgctggga ggaaaggccg ccctgacact gtctggcgtg      240
cagcctgaag atgaggccga gtactactgc gccctgtggt acgccaacct gtgggtgttc      300
ggcggaggca ccaagctgac agtccta                                          327

```
<210> SEQ ID NO 207
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 207
```
gaggtgcaat tggtggaaag cggaggcggc ctcgtgaagc tggcggatc tctgagactg        60 agctgtgccg ccagcggctt caccttcagc aacgcctgga tgcactgggt gcgccaggcc      120
cctggaaaag gactcgagtg ggtgggacg atcaagagca agaccgatgg cggcaccacc       180
gactatgccg cccctgtgaa gggccggttc accatcagca gggacgacag caagaacacc      240
ctgtacctgc agatgaacag cctgaaaacc gaggacaccg ccgtgtacta ctgcaccacc      300
ccctgggagt ggtcttggta cgactattgg ggccagggca ccctcgtgac cgtgtcctct      360
gctagc                                                                  366

```
<210> SEQ ID NO 208
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 208
```
gaggtgcaat tggtggaaag cggaggcggc ctcgtgaagc tggcggatc tctgagactg        60 agctgtgccg ccagcggctt caccttcagc aacgcctgga tgagctgggt gcgccaggcc     120
cctggaaaag gactcgagtg ggtgtcccgg atcaagagca agaccgatgg cggcaccacc      180
gactatgccg cccctgtgaa gggccggttc accatcagca gggacgacag caagaacacc      240
ctgtacctgc agatgaacag cctgaaaacc gaggacaccg ccgtgtacta ctgcaccacc      300
ccctgggagt ggtcttggta cgactattgg ggccagggca ccctcgtgac cgtgtcctct      360
gctagc                                                                  366

```
<210> SEQ ID NO 209
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 209
```
gaggtgcaat tggtggaaag cggaggcggc ctcgtgaagc tggcggatc tctgagactg        60 agctgtgccg ccagcggctt caccttcagc aacgcctgga tgagctgggt gcgccaggcc     120
cctggaaaag gactcgagtg ggtgggatct atcaagagca agaccgacgg cggcaccacc      180
gactatgccg cccctgtgaa gggccggttc accatcagca gggacgacag caagaacacc      240
ctgtacctgc agatgaacag cctgaaaacc gaggacaccg ccgtgtacta ctgcaccacc    300
ccctgggagt ggtcttggta cgactattgg ggccagggca ccctcgtgac cgtgtcctct    360
gctagc                                                                366

<210> SEQ ID NO 210
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 210
gaggtgcaat tggtggaaag cggaggcggc ctcgtgaagc ctggcggatc tctgagactg     60
agctgtgccg ccagcggctt caccttcagc aacgcctgga tgagctgggt cgcccaggcc    120
cctggaaaag gactcgagtg ggtgggacgg atcaagagca gaccgatgg cggcaccacc     180 gactatgccg cccctgtgaa gggccggttc accatcagca gggacgacag caagaacacc    240
ctgtacctgc agatgaacag cctgaaaacc gaggacaccg ccgtgtacta ctgcaccacc    300
ccctacgagt ggtcttggta cgactactgg ggccagggca ccctcgtgac cgtgtcatct    360
gctagc                                                                366

<210> SEQ ID NO 211
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 211
gaggtgcaat tggtggaaag cggaggcggc ctcgtgaagc ctggcggatc tctgagactg     60
agctgtgccg ccagcggctt caccttcagc aacgcctgga tgagctgggt cgcccaggcc    120
cctggaaaag gactcgagtg ggtgggacgg atcaagagca gaccgatgg cggcaccacc     180 gactatgccg cccctgtgaa gggccggttc accatcagca gggacgacag caagaacacc    240
ctgtacctgc agatgaacag cctgaaaacc gaggacaccg ccgtgtacta ctgcaccacc    300
ccctgggagt actcttggta cgactactgg ggccagggca ccctcgtgac cgtgtcatct    360
gctagc                                                                366

<210> SEQ ID NO 212
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 212
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctgaatg gatgggcatc attaacccaa gcggtggctc tacctcctac    180
gcgcagaaat tccagggtcg cgtcacgatg accgtgaca ctagcacctc taccgttat    240 atggagctgt ccagcctgcg ttctgaagat actgcagtgt actactgtgc acgcaactac    300

```
actatcgttg tttctccgtt cgactattgg ggtcaaggca ccctcgtaac ggtttcttct    360
gctagc                                                               366

<210> SEQ ID NO 213
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 213
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctggaatg gatgggcatc attaacccaa gcggtggctc tacctcctac    180
gcgcagaaat tccagggtcg cgtcacgatg acccgtgaca ctagcacctc taccgtttat    240
atggagctgt ccagcctgcg ttctgaagat actgcagtgt actactgtgc acgcaactac    300
ttcatcggtt ctgttgctat ggactattgg ggtcaaggca ccctcgtaac ggtttcttct    360
gctagc                                                               366

<210> SEQ ID NO 214
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 214
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctggaatg gatgggcatc attaacccaa gcggtggctc tacctcctac    180
gcgcagaaat tccagggtcg cgtcacgatg acccgtgaca ctagcacctc taccgtttat    240
atggagctgt ccagcctgcg ttctgaagat actgcagtgt actactgtgc acgcggtctg    300
acttactcta tggactattg gggtcaaggc accctcgtaa cggtttcttc tgctagc       357

<210> SEQ ID NO 215
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 215
gatattgtta tgactcaatc tccactgtct ctgccggtga ctccaggcga accggcgagc     60
atttcttgcc gttccagcca gtctctgctg cactccaacg gctacaacta tctcgattgg    120
tacctgcaaa aaccgggtca gagccctcag ctgctgatct acctgggctc taaccgcgct    180
tccggtgtac cggaccgttt cagcggctct ggatccggca ccgatttcac gttgaaaatc    240
agccgtgttg aagcagaaga cgtgggcgtt tattactgta tgcaggcact gcagattcca    300
aacacttttg gtcaaggcac caaggtcgaa attaaacgta cg                       342
```

<210> SEQ ID NO 216
<211> LENGTH: 354
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 216

| | | | | | |
|---|---|---|---|---|---|
| gaggtgcaat | tgttggagtc | tgggggaggc | ttggtacagc | ctgggggtc | cctgagactc | 60 |
| tcctgtgcag | cctccggatt | cacctttagc | agttatgcca | tgagctgggt | ccgccaggct | 120 |
| ccagggaagg | ggctggagtg | ggtctcagct | attagtggta | gtggtggtag | cacatactac | 180 |
| gcagactccg | tgaagggccg | gttcaccatc | tccagagaca | attccaagaa | cacgctgtat | 240 |
| ctgcagatga | acagcctgag | agccgaggac | acggccgtat | attactgtgc | gaaatacgct | 300 |
| tacgctctgg | actactgggg | ccaaggaacc | ctggtcaccg | tctcgagtgc | tagc | 354 |

<210> SEQ ID NO 217
<211> LENGTH: 327
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 217

| | | | | | |
|---|---|---|---|---|---|
| gaaatcgtgt | taacgcagtc | tccaggcacc | ctgtctttgt | ctccagggga | aagagccacc | 60 |
| ctctcttgca | gggccagtca | gagtgttagc | agcagctact | tagcctggta | ccagcagaaa | 120 |
| cctggccagg | ctcccaggct | cctcatctat | ggagcatcca | gcagggccac | tggcatccca | 180 |
| gacaggttca | gtggcagtgg | atccgggaca | gacttcactc | tcaccatcag | cagactggag | 240 |
| cctgaagatt | ttgcagtgta | ttactgtcag | cagcatggca | gcagcagcac | gttcggccag | 300 |
| gggaccaaag | tggaaatcaa | acgtacg | | | | 327 |

<210> SEQ ID NO 218
<211> LENGTH: 366
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 218

| | | | | | |
|---|---|---|---|---|---|
| caggtgcaat | tggttcaatc | tggtgctgaa | gtaaaaaaac | cgggcgcttc | cgttaaagtg | 60 |
| agctgcaaag | catccggata | caccttcact | tcctattaca | tgcactgggt | tcgtcaagcc | 120 |
| ccgggccagg | gtctggaatg | gatgggcatc | attaacccaa | gcggtggctc | tacctcctac | 180 |
| gcgcagaaat | tccagggtcg | cgtcacgatg | acccgtgaca | ctagcacctc | taccgtttat | 240 |
| atggagctgt | ccagcctgcg | ttctgaagat | actgcagtgt | actactgtgc | acgcggtgac | 300 |
| ttctctgctg | gtcgtctgat | ggactattgg | ggtcaaggca | ccctcgtaac | ggtttcttct | 360 |
| gctagc | | | | | | 366 |

<210> SEQ ID NO 219
<211> LENGTH: 345
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 219
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcact gcagacccca   300
ccaattacct ttggtcaagg caccaaggtc gaaattaaac gtacg                   345

<210> SEQ ID NO 220
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 220
caggtgcaat tggttcaatc tggtgctgaa gtaaaaaaac cgggcgcttc cgttaaagtg    60
agctgcaaag catccggata caccttcact cctattaca tgcactgggt tcgtcaagcc   120
ccgggccagg gtctggaatg gatgggcatc attaacccaa gcgtggctc tacctcctac   180 gcgcagaaat tccagggtcg cgtcacgatg acccgtgaca ctagcacctc taccgtttat   240
atggagctgt ccagcctgcg ttctgaagat actgcagtgt actactgtgc acgcggtgac   300
tacaacgctt tcgactattg gggtcacggc accctcgtaa cggtttcttc tgctagc     357

<210> SEQ ID NO 221
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 221
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcatg gcatagccca   300
acttttggtc aaggcaccaa ggtcgaaatt aaacgtacg                          339

<210> SEQ ID NO 222
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 222

```
caggtgcaat tggttcaatc tggtgctgaa gtaaaaaaac cgggcgcttc cgttaaagtg    60
agctgcaaag catccggata caccttcact tcctattaca tgcactgggt tcgtcaagcc   120
ccgggccagg gtctggaatg gatgggcatc attaacccaa gcggtggctc tacctcctac   180
gcgcagaaat tccagggtcg cgtcacgatg acccgtgaca ctagcacctc taccgtttat   240
atggagctgt ccagcctgcg ttctgaagat actgcagtgt actactgtgc acgcggtgct   300
acttacacta tggactattg gggtcaaggc accctcgtaa cggtttcttc tgctagc      357

<210> SEQ ID NO 223
<211> LENGTH: 342
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 223
gatattgtta tgactcaatc tccactgtct ctgccggtga ctccaggcga accggcgagc    60
atttcttgcc gttccagcca gtctctgctg cactccaacg gctacaacta tctcgattgg   120
tacctgcaaa aaccgggtca gagccctcag ctgctgatct acctgggctc taaccgcgct   180
tccggtgtac cggaccgttt cagcggctct ggatccggca ccgatttcac gttgaaaatc   240
agccgtgttg aagcagaaga cgtgggcgtt tattactgta tgcaggcact gcagacccca   300
attacttttg gtcaaggcac caaggtcgaa attaaacgta cg                      342

<210> SEQ ID NO 224
<211> LENGTH: 1344
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 224
caggtgcagc tgcagcagtc tggcgccgag ctcgtgaaac tggcgcctc cgtgaagatc     60 agctgcaagg ccagcggcta cagcttcacc ggctacttca tgaactgggt caagcagagc   120
cacggcaaga gcctggaatg gatcggcaga atccacccct acgacggcga caccttctac   180
aaccagaact tcaaggacaa ggccaccctg accgtggaca gagcagcaa caccgcccac   240 atggaactgc tgagcctgac cagcgaggac ttcgccgtgt actactgcac cagatacgac   300
ggcagccggg ccatggatta ttggggccag ggcaccaccg tgacagtgtc cagcgctagc   360
accaagggcc cctccgtgtt ccccctggcc ccagcagca agagcaccag cggcggcaca   420
gccgctctgg gctgcctggt caaggactac ttccccgagc ccgtgaccgt gtcctggaac   480
agcggagccc tgacctccgg cgtgcacacc ttccccgccg tgctgcagag ttctggcctg   540
tatagcctga gcagcgtggt caccgtgcct tctagcagcc tgggcaccca gacctacatc   600
tgcaacgtga accacaagcc cagcaacacc aaggtggaca gaaggtgga gcccaagagc   660 tgcgacaaaa ctcacacatg cccaccgtgc ccagcacctg aagctgcagg ggaccgtca    720 gtcttcctct tccccccaaa acccaaggac accctcatga tctcccggac ccctgaggtc   780
acatgcgtgg tggtggacgt gagccacgaa gaccctgagg tcaagttcaa ctggtacgtg   840
gacggcgtga aggtgcataa tgccaagaca aagccgcggg aggagcagta caacagcacg   900
taccgtgtgg tcagcgtcct caccgtcctg caccaggact ggctgaatgg caaggagtac   960
```

-continued

| | |
|---|---|
| aagtgcaagg tctccaacaa agccctcggc gcccccatcg agaaaaccat ctccaaagcc | 1020 |
| aaagggcagc cccgagaacc acaggtgtgc accctgcccc catcccggga tgagctgacc | 1080 |
| aagaaccagg tcagcctctc gtgcgcagtc aaaggcttct atcccagcga catcgccgtg | 1140 |
| gagtggggaga gcaatgggca gccggagaac aactacaaga ccacgcctcc cgtgctggac | 1200 |
| tccgacggct ccttcttcct cgtgagcaag ctcaccgtgg acaagagcag gtggcagcag | 1260 |
| gggaacgtct tctcatgctc cgtgatgcat gaggctctgc acaaccacta cacgcagaag | 1320 |
| agcctctccc tgtctccggg taaa | 1344 |

<210> SEQ ID NO 225
<211> LENGTH: 2073
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 225

| | |
|---|---|
| caggtgcagc tgcagcagtc tggcgccgag ctcgtgaaac ctggcgcctc cgtgaagatc | 60 |
| agctgcaagg ccagcggcta cagcttcacc ggctacttca tgaactgggt caagcagagc | 120 |
| cacggcaaga gcctggaatg gatcggcaga atccacccct acgacggcga caccttctac | 180 |
| aaccagaact tcaaggacaa ggccaccctg accgtggaca gagcagcaa caccgcccac | 240 |
| atggaactgc tgagcctgac cagcgaggac ttcgccgtgt actactgcac cagatacgac | 300 |
| ggcagccggg ccatggatta ttggggccag ggcaccaccg tgacagtgtc cagcgctagc | 360 |
| acaaagggcc ccagcgtgtt ccctctggcc cctagcagca gagcacatc tggcggaaca | 420 |
| gccgccctgg gctgcctcgt gaaggactac tttcccgagc ctgtgaccgt gtcctggaac | 480 |
| tctggcgccc tgacaagcgg cgtgcacacc tttccagccg tgctgcagag cagcggcctg | 540 |
| tactctctga gcagcgtggt caccgtgcct agcagcagcc tgggcaccca gacctacatc | 600 |
| tgcaacgtga accacaagcc cagcaacacc aaagtggaca agaaggtgga gcccaagagc | 660 |
| tgtgatggcg gaggaggggtc cggaggcgga ggatccgaag tgcagctggt ggaaagcggc | 720 |
| ggaggcctgg tgcagcctaa gggctctctg aagctgagct gtgccgccag cggcttcacc | 780 |
| ttcaacacct acgccatgaa ctgggtgcgc caggcccctg gcaaaggcct ggaatgggtg | 840 |
| gcccggatca gaagcaagta caacaattac gccacctact acgccgacag cgtgaaggac | 900 |
| cggttcacca tcagccggga cgacagccag agcatcctgt acctgcagat gaacaacctg | 960 |
| aaaaccgagg acaccgccat gtactactgc gtgcggcacg gcaacttcgg caacagctat | 1020 |
| gtgtcttggt ttgcctactg gggccagggc accctcgtga cagtgtctgc tgctagcgtg | 1080 |
| gccgctccct ccgtgtttat ctttccccca tccgatgaac agctgaaaag cggcaccgcc | 1140 |
| tccgtcgtgt gtctgctgaa caatttttac cctagggaag ctaaagtgca gtggaaagtg | 1200 |
| gataacgcac tgcagtccgg caactcccag gaatctgtga cagaacagga ctccaaggac | 1260 |
| agcacctact ccctgtcctc cacccctgaca ctgtctaagg ctgattatga gaaacacaaa | 1320 |
| gtctacgcct gcgaagtcac ccatcagggc ctgagctcgc ccgtcacaaa gagcttcaac | 1380 |
| aggggagagt gtgacaagac ccacacctgt cccccttgtc ctgcccctga agctgctggc | 1440 |
| ggcccttctg tgttcctgtt ccccccaaag cccaaggaca ccctgatgat cagccggacc | 1500 |
| cccgaagtga cctgcgtggt ggtggatgtg tcccacgagg accctgaagt gaagttcaat | 1560 |

```
tggtacgtgg acggcgtgga agtgcacaac gccaagacaa agccgcggga ggagcagtac      1620
aacagcacgt accgtgtggt cagcgtcctc accgtcctgc accaggactg gctgaatggc      1680
aaggagtaca agtgcaaggt ctccaacaaa gccctcggcg cccccatcga gaaaaccatc      1740
tccaaagcca aagggcagcc ccgagaacca caggtgtaca ccctgccccc atgccgggat      1800
gagctgacca agaaccaggt cagcctgtgg tgcctggtca aaggcttcta tcccagcgac      1860
atcgccgtgg agtgggagag caatgggcag ccggagaaca actacaagac cacgcctccc      1920
gtgctggact ccgacggctc cttcttcctc tacagcaagc tcaccgtgga caagagcagg      1980
tggcagcagg ggaacgtctt ctcatgctcc gtgatgcatg aggctctgca caaccactac      2040
acgcagaaga gcctctccct gtctccgggt aaa                                   2073
```

<210> SEQ ID NO 226
<211> LENGTH: 654
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 226

```
gacatcgagc tgacccagag ccctgcctct ctggccgtgt ctctgggaca gagagccatc       60
atcagctgca aggccagcca gagcgtgtcc tttgccggca cctctctgat gcactggtat      120
caccagaagc ccggccagca gcccaagctg ctgatctaca gagccagcaa cctggaagcc      180
ggcgtgccca agatttttc ggcagcggc agcaagaccg acttcaccct gaacatccac      240
cccgtggaag aagaggacgc cgccacctac tactgccagc agagcagaga gtaccccctac      300 accttcggcg gaggcaccaa gctggaaatc aagcgtacgg tggctgcacc atctgtcttc      360
atcttcccgc catctgatga gcagttgaaa tctggaactg cctctgttgt gtgcctgctg      420
aataacttct atcccagaga ggccaaagta cagtggaagg tggataacgc cctccaatcg      480
ggtaactccc aggagagtgt cacagagcag gacagcaagg acagcaccta cagcctcagc      540
agcaccctga cgctgagcaa agcagactac gagaaacaca agtctacgc ctgcgaagtc      600 acccatcagg gcctgagctc gcccgtcaca aagagcttca acaggggaga gtgt            654
```

<210> SEQ ID NO 227
<211> LENGTH: 209
<212> TYPE: PRT
<213> ORGANISM: Homo sapiens

<400> SEQUENCE: 227

```
Arg Ile Ala Trp Ala Arg Thr Glu Leu Leu Asn Val Cys Met Asn Ala
  1               5                  10                  15

Lys His His Lys Glu Lys Pro Gly Pro Glu Asp Lys Leu His Glu Gln
                 20                  25                  30

Cys Arg Pro Trp Arg Lys Asn Ala Cys Cys Ser Thr Asn Thr Ser Gln
             35                  40                  45

Glu Ala His Lys Asp Val Ser Tyr Leu Tyr Arg Phe Asn Trp Asn His
         50                  55                  60

Cys Gly Glu Met Ala Pro Ala Cys Lys Arg His Phe Ile Gln Asp Thr
 65                  70                  75                  80

Cys Leu Tyr Glu Cys Ser Pro Asn Leu Gly Pro Trp Ile Gln Gln Val
                 85                  90                  95

Asp Gln Ser Trp Arg Lys Glu Arg Val Leu Asn Val Pro Leu Cys Lys
```

```
                100             105             110
Glu Asp Cys Glu Gln Trp Trp Glu Asp Cys Arg Thr Ser Tyr Thr Cys
            115                 120                 125
Lys Ser Asn Trp His Lys Gly Trp Asn Trp Thr Ser Gly Phe Asn Lys
        130                 135                 140
Cys Ala Val Gly Ala Ala Cys Gln Pro Phe His Phe Tyr Phe Pro Thr
145                 150                 155                 160
Pro Thr Val Leu Cys Asn Glu Ile Trp Thr His Ser Tyr Lys Val Ser
                165                 170                 175
Asn Tyr Ser Arg Gly Ser Gly Arg Cys Ile Gln Met Trp Phe Asp Pro
            180                 185                 190
Ala Gln Gly Asn Pro Asn Glu Glu Val Ala Arg Phe Tyr Ala Ala Ala
        195                 200                 205
Met
```

<210> SEQ ID NO 228
<211> LENGTH: 214
<212> TYPE: PRT
<213> ORGANISM: Homo sapiens

<400> SEQUENCE: 228

```
Thr Met Cys Ser Ala Gln Asp Arg Thr Asp Leu Leu Asn Val Cys Met
1               5                   10                  15
Asp Ala Lys His His Lys Thr Lys Pro Gly Pro Glu Asp Lys Leu His
            20                  25                  30
Asp Gln Cys Ser Pro Trp Lys Lys Asn Ala Cys Cys Thr Ala Ser Thr
        35                  40                  45
Ser Gln Glu Leu His Lys Asp Thr Ser Arg Leu Tyr Asn Phe Asn Trp
    50                  55                  60
Asp His Cys Gly Lys Met Glu Pro Ala Cys Lys Arg His Phe Ile Gln
65                  70                  75                  80
Asp Thr Cys Leu Tyr Glu Cys Ser Pro Asn Leu Gly Pro Trp Ile Gln
                85                  90                  95
Gln Val Asn Gln Ser Trp Arg Lys Glu Arg Phe Leu Asp Val Pro Leu
            100                 105                 110
Cys Lys Glu Asp Cys Gln Arg Trp Trp Glu Asp Cys His Thr Ser His
        115                 120                 125
Thr Cys Lys Ser Asn Trp His Arg Gly Trp Asp Trp Thr Ser Gly Val
    130                 135                 140
Asn Lys Cys Pro Ala Gly Ala Leu Cys Arg Thr Phe Glu Ser Tyr Phe
145                 150                 155                 160
Pro Thr Pro Ala Ala Leu Cys Glu Gly Leu Trp Ser His Ser Tyr Lys
                165                 170                 175
Val Ser Asn Tyr Ser Arg Gly Ser Gly Arg Cys Ile Gln Met Trp Phe
            180                 185                 190
Asp Ser Ala Gln Gly Asn Pro Asn Glu Glu Val Ala Arg Phe Tyr Ala
        195                 200                 205
Ala Ala Met His Val Asn
    210
```

<210> SEQ ID NO 229
<211> LENGTH: 220
<212> TYPE: PRT
<213> ORGANISM: Homo sapiens

<400> SEQUENCE: 229

```
Ser Ala Arg Ala Arg Thr Asp Leu Leu Asn Val Cys Met Asn Ala Lys
1               5                   10                  15

His His Lys Thr Gln Pro Ser Pro Glu Asp Leu Tyr Gly Gln Cys
            20              25                  30

Ser Pro Trp Lys Lys Asn Ala Cys Cys Thr Ala Ser Thr Ser Gln Glu
            35              40                  45

Leu His Lys Asp Thr Ser Arg Leu Tyr Asn Phe Asn Trp Asp His Cys
        50                  55                  60

Gly Lys Met Glu Pro Thr Cys Lys Arg His Phe Ile Gln Asp Ser Cys
65              70                  75                  80

Leu Tyr Glu Cys Ser Pro Asn Leu Gly Pro Trp Ile Arg Gln Val Asn
                85                  90                  95

Gln Ser Trp Arg Lys Glu Arg Ile Leu Asn Val Pro Leu Cys Lys Glu
            100                 105                 110

Asp Cys Glu Arg Trp Trp Glu Asp Cys Arg Thr Ser Tyr Thr Cys Lys
        115                 120                 125

Ser Asn Trp His Lys Gly Trp Asn Trp Thr Ser Gly Ile Asn Glu Cys
        130                 135                 140

Pro Ala Gly Ala Leu Cys Ser Thr Phe Glu Ser Tyr Phe Pro Thr Pro
145                 150                 155                 160

Ala Ala Leu Cys Glu Gly Leu Trp Ser His Ser Phe Lys Val Ser Asn
                165                 170                 175

Tyr Ser Arg Gly Ser Gly Arg Cys Ile Gln Met Trp Phe Asp Ser Ala
                180                 185                 190

Gln Gly Asn Pro Asn Glu Glu Val Ala Lys Phe Tyr Ala Ala Ala Met
            195                 200                 205

Asn Ala Gly Ala Pro Ser Arg Gly Ile Ile Asp Ser
            210                 215                 220

<210> SEQ ID NO 230
<211> LENGTH: 208
<212> TYPE: PRT
<213> ORGANISM: Mus musculus

<400> SEQUENCE: 230

Thr Arg Ala Arg Thr Glu Leu Leu Asn Val Cys Met Asp Ala Lys His
1               5                   10                  15

His Lys Glu Lys Pro Gly Pro Glu Asp Asn Leu His Asp Gln Cys Ser
            20                  25                  30

Pro Trp Lys Thr Asn Ser Cys Cys Ser Thr Asn Thr Ser Gln Glu Ala
            35                  40                  45

His Lys Asp Ile Ser Tyr Leu Tyr Arg Phe Asn Trp Asn His Cys Gly
        50                  55                  60

Thr Met Thr Ser Glu Cys Lys Arg His Phe Ile Gln Asp Thr Cys Leu
65              70                  75                  80

Tyr Glu Cys Ser Pro Asn Leu Gly Pro Trp Ile Gln Gln Val Asp Gln
                85                  90                  95

Ser Trp Arg Lys Glu Arg Ile Leu Asp Val Pro Leu Cys Lys Glu Asp
            100                 105                 110

Cys Gln Gln Trp Trp Glu Asp Cys Gln Ser Ser Phe Thr Cys Lys Ser
        115                 120                 125

Asn Trp His Lys Gly Trp Asn Trp Ser Ser Gly His Asn Glu Cys Pro
        130                 135                 140

Val Gly Ala Ser Cys His Pro Phe Thr Phe Tyr Phe Pro Thr Ser Ala
```

| | | | | | | | | | | |
|---|---|---|---|---|---|---|---|---|---|---|
| 145 | | | | 150 | | | | 155 | | 160 |

Ala Leu Cys Glu Glu Ile Trp Ser His Ser Tyr Lys Leu Ser Asn Tyr
                165                170                175

Ser Arg Gly Ser Gly Arg Cys Ile Gln Met Trp Phe Asp Pro Ala Gln
                180                185                190

Gly Asn Pro Asn Glu Glu Val Ala Arg Phe Tyr Ala Glu Ala Met Ser
                195                200                205

<210> SEQ ID NO 231
<211> LENGTH: 213
<212> TYPE: PRT
<213> ORGANISM: Macaca fascicularis

<400> SEQUENCE: 231

Glu Ala Gln Thr Arg Thr Ala Arg Ala Arg Thr Glu Leu Leu Asn Val
1                5                10                15

Cys Met Asn Ala Lys His His Lys Glu Lys Pro Gly Pro Glu Asp Lys
                20                25                30

Leu His Glu Gln Cys Arg Pro Trp Lys Lys Asn Ala Cys Cys Ser Thr
                35                40                45

Asn Thr Ser Gln Glu Ala His Lys Asp Val Ser Tyr Leu Tyr Arg Phe
   50                    55                60

Asn Trp Asn His Cys Gly Glu Met Ala Pro Ala Cys Lys Arg His Phe
65                70                75                80

Ile Gln Asp Thr Cys Leu Tyr Glu Cys Ser Pro Asn Leu Gly Pro Trp
                85                90                95

Ile Gln Gln Val Asp Gln Ser Trp Arg Lys Glu Arg Val Leu Asn Val
                100                105                110

Pro Leu Cys Lys Glu Asp Cys Glu Arg Trp Trp Glu Asp Cys Arg Thr
                115                120                125

Ser Tyr Cys Lys Ser Asn Trp His Lys Gly Trp Asn Trp Thr Ser Gly
   130                    135                140

Phe Asn Lys Cys Pro Val Gly Ala Ala Cys Gln Pro Phe His Phe Tyr
145                150                155                160

Phe Pro Thr Pro Thr Val Leu Cys Asn Glu Ile Trp Thr Tyr Ser Tyr
                165                170                175

Lys Val Ser Asn Tyr Ser Arg Gly Ser Gly Arg Cys Ile Gln Met Trp
                180                185                190

Phe Asp Pro Ala Gln Gly Asn Pro Asn Glu Glu Val Ala Arg Phe Tyr
                195                200                205

Ala Ala Ala Met Ser
   210

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246
<211> LENGTH: 2076
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 246

```
caggtgcaat tggttcaatc tggtgctgaa gtaaaaaaac cgggcgcttc cgttaaagtg      60
agctgcaaag catccggata caccttcact tcctattaca tgcactgggt tcgtcaagcc     120
ccgggccagg gtctggaatg gatgggcatc attaacccaa gcggtggctc tacctcctac     180
gcgcagaaat tccagggtcg cgtcacgatg acccatgaca ctagcacctc taccgtttat     240
atggagctgt ccagcctgcg ttctgaagat actgcagtgt actactgtgc acgctctttc     300
ttcactggtt tccatctgga ctattggggt caaggcaccc tcgtaacggt ttcttctgct     360
agcacaaagg gccccagcgt gttccctctg gcccctagca gcaagagcac atctggcgga     420
acagccgccc tgggctgcct cgtgaaggac tactttcccg agcctgtgac cgtgtcctgg     480
aactctggcg ccctgacaag cggcgtgcac acctttccag ccgtgctgca gagcagcggc     540
ctgtactctc tgagcagcgt ggtcaccgtg cctagcagca gcctgggcac ccagacctac     600
atctgcaacg tgaaccacaa gcccagcaac accaaagtgg acaagaaggt ggagcccaag     660
agctgtgatg cggaggagg gtccggaggc ggaggatccg aggtgcagct gctggaatct     720
ggcggcggac tggtgcagcc tggcggatct ctgagactga gctgtgccgc agcggcttc     780
accttcagca cctacgccat gaactgggtg cgccaggccc ctggcaaagg cctggaatgg     840
gtgtcccgga tcagaagcaa gtacaacaac tacgccacct actacgccga cagcgtgaag     900
ggccggttca ccatcagccg ggacgacagc aagaacaccc tgtacctgca gatgaacagc     960
ctgcgggccg aggacaccgc cgtgtactat tgtgtgcggc acggcaactt cggcaacagc    1020
tatgtgtctt ggtttgccta ctggggccag ggcaccctcg tgaccgtgtc aagcgctagt    1080
gtggccgctc cctccgtgtt tatctttccc ccatccgatg aacagctgaa agcggcacc    1140
gcctccgtcg tgtgtctgct gaacaatttt taccctaggg aagctaaagt gcagtggaaa    1200
gtggataacg cactgcagtc cggcaactcc caggaatctg tgacagaaca ggactccaag    1260
gacagcacct actccctgtc ctccaccctg acactgtcta aggctgatta tgagaaacac    1320
aaagtctacg cctgcgaagt cacccatcag ggcctgagct cgcccgtcac aaagagcttc    1380
aacaggggag agtgtgacaa gacccacacc tgtccccctt gtcctgcccc tgaagctgct    1440
ggcggccctt ctgtgttcct gttccccca aagcccaagg acaccctgat gatcagccgg    1500
accccgaag tgacctgcgt ggtggtggat gtgtcccacg aggaccctga agtgaagttc    1560
aattggtacg tggacggcgt ggaagtgcac aacgccaaga caaagccgcg ggaggagcag    1620
tacaacagca cgtaccgtgt ggtcagcgtc ctcaccgtcc tgcaccagga ctggctgaat    1680
ggcaaggagt acaagtgcaa ggtctccaac aaagccctcg cgcccccat cgagaaaacc    1740
atctccaaag ccaagggca gccccgagaa ccacaggtgt acaccctgcc ccatgccgg    1800
gatgagctga ccaagaacca ggtcagcctg tggtgcctgg tcaaaggctt ctatcccagc    1860
gacatcgccg tggagtggga gagcaatggg cagccggaga caactacaa gaccacgcct    1920
cccgtgctgg actccgacgg ctccttcttc ctctacagca agctcaccgt ggacaagagc    1980
```

| | |
|---|---|
| aggtggcagc agggggaacgt cttctcatgc tccgtgatgc atgaggctct gcacaaccac | 2040 |
| tacacgcaga agagcctctc cctgtctccg ggtaaa | 2076 |

<210> SEQ ID NO 247
<211> LENGTH: 1347
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 247

| | |
|---|---|
| caggtgcaat tggttcaatc tggtgctgaa gtaaaaaaac cgggcgcttc cgttaaagtg | 60 |
| agctgcaaag catccggata caccttcact tcctattaca tgcactgggt tcgtcaagcc | 120 |
| ccgggccagg gtctggaatg gatgggcatc attaacccaa gcggtggctc tacctcctac | 180 |
| gcgcagaaat tccagggtcg cgtcacgatg acccatgaca ctagcacctc taccgtttat | 240 |
| atggagctgt ccagcctgcg ttctgaagat actgcagtgt actactgtgc acgctctttc | 300 |
| ttcactggtt tccatctgga ctattggggt caaggcaccc tcgtaacggt ttcttctgct | 360 |
| agcaccaagg gcccctccgt gttccccctg gccccagca gcaagagcac cagcggcggc | 420 |
| acagccgctc tgggctgcct ggtcaaggac tacttccccg agcccgtgac cgtgtcctgg | 480 |
| aacagcggag ccctgacctc cggcgtgcac accttccccg ccgtgctgca gagttctggc | 540 |
| ctgtatagcc tgagcagcgt ggtcaccgtg ccttctagca gcctgggcac ccagacctac | 600 |
| atctgcaacg tgaaccacaa gcccagcaac accaaggtgg acaagaaggt ggagcccaag | 660 |
| agctgcgaca aaactcacac atgcccaccg tgcccagcac ctgaagctgc aggggggaccg | 720 |
| tcagtcttcc tcttcccccc aaaacccaag gacaccctca tgatctcccg gacccctgag | 780 |
| gtcacatgcg tggtggtgga cgtgagccac gaagaccctg aggtcaagtt caactggtac | 840 |
| gtggacggcg tggaggtgca taatgccaag acaaagccgc gggaggagca gtacaacagc | 900 |
| acgtaccgtg tggtcagcgt cctcaccgtc ctgcaccagg actggctgaa tggcaaggag | 960 |
| tacaagtgca aggtctccaa caaagccctc ggcgcccca tcgagaaaac catctccaaa | 1020 |
| gccaaagggc agccccgaga accacaggtg tgcaccctgc ccccatcccg ggatgagctg | 1080 |
| accaagaacc aggtcagcct ctcgtgcgca gtcaaaggct tctatcccag cgacatcgcc | 1140 |
| gtggagtggg agagcaatgg gcagccggag aacaactaca agaccacgcc tcccgtgctg | 1200 |
| gactccgacg gctccttctt cctcgtgagc aagctcaccg tggacaagag caggtggcag | 1260 |
| caggggaacg tcttctcatg ctccgtgatg catgaggctc tgcacaacca ctacacgcag | 1320 |
| aagagcctct ccctgtctcc gggtaaa | 1347 |

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261
<211> LENGTH: 360
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic polynucleotide"

<400> SEQUENCE: 261
gaggtgcaat tggttgaatc tggtggtggt ctggtaaaac cgggcggttc cctgcgtctg    60
agctgcgcgg cttccggatt caccttctcc aacgcgtgga tgagctgggt tcgccaggcc   120
ccgggcaaag gcctcgagtg ggttggtcgt atcaagtcta aaactgaggg tggcaccacg   180
gattacgcgg ctccagttaa aggtcgtttt accatttccc gcgacgatag caaaaacact   240
ctgtatctgc agatgaactc tctgaaaact gaagacaccg cagtctacta ctgtactacc   300
ccgtgggaat ggtcttggta cgattattgg ggccagggca cgctggttac ggtgtcttcc   360

<210> SEQ ID NO 262
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 262
gaggtgcaat tggttgaatc tggtggtggt ctggtaaaac cgggcggttc cctgcgtctg    60
agctgcgcgg cttccggatt caccttctcc aacgcgtgga tgagctgggt tcgccaggcc   120
ccgggcaaag gcctcgagtg ggttggtcgt atcaagtcta aaactcaggg tggcaccacg   180
gattacgcgg ctccagttaa aggtcgtttt accatttccc gcgacgatag caaaaacact   240
ctgtatctgc agatgaactc tctgaaaact gaagacaccg cagtctacta ctgtactacc   300
ccgtgggaat ggtcttggta cgattattgg ggccagggca cgctggttac ggtgtcttcc   360

<210> SEQ ID NO 263
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 263
gaggtgcagc tgctggaatc tggcggcgga ctggtgcagc ctggcggatc tctgagactg    60
agctgtgccg ccagcggctt caccttcagc acctacgcca tgaactgggt gcgccaggcc   120
cctggcaaag gcctggaatg ggtgtcccgg atcagaagca agtacaacaa ctacgccacc   180
tactacgccg acagcgtgaa gggccggttc accatcagcc gggacgacag caagaacacc   240
ctgtacctgc agatgaacag cctgcgggcc gaggacaccg ccgtgtacta ttgtgtgcgg   300
cacggcaact cggcgccag ctatgtgtct tggtttgcct actggggcca gggcaccctc   360
gtgaccgtgt caagc                                                    375

<210> SEQ ID NO 264
<211> LENGTH: 375
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
```

<400> SEQUENCE: 264

```
gaggtgcagc tgctggaatc tggcggcgga ctggtgcagc ctggcggatc tctgagactg    60
agctgtgccg ccagcggctt caccttcagc acctacgcca tgaactgggt gcgccaggcc   120
cctggcaaag gcctggaatg gatgtcccgg atcagaagca agtacaacaa ctacgccacc   180
tactacgccg acagcgtgaa gggccggttc accatcagcc gggacgacag caagaacacc   240
ctgtacctgc agatgaacag cctgcgggcc gaggacaccg ccgtgtacta ttgtgtgcgg   300
cacggcaact cggcaacgc ctatgtgtct tggtttgcct actggggcca gggcaccctc    360
gtgaccgtgt caagc                                                    375
```

<210> SEQ ID NO 265
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 265

```
gaggtgcaat tggttgaatc tggtggtggt ctggtaaaac cgggcggttc cctgcgtctg    60
agctgcgcgg cttccggatt caccttctcc aacgcgtgga tgagctgggt tcgccaggcc   120
ccgggcaaag gcctcgagtg ggttggtcgt atcaagtcta aaactgacgg tggcaccacg   180
gattacgcgg ctccagttaa aggtcgtttt accatttccc gcgacgatag caaaaacact   240
ctgtatctgc agatgaactc tctgaaaact gaagacaccg cagtctacta ctgtactacc   300
ccgtgggaat ggtcttggta cgattattgg ggccagggca cgctggttac ggtgtcttcc   360
gctagcacaa agggcccta g cgtgttccct ctggcccca gcagcaagag cacaagcggc   420
ggaacagccg ccctgggctg cctcgtgaag gactacttcc ccgagcccgt gacagtgtct   480
tggaacagcg gagccctgac aagcggcgtg cacactttcc ctgccgtgct gcagagcagc   540
ggcctgtact ccctgagcag cgtggtcacc gtgcctagca gcagcctggg cacccagacc   600
tacatctgca acgtgaacca caagcccagc aacaccaaag tggacaagaa ggtggagccc   660
aagagctgtg atgcggagg agggtccgga ggcggaggat ccgaggtgca gctgctggaa   720
tctggcggcg gactggtgca gcctggcgga tctctgagac tgagctgtgc cgccagcggc   780
ttcaccttca gcacctacgc catgaactgg gtgcgccagg ccctggcaa aggcctggaa   840
tgggtgtccc ggatcagaag caagtacaac aactacgcca cctactacgc cgacagcgtg   900
aagggccggt tcaccatcag ccgggacgac agcaagaaca ccctgtacct gcagatgaac   960
agcctgcggg ccgaggacac cgccgtgtac tattgtgtgc ggcacggcaa cttcggcgcc  1020
agctatgtgt cttggtttgc ctactggggc cagggcaccc tcgtgaccgt gtcaagcgct  1080
agtaccaagg gcccagcgt gttcccctg gcacccagca gcaagagcac atctggcgga   1140
acagccgctc tgggctgtct ggtgaaagac tacttccccg agcccgtgac cgtgtcttgg  1200
aactctggcg ccctgaccag cggcgtgcac acctttccag ccgtgctgca gagcagcggc  1260
ctgtactccc tgtcctccgt ggtcaccgtg cctctagct ccctgggaac acagacatat   1320
atctgtaatg tcaatcacaa gccttccaac accaaagtcg ataagaaagt cgagcccaag  1380
agctgcgaca aaactcacac atgcccaccg tgcccagcac ctgaagctgc agggggaccg  1440
tcagtcttcc tcttcccccc aaaacccaag gacaccctca tgatctcccg gacccctgag  1500
gtcacatgcg tggtggtgga cgtgagccac gaagaccctg aggtcaagtt caactggtac  1560
```

```
gtggacggcg tggaggtgca taatgccaag acaaagccgc gggaggagca gtacaacagc    1620
acgtaccgtg tggtcagcgt cctcaccgtc ctgcaccagg actggctgaa tggcaaggag    1680
tacaagtgca aggtctccaa caaagccctc ggcgccccca tcgagaaaac catctccaaa    1740 gccaagggc agccccgaga accacaggtg tacaccctgc ccccatgccg ggatgagctg     1800
accaagaacc aggtcagcct gtggtgcctg gtcaaaggct tctatcccag cgacatcgcc    1860
gtggagtggg agagcaatgg gcagccggag aacaactaca agaccacgcc tcccgtgctg    1920
gactccgacg gctccttctt cctctacagc aagctcaccg tggacaagag caggtggcag    1980
caggggaacg tcttctcatg ctccgtgatg catgaggctc tgcacaacca ctacacgcag    2040
aagagcctct ccctgtctcc gggtaaa                                        2067
```

<210> SEQ ID NO 266
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 266

```
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc    120
ccgggcaaag gcctcgagtg ggttggtcgt atcaagtcta aaactgacgg tggcaccacg    180
gattacgcgg ctccagttaa aggtcgtttt accatttccc gcgacgatag caaaaacact    240
ctgtatctgc agatgaactc tctgaaaact gaagacaccg cagtctacta ctgtactacc    300
ccgtgggaat ggtcttggta cgattattgg ggccagggca cgctggttac ggtgtcttcc    360
gctagcacca agggcccctc cgtgttcccc ctggccccca gcagcaagag caccagcggc    420
ggcacagccg ctctgggctg cctggtcaag gactacttcc ccgagcccgt gaccgtgtcc    480
tggaacagcg gagccctgac ctccggcgtg cacaccttcc ccgccgtgct gcagagttct    540
ggcctgtata gcctgagcag cgtggtcacc gtgccttcta gcagcctggg cacccagacc    600
tacatctgca acgtgaacca caagcccagc aacaccaagg tggacaagaa ggtggagccc    660
aagagctgcg acaaaactca cacatgccca ccgtgcccag cacctgaagc tgcagggga   720 ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcggggagga gcagtacaac    900 agcacgtacc gtgtggtcag cgtcctcacc gtcctgcacc aggactggct gaatggcaag    960
gagtacaagt gcaaggtctc caacaaagcc ctcggcgccc ccatcgagaa aaccatctcc   1020
aaagccaaag gcagccccg agaaccacag gtgtgcaccc tgcccccatc ccgggatgag   1080
ctgaccaaga accaggtcag cctctcgtgc gcagtcaaag gcttctatcc cagcgacatc   1140
gccgtggagt gggagagcaa tgggcagccg gagaacaact acaagaccac gcctcccgtg   1200
ctggactccg acggctcctt cttcctcgtg agcaagctca ccgtggacaa gagcaggtgg   1260
cagcagggga acgtcttctc atgctccgtg atgcatgagg ctctgcacaa ccgcttcacg   1320
cagaagagcc tctccctgtc tccgggtaaa                                    1350
```

<210> SEQ ID NO 267

```
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 267
caggccgtcg tgacccagga acccagcctg acagtgtctc ctggcggcac cgtgaccctg      60
acatgtggca gttctacagg cgccgtgacc accagcaact acgccaactg ggtgcaggaa     120
aagcccggcc aggccttcag aggactgatc ggcggcacca caagagagc ccctggcacc      180
cctgccagat tcagcggatc tctgctggga ggaaaggccg ccctgacact gtctggcgcc     240
cagccagaag atgaggccga gtactactgc gccctgtggt acagcaacct gtgggtgttc     300
ggcggaggca ccaagctgac agtcctaggt caacccaagg ctgccccag cgtgaccctg      360
ttccccccca gcagcgagga actgcaggcc aacaaggcca cctggtctg cctgatcagc      420
gacttctacc caggcgccgt gaccgtggcc tggaaggcca cagcagccc cgtgaaggcc      480
ggcgtggaga ccaccacccc cagcaagcag agcaacaaca gtacgccgc cagcagctac      540
ctgagcctga cccccgagca gtggaagagc acaggtcct acagctgcca ggtgacccac      600
gagggcagca ccgtggagaa aaccgtggcc cccaccgagt gcagc                    645

<210> SEQ ID NO 268
<211> LENGTH: 2067
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 268
gaggtgcaat tggttgaatc tggtggtggt ctggtaaaac cgggcggttc cctgcgtctg      60
agctgcgcgg cttccggatt caccttctcc aacgcgtgga tgagctgggt tcgccaggcc     120
ccgggcaaag cctcgagtg ggttggtcgt atcaagtcta aaactgacgg tggcaccacg      180
gattacgcgg ctccagttaa aggtcgtttt accatttccc gcgacgatag caaaaacact     240
ctgtatctgc agatgaactc tctgaaaact gaagacaccg cagtctacta ctgtactacc     300
ccgtgggaat ggtcttggta cgattattgg ggccagggca cgctggttac ggtgtcttcc     360
gctagcacaa agggcctag cgtgttccct ctggccccca gcagcaagag cacaagcggc      420
ggaacagccg ccctgggctg cctcgtgaag gactacttcc ccgagcccgt gacagtgtct     480
tggaacagcg gagccctgac aagcggcgtg cacactttcc ctgccgtgct gcagagcagc     540
ggcctgtact ccctgagcag cgtggtcacc gtgcctagca gcagcctggg cacccagacc     600
tacatctgca acgtgaacca caagcccagc aacaccaaag tggacaagaa ggtggagccc     660
aagagctgtg atggcggagg agggtccgga ggcggaggat ccgaggtgca gctgctggaa     720
tctggcggcg gactggtgca gcctggcgga tctctgagac tgagctgtgc cgccagcggc     780
ttcaccttca gcacctacgc catgaactgg gtgcgccagg cccctggcaa aggcctggaa     840
tgggtgtccc ggatcagaag caagtacaac aactacgcca cctactacgc cgacagcgtg     900
aagggccggt tcaccatcag ccgggacgac agcaagaaca ccctgtacct gcagatgaac     960
agcctgcggg ccgaggacac cgccgtgtac tattgtgtgc ggcacggcaa cttcggcaac    1020
gcctatgtgt cttggtttgc ctactggggc cagggcaccc tcgtgaccgt gtcaagcgct    1080
```

```
agtaccaagg gccccagcgt gttcccctg gcacccagca gcaagagcac atctggcgga    1140
acagccgctc tgggctgtct ggtgaaagac tacttccccg agcccgtgac cgtgtcttgg    1200
aactctggcg ccctgaccag cggcgtgcac acctttccag ccgtgctgca gagcagcggc    1260
ctgtactccc tgtcctccgt ggtcaccgtg ccctctagct ccctgggaac acagacatat    1320
atctgtaatg tcaatcacaa gccttccaac accaaagtcg ataagaaagt cgagcccaag    1380
agctgcgaca aaactcacac atgcccaccg tgcccagcac ctgaagctgc aggggaccg    1440 tcagtcttcc tcttccccc aaaacccaag gacaccctca tgatctcccg gacccctgag    1500
gtcacatgcg tggtggtgga cgtgagccac gaagaccctg aggtcaagtt caactggtac    1560
gtggacggcg tggaggtgca taatgccaag acaaagccgc gggaggagca gtacaacagc    1620
acgtaccgtg tggtcagcgt cctcaccgtc ctgcaccagg actggctgaa tggcaaggag    1680
tacaagtgca aggtctccaa caaagccctc ggcgccccca tcgagaaaac catctccaaa    1740
gccaaagggc agccccgaga accacaggtg tacaccctgc ccccatgccg ggatgagctg    1800
accaagaacc aggtcagcct gtggtgcctg gtcaaaggct tctatcccag cgacatcgcc    1860
gtggagtggg agagcaatgg gcagccggag aacaactaca agaccacgcc tcccgtgctg    1920
gactccgacg gctccttctt cctctacagc aagctcaccg tggacaagag caggtggcag    1980
caggggaacg tcttctcatg ctccgtgatg catgaggctc tgcacaacca ctacacgcag    2040
aagagcctct ccctgtctcc gggtaaa                                         2067

<210> SEQ ID NO 269
<211> LENGTH: 2070
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 269
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctggaatg gatgggcatc attaacccaa gcggtggccc tacctcctac    180
gcgcagaaat tccagggtcg cgtcacgatg acccgtgaca ctagcacctc taccgtttat    240
atggagctgt ccagcctgcg ttctgaagat actgcagtgt actactgtgc acgcggtgac    300
ttcgcttggc tggactattg gggtcaaggc accctcgtaa cggtttcttc tgctagcaca    360
aagggcccca gcgtgttccc tctggcccct agcagcaaga gcacatctgg cggaacagcc    420
gccctgggct gcctcgtgaa ggactacttt cccgagcctg tgaccgtgtc ctggaactct    480
ggcgccctga caagcggcgt gcacaccttt ccagccgtgc tgcagagcag cggcctgtac    540
tctctgagca gcgtggtcac cgtgcctagc agcagcctgg gcacccagac ctacatctgc    600
aacgtgaacc acaagcccag caacaccaaa gtggacaaga aggtggagcc caagagctgt    660
gatggcggag agggtccgg aggcggagga tccgaggtgc agctgctgga atctggcggc    720
ggactggtgc agcctggcgg atctctgaga ctgagctgtg ccgccagcgg cttcaccttc    780
agcacctacg ccatgaactg ggtgcgccag gcccctggca aaggcctgga atgggtgtcc    840
cggatcagaa gcaagtacaa caactacgcc acctactacg ccgacagcgt gaagggccgg    900
ttcaccatca gccgggacga cagcaagaac accctgtacc tgcagatgaa cagcctgcgg    960
```

| | | | | |
|---|---|---|---|---|
| gccgaggaca | ccgccgtgta | ctattgtgtg | cggcacggca | acttcggcgc cagctatgtg | 1020 |
| tcttggtttg | cctactgggg | ccagggcacc | ctcgtgaccg | tgtcaagcgc tagtgtggcc | 1080 |
| gctccctccg | tgtttatctt | tcccccatcc | gatgaacagc | tgaaaagcgg caccgcctcc | 1140 |
| gtcgtgtgtc | tgctgaacaa | ttttacccct | agggaagcta | aagtgcagtg gaaagtggat | 1200 |
| aacgcactgc | agtccggcaa | ctcccaggaa | tctgtgacag | aacaggactc caaggacagc | 1260 |
| acctactccc | tgtcctccac | cctgacactg | tctaaggctg | attatgagaa acacaaagtc | 1320 |
| tacgcctgcg | aagtcaccca | tcagggcctg | agctcgcccg | tcacaaagag cttcaacagg | 1380 |
| ggagagtgtg | acaagaccca | cacctgtccc | ccttgtcctg | cccctgaagc tgctggcggc | 1440 |
| ccttctgtgt | tcctgttccc | cccaaagccc | aaggacaccc | tgatgatcag ccggaccccc | 1500 |
| gaagtgacct | gcgtggtggt | ggatgtgtcc | cacgaggacc | ctgaagtgaa gttcaattgg | 1560 |
| tacgtggacg | gcgtggaagt | gcacaacgcc | aagacaaagc | cgcgggagga gcagtacaac | 1620 |
| agcacgtacc | gtgtggtcag | cgtcctcacc | gtcctgcacc | aggactggct gaatggcaag | 1680 |
| gagtacaagt | gcaaggtctc | caacaaagcc | ctcggcgccc | catcgagaa aaccatctcc | 1740 |
| aaagccaaag | ggcagccccg | agaaccacag | gtgtacaccc | tgcccccatg ccgggatgag | 1800 |
| ctgaccaaga | accaggtcag | cctgtggtgc | ctggtcaaag | gcttctatcc cagcgacatc | 1860 |
| gccgtggagt | gggagagcaa | tgggcagccg | gagaacaact | acaagaccac gcctcccgtg | 1920 |
| ctggactccg | acggctcctt | cttcctctac | agcaagctca | ccgtggacaa gagcaggtgg | 1980 |
| cagcagggga | acgtcttctc | atgctccgtg | atgcatgagg | ctctgcacaa ccactacacg | 2040 |
| cagaagagcc | tctccctgtc | tccgggtaaa | | | 2070 |

<210> SEQ ID NO 270
<211> LENGTH: 1341
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 270

| | | | | |
|---|---|---|---|---|
| caggtgcaat | tggttcaatc | tggtgctgaa | gtaaaaaaac | cgggcgcttc cgttaaagtg | 60 |
| agctgcaaag | catccggata | caccttcact | tcctattaca | tgcactgggt tcgtcaagcc | 120 |
| ccgggccagg | gtctggaatg | gatgggcatc | attaacccaa | gcggtggccc tacctcctac | 180 |
| gcgcagaaat | tccagggtcg | cgtcacgatg | acccgtgaca | ctagcacctc taccgtttat | 240 |
| atggagctgt | ccagcctgcg | ttctgaagat | actgcagtgt | actactgtgc acgcggtgac | 300 |
| ttcgcttggc | tggactattg | gggtcaaggc | accctcgtaa | cggtttcttc tgctagcacc | 360 |
| aagggcccct | ccgtgttccc | cctggccccc | agcagcaaga | gcaccagcgg cggcacagcc | 420 |
| gctctgggct | gcctggtcaa | ggactacttc | cccgagcccg | tgaccgtgtc ctggaacagc | 480 |
| ggagccctga | cctccggcgt | gcacaccttc | cccgccgtgc | tgcagagttc tggcctgtat | 540 |
| agcctgagca | gcgtggtcac | cgtgccttct | agcagcctgg | gcacccagac ctacatctgc | 600 |
| aacgtgaacc | acaagcccag | caacaccaag | gtggacaaga | aggtggagcc caagagctgc | 660 |
| gacaaaactc | acacatgccc | accgtgccca | gcacctgaag | ctgcaggggg accgtcagtc | 720 |
| ttcctcttcc | ccccaaaacc | caaggacacc | ctcatgatct | cccggacccc tgaggtcaca | 780 |
| tgcgtggtgg | tggacgtgag | ccacgaagac | cctgaggtca | agttcaactg gtacgtggac | 840 |
| ggcgtggagg | tgcataatgc | caagacaaag | ccgcgggagg | agcagtacaa cagcacgtac | 900 |

```
cgtgtggtca gcgtcctcac cgtcctgcac caggactggc tgaatggcaa ggagtacaag    960
tgcaaggtct ccaacaaagc cctcggcgcc cccatcgaga aaccatctc caaagccaaa    1020 gggcagcccc gagaaccaca ggtgtgcacc ctgcccccat cccgggatga gctgaccaag    1080
aaccaggtca gcctctcgtg cgcagtcaaa ggcttctatc ccagcgacat cgccgtggag    1140
tgggagagca atgggcagcc ggagaacaac tacaagacca cgcctcccgt gctggactcc    1200
gacggctcct tcttcctcgt gagcaagctc accgtggaca gagcaggtg gcagcagggg    1260 aacgtcttct catgctccgt gatgcatgag gctctgcaca accactacac gcagaagagc    1320
ctctccctgt ctccgggtaa a                                              1341
```

<210> SEQ ID NO 271
<211> LENGTH: 657
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 271

```
gatattgtta tgactcaatc tccactgtct ctgccggtga ctccaggcga accggcgagc    60
atttcttgcc gttccagcca gtctctgctg cactccaacg gctacaacta tctcgattgg    120
tacctgcaaa aaccgggtca gagccctcag ctgctgatct acctgggctc taaccgcgct    180
tccggtgtac cggaccgttt cagcggctct ggatccggca ccgatttcac gttgaaaatc    240
agccgtgttg aagcagaaga cgtgggcgtt tattactgta tgcaggcaag cattatgcag    300
cggacttttg gtcaaggcac caaggtcgaa attaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt     657
```

<210> SEQ ID NO 272
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 272

```
caggccgtcg tgacccagga acccagcctg acagtgtctc ctggcggcac cgtgaccctg    60
acatgtggca gttctacagg cgccgtgacc accagcaact acgccaactg ggtgcaggaa    120
aagcccggcc aggccttcag aggactgatc ggcggcacca acaagagagc ccctggcacc    180
cctgccagat tcagcggatc tctgctggga ggaaaggccg ccctgacact gtctggcgcc    240
cagccagaag atgaggccga gtactactgc gccctgtggt acagcaacct gtgggtgttc    300
ggcggaggca ccaagctgac agtgctgagc agcgcttcca ccaaaggccc ttccgtgttt    360
cctctggctc ctagctccaa gtccacctct ggaggcaccg ctgctctcgg atgcctcgtg    420
aaggattatt ttcctgagcc tgtgacagtg tcctggaata gcggagcact gacctctgga    480
```

-continued

```
gtgcatactt tccccgctgt gctgcagtcc tctggactgt acagcctgag cagcgtggtg    540
acagtgccca gcagcagcct gggcacccag acctacatct gcaacgtgaa ccacaagccc    600
agcaacacca aggtggacaa gaaggtggaa cccaagtctt gt                       642
```

<210> SEQ ID NO 273
<211> LENGTH: 2070
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 273

```
caggtgcaat tggttcaatc tggtgctgaa gtaaaaaaac cgggcgcttc cgttaaagtg     60
agctgcaaag catccggata caccttcact tcctattaca tgcactgggt tcgtcaagcc    120
ccgggccagg gtctgaatg gatgggcatc attaacccaa gcggtggccc tacctcctac    180
gcgcagaaat tccagggtcg cgtcacgatg acccgtgaca ctagcacctc taccgtttat    240
atggagctgt ccagcctgcg ttctgaagat actgcagtgt actactgtgc acgcggtgac    300
ttcgcttggc tggactattg gggtcaaggc accctcgtaa cggtttcttc tgctagcaca    360
aagggcccca gcgtgttccc tctggcccct agcagcaaga gcacatctgg cggaacagcc    420
gccctgggct gcctcgtgaa ggactacttt cccgagcctg tgaccgtgtc ctggaactct    480
ggcgccctga caagcggcgt gcacaccttt ccagccgtgc tgcagagcag cggcctgtac    540
tctctgagca gcgtggtcac cgtgcctagc agcagcctgg gcacccagac ctacatctgc    600
aacgtgaacc acaagcccag caacaccaaa gtggacaaga aggtggagcc caagagctgt    660
gatggcggag gagggtccgg aggcggagga tccgaggtgc agctgctgga atctggcggc    720
ggactggtgc agcctggcgg atctctgaga ctgagctgtg ccgccagcgg cttcaccttc    780
agcacctacg ccatgaactg ggtgcgccag gcccctggca aaggcctgga atgggtgtcc    840
cggatcagaa gcaagtacaa caactacgcc acctactacg ccgacagcgt gaagggccgg    900
ttcaccatca gccgggacga cagcaagaac accctgtacc tgcagatgaa cagcctgcgg    960
gccgaggaca ccgccgtgta ctattgtgtg cggcacggca acttcggcaa cgcctatgtg   1020
tcttggtttg cctactgggg ccagggcacc ctcgtgaccg tgtcaagcgc tagtgtggcc   1080
gctccctccg tgtttatctt tccccccatcc gatgaacagc tgaaaagcgg caccgcctcc   1140
gtcgtgtgtc tgctgaacaa ttttttacccct agggaagcta aagtgcagtg gaaagtggat   1200
aacgcactgc agtccggcaa ctcccaggaa tctgtgacag aacaggactc caaggacagc   1260
acctactccc tgtcctccac cctgacactg tctaaggctg attatgagaa acacaaagtc   1320
tacgcctgcg aagtcaccca tcagggcctg agctcgcccg tcacaaagag cttcaacagg   1380
ggagagtgtg acaagaccca cacctgtccc ccttgtcctg cccctgaagc tgctggcggc   1440
ccttctgtgt tcctgttccc cccaaagccc aaggacaccc tgatgatcag ccggacccc     1500 gaagtgacct gcgtggtggt ggatgtgtcc cacgaggacc ctgaagtgaa gttcaattgg   1560
tacgtggacg gcgtggaagt gcacaacgcc aagacaaagc cgcgggagga gcagtacaac   1620
agcacgtacc gtgtggtcag cgtcctcacc gtcctgcacc aggactggct gaatggcaag   1680
gagtacaagt gcaaggtctc caacaaagcc ctcggcgccc ccatcgagaa aaccatctcc   1740
aaagccaaag gcagccccg agaaccacag gtgtacaccc tgcccccatg ccgggatgag   1800
ctgaccaaga accaggtcag cctgtggtgc ctggtcaaag gcttctatcc cagcgacatc   1860
```

| | | | | | |
|---|---|---|---|---|---|
| gccgtggagt | gggagagcaa | tgggcagccg | gagaacaact | acaagaccac | gcctcccgtg | 1920
| ctggactccg | acggctcctt | cttcctctac | agcaagctca | ccgtggacaa | gagcaggtgg | 1980
| cagcagggga | acgtcttctc | atgctccgtg | atgcatgagg | ctctgcacaa | ccactacacg | 2040
| cagaagagcc | tctccctgtc | tccgggtaaa | | | | 2070